US009101598B2

(12) United States Patent
Bublot et al.

(10) Patent No.: US 9,101,598 B2
(45) **Date of Patent: *Aug. 11, 2015**

(54) RECOMBINANT GALLID HERPESVIRUS 3 (MDV SEROTYPE 2) VECTORS EXPRESSING ANTIGENS OF AVIAN PATHOGENS AND USES THEREOF

(71) Applicants: Michel Bublot, Chaponost (FR); Teshome Mebatsion, Watkinsville, GA (US); Joyce Pritchard, Gainesville, GA (US); Perry Linz, Jefferson, GA (US)

(72) Inventors: Michel Bublot, Chaponost (FR); Teshome Mebatsion, Watkinsville, GA (US); Joyce Pritchard, Gainesville, GA (US); Perry Linz, Jefferson, GA (US)

(73) Assignee: MERIAL, INC., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/689,572

(22) Filed: Nov. 29, 2012

(65) Prior Publication Data

US 2014/0147465 A1 May 29, 2014

Related U.S. Application Data

(60) Provisional application No. 61/564,877, filed on Nov. 30, 2011, provisional application No. 61/694,957, filed on Aug. 30, 2012.

(51) Int. Cl.

| | |
|---|---|
| ***A61K 39/245*** | (2006.01) |
| ***A61K 39/17*** | (2006.01) |
| ***A61K 39/295*** | (2006.01) |
| ***A61K 39/12*** | (2006.01) |
| ***C12N 15/869*** | (2006.01) |
| ***C12N 15/38*** | (2006.01) |
| ***C12N 15/45*** | (2006.01) |
| *A61K 39/00* | (2006.01) |

(52) U.S. Cl.

CPC ............... *A61K 39/295* (2013.01); *A61K 39/12* (2013.01); *A61K 2039/53* (2013.01); *C12N 2710/16334* (2013.01); *C12N 2710/20034* (2013.01); *C12N 2760/18134* (2013.01)

(58) Field of Classification Search

CPC . A61K 39/12; A61K 39/295; A61K 2039/53; C12N 2710/16334; C12N 2710/20034; C12N 2760/18134

See application file for complete search history.

(56) References Cited

U.S. PATENT DOCUMENTS

| | | | | |
|---|---|---|---|---|
| 5,187,087 | A | 2/1993 | Sondermeijer et al. | |
| 5,853,733 | A | 12/1998 | Cochran et al. | |
| 5,980,906 | A * | 11/1999 | Audonnet et al. | 424/199.1 |
| 6,183,753 | B1 | 2/2001 | Cochran et al. | |
| 2002/0081316 | A1 * | 6/2002 | Cochran et al. | 424/199.1 |
| 2013/0101619 | A1 * | 4/2013 | Cook et al. | 424/199.1 |
| 2014/0147457 | A1 | 5/2014 | Bublot et al. | |

FOREIGN PATENT DOCUMENTS

| | | |
|---|---|---|
| EP | 1 298 139 | 2/2003 |
| WO | WO-A-87/04463 | 7/1987 |

OTHER PUBLICATIONS

Heidari M, Huebner M, Kireev D, Silva RF. Transcriptional profiling of Marek's disease virus genes during cytolytic and latent infection. Virus Genes. Apr. 2008;36(2):383-92. Epub Feb. 12, 2008.*

Yao Y, Zhao Y, Xu H, Smith LP, Lawrie CH, Sewer A, Zavolan M, Nair V. Marek's disease virus type 2 (MDV-2)-encoded microRNAs show no sequence conservation with those encoded by MDV-1. J Virol. Jul. 2007;81(13):7164-70. Epub Apr. 25, 2007.*

Bublot M, Laplace E, Audonnet JC. Non-essential loci in the BamHI-I and -F fragments of the HVT FC126 genome. Acta Virol. Apr.-Jun. 1999;43(2-3):181-5.*

Lemiere S, Wong SY, Saint-Gerand AL, Goutebroze S, Le Gros FX. Compatibility of turkey herpesvirus-infectious bursal disease vector vaccine with Marek's disease rispens vaccine injected into day-old pullets. Avian Dis. Mar. 2011;55(1):113-8.*

Lemiere S, Fernandez R, Pritchard N, Cruz-Coy J, Rojo F, Wong Sy, Saint-Gerand Al, Gauthier Jc, Perozo F. Concomitant turkey herpesvirus-infectious bursal disease vector vaccine and oil-adjuvanted inactivated Newcastle disease vaccine administration: consequences for vaccine intake and protection. Avian Dis. 2011 Dec;55(4):642-9.*

Goutebroze S, Curet M, Jay Ml, Roux C, Le Gros Fx. Efficacy of a recombinant vaccine Hvt-VP2 against Gumboro disease in the presence of maternal antibodies.Br Poult Sci. 2003 Dec;44(5):824-5.*

Seal Bs, King Dj, Sellers Hs. The avian response to Newcastle disease virus. Dev Comp Immunol. 2000 Mar-Apr;24(2-3):257- 68.*

Darteil R, Bublot M, Laplace E, Bouquet Jf, Audonnet Jc, Rivière M. Herpesvirus of turkey recombinant viruses expressing infectious bursal disease virus (Ibdv) VP2 immunogen induce protection against an Ibdv virulent challenge in chickens. Virology. 1995 Aug 20;211(2):481-90.*

(Continued)

*Primary Examiner* — Benjamin P Blumel
*Assistant Examiner* — Rachel Gill
(74) *Attorney, Agent, or Firm* — Judy Jarecki-Black; Ruoying Chen; Merial, Inc.

(57) ABSTRACT

The present invention provides recombinant Gallid herpesvirus 3 (MDV-2) vectors that contain and express antigens of avian pathogens, recombinant Gallid herpesvirus 3 (MDV-2) vectors that contain a mutated gC gene, compositions comprising the recombinant Gallid herpesvirus 3 (MDV-2) vectors, polyvalent vaccines comprising the recombinant Gallid herpesvirus 3 (MDV-2) vectors and one or more wild type viruses or recombinant vectors. The present invention further provides methods of vaccination against a variety of avian pathogens and method of producing the recombinant Gallid herpesvirus 3 (MDV-2) vectors.

10 Claims, 37 Drawing Sheets

(56) References Cited

OTHER PUBLICATIONS

Senne DA, King DJ, Kapczynski DR. Control of Newcastle disease by vaccination. Dev Biol (Basel). 2004;119:165-70.*
Jarosinski Kw, et. al. PLoS One. 2012;7(5):e37428. Epub May 21, 2012.*
Sharma Jm, et. al. Avian Dis. Jul-Sep 2002;46(3):613-22.*
Taylor J, Edbauer C, Rey-Senelonge A, Bouquet JF, Norton E, Goebel S, Desmettre P, Paoletti E. Newcastle disease virus fusion protein expressed in a fowlpox virus recombinant confers protection in chickens. J Virol. Apr. 1990;64(4):1441-50.*
Liu HL, et. al. NCBI GenBank Direct Submission, Acc. No. AAP97877, Sub. Jul. 29, 2003.*
"Codon optimization to PCR". Beckman-Coulter. Nature. vol. 25: Oct. 2, 2003. p. 540.*
Taylor J, et. al. Newcastle disease virus fusion protein F-0 (NDFF) gene, complete cds. GenBank Acc. No. M33855. Dep. Aug. 2, 1993. Pub. In. J Virol. Apr. 1990;64(4):1441-50.*
Taylor J, et. al. Fusion protein F-0 precursor (NDFF) [Newcastle disease virus]. GenBank Acc. No. AAA46675. Dep. Aug. 2, 1993. Pub. In. J Virol. Apr. 1990;64(4):1441-50.*
Rahaus M, Augustinski K, Castells M, Desloges N. Application of a new bivalent Marek's disease vaccine does not interfere with infectious bronchitis or Newcastle disease vaccinations and proves efficacious. Avian Dis. Jun. 2013;57(2 Suppl):498-502.*
FAQ's on Viral Tumor Diseases. AAAP Tumor Virus Committee. 2012.*
Efficacy Studies (including Interference Studies). Internal USDA Document; provided by Applicant Dec. 22, 2014.*
CVB Policy, Evaluation and Licensing—Reviewers Manual. Internal USDA Document; provided by Applicant Dec. 22, 2014.*
Witter RL, Bacon LD, Calvert JG. Partial inhibition by turkey herpesvirus of serotype 2 Marek's disease virus plaque formation and in vivo infectivity. Avian Dis. Oct.-Dec. 1994;38(4):800-9.*
Bublot et al J.Comp. Path.2007,vol. 137, S81-S84, "Use of a Vectored Vaccine against Infectious Bursal Disease of Chickens in the Face of High-Titred maternally Derived Antibody".
Petherbridge, et al., J. Virol. Methods 158, 11-17, 2009, "Cloning of Gallid herpesvirus 3 (Marek's disease virus serotype-2) genome as infectious bacterial artificial chromosomes for analysis of viral gene functions".
Jarosinski, et al., J. of Virology 81, 10575-10587, 2007, "Horizontal Transmission of Marek's Disease Virus Requires $U_S2$, the $U_L13$ protein Kinase, and gC".
Jarosinski, et al., J. of Virology 84, 7911-7916, 2010, "Further analysis of Marek's disease virus horizontal transmission confirms that $U_L44$ (gC) and $U_L13$ protein kinase activity are essential, while $U_S2$ is nonessential".
Johnson et al, 2010 Avian Dis 54, 1251-1259, "Protection Against Infectious Laryngotracheitis by In Ovo Vaccination with Commercially Available Viral Vector Recombinant Vaccines".
Morgan et al 1992, Avian dis. 36, 858-70, "Protection of Chickens from Newcastle and Marek's Diseases with a Recombinant Herpesvirus of Turkeys Vaccine Expressing the Newcastle Disease Virus Fusion Protein".
Rudolf Heine 2011; Issues of the Poultry Recombinant Viral Vector Vaccines which May Cause an Effect on the Economic Benefits of those Vaccines; paper presented at the XVII World Veterinary Poultry Association (WVPA) Congress in Cancan, Mexico, Aug. 14-18, 2011.
Singh et al., Research in Veterinary Science 89, 140-145, 2010, "Comparative efficacy of BAC-derived recombinant SB-1 vaccine and the parent wild type strain in preventing replication, shedding and disease induced by virulent Marek's disease virus".
Slacum et al, 2009, The compatibility of HVT recombinants with other Marek's disease vaccines, 58th Western Poultry Disease Conference, Sacramento, CA, USA, Mar. 23rd-25th, p. 84.
Spatz et al, Virus Gene 42, 331-338, 2011, "Comparative genomic sequence analysis of the Marek's disease vaccine strain SB-1".
Witter et al, 1984, Avian Pathology 13, 75-92, "Polyvalent Marek's disease vaccines: safety, efficacy and protective synergism in chickens with maternal antibodies".

* cited by examiner

Figure 1

| SEQ ID NO: | Type | Gene Description |
|---|---|---|
| 1 | DNA | NDV F codon-optimized gene from modified wt VIId |
| 2 | Protein | NDV F protein of codon-optimized NDV-F gene of modified wt VIId |
| 3 | DNA | NDV-F DNA wt VIId in SB-1 construct |
| 4 | DNA | NDV-F DNA with GenBank accession No. AY337464.1 |
| 5 | Protein | NDV-F protein with GenBank accession No. AAP97877.1 |
| 6 | DNA | NDV-F DNA wildtype V (CA02 strain) with GenBank accession No. EF520718 |
| 7 | Protein | NDV-F protein wildtype V (CA02 strain) with GenBank accession No. ABS84266 |
| 8 | DNA | NDV-F codon-optimized gene from modified wildtype V (CA02 strain) |
| 9 | Protein | NDV-F protein of codon-optimized NDV-F gene of modified wildtype V (CA02 strain) in vSB1-008 and vSB1-009 |
| 10 | DNA | MCMV IE promoter |
| 11 | DNA | SV40 PolyA |
| 12 | DNA | SV40 promoter |
| 13 | DNA | Synthetic PolyA |
| 14 | DNA | SB-1 genome HQ840738.1 |
| 15 | Oligo | MB080 primer: CGA ACA AAC TTC ATC GCT ATG C |
| 16 | Oligo | MB081 primer: TAA CTC AAA TGC GAA GCG TTG C |
| 17 | Oligo | SB-1 US10 primer: TCA ACG TGC GAC AAT CGT CTG |
| 18 | Oligo | SB-1 SORF4 primer: ATG TGG AGG AAC GAT CCT ATA |
| 19 | Oligo | ALLNDVFprimer: ATG GCT TGG GAA TAA TAC |
| 20 | Oligo | mCMVF primer: AAC TCC GCC CGT TTT ATG |
| 21 | Oligo | SV40tailR primer: TCG ACT CTA GAG GAT CCG |
| 22 | Oligo | newSB-1 UL55R primer: ATGGCTATAGAGGGACTGTGT |
| 23 | Oligo | New SB-1 ORF5F primer: GATCTCAACGCTATACCGGCG |
| 24 | Oligo | OptF primer: ACT GAC AAC ACC CTA CAT GGC |
| 25 | Oligo | VIIoptF RP primer: GCC AGC ACC AGG CTC AGG G |
| 26 | Oligo | SV40promoterF primer: AGC TTG GCT GTG GAA TGT |
| 27 | Oligo | SB1 43.F primer: GCT CTC GGA GAC GCG GCT CGC |
| 28 | Oligo | SB1 45.R primer: GCT CTT GTA ACA TCG CGG ACG |
| 29 | Oligo | SV40 promoter F primer: AGC TTG GCT GTG GAA TGT |
| 30 | Oligo | HVTUS10 FP primer: CCG GCA ACA TAC ATA ATG TG |
| 31 | Oligo | HVTUS10 RP primer: GGC ACT ATC CAC AGT ACG |
| 32 | Oligo | CaoptF RP primer: GCC AGC ACC AGG CTC ATC A |
| 33 | Oligo | SynTailR primer: ATG TTC TGG CAC CTG CAC |
| 34 | DNA | Gene coding for glycoprotein C of SB-1 strain GenBank accession No.HQ840738 |
| 35 | Protein | Glycoprotein C of SB-1 strain GenBank accession No. AEI00252 |

Figure 1 (continued)

| SEQ ID NO: | Type | Gene Description |
|---|---|---|
| 36 | DNA | Plasmid pSB1 44cds (for gC deletion) |
| 37 | DNA | Partial plasmid pSB1 44 cds SV FCAopt (for vSB1-009) |
| 38 | DNA | Partial plasmid pHM103+Fopt DNA sequence (for vHVT114) |
| 39 | DNA | IBDV DNA encoding VP2 protein |
| 40 | Protein | IBDV VP2 protein |
| 41 | DNA | Partial plasmid sequence of SB-1 US10mFwt SbfI (for vSB1-004) |
| 42 | DNA | Partial plasmid sequence of SB1 UL55 SVFopt syn tail SbfI (for vSB1-006) |
| 43 | DNA | Partial plasmid sequence of pSB1 44 cds SVOptF (for vSB1-007) |
| 44 | DNA | Partial plasmid sequence of SB-1 UL55 CaFopt syn tail SbfI (for vSB1-008) |
| 45 | DNA | Partial plasmid sequence of pHVT US2 SV- Fopt-synPA (for vHVT306) |
| 46 | DNA | Partial plasmid pCD046+NDV-F VII YZCQ sequence (vHVT112) |
| 47 | DNA | Partial plasmid pCD046+NDV Texas F sequence (for vHVT113) |
| 48 | DNA | Partial plasmid pHM119 sequence (for vHVT039) |
| 49 | DNA | NDV-F Wtnm-Texas wildtype DNA sequence |
| 50 | protein | NDV-F protein from Wtnm-Texas wildtype |
| 51 | DNA | NDV-F YZCQ wildtype DNA sequence |
| 52 | protein | NDV-F protein from wildtype YZCQ strain |
| 53 | DNA | NDV-F Texas wildtype DNA sequence |
| 54 | protein | NDV-F protein from wildtype Texas strain |
| 55 | DNA | MDV gB promoter |
| 56 | DNA | Partial plasmid HVT SORF3-US2 gpVar-Ewtsyn sequence (vHVT202) |
| 57 | DNA | Partial plasmid SB1US2 gpVIIdwtsyn sequence (vSB1-010) |
| 58 | DNA | IBDV DNA encoding VP2 protein of IBDV E strain |
| 59 | protein | IBDV VP2 protein of IBDV E strain |
| 60 | DNA | Guinea pig CMV promoter |
| 61 | oligo | primer HM101 |
| 62 | oligo | Primer HM102 |
| 63 | oligo | primer F-ATG |
| 64 | oligo | Primer F-STOP |

Schematic diagram of SB-1 genome organization

The UL44 (gC), UL55/LORF5 and US10/SORF4 insertion sites are shown

Immunofluorescent staining of recombinant vSB1-004 virus expressing NDV-F protein Schematic representation of primer binding sites vSB1-004 Identity PCR Lane 1: no template
Lane 2: HVT FC126
Lane 3: SB-1 parental virus
Lane 4: vSB1-004

Immunofluorescent staining of recombinant vSB1-006 virus expressing NDV-F protein Schematic representation of primer binding sites Figure 8
vSB1-006 Identity PCR Results
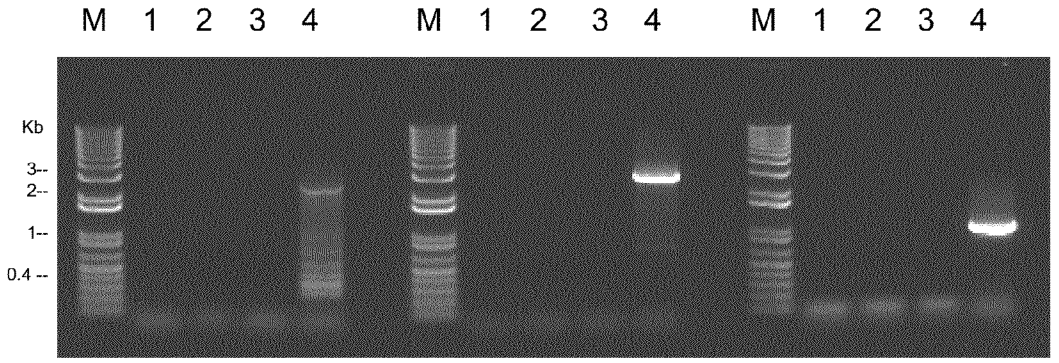
newSB-1ORF5F+VIIoptF.RP SV40promoterF+newSB-1UL55R OptFprimer+newSB-1UL55R
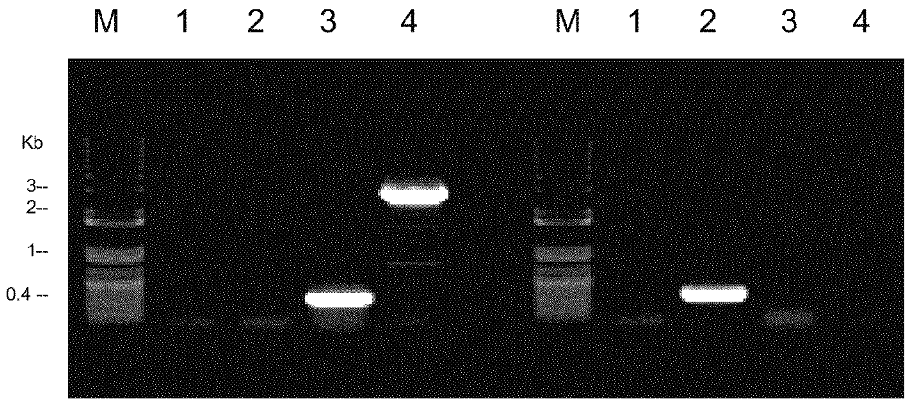
New SB1LOrf5F + New SB1UL55R MB080 + MB081
Lane 1: no template
Lane 2: HVT FC126
Lane 3: parent SB-1
Lane 4: vSB1-006

Immunofluorescent staining of recombinant SB1-007 virus
expressing NDV-F protein Schematic diagram of primer location on pSB1 44 cds SVOptF donor plasmid vSB1-007 Identity PCR

| | | | |
|---|---|---|---|
| Lane1:vSB1-007 | Lane1:vSB1-007 | Lane1:vSB1-007 | Lane1:vSB1-007 |
| Lane2:pSB1 44 cds SV optF | Lane2:pSB1 44 cds SV optF | Lane2:pSB1 44 cds SV optF | Lane2:HVT |
| Lane3:SB-1, | Lane3:SB-1, | Lane3:SB-1 | Lane3:SB-1 |
| Lane4:Water | Lane4:Water | Lane4:Water | Lane4:Water |

Immunofluorescent staining of recombinant SB1-008 virus expressing NDV-F protein Schematic representation of primer binding sites SB-1 UL55 SVCaFsyn tail SbfI rc 6867 bp Figure 14
vSB1-008 Identity PCR Results
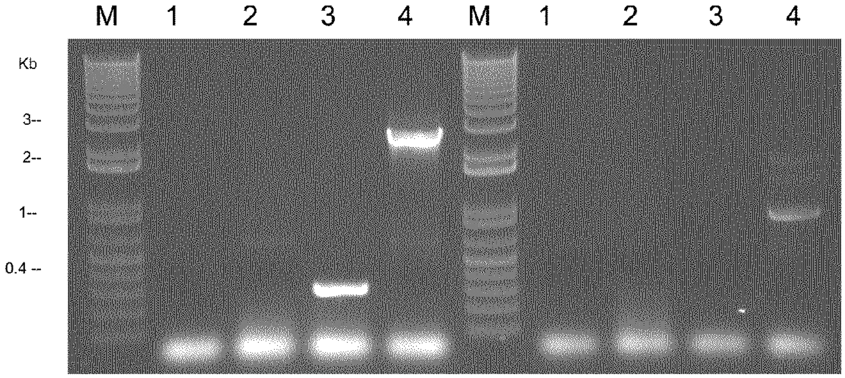
New SB1-UL55R + New SB1-ORF5F
New SB1-ORF5F + CaFopt R.P.
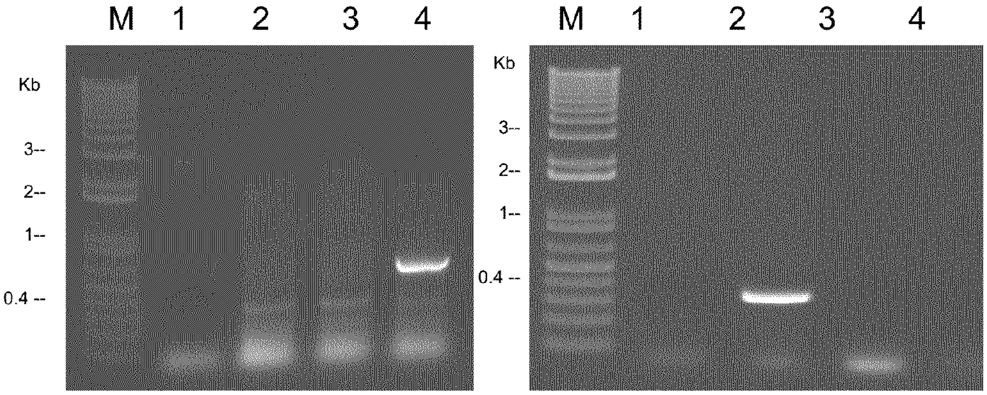
SynTail R + optF
MB080 + MB081
Lane 1: no template
Lane 2: HVT FC126
Lane 3: parent SB-1
Lane 4: vSB1-008

Western blot analysis of immunoprecipitated sample
from vSB1-009 infected cells

Lane M: pre-stained protein standard (Invitrogen, SeeBlue)
Lane 1: uninfected CEF
Lane 2: vSB1-009 pre-MSV stock Immunoprecipitation and Western Blot of vHVT114

Lane M: Pre-Stained Standard (SeeBlue, Invitrogen)
Lane 1: CEF
Lane 2: vHVT114

Figure 17
FIG. 17A
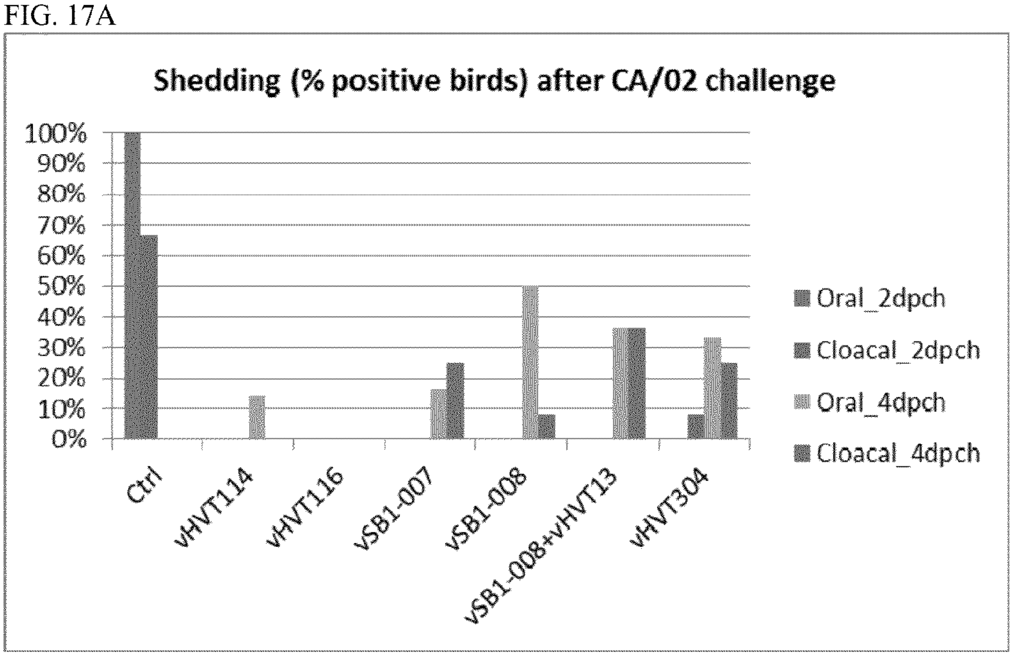
FIG. 17B
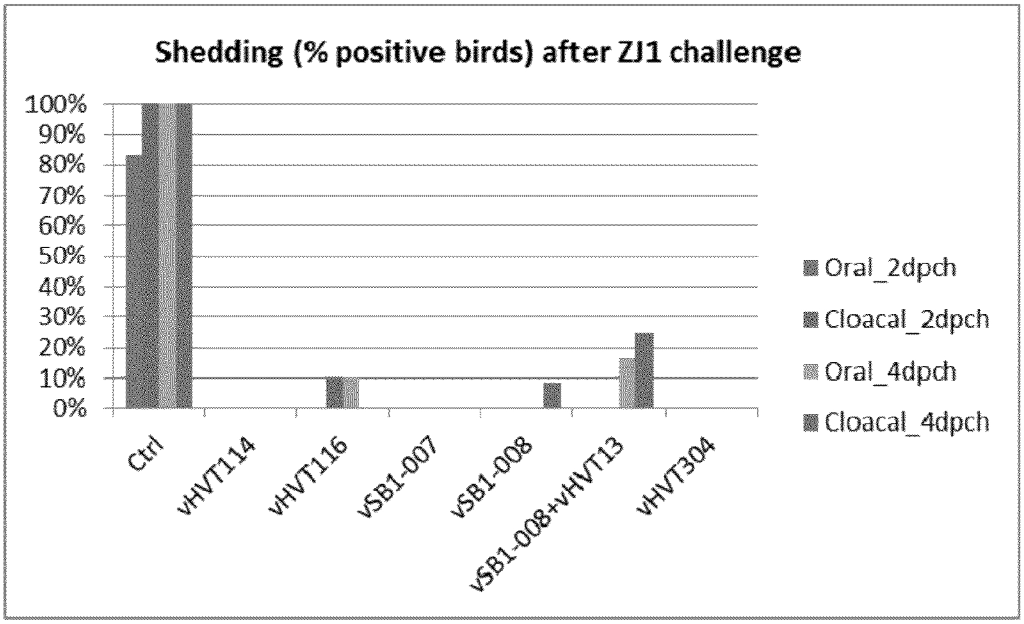
Shedding (% positive birds) after CA/02 challenge
- Oral_2dpch
- Cloacal_2dpch
- Oral_4dpch
- Cloacal_4dpch
Groups: Ctrl, vHVT114, vHVT116, vSB1-007, vSB1-008, vSB1-008+vHVT13, vHVT304
Shedding (% positive birds) after ZJ1 challenge
- Oral_2dpch
- Cloacal_2dpch
- Oral_4dpch
- Cloacal_4dpch
Groups: Ctrl, vHVT114, vHVT116, vSB1-007, vSB1-008, vSB1-008+vHVT13, vHVT304

Figure 18
FIG. 18A
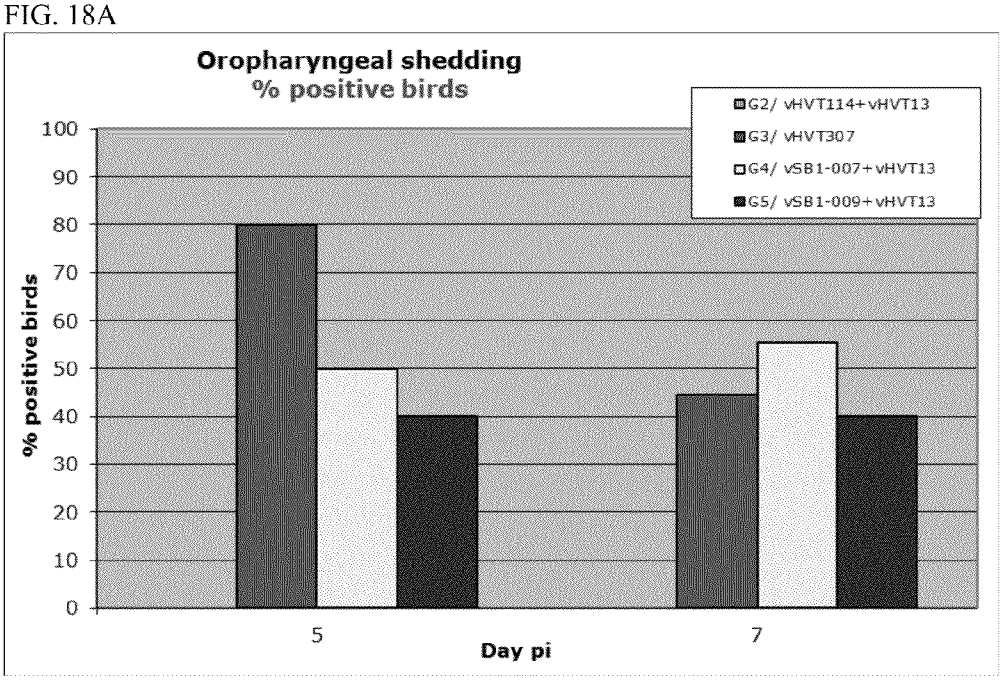
FIG. 18B
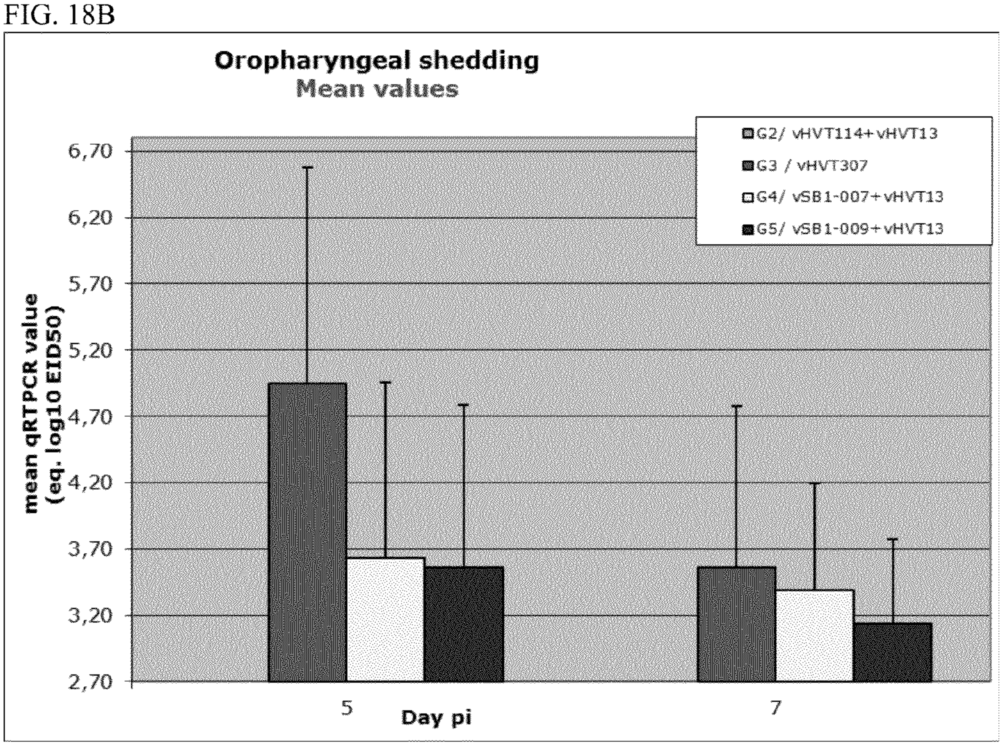

Figure 19A

DNA sequence alignment of NDV-F genes

```
                           1                                                50
SEQ ID NO:1      (1)   --------------------------------ATGGGCAGCAAGCCCAGC
SEQ ID NO:3      (1)   --------------------------------ATGGGCTCCAAACCTTCT
SEQ ID NO:4      (1)   CTGGATCCCGGTTGGCTCATTCAGGACGCAATATGGGCTCCAAACCTTCT
SEQ ID NO:8      (1)   --------------------------------ATGGGCAGCAAGCCCAGC
SEQ ID NO:49     (1)   --------------------------------ATGGGCTCCAGATCTTCT
SEQ ID NO:51     (1)   --------------------------------ATGGGCTCCAGATCTTCT
SEQ ID NO:53     (1)   --------------------------------ATGGGCTCTAAACCTTCT

                       51                                              100
SEQ ID NO:1     (19)   ACAAGAATCCCAGCCCCCCTGATGCTGATCACCCGCATCATGCTGATCCT
SEQ ID NO:3     (19)   ACCAGGATCCCAGCACCTCTGATGCTGATCACCCGGATTATGCTGATATT
SEQ ID NO:4     (51)   ACCAGGATCCCAGCACCTCTGATGCTGATCACCCGGATTATGCTGATATT
SEQ ID NO:8     (19)   ACCTGGATCAGCGTGACCCTGATGCTGATCACCAGAACCATGCTGATCCT
SEQ ID NO:49    (19)   ACCAGGATCCCGGTACCTCTAATGCTGATCATCCGAACCGCGCTGACACT
SEQ ID NO:51    (19)   ACCAGGATCCCGGTACCTCTAATGCTGATCATCCGAACCGCGCTGACACT
SEQ ID NO:53    (19)   ACCAGGATCCCAGCACCTCTGATGCTGATCACCCGGATTATGCTGATATT

                       101                                             150
SEQ ID NO:1     (69)   GGGCTGCATCAGACCCACAAGCTCCCTGGATGGACGCCCCCTGGCCGCTG
SEQ ID NO:3     (69)   GGGCTGTATCCGTCCGACAAGCTCTCTTGACGGCAGGCCTCTTGCAGCTG
SEQ ID NO:4    (101)   GGGCTGTATCCGTCCGACAAGCTCTCTTGACGGCAGGCCTCTTGCAGCTG
SEQ ID NO:8     (69)   GAGCTGCATCTGCCCCACAAGCAGCCTGGACGGCAGACCCCTGGCCGCTG
SEQ ID NO:49    (69)   GAGCTGTATCCGTCTGACAAGCTCTCTTGATGGCAGGCCTCTTGCGGCTG
SEQ ID NO:51    (69)   GAGCTGTATCCGTCTGACAAGCTCTCTTGATGGCAGGCCTCTTGCGGCTG
SEQ ID NO:53    (69)   GGACTGTATCCGTCCGACAAGCTCTCTTGACGGCAGGCCTCTTGCAGCTG

                       151                                             200
SEQ ID NO:1    (119)   CCGGCATCGTGGTGACCGGCGACAAGGCCGTGAACGTGTACACCAGCAGC
SEQ ID NO:3    (119)   CAGGAATTGTAGTAACAGGAGATAAGGCAGTCAATGTATACACTTCGTCT
SEQ ID NO:4    (151)   CAGGAATTGTAGTAACAGGAGATAAGGCAGTCAATGTATACACTTCGTCT
SEQ ID NO:8    (119)   CCGGCATCGTGGTGACCGGCGACAAGGCCGTGAACATCTACACCAGCAGC
SEQ ID NO:49   (119)   CAGGGATCGTGGTAACAGGAGATAAAGCAGTCAACATATACACCTCATCC
SEQ ID NO:51   (119)   CAGGGATCGTGGTAACAGGAGATAAAGCAGTCAACATATACACCTCATCC
SEQ ID NO:53   (119)   CAGGAATTGTAGTAACAGGAGATAAGGCAGTCAATGTATATACCTCGTCT

                       201                                             250
SEQ ID NO:1    (169)   CAGACCGGCAGCATCATCGTGAAGCTGCTGCCCAACATGCCCAGAGACAA
SEQ ID NO:3    (169)   CAGACAGGGTCAATCATAGTCAAGTTGCTCCCGAATATGCCCAGGGATAA
SEQ ID NO:4    (201)   CAGACAGGGTCAATCATAGTCAAGTTGCTCCCGAATATGCCCAGGGATAA
SEQ ID NO:8    (169)   CAGACCGGCAGCATCATCATCAAGCTGCTGCCCAACATGCCCAAGGACAA
SEQ ID NO:49   (169)   CAGACAGGGTCAATCATAGTTAAGTTACTCCCGAATATGCCCAAGGACAA
SEQ ID NO:51   (169)   CAGACAGGGTCAATCATAGTTAAGTTACTCCCGAATATGCCCAAGGACAA
SEQ ID NO:53   (169)   CAGACAGGGTCAATCATAGTCAAGTTGCTCCCGAATATGCCCAAGGATAA
```

Figure 19B

```
              251                                                   300
SEQ ID NO:1   (219) AGAGGCCTGCGCCAAGGCCCCCCTGGAAGCCTACAACAGAACCCTGACCA
SEQ ID NO:3   (219) GGAGGCGTGTGCAAAAGCCCCATTAGAGGCATATAACAGAACACTGACTA
SEQ ID NO:4   (251) GGAGGCGTGTGCAAAAGCCCCATTAGAGGCATATAACAGAACACTGACTA
SEQ ID NO:8   (219) AGAGGCCTGCGCCAAGGCCCCCCTGGAAGCCTACAACAGAACCCTGACCA
SEQ ID NO:49  (219) AGAGGTGTGTGCAAAAGCCCCATTGGAGGCATACAACAGGACACTGACTA
SEQ ID NO:51  (219) AGAGGTGTGTGCAAAAGCCCCATTGGAGGCATACAACAGGACACTGACTA
SEQ ID NO:53  (219) GGAGGCGTGTGCGAAAGACCCATTAGAGGCATATAACAGAACACTGACTA

              301                                                   350
SEQ ID NO:1   (269) CCCTGCTGACCCCCCTGGGCGACAGCATCAGAAAGATCCAGGGCTCCGTG
SEQ ID NO:3   (269) CTTTGCTCACTCCTCTTGGCGACTCCATCCGCAAGATCCAAGGGTCTGTG
SEQ ID NO:4   (301) CTTTGCTCACTCCTCTTGGCGACTCCATCCGCAAGATCCAAGGGTCTGTG
SEQ ID NO:8   (269) CCCTGCTGACCCCCCTGGGCGACAGCATCAGAAGAATCCAGGGCAGCGCC
SEQ ID NO:49  (269) CTTTACTCACCCCCCTTGGTGATTCTATCCGCAGGATACAAGAGTCTGTG
SEQ ID NO:51  (269) CTTTACTCACCCCCCTTGGTGATTCTATCCGCAGGATACAAGAGTCTGTG
SEQ ID NO:53  (269) CTTTGCTCACTCCTCTTGGCGAATCCATCCGCAAGATCCAAGGGTCTGTG

              351                                                   400
SEQ ID NO:1   (319) AGCACAAGCGGCGGAGGAAAGCAGGGCAGACTGATCGGCGCCGTGATCGG
SEQ ID NO:3   (319) TCCACATCTGGAGGAGGCAAGCAAGGCCGCCTGATAGGTGCTGTTATTGG
SEQ ID NO:4   (351) TCCACATCTGGAGGAAGGAGACAAAAACGCTTTATAGGTGCTGTTATTGG
SEQ ID NO:8   (319) ACCACAAGCGGCGGAGGAAAGCAGGGCAGACTGGTGGGCGCTATCATCGG
SEQ ID NO:49  (319) ACTACTTCCGGAGGAAGGAGACAGAGACGCTTTATAGGTGCCATTATCGG
SEQ ID NO:51  (319) ACTACTTCCGGAGGAGGCAAGCAAGGCCGCCTGATAGGTGCCATTATCGG
SEQ ID NO:53  (319) TCCACGTCTGGAGGAGGCAAGCAAGGCCGCCTGATAGGTGCTGTTATTGG

              401                                                   450
SEQ ID NO:1   (369) CAGCGTGGCCCTGGGAGTGGCTACAGCTGCCCAGATTACCGCTGCAGCCG
SEQ ID NO:3   (369) CAGTGTAGCTCTTGGGGTTGCAACAGCGGCACAGATAACAGCAGCTGCGG
SEQ ID NO:4   (401) CAGTGTAGCTCTTGGGGTTGCAACAGCGGCACAGATAACAGCAGCTGCGG
SEQ ID NO:8   (369) GAGCGTGGCCCTGGGCGTGGCCACAGCTGCCCAGATTACCGCTGCAGCCG
SEQ ID NO:49  (369) CAGTGTAGCTCTTGGGGTTGCGACAGCTGCACAGATAACAGCAGCTTCGG
SEQ ID NO:51  (369) CAGTGTAGCTCTTGGGGTTGCGACAGCTGCACAGATAACAGCAGCTTCGG
SEQ ID NO:53  (369) TAGTGTAGCTCTTGGGGTTGCAACAGCGGCACAAATAACAGCAGCTGCGG

              451                                                   500
SEQ ID NO:1   (419) CCCTGATCCAGGCCAACCAGAACGCCGCCAACATCCTGAGACTGAAAGAG
SEQ ID NO:3   (419) CCCTAATACAAGCCAACCAGAATGCCGCCAACATCCTCCGGCTTAAGGAG
SEQ ID NO:4   (451) CCCTAATACAAGCCAACCAGAATGCCGCCAACATCCTCCGGCTTAAGGAG
SEQ ID NO:8   (419) CCCTGATTCAGGCCAATCAGAACGCCGCCAACATCCTGAGACTGAAAGAG
SEQ ID NO:49  (419) CCCTGATACAAGCCAACCAGAATGCTGCCAACATCCTCCGGCTTAAAGAG
SEQ ID NO:51  (419) CCCTGATACAAGCCAACCAGAATGCTGCCAACATCCTCCGGCTTAAAGAG
SEQ ID NO:53  (419) CCCTAATACAAGCCAACCAGAATGCTGCCAACATCCTTCGGCTTAAGGAG

              501                                                   550
SEQ ID NO:1   (469) AGCATTGCCGCCACCAACGAGGCCGTGCACGAAGTGACCGACGGCCTGAG
SEQ ID NO:3   (469) AGCATTGCTGCAACCAATGAAGCTGTGCATGAAGTCACCGACGGATTATC
SEQ ID NO:4   (501) AGCATTGCTGCAACCAATGAAGCTGTGCATGAAGTCACCGACGGATTATC
SEQ ID NO:8   (469) AGCATTGCCGCCACCAACGACGCCGTGCACGAAGTGACAAACGGACTGTC
SEQ ID NO:49  (469) AGCATTGCTGCAACCAATGAAGCTGTGCACGAGGTCACTGACGGATTATC
SEQ ID NO:51  (469) AGCATTGCTGCAACCAATGAAGCTGTGCACGAGGTCACTGACGGATTATC
SEQ ID NO:53  (469) AGCATTGCTGCAACCAATGAAGCTGTGCATGAAGTCACCGACGGATTATC
```

Figure 19C

```
                         551                                              600
SEQ ID NO:1       (519)  CCAGCTGTCCGTGGCCGTGGGCAAGATGCAGCAGTTCGTGAACGACCAGT
SEQ ID NO:3       (519)  ACAACTATCAGTGGCAGTTGGGAAGATGCAGCAGTTTGTCAATGACCAGT
SEQ ID NO:4       (551)  ACAACTATCAGTGGCAGTTGGGAAGATGCAGCAGTTTGTCAATGACCAGT
SEQ ID NO:8       (519)  CCAGCTGGCTGTCGCTGTCGGCAAGATGCAGCAGTTCGTGAACAACCAGT
SEQ ID NO:49      (519)  ACAACTAGCAGTGGCAGTAGGGAAGATGCAACAGTTTGTCAATGACCAGT
SEQ ID NO:51      (519)  ACAACTAGCAGTGGCAGTAGGGAAGATGCAACAGTTTGTCAATGACCAGT
SEQ ID NO:53      (519)  ACAACTATCAGTGGCAGTTGGGAAGATGCAGCAGTTTGTCAATGACCAGT

                         601                                              650
SEQ ID NO:1       (569)  TCAACAACACCGCCAGAGAGCTGGACTGCATCAAGATCACCCAGCAGGTG
SEQ ID NO:3       (569)  TTAATAATACGGCGCGAGAATTGGACTGTATAAAAATCACACAACAGGTT
SEQ ID NO:4       (601)  TTAATAATACGGCGCGAGAATTGGACTGTATAAAAATCACACAACAGGTT
SEQ ID NO:8       (569)  TCAACAACACCGCCAGAGAGCTGGACTGCATCAAGATCGCCCAGCAGGTG
SEQ ID NO:49      (569)  TCAATAATACAGCGCAAGAATTGGACTGTATAAAAATTGCACAGCAGGTC
SEQ ID NO:51      (569)  TCAATAATACAGCGCAAGAATTGGACTGTATAAAAATTGCACAGCAGGTC
SEQ ID NO:53      (569)  TTAATAATACAGCGCGAGAATTGGACTGTATAAAAATCACACAACAGGTT

                         651                                              700
SEQ ID NO:1       (619)  GGCGTGGAGCTGAACCTGTACCTGACCGAGCTGACCACAGTGTTCGGCCC
SEQ ID NO:3       (619)  GGTGTAGAACTCAACCTATACCTAACTGAATTGACTACAGTATTCGGGCC
SEQ ID NO:4       (651)  GGTGTAGAACTCAACCTATACCTAACTGAATTGACTACAGTATTCGGGCC
SEQ ID NO:8       (619)  GGCGTGGAGCTGAACCTGTACCTGACCGAGCTGACCACAGTGTTCGGCCC
SEQ ID NO:49      (619)  GGTGTAGAACTCAACTTGTACCTAACTGAATTGACTACAGTATTTGGGCC
SEQ ID NO:51      (619)  GGTGTAGAACTCAACTTGTACCTAACTGAATTGACTACAGTATTTGGGCC
SEQ ID NO:53      (619)  GGTGTAGAACTCAACCTATACCTAACTGAATTGACTACAGTATTCGGGCC

                         701                                              750
SEQ ID NO:1       (669)  CCAGATCACAAGCCCAGCCCTGACACAGCTGACCATCCAGGCCCTGTACA
SEQ ID NO:3       (669)  ACAGATCACCTCCCCTGCATTAACTCAGCTGACCATCCAGGCACTTTATA
SEQ ID NO:4       (701)  ACAGATCACCTCCCCTGCATTAACTCAGCTGACCATCCAGGCACTTTATA
SEQ ID NO:8       (669)  CCAGATCACAAGCCCCGCTCTGACCCAGCTGACAATCCAGGCCCTGTACA
SEQ ID NO:49      (669)  ACAAATCACTTCCCCTGCCTTAACTCAGCTGACTATCCAAGCGCTTTACA
SEQ ID NO:51      (669)  ACAAATCACTTCCCCTGCCTTAACTCAGCTGACTATCCAAGCGCTTTACA
SEQ ID NO:53      (669)  ACAGATCACCTCCCCTGCATTAACTCAGCTGACCATCCAGGCACTTTATA

                         751                                              800
SEQ ID NO:1       (719)  ACCTGGCTGGCGGCAACATGGACTATCTGCTGACAAAGCTGGGAATCGGC
SEQ ID NO:3       (719)  ATTTAGCTGGTGGCAATATGGATTACTTATTAACTAAGTTAGGTATAGGG
SEQ ID NO:4       (751)  ATTTAGCTGGTGGCAATATGGATTACTTATTAACTAAGTTAGGTATAGGG
SEQ ID NO:8       (719)  ACCTGGCTGGCGGCAACATGGACTATCTGCTGACTAAGCTGGGAGTGGGC
SEQ ID NO:49      (719)  ATCTAGCTGGTGGTAATATGGATTACTTGCTGACTAAGTTAGGTGTAGGG
SEQ ID NO:51      (719)  ATCTAGCTGGTGGTAATATGGATTACTTGCTGACTAAGTTAGGTGTAGGG
SEQ ID NO:53      (719)  ATTTAGCTGGTGGCAATATGGATTACTTATTAACTAAGTTAGGTATAGGG

                         801                                              850
SEQ ID NO:1       (769)  AACAACCAGCTGTCCAGCCTGATCGGAAGCGGCCTGATCACCGGCTACCC
SEQ ID NO:3       (769)  AACAATCAACTCAGCTCGTTAATTGGTAGCGGCCTGATCACTGGTTACCC
SEQ ID NO:4       (801)  AACAATCAACTCAGCTCGTTAATTGGTAGCGGCCTGATCACTGGTTACCC
SEQ ID NO:8       (769)  AACAACCAGCTGTCCAGCCTGATCGGGTCCGGGCTGATCACAGGCAACCC
SEQ ID NO:49      (769)  AACAACCAACTCAGCTCATTAATTGGTAGCGGCTTGATCACCGGCAACCC
SEQ ID NO:51      (769)  AACAACCAACTCAGCTCATTAATTGGTAGCGGCTTGATCACCGGCAACCC
SEQ ID NO:53      (769)  AACAATCAACTCAGCTCATTAATTGGCAGCGGCCTGATCACTGGTTACCC
```

Figure 19D

```
                          851                                              900
SEQ ID NO:1     (819)   CATCCTGTACGACAGCCAGACACAGCTGCTGGGCATCCAGGTGAACCTGC
SEQ ID NO:3     (819)   TATACTGTATGACTCACAGACTCAACTCTTGGGCATACAAGTGAATTTAC
SEQ ID NO:4     (851)   TATACTGTATGACTCACAGACTCAACTCTTGGGCATACAAGTGAATTTAC
SEQ ID NO:8     (819)   CATCCTGTACGACAGCCAGACACAGCTGCTGGGCATCCAGATCAACCTGC
SEQ ID NO:49    (819)   TATTCTGTACGACTCACAGACTCAGATCTTGGGTATACAGGTAACTTTGC
SEQ ID NO:51    (819)   TATTCTGTACGACTCACAGACTCAGATCTTGGGTATACAGGTAACTTTGC
SEQ ID NO:53    (819)   TATATTGTATGACTCACAGACTCAACTCTTGGGCATACAAGTGAATTTGC

                          901                                              950
SEQ ID NO:1     (869)   CCAGCGTGGGCAACCTGAACAACATGCGCGCCACCTACCTGGAAACCCTG
SEQ ID NO:3     (869)   CCTCAGTCGGGAACTTAAATAATATGCGTGCCACCTATTTGGAGACCTTA
SEQ ID NO:4     (901)   CCTCAGTCGGGAACTTAAATAATATGCGTGCCACCTATTTGGAGACCTTA
SEQ ID NO:8     (869)   CATCCGTGGGAAGCCTGAACAACATGAGAGCCACCTACCTGGAAACCCTG
SEQ ID NO:49    (869)   CTTCAGTTGGGAACCTGAATAATATGCGTGCCACCTACCTGGAGACCTTA
SEQ ID NO:51    (869)   CTTCAGTTGGGAACCTGAATAATATGCGTGCCACCTACCTGGAGACCTTA
SEQ ID NO:53    (869)   CCTCAGTCGGGAACTTAAATAATATGCGTGCCACCTATTTAGAGACCTTA

                          951                                             1000
SEQ ID NO:1     (919)   AGCGTGTCCACCACCAAGGGCTACGCCAGCGCCCTGGTGCCCAAGGTGGT
SEQ ID NO:3     (919)   TCTGTAAGTACAACCAAAGGATATGCCTCAGCACTTGTCCCGAAAGTAGT
SEQ ID NO:4     (951)   TCTGTAAGTACAACCAAAGGATATGCCTCAGCACTTGTCCCGAAAGTAGT
SEQ ID NO:8     (919)   AGCGTGTCCACCACCAAGGGCTTCGCCAGCGCCCTGGTGCCCAAGGTGGT
SEQ ID NO:49    (919)   TCTGTAAGCACAACCAAGGGATTTGCCTCAGCACTTGTCCCAAAAGTGGT
SEQ ID NO:51    (919)   TCTGTAAGCACAACCAAGGGATTTGCCTCAGCACTTGTCCCAAAAGTGGT
SEQ ID NO:53    (919)   TCTGTAAGTACAGCCAAAGGATATGCCTCAGCACTTGTTCCAAAAGTAGT

                          1001                                            1050
SEQ ID NO:1     (969)   GACACAGGTGGGCAGCGTGATCGAGGAACTGGACACCAGCTACTGCATCG
SEQ ID NO:3     (969)   GACACAAGTCGGTTCCGTGATAGAAGAGCTTGACACCTCATACTGTATAG
SEQ ID NO:4    (1001)   GACACAAGTCGGTTCCGTGATAGAAGAGCTTGACACCTCATACTGTATAG
SEQ ID NO:8     (969)   GACACAGGTGGGCAGCGTGATCGAGGAACTGGACACCAGCTACTGCATCG
SEQ ID NO:49    (969)   GACACAGGTCGGTTCCGTGATAGAAGAACTTGACACCTCATACTGTATAG
SEQ ID NO:51    (969)   GACACAGGTCGGTTCCGTGATAGAAGAACTTGACACCTCATACTGTATAG
SEQ ID NO:53    (969)   GACACAAGTCGGTTCTGTGATAGAAGAGCTTGACACCTCATACTGTATAG

                          1051                                            1100
SEQ ID NO:1    (1019)   AGAGCGACCTGGACCTGTACTGCACCAGAATCGTGACCTTCCCAATGAGC
SEQ ID NO:3    (1019)   AGTCCGATCTGGATTTATATTGTACTAGAATAGTGACATTCCCCATGTCC
SEQ ID NO:4    (1051)   AGTCCGATCTGGATTTATATTGTACTAGAATAGTGACATTCCCCATGTCC
SEQ ID NO:8    (1019)   AGAGCGACATCGACCTGTACTGCACCAGAGTGGTGACCTTCCCAATGAGC
SEQ ID NO:49   (1019)   GGACCGACTTGGATTTATACTGTACAAGAATAGTGACATTCCCTATGTCT
SEQ ID NO:51   (1019)   GGACCGACTTGGATTTATACTGTACAAGAATAGTGACATTCCCTATGTCT
SEQ ID NO:53   (1019)   AGTCCGATCTGGATTTATATTGTACTAGAATAGTGACATTCCCCATGTCC

                          1101                                            1150
SEQ ID NO:1    (1069)   CCCGGCATCTACAGCTGCCTGAGCGGCAACACCAGCGCCTGCATGTACAG
SEQ ID NO:3    (1069)   CCAGGTATTTATTCCTGTTTGAGCGGCAACACATCAGCTTGCATGTATTC
SEQ ID NO:4    (1101)   CCAGGTATTTATTCCTGTTTGAGCGGCAACACATCAGCTTGCATGTATTC
SEQ ID NO:8    (1069)   CCCGGCATCTACAGCTGCCTGAGCGGCAACACCAGCGCCTGCATGTACAG
SEQ ID NO:49   (1069)   CCTGGTATTTATTCTTGTCTGAGCGGTAATACATCGGCTTGCATGTATTC
SEQ ID NO:51   (1069)   CCTGGTATTTATTCTTGTCTGAGCGGTAATACATCGGCTTGCATGTATTC
SEQ ID NO:53   (1069)   CCAGGTATTTATTCCTGTTTAAGCGGCAACACATCAGCTTGCATGTATTC
```

Figure 19E

```
                       1151                                              1200
SEQ ID NO:1   (1119)   CAAGACCGAAGGCGCACTGACAACACCCTACATGGCCCTGAAGGGAAGCG
SEQ ID NO:3   (1119)   AAAGACTGAAGGCGCACTCACTACGCCGTATATGGCCCTTAAAGGCTCAG
SEQ ID NO:4   (1151)   AAAGACTGAAGGCGCACTCACTACGCCGTATATGGCCCTTAAAGGCTCAG
SEQ ID NO:8   (1119)   CAAGACCGAAGGAGCACTGACAACACCCTACATGGCCCTGAAGGGAAGCG
SEQ ID NO:49  (1119)   AAAGACTGAAGGCGCACTTACTACGCCATATATGGCTCTCAAAGGCTCAG
SEQ ID NO:51  (1119)   AAAGACTGAAGGCGCACTTACTACGCCATATATGGCTCTCAAAGGCTCAG
SEQ ID NO:53  (1119)   AAAGACTGAAGGCGCACTCACTACGCCGTATATGGCCCTTAAAGGCTCAG

                       1201                                              1250
SEQ ID NO:1   (1169)   TGATCGCCAACTGCAAGATCACCACCTGCAGATGCACCGACCCCCCAGGC
SEQ ID NO:3   (1169)   TTATTGCCAATTGTAAAATAACAACATGTAGATGTACAGACCCTCCTGGT
SEQ ID NO:4   (1201)   TTATTGCCAATTGTAGGATAACAACATGTAGATGTACAGACCCTCCTGGT
SEQ ID NO:8   (1169)   TGATCGCCAACTGCAAGATGACCACCTGCAGATGCGCCGACCCCCCAGGC
SEQ ID NO:49  (1169)   TTATTGCCAATTGCAAGCTGACAACATGTAGATGTGCAGATCCCCCAGGT
SEQ ID NO:51  (1169)   TTATTGCCAATTGCAAGCTGACAACATGTAGATGTGCAGATCCCCCAGGT
SEQ ID NO:53  (1169)   TTATTGCCAATTGTAAGATAACAACATGTAGATGTACAGACCCTCCTGGT

                       1251                                              1300
SEQ ID NO:1   (1219)   ATCATCAGCCAGAACTACGGCGAGGCCGTGAGCCTGATCGATCGCCATTC
SEQ ID NO:3   (1219)   ATCATATCGCAAAATTATGGAGAAGCTGTATCCCTGATAGATAGACATTC
SEQ ID NO:4   (1251)   ATCATATCGCAAAATTATGGAGAAGCTGTATCCCTGATAGATAGACATTC
SEQ ID NO:8   (1219)   ATCATCAGCCAGAACTACGGCGAGGCCGTGAGCCTGATCGACAAACATTC
SEQ ID NO:49  (1219)   ATCATATCGCAAAATTATGGAGAAGCTGTGTCCTTAATAGATAGGCACTC
SEQ ID NO:51  (1219)   ATCATATCGCAAAATTATGGAGAAGCTGTGTCCTTAATAGATAGGCACTC
SEQ ID NO:53  (1219)   ATCATATCGCAAAATTATGGAGAAGCTGTATCCCTGATAGATAGACATTC

                       1301                                              1350
SEQ ID NO:1   (1269)   CTGTAACGTGCTGTCCCTGGACGGCATCACACTGAGACTGAGCGGCGAGT
SEQ ID NO:3   (1269)   GTGCAATGTCTTATCATTAGACGGGATAACTCTAAGGCTCAGTGGGGAAT
SEQ ID NO:4   (1301)   GTGCAATGTCTTATCATTAGACGGGATAACTCTAAGGCTCAGTGGGGAAT
SEQ ID NO:8   (1269)   CTGTAGCGTGCTGTCCCTGGATGGCATCACACTGAGACTGAGCGGCGAGT
SEQ ID NO:49  (1269)   ATGCAACGTCTTATCCTTAGACGGGATAACTCTGAGGCTCAGTGGGGAAT
SEQ ID NO:51  (1269)   ATGCAACGTCTTATCCTTAGACGGGATAACTCTGAGGCTCAGTGGGGAAT
SEQ ID NO:53  (1269)   GTGCAATGTCTTATCATTAGACGGGATAACTCTGAGGCTCAGTGGAGAAT

                       1351                                              1400
SEQ ID NO:1   (1319)   TCGATGCCACCTACCAGAAGAACATCAGCATCCTGGACAGCCAGGTGATC
SEQ ID NO:3   (1319)   TTGATGCAACTTATCAAAAGAACATCTCAATACTAGATTCTCAAGTCATC
SEQ ID NO:4   (1351)   TTGATGCAACTTATCAAAAGAACATCTCAATACTAGATTCTCAAGTCATC
SEQ ID NO:8   (1319)   TCGACGCCACCTACCAGAAGAACATCAGCATCCTGGACAGCCAGGTGATC
SEQ ID NO:49  (1319)   TTGATGCAACCTATCAAAAGAATATCTCTATACTAGATTCTCAAGTTATA
SEQ ID NO:51  (1319)   TTGATGCAACCTATCAAAAGAATATCTCTATACTAGATTCTCAAGTTATA
SEQ ID NO:53  (1319)   TTGATGCAACTTATCAAAAGAACATCTCAATACTAGATTCTCAAGTCATC

                       1401                                              1450
SEQ ID NO:1   (1369)   GTGACCGGCAACCTGGACATCAGCACCGAGCTGGGCAACGTGAATAACAG
SEQ ID NO:3   (1369)   GTGACAGGCAATCTTGATATATCAACTGAACTTGGAAACGTCAACAATTC
SEQ ID NO:4   (1401)   GTGACAGGCAATCTTGATATATCAACTGAACTTGGAAACGTCAACAATTC
SEQ ID NO:8   (1369)   GTGACCGGCAACCTGGACATCAGCACCGAGCTGGGCAACGTGAACAACAG
SEQ ID NO:49  (1369)   GTGACAGGCAATCTTGATATATCAACTGAGCTTGGGAATGTCAACAACTC
SEQ ID NO:51  (1369)   GTGACAGGCAATCTTGATATATCAACTGAGCTTGGGAATGTCAACAACTC
SEQ ID NO:53  (1369)   GTGACAGGCAATCTTGATATATCAACTGAACTTGGAAACGTCAACAATTC
```

Figure 19F

```
                        1451                                              1500
SEQ ID NO:1   (1419) CATCAGCAACGCCCTGGACAGACTGGCCGAGAGCAACAGCAAGCTGGAAA
SEQ ID NO:3   (1419) AATCAGCAATGCCTTGGATAGGTTGGCAGAAAGCAACAGCAAGCTAGAAA
SEQ ID NO:4   (1451) AATCAGCAATGCCTTGGATAGGTTGGCAGAAAGCAACAGCAAGCTAGAAA
SEQ ID NO:8   (1419) CATCAGCAGCACCCTGGACAAGCTGGCCGAGTCCAACAACAAGCTGAACA
SEQ ID NO:49  (1419) AATAAGTAATGCCCTGAATAAGTTAGAGGAAAGCAACAGCAAACTAGACA
SEQ ID NO:51  (1419) AATAAGTAATGCCCTGAATAAGTTAGAGGAAAGCAACAGCAAACTAGACA
SEQ ID NO:53  (1419) AATCAGCAATGCCTTGGATAAGTTGGCAAAAAGCAACAGCAAGCTAGAAA

                        1501                                              1550
SEQ ID NO:1   (1469) AAGTGAACGTGCGCCTGACATCCACTTCCGCTCTGATCACCTACATCGTG
SEQ ID NO:3   (1469) AAGTCAATGTCAGACTAACCAGCACATCTGCTCTCATTACCTATATTGTT
SEQ ID NO:4   (1501) AAGTCAATGTCAGACTAACCAGCACATCTGCTCTCATTACCTATATTGTT
SEQ ID NO:8   (1469) AAGTGAACGTGAACCTGACCAGCACAAGCGCCCTGATCACCTACATCGTG
SEQ ID NO:49  (1469) AAGTCAATGTCAAACTGACCAGCACATCTGCTCTCATTACCTACATCGTT
SEQ ID NO:51  (1469) AAGTCAATGTCAAACTGACCAGCACATCTGCTCTCATTACCTACATCGTT
SEQ ID NO:53  (1469) AAGTCAATGTCAGACTAACCAGCACATCCGCTCTCATTACCTATATTGTT

                        1551                                              1600
SEQ ID NO:1   (1519) CTGACCGTGATCAGCCTGGTGTTCGGCGCCCTGAGCCTGGTGCTGGCCTG
SEQ ID NO:3   (1519) CTAACTGTCATTTCTCTAGTTTTCGGTGCACTTAGTCTGGTGTTAGCGTG
SEQ ID NO:4   (1551) CTAACTGTCATTTCTCTAGTTTTCGGTGCACTTAGTCTGGGTTTAGCGTG
SEQ ID NO:8   (1519) CTGGCCATCGTGTCCCTGGCCTTCGGCGTGATCAGCCTGGTGCTGGCCTG
SEQ ID NO:49  (1519) TTAACTGTCATATCTCTTGTTTTTGGTGTACTTAGCCTGGTTCTAGCATG
SEQ ID NO:51  (1519) TTAACTGTCATATCTCTTGTTTTTGGTGTACTTAGCCTGGTTCTAGCATG
SEQ ID NO:53  (1519) CTGACTGTCATTTCTCTAGTTTTCGGTGCACTAAGTCTGGGTTTAACATG

                        1601                                              1650
SEQ ID NO:1   (1569) CTACCTGATGTACAAGCAGAAGGCCCAGCAGAAAACCCTGCTGTGGCTGG
SEQ ID NO:3   (1569) TTACCTGATGTACAAACAGAAGGCACAACAAAGACCTTGCTATGGCTTG
SEQ ID NO:4   (1601) TTACCTGATGTACAAACAGAAGGCACAACAAAGACCTTGCTATGGCTTG
SEQ ID NO:8   (1569) CTACCTGATGTACAAGCAGAGAGCCCAGCAGAAAACCCTGCTGTGGCTGG
SEQ ID NO:49  (1569) CTACCTGATGTACAAGCAAAAGGCACAACAAAGACCTTGTTATGGCTTG
SEQ ID NO:51  (1569) CTACCTGATGTACAAGCAAAAGGCACAACAAAGACCTTGTTATGGCTTG
SEQ ID NO:53  (1569) TTACCTGATGTACAAACAAAAGGCACAACAAAGACCTTGCTATGGCTTG

                        1651                                          1697
SEQ ID NO:1   (1619) GCAACAACACCCTGGACCAGATGAGAGCCACCACCAGAGCCTGATGA
SEQ ID NO:3   (1619) GGAATAATACCCTCGATCAGATGAGAGCCACTACAAGAGCATGA---
SEQ ID NO:4   (1651) GGAATAATACCCTCGATCAGATGAGAGCCACTACAAGAGCATGAA--
SEQ ID NO:8   (1619) GCAATAACACCCTGGACCAGATGAGGGCCACCACCAGAACCTGATGA
SEQ ID NO:49  (1619) GGAATAATACCCTTGATCAGATGAGAGCCACTACAAAAATATGA---
SEQ ID NO:51  (1619) GGAATAATACCCTTGATCAGATGAGAGCCACTACAAAAATATGA---
SEQ ID NO:53  (1619) GGAATAATACCCTCGATCAGATGAGAGCCACTACAAGAGCATGA---
```

Figure 19G

| | SEQ:1 | SEQ:3 | SEQ:4 | SEQ:8 | SEQ:49 | SEQ:51 | SEQ:53 |
|---|---|---|---|---|---|---|---|
| SEQ:1 | 100% | 72% | 72% | 92% | 71% | 71% | 71% |
| SEQ:3 | | 100% | 99% | 69% | 88% | 89% | 98% |
| SEQ:4 | | | 100% | 69% | 88% | 88% | 97% |
| SEQ:8 | | | | 100% | 70% | 71% | 69% |
| SEQ:49 | | | | | 100% | 99% | 88% |
| SEQ:51 | | | | | | 100% | 88% |
| SEQ:53 | | | | | | | 100% |

Figure 20A

The DNA sequence alignment between SEQ ID NO:3 and SEQ ID NO:4 (AY337464.1) to highlight the differences at nucleotide level:

```
SEQ ID NO:3  1     ATGGGCTCCAAACCTTCTACCAGGATCCCAGCACCTCTGATGCTGATCACCCGGATTATG  60
SEQ ID NO:4  33    ............................................................  92

SEQ ID NO:3  61    CTGATATTGGGCTGTATCCGTCCGACAAGCTCTCTTGACGGCAGGCCTCTTGCAGCTGCA  120
SEQ ID NO:4  93    ............................................................  152

SEQ ID NO:3  121   GGAATTGTAGTAACAGGAGATAAGGCAGTCAATGTATACACTTCGTCTCAGACAGGGTCA  180
SEQ ID NO:4  153   ............................................................  212

SEQ ID NO:3  181   ATCATAGTCAAGTTGCTCCCGAATATGCCCAGGGATAAGGAGGCGTGTGCAAAAGCCCCA  240
SEQ ID NO:4  213   ............................................................  272

SEQ ID NO:3  241   TTAGAGGCATATAACAGAACACTGACTACTTTGCTCACTCCTCTTGGCGACTCCATCCGC  300
SEQ ID NO:4  273   ............................................................  332

SEQ ID NO:3  301   AAGATCCAAGGGTCTGTGTCCACATCTGGAGGAGGCAAGCAAGGCCGCCTGATAGGTGCT  360
SEQ ID NO:4  333   .................................A.G.GA...AAA...T.T.........  392

SEQ ID NO:3  361   GTTATTGGCAGTGTAGCTCTTGGGGTTGCAACAGCGGCACAGATAACAGCAGCTGCGGCC  420
SEQ ID NO:4  393   ............................................................  452

SEQ ID NO:3  421   CTAATACAAGCCAACCAGAATGCCGCCAACATCCTCCGGCTTAAGGAGAGCATTGCTGCA  480
SEQ ID NO:4  453   ............................................................  512

SEQ ID NO:3  481   ACCAATGAAGCTGTGCATGAAGTCACCGACGGATTATCACAACTATCAGTGGCAGTTGGG  540
SEQ ID NO:4  513   ............................................................  572

SEQ ID NO:3  541   AAGATGCAGCAGTTTGTCAATGACCAGTTTAATAATACGGCGCGAGAATTGGACTGTATA  600
SEQ ID NO:4  573   ............................................................  632

SEQ ID NO:3  601   AAAATCACACAACAGGTTGGTGTAGAACTCAACCTATACCTAACTGAATTGACTACAGTA  660
SEQ ID NO:4  633   ............................................................  692

SEQ ID NO:3  661   TTCGGGCCACAGATCACCTCCCCTGCATTAACTCAGCTGACCATCCAGGCACTTTATAAT  720
SEQ ID NO:4  693   ............................................................  752

SEQ ID NO:3  721   TTAGCTGGTGGCAATATGGATTACTTATTAACTAAGTTAGGTATAGGGAACAATCAACTC  780
SEQ ID NO:5  753   ............................................................  812

SEQ ID NO:3  781   AGCTCGTTAATTGGTAGCGGCCTGATCACTGGTTACCCTATACTGTATGACTCACAGACT  840
SEQ ID NO:4  813   ............................................................  872

SEQ ID NO:3  841   CAACTCTTGGGCATACAAGTGAATTTACCCTCAGTCGGGAACTTAAATAATATGCGTGCC  900
SEQ ID NO:4  873   ............................................................  932

SEQ ID NO:3  901   ACCTATTTGGAGACCTTATCTGTAAGTACAACCAAAGGATATGCCTCAGCACTTGTCCCG  960
SEQ ID NO:4  933   ............................................................  992

SEQ ID NO:3  961   AAAGTAGTGACACAAGTCGGTTCCGTGATAGAAGAGCTTGACACCTCATACTGTATAGAG  1020
SEQ ID NO:4  993   ............................................................  1052

SEQ ID NO:3  1021  TCCGATCTGGATTTATATTGTACTAGAATAGTGACATTCCCCATGTCCCCAGGTATTTAT  1080
SEQ ID NO:4  1053  ............................................................  1112

SEQ ID NO:3  1081  TCCTGTTTGAGCGGCAACACATCAGCTTGCATGTATTCAAAGACTGAAGGCGCACTCACT  1140
SEQ ID NO:4  1113  ............................................................  1172

SEQ ID NO:3  1141  ACGCCGTATATGGCCCTTAAAGGCTCAGTTATTGCCAATTGTAAAATAACAACATGTAGA  1200
SEQ ID NO:4  1173  ...........................................GG...............  1232

SEQ ID NO:3  1201  TGTACAGACCCTCCTGGTATCATATCGCAAAATTATGGAGAAGCTGTATCCCTGATAGAT  1260
SEQ ID NO:4  1233  ............................................................  1292
```

Figure 20B

```
SEQ ID NO:3  1261  AGACATTCGTGCAATGTCTTATCATTAGACGGGATAACTCTAAGGCTCAGTGGGGAATTT  1320
SEQ ID NO:4  1293  ............................................................  1352

SEQ ID NO:3  1321  GATGCAACTTATCAAAAGAACATCTCAATACTAGATTCTCAAGTCATCGTGACAGGCAAT  1380
SEQ ID NO:4  1353  ............................................................  1412

SEQ ID NO:3  1381  CTTGATATATCAACTGAACTTGGAAACGTCAACAATTCAATCAGCAATGCCTTGGATAGG  1440
SEQ ID NO:4  1413  ............................................................  1472

SEQ ID NO:3  1441  TTGGCAGAAAGCAACAGCAAGCTAGAAAAAGTCAATGTCAGACTAACCAGCACATCTGCT  1500
SEQ ID NO:4  1473  ............................................................  1532

SEQ ID NO:3  1501  CTCATTACCTATATTGTTCTAACTGTCATTTCTCTAGTTTTCGGTGCACTTAGTCTGGTG  1560
SEQ ID NO:4  1533  ..........................................................GT  1592

SEQ ID NO:3  1561  TTAGCGTGTTACCTGATGTACAAACAGAAGGCACAACAAAAGACCTTGCTATGGCTTGGG  1620
SEQ ID NO:4  1593  ............................................................  1652

SEQ ID NO:3  1621  AATAATACCCTCGATCAGATGAGAGCCACTACAAGAGCATGA  1662
SEQ ID NO:4  1653  ..........................................  1694
```

Figure 21A

Protein sequence alignment of NDV-F

```
                       1                                                50
SEQ ID NO:2      (1)   MGSKPSTRIPAPLMLITRIMLILGCIRPTSSLDGRPLAAAGIVVTGDKAV
SEQ ID NO:5      (1)   MGSKPSTRIPAPLMLITRIMLILGCIRPTSSLDGRPLAAAGIVVTGDKAV
SEQ ID NO:50     (1)   MGSRSSTRIPVPLMLIIRTALTLSCIRLTSSLDGRPLAAAGIVVTGDKAV
SEQ ID NO:52     (1)   MGSRSSTRIPVPLMLIIRTALTLSCIRLTSSLDGRPLAAAGIVVTGDKAV
SEQ ID NO:54     (1)   MGSKPSTRIPAPLMLITRIMLILDCIRPTSSLDGRPLAAAGIVVTGDKAV
SEQ ID NO:7      (1)   MGSKPSTWISVTLMLITRTMLILSCICPTSSLDGRPLAAAGIVVTGDKAV
SEQ ID NO:9      (1)   MGSKPSTWISVTLMLITRTMLILSCICPTSSLDGRPLAAAGIVVTGDKAV

                       51                                              100
SEQ ID NO:2     (51)   NVYTSSQTGSIIVKLLPNMPRDKEACAKAPLEAYNRTLTTLLTPLGDSIR
SEQ ID NO:5     (51)   NVYTSSQTGSIIVKLLPNMPRDKEACAKAPLEAYNRTLTTLLTPLGDSIR
SEQ ID NO:50    (51)   NIYTSSQTGSIIVKLLPNMPKDKEVCAKAPLEAYNRTLTTLLTPLGDSIR
SEQ ID NO:52    (51)   NIYTSSQTGSIIVKLLPNMPKDKEVCAKAPLEAYNRTLTTLLTPLGDSIR
SEQ ID NO:54    (51)   NVYTSSQTGSIIVKLLPNMPKDKEACAKDPLEAYNRTLTTLLTPLGESIR
SEQ ID NO:7     (51)   NIYTSSQTGSIIIKLLPNMPKDKEACAKAPLEAYNRTLTTLLTPLGDSIR
SEQ ID NO:9     (51)   NIYTSSQTGSIIIKLLPNMPKDKEACAKAPLEAYNRTLTTLLTPLGDSIR

                       101                                             150
SEQ ID NO:2    (101)   KIQGSVSTSGGGKQGRLIGAVIGSVALGVATAAQITAAAALIQANQNAAN
SEQ ID NO:5    (101)   KIQGSVSTSGGRRQKRFIGAVIGSVALGVATAAQITAAAALIQANQNAAN
SEQ ID NO:50   (101)   RIQESVTTSGGRRQRRFIGAIIGSVALGVATAAQITAASALIQANQNAAN
SEQ ID NO:52   (101)   RIQESVTTSGGGKQGRLIGAIIGSVALGVATAAQITAASALIQANQNAAN
SEQ ID NO:54   (101)   KIQGSVSTSGGGKQGRLIGAVIGSVALGVATAAQITAAAALIQANQNAAN
SEQ ID NO:7    (101)   RIQGSATTSGGRRQKRFVGAIIGSVALGVATAAQITAAAALIQANQNAAN
SEQ ID NO:9    (101)   RIQGSATTSGGGKQGRLVGAIIGSVALGVATAAQITAAAALIQANQNAAN

                       151                                             200
SEQ ID NO:2    (151)   ILRLKESIAATNEAVHEVTDGLSQLSVAVGKMQQFVNDQFNNTARELDCI
SEQ ID NO:5    (151)   ILRLKESIAATNEAVHEVTDGLSQLSVAVGKMQQFVNDQFNNTARELDCI
SEQ ID NO:50   (151)   ILRLKESIAATNEAVHEVTDGLSQLAVAVGKMQQFVNDQFNNTAQELDCI
SEQ ID NO:52   (151)   ILRLKESIAATNEAVHEVTDGLSQLAVAVGKMQQFVNDQFNNTAQELDCI
SEQ ID NO:54   (151)   ILRLKESIAATNEAVHEVTDGLSQLSVAVGKMQQFVNDQFNNTARELDCI
SEQ ID NO:7    (151)   ILRLKESIAATNDAVHEVTNGLSQLAVAVGKMQQFVNNQFNNTARELDCI
SEQ ID NO:9    (151)   ILRLKESIAATNDAVHEVTNGLSQLAVAVGKMQQFVNNQFNNTARELDCI

                       201                                             250
SEQ ID NO:2    (201)   KITQQVGVELNLYLTELTTVFGPQITSPALTQLTIQALYNLAGGNMDYLL
SEQ ID NO:5    (201)   KITQQVGVELNLYLTELTTVFGPQITSPALTQLTIQALYNLAGGNMDYLL
SEQ ID NO:50   (201)   KIAQQVGVELNLYLTELTTVFGPQITSPALTQLTIQALYNLAGGNMDYLL
SEQ ID NO:52   (201)   KIAQQVGVELNLYLTELTTVFGPQITSPALTQLTIQALYNLAGGNMDYLL
SEQ ID NO:54   (201)   KITQQVGVELNLYLTELTTVFGPQITSPALTQLTIQALYNLAGGNMDYLL
SEQ ID NO:7    (201)   KIAQQVGVELNLYLTELTTVFGPQITSPALTQLTIQALYNLAGGNMDYLL
SEQ ID NO:9    (201)   KIAQQVGVELNLYLTELTTVFGPQITSPALTQLTIQALYNLAGGNMDYLL
```

Figure 21B

```
                    251                                                300
SEQ ID NO:2   (251) TKLGIGNNQLSSLIGSGLITGYPILYDSQTQLLGIQVNLPSVGNLNNMRA
SEQ ID NO:5   (251) TKLGIGNNQLSSLIGSGLITGYPILYDSQTQLLGIQVNLPSVGNLNNMRA
SEQ ID NO:50  (251) TKLGVGNNQLSSLIGSGLITGNPILYDSQTQILGIQVTLPSVGNLNNMRA
SEQ ID NO:52  (251) TKLGVGNNQLSSLIGSGLITGNPILYDSQTQILGIQVTLPSVGNLNNMRA
SEQ ID NO:54  (251) TKLGIGNNQLSSLIGSGLITGYPILYDSQTQLLGIQVNLPSVGNLNNMRA
SEQ ID NO:7   (251) TKLGVGNNQLSSLIGSGLITGNPILYDSQTQLLGIQINLPSVGSLNNMRA
SEQ ID NO:9   (251) TKLGVGNNQLSSLIGSGLITGNPILYDSQTQLLGIQINLPSVGSLNNMRA

                    301                                                350
SEQ ID NO:2   (301) TYLETLSVSTTKGYASALVPKVVTQVGSVIEELDTSYCIESDLDLYCTRI
SEQ ID NO:5   (301) TYLETLSVSTTKGYASALVPKVVTQVGSVIEELDTSYCIESDLDLYCTRI
SEQ ID NO:50  (301) TYLETLSVSTTKGFASALVPKVVTQVGSVIEELDTSYCIGTDLDLYCTRI
SEQ ID NO:52  (301) TYLETLSVSTTKGFASALVPKVVTQVGSVIEELDTSYCIGTDLDLYCTRI
SEQ ID NO:54  (301) TYLETLSVSTAKGYASALVPKVVTQVGSVIEELDTSYCIESDLDLYCTRI
SEQ ID NO:7   (301) TYLETLSVSTTKGFASALVPKVVTQVGSVIEELDTSYCIESDIDLYCTRV
SEQ ID NO:9   (301) TYLETLSVSTTKGFASALVPKVVTQVGSVIEELDTSYCIESDIDLYCTRV

                    351                                                400
SEQ ID NO:2   (351) VTFPMSPGIYSCLSGNTSACMYSKTEGALTTPYMALKGSVIANCKITTCR
SEQ ID NO:5   (351) VTFPMSPGIYSCLSGNTSACMYSKTEGALTTPYMALKGSVIANCRITTCR
SEQ ID NO:50  (351) VTFPMSPGIYSCLSGNTSACMYSKTEGALTTPYMALKGSVIANCKLTTCR
SEQ ID NO:52  (351) VTFPMSPGIYSCLSGNTSACMYSKTEGALTTPYMALKGSVIANCKLTTCR
SEQ ID NO:54  (351) VTFPMSPGIYSCLSGNTSACMYSKTEGALTTPYMALKGSVIANCKITTCR
SEQ ID NO:7   (351) VTFPMSPGIYSCLSGNTSACMYSKTEGALTTPYMALKGSVIANCKMTTCR
SEQ ID NO:9   (351) VTFPMSPGIYSCLSGNTSACMYSKTEGALTTPYMALKGSVIANCKMTTCR

                    401                                                450
SEQ ID NO:2   (401) CTDPPGIISQNYGEAVSLIDRHSCNVLSLDGITLRLSGEFDATYQKNISI
SEQ ID NO:5   (401) CTDPPGIISQNYGEAVSLIDRHSCNVLSLDGITLRLSGEFDATYQKNISI
SEQ ID NO:50  (401) CADPPGIISQNYGEAVSLIDRHSCNVLSLDGITLRLSGEFDATYQKNISI
SEQ ID NO:52  (401) CADPPGIISQNYGEAVSLIDRHSCNVLSLDGITLRLSGEFDATYQKNISI
SEQ ID NO:54  (401) CTDPPGIISQNYGEAVSLIDRHSCNVLSLDGITLRLSGEFDATYQKNISI
SEQ ID NO:7   (401) CADPPGIISQNYGEAVSLIDKHSCSVLSLDGITLRLSGEFDATYQKNISI
SEQ ID NO:9   (401) CADPPGIISQNYGEAVSLIDKHSCSVLSLDGITLRLSGEFDATYQKNISI

                    451                                                500
SEQ ID NO:2   (451) LDSQVIVTGNLDISTELGNVNNSISNALDRLAESNSKLEKVNVRLTSTSA
SEQ ID NO:5   (451) LDSQVIVTGNLDISTELGNVNNSISNALDRLAESNSKLEKVNVRLTSTSA
SEQ ID NO:50  (451) LDSQVIVTGNLDISTELGNVNNSISNALNKLEESNSKLDKVNVKLTSTSA
SEQ ID NO:52  (451) LDSQVIVTGNLDISTELGNVNNSISNALNKLEESNSKLDKVNVKLTSTSA
SEQ ID NO:54  (451) LDSQVIVTGNLDISTELGNVNNSISNALDKLAKSNSKLEKVNVRLTSTSA
SEQ ID NO:7   (451) LDSQVIVTGNLDISTELGNVNNSISSTLDKLAESNNKLNKVNVNLTSTSA
SEQ ID NO:9   (451) LDSQVIVTGNLDISTELGNVNNSISSTLDKLAESNNKLNKVNVNLTSTSA

                    501                                                550
SEQ ID NO:2   (501) LITYIVLTVISLVFGALSLVLACYLMYKQKAQQKTLLWLGNNTLDQMRAT
SEQ ID NO:5   (501) LITYIVLTVISLVFGALSLGLACYLMYKQKAQQKTLLWLGNNTLDQMRAT
SEQ ID NO:50  (501) LITYIVLTVISLVFGVLSLVLACYLMYKQKAQQKTLLWLGNNTLDQMRAT
SEQ ID NO:52  (501) LITYIVLTVISLVFGVLSLVLACYLMYKQKAQQKTLLWLGNNTLDQMRAT
SEQ ID NO:54  (501) LITYIVLTVISLVFGALSLGLTCYLMYKQKAQQKTLLWLGNNTLDQMRAT
SEQ ID NO:7   (501) LITYIVLAIVSLAFGVISLVLACYLMYKQRAQQKTLLWLGNNTLDQMRAT
SEQ ID NO:9   (501) LITYIVLAIVSLAFGVISLVLACYLMYKQRAQQKTLLWLGNNTLDQMRAT
```

Figure 21C

```
                          551
SEQ ID NO:2  (551) TRA-
SEQ ID NO:5  (551) TRA-
SEQ ID NO:50 (551) TKI-
SEQ ID NO:52 (551) TKI-
SEQ ID NO:54 (551) TRA-
SEQ ID NO:7  (551) TRT-
SEQ ID NO:9  (551) TRT-
```

| | SEQ:2 | SEQ:5 | SEQ:50 | SEQ:52 | SEQ:54 | SEQ:7 | SEQ:9 |
|---|---|---|---|---|---|---|---|
| SEQ:2 | 100% | 99% | 92% | 93% | 98% | 91% | 92% |
| SEQ:5 | | 100% | 93% | 92% | 98% | 92% | 91% |
| SEQ:50 | | | 100% | 99% | 92% | 92% | 91% |
| SEQ:52 | | | | 100% | 92% | 91% | 92% |
| SEQ:54 | | | | | 100% | 90% | 91% |
| SEQ:7 | | | | | | 100% | 99% |
| SEQ:9 | | | | | | | 100% |

Figure 22

Protein sequence alignment of IBDV VP2

```
                  1                                                50
SEQ ID NO:40   (1) MTNLQDQTQQIVPFIRSLLMPTTGPASIPDDTLEKHTLRSETSTYNLTVG
SEQ ID NO:59   (1) MTNLQDQTQQIVPFIRSLLMPTTGPASIPDDTLEKHTLRSETSTYNLTVG

                  51                                              100
SEQ ID NO:40  (51) DTGSGLIVFFPGFPGSIVGAHYTLQSNGNYKFDQMLLTAQNLPASYNYCR
SEQ ID NO:59  (51) DTGSGLIVFFPGFPGSIVGAHYTLQSNGNYKFDQMLLTAQNLPASYNYCR

                  101                                             150
SEQ ID NO:40 (101) LVSRSLTVRSSTLPGGVYALNGTINAVTFQGSLSELTDVSYNGLMSATAN
SEQ ID NO:59 (101) LVSRSLTVRSSTLPGGVYALNGTINAVTFQGSLSELTDVSYNGLMSATAN

                  151                                             200
SEQ ID NO:40 (151) INDKIGNVLVGEGVTVLSLPTSYDLGYVRLGDPIPAIGLDPKMVATCDSS
SEQ ID NO:59 (151) INDKIGNVLVGEGVTVLSLPTSYDLGYVRLGDPIPAIGLDPKMVATCDSS

                  201                                             250
SEQ ID NO:40 (201) DRPRVYTITAADDYQFSSQYQPGGVTITLFSANIDAITSLSIGGELVFQT
SEQ ID NO:59 (201) DRPRVYTITAADNYQFSSQYQTGGVTITLFSANIDAITSLSVGGELVFKT

                  251                                             300
SEQ ID NO:40 (251) SVQGLVLGATIYLIGFDGTAVITRAVAADNGLTAGTDNLMPFNLVIPTNE
SEQ ID NO:59 (251) SVQSLVLGATIYLIGFDGTAVITRAVAANNGLTAGIDNLMPFNLVIPTNE

                  301                                             350
SEQ ID NO:40 (301) ITQPITSIKLEIVTSKSGGQAGDQMSWSASGSLAVTIHGGNYPGALRPVT
SEQ ID NO:59 (301) ITQPITSIKLEIVTSKSDGQAGEQMSWSASGSLAVTIHGGNYPGALRPVT

                  351                                             400
SEQ ID NO:40 (351) LVAYERVATGSVVTVAGVSNFELIPNPELAKNLVTEYGRFDPGAMNYTKL
SEQ ID NO:59 (351) LVAYERVATGSVVTVAGVSNFELIPNPELAKNLVTEYGRFDPGAMNYTKL

                  401                                             450
SEQ ID NO:40 (401) ILSERDRLGIKTVWPTREYTDFREYFMEVADLNSPLKIAGAFGFKDIIRA
SEQ ID NO:59 (401) ILSERDRLGIKTVWPTREYTDFREYFMEVADLNSPLKIAGAFGFKDIIRA

                  451
SEQ ID NO:40 (451) IRR-
SEQ ID NO:59 (451) IRR-
```

SEQ ID NO:40 is 98% identical to SEQ ID NO:59

Figure 23A

DNA sequence alignment of IBDV VP2 genes

```
                   1                                                50
SEQ ID NO:39    (1) ATGACAAACCTGCAAGATCAAACCCAACAGATTGTTCCGTTCATACGGAG
SEQ ID NO:58    (1) ATGACAAACCTGCAAGATCAAACCCAACAGATTGTTCCGTTCATACGGAG

                   51                                               100
SEQ ID NO:39   (51) CCTTCTGATGCCAACAACCGGACCGGCGTCCATTCCGGACGACACCCTGG
SEQ ID NO:58   (51) CCTTCTGATGCCAACAACCGGACCGGCGTCCATTCCGGACGACACCCTGG

                   101                                              150
SEQ ID NO:39  (101) AGAAGCACACTCTCAGGTCAGAGACCTCGACCTACAATTTGACTGTGGGG
SEQ ID NO:58  (101) AGAAGCACACTCTCAGGTCAGAGACCTCGACCTACAATTTGACTGTGGGG

                   151                                              200
SEQ ID NO:39  (151) GACACAGGGTCAGGGCTAATTGTCTTTTTCCCTGGATTCCCTGGCTCAAT
SEQ ID NO:58  (151) GACACAGGGTCAGGGCTAATTGTCTTTTTCCCTGGATTCCCTGGCTCAAT

                   201                                              250
SEQ ID NO:39  (201) TGTGGGTGCTCACTACACACTGCAGAGCAATGGGAACTACAAGTTCGATC
SEQ ID NO:58  (201) TGTGGGTGCTCACTACACACTGCAGAGCAATGGGAACTACAAGTTCGATC

                   251                                              300
SEQ ID NO:39  (251) AGATGCTCCTGACTGCCCAGAACCTACCGGCCAGCTACAACTACTGCAGA
SEQ ID NO:58  (251) AGATGCTCCTGACTGCCCAGAACCTACCGGCCAGCTACAACTACTGCAGG

                   301                                              350
SEQ ID NO:39  (301) CTAGTGAGTCGGAGTCTCACAGTGAGGTCAAGCACACTCCCTGGTGGCGT
SEQ ID NO:58  (301) CTAGTGAGTCGGAGTCTCACAGTAAGGTCAAGCACACTCCCTGGTGGCGT

                   351                                              400
SEQ ID NO:39  (351) TTATGCACTAAACGGCACCATAAACGCCGTGACCTTCCAAGGAAGCCTGA
SEQ ID NO:58  (351) TTATGCACTAAACGGCACCATAAACGCCGTGACCTTCCAAGGAAGCCTGA

                   401                                              450
SEQ ID NO:39  (401) GTGAACTGACAGATGTTAGCTACAATGGGTTGATGTCTGCAACAGCCAAC
SEQ ID NO:58  (401) GTGAACTGACAGATGTTAGCTACAACGGGTTGATGTCTGCAACAGCCAAC

                   451                                              500
SEQ ID NO:39  (451) ATCAACGACAAAATTGGGAATGTCCTGGTAGGGGAAGGGGTCACTGTCCT
SEQ ID NO:58  (451) ATCAACGACAAAATTGGGAACGTCCTAGTAGGGGAAGGGGTAACCGTCCT

                   501                                              550
SEQ ID NO:39  (501) CAGCCTACCCACATCATATGATCTTGGGTATGTGAGGCTTGGTGACCCCA
SEQ ID NO:58  (501) CAGCTTACCCACATCATATGATCTTGGGTATGTGAGGCTTGGTGACCCCA

                   551                                              600
SEQ ID NO:39  (551) TTCCCGCTATAGGGCTTGACCCAAAAATGGTAGCTACATGCGACAGCAGT
SEQ ID NO:58  (551) TACCCGCTATAGGGCTTGACCCAAAAATGGTAGCAACATGTGACAGCAGT

                   601                                              650
SEQ ID NO:39  (601) GACAGGCCCAGAGTCTACACCATAACTGCAGCCGATGATTACCAATTCTC
SEQ ID NO:58  (601) GACAGGCCCAGAGTCTACACCATAACTGCAGCCGATAATTACCAATTCTC
```

Figure 23B

```
                          651                                              700
SEQ ID NO:39    (651)  ATCACAGTACCAACCAGGTGGGGTAACAATCACACTGTTCTCAGCCAACA
SEQ ID NO:58    (651)  ATCACAGTACCAAACAGGTGGGGTAACAATCACACTGTTCTCAGCCAACA

                          701                                              750
SEQ ID NO:39    (701)  TTGATGCTATCACAAGCCTCAGCATTGGGGGAGAGCTCGTGTTTCAAACA
SEQ ID NO:58    (701)  TTGATGCCATCACAAGTCTCAGCGTTGGGGGAGAGCTCGTGTTCAAAACA

                          751                                              800
SEQ ID NO:39    (751)  AGCGTCCAAGGCCTTGTACTGGGCGCCACCATCTACCTTATAGGCTTTGA
SEQ ID NO:58    (751)  AGCGTCCAAAGCCTTGTACTGGGCGCCACCATCTACCTTATAGGCTTTGA

                          801                                              850
SEQ ID NO:39    (801)  TGGGACTGCGGTAATCACCAGAGCTGTAGCCGCAGATAATGGGCTGACGG
SEQ ID NO:58    (801)  TGGGACTGCGGTAATCACCAGAGCTGTGGCCGCAAACAATGGGCTGACGG

                          851                                              900
SEQ ID NO:39    (851)  CCGGCACCGACAATCTTATGCCATTCAATCTTGTCATTCCAACCAATGAG
SEQ ID NO:58    (851)  CCGGCATCGACAATCTTATGCCATTCAATCTTGTGATTCCAACCAATGAG

                          901                                              950
SEQ ID NO:39    (901)  ATAACCCAGCCAATCACATCCATCAAACTGGAGATAGTGACCTCCAAAAG
SEQ ID NO:58    (901)  ATAACCCAGCCAATCACATCCATCAAACTGGAGATAGTGACCTCCAAAAG

                          951                                             1000
SEQ ID NO:39    (951)  TGGTGGTCAGGCAGGGGATCAGATGTCATGGTCGGCAAGTGGGAGCCTAG
SEQ ID NO:58    (951)  TGATGGTCAGGCAGGGGAACAGATGTCATGGTCGGCAAGTGGGAGCCTAG

                          1001                                            1050
SEQ ID NO:39   (1001)  CAGTGACGATCCATGGTGGCAACTATCCAGGGGCCCTCCGTCCCGTCACA
SEQ ID NO:58   (1001)  CAGTGACGATCCATGGTGGCAACTATCCAGGAGCCCTCCGTCCCGTCACA

                          1051                                            1100
SEQ ID NO:39   (1051)  CTAGTAGCCTACGAAAGAGTGGCAACAGGATCCGTCGTTACGGTCGCTGG
SEQ ID NO:58   (1051)  CTAGTGGCCTACGAAAGAGTGGCAACAGGATCTGTCGTTACGGTCGCTGG

                          1101                                            1150
SEQ ID NO:39   (1101)  GGTGAGTAACTTCGAGCTGATTCCAAATCCTGAACTAGCAAAGAACCTGG
SEQ ID NO:58   (1101)  GGTGAGCAACTTCGAGCTGATCCCAAATCCTGAACTAGCAAAGAACCTGG

                          1151                                            1200
SEQ ID NO:39   (1151)  TTACAGAATACGGCCGATTTGACCCAGGAGCCATGAACTACACAAAATTG
SEQ ID NO:58   (1151)  TTACAGAATATGGCCGATTTGACCCAGGAGCCATGAACTACACGAAATTG

                          1201                                            1250
SEQ ID NO:39   (1201)  ATACTGAGTGAGAGGGACCGTCTTGGCATCAAGACCGTCTGGCCAACAAG
SEQ ID NO:58   (1201)  ATACTGAGTGAGAGGGACCGCCTTGGCATCAAGACCGTCTGGCCAACAAG

                          1251                                            1300
SEQ ID NO:39   (1251)  GGAGTACACTGATTTTCGTGAGTACTTCATGGAGGTGGCCGACCTCAACT
SEQ ID NO:58   (1251)  GGAGTACACTGACTTTCGTGAGTACTTCATGGAGGTGGCCGACCTCAACT
```

Figure 23C

```
                     1301                                             1350
SEQ ID NO:39 (1301) CTCCCCTGAAGATTGCAGGAGCATTTGGCTTCAAAGACATAATCCGGGCT
SEQ ID NO:58 (1301) CTCCCCTGAAGATTGCAGGAGCATTTGGCTTCAAAGACATAATCCGGGCC

                     1351        1362
SEQ ID NO:39 (1351) ATAAGGAGGTAA
SEQ ID NO:58 (1351) ATAAGGAGGTGA
```

SEQ ID NO:39 is 97% identical to SEQ ID NO:58

Figure 24

The protein sequence alignment between SEQ ID NO:2 and SEQ ID NO:5 (AAP97877.1) to highlight the differences at amino acid level:

```
SEQ ID NO:2  1    MGSKPSTRIPAPLMLITRIMLILGCIRPTSSLDGRPLAAAGIVVTGDKAVNVYTSSQTGS  60
SEQ ID NO:5  1    ............................................................  60

SEQ ID NO:2  61   IIVKLLPNMPRDKEACAKAPLEAYNRTLTTLLTPLGDSIRKIQGSVSTSGGGKQGRLIGA  120
SEQ ID NO:5  61   ...................................................RR.K.F...  120

SEQ ID NO:2  121  VIGSVALGVATAAQITAAAALIQANQNAANILRLKESIAATNEAVHEVTDGLSQLSVAVG  180
SEQ ID NO:5  121  ............................................................  180

SEQ ID NO:2  181  KMQQFVNDQFNNTARELDCIKITQQVGVELNLYLTELTTVFGPQITSPALTQLTIQALYN  240
SEQ ID NO:5  181  ............................................................  240

SEQ ID NO:2  241  LAGGNMDYLLTKLGIGNNQLSSLIGSGLITGYPILYDSQTQLLGIQVNLPSVGNLNNMRA  300
SEQ ID NO:5  241  ............................................................  300

SEQ ID NO:2  301  TYLETLSVSTTKGYASALVPKVVTQVGSVIEELDTSYCIESDLDLYCTRIVTFPMSPGIY  360
SEQ ID NO:5  301  ............................................................  360

SEQ ID NO:2  361  SCLSGNTSACMYSKTEGALTTPYMALKGSVIANCKITTCRCTDPPGIISQNYGEAVSLID  420
SEQ ID NO:5  361  ..................................R.........................  420

SEQ ID NO:2  421  RHSCNVLSLDGITLRLSGEFDATYQKNISILDSQVIVTGNLDISTELGNVNNSISNALDR  480
SEQ ID NO:5  421  ............................................................  480

SEQ ID NO:2  481  LAESNSKLEKVNVRLTSTSALITYIVLTVISLVFGALSLVLACYLMYKQKAQQKTLLWLG  540
SEQ ID NO:5  481  .......................................G....................  540

SEQ ID NO:2  541  NNTLDQMRATTRA  553
SEQ ID NO:5  541  .............  553
```

Note: the changes between amino acid positions 112 to 117 were introduced to change the velogenic F-cleavage site sequence to a lentogenic F-cleavage site sequence. The changes at amino acid positions 395 and 520 were made to keep the amino aacid sequence between the wt VIId NDV-F of the present invention and codon-optimized NDV-F the same. The codon optimized NDV-F VIId was based on a consensus sequence of VIId NDV strains.

Figure 25

The protein sequence alignment between SEQ ID NO:2 and SEQ ID NO:9 to highlight the differences at amino acid level:

| | | | |
|---|---|---|---|
| SEQ ID NO:2 | 1 | MGSKPSTRIPAPLMLITRIMLILGCIRPTSSLDGRPLAAAGIVVTGDKAVNVYTSSQTGS | 60 |
| SEQ ID NO:9 | 1 | .......**W**.**SVT**......**T**....**S**..**C**........................**I**........ | 60 |
| SEQ ID NO:2 | 61 | IIVKLLPNMPRDKEACAKAPLEAYNRTLTTLLTPLGDSIRKIQGSVSTSGGGKQGRLIGA | 120 |
| SEQ ID NO:9 | 61 | ..**I**.......**K**.............................**R**....**AT**..........**V**.. | 120 |
| SEQ ID NO:2 | 121 | VIGSVALGVATAAQITAAAALIQANQNAANILRLKESIAATNEAVHEVTDGLSQLSVAVG | 180 |
| SEQ ID NO:9 | 121 | **I**.........................................**D**......**N**.....**A**.... | 180 |
| SEQ ID NO:2 | 181 | KMQQFVNDQFNNTARELDCIKITQQVGVELNLYLTELTTVFGPQITSPALTQLTIQALYN | 240 |
| SEQ ID NO:9 | 181 | .......**N**..............**A**..................................... | 240 |
| SEQ ID NO:2 | 241 | LAGGNMDYLLTKLGIGNNQLSSLIGSGLITGYPILYDSQTQLLGIQVNLPSVGNLNNMRA | 300 |
| SEQ ID NO:9 | 241 | ..............**V**................**N**..............**I**......**S**...... | 300 |
| SEQ ID NO:2 | 301 | TYLETLSVSTTKGYASALVPKVVTQVGSVIEELDTSYCIESDLDLYCTRIVTFPMSPGIY | 360 |
| SEQ ID NO:9 | 301 | .............**F**............................**I**......**V**.......... | 360 |
| SEQ ID NO:2 | 361 | SCLSGNTSACMYSKTEGALTTPYMALKGSVIANCKITTCRCTDPPGIISQNYGEAVSLID | 420 |
| SEQ ID NO:9 | 361 | ...................................**M**.....**A**.................. | 420 |
| SEQ ID NO:2 | 421 | RHSCNVLSLDGITLRLSGEFDATYQKNISILDSQVIVTGNLDISTELGNVNNSISNALDR | 480 |
| SEQ ID NO:9 | 421 | **K**...**S**..................................................**ST**..**K** | 480 |
| SEQ ID NO:2 | 481 | LAESNSKLEKVNVRLTSTSALITYIVLTVISLVFGALSLVLACYLMYKQKAQQKTLLWLG | 540 |
| SEQ ID NO:9 | 481 | .....**N**..**N**....**N**.............**AIV**..**A**..**VI**............**R**.......... | 540 |
| SEQ ID NO:2 | 541 | NNTLDQMRATTR | 552 |
| SEQ ID NO:9 | 541 | ............ | 552 |

SEQUENCE LISTING

```
<160> NUMBER OF SEQ ID NOS: 64

<210> SEQ ID NO 1
<211> LENGTH: 1665
<212> TYPE: DNA
<213> ORGANISM: artificial sequence
```

-continued

<220> FEATURE:
<223> OTHER INFORMATION: NDV-F codon-optimized gene from modified wt VIId

<400> SEQUENCE: 1

```
atgggcagca agcccagcac aagaatccca gccccccctga tgctgatcac ccgcatcatg     60
ctgatcctgg gctgcatcag acccacaagc tccctggatg gacgcccccct ggccgctgcc    120
ggcatcgtgg tgaccggcga caaggccgtg aacgtgtaca ccagcagcca gaccggcagc    180
atcatcgtga agctgctgcc caacatgccc agagacaaag aggcctgcgc caaggccccc    240
ctggaagcct acaacagaac cctgaccacc ctgctgaccc ccctgggcga cagcatcaga    300
aagatccagg gctccgtgag cacaagcggc ggaggaaagc agggcagact gatcggcgcc    360
gtgatcggca gcgtggccct gggagtggct acagctgccc agattaccgc tgcagccgcc    420
ctgatccagg ccaaccagaa cgccgccaac atcctgagac tgaaagagag cattgccgcc    480
accaacgagg ccgtgcacga agtgaccgac ggcctgagcc agctgtccgt ggccgtgggc    540
aagatgcagc agttcgtgaa cgaccagttc aacaacaccg ccagagagct ggactgcatc    600
aagatcaccc agcaggtggg cgtggagctg aacctgtacc tgaccgagct gaccacagtg    660
ttcggccccc agatcacaag cccagccctg acacagctga ccatccaggc cctgtacaac    720
ctggctggcg gcaacatgga ctatctgctg acaaagctgg gaatcggcaa caaccagctg    780
tccagcctga tcggaagcgg cctgatcacc ggctacccca tcctgtacga cagccagaca    840
cagctgctgg gcatccaggt gaacctgccc agcgtgggca acctgaacaa catgcgcgcc    900
acctacctgg aaaccctgag cgtgtccacc accaagggct acgccagcgc cctggtgccc    960
aaggtggtga cacaggtggg cagcgtgatc gaggaactgg acaccagcta ctgcatcgag   1020
agcgacctgg acctgtactg caccagaatc gtgaccttcc caatgagccc cggcatctac   1080
agctgcctga gcggcaacac cagcgcctgc atgtacagca agaccgaagg cgcactgaca   1140
acaccctaca tggccctgaa gggaagcgtg atcgccaact gcaagatcac cacctgcaga   1200
tgcaccgacc ccccaggcat catcagccag aactacggcg aggccgtgag cctgatcgat   1260
cgccattcct gtaacgtgct gtccctggac ggcatcacac tgagactgag cggcgagttc   1320
gatgccacct accagaagaa catcagcatc ctggacagcc aggtgatcgt gaccggcaac   1380
ctggacatca gcaccgagct gggcaacgtg aataacagca tcagcaacgc cctggacaga   1440
ctggccgaga gcaacagcaa gctggaaaaa gtgaacgtgc gcctgacatc cacttccgct   1500
ctgatcacct acatcgtgct gaccgtgatc agcctggtgt tcggcgccct gagcctggtg   1560
ctggcctgct acctgatgta caagcagaag gcccagcaga aaccctgct gtggctgggc   1620
aacaacaccc tggaccagat gagagccacc accagagcct gatga                   1665
```

<210> SEQ ID NO 2
<211> LENGTH: 553
<212> TYPE: PRT
<213> ORGANISM: artificial sequence
<220> FEATURE:
<223> OTHER INFORMATION: NDV-F protein of modified wt VIId of codon-optimized gene

<400> SEQUENCE: 2

```
Met Gly Ser Lys Pro Ser Thr Arg Ile Pro Ala Pro Leu Met Leu Ile
1               5                   10                  15

Thr Arg Ile Met Leu Ile Leu Gly Cys Ile Arg Pro Thr Ser Ser Leu
            20                  25                  30
```

-continued

```
Asp Gly Arg Pro Leu Ala Ala Ala Gly Ile Val Val Thr Gly Asp Lys
        35                  40                  45

Ala Val Asn Val Tyr Thr Ser Ser Gln Thr Gly Ser Ile Ile Val Lys
    50                  55                  60

Leu Leu Pro Asn Met Pro Arg Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Lys Ile Gln Gly Ser Val Ser Thr Ser Gly Gly Gly
            100                 105                 110

Lys Gln Gly Arg Leu Ile Gly Ala Val Ile Gly Ser Val Ala Leu Gly
        115                 120                 125

Val Ala Thr Ala Ala Gln Ile Thr Ala Ala Ala Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ser
                165                 170                 175

Val Ala Val Gly Lys Met Gln Gln Phe Val Asn Asp Gln Phe Asn Asn
            180                 185                 190

Thr Ala Arg Glu Leu Asp Cys Ile Lys Ile Thr Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Tyr
            260                 265                 270

Pro Ile Leu Tyr Asp Ser Gln Thr Gln Leu Leu Gly Ile Gln Val Asn
        275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Tyr Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Ala Leu Lys Gly Ser Val Ile Ala Asn Cys Lys Ile Thr Thr Cys Arg
385                 390                 395                 400

Cys Thr Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
```

-continued

```
    450                 455                 460

Thr Glu Leu Gly Asn Val Asn Asn Ser Ile Ser Asn Ala Leu Asp Arg
465                 470                 475                 480

Leu Ala Glu Ser Asn Ser Lys Leu Glu Lys Val Asn Val Arg Leu Thr
                485                 490                 495

Ser Thr Ser Ala Leu Ile Thr Tyr Ile Val Leu Thr Val Ile Ser Leu
            500                 505                 510

Val Phe Gly Ala Leu Ser Leu Val Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Arg Ala
545                 550


<210> SEQ ID NO 3
<211> LENGTH: 1662
<212> TYPE: DNA
<213> ORGANISM: artificial sequence
<220> FEATURE:
<223> OTHER INFORMATION: NDV-F DAN wt VIId

<400> SEQUENCE: 3

atgggctcca aaccttctac caggatccca gcacctctga tgctgatcac ccggattatg      60

ctgatattgg gctgtatccg tccgacaagc tctcttgacg gcaggcctct tgcagctgca     120

ggaattgtag taacaggaga taaggcagtc aatgtataca cttcgtctca gacagggtca     180

atcatagtca agttgctccc gaatatgccc agggataagg aggcgtgtgc aaaagcccca     240

ttagaggcat ataacagaac actgactact ttgctcactc ctcttggcga ctccatccgc     300

aagatccaag ggtctgtgtc cacatctgga ggaggcaagc aaggccgcct gataggtgct     360

gttattggca gtgtagctct tggggttgca acagcggcac agataacagc agctgcggcc     420

ctaatacaag ccaaccagaa tgccgccaac atcctccggc ttaaggagag cattgctgca     480

accaatgaag ctgtgcatga agtcaccgac ggattatcac aactatcagt ggcagttggg     540

aagatgcagc agtttgtcaa tgaccagttt aataatacgg cgcgagaatt ggactgtata     600

aaaatcacac aacaggttgg tgtagaactc aacctatacc taactgaatt gactacagta     660

ttcgggccac agatcacctc ccctgcatta actcagctga ccatccaggc actttataat     720

ttagctggtg gcaatatgga ttacttatta actaagttag gtatagggaa caatcaactc     780

agctcgttaa ttggtagcgg cctgatcact ggttacccta tactgtatga ctcacagact     840

caactcttgg gcatacaagt gaatttaccc tcagtcggga acttaaataa tatgcgtgcc     900

acctatttgg agaccttatc tgtaagtaca accaaaggat atgcctcagc acttgtcccg     960

aaagtagtga cacaagtcgg ttccgtgata gaagagcttg acacctcata ctgtatagag    1020

tccgatctgg atttatattg tactagaata gtgacattcc ccatgtcccc aggtatttat    1080

tcctgtttga gcggcaacac atcagcttgc atgtattcaa agactgaagg cgcactcact    1140

acgccgtata tggcccttaa aggctcagtt attgccaatt gtaaaataac aacatgtaga    1200

tgtacagacc ctcctggtat catatcgcaa aattatggag aagctgtatc cctgatagat    1260

agacattcgt gcaatgtctt atcattagac gggataactc taaggctcag tggggaattt    1320

gatgcaactt atcaaaagaa catctcaata ctagattctc aagtcatcgt gacaggcaat    1380

cttgatatat caactgaact tggaaacgtc aacaattcaa tcagcaatgc cttggatagg    1440

ttggcagaaa gcaacagcaa gctagaaaaa gtcaatgtca gactaaccag cacatctgct    1500
```

ctcattacct atattgttct aactgtcatt tctctagttt tcggtgcact tagtctggtg 1560
ttagcgtgtt acctgatgta caaacagaag gcacaacaaa agaccttgct atggcttggg 1620
aataataccc tcgatcagat gagagccact acaagagcat ga 1662

<210> SEQ ID NO 4
<211> LENGTH: 1695
<212> TYPE: DNA
<213> ORGANISM: artificial sequence
<220> FEATURE:
<223> OTHER INFORMATION: NDV-F DNA with GenBank accession No. AY337464.1

<400> SEQUENCE: 4
ctggatcccg gttggctcat tcaggacgca atatgggctc caaaccttct accaggatcc 60
cagcacctct gatgctgatc acccggatta tgctgatatt gggctgtatc cgtccgacaa 120
gctctcttga cggcaggcct cttgcagctg caggaattgt agtaacagga gataaggcag 180
tcaatgtata cacttcgtct cagacagggt caatcatagt caagttgctc ccgaatatgc 240
ccagggataa ggaggcgtgt gcaaaagccc cattagaggc atataacaga acactgacta 300
ctttgctcac tcctcttggc gactccatcc gcaagatcca agggtctgtg tccacatctg 360
gaggaaggag acaaaaacgc tttataggtg ctgttattgg cagtgtagct cttggggttg 420
caacagcggc acagataaca gcagctgcgg ccctaataca agccaaccag aatgccgcca 480
acatcctccg gcttaaggag agcattgctg caaccaatga agctgtgcat gaagtcaccg 540
acggattatc acaactatca gtggcagttg ggaagatgca gcagtttgtc aatgaccagt 600
ttaataatac ggcgcgagaa ttggactgta taaaaatcac acaacaggtt ggtgtagaac 660
tcaacctata cctaactgaa ttgactacag tattcgggcc acagatcacc tcccctgcat 720
taactcagct gaccatccag gcactttata atttagctgg tggcaatatg gattacttat 780
taactaagtt aggtataggg aacaatcaac tcagctcgtt aattggtagc ggcctgatca 840
ctggttaccc tatactgtat gactcacaga ctcaactctt gggcatacaa gtgaatttac 900
cctcagtcgg gaacttaaat aatatgcgtg ccacctattt ggagacctta tctgtaagta 960
caaccaaagg atatgcctca gcacttgtcc cgaaagtagt gacacaagtc ggttccgtga 1020
tagaagagct tgacacctca tactgtatag agtccgatct ggatttatat tgtactagaa 1080
tagtgacatt ccccatgtcc ccaggtattt attcctgttt gagcggcaac acatcagctt 1140
gcatgtattc aaagactgaa ggcgcactca ctacgccgta tatggccctt aaaggctcag 1200
ttattgccaa ttgtaggata acaacatgta gatgtacaga ccctcctggt atcatatcgc 1260
aaaattatgg agaagctgta tccctgatag atagacattc gtgcaatgtc ttatcattag 1320
acgggataac tctaaggctc agtggggaat ttgatgcaac ttatcaaaag aacatctcaa 1380
tactagattc tcaagtcatc gtgacaggca atcttgatat atcaactgaa cttggaaacg 1440
tcaacaattc aatcagcaat gccttggata ggttggcaga aagcaacagc aagctagaaa 1500
aagtcaatgt cagactaacc agcacatctg ctctcattac ctatattgtt ctaactgtca 1560
tttctctagt tttcggtgca cttagtctgg gtttagcgtg ttacctgatg tacaaacaga 1620
aggcacaaca aaagaccttg ctatggcttg ggaataatac cctcgatcag atgagagcca 1680
ctacaagagc atgaa 1695

<210> SEQ ID NO 5
<211> LENGTH: 553
<212> TYPE: PRT

<213> ORGANISM: artificial sequence
<220> FEATURE:
<223> OTHER INFORMATION: NDV-F protein with GenBank accession No.
AAP97877.1

<400> SEQUENCE: 5

```
Met Gly Ser Lys Pro Ser Thr Arg Ile Pro Ala Pro Leu Met Leu Ile
1               5                   10                  15

Thr Arg Ile Met Leu Ile Leu Gly Cys Ile Arg Pro Thr Ser Ser Leu
            20                  25                  30

Asp Gly Arg Pro Leu Ala Ala Ala Gly Ile Val Val Thr Gly Asp Lys
        35                  40                  45

Ala Val Asn Val Tyr Thr Ser Ser Gln Thr Gly Ser Ile Ile Val Lys
    50                  55                  60

Leu Leu Pro Asn Met Pro Arg Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Lys Ile Gln Gly Ser Val Ser Thr Ser Gly Gly Arg
            100                 105                 110

Arg Gln Lys Arg Phe Ile Gly Ala Val Ile Gly Ser Val Ala Leu Gly
        115                 120                 125

Val Ala Thr Ala Ala Gln Ile Thr Ala Ala Ala Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ser
                165                 170                 175

Val Ala Val Gly Lys Met Gln Gln Phe Val Asn Asp Gln Phe Asn Asn
            180                 185                 190

Thr Ala Arg Glu Leu Asp Cys Ile Lys Ile Thr Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Tyr
            260                 265                 270

Pro Ile Leu Tyr Asp Ser Gln Thr Gln Leu Leu Gly Ile Gln Val Asn
        275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Tyr Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380
```

-continued

```
Ala Leu Lys Gly Ser Val Ile Ala Asn Cys Arg Ile Thr Thr Cys Arg
385                 390                 395                 400

Cys Thr Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
    450                 455                 460

Thr Glu Leu Gly Asn Val Asn Asn Ser Ile Ser Asn Ala Leu Asp Arg
465                 470                 475                 480

Leu Ala Glu Ser Asn Ser Lys Leu Glu Lys Val Asn Val Arg Leu Thr
                485                 490                 495

Ser Thr Ser Ala Leu Ile Thr Tyr Ile Val Leu Thr Val Ile Ser Leu
            500                 505                 510

Val Phe Gly Ala Leu Ser Leu Gly Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Arg Ala
545                 550
```

```
<210> SEQ ID NO 6
<211> LENGTH: 1662
<212> TYPE: DNA
<213> ORGANISM: artificial sequence
<220> FEATURE:
<223> OTHER INFORMATION: NDV-F DNA wildtype V (CA02 strain) with GenBank
      accession No. EF520718

<400> SEQUENCE: 6

atgggctcca aaccttctac ctggatctca gtaactctga tgctgatcac tcggaccatg     60

cttatactta gctgtatctg tccgacaagc tctcttgacg gtagacctct cgcagccgca    120

gggattgtgg tgacgggaga taaagcagtc aatatataca cttcatctca aacagggtca    180

atcatcatca agttactccc aaatatgccc aaggataaag aagcgtgcgc aaaagcccca    240

ttggaagcat acaatagaac actgaccact ttactcaccc ctcttggtga ctctatccgc    300

agaatacaag ggtctgcgac tacatctgga ggaaggagac agaaacgctt tgtaggtgcc    360

attatcggca gtgtagctct tggggttgca acagctgcac agataacagc agccgcagct    420

ctgatacaag ccaaccaaaa tgctgccaac atcctccggc ttaaggagag cattgctgca    480

accaatgacg ctgtacacga ggtcactaac ggattatcac aactagcggt ggcggtcggg    540

aagatgcagc agtttgttaa taaccagttt aataatacgg cgcgagaatt ggactgcata    600

aaaattgcac aacaagtggg cgtcgaactc aatttgtatc taactgaatt gaccacagtg    660

ttcgggccac aaatcacctc ccctgcttta actcagctga ctatccaggc actttataat    720

ttagccggtg gcaatatgga ttacctgttg actaagttgg gtgtagggaa taatcaactc    780

agttcgttaa ttggtagtgg cttgataact ggcaacccta tactatatga ctcacagacc    840

caactcttag gcatacagat aaatttaccc tcagtcggga gcctaaataa tatgcgtgcc    900

acctacttgg agaccttatc cgtaagcacg accaaagggt tcgcctcagc acttgtcccg    960

aaagttgtga cgcaagtcgg ctctgtgata gaagaacttg acacctcata ttgtatagaa   1020

tccgatatag atctatattg tacaagggta gtgacattcc ccatgtctcc tggtatttac   1080
```

```
tcctgtctga gcggcaatac gtcagcttgt atgtattcaa agaccgaagg tgcactcact   1140

acaccataca tggccctcaa aggctcagtt attgccaatt gcaagatgac tacatgcaga   1200

tgcgcagatc ccccaggtat catatcacag aattatgggg aagctgtgtc tctaatagat   1260

aaacattcat gcagtgtctt gtccctagac gggataactc tgaggctcag tggggaattt   1320

gatgcgacct atcaaaagaa catctcaata ctagattctc aagtcatcgt gacaggaaat   1380

ctcgatatat caactgagct tgggaatgtt aacaactcga taagcagtac cctggacaaa   1440

ttagcagaaa gcaacaacaa gctaaacaag gtcaatgtaa acctaaccag cacatctgct   1500

ctcatcactt atattgtctt agctatcgta tctcttgctt tcggcgtaat tagcctggtt   1560

ctagcatgct acctgatgta taaacaaaga gcacaacaaa agaccttact atggctcggg   1620

aacaacaccc ttgatcagat gagagccacc acaagaacct ga                      1662
```

<210> SEQ ID NO 7
<211> LENGTH: 553
<212> TYPE: PRT
<213> ORGANISM: artificial sequence
<220> FEATURE:
<223> OTHER INFORMATION: NDV-F protein wildtype V (CA02 strain) with
      GenBank accession No. ABS84266

<400> SEQUENCE: 7

```
Met Gly Ser Lys Pro Ser Thr Trp Ile Ser Val Thr Leu Met Leu Ile
1               5                   10                  15

Thr Arg Thr Met Leu Ile Leu Ser Cys Ile Cys Pro Thr Ser Ser Leu
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Ile Lys
    50                  55                  60

Leu Leu Pro Asn Met Pro Lys Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Gly Ser Ala Thr Thr Ser Gly Gly Arg
            100                 105                 110

Arg Gln Lys Arg Phe Val Gly Ala Ile Ile Gly Ser Val Ala Leu Gly
        115                 120                 125

Val Ala Thr Ala Ala Gln Ile Thr Ala Ala Ala Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Asp Ala Val His Glu Val Thr Asn Gly Leu Ser Gln Leu Ala
                165                 170                 175

Val Ala Val Gly Lys Met Gln Gln Phe Val Asn Asn Gln Phe Asn Asn
            180                 185                 190

Thr Ala Arg Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255
```

```
Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Ile Asn
        275                 280                 285

Leu Pro Ser Val Gly Ser Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Ile Asp Leu Tyr Cys Thr Arg Val Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Ala Leu Lys Gly Ser Val Ile Ala Asn Cys Lys Met Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Lys His Ser Cys Ser Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
    450                 455                 460

Thr Glu Leu Gly Asn Val Asn Asn Ser Ile Ser Ser Thr Leu Asp Lys
465                 470                 475                 480

Leu Ala Glu Ser Asn Asn Lys Leu Asn Lys Val Asn Val Asn Leu Thr
                485                 490                 495

Ser Thr Ser Ala Leu Ile Thr Tyr Ile Val Leu Ala Ile Val Ser Leu
            500                 505                 510

Ala Phe Gly Val Ile Ser Leu Val Leu Ala Cys Tyr Leu Met Tyr Lys
        515                 520                 525

Gln Arg Ala Gln Gln Lys Thr Leu Leu Trp Leu Gly Asn Asn Thr Leu
    530                 535                 540

Asp Gln Met Arg Ala Thr Thr Arg Thr
545                 550
```

<210> SEQ ID NO 8
<211> LENGTH: 1665
<212> TYPE: DNA
<213> ORGANISM: artificial sequence
<220> FEATURE:
<223> OTHER INFORMATION: NDV-F codon-optimized gene from modified wildtype V (CA02 strain)

<400> SEQUENCE: 8

```
atgggcagca agcccagcac ctggatcagc gtgaccctga tgctgatcac cagaaccatg      60

ctgatcctga gctgcatctg ccccacaagc agcctggacg gcagacccct ggccgctgcc     120

ggcatcgtgg tgaccggcga caaggccgtg aacatctaca ccagcagcca gaccggcagc     180

atcatcatca agctgctgcc caacatgccc aaggacaaag aggcctgcgc caaggccccc     240

ctggaagcct acaacagaac cctgaccacc ctgctgaccc ccctgggcga cagcatcaga     300
```

```
agaatccagg gcagcgccac cacaagcggc ggaggaaagc agggcagact ggtgggcgct    360
atcatcggga gcgtggccct gggcgtggcc acagctgccc agattaccgc tgcagccgcc    420
ctgattcagg ccaatcagaa cgccgccaac atcctgagac tgaaagagag cattgccgcc    480
accaacgacg ccgtgcacga agtgacaaac ggactgtccc agctggctgt cgctgtcggc    540
aagatgcagc agttcgtgaa caaccagttc aacaacaccg ccagagagct ggactgcatc    600
aagatcgccc agcaggtggg cgtggagctg aacctgtacc tgaccgagct gaccacagtg    660
ttcggccccc agatcacaag ccccgctctg acccagctga caatccaggc cctgtacaac    720
ctggctggcg gcaacatgga ctatctgctg actaagctgg gagtgggcaa caaccagctg    780
tccagcctga tcgggtccgg gctgatcaca ggcaacccca tcctgtacga cagccagaca    840
cagctgctgg gcatccagat caacctgcca tccgtgggaa gcctgaacaa catgagagcc    900
acctacctgg aaaccctgag cgtgtccacc accaagggct tcgccagcgc cctggtgccc    960
aaggtggtga cacaggtggg cagcgtgatc gaggaactgg acaccagcta ctgcatcgag   1020
agcgacatcg acctgtactg caccagagtg gtgaccttcc caatgagccc cggcatctac   1080
agctgcctga gcggcaacac cagcgcctgc atgtacagca agaccgaagg agcactgaca   1140
acaccctaca tggccctgaa gggaagcgtg atcgccaact gcaagatgac cacctgcaga   1200
tgcgccgacc ccccaggcat catcagccag aactacggcg aggccgtgag cctgatcgac   1260
aaacattcct gtagcgtgct gtccctggat ggcatcacac tgagactgag cggcgagttc   1320
gacgccacct accagaagaa catcagcatc ctggacagcc aggtgatcgt gaccggcaac   1380
ctggacatca gcaccgagct gggcaacgtg aacaacagca tcagcagcac cctggacaag   1440
ctggccgagt ccaacaacaa gctgaacaaa gtgaacgtga acctgaccag cacaagcgcc   1500
ctgatcacct acatcgtgct ggccatcgtg tccctggcct tcggcgtgat cagcctggtg   1560
ctggcctgct acctgatgta caagcagaga gcccagcaga aaaccctgct gtggctgggc   1620
aataacaccc tggaccagat gagggccacc accagaacct gatga                   1665
```

```
<210> SEQ ID NO 9
<211> LENGTH: 553
<212> TYPE: PRT
<213> ORGANISM: artificial sequence
<220> FEATURE:
<223> OTHER INFORMATION: NDV-F protein of codon-optimized NDV-F gene of
      modified wildtype V (CA02 strain)

<400> SEQUENCE: 9

Met Gly Ser Lys Pro Ser Thr Trp Ile Ser Val Thr Leu Met Leu Ile
1               5                   10                  15

Thr Arg Thr Met Leu Ile Leu Ser Cys Ile Cys Pro Thr Ser Ser Leu
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Ile Lys
    50                  55                  60

Leu Leu Pro Asn Met Pro Lys Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Gly Ser Ala Thr Thr Ser Gly Gly Gly
            100                 105                 110

Lys Gln Gly Arg Leu Val Gly Ala Ile Ile Gly Ser Val Ala Leu Gly
```

-continued

```
        115                 120                 125

Val Ala Thr Ala Ala Gln Ile Thr Ala Ala Ala Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Asp Ala Val His Glu Val Thr Asn Gly Leu Ser Gln Leu Ala
                165                 170                 175

Val Ala Val Gly Lys Met Gln Gln Phe Val Asn Asn Gln Phe Asn Asn
            180                 185                 190

Thr Ala Arg Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Ile Asn
        275                 280                 285

Leu Pro Ser Val Gly Ser Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Ile Asp Leu Tyr Cys Thr Arg Val Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Ala Leu Lys Gly Ser Val Ile Ala Asn Cys Lys Met Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Lys His Ser Cys Ser Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
    450                 455                 460

Thr Glu Leu Gly Asn Val Asn Asn Ser Ile Ser Ser Thr Leu Asp Lys
465                 470                 475                 480

Leu Ala Glu Ser Asn Asn Lys Leu Asn Lys Val Asn Val Asn Leu Thr
                485                 490                 495

Ser Thr Ser Ala Leu Ile Thr Tyr Ile Val Leu Ala Ile Val Ser Leu
            500                 505                 510

Ala Phe Gly Val Ile Ser Leu Val Leu Ala Cys Tyr Leu Met Tyr Lys
        515                 520                 525

Gln Arg Ala Gln Gln Lys Thr Leu Leu Trp Leu Gly Asn Asn Thr Leu
    530                 535                 540
```

Asp Gln Met Arg Ala Thr Thr Arg Thr
545 550

<210> SEQ ID NO 10
<211> LENGTH: 1411
<212> TYPE: DNA
<213> ORGANISM: artificial sequence
<220> FEATURE:
<223> OTHER INFORMATION: MCMV IE promoter

<400> SEQUENCE: 10
aattcaatag tggatccccc aactccgccc gttttatgac tagaaccaat agtttttaat 60
gccaaatgca ctgaaatccc ctaatttgca aagccaaacg cccccctatgt gagtaatacg 120 gggacttttt acccaatttc ccacgcggaa agccccctaa tacactcata tggcatatga 180
atcagcacgg tcatgcactc taatggcggc ccatagggac tttccacata gggggcgttc 240
accatttccc agcatagggg tggtgactca atggccttta cccaagtaca ttgggtcaat 300
gggaggtaag ccaatgggtt tttcccatta ctggcaagca cactgagtca aatgggactt 360
tccactgggt tttgcccaag tacattgggt caatgggagg tgagccaatg ggaaaaaccc 420
attgctgcca agtacactga ctcaataggg actttccaat gggtttttcc attgttggca 480
agcatataag gtcaatgtgg gtgagtcaat agggactttc cattgtattc tgcccagtac 540
ataaggtcaa tagggggtga atcaacagga aagtcccatt ggagccaagt acactgcgtc 600
aatagggact ttccattggg ttttgcccag tacataaggt caatagggga tgagtcaatg 660
ggaaaaaccc attggagcca agtacactga ctcaataggg actttccatt gggttttgcc 720
cagtacataa ggtcaatagg gggtgagtca acaggaaagt tccattggag ccaagtacat 780
tgagtcaata gggactttcc aatgggtttt gcccagtaca taaggtcaat gggaggtaag 840
ccaatgggtt tttcccatta ctggcacgta tactgagtca ttagggactt tccaatgggt 900
tttgcccagt acataaggtc aataggggtg aatcaacagg aaagtcccat tggagccaag 960
tacactgagt caatagggac tttccattgg gttttgccca gtacaaaagg tcaatagggg 1020
gtgagtcaat gggtttttcc cattattggc acgtacataa ggtcaatagg ggtgagtcat 1080
tgggtttttc cagccaattt aattaaaacg ccatgtactt tcccaccatt gacgtcaatg 1140
ggctattgaa actaatgcaa cgtgaccttt aaacggtact ttcccatagc tgattaatgg 1200
gaaagtaccg ttctcgagcc aatacacgtc aatgggaagt gaaagggcag ccaaaacgta 1260
acaccgcccc ggttttcccc tggaaattcc atattggcac gcattctatt ggctgagctg 1320
cgttctacgt gggtataaga ggcgcgacca gcgtcggtac cgtcgcagtc ttcggtctga 1380
ccaccgtaga acgcagagct cctcgctgca g 1411

<210> SEQ ID NO 11
<211> LENGTH: 217
<212> TYPE: DNA
<213> ORGANISM: artificial sequence
<220> FEATURE:
<223> OTHER INFORMATION: SV40 PolyA

<400> SEQUENCE: 11
ggggatccag acatgataag atacattgat gagtttggac aaaccacaac tagaatgcag 60
tgaaaaaaat gctttatttg tgaaatttgt gatgctattg ctttatttgt aaccattata 120
agctgcaata aacaagttaa caacaacaat tgcattgatt ttatgtttca ggttcagggg 180
gaggtgtggg aggtttttc ggatcctcta gagtcga 217

<210> SEQ ID NO 12
<211> LENGTH: 368
<212> TYPE: DNA
<213> ORGANISM: artificial sequence
<220> FEATURE:
<223> OTHER INFORMATION: SV40 promoter

<400> SEQUENCE: 12
caattcgagc tcggtacagc ttggctgtgg aatgtgtgtc agttagggtg tggaaagtcc 60
ccaggctccc cagcaggcag aagtatgcaa agcatgcatc tcaattagtc agcaaccagg 120
tgtggaaagt ccccaggctc cccagcaggc agaagtatgc aaagcatgca tctcaattag 180
tcagcaacca tagtcccgcc cctaactccg cccatcccgc ccctaactcc gcccagttcc 240
gcccattctc cgccccatgg ctgactaatt ttttttattt atgcagaggc cgaggccgcc 300
tcggcctctg agctattcca gaagtagtga ggaggctttt ttggaggcct aggcttttgc 360
aaaaagct 368

<210> SEQ ID NO 13
<211> LENGTH: 154
<212> TYPE: DNA
<213> ORGANISM: artificial sequence
<220> FEATURE:
<223> OTHER INFORMATION: Synthetic PolyA

<400> SEQUENCE: 13
aataaaatat ctttattttc attacatctg tgtgttggtt ttttgtgtga atcgatagta 60
ctaacatacg ctctccatca aaacaaaacg aaacaaaaca aactagcaaa ataggctgtc 120
cccagtgcaa gtgcaggtgc cagaacattt ctct 154

<210> SEQ ID NO 14
<211> LENGTH: 165994
<212> TYPE: DNA
<213> ORGANISM: artificial sequence
<220> FEATURE:
<223> OTHER INFORMATION: SB-1 genome HQ840738.1

<400> SEQUENCE: 14
ataccaaaac tctcgcggcg gcgaactgaa taaaaaaaat tcaccctaac cctaacccta 60
aaggcctaac cctaacccta aaggcctaac cctaacccta acggcctaac cctaacccta 120
accctaaccc taaccctaac cctaacccta accctaaccc taaccctaac cctaacccta 180
accctaaccc taaccaactt aatatccccc cctgcatttc accccccccc caaaaaagga 240
acatagcaca acaattaacg cggctgggcc gcagcctccc gccgccacag gtgcactcag 300
cccgcgggct gccgcacccc gcgaactgtc ggctacaggc agaatgaacg cgcagcattg 360
cgcggacaca gtgggtgacc gaagcacacc accacagact ctgaccctgc catagccccg 420
accgtgaaat gaggcccggc gaggcctaac agtcaccccg accgtgatac atgacaccaa 480
cgctgcccgt tacattaaaa ggtcctagcc ctacatgccg taaccgccaa agccgctacc 540
cttaatatgt cctgaccccg actatggact attaccctaa ccctgaaagg ccataacagt 600
gaccctaaca gtcctgacgc cgaccccgag aggccctaac cgccaccgta aacggccctg 660
gcccaagccc ttaatgtggc cctaacaggc actaaaacga ataagacagg ccctaacccc 720
gaccgtgatg acaggccgaa cccccgaccc taacagaccc tatcgcgggg tccaataatc 780
cgctttccca ccccgtcctt caacggaaga gtgcgtgctt cagacccgcg gacccgggca 840

-continued

```
acttgtaccc ggccccgagc gtctctgtgc aacgcactac attgaaagta aacaacaggt    900
aggcggtgtc gactcaggtc tgtgcgaacg ccaaccgctt tcaagaacgg aggctacgcg    960
cagtcacgaa tgaggaagtg gttttgtgag gccgatcccc tttcctgttt ttttgagact   1020
cgcagccgat tccgagagga ccgggagcgc acgacgatgg gctcccgcct tacagttttc   1080
tccgcgaaca ccgtactcct gctgggaagg taagccgcgg tccactgttt acttcccgtg   1140
caagcacttc cgcgtacgcg attgtccggc acgtccggac gcgcttaatt tccgtgtcct   1200
gactgcatcc ggcgactaca gcgccgcatc ccccctcaa cccccccccc gtagattcca   1260
tggccgagtc cgccacaccg gctttttgga atttcgcggg gggctggcgg agaccgcctc   1320
tgtcccggcg ctcgggaagt gcgtacagga tgtttttctt tttccggcag cggtgcagca   1380
atggcgggga cgcaggacgc ttgggaaccg cggaccgcag cctttgcgtc gccgccggga   1440
gacggcggct tcatcgcgca cgcgggcgct cctagccccg acccgggctg aagccgtcgg   1500
ccagtacgaa taaaaacgcc catggaatgc tgctacgaga cgcgtccgtc cgtccgtccg   1560
tctggctcgc gcgcgagcgc atgcgcgcac atccgccgtt tccgtaaaca ccggaacgac   1620
accctcgccg gccccgaccc tcaatccgcg gcacgccctg accctataac cattacacgc   1680
cccgccctaa ttccgagaga ccttaacccc taacctaacc ctgttaccct acccctaaca   1740
ggccctaacc ctgacgggga gggggaacgc ctccttaaca gactaacaat aatgggggg   1800
gggaggaggg tcgctcctag ccctaacggg cccaaccttc gcgcctaccc taccctgcc    1860
aggccctaac cctactcggg ggggggaggg gggatgggaa cctaagcgtg gcaggtcgaa   1920
ccgtgtgggg ggggccctgc ccgtaacaga ccccagcccc taccccttacg ggccccaacc  1980
cttacaagac cctaacctta gtactcggtg ggagcctaac ccgaataggg cctgacatta   2040
ataggcccta ataacccta cacctgtgac cacgaactct gataggccat aaccctgacc    2100
ttgacaggtc ctaaccccgg gcccctaagc caaacgccgc ccttgagacc ctaaccccga   2160
ggccttaacc ctgacccaga gaacctaaca ctgataggcc ttcgcgctct tagtctctga   2220
tcataatcac cccgacccta aagacccgat ccagaagcct aaccccgacc ctaaagaccc   2280
gatccagaag cctaaccccg accctgaccc taaccctgcc cctaaaggcc taaccccgac   2340
cctgcacctg agcttgcccc taaaggccta accccgaccc cgacactacc cctaaaggcc   2400
taaccccgac aacgacacta cccctacagg cctaaccccg acaacgacac taccccctaaa  2460
ggcctaaccc taaacccgac actacccta aaggtctaac cccgaactcg acccgacccc    2520
taaacgccta accacgaccc cgagactgcc cctaaaggcc taaccctaaa ccagacacaa   2580
cccctaaagg cctaaccccg aacccgaccc gaccccctaaa cgcctaactt tggaccccaa  2640
ccctaacctt aacggcatat ccctgtccat gaccctgaca cccgaccctg gcactaaccc   2700
ttaccccgag cccctgcccc taagggccca accatcaccc taaaggcccg accctgcccc   2760
taaagaccta agcatgacct taaaggccta accctgacca tgaccctaag ggcccgaccc   2820
taaccctaac ctagtaccct ccttccacac cccccccccg aaaaccgagc atagcccaac   2880
aatgaactcg gccggtttaa agatttattt cgatgcgatg cgcggtcacg cccaccacaa   2940
aaatagaccc tgcaatattg atgccggaac cagcccatcg cagagcgggc gaccgctaca   3000
cgggacgcgt attcgtcggg accgcctttc tccggcaggt agcctacacg tacctcacta   3060
tggccataaa gatgcagcca tagagaggta cgtgaagaag acccgtcgga atcagaagca   3120
acatttcagg acgtacgact cgagccggac atgataccag acaccggagt ccacagcgac   3180
cgcgatttcc tctgcgccta ccctcggccg acgaacaacg ccgagggtag gcgtcgagaa   3240
```

-continued

```
aatcgcgacc gagggtgcgc cctcgttcca cgcgatcccg cagaacgctt cgcgcccagt   3300
ctccgtccat cgacgtggtg cttgatgaca ggatccacct ctaacaccac gcgatgcgct   3360
ccgcagcgcc ttcgtcccgg agtagagcgc catctccttc ctccagcacg gtgctcgacg   3420
cggcaataca aaagtctcac gcctcgaaca ccggacgaag gagggaactg cgcgcgtctg   3480
gactttaccg gggcggcttc gtcccgcggc gttccggatg acgtttcgag ggcccactcc   3540
atccttcggt gcggtgcccg agaagggatg acgacctctc acacacagca caaaggacgg   3600
cgctgggctc cgtccgatgc tctcgatctc aggcagcacg gcaccgatcc ggagagcgcg   3660
tcgcacgtcg cgtcctaccc ccggagtagt gcatgacggt tactccccgg caagcactcg   3720
tccgaaggag gacacgccac gcgacccgat tcccagccgc ttcgcgcccg gctacttctt   3780
cgcctgcagt ccgccggcag ggctcgagca aacaaactcc catctttccc tgacggcatc   3840
taaccgttaa aatacgacgt caggcaccgt aagggaaaaa atggaagcag ttcggagtac   3900
agacgcctaa ccacgggccc tctctcgccc ctccgcgtcc gatatgcaga tcggtgagag   3960
tactgatcgt ctcatatccg caacgaagac ttcgggatcg atagacgtta tccttcccgc   4020
cccccccccc ccacatagga acctctgttc catcgccatc tgttacaaaa aagggcgagc   4080
ctatccactg gcaacgagcg agaacacagc taggcctccc aggtcgtaac aagccactta   4140
cgtcgtcgcg ggggaaggtc ggtccatttc gctcctattc cgcaccttcg tttggaacag   4200
aagcattaca cacaccgcca tttccccgcg ggcagaattc tagtcttttt gtggttatgc   4260
tcccacctac ccgcacagac acgtactcac ctctcacgat ccagcatatc gccgtaagat   4320
ttacagacat tcctccctcc ccacccaacc gaacactgca cagcggcagc ctaaaagtcg   4380
ctctgcggtc gcatatcccc cccacccccc ttcgatggtc cggtgtacgg agacctctca   4440
cacaacacag gacaccgtac cacggaccat ccgaacggcg ggcgaacagt cacgcaggac   4500
gtggacacga gtcctgcgct cgcacaggca gctgggcggc ggtgctgtct tcctccgacg   4560
gacagcctac aagcaagcca ctaggactac cgatacgacc agagtgacgt gcgtgtaaga   4620
cggcccagga cgaagtcccg cgccccgccg aaaataacag caccgacctg aaagagacca   4680
cgtcttaccc aacagccgac ccccgaacga tgcacgctcc caagagtcgg ccgtaggaga   4740
gcacgcgccc ccccatactc ggcgcgcgta cccgcggcca tccctgcagc gcggcccggc   4800
ctcgttgcga ttcagtgaac gtaccgcgcg ccatctccgt ccatcggcgt ggtgctcgat   4860
cccgtcattc ggtgatctca agcaccccgc gaaggaggaa gcggagcgtg taacgatttc   4920
cgcggcgcgc gacgacgccg cgccgtcccg tccgacgttt ggaacgccgc ctcggtcctt   4980
gcgcgcagta cttgagacga tacgtgttaa aatctcaggc accacgctaa ggacggagca   5040
gagctcggtt cgcttcgctc gcgcgccgac gcatctctgc ttcgcagaac ctgttttgaa   5100
aagaccgcag cgaccaccgc gtgctaccct cggagggggg catgaggacg gcgcccgata   5160
ctcccgtgca caccgccgag gggggacacg gcgcgcgcgc cgatgctcag ccggttcttc   5220
gcccagagcc ctcccaacct tgtcccacac gacggggagc ggcacgggga atcaattcgt   5280
ctttctctcc gcaggcattg cacaacggca atgacacgtg caatgccagc ctgagagaaa   5340
acatacgaac agtcccgagt tccgagtagt aactctcgct ttcgcgccct tccccgactc   5400
gttccgagca tatcaggcga tacgaggcat ttcgcgcgcg tcgccctgtc cgtcccggtt   5460
gtcctagaac gtgacacctc taggggaccc gggaaggact ggacgacgcg ccgtcgtgcg   5520
gtccgaccgc aatacggcgt cgttacccct tcctcacaac acctgatctc gtggcctaaa   5580
```

-continued

```
tacccgctca tcgccccgca tccgacgcct ctacctcccc tttgtcccca accgagaaac   5640
ctatccgggg cccgctaagg tcgaaccgcc gagactccgt cgtccggcta ttacccgcca   5700
taacaagtcg ctagtcgaag gatggaatcg cagcggtccg agcggctctc ctctgatatc   5760
ccggcacggc ctattgggat taaggtccgg gcctattcag attacggtta gagtcctcga   5820
gaaacatttc agtctctctg gcatctgaca acggctacgc gccactcaga tgccaaaaca   5880
gactggatgc gtttccaaag gccatcgtgt ctaacaaagg ccagtccctg taactaggcc   5940
aaacatctca tcaccgtcca agtcacaggt acttcaggtt tacggtcgtc tgctatctac   6000
aacgaagaat tcagagccga tctcgccagg gccccttctc ccccctccct tcttcccccc   6060
tcccttctcc ccccctccct tctcccccct cccttcttcc cccctccctt cttcccccct   6120
cccttcttcc cccctccctt cttcccccct cccttcttcc cccctccctt cttcccccct   6180
cccttcttcc cccctccctt cttcccccct cccttcttcc tcccttcccc ccccctcccc   6240
tcttcctccc ttcccctcc cttccccccc tcccttcccc ccctcccttc cccccctccc   6300
ttcccccccct cccttcccc cctcccttcc ccccttcccc cttcccctct tctccccccc   6360
ccctccccac tccctccctt cttcccccctt ctcccacctc cgttcagcct tccccctccc   6420
ccctcccttc tccccccctcc gttcagcctt cccccctcccc cctcccttct cccccctccg   6480
ttcagacttc ctcctcccca atcgcccccc ttcgcaactt gcgaaatcta gtctaacacg   6540
ggtttactta cgcggtttac attcacacag cgggtgcatg ttttccgctg acatttccca   6600
agccggccac aagaaacgaa gcaaaaaaaa aaaagatagg ggtattaatg cgcgccaccc   6660
gtcgctacgc agcccgactc caaatttcga ataatgccct tctaggcatt ggaccgccgc   6720
cccactcccc gcgcaatatc taggcttaat cgccaagatt gaccacgtat cccttatcgc   6780
gccggccgtt caggccctcc cccccccccc acgcctctcg actctttttt ttttccatgg   6840
gccgtccaga ctgagacgac acgtagattc gcggtcgtcc cagaataaag gatgaccccg   6900
cgatgcccat tcccactcgc ccgacgtctc cctccgattc aaaagtactg cggcacgacc   6960
tgcgatggaa gggaaaaaca caccaaacgg ccttaagttt tccggtttgc ctttcccttc   7020
catcgcaaat agcccgcaaa agaaggatcg catttccggc cccgtccggc catcgcgact   7080
catccaccgg ccaaacgggg atatcggacc gcgagacttt aacggctatg tatttcccca   7140
cccgctcttc tcagaggaat ccccgatgca atctagaagc ttatcgttca gagcgtttcg   7200
ggcacggaac ttcctgagaa tatagatcat ctctcagggt gcaccgtacc acacaacgtt   7260
tctgtgggaa aacggaaggc cagtcacttt cacgtagacc cctcaggata cccataacag   7320
aaaaactcag ccccccctcc cctcacgacc attttcctac gtggaatgca ctacaagtac   7380
ctgacatttt gcaaacaggg cgccgagacg tccgatgggg ttccagcttc cgtggcggac   7440
gaaccaacac cagtgtgggc gttcgcatct cccccccccct cccccccccc catacatgaa   7500
agacctacga ttactgcata ggaccccgct cctgggacaa atactccgga aacctccagg   7560
gatcggaaat ttatttagaa ggggggtggg gtacagggca tgcttgctta ggatctgctc   7620
gaaacttgac tataaaaggc aatctgacta gaatcgccaa aggcgatagg tctcagaaga   7680
aaagtaggac gcgcgggggga gggataattg tttacgcggg ggggaagata aatggcccac   7740
ggcggaaacg agaaagcgcg gggggggggtt aggccttgga agggggaaag acgcattcgc   7800
gcatgtcaga attaagatgg cttccctata agacgaacgc acggtttaac agaaaagcgg   7860
acatcacgcc ggggtcgaac gcgggaaaat aaaaccgttg cggggggggg ggggagtccg   7920
aaccgtgcgg cgggaaggct ccgagtccga ccggaaacgg aaaaaggcgg cacggcacgg   7980
```

-continued

```
ggcgctcaac gcacagggga taggaagaat ttcccctcgg cccgcggatt cggatcgcgc   8040
tcgcgatcca ccttttctcc gccgactcgc cgaccgcccg gaacgccggt acttacgcgc   8100
tggagaagcc ccgtattact cttcttcccg gattcggccc cggcgcttct gcgtctgcgc   8160
ggcggacata cgcagttgcg cttccgtcga cgtattcaat gtaaacaagg aagtcggccc   8220
tgcgacttcc gcgatcgcga tcgcgaaccg gtaaacaacg caggggggagc gcggagcgcg  8280
ggcgcgggca gggagttaac ctcgcgatcc gaccgcgcat tcggatgtgc gggtcgggggg  8340
cgtagagata acgcggcgtt tccgctccgg gccggagagg ctggcgggcg ggtctctccg   8400
tacattcttt ttttttgcaa acgcgccgct gcgcgcctaa acgccgcagc ggcgcgaaac   8460
gcccgcgctc tctaagcgtc cgaaggccgt acggacaccg gtgcgtccgg gcgctcggcc   8520
gggcgaacgg cggagctttt ctttctcttt tcagtctcgg agaaaacggc ccggtgcaca   8580
cctcctctcg ggagcgtcgc aggaaagtaa gttcgtgtca ctcaccaccc cccccccccc   8640
gccatcgaca cggagtctga gcatgagggc tttaataaac cgatttgaac gtgctacgac   8700
gagagtccgt gcaagtgttc gcgctcgcgc ctatacgtac tacgacagcc gctctgtagc   8760
cgcggtgtgt gtgggggtgt gtgggggtgt gtgtgggggt gtgtgtgggt gtgcgcgcgg   8820
ccgggacggg attcctgatt ccgtagcact tcatctcgaa tgtggaattc ggttccgacg   8880
ggggccgtta acacatatac gcgacactgg tcggaactcg cgacttccac ggtcgccgcg   8940
taagtcagtg gtgcttatac gtgggaacga agcgaggcta agtagcaggt cgcgaacaag   9000
gaggtggacc gcggggctgt ttatatcgca tctgcgtctc ccgcggggcc ggtgagctaa   9060
cggctcctcc ccgtcgcgaa actgtatccc ccgcacaaac acctggacga tccgcgagcg   9120
acttatgatg cgcgtgcccc tcccccaact aacccttcgc gcgcaccgcg ggcctcggcg   9180
cggtacgttc tccacaacac taatcgcacg cattcccggt cgcccgtcgc ccccccccctc  9240
gcacatcccg cctcgggggga gaggagagga caaagtacgt tccccgactt acgcgacgga  9300
ctcccccgcc cgcgccatcg ccagacaccg aaacgggacc gaagcgagaa agacttttta   9360
ataaacacgt tcatacgcac tacgacgaga ccgctcgcac gcggtctcgt acacgcacgt   9420
acaccttaac gatcgacgca ctgtacgcga gggctaagag cgggcgagcg atccaccccg   9480
tttcgcaaga aacgacgcgt cccgggcgcg gctccgctaa gcattcgttt acacggcagt   9540
ttcggcgtct ccctcctccg gtcgtccgta ggagccctct gcgtttcccc gcacggccct   9600
cgaaaccaaa ctccacagac tcttccagac gtttgcgacg ctaggctggc ccggggcgcg   9660
gacgcggtct gagggcttga gccggtggct gcagctcgtg agagcgtgtt cgaactctga   9720
aacgtaaaac ggtccggctc gattccggat aacgcaaacg tcttttcccc tcccccccga   9780
tccggcaggc gagaccttcc cactcaacct cggtcccgca cgggcttggg gggggggggg   9840
ggagggaaat agccggccga accctactcg ggcccggacc caaacgacat cgctccaaaa   9900
gagagcgttc cgtttgacgg agcccgcggt gcgtacctgc acgggattcc ggatcccgat   9960
cccatagcga ccaatctcga atactgaact ccgttgttcc gtcggaggcc gttaacacat  10020
ataggggcaa ttggtctggg ctcacgattt tcattgtcgc cgcaaaagtg agtgtgcttg  10080
tgtgtgcaac aaagcgagac cctctaccct gttcgtgagg agagggtcgc ggggttgcat  10140
atatgtggca tatgcgttga tcacgggacc ggtgagctga caactcctcc ccgtcaggga  10200
actctattcc ccgcattacc acatggacgg gccgcggcgt cgcggcgttt cccacacccc  10260
tccaccgacc atgccccacc cccgctctcg ttcgagaggc cgtcccctcc cccatttcgt  10320
```

tccgcctcgt ccagagccag cgcgggactt cactttttcc ccatccctct actcctatct 10380
cgttgcccag cccacgatcg ctatgtacgc gttctctccg aggccggctc gcgccgagcc 10440
ggccagacaa agtcacttcg gaactgacgc cgaagtgagt gctgaacggt tgagggggcg 10500
gcgtatcgcg gataagctat tctcctcgga gtctttttgc ggcaggccgc aagcttcctc 10560 gtaccccct ttcggggttc gctagaactc gatcgaaacc cgagacgagt tactactgag 10620
ccgatcccta cagctcggga ccgctcccga acagaacgcg gcctcatcgg gttctttcgt 10680
agagcgccgc aagggcagaa acggaccgac gcgcgtccga gactcatccc gagctcacgc 10740
cgaacggctt tattgctccg cttccgaacg agagagcggt cctatctcga ccggcccgtt 10800
ttcaatcgat tcccgaggtt ccgacctcgc cgcgggtgcg gggccggggg gaaagtcggg 10860
gggcgacccg cgaccgtgtt ccgcgagcgg cgttcggccg cgtcgccgac gcggggtcgg 10920
atctcgttct cgtgcgaggg atcgggacga tccgcggacg agaacgatgg ggcgtcctcc 10980
ctcgacgtcc gacggttccg gacgccgcga gggtcgcggc ccgaaggcgg agatgccgag 11040
ctcggccagt tcgatgccct cggtacccat ccccccttcca cccgtcggcg acccccgcga 11100
acgcgagccg tagacgacgt tctcgggacg gcgcgcgatc gcttcccggc cgcctgcgat 11160
cccaacggga cgggttcgtt cgccgcgcgg ttcgcccggc ggtaaaagaa cgaccagaaa 11220
atccgatccg cgacggcggg cgctttatta ccgcggtccc gcgctttcgg acggcgggcc 11280
ggccagcgga acgacggtcc ccgccggacc tccgctcgcg tatttgtagg ccggaggtcc 11340
ccgaatccgc ccccgtggga ggggggcggc gtttctagcc cccggcgcgg gccgcggccg 11400
gacacgaaca cgtggcatag gatcccgctt cccgattggc ccggacgggc gttcgcacct 11460
tgcgccaata atatattata tatataatct tatattggtt cgcggtgcga acgctgacgc 11520
gttcgccccg ctcgtttgca ttgcatcacg tgatcgttac gccctcacga ccggcccggt 11580
cataagaagc ggaggcgccg gatctccgct tagagcgccg gtccggcgct tcccgcgaac 11640
ggacgcaagg tggcggcaga ggataagcga tcgccgaacg agagccccgt cgggagcgat 11700
cccggatcgg acgccgcggc gaacgcgtag gtttcggccg tctccccctt cccttccccc 11760
acacatcctc ccgcccccca caacctcctc cccggcggcc tcggacggcg cctcccccgc 11820
tcttcccgaa ctgcaggccg gccggctacc ctccctcccc cctctcctcc ttcccccccct 11880 ccccccttctt ctcccgtccg accggcccgg cggaacgcga tgcggcgggg gaaaaggcgc 11940
cgatccgacg gacgcgatcg cgacccgacc gctgatccgc gcgcccctcc ggacgccgag 12000
agggatgcgg agcgcgagag cggagccggg gacggagggg gcgacccgga cgccggagag 12060
aacgacgccg gagggcgcgg accgggcgcg gacccgggcg acgacccggg cgacgacccg 12120
ggcgacgacc cgggcgacga cccgggcgcg gacgcgggcg cggacgcgga cgaggcgcac 12180
gcgcgcctgc tccggcgcgc cgagcgcgaa aacaagaaac tccgaagggg atgtaattta 12240
gtgtttacta taagcaacaa aaccctagta gtcggaacat gttttatgct tgcggcaggt 12300
gtactagtcg gtgcaagtgg tgctgaccac gagactgcat gcaacaaaac taatttgctg 12360
ttggtatttg ttactgccct cttgacacga tttatttgaa acggtaacga atgctcgtgt 12420
actttataat tgcatgcccg attacaatct gttctgtaag aatagttata cgtagcgtgt 12480
tttacatagt cttcgatgta tagaagagac gcagtcaact tgccggtgcc gtgaaattgt 12540
ctccacacta tgatgttttt actgttacaa ggtaattaaa gaccttcgag tttttcactc 12600
cacttgtgtg acgctccttc gattatgaga gtacaatgtc gtctaagggg gatgtggatc 12660
accacgcggg ttatggggtg gcactcgcaa ttattgctct attgctcgta catgctactg 12720

-continued

```
cactgattat ggtgagtgtc tttttacctc tgtcccatca gtaattgcta aacaatgatt  12780
gttttaatgc caaaaatctt tttttagatc ttttctgatg tcaaattcag accagtttca  12840
caggatctta gtacgcagta cccatctcat aagcattatg atgatgcgta ctcgccacat  12900
atgtctgggg tagaccacgg ccattcggat gtatggacta acactgtaaa tgacccatcc  12960
ggcggaataa actcaaattt gcctggtgcg aagagcgtgg agaagatcta tcctagcgta  13020
gaaccaagta cgtcgcatga caaagtgtcg tatggaaatg catggggagg ggacataaac  13080
accggcagtg tttcaccttc tgatgacaaa gcattgcccg ccactgtcga accatcgacg  13140
gacatcgttt ccatcgcgat cacggggagc agtttaaacg gagaaagtag ttggcggatt  13200
tctaaggatg gcccgcgtcg ggtttataca ccacaccaga ctaaaagaag tcctcctcag  13260
atcgatggca cgcgtttatc tactagaacg gcatacttga gtgtgtggga tgaacaggag  13320
gggattttta aaacgttccc ggccaatgct gctgcattca atttattgga cgctaatcag  13380
ttagagaaag cgcgccgtga agttttttttc gttgtgtcgg tgtggcatgg aaatacgaac  13440
gaaacccgta tatttttatc cgccacgagg ctactgacgc gaatgatgtc cacatcgctc  13500
gtcgtttatc tttcctggga ctctcgaggg gccctgggga cgacaactga tgcggctttt  13560
ctggcacgga gcgtaaatat atcccagttc ctgaccgctg taccaccaca ttcgcaagtt  13620
cgttgtatgg gccattcatt aggaatgtat acttgcggtt ccatctgtag acaatataat  13680
agtgtaggta cgaccagatg caaaagcatt ttaagtattg atccttacgg cgcctcatca  13740
cccgagtctc atgtatcctc ggcagacagc tcaaatacaa tacgctttga tgccgactat  13800
gttgcgattt tcgcaacaag taagtggcac ttgaacacgt ccgattcaaa cgcagacgaa  13860
tatataatag tagatggctt gaatgcaaat gctgtgtgtg tcgatcccta cgagtggagt  13920
gtcttattgt gtgttagcaa tcgccaacga aatgccgttt gtgagcgatt cggtgctaac  13980
aacgtaacga ctaccggcga ccctgcggaa gacggttcgg aaacatgcat gcgaatactc  14040
cctatactat cggtgctgca gtcgctcgat aagaattctg cgtatccgct gttacgtatg  14100
gatccgccgg gagcttctgc agcggtacca tccttaccgt ccacatggaa tatctacgtg  14160
atgggaaagg attacagata ttctacttat ggaaaaaatg agagcctgtg gtattctagc  14220
gccgtgcata tgggaggacc gggattcttt cctgcgtcgg tatttactgt gtttcttccc  14280
tcgggtatac ccgctgtggt atccaatgtc gtgcaacaca gtagcatcag ttacggagat  14340
gtagcggttc attccgcttt cttaactgat aggtccctct actacccccg agtgatggtc  14400
caaacatccg ggcctatttt atctgcctat tcttggagag cgcgactgca taatgacagc  14460
ctctatttat taccacttcc agaacaggag ataatgcaat acaaatgcgc agttgcacag  14520
ggaagctatg catgtagtcc cacaggcccg atcttgacaa ctgttatgtg gcgttcactg  14580
ttattcgcgg gcagatcttc gccggtgccc ccaaacggta gttgtttgac ttatatcccc  14640
gctaacacaa tcatccggag ccggtccccc attgaaatag gccctcgaag tattataact  14700
gcatcgtttc agctaagcag acaattaatg gctatgacgc tcgaaaatca tttcacgtcc  14760
acgaaccgga ctctattgac atttcatgat gtgtgccacg acactgctat ggagtcggat  14820
atatacttcg agtataactg gttaggcgca tcgatgaaca ttaccatact gaaccccggc  14880
ctctatacgt ttagatggtt tttcccattt gaggttttcg taatgccggt ggtagttacg  14940
cctcccaagt ccagagcgga taccgtcacg atcgctcccg taggactata accctgttgg  15000
acaaataaag tatacagact gttcaaactg tgtagtgagt ccatcttagt cgtactggat  15060
```

gcaaacgagc ccaataaagt gtaacagttg ggaaaacttt aactgtcgtg ggataaccct 15120
tataatgtta tagtgcagtg actgacttgt aagcaaacat tgactggaag ttagcttata 15180
ctgtacttcg tcgagactgc cgttgccgac tgtacgatgg agcggcctct cgatcgtgac 15240
tatcaaagtg cgataacgtg cttgacgtgc gagagagtac tttttgtcg cctctgacat 15300 gggcaggttc gtggcgataa ctccaactac atcaatgcca agaggtttaa gcgttaggtc 15360
gccggtttaa atactcattc ggaagccgtg ggtggcgcct cgcgtacccc agaccgttgt 15420
gttataaaac ccagactcgt cgccacacat gtaggcaaaa aaatgactag cgaaagagct 15480
cttgcgctag cacccggtcg ggcggccacg gcagatttct acgaagtgga tccggtatat 15540
cggcgagact tcgcacgccg gcttttacaa cgtaagttcc agcttgtcgt gttgtagagg 15600
tatttactac tctgatcttc acctaattag caccatgccg tttgtattta ggtttattcc 15660
ccaagacgct tgccgccgtc agggaatcgg agggaggccg aaacacgcgc ccgcccaaaa 15720
cagatctgtg tacgcttttg cgcataatcg cgcatcatga gaccccgcac attttcaccc 15780
caggtcccag actcccgaaa tcctcagcaa ttgtcgacgg gctatgggta gcgtgtcgag 15840
gacttgcggc agagtgcatg ttcgatggcc gggcgacaat agagttagca gaacgcctcg 15900
caacttcatg gttgacggcc ataagattaa ttctagtttg gcatcccgtg tatgccctcg 15960
gccagcaaca cgaaccactc gagcggatat gtcgccaagg tcgagaatat attgctatgc 16020
tctcgggaac gattcaaaca tcgtatgcga catggccgtt ttggcaaatg atgcaacgat 16080
gcttagattg gtgctgctca tttcacatcc ccgatgaccg ttcttgtgag cacggatctc 16140
cacgtctggg gatccaacta gagggcgaaa accagatatt cgcgccaagt ttggggctct 16200
actccgctgt aatggcatgg accccaattc catgtcacgt acaggttcct gtatttccga 16260
gacctggcga atcggacgat gtctcgaccc cgcctagtgg ggcacagata ggacgggtgc 16320
gacctcacag tcttcaaagg ctggcactaa aacacagacc tattgatgcc gatgtacata 16380
gacccatgcc gttaggccgg ccactccctt caatgcatat ggacgatcca gacgatccgc 16440
aacctggacc ctccggacaa ggccgggcgc ccagaactcc aactctggaa ggagtccggg 16500
tcgcagaaca accggtaagt cttcgccgcg caagaacacc accgccgccg ctcaatgtcg 16560
acgaagacga caacgatctt cctcccggcc aacccccccg ccctcatctt cgaactcccc 16620
catcatcacc atcgtcctcc gagactgaaa tcgatgagga acttaacgcg caacccgatc 16680
cttggggtac aaaccgtagc tctacccccta cagataactc ctctgccagt gaggatgaag 16740
ccagagggag cgggttgccc cgaccattgc gcagcgcgac tactgaaccg cgcgtaacgc 16800
gtagaagccg ccgtgaggct cgcagccgga gccgaagtcg gtctggagac cggaggtggg 16860
gaccgtcccg attaaggtca atgcctggac gcaggagagc ttctcgacaa gatacagtac 16920
ttgtagacag ttctgaagag gaaccgtagc cgtttgtagt cagggttcta gttaagtagg 16980
cgccgcgcga tttacgaatt agtacatttg ggccctgccg cgcagcgagc gtctcacgac 17040
tgcgatagtc atgcacgttt cgctggtatg ggtgctgtgt ttgcttttcg gaactagtgg 17100
gggtgtttta aagtggtctg acgttgactt gtcgcgggga ttcatttcgg tcccaaatgt 17160
aagttcgctt atgcttttag actgcgctcc aaattcgata ctctcaactg ccagattcgc 17220
cgatctgaca acagatgatg tccctaccgg tatatttatt aagatcaatt gcagcgttcc 17280
ggaattcatt ttatggtatg ggtctaaaag cgtggcggcg cggctcaacc caattattgc 17340
aagcgcttta atgatggacg atgttttaaa gagcggattg gacgattccg tgaaggcgga 17400
acttcgcgtg tttttaaaaa gaatatccga acggctacct tggagctctc tccggaaaag 17460
acacggttgt ctgaacctgg acgcacctta tgacttctcc tgttatggct cggcacggct 17520
cgacagattt gaacgagaca tcgaggacga tggccgcgga atgtcatgcc gagctaaatc 17580
aacccgagct aaagcggccc gcaccaacgc catcgaggga tagttcggcc gcgattaaaa 17640
agcgtcgccg gccgatcgga cctccgcccg gtttcgcgcc actgggcgat aatgcgccat 17700
ccccacaggg tgaaactgac gcgtacggac atcaactgtc gatgaccgaa aacgtccgcg 17760
ctgaattgtg gcctgttata gccgagtctt acaacataga ctggagttgg aaagattggc 17820
tgctccccga attatgctgt cctaacggct ccaagttgtt ggcggaatac gaacgccgtg 17880
ctgcggtaga agacgtcttt cctccgcgag cagatatttt cgcgtggact aagtactgcg 17940
ctccgcccga cgtcaaagtt gtgatcgtcg ggcaagaccc gtacgttcat ccgggacaag 18000
ctcacggctt ggcatttagc gtcaagcgcg gcattacaat tcctcctagt ctgcagaata 18060
tattttcggc agtcaaggcg tgctatccct cgatcgaact cggagcccac ggatgtctag 18120
aagactgggc taaacgcgga gtcctgttac taaattccgt tttgacagta aagaaggggg 18180
agcccggatc tcatcactct ctaggatggc aaactctggt gcgaaacgtg cttcgaagac 18240
tgtcgttgtc gactcgaggc atagtcttca tgttatgggg agcgcgggca cagactatat 18300
attttcaaac ggatcgcgac gatcgacatt tggtgctgaa atacagtcac ccgtctcctt 18360
tatcccggag accgtttgcg tcctgcacgc actttaaaga cgccaacgag ttcctctgta 18420
aaagcggtaa agggggcata gactggagca ttggcgcgta agtgacggaa gggttaatca 18480
tcacatgcgt acaaaagtcg cagcgctcta ggacttgtcg ctttctgcgc gcgcaatgaa 18540
cgataccgca ccttctgttt tggcagtatt atccaactgg ggttggaaga gcacaccctt 18600
gggcaccgta ggccccgtcc cgattcgcga cgagactgag tgcgcgcgcg aagaccttcc 18660
ggcacatgat tgcgaccact ggtgtaaaac cgccaatgca gaaaacggac ctatggcacc 18720
ctccccgggg aatcgagatt ttgcgggaaa ccaagaatac acacatttcg acactctgtt 18780
tatggtctcg tctctcgacg aattgggaag acgtcaactg acagatacta tacggagaga 18840
tctaaggcat tctctggcca agtttacaat agcttgtact aaaacctcct cgttttcttc 18900
ctcgcacgcc acgaaaaagg ttcgcgcgaa aatgtttcaa agagggcgtc agagcaacaa 18960
gagcttgcag atgtttattt tatgccgcag ggcacacgct aaacatatcc gggcccaact 19020
gcaagcggta attcaagctc gaaaaccccg caagtattac acccgcgccg tggacggaac 19080
tacgcatccg gtggtgcccg tctttgtata cgagtttgcc gccatagacg ttgtcagttt 19140
gcatcgagac aacgtgatag aggtagacac tcccggctcg tgagcttctc gccgctcatc 19200
atgttcgtcg tttcggcagc tttagcatcc gcatcagact acgccgcgtt tttgcgggac 19260
aacaagcaag ctgctcgcaa gctgcagttt ccgttgtccc cgatgccgag ccaacggatc 19320
ccgcatctgt ctaaggatgg caggactgca gtcgcccggg aaacggggtc gagcgaggtt 19380
atgtcagcga gcggacagaa cgcgtcgacc cgaccggtcg acgctcgttt cgccaaccta 19440
gacaccgaga aatgacaaga agcatctaaa acgcgcttga ttgtcgagtg gctgaataaa 19500
atctttattg atcgactcgc tttcctattt ctgatttaat aaccatagat ggggcgggga 19560
atctataaaa taggcaaggt ccgcgcggat tcgagcacat cgaccgcgtc cgcgacacag 19620
catgcaagtg gcgacgaacg gtcctcaggc atgcacgact ggtctatctg tatatctgcc 19680
tcgcggatcg cttccgtgag aaggtcttcc tcgtacccgg ttgagaaagc gtccactttc 19740
gagggtccgt acccgtgcac agcgccaatt tcgtgcgctt cgatgcactt actaatctcg 19800

-continued

```
ggcgcgtttt cgggcagaga tcttatcgga tcgcagctct gtcgatgcgc atctttatta  19860
gggtctgcga tcgcttggca atacaatcgc gcgctggatt cgtgaccgac ccgcattgca  19920
ttggctgttt gtgtcaaaga gccgggctta ccgtagatgg tgatcgttat gtacagtgac  19980
gttcccatcc acataacggt taaaattcct ccggaactgc tgtataagta ggcatccggc  20040
cccgtcacgg tacacgtagc aaatggtatg acgcacaggg attcgggcag aaaggagagc  20100
ggcgcggcat ggtattcggc gccgcactcg ccgacgcgta gaagataaga gcaaatgtcc  20160
gcgccgctgt cgacaatgat cagggtacct accggtcctc gctgtatgat aaagttcgac  20220
gatgggatat gatcgcatct ggtcatctta ccaacggcaa tcgagcgcgt accgcctgca  20280
catgagcaaa ccatctgctc ataaggaggc attgtccacg cgggctgagc agtgacgttc  20340
tcaagcgtat acgcgatgaa cgtggacccc atcatatcca cgtctcatgt gacggcccta  20400
tgcttcatgg ccctagttag tatacaatgt ggactttcgg atcccggagg gcggctaata  20460
agtgcgcgct gatattgtta tcatccctag tatgcgtttc ccgaagtggg ttaatgttca  20520
tcctcagaaa cttagaggag gtcactcgag acatggccac gtagacgctg ctgagtttga  20580
tgcccgattg ggcaaaacat atagcaaccc tctcaaggct aagcccttgc gatctggcga  20640
tagtcatcgc cagtttggag cttattccgt agtcggcggt tacggccatc cggagttcct  20700
gatcgtctac cgtttcgaca aaatcattga cgttggtgtt aattgctgcc atgaaaccgt  20760
gttgatcttt caaaaccagg gtcggcatgt gaagttcccc gagcgcttcc gcgacctggg  20820
gatgtatctt acgtctaata ggctcgtctg caaatgtgtt aattctagcg tatgtgtaac  20880
ccatgagagt gtagctgtcc gtctgcaaag cgagcgatag cattcctccg cgcatgctat  20940
ttataaatat ttcgcaccct ttaaagctca cgttgtcgac ataactatcg aatctggacg  21000
ctgcaaactt ttgcccgaat agctccgtca ggatagaata cctgcccata aacatgctct  21060
taagcatgct gaactgggta tatatctccg cagaagtttc tgcgcgtcca aattcgtaat  21120
tgcaataaag catgtctatc atctggtcgt cgaaatccat aaatagggca tcgtctgtat  21180
cctccacatg actgatttgg tcattagcta tacaatctaa ttccttctca ctgccatagc  21240
ggtgtcctgg aatcgcgaac gactccctct gctccgctct atccggaggt tgccgtcccg  21300
gatagagcag cgcagaggta agcatcgcca atctatcgta cgcgctttta acagaattgt  21360
ctggaagacc ctgccgttgc agatagttgt agaactgtat catgccgttg aaaagcagtt  21420
gagataagaa acggtacacg tattctacag acccatctcc gtgcgtcttt atgaaggaat  21480
cgtctttcaa tacggataga aatgtctcga acgtcccgca aaagccgaaa acccacttcc  21540
gaagtcgggt agtaacagcc acttggctgt ttaagacata ggcaatatct acacacgata  21600
ccgcgagccc ctgttggctg cgaatttcac atttggcctg tgtggcatct tggtcgcgac  21660
tttgcgacca gttgctcaag cgtcccgcat tggcagcaag ccatttttcc aacgtaacgt  21720
gcggttggtt ggcagcagta cgatatcgtt cgaaactatc caaactgacg aaggtataag  21780
ccggcagggt aaacactaca aatttcgtat ttccggacgt tttcaggtag tcgtgtaatc  21840
tgctcatgta cgcgctgact tctttatggg acgaatacag acgcgtccat cccggaaggt  21900
tcgcgggatt gttgatgtat gcttctggga cgacgaaact atctacgatc cgagcgtgct  21960
cctcggttat gggaagacca tactctaagg tcttgaggag gtccccgaac tcgggttcgg  22020
tgcaccgttt gttattaatg aatatcgccc agttcttgga cagttctaag tacgagcgca  22080
acgtctggtt gcatataata tacgtaagaa tattttcgct cgtacgcaca ttacacttca  22140
gcttgctatg ctcaaatgtg gactccaaag aattcgtttg cgtgggcgac ccgacgcata  22200
```

tcaataccgg cctccttctt ctacagtact gcggcgtgcg gtaaacggcg tttgtgagcc 22260
accaactgta tacgatagcc gtaagcaaat actttcccag aagtccagcc tcgtctatga 22320
cgattatgtt actgcgagtg aacgagggca tcgaaccatg tatgccgaag attgtccacg 22380
ccatactacc gcgaggcttg cttagcagat cctctaacgc gcgaatcatt tcaaaccgcc 22440
ctggcccgac ctcgttagac accgccttca aggcgcattt tgtaatgtcg gataaaacgt 22500
cccaataata cactatatcc tttttctgca attctttcat cgtcggtggg ctggtcggac 22560
atacgtactg atattttccc aaattcgctt gaatgtgatt acctttaaac ccgaattcct 22620
gaaatatcgt gtttatgtgc tgcgatgtgt atgaattgct aagcttgcaa taaatattct 22680
gcgctgcgac ctttgtcgtg ccggtgataa tacagtccaa gatttcggat agcatctgta 22740
tgcacgtgct ttttcctgag cccgcatttc cgcttattaa gtaaacggcg aaaggtagct 22800
cgcggagttc tagatccaac gggctttcta gttttgacgc gttcataaaa tacgatagcg 22860
gggggactat atcatcgctc accgatgcgt ccgccaggct ccttacacgc gcaatgatag 22920
tctgtatccc gtgcatcgca gtgaaattta gatacgttgc ctcactgaag aaatcgttct 22980
cccgcgacat cgtcggtctt ggggaagacg ggagtgacga atctacgtat cttttagggt 23040
cggggctggc gtgttgttta tttccgatgg agagctcaga cgttcgggcc gcacgcagtc 23100
ccgccctaaa acaaattcga cggccgcagt tgcaatctgt cacgcgccaa tggaaacttt 23160
caagcgacgg cgattcgcaa cagtccctgg aacaggactg gataataatt caccctactc 23220
gccaaacacg tatgttcaaa gaggtcctca ccgggcaatt gggatataca gatggacagg 23280
gcatatataa ctcggtacga tctacagaag ccgcgattcg gcagattcaa agtaccattc 23340
tcaccctttc tttagatgcg gtcagatatg acgacttgaa agaggattgg tcgaagcata 23400
tggataggcg tgggatgtcg gccaaggaaa tcgcaaaaaa gtatggcgtt catagtgaag 23460
ccgaagctgt tagaatggca aagggggtgt tttcaacttg gcgtaaaact cttcaaatga 23520
ccttaataga attggttcgg cacgcaacag attgcttcgc cgcggccgag aaaaccacgt 23580
cctgcttctc taaatacata gactggatct gctgtttagg tatcgttccg gtcgtcagaa 23640
gcgagcgctc tatgcaggcg tcgcggccgg atagcaactg cagagatcgc gctaccattc 23700
gcccgaattg ggtattcagc gatgccaccg ctaagctact agttgcggat agcgttatgg 23760
cccgcgcaca acaaatcgcg gattacttaa ctgcatccat gcaagcactg actgtgatag 23820
aatacgatag ggcccagata gaatataatt tcttaaaacg tgaacttcgc gttaaggacg 23880
tgttgagcgg cgaacgtggc gagtgtatcg ttatttggag accggtaatg aacgacggag 23940
gggtaatttt tgattcgccc atgcagagaa tctacaagga gatgattgaa tgtcacgatt 24000
tgcggatgca tgcggcgctg tgtcggctag taaacacggc ccctataaag gtcctcatcg 24060
ggaaacgcga tgaggatagt aaaagcatgg ccggggctca aagagcaatc gataaagttc 24120
tgggagacca aactgaaacg gcggcgagct ctgccgcctc taggttggtc aagcttataa 24180
ttggcctcaa aggtatgcgt catgtcggcg atatcacaga tagagtgcgg gattacttgg 24240
aggaaaccgg cggacattta ttggatgcct cgcccgtgga tacatctcag cctggcttcg 24300
ggcgcgctaa tcgaccacag agttctacga tatccgatgg aacttgctcc aataccgcta 24360
gactacgtga tgcgttccac gcgtccgtcg tgacgagtat aaacgaaatg ttagagggct 24420
atataaataa acttttccat accgtggaag ggttaaaggc ggccaataaa gacttatctg 24480
caaaattaag ctctaaagaa atagagctcg acagaatacg cacggaagcc ctgatctcag 24540

-continued

```
aacgggcgcg agctgacgcc tcgtgcgatc ctcactgcaa tccaaccatg gaaactttgg  24600
tgcgcgagct aaaacatgac gtaattgacg taaccaatgc aatggaggat gagtcctata  24660
tcgcgaatag cttccagtct caatacatac catcatacga tggcgatttg aaacggctct  24720
ctaacatttg ggaacaggaa atgttgaggt gctttaagat gactcgtatc accagtaatc  24780
aaggtcgaga ggtttcgatc tcctactcaa atagcgctat aactttatta ctcgcccccct  24840
atttcttctc cgtgttgcag atctatgata ttggtgcgat ggtcacgagc caagacgttt  24900
acaagtcgga ggaggagtta tgtaattccg tgcttgaaaa aacccgactt tgtacatatc  24960
tggatgattt ggctctcgtc tttgaggccg atgtgaaaag agctgtcgcg aagtattcgc  25020
tccgtgcggg taacgccgaa atagacttag cgcccgagga gttttcgtac ggctctcatg  25080
gaagcaaatg cgagacacgg ttttcatccg ctagacacga gcgacacgtt ggacgctcta  25140
gttttaagca cgctaaatgg agaagtcggc caaaacgaga ccgtagaaga actaatttgg  25200
caaccgacgg cgcggatgat gatggagatc cgagagattc aaggcggtcc tactcaattc  25260
acgggcgtct ccgtgagtaa acttcgcgtg gcaagatgtg atacgcgctt tcatctgact  25320
ttaaccggag ccgacttgga tgatgaaatg gcaagtgacg tataccacag tcagtgcata  25380
gttaattcgg cgttcaaagg tttcgtcttt atggttctca cggttacgga agatatagtg  25440
cggacgatag gggttccacc ccctctgcta aaatacaggc tcgtgttcta taacccatct  25500
gaacatttgg acttcgcatt atgtttgctc gtagcctatt tggagaatct ccatgcaagc  25560
gcctgcgacg taactttttt cgtacaggtt caatcttttc tgagatacgc atggacacgg  25620
gtgacgccaa tgaccaaaat gcgcagattt ttatgcgcca cgaacgtttg gttactaaac  25680
actttgatgt cgatggggtc ctgtagccca ttcgacggag atcgagtact cccccattat  25740
gcgatataca gacatttgtg ttctaccagt ggcgtctgcg acgtgttact aaccttgttt  25800
gaacccgata cacggcaggt acgtgaccgc acgcacggca agggacttgt catgctcaac  25860
agaggaatta tgaataaggc ttttcggcag acatggatta gtgatacggt ctacgattgg  25920
tggaccggcg aacgcgagaa gttgatcgga gaagaatctc tgttcaacac gtataatata  25980
tgaataaagt atgacaggca ctgctataaa tagaccgtgg tttcttagcg ttttcattta  26040
tttattgcgg acgaacagaa acctgtacgg ctctacgtcg aatgtgaatt tgctgagatc  26100
gacgttaggc catttcgatg ttagagcacc gatcagtaat ctcgaaaaaa tggacattat  26160
tggtttcata tgatcgatgc acgcgatggc agggagaatt acttgtcccc cttcgaaaag  26220
tgaacacgtg agaggtgcta tgctgccgtc cacagtcacg gtgtggacgg cgtcgttact  26280
gaaggcgctc gtatcgaatc tagctgccgc ccgtagtccc aaagccgtga tatagtgagt  26340
gtggtcgcgc gattctgcgg gacagctcca aaagcaggcg tctccgcggg cttcgaaagc  26400
cgcggtcacg agctcttcga acactgcacg cgatcgttct tggattgtcc gtagggactc  26460
gtcggaatcg ttgcatgcgg aaatttcttc taaaagggca gacaaggctt tcttaacttg  26520
gcccgcaaac gcaggtcggg ccggaaaccc cacgaaatct gtttcccgct tagtttcgtt  26580
ccacagccag taacaattgg cattccacga tactgcatga gtgtataccc cttccattcg  26640
aaactctaat ctgatatctt cgggaaaccg tagcccgact gacgtggcta atttgttagc  26700
gctcttaccg caagcgactc gtagtgtttc taaagcggtt tctgttcctt tagaggaatg  26760
cagaacgttg ttggccccgt ccgtgaatgt cccccacagt ccatctttga cgtaggtaca  26820
cggggcgaat ccgagagccg acgcggtagc ttctacctcg agactaatat gattcccgat  26880
acagataata gctctataaa catcttcacg cactcttttc aataggcctc cgaactctat  26940
```

```
gatgggctgc ttcaaccagt ttttctcgcg ctgcagtcga gcttttaccg cggcgcgcaa  27000
ccgggaatga tcgggaaaca gtcctagata tagagtcgca aaaaaggcgc taaaatcaaa  27060
ctttgcgata tacgcttgct ctatgaaagt cggttcccgg aaaatacaag ttatccgccc  27120
agccgtccag tcgtcggcta cctgacgccg cgtactgctt gtgcgccctt ttaaattttc  27180
gagtacgtct ataccagggg tcggatgggt ttccggatgc caaggagcaa gcaggtggaa  27240
ggttctcggt ccggccagtg gccacaggcc atcggtctcc gaatagctgc cgacggcctt  27300
tctgatggcc gaggggggccg ccgtagatgt tttcaagagc ggccaaaggg gaaatccgat  27360
agtgcaggca tagtcaacgt cctcgccgcg cggactggtt tcggggccaa tatatacaaa  27420
tataggggcc agcctttttt ccgagtcatc ggctagagag tatattttttt tgtgccactg  27480
cgcatagatg gccaataatg ccgtgagaga aaattcggcg ggtgtcgtaa ccaagcagtc  27540
aaaagacgtc ggaaccggag ccgcggtttt tatgggtgcc tgtgagtcgg gtaatgatag  27600
aacgcgttcg acgatagtga atattctatt cgtatttccc catttgattt tcttggacct  27660
gcgacccact gttttatatt cgcggatgaa ccggtcttcc tttgtgtaaa tttcgatacg  27720
ggagtcgaat tccgggatcg tgtcgtcgtg tttaagagcc gacaatttaa tgtgggctag  27780
gtgcgcgccc tcagtatact ccatagccgt ggatacgagg cgtgattctt ctacgtgcac  27840
ggcaccgtcc gtttttagta gccccggacg gggagcacat cgatcgcccg gcagaggttc  27900
gcacgatata actaatcccg ttgttgtgtc tacgtacata tcgacgggtg cgaagtatgc  27960
atgataaccg agcttaattc tcaattttgc cagcgtcacg gcgagcagcg ctttccatag  28020
agcgtgctgg tccggcctgc aagacggcca aactcccgtc acagatccgg cactggccat  28080
aatcgccagt gccgcgtcgg ttactgaatc cggattcaat ccccaagctc tcgcgataga  28140
ccgtcccgat acgtttaccg tagagtaatg tgcagaatac gtaccgcact catttctaaa  28200
aagcaagtaa cacagtgcgg taagaccatc ggtgcggtct ctactagtcc atactctata  28260
caaagtggta tagcaaatac acccccggat tttctgtacc gccacagtat tagcctcagc  28320
cattgttgac ataactaggt tcgctgcgta cgccttacaa actgtgaaaa tctatagcgc  28380
cctctacacg aggccagcac gccgggggaa cttctgccaa aaccgtctcc aggtccaaaa  28440
tgtcgtggta tatgcccaat tccgcgtcca agcgagattt cactagcgcg taccacttag  28500
ggcgtcgaat ctcgtagcgc gttttgcgga acgacgcttt gtttttcata aggagtgtgt  28560
aaagcgcgcg gtgcgttttg atcgacgttc tatctatccc cgccccatcc aacaaagctt  28620
ctatctccgc ctttcggaga ttcttaactt tggtgccacc cggaaacgtc gtcgcgctct  28680
ttacaaggcg taacccatac agtatttccc atgtgacttt aaaaacagaa aaggcgtggt  28740
tctcctccgt ctgccggccc aagggatacc tcgcgagacc acttaacgcg cttttcgttg  28800
ttttgactga tcgtttagag gcagtacggg catccagcag ataacatcgc gtgacttcca  28860
ataccgaacg aataaaagta tcgtactcat tttgcatcac acgcagcatc gataatggat  28920
ctaaattttt agctgttccc tctaaagggt taatacccaa cgaggtcgcc catctgcagc  28980
ataaccgata taagtgccac cttccagaca cgttgaaatc ggccgttatt gcgacggtac  29040
ccagccctcc atcgggcccg attattggta agctgcctga tgcgtaatac tgataaatac  29100
gacagaacac ctcttcacta taaagagcgg ccggcgttgc gcgacacgct tccaacatcg  29160
taatatttat aaattgttct ctagtaagcg gttctgccag tttagttaat aattgcgcaa  29220
gatcgctcgg cgatccgtca tgtcttagat atttatgaat aaacggctcc accatctcat  29280
```

-continued

```
tgtcgatcag atcagcctgg atttgaccgc aggcaatttt acggaggtgt ttcaaatctc  29340
gttgagcgat aagggcgtct gccgttaaat ccgctaagaa ggcgcagaag gtttcagcgt  29400
ccaattgaga gtcagatccg tcaaatctga cgcttattag attcgcgtca agtaaggcgt  29460
ggagaatatt gatgctgtcg ctaagattgt tgagggtgca ccgttcaaac aaatgcttgt  29520
acttaaatcg tgggaaaatg tataacgcgt cggcggactt gaaagtcgga acgcaatctc  29580
ttctgaaatt gttacacaac atattggtcg cgcatacgaa ttgcgccggc catcctcccc  29640
cactggcgat gacgtggttt agtagcatgg gtgtgaaaac tggctccgaa cgagctcccg  29700
atgcatctat gtaaaccaag acttcgttac ggcgtaacga tcggattcta cctaaagatt  29760
gatagaccga aaccatatcg ggcccgtttc gcgtcggctt aatatacgcg aacatgctgt  29820
ggaagtggga gctgataaaa cttaggccta ctgttactac ggtagtgtag atgacaactc  29880
ggtaacgagt ccatgaattt atatcaattg gtatatcacg ggtggaattt aagaccagga  29940
cagaatcggt aaatatgagg cagaagcgtg ccgccgcttc cgagaatgaa attgtcgagg  30000
aaaataagca aatgttcaac ccgcccgcga gtcttctgct gagttcagaa aaaaacgtcg  30060
tctcagtcac gcttctatgc cgagagtggg taccgtcagc cccgtgttta ggtgtgggtc  30120
gtacatgaaa acaatctgat tggtcgctat tcatgacgga gagaagtgta tctgttccca  30180
gattgcggag gatggtacat gatctcttag aaaacccagg ggctgcgtat tcgcccacga  30240
tgacatgtat gttatcttct cctctcatgc ttgccaacat atctaccagt tgtgtattta  30300
ttgtagcgtc cattgctatg atcctcgggc aattacgtaa cagagtcgtt agtatcgaat  30360
cgactctgga cagatgcctc atggttggag agtaaagttg actaatggtc gacatgactt  30420
cgtccagtat gatgatttca taccgtccga gcaagtcagg gtctatgcga tgcaaagatt  30480
cgatttggat caacagtctg taaaactctc tgcctcgtat gctgtagtca ctagccgtca  30540
aatagttgcc gaaccccgac agcccggcat tgctcagttt gtcgaataat gtgttcgtaa  30600
aacttcgcct acaggacaca accaaaacgc tcgtgtccgg attatataaa atacgctgca  30660
accagtctat gagagcagtt gtcttgccgg atcccatagg cgcgcgcact acaagtacat  30720
tgcgcgctct cgaggacagt ggcggcggaa aagtaacggg cccgtcggat tggcgctcgg  30780
tcgttactcc gggtctgttc ttagctatcc aatctatgag accttctccg tataatatcc  30840
tcgacaaaga ggcgctacag acatagtcta tcattttctg tgcggtcgat gctctaacgt  30900
cgccgagacc ggtgctccgg gtgaggatta cgttctgacg accagagaac cgtctacgat  30960
cgtcgctatg tcaaaaggac cgcgatcgga aggagcccgg agaggagcag atcatataga  31020
ctacattcac aaaaagatgt gggttgtcca ggcggcgtgt ttttctgtcg ccgtcttggt  31080
tttcctagga accctgatag ctgcatctat aaacatgacc gaaggtttcc catgcttttt  31140
tgcggccgtc gtggactacg ggatgacgaa cgtgacgctt gtgcatacgg gcatgaccaa  31200
tccgaggctg ggaggcgtag ttcctgtgct gtttttccaa accaaagccg tggcgtttct  31260
cttctattcg gcgagcgtcg tttttgtatg catcacgtgt tatatcgccg taggcgccat  31320
cataactagc aagaaacgag tgggtgctgc gtataccgga aggggcgcgt tcgtcctttc  31380
acttatggca tcgccctcga caattttgtt gggtactgtg tcgatttggc ttcttcaagc  31440
ggtagttata gtcctagccc acaaacttat tgtactagcc gcggcggttt atttagtgca  31500
cttctcgact ataacgtttt tttatgggta tttctgtgga aggggcgttg acagtaaagt  31560
atatgcggaa gacatcgctg ctgcgaaaaa cgtagacgcc ggtctgcaca gattaattgg  31620
aaacgggcgg gcggtcatga tcaacttggt ttcgatcgta tacagtatgc ttctgataat  31680
```

ggcgtctcta atgttaggca tgttactagc aaacagcttt accttaaagt tttggcatgt 31740
catcgttacc gtcctcataa cttcctcagt cttaacccta atgtatcttt tagtactcga 31800
gttcctagtg gcgcggtacg tgcacatgat tttgggtgcg tacataggcc ttctgatcgc 31860
ctatgggatg ctctggacca cctcatgtga ttatgtcaac cggttctact tcgcgatggg 31920
cgtaggagcc ggcaacttac gcactgcctg tcacagcgtg ctggcgtttt tcaccgtact 31980
gattgtagcg ggcatgattg ttcgcctaat ccgggccggg ttgtatcacc gtaggcgatc 32040
tactcgtgca tacgccaaag ccaggcagtt acaaagaaat gtaaaggaga gattgagacg 32100
aatgagtcgg ggacgcgatc gtcccgatag ccgagctgag gacgagcggg cgcttacgca 32160
aacccaatat agcgaaacat cagacgacga gactatatat gatcgcgttt attcggggtc 32220
tgatagtgaa tgggatgaat aggaacgccc gaaacataat aaaacgctaa atctacaagt 32280
gattgtcgcg cgacttattt atcactataa cgtatcgtta cattgttccc gaccgtcctt 32340
aaatctgaaa agcgtctttc ctctcgcgca agtacttcca gctaagacag tatcggaatg 32400
gataagaggg tcggaggacc taagaccgtc caaatcgacg gtatcgtatt gctcgtcgtc 32460
gagctcaatt acatgtcccg ttttggtcag aacggtgttt cgtttccgac agcgtcggaa 32520
cagttccgtt acggatattg cttggcccat acttgctgca cgagttcacc gaacgcacgg 32580
tatccggcct cttctacttc accgtagaat gtaacgtcca cgaccacggg agtgatgagg 32640
aggagaacgg gaatcgcttg ttcggggtct attttgacgc ttggagtggg ttctccagtg 32700
tttccttcgg agatcgtcag gcgtctacct aattcgccag gtcgtctgcg gcggcctata 32760
aacgtggcga ggtgtgggat gaccgggttg ctttcaaagt aattagaagc tacgtagttc 32820
tgaacgaaaa tctgcttgaa atttggatgt cgtgggttgg caaatatggg cacaaggaca 32880
gattgttctc cggtactcca gcatagcggg tgtatcgcgt tcgtttgcag atcaggttcg 32940
ccaaacagcc atacgcgaga actgcagttc ttattggagg ccaagtgacg cgaatcaaag 33000
tcgttccgtt taatgtttga tgaaatggcg cggaagcgtg atagccccac tttccagtcg 33060
tcgtcacatg tgattagcgc ctcctttgcc ttaggaaaat cgtcaggttt aaaatagtcc 33120
acgcaaggat gattgatggc gtataagaat cttcggagcg ctgcgacggt tcttgtttgt 33180
aataggcgtt cgtaacattg agatagctcg cttcgacatt ccgggtaaaa cgcgtatttg 33240
gccctacact ttatttcgta cgtttctatg gagtggtcgg ggagggcagg cgtaaggatt 33300
ccgcgtgcgc tgcgagggca taccgccata tcgagggatg ctccgagcat cccggttctg 33360
gcgtctatca tcagaccgca cgcgtatttg tcagaggcgg atgagacggt gattgtctcg 33420
tccggtacgc gtgcattttc gagcacccga gaaggttcgc gaggcctgta cctggggttc 33480
tccagacaat aggtctctat gagcgctctc gcgagcggct cgttacgcgt tccgaagact 33540
acgctttcgg gcattccttg cgccgtgatt tcggcaggtc ttatgccaac ggtgtttatc 33600
cgtccatcgg cggtccactt caatgtcgat gcggtcaaca gccattgtct aagtacgtgc 33660
catagctcgc agtccgcttg cggtctggtg agagtttcta caattttaca ccagaaaagc 33720
gcatgattag acggcgacgt tgcatttgcg cccgattcat acaggagctt gtcttccgcc 33780
tctaggagag aagaatatga agatgccggc caacgtccct ctgaaatgcc tcgtttgata 33840
acgtccgtta tgtacaataa gcggtgatac agcgggtgtg gcgagggccc cgattgcttc 33900
gggtcgacat tccgtaatat atagtcgctg aaggtataat cgaccacaac actgtagcat 33960
acggtatcgt aaggtttgga ctgcactgct tctgcgtgct cggcgcaagc gaagaccttt 34020

-continued

```
ggacacgatt taaattcgga ctccttttta cgtttccgtg gcccgttctc gccgagacgg  34080
aacattgcgg tggagtctat ttccataaca gccgtgtagc ggccctcgct tctgagttcg  34140
agtgacagta aagtgcaacg agctcgaaaa gattgcttaa atatggcggg actctcaatg  34200
aatcaaatag cttcctgtgc gtcacttcat atccttctaa atatttctca aacgcgaccc  34260
tgtggtgaga gccgtgtagc tgcgaacgaa tcttttcggc tcgttcccac gggataccga  34320
ttttggcagt taacggggta gctggaaata agtactggta cagcatacac cgatacgcta  34380
acatgtctaa aagatagtcg gccggcatca ttttatggta ataaaaatgc accgggtttc  34440
cggggatggc aaagtcccgc gtaaaattca tcccggcggc tagaagcact tccatcagtg  34500
attggcccag tgcgtacata tctatagcga caccttcatc actggacagt tgacttgaac  34560
cccgctccaa gcccgtcccg tttaaggctt taaccagcaa ttcgcagggc tgcgtttgcc  34620
catgccccag cactaaatca aatacaggtc taatgtttgc tctagacact tttactgaat  34680
atactcgatc ggagtctaca gttatgtcga atcgggcttt cgtaatggtg gagtttgtgt  34740
taagtaacgc caagctaaaa tcgccgatta cggcctccac tataataggg ttagaccctt  34800
ccctgacgtt gacgaaaatg ttcccgcact taatatccaa atgagtcagt ccgcaggaca  34860
cgttcaagta cacaacggct ctgccgaggc ccatgaacgc tttttctatg gccctccaat  34920
ggcgtgcagt tttatccatc ttcctcagtc gatggcagta cgagtccatg tccatgtcat  34980
acgctggaaa taccagttcc ctggatggta tcgaaaaggc cagtaatgaa atcacgctat  35040
tgagcgctag agttgacctt gcccgacaag cgcattcgcc ggctatcagt gtcataagca  35100
attcggtctt gaaacactcg aacacctttt tgacggctac atttgcaccc ttaaatactt  35160
taacttctcc atagctcccg cttcccgcat atattggcgt ttcttgcagg tcgatggtgc  35220
tgtaatgtaa gcccggggag atatcgaaaa tgagcgatgt tatattcttt atgcgagata  35280
gagtgaaaat atgatccggc aaagatggtc ttgatagcaa aatgtcagat gttttcctag  35340
atatatgttt gcgtctccta tagaattgtt ttaggcatct cctaatgttg acggagatgt  35400
gttgtttgtg gtcctttttt ctacacgaat ctcttcgggg ggcactgaat gttccctgca  35460
gatcgtctgt tgtgcttgag tatcccttag gcccgctgaa gtcttcttgg tcgctgatgt  35520
cggaaagcca tttaacgtga ggacactcgt cgttttcgcg gccgcgcccc ggctttctgg  35580
ctttgaggtc aagatccatt ttgacagcag cgcctcgcac tctgcgtcca attctatgtc  35640
tggaaggcga tcgctgatgt cgtcgctgat ttgcgttaag atgtcttcgt ttgctagaat  35700
gtcctcttcg gcacgatcca actgtgactg gagcctaggg tttaaaaacc ttcggttcgc  35760
atctaagacg atgcggcggt ccacctgttc gtctatgtgg cgttggataa ttctcgactt  35820
tctatgagct tcttcgatcc gcatgttcga gtgcaactgg gttttgtagt cactgtgggc  35880
gtttctggct gacgttaacg cttcgatgag ttctgggtcg tccgcttcta caccttggga  35940
caaaagtgtc aaggtgcgtt ccttataaat tttctcccgc gttcgacact cggccaatat  36000
ttgacgcctg cgtctgcgta ttgtgttaac ggcgaacatc gctcgacgag attcgtagtc  36060
tggcgattac cgactccgta aagatgttcg gaggcgcgct cggagaatcg gcgaagaagc  36120
actttgaacg cctgctgaga gataggaacg agcgtttagg tgcgagccgt aaaaatgaat  36180
gcctcgcgcg cggcgggagt ttagtcgacg ccccctttct aaattttgcg atttcggtcc  36240
caaggcgaca tcagacagtg atgcccgctg tcggtacatt gcatgactgc tgcgacggta  36300
ctggtattta ctccgcgatc gctacacgcc tgctgtatgc tggtatcgta agcagcgaat  36360
ttggtgaagt gcgacgcgag tcgttatcta acggtcacat atcgaaaagg aatcgggagg  36420
```

cgttgcttgc gccgactctg acacgcgtcg ccaattccat aacatttcac gagtacgacg 36480
atgcacaatg cgcggcgcat cgcaacgcgt attacagtac gatgaacact ttcgggtcta 36540
tgaggacatc tgacgcgttt caacagctgg cgtcctttat cgatcgattt tcaaaattat 36600
tagctgcctc gtttaaagac gtgaatattt tggacagaaa taacgctccc aaacgagcac 36660
gaataaccgc tccctcgtac gataagcctc atggcacgct ggagctgttt cagaaaatga 36720
tactgatgca cgccacttat ttcttaacgt ccgttttact tgaagaccac gcggaacgtg 36780
ctgaacgttt gctccgtgtc atatttgata tcccagactt ttcggacgcg gccactagac 36840
atttccgaca aagggcgact gtttttctag ttcctaggag acatgggaaa acttggtttt 36900
tggtgccctt gatagcactg gccatgtcgt cttttgaagg tatccgtatt ggatacacgt 36960
cacatattcg gaaagcgata gaacccgttt ttgaagaaat tggggatcgt ctcagacgct 37020
ggtttggtac tcagtgtgtg gatcacgtta aaggagaaac cataacgttt tcgtttccta 37080
gcggatcgag aagtacggta acgtttgcct ccagccataa tacaaacgtg agtattgcat 37140
tcaaaaccgt tgtgtcggat ggtccccccc ctatacacac acccgtgata gtctaataca 37200
cccttgaacc agtatcgaac tccacatctc cggcaggtag accaaatgcc atccgcatga 37260
atttacggga atcttcctac tgtctacctc ggcttcgatt aactcttcga gccgttctgt 37320
aatgcacgcc ttcgtgccgc tattaccgac cactcggacg gcatttaccg tgtccatgaa 37380
taaaacgcaa cagaggcttt tttccccttt gacttgtata tctgtctgtc gggctttcat 37440
ccacatacac ggacctctgc aaacacaagc ctgcccgagc gatccgcact cccatctcac 37500
gttacaaaca tccacgtgaa ggtcgaaatg cccacggcat tccgcacagc cgctccggtg 37560
gttaagaaat tttgctagag tagcgcccag agaacgttgc tgccaaccgg cgggacatat 37620
agatagcaaa ctctcttcca tcctgaggta ataaaacctg cgtttggaaa gggaccacca 37680
agctccaata gatatcgcta tacagttgtg tggatcgtct ggcggctgcg tgcgttggac 37740
tagggaattt atgtccggtg cgatacaaga gatagttgac aaaggttcta tggcgacgtc 37800
cggaagaccg atacaggtcc tactaggagc gacgtcagaa aagaaaataa gatctgcgga 37860
agatccgtcg cgcagaatgg gggttatgcg taaagcggca gtcacggaat aggcgcgcgt 37920
cccgttgact aagaacaaga gttgaaaagt gtttctgtcc aagtacatct cctttggtcg 37980
cgtaaggtac atgaatatct ccacccattt cgtcttttgc ggccgagcgc ccagcggtac 38040
gtacgtacat aacgtaaagt ctaacgtggt taatgcgacc aacacagcta gacgcgattc 38100
ggcccgaagc gtgcgccata cgcaaatgcg gtcatttaac ttattaacga actcaactgc 38160
cgccgtatcg caagtccgtt ctgaacgacg cggcgatccg ggcgtccttc gtcttcgcgt 38220
agtcatcgtc ccacatctgt atgacgctac cgctaattga atattcgagt cttggcaggg 38280
cgctcatgga aaagataatg tagtgttgct gctgcagagg cgcgataaaa ccgcgtccgc 38340
ccgcgccaga ggccaattga actcggcgcc ggcatgcgct gctaacatga accccgcggg 38400
caacacgatt gcaacgcgca tacgttcatc ataacctacg caaatatacg cataactttc 38460
tccaggaaga aatctttcac acgttgcgcg cgatacgaac cattcgggga atgcgcaggt 38520
tctaatagat tcgtcgcccg gcccgccggg cgacaaatgc gctgcgtcac gcaaaataac 38580
tgggataggc ctcttattta acatcataca ttctccgccc gcgctataat aatcaaatag 38640
gaaaagattc ggcgtcctag tagcgacggg ttggtagtcg cctcccagga cttcggcatt 38700
gtttccagtc gtatgtatgt aatatgtttt tcctccagtg cgcttaacat gcctggccag 38760

-continued

```
aaacgagatg ctcgcggacc taagagcgcc tactgaaaac ttctcaggcg aagaactcgc  38820
gattgcctgt agaactgcgc gtactgaatg gggtgtgcgg cttgcgattt ctgccacgca  38880
ctgaacgtct cgcgcataca cgtcgtagct gatcagctga tatagattgg gccctgtttt  38940
caacgcttcc ccaactgccc ttatgacaca cgcagagaca tacgacttga aattaatcat  39000
taattcggtt tcggagcccg gagaaaacgc acgcagttgg ttttcctctg cttttaataa  39060
gggagcagcc aaaataggag cttccgttgc gatttcggtc tttcttcttt gtggtagacg  39120
agaggggtga tcgacgcctt cttccataca agcggtagcg agtaaattgc tcaacgaaga  39180
tggaattgtg gcagaatcgg aggaacggcc ccctaaggca atcgaccgct catacgatat  39240
aagataaagt gtttttttgg tcatggagtg ggtacgtgga acgatggata tgcccccgca  39300
cctccaccgg ttcgcaattg tgagcccgtc cgccaaaatg ccgaccgcag aagataggag  39360
gtctttgggg cttaacgaat tttgcgatgg ttcatcgaac atgagaatgt cttccaaatt  39420
caatgcagtc cctgtagatt gctggtcctt attacggccc tccaagcccc tccgagtgtc  39480
gtggtttctg gcaaaccttc ctttgcccac gggctcgaga ccatctatga cggctttctg  39540
tgacacgctg ctactgggtg tgcacaaatt attttccaaa caagctatcg ccccttggcg  39600
caatccggac actacgctgg cgtgtatatt ctccgccggc cgttttgcgc ttaccggcgc  39660
tcgcctggtg atagcctcgg ctgccttctt aatgagattt gcgatctcta tattgtctgt  39720
ctctagtcgc gtgtcgagag taggagtgtc gaagacgttc ggagaatctg ttacttgccg  39780
cataatgtca aactgaccgg gcagttcgac ggcggataaa cacgcctcta atttagcccc  39840
caattctata acagccgacg gtaattcgac ctcgtatctc ttagtatatc gtatgaattg  39900
acggaagagc gtctttaagc ggttcgcatc gatatcgtat cgagtacctg gaggaactaa  39960
ttcctcttga ctaaacagta aatccatgta cgcttcgtac tctccggttt ccctatcctg  40020
tacgttaaag cgaatagcca cggatgtaaa cggatcaaag cggttcttag aatcatattg  40080
tatgggaaga ctcatgaaca atccaccttg atcgtttcga ttgagcgtcg cgaaaagttt  40140
ggcgtggccc gggacatgag gtatcaagag tatgtgtagt gcgccagagg gaacgtaggc  40200
tgccggtgat tcgcgccaac cggaacattt accggtggca ttatagcgca tctgaacact  40260
taccggaatc ggcagcgatt ggtaagcact gctgggtact ctctgtgccg catccttaaa  40320
acgggcgata tctatccccg ctgccgacaa acactcatcc ggtaagagga catgcgtcag  40380
tacgtgccga ttggggccgt gtttgggagt agatagcgaa tacgcggtct cgctctctat  40440
atgcgcctcc atcctgcacc ggaatggcga gtcgggtcct gcggtctaga tagcgtcgcg  40500
tcgccgttaa tgcgaggggc tatgccttta cggaccctct cgactcagca ttgcttgttt  40560
ttgtttctgc agagcattcg cggccaagat ttcaacttgc tctttgtcga cgaggcgaat  40620
ttcatacgtc cggatgccgt gcagacaata atagggtttc tgaatcaagc gaattgcaaa  40680
ataattttcg tgtcgtctac gaacagcggt aaggcgagca cgagtttctt atacggtctg  40740
aagggatcgg ccgacgatct cctaaacgtg gtgacgtata tatgcgacga acacatgaaa  40800
catgtgacga attatactaa cgctacgtca tgttcgtgct atgttctgaa caagcccgtg  40860
ttcattacga tggatggggc catgcgtcgc acggctgaaa tgtttctccc cgactctttt  40920
atgaaggaaa taatagggggg tatcaccatg gatagaaaca cgtgccaggg agaccggggg  40980
gtttttactg cttctgctgt tgagcggctt cttctatata ggccgtcgac tgtacggaat  41040
caggatatcc tctcgcgaga cttatacgtg tatgtcgatc cggcgtttac tgccaacacc  41100
agagcctccg gaacggggat agccgtaatc ggtaggtatg gagcagatta catcattttc  41160
```

```
ggccttgagc actttttctt gcgggccctg acgggagagt ccgcggatgc cataggagag  41220
tgtgccgcgc agtgtatcgc gcaaatctgc gcgatacact gcgagcgttt cggaacgata  41280
agagtggccg tggaagggaa tagcaaccaa gattcagcgg tagcaatagc tactagaatt  41340
tcgatcgacc tggcctcgta cgtgcagtcc ggagtggcac cggcgccaca cgacgtttgt  41400
ttttaccaca gcaagcctgc cggcagcaac gtcgaatatc ccttttttcct cttacagcgc  41460
cagaaaactg cggcgtttga tttttttatc gcccgcttca actcgggtcg agtactagct  41520
tctcaagatt tggtttctac cacgattagc ctgtccaccg atccggtcga gtatttgacc  41580
aaacaattga cgaacctctc ggaggtggtc accggcgcga caggcacaag aacgttctct  41640
ggcaaaaaag ggggctacga cgataccgtt gtggccttgg taatggcggt atatatatct  41700
gcccacgcgt cggacgcgac gttcgctcct ataagaggag tcgaggccac gtgtcgcggc  41760
ccaacagaag cgtgaccggc cccgaagcgt gaaatatatc tgccgcgtcg caggaaaagc  41820
taaccaataa gcagactcgc ataagcacaa accgtttatt agaaggctac ccgatgaata  41880
aagttatttt aattccagtt agaaataacg ggacataggt ctccgacttt tatactcgcg  41940
ggcccgtcga acgtgcacac tttcaatagc gggcgcagcg ctagcatgtc ccctagatgc  42000
agagccatgg taatccacga agacagggct tcgtaaatgg gatatctgcg ccacgcgtct  42060
tgcaaaggcg ggggtctcgg aattctgatg agctgaccta ctgctctcgt ggccgtctgg  42120
agacccacca gggcgttgac gtaaccgtca gacgctccca aagtaagcaa cgtcggtatc  42180
agagcatata ggagcatgtt accttcgtcg atagcgaaaa tcatgtttag caataaggtt  42240
ctcactgcag actccgacgc atccagacta tggagcgtcg gactaatggt ataggttttc  42300
ccgttatatg taatggattc cgcttcacgg ctcgtagggg gaggcgctag ccctccgccg  42360
atcgctatcc cttccgtggc tcgagatagc gtcttagcaa taatttcacg tgcgagtctc  42420
gccggaacgg ttgatggaaa taaaagttcg gtatcgatcg attccaaccg gatacgggag  42480
caaacgttag ggaaaagcgg aggtatcagg catacagcat ccccgttaca taggtcgaac  42540
gggccggtgt tttgaagtgc caggcctgaa ggaatggtcc ccattcccaa aactacagca  42600
ctcattcgac cgggtagcgc gcgggtgacg acggccgcaa atcgtcgttt gtaggtcgat  42660
agcagactca gcgtatcagg ttcggcccca gcgatgtagt atgacttata atctacttct  42720
ttgagcagca ctctggctct gacggacggt aaaaaaagaa ctcgcccctc acatcgttga  42780
agtaggttcg cgtcgcacgt agaaagcccg caggggagct cgatctctac tgtcgtacca  42840
ttagaagcgg ccataacggt accgctggcg gtttattttc ggtaccgacg gcggcagcgg  42900
ataagtgtat aggaaccagg ccgagccgct gtcaggtcaa gcacgtagac cgcggaaggt  42960
tagcgatcgg cgagctggca gttcagcatg caggcaagca tccaccgatc ggcgaagcgt  43020
ctttgattaa gtattgagcc aagtgcgttt ctgggttatc cgcacccccct gcgaaatacg  43080
tgcggagcaa agctttgtcg gtagcgcaaa gtagcggata ggcttcctga aatagggaac  43140
aaggatcttc gattaattcc gtagatccga ctggtcgttt gaactgtact tctccgtccg  43200
acgcgaatgc tgccacggca gaaccggctt cgctgattag tttatccaag caccggcttt  43260
tgcagcacac ttctgccggg gtaaaaaatt tataggtggg actgaagagg ggagacgccc  43320
cgctcaaatt gtaagttccg ttatagagct tgtccgcgta agagaatttt tgcgaagccc  43380
acggattgtt ggttgcgcgg aacggataag cgggatcccc ctgccggtga tcgtacatga  43440
gtttctcgat atcggatact tcctcgtccg aatgtatcgc cccggccgcc ctccctctcg  43500
```

-continued

```
ggttacacgg ggttcgaaag tactccaggt ctgcggaaac gggtgtaggg atgaactcgc  43560
atatggacat ttggccatgt tccagcccgt cggggagcat gggcatcagt gtacctagaa  43620
aggggacagt tctttgcgga gctgttctct gtccgcgcgt tgctgctttc cgtagaaagt  43680
catcggcttc ggggtttata aggggggcg agccccgtgt caaatgcagg ctttggacag  43740
tgttccccat atccgtcgta gcgtttcgta agagtaaagg ggtacaagtg gccgtatacc  43800
ccacgcccaa atcaacgtta gctcgtggtt gtgtcagaga aaactgcacc ccccctgcgt  43860
gcgggcgctt cgagacagac acctgtccga gaaaaaacga ttcggacgcc cgttcggcaa  43920
acaggcccat atctgctagg aacctatctt gtcgtacgac ggtaaatgca attcccggat  43980
ggaaccccgt tctcaactga tgatacaggc ctataggagt gagtttgaaa tatcctgcca  44040
tcagcgcgta cgacatttcg ttgggcccgc atctactttc gcatatgtac tgtgccacgg  44100
gctggcggaa cgtagaataa taattggcgc ccaaaaactg tggaacggga ggagctctgc  44160
cgagcagcgt acgcgcgttc ccggccaact ccccgactgc cgttagatgg tcctgacagg  44220
cgaacaaagc gttaactgga acgggataga agtacgtgcc ggcagcgatc gtctcatcat  44280
tgcatgggta ggccatcatt aaaagcccat ggtgtaacgc gccatcgaac gttcgcatat  44340
gccttgtcgc cgatgacgtg ccgcctacat ccggggtggt tccgtagaga atcgccgttg  44400
tccgctccgc catattgttc accgtttcct gcagagttag aagcgcgtcc gcatccacca  44460
atattctggc gttgtgtagc agcacgttaa acgtgttggg gacaagattt ctagcgttca  44520
acgggtgcct cgggtcttct gcgcccaggg gaggctcctc gtcgggttgg atgtcgggaa  44580
tgatcacaga ttgagacgta gcgtagatgt tgtcgaaacg gatgcccatg gtgcaacact  44640
gacccctgga aaatgccggg accatcacgt aataataaat tttcgatagg attgaccatt  44700
catgggtatg atgaggcgcg aacgtttgtc gatcggcgtc tcctacaggc ctgttatgga  44760
ctaaaacgtt gccggtgcgt tcaaaatccg catcctgcaa ttccagccac ggccgcacag  44820
cgtaattttc gtcgcttccc acgttcaaat acaagtttct atcgcgcacg ccgtgcgctt  44880
gatacatcag gggtcacag tcccacagta gggggggtag gatcgctcta tcgattaagg  44940
cgtggtttaa ttcctcatta ctctgcccgg tcagtgagtc tgtctgaacg gtataatcct  45000
ttacaatcga ccgcagcgcg cgaacgtgcc gcatcagctc tttgtagata ttcgtacagt  45060
cctcagggag ttcaccgctg cataaatagg tatcgatgaa tgcgaccatg tgaaagttat  45120
tgacgaatgc tactcgtttg cagttgtccc agtaactccg tatacattga atgatcagtc  45180
gcatcagtat accgaaatta cgttcgctgc cgtgaattac ggcttcgatt acataaaacg  45240
cagtggggta gctaacgtct gagaacgttg cacatacggc attgattgtg gaagcgctca  45300
ttttgtggcg actggatgcg agctcttggc cgagcgcatc tctaaagtcg ctactgcaga  45360
gaggtagcgg aatattacag ttgcaaaccc gccaggaggc ggcgatcgac gccatcactt  45420
gcggaacgtt atgcggcccc gggagctcta catctcccgg gaccacaaaa aagtcaaacg  45480
cgggatgcaa ctccatagat agatgtggat ttccggccga taggaattgc tcttgactca  45540
tatggcattc atctacccac cggggcgacc cgcagagcac gtctccgatg ttctcgaaaa  45600
accgacggct agcttcccgt agaggcaagg ccggcgggtt cgtcacatac gccccgaaaa  45660
cacacgttaa atcgcgtctg tcgcgacgta aatgactaac cgtcgcttcg atatccaaaa  45720
aggatgagtg gcacacggtt ccaatagcat ccgataaaca tacgctaatt atctggttgt  45780
ctttgttatg gaaatatagc tcccgtggcg ggaacccgcg cacatctcct tgacatccag  45840
gcccgggcgc atagtcccca atatgccgcg cataacggtc cgcccgtttc tgatatagtc  45900
```

-continued

```
ccaaaggcat cacgaacgtt aaatctatgt gtccgattaa agggtactgg acttgcgttg  45960
cttgataaac gcgccgttcc atggcttcta gaaaaattaa cttatcccca atggtcacca  46020
attccgcagg cacttctgcc gtttgggga catcgtcgtc tccccgtacg acttcatctg  46080
tacgatcgat gatgtcgttt tcgtcgagat tgagaatata gcgtgcgatg tcgtccatgt  46140
tgcgtatggc tttgcccatc actacggcgg ttactaggtt tgttcccgat attatcattt  46200
ctccatatgt aacgggcacc ctagcagacg tatccgccat gtctagaatt cctgatagca  46260
gtttttgcct caccatgctc gttgttacta gtacgccatc tacgaggcgc cctttcgaat  46320
cggaatgggt cagcctcggc attgcaattg tctgatgagt agagttaacc atcttggcga  46380
ggaatgagac tatactgtct ttgctcgcac cggctttgct catgatgaag gtatcgttac  46440
acactctgcg tttgagctct gataccaaat tcgctcgcat tacctgcccg tttacccttc  46500
cttctgtcgt gctgcgcgaa aggggtatca gtagcggagt cggcggagcc ttttccatca  46560
gtattctaag catctgatcg accgtgcccc gctcaaacga atccaatatc gttctcacgt  46620
ttcgagctaa ttgctgtatg gctctcagtc tcaggtggtt agatattgcc gttccatcta  46680
aagatacttc agataataat gcgagtgctt ccgccgcaac gacaaaggcc gcgcttaacg  46740
atcgcttgca tacgcgcttt accatgtaag tgtaaagcgg ttgatcggca ggatggggcc  46800
cctcgcgcgc aatcatgggt tgctgtattt caaattgcac ggttccttcg cgcatgtata  46860
gcagatcggg agcacgcgtg cagacgcatg cgactgagag ccccgtttcg agaaatctga  46920
tcaaagacaa tgtattgcag taggttccga gaagaatatc gaactgggcc gaatagcgtc  46980
cgttgtcatc ggaactgaat tgtttgaaat agtcgaacat gcatcgatgg gatgtcattt  47040
ctatagcagt caggagtcta cctgtaggcg ctaacgttgc tcctacgttg aatggtgtcg  47100
aaattgcaca cggtgcgatt ggcggacagt cggtcgccgg aggacagcgg catccggcca  47160
tggtcgtcaa cgggccgcgt ccgatgtaag gactaattgc caccgtgact atccgatgct  47220
atgcgtgatc cagggcatct agtaacgttt ggtcgcgtcg aaggtcacgt taccggctgt  47280
tcgaatgcga cgcaaatgat agccgatatt gtaggagaga cgtgacgtgg agaatgcgcg  47340
agttctagca acacgaacga aattgcatat tagactttaa cgatgcaggt tttatctac  47400
acaatgaagt cgcgagtgcg cgtgccctta tatgtgcaag tttccgcccc taatcagaac  47460
ggaacgcacg tctttatcag tgctcgtgtc cacaaacgag ggaggagaaa tcccagtgcg  47520
tccgacacag ctactgtagc gtaggtgatg gtagctccca ttaacaggta taccacagct  47580
ccgtctgtct tatcgttttc ctctaattgt aaaactttct ccatgaatct cggatcttga  47640
aacaccatgc ggtaagaaaa tactccgaat atcaccgccc ccaacgtaga cagaatacca  47700
acgaagattt gctggcagtt atccataggc atgacatcat tctttatgtt tctgtacatg  47760
taataagttt cgaggagtaa ggtaccatag aacactgcgg taatggtcgc gcccaggatc  47820
agaaaacgat tgtcgtgccc gtccatcgcg tacaccagaa atataataca acacgagggt  47880
cggagaacaa atgcagatag ccaagagagc acaacatacc gagtaaattt ggggttcatg  47940
tcacagcttt tcgaaatagt gaaaattgaa cctgataagt aagaggacat cgtggcatac  48000
tcggccgcat cttcgcaatc gatatcgtcc gaaacgcgtg taactattga ctccgtgtct  48060
tgcatattcg tctctaactg ttcatcgcca atatagtcga ggagaatatc gcaatcggtc  48120
ggttttgttg tatggtatcc acgcctgtac caaggcatag tgccactcga gaaggaccgt  48180
ttctggccac acgtaacgac tttgtcttct actaaagacc acccggactc ggtacagacc  48240
```

-continued

```
caagctagag ctcgagaccg cggaaaatgg atatcaaata cgaacagaag atcttgtata  48300
gaaacgtcca cttttatatc tcggaatgcg gccgcatagc ttatttcttc tgcggtggtt  48360
gtctcatggc ggtcgggcga ccgcctaccg atgactcgca ggcagagttt gcaaaatttg  48420
ggctggctct tcgaggcgat ggagagtcta aacccttggc agcttatgta cggcgggaat  48480
tgcttcgtag aggaatgaaa tgggcgctgc ctcccggcga cgatgaatta ttcatcgact  48540
gtatggcctt tttgaatcta gacggggcgt gcagtgaacg tgagatttgc gatcttgttt  48600
gcctggaaac gtatgatccg gagatcacaa aacacatggt atccacgaac gtcatttctg  48660
gattgttgat ccagacggcg catgagtcgc cgcgggactg cgtgatccac ctgcccgggg  48720
ccccacaagt tacagacgca cattccaatg ctgtgtacga atgtaattct ggtgcattcg  48780
tgctaacttg cgcaactttg gtggaactgc ccacgtctct gaacgatctc gtcgaagggt  48840
tgtttgacgg tgtccccatc cccagagatg cgctctcgtc gaggtcgctt agtagacgaa  48900
cgaacgtgat tatcacgtct accaaagccg cggaaacgac gactatacag cggatgcatg  48960
tcccgcgaca taaacagagg ggcaacttaa acaccatcgc agctactttg cgaccggtga  49020
aaaaacacgc gcggtttagc ccgttcgtgc aagtaaagta tatacctcgc gtactcaaaa  49080
tatggagttg tgattcagat agccattcgc cgtccctaaa ggagttgcgg gaattgtttt  49140
gtaaagtgga catggtccgt agagaaaaca tgtacgcaga atcgcaattg gaaccagagt  49200
ccgtcacaag tgaactggtt ctgatagtcg atactgtatt tgggagaccg ctcgcaccat  49260
ttattggcgt cgggtcggaa aacatacgcg tctcacattt ccaaaagttc ttactgctcc  49320
agggcgtcct tatattaaat cgtttgccga attgctacgg accgcttcgg gagctgtgca  49380
ttcagcatgc acctgccggt gaagagtcgc ctcctctggt atccgactct gttatcgcag  49440
acatggcgaa ccatatgttt agggtcgccg tatttattgg catggttgtg gaaatagttg  49500
cgggatgtgt atcttttgca tcagaagaac tcgaaacgcg atttcccagt gcgaccgcgt  49560
ttacggatgc tggcattcta ctgaacggca tagaagcctc gccgaagcca aattgcttgt  49620
cggaacttaa aacacgcaaa ctcgctctta tcctggacgg tatttataga gacatggatc  49680
ctatagacgt tgctctacag gaatcggtgg ggctaaatac agcagagtta ttatccgcag  49740
caatagatat ctcggttatg tctgcatttg agcattcggg atggtgtagc ggctacatgg  49800
aacactttgt ttcattgcta gatgcccgtc tgagagaggg agggtgcttg gcaatattcc  49860
ggtagctttg tagcacagcg gcgagacgcg cataggcgtg ccgggcatat acagaacgta  49920
agccaagctg gagtttgtgt aagtatgtgc tctacagcgt gcgggaaggg cggttcgcga  49980
ataaacacaa cagtacaggt tcgacggtta gaaagtttcc agagtttatt aattagattg  50040
gcccctcaag atcgtctttg cgtcttaatt tctcatatcc atggtaccta aagttgctga  50100
caagcatttt ggcggtgaca atcgctatag ctgcggctat tagtacaccc gctgcagtag  50160
ttgcgatgta ggtcgccgag aggatggcaa tgcgctgcga ctcaaacgct aggatcctca  50220
cgactgtgcc atttggatac agcaatagtg acgtgccata caggttactg gtggtggggt  50280
tgaaatagcg cacggacgaa ttgcctgctg ctagcaattc ccgctgcaaa tcgcgcgatg  50340
agatataaat cgcatgtcga acgtggccgc ttgcggaata tcgcagcagc acgcagccgc  50400
aatacggaca ttcttttccc agaggcctag gtaaaaccgc aggactgatt atacctgatg  50460
tcgacgtgca cggcagcctg gcatatgtta tgtaaagttg gttgtttaca tcaacgccgt  50520
ctacggtata cacgatccct ctgaccccgg cccgccttgt tacaatgtag ctacctatac  50580
cggagatggg taacaccaga agagtgtcgg attctaacct atcagtgccc gaacattcca  50640
```

```
aaacctccga cgcgtatgta gcaactgttc tccctattga tgttcgcagc tttgcaatta  50700
ctgattccgc cttggcctgc agatcttctt cgattctgac cccctgagaa gtattctcta  50760
aatactcctc tattactgga cggtaaacca cattggccat cgcgtatacc ctgtgacgcc  50820
gctcggaaat gtcgatcctc aatgatgtca tgcacggcgt atacgcgtcc aaaatatgta  50880
cgggctcagt gctgcgagtg agtctgatat acatgtcttg caccgttaat tcagcggccg  50940
cgatgtgttc ttcagtacac atcgatgatg caaataacag agatttgcgt gcgttatgcg  51000
atgcgcgcca ttccatcggc gaccgctgaa aaacgctgtc gaatgcataa tacagggcgt  51060
gtctcgtgga agcattccac gagatcgcgt ccctgacgga ttcttcgtgg agagacgtga  51120
taaaatttag tgcgaggtcg gaaattcgcg ccccccattc gcccttctcc cgaggtatgt  51180
cgaacgcgta cacggaccgg aataggtaca actgtcgcgc aatacctaaa gaatgcgtcc  51240
ccctcgatac atcgctaatt tttttttca atacggatgt tagtatagca gctttttcat  51300
tccatacatg tgtccgcgat aataagaagc acgtgccggg gtccgtgctc ggggcaaaat  51360
tgcaaagtgc cgcggcgatt actttcagat ctgcctccct tttaattaat tcatcgaggg  51420
agacgtagcc agacttaaaa gcggcgtgta cggacgcaac aagcgccaga aacaaacgcg  51480
tcgttacgat cctaaagccg tggatataat tactagtaga tgcgggcata gaggcagaaa  51540
taaaaagccg ggagtgcgct tgagtgatat gaagattata atctaatagg tcatctacac  51600
tcgaaaccat atctgcgtgg gcctttaatt ccatatccga ggcgttctga tatgttccca  51660
gtaggtatgt cgaaaggaga tgtcgagagg atccgttcat cgggtcatac tgcttcatcg  51720
gtggccacag caaagtcatg ttggtagtcc ccgacgataa tattagttcc acaggcgatg  51780
cggcttccat agagatcgta acggaggcga attgcactcc taccttcatt aagacctccg  51840
cggtatttga accgaatatc gtcgtccgca cgtgggcata atctgtcggg actagtgtgt  51900
ccatggggtc cacgaagcat gcacgctttg caaaagctcc cgataattcg ctgttgagaa  51960
taaaacggtt ctccggagtg aagaagtcat tcggctttat attttctaac actgttggcg  52020
ggtttgcgcc agtaggttgt gacttggcac caccgtgagc ttttggaccg ggtttgtccg  52080
gtgtcttttt ttcgtctcgt cgatgggata atacggctgc cgtcaacgag taatcgaggt  52140
ccggcttcgc gttcaaaact ttgatcaggt tattagacgt tagcagccta gatatcggtc  52200
gtttgaagaa aaccatttgc ttcacttcac ttattggtaa atgaaagaga atgccgctcg  52260
ccggcgtaga tgctcctata tatacaaatg tcgcattgtc gcgtacccag gacgtcgggc  52320
tagtagcatt ttcatcggcc gatgaaaagt ccaattttac ggacggcggt ctccggatgt  52380
ctagcagcga ccatacggag gggatattat ccgaggtggg ggctcccggg gaagatgcga  52440
gcgctagcag taataaggtg cataccgcca ttccgattac gcggcgtcgg tcgttgcctc  52500
tgcgtatcgc tagttcgagc tcgggtttcc gaagcaacgt aacacacata tcctatagtg  52560
tacaatgttt cgatgcaact gaaagcaacg agctaaagcg aagatgtttt gcaggcgaca  52620
agggcatgca ttaatgcaca ctcgtccgaa atgtcgtagt ctcaaatgtc catctcctta  52680
ttgaatgcct gaacgtccgc ctcgatctca aatacatcat tccagctcat atgcgttatt  52740
aatctttccg ccattgaatc cataagatac tctgcacatt tctggaccga catgtcgctg  52800
acatcaagcc gctcgacatt gatgttcctc agtttcatca acatccccca caatatccac  52860
ccgtataccg ttaacaggct accatcttca ctgcataatt ctttccgctt aaaaattggc  52920
aaaagcgtgt gctgcaatga cacccggcta ccatggtaac ctgaacgggg accatctata  52980
```

-continued

```
aatgtagagg ccatcgatgc atcaaaccac gggagctgca tccactctgt ttcccattcg  53040
tctttactgt aaggacaaat gcaattcgca tacgcgacgg tatctgctaa agccgaatat  53100
gccgcattga gcgccctgag catgcgcacg tctgtagttt cccccgctct gttcctggcc  53160
gataggcgct tcaggtgctc ggtttcgtcg ggcaaatgtg ctattaccaa gttgcagccg  53220
ggcggttcgt ggggcaaccg tgtaatcgca ctaatcaaca tttccagaga acaatcgcca  53280
atcagatgtc gggcgatggg aaagcagacg gtagctgaaa caggatggcg atcaactatt  53340
aatataagag atgggttgcc ccgtgttccg gctaattgat gacatttaga tgatattcgt  53400
tcgtgtagta caatgaaggg atcggcaaat ttggcctgca aagccattac gatcatgcta  53460
gactgaaata gagataattc tccccgacgc cggcgttcgg aagcgtcatt cacagctgca  53520
actaaatcgg taaaatagcg acgccaatat ttcagaggct caaaaacttt cagcacgggt  53580
actcccgtcg cagagtggct cggcacttcg tttaacatcg acgttttacc tatagccaat  53640
ggcccgtcga ggtagacgcg gatcagctgc gcggatgtca tctgagaggg cattaccgac  53700
cacggccgca cgtccgacat gtccggcgcg caagaaaact gctcgtagac gatataaccg  53760
gcggagaagc acttctggac gctcaagtta ccgtgcggct gttaacctca agagaactct  53820
agcggccggc gttcgatgtc acgcacgttt ttaccaaaag ctctacgcag aatctatgca  53880
ccttcgaact caggccgatg attggacggg gcgggcccta tctaagattt taggaaaaat  53940
tatggggttt gatgtattta aagcggcaac tgatttccga ttggtctttg aagtaaatct  54000
ggggcggcga aaaccggact gcatttgcat gattaggtgc ccccgcggtc tatgggaggc  54060
aagttgtgat ggcgcttgcg tcatcattga gttgaagact tgtaggttct ccaataatct  54120
aggaacggcc agcaaaaagg aacagcgcct cactggaaca aaacagctct tggattcaaa  54180
attgctgatt gactatttag cgcccgtagg ttcggagcgt attttcatct gcccgttact  54240
agtattcgtg tccaggagaa aattaaacgt gttgcgtgta acctgcctca gaagaaacgt  54300
cgtaagtacc gatttccatc gtctcgcaac tttaataacg cttgcatcgg aatataagat  54360
taaacaggtc gacaggcgca gaacggctgt tcggaaaccg gctcagtgtg caagaaattt  54420
cgcaagtctt gagaacgcgc ggcgagacga tcgatcggaa gaggtcgaga tacacacttt  54480
tcctaactgt agtattgtcc taccacctcg taccattcta cccggagccg cgaatacgac  54540
aatgcaccgt ttggcaagta ttgttagctg cttggtacgg aagcagtaac cgaaatcaac  54600
ggcaccctac gaccagctat gttacacggt gcaatccgcg gcccttctcc cgttactttc  54660
ttgctccgca gcccttgtcc aacgtcagtt gtccgtaggc actgcagcaa agcatggcga  54720
gctttgcctg ggatgcaaga attttgacag acccgggccc ggaatctcac ccggctgatg  54780
taaagaattt catagcacct ccctggcctc tgcacttctg gagggaacct atatttagcg  54840
gcaatcttgg ggatgcggaa cggcaactgg caatcgttaa ggcgcgaaac agtgccgcga  54900
ttgcagcgtt aactagtttg gacgaccgta ctgatttaat tgcggtagaa gtggagcgtc  54960
ggcttcgacc actagaagat aaaatggaac agatcgcaac gactttggcg gatttggaac  55020
gagctgcttc tgcggctgaa cttgccgacg ccgcagccga tgaggctcaa aatgtcgtcg  55080
attcgaacga atgccaaaaa aacattggta gcgctgcgag tcgcgaggtc caaatagtca  55140
ggaacgatcc gtcgctaaga tacgactcta acctgtcggt ggatctgctg aatattatct  55200
atgccagcag gggcgctgcg aattcgggag tggcgttcgg tacatggtac cgtactttac  55260
aaaactccct tattgcggaa aatcccagcg ctgcgcggaa gatagattat cgcgatggaa  55320
gaatgtcgcg gaccttcatt gcaacggcga taacgtcctt acagtcatgt gggcgcttat  55380
```

-continued

```
atgtggggac gcgtaactat tcttctttag aatctgcagt tctatgtctg tatgcgtttt  55440
atacaaaaac gggagctaat gtgtcccatc caagttcttt taagagtgca ttagaatctg  55500
ttcccattta tctggatcac atgtcagcga gcctcgctag cactgatacc aggcaaatct  55560
acgggttcga taccgggaaa ttgccgaagg atagtttcgc cgccccgtcc ggaaaatacg  55620
aacggggcgc gctaagtgat catagcgtat tgagagctct agcaaattct cgcgtgttgc  55680
ctcctagtgc ggggtcgatc ccccgtggag acgtagcccc agagctagat gccgaccaga  55740
gcgttcgtaa cgacgaagtc aacgctgccg ccgcagcgct actgggacga gcccaacccc  55800
tcttccttat ggaggatcag acgttgctga gagccacttt ggacacaatc gtggcattgc  55860
ttttacttcg ccgtctactt tggaatacga atatatattc agctagagtt aaaaaccagt  55920
tccaactggg ggcgttcgtt ccaggcgtgc ctccagattt aaccgtagga gcctcagtag  55980
acacgccggg ggatgtaatt aagagtgacg ggagaaactt aacctttttta tttcagagat  56040
acgtagttcc cgtatatagt gttgtcaaag ggatagagct cacacaactc tttccggggc  56100
tggtagcgtt gtgtttggac gtcccgtttt ccgatcgagg gttatatagc accaggacgc  56160
cgccatcgcg tatcattgac gtttcgctga gtaaatatca ggcctccctc gtgaaattga  56220
tttccttaga gcttcaaaat cgttcccgcg ctaatgttgt atctgtttgc gaggtgatcg  56280
cgactcacga tttggtgact ctgcagtatg agcgaggctt ggaatcgctg atgcaagtcc  56340
agcgtccccg cacccgcttt tttgaaacca agaaggcttt ggcgttcaat gtggaaacgg  56400
attacgatct gctttatttc gtgtgtttag ggtatattcc gaggtccgta tctgcatcgt  56460
gaaatatacg caaaatattg gcacgtgtcc agcttaaaca acagtttagt agaaatgaat  56520
ccgacggaga aatattcctc ggtatatgtc gccggatatt tgtttttgta cggtgcagat  56580
gatggcagcg aactgcacat cgaccgcgag gatattcgag ctgcaattcc gacacctgct  56640
cctttgccca taaacataga tcatatacgg aactgtaccg tcggagccgt tctggcacta  56700
acggacgacg aacacgggct gttcttttta ggaaaaataa attgcccggt gatgatacgc  56760
acgctcgaga cggccgctag tcaggaaata ttcagcgaat tcgataatct caaaacagag  56820
gagagggtat tgtatttgat aacgaactat ctaccatcgg tgtcgttatc ttccaaacgt  56880
cttgaacccg gggaaaaggc cgacaaaagt tttctggcac acgtagcttt gtgtttattg  56940
gggaaacgaa tcgggactat cgttacatac gatcttactc cggaaaatgc cattgaaccg  57000
ttcaggaagc tttcccctac taccaagacg gccctactat ccgaggggca agaaacagag  57060
cggctcttag gcgataaggt ctggcatcct agtaaagagg cgatgtcaac cgcgttgttg  57120
ggcaccgctc tgaacaatat gttattaaga gatagatggc gcactatttc cagccgaaga  57180
cgcatggctg gtatatccgg ccagaagtac ttgcaggcgt cagccttgac cgcactggcc  57240
gagtcgatga cgtccaataa cgcatcaacg atccatccaa tcggcgaaac cgcaaactcg  57300
gacggcatac aaaaggatga tcgaattgaa gtgtgcgcca cttcgccgca aacgaacaaa  57360
accttagagt ccagagcatt ttcgggaggg agtgggttcg ccgggactca tgcgatctct  57420
ccaccgcccc agatgagcgc acaatcgcca accgagatgt ctatgaatac taaatctcat  57480
ttcccccccg gcgacgattt catttgggtt cctatgaaaa gctacaacga actggtgtcg  57540
agacaggcca cgcacgcaat taatgccccc gaagctgcag tggggagcca ggcaccgtat  57600
agttcctctc cgttaatgat tccggcgcac ttgggacagc atgctcacat tgggggatat  57660
ggacatgcct ccaacccgca atttgcatcg gggccataa attacatggg cgggtttcca  57720
```

-continued

```
tatgctctgc ctatccaccc cgttccaacc ggccaatcgt ctttggaaac caagctgtcg  57780
gctctactgg attgtatgac gagggagaaa aaatcagtcg atggggatcg cggacgtgac  57840
gacatgttct ctggccaaga agaacgaggc cggcgcgggc gcaagcgccc gtacaactgt  57900
gacaaatctc ccgagcagga accttattat ccaggcgaat tccagcagtc cgagcatcgt  57960
aacttaagat gcgaagacgg catcgaatac gggcgagacg cgactcaaac gaggcccgcc  58020
ctggcgggcc tcgtgaacgc tgttacgtct ttgcagaaag aagttgaacg gttaaacgga  58080
agggcgcaag cccattcgat accggccgta cagcatatgc aaggaatggg aaccggattc  58140
caggcccccg tatactacgc ataccctcct ctcccaatac cacatgtatt ttcgcggccg  58200
ccagaagacg gccgcccaat ttcttccggg gagggaaggg cctcgctagg tagcgccacg  58260
ggcactcctc cgtctggatc ggtacctccg aacgcttctc aagaacgtgt cgatgcagct  58320
cctaaaagcg acaccgttca gtcgcaagat actgtgaacg ccagtacgat cgccaatgta  58380
catcgcgccg acgatgcagg cgcggatatt ttcattaaac aaatgatggc ttaaatgatg  58440
gcaggggatc cgctatgtcg acgtataagt ttatacattt tgcgaccgca atagcaaata  58500
aaagtaaaat aatcgtatgc gcacgtgaga atttatttat cgagaaacag catcgcgcta  58560
aacggcatcg tcctccgaat cagagtacac aggcgataat ctatcgtagt gctggccact  58620
actttttagc ctcagctttg ttaggtgatt agaaagaata gcagtggtgc ctcttgtttt  58680
tttgcgcaaa tcattttcgt ggcgttcctc tgcggacacc aacgccatat attttatcat  58740
ttctcgagcc ttctgtaatt tttttttatc gattggtgcc ttttccgagt ccggttcttc  58800
tccgtgcaac tcgcgcgttg cctgggactt tagctcttcc gtcgtcactg gatatagggc  58860
tttcatcggg ttgcctctaa gcttgtttac gtaccagtaa gctagaaacg cagccacgag  58920
tcctgctata attatcaatc ctaccgctaa agctccgaac gggttagaca taaaagcgga  58980
cactccagat acggtagcca ccacggcacc ggcggcaccc acaacgacct tccctatggc  59040
ctgaccgact tgccccatac cgttgaacaa ttccgccagg ccgttcataa aagcgtaatt  59100
tgtatctact tctattactt tatttatgtc ataaaatttt agttcgtgca actggttgcg  59160
gcgagccacc tcggcatagt ccaatacccc gacatctcgc aactcctctt tcgtgtagac  59220
cgacagagga agaatttctc tgtcttctaa cagtgttaag ttcaggtcta caaacgtgct  59280
ggctgtctgt atatcagcaa cctctaccat cttaacaaag ttatagtctt cgaacagagc  59340
gtatgcggat ccaaacagga agtatctccg ctggttagcc gtacacggtt ctacggcctc  59400
cagtgttggg agtagctcgt tattttcgcc gagctggcct tgtatcctcc cctggttctc  59460
gccatacgaa aacaagacca gcgggcggct gtagcacata ttagtagacg tggcgaccct  59520
catggaattc tgcaatgtta ccgattccgc gtcgatccca gtacaagtag acacggcggt  59580
cacatcccct aacattttag ccgctacgcg tctccctaag gtagcgctcg cgatggcgct  59640
cgggttaatt ttcatccctt cctgccataa agccagttct ttattttgta attcgcacca  59700
ggccgtggcg attcggctga acatgtcgtt gatatgagtc tgtatatggt cgtagagaaa  59760
ttggagcatg gcgaattgga cggacgaagt agatcttatc gtagcgcctt cgttcagcgc  59820
cagtttttcc ttcggcgcat tacggagctc tcgccgcaaa cgggacaagg agacatttgt  59880
tttattggaa agagcatgct tattatgtac taggtctagc agctcgtctg tcctgttgtc  59940
cctcatcagt tctcttagat acatgtgagc cagagatttc gacataacgg gctgatacgc  60000
cacaagaaat ccaccgaggg ccaaaaaata ttggaccttc ccgaccttga cgtggctgtc  60060
gttatatttt tgcgcgaata tgcgcttgat tgttgtttca gcgtcgcgct ttacgcactg  60120
```

-continued

```
acctagcctg atacgatccg gatcgaattc agtggtattg ctgataaatg ttgacgatag  60180
ctcgcgggcc atgaatctat acttgccgtt aaccgttgcg cgcaacattt cagtaacatc  60240
tttccattta accatcgagc atacacgagc ggtctttgct gcccagtccc acccaaccgt  60300
aaaatgtgga gtgacgagga agttacgctt gacgggtatg ctcgccttct gacgcttgct  60360
cagatccatt gggaaatagc cgtctatctg cctaaattgt tctagcggat agcccatggg  60420
ttcggcggcg gcctcgggcg gggcgacgcc ataaaacggg gacatatttg cgatatctcc  60480
gttcgccatt gcaaaatacg agtatgggaa tgcagccctg gcatccattt cttccactat  60540
gcagttgaca gacgtccccg tccgatatac ccacggagac ccccatacgg tataagtgtc  60600
gttggtcgta tgccacgcct tggactcggg ggtgttgaat tttgacggtt gtagaagtac  60660
ctgtttttct ccggcgtcgc cgtcgtatgc ctcgacgtat acattgtttc tcaggtatcg  60720
cgctttggag gaacatctcc ctttcgcgtc gattacatcc gtaatttctt cgatggaaac  60780
gggagtccta tctgtaaacc tgttggtgat ttgtctgtac gtcgtcccgg tccaggtcgt  60840
cgtttgtata acgttcttat aataaagcgt gactttgaat ttgtatgggt ttatattctc  60900
tttgaagagt atagcaattc cttctcccca ttcggtggcc tttagcggtt cggggcattt  60960
tcgcggcggt tctaaccgga ccacggtcgt accgaccgcc ggtgggcaga gaaaaaatga  61020
ggactcgtct tcagacagct gtacgctcga gactgcttcc cgcgacgtta cgttttgggc  61080
cctcgcgact cggccgaaga agtagaaaac cacagatatg aaaagtggaa cgcagatccc  61140
actgaaatgg ttcattacgg gttgatctta acgagtctca tcgatagtgt ggaaaggcgc  61200
gccgcggtac gaaagatatc gcactggtca agtgggggtg tggtcatggt ttgttcgttc  61260
cgcacgtatc tgatccgcag ccgcgggagc catgtactgc agaatggaat agagcagcga  61320
gaaaacatcc gcatcaagga ttacggtcac gttgtctgat tccgcaccga ggaccgttat  61380
gagagggcat tctgtttcat atgtgacgta tattccatcc tcccatatgt attccacgtt  61440
aacattgagc ggcaagcaat ctgcacgacg caggtgcaat tcaccgcagc tgaacgcgga  61500
agaaaataaa gttgtcgcca aaatcacctc ttttatatat ttccaagcca ttctatgggc  61560
cgcggttata ctatctatgc cgtcgaagtc gtaaaaccct ctgaatttac tgacgatcca  61620
gtcagacgaa ctgcaactat gaatcataaa tcgcgctatt tcctccttca aatgcggcaa  61680
tagaccaacg ttctctacac tgaaatatag cgctgtattc gaaggttggg cgaacctatg  61740
tacatcgtga ttaaacatcg ggccgtttaa caaccgaaaa aatttgtgag ttaggctggg  61800
gagcatcgcg ggatctattc tgtgcttaag taatgacgtt tgcatgaaac ggtgggcgtc  61860
gaacgcatca gcggtgatgc gattatcgat gatattcgta catcgtttcc taatggcttc  61920
caataaccta ttcctggagc ggaacccatt gaataatgtc gtgtatgagt ctatcaatat  61980
ttcaccgtat acgttaaccc gcagcatttt ttccagctcc tttctttgct ctgtaataca  62040
tttatccaaa cttgcgaggg atcttttact taggcgctct gcgtacattt tgcgtctccg  62100
agcaacgtca gccgatgccg atcgtaccaa ctctaaccag tcgtagtgct cgcggacatc  62160
gggtaacggg gtaacccctt cgcgaatccg tagatgctcg gagttactaa aatcgtcctc  62220
gggcgcgccg tcgccgtcct ggcatagggg accatttctc gtgctatgcg aagtcacttg  62280
ttctaaagta gtcttcagcg cgtcttgcgc cgcctcctcc gggtacaata aacgttttag  62340
cagaggagtc gacatatgat gatcgtaaca tgctcttatc agcgcttcta tgatgtcgtc  62400
tggcgctacc gccctacccc ccagaagcaa tctgtcggcc gcattcatat tctcgatttc  62460
```

-continued ttgtgcaaac acccgttcga aatgatccat gcgccgcccg aataccgtca tttccacgac 62520
ggatgttctc agatcgaaaa gacgctcttt gaatgctaaa tcttcgaggt tgtccgcaaa 62580
cgagtcaatc gtgtttgctc tcggttggtt aggtttgcgt tcggacgagg caatccagaa 62640
ttgcagctcg ctaatggcat acagattccc cgatgccggc aaaaaaacgt tatgcgcgtc 62700
caggacggcg gttgccgcat cggcgacaga cactgtatcg ccgctacctc cgggatcctt 62760
gtctcccctt gtcggtctaa tgagcgaaag tgccgcttgt acaaccgaac gcttttcgtc 62820
ggacagacaa gcggcatgtg ggatgtgcgc taccatgtca tctgggtgga cgcggagaac 62880
gatctgctta gttacatgat tacatatttt tccgattatg cgcttatgtg ccgagtctcc 62940
actgtttgcc gtcacgcata gttcttcaaa acaaacggag catggttgtg acgggtcgca 63000
caactccggc gaaacgaccg atcccgcgcc cagagtttcg attagatatc gatccagggc 63060
caacataaag ttttctgcgg ttcccgcttt tacgattagg tgacagtaat tgagttgctt 63120
caatatgttt tctacgtcgt gtaggaattt aatctcggtc cgcaccgaac cgccgtaagt 63180
atccaattcg acgacttcgt gatacggaca gtccccggat atggtcatcg acttaataaa 63240
aaagccgtgt acatctccgg tgtctgtaaa ctcgcacagc gcacgcagca gcacttctcc 63300
gtctagtcga gctctacgca gagctaacca caaaccgtag ctaaggggac taatattcct 63360
ctcgagttgc tccgtcagcc caggagccat taggttttcc aaatagcgta ccatgagcac 63420
atttaatttc agcggcttga tcattcgcac acctactctc ggatcgcatc tcttcagcag 63480
ctctacttga aacaagtacg attgcaactg accccataca gcgagcagtt tctgactagc 63540
gaatatactg tctcgctcaa cgtctagcgc ttgtgcgttt ccgtgaggca tatccaacgt 63600
ctcggttcgc ctcgtctacg ctgaattgga cctgagtcgg agggagagca tgatgatatt 63660
tataggggtt agccgataac gccccatccg gaataagacc cacaaagcga tataagaaag 63720
agtatgctgt atatttcata tttccgtata caggttgaaa agccgacaat gacgtagtat 63780
ctatcttgat aaggctatgc gagcaggccc catccgggat atgagctagg tagttcgata 63840
caaaagtaaa cgcgtttaga cccaaacaca gattttaaaa gcccgcaacc cacgtactgg 63900
gacaacaata cacgcggtta tagcatatcc accgatagtc ctggagcccg cttttcggga 63960
acgggctcca agtcaaaaac gtccgaacac ggacgtttca aagttggctc taatatggac 64020
gggccgtccg cgcgtctttc cgtattctca tcaagagcat cgtaattaaa cgtaggtccg 64080
tccagcggga gagccttcga catatcgacc atctctttcg ctaatatcgc ggcagcatcg 64140
acactccaac cgccctcgca tccctctacc tgcttgttaa gttcatctat caaagatgag 64200
atgtacgcat cgttagttat ttccatccag tcatccagtt ccatttgccg tacacgatct 64260
ccaaccattt tcaacgcgat catatatacg gcggcatgag gcgctccgca ctcctcagat 64320
aaaaccgccc gggctctatc cacgagcgtg gtttccttca agcccgagga aaatccagtc 64380
tgttccgata caaagccgac cctaggacat gccatgacga aacggtgggt tctattaaaa 64440
gacattatgg agcagacgtt tctcccaccc attatgttgc cccagttgcc ggattggaat 64500
acttttgtgc taccggccat tccgtgatat ttactgatgc tgacggctat cacaacaaag 64560
ggtttagagg ccatgatagg accgacgaga ttagtagatg aaaaggcagc acaccatgct 64620
tccttatgat cacagatatt ttttagcagt tgctgggcgg ctggtgccac atctgaccct 64680
tgtgtgagga tatgttcgat ccagggcagg accatagccg gatccctagg tcgcttggag 64740
gttgcaacca aagccgaaat cgtgttgata aagaaatgct tatgtgaaca gtacctcagg 64800
atggtattcg ctagataaaa ttgagccagc tccccgaagc atgtaggact gatgttaatg 64860

-continued taattcatat cggcgtagct attggtaaac cttttaatga atgacgtgtt ctcctcggca 64920
tctttggaga gtataccggc cggcaactga ttgcgttgta agaggatcca aaaccagaga 64980
gcattgggag tcgtgccatt aggcatctta acattcggaa aaagttgcgt gtgataccgt 65040
ttgagcgcaa agccgagagg gccattgagc acatgcatcg cttttgccgg ccgttgatac 65100
gcttctatca tgcccgccag ccgggatttt gtagcgtcgg agacggtact ggaaacgcct 65160
ccgacgaaca taactttatt cttcacttta aattcccgga atatctcaaa tgtaactttc 65220
actagatctc cttccatgtg caccgccagc ggatcatgct gagatttgct aggatcggga 65280
acggagattt gttgatcctc taaggtcacc gttatgtttt tagatgtgat gaacccggcg 65340
ttttgcaagt ccagtacgcg ccgcctgagt accgcttgga actgagtcct aaaatttcta 65400
gcctctactt gttgcccgtg cattatcata gagcactggc ttaacgccat atcttgaacg 65460
acggcaatta tcgtgcgcct ggataaaaat gagagcacgg gacatatgcc tgacgaatac 65520
ggctctattg ccagcgaaag ggtatgggtt gcatcaccta gcccttcgcg tatgttatat 65580
tctctgattt ctgtcaaatt tcgcatcagc tggccagctt cgctctcgat tatattagcc 65640
attgtcgata gagcacgcat aaacgatttg ccatcccgga tgatggcatc tgcgggtgtc 65700
atgtctgctg ggtcctcgca tgtcagcaaa ccttcttttt ctaacgcttt cattactctt 65760
tcgaccgtca gcttgtacgt gtcctgcatt acactgcggc tcgtctctcc ctccgatcgt 65820
ttgagagtcg agaatggggc gtagcttccc agcgcgttca cgtcgcagta gttattcgtc 65880
atagatccaa agagccccat agccccacgc atctgatacc cgaatttcgg caatcgatat 65940
tctaagcgct taattgtggt atgggcgcaa taaatacgcg acgctttgtc gcacaaatcg 66000
catggtacgt ccgcgtccat ggcagatgaa acaaatttca cggtatctaa atcgtgatgg 66060
caagcttgag atccgccgtc acacctctcc aggtagaaca agaatcttgc cagcaattgc 66120
ggacaaaacc cacacgccaa aattaggtaa tctaacgagt attccgacgg gctggccgat 66180
gtggctttgg acaaatcttc gcccggaatc ggcttgccgt ctctatcgat taacgggttt 66240
gaggccaaat gcggcgcggc tatttggaaa aaccgataaa acgaggctgc ggtcgtactt 66300
gtgtcttttc cgtctgcgct actcgcttct cccacctcgg tcatgtatat aaccgaattc 66360
gaactaaaca ccattgcccc gaccagtcct gccacgcggg ccatatacgc agacagcgct 66420
tccactctat ctgtatatcc gatcggactg caatagaggg gccatttctt tacatcgggt 66480
atagactcct cgtagaccga tgtcgcgatt acgttttcta tggacagagt agcgtcggat 66540
gccattagag aagccgtcct acgttcatac cccccgccag atagctccat gccttccttt 66600
ttccccgctt tatactgcga tttcgaagca gattcgatgg gagtgaatgc gttaaaagct 66660
gtatctgcgg gtaacaatgt tccctcgtga ttttcgtcaa agcttaaatg ggcggcacag 66720
cgcgcaatcg cgtctacatt gcgaacgcga aggcctacgg ccgcggtact gagcacataa 66780
ccgtgtaata gacgacataa ggaatcatta tagaaagcct ttggcataag agctccctcg 66840
cctagtgctc taggcttcgt actaaatgga tcgctggcaa cgcggttgaa gtccgggaaa 66900
accaagtgca ggggatataa cggtattcta cgaacatcga cgccattaat gctcacgact 66960
ccagtaccac cgtaatgtaa atatgagttg cagaggtaca cggcctcttt aaataattcg 67020
gtcactacta agtagagcat agtttcttga ggattcattc cgagattatc gcatatttgc 67080
tcgccggttg tttcgaacga cgtggctacc gggggcgaat aggtgctgta gccgaatctt 67140
cctcgtgcca aatcacatgc tttagtcaga ttcggagcct tcgtgcacgg ttttatacat 67200

-continued

```
tctccgccgt gaaacacaaa cacgcacgga tggtaatgcg tcggaacgag cttgagagta  67260
gttgatccgc tacccagacc cgttgtcttc gttcctgcaa cagctgccac gttccacatg  67320
aaatccgctt caactgtaag acctgaaacg agaggcaata tcgcatcctc gcagtcattg  67380
ctcttggccg cgaagatcga gagatcttca gctggcatgc tgctcgtggg tgcagcatat  67440
acatatccta tcggcccccc ggtgatctta acgcttttcc ctacatccat ggttaaggtg  67500
tcagcgttta tccggtagac tgtacaacgg aatggcaagg ggcgatgtgc cttccaaagc  67560
tgcgaacgcc ggcttcgcca ggagatggca ctttgacttt ctcgtgccgg atgttttaaa  67620
gccagaggac ctccaaagga tatgacgcaa cacttcctaa agtgcgccac gaaacacgtc  67680
gcgcatattg tatgttttat aagtcctcga cttcaaactt gccttctctg taagccgata  67740
tgtcagtaga tggggctaga actttttca acccgtacct cggtgcacga aagaggggac  67800
gggatgaaga tagtaccata ccgccgctaa gtagaccgcg ggacggggag agataccttc  67860
ggcaacatcg caatgcgatt acctatatag cgactataga cgaatttaaa tatatcgccc  67920
ccaaatgctt agacgcggcg gaaataaagc agcggggcac tcatatcggc aaattgaaac  67980
gctcgcctat actgtacaaa aacggagagg aacgtgagtt cttgaatttc gaggctttgg  68040
gggacgcgtg gccacggaga tgttttagct ggaataacgt atcattctta cccacggaat  68100
tcgacccgcg tttttctagg tttcatgtgt acgatatgat tgaaacggta gagtttgcaa  68160
atggggcaac aggcagagat aaaaaccgtt ttctggagct attgcggcct atgggcacga  68220
ttattaccat gatgggaatg actgaatgcg gcaggcgcgt ggctgtgcat gtctacggcg  68280
tcaaaccata cttctatatg cgtaagatcg atgtagacac cgcctgcggg agtcgatcca  68340
cccgcggact cgctgagcag atggcgagcg tggtacgctc gtctgtgaac gaaagcgcaa  68400
gaaaacgatt ttacggctca agcactgtga cggccgactg tttcgaagtg gacgtggtac  68460
gtcgtaagga tatttatttc tacgggacag attgcgaaga gtattaccgg attaggtgtc  68520
agagcggcaa attcgttgcg ctcatatgtg ataactttca cccctccata attaaatacg  68580
aaggcagtgt cgatacaatt actcgaatgg tgctggacaa cgccggattt agtacatttg  68640
gatggtattc cctaaaaatt gggaattgcg gtgagaaagt acaagttcga gcgccccagc  68700
accatgttac ttcatgcgac atcgaaatta attgtacggt ggacaatttg attggtcatc  68760
cagaggacga tcactggccc gattacaagc tcctatgctt tgatatcgaa tgcaaatccg  68820
ggggagcgaa cgaatgcgca tttccggtgg ccacgaacga ggaggatgta gtcattcaga  68880
tctcgtgtct gatgtattcg gttcgacaaa agcaattaga acatgcgctg ttgtttgccc  68940
tcggttcatg tgatcttccc gaaaccttcc aagagacgtt tcgtgatacc tatggcgttt  69000
tgcccgaagt cctcgaattc gacagtgaat tcgaactgct gttggcgttc atgacttttg  69060
tcaagcagta cgccccggaa ttcgtaacgg ggtataatat agtcaatttc gattgggcgt  69120
tcatagtgaa taagttgacc accgtttacg gtattagatt ggacggatac ggggttatta  69180
accaaagagg gacgttcaaa gtatgggatg ccggggcaaa cgcatttcaa aaaaaaggga  69240
aatttaaggc caccggaata atcgctttag atatgtattg catagccacc gagaagttga  69300
agctgcaaag ttacaagtta gacgtggtgg cggaagccgc gttgggggag cggaaaaagg  69360
agctgtcgta taaagaaata ccaacgcact ttgcggcagg tcccagccaa cgtggaatta  69420
taggagaata ctgttttcag gattcgttgt tggtagggaa attatttttc aaatacgttc  69480
ctcatttgga actgtcagcg atagcaaaat tagccgggat attgctatcg cgagcggtat  69540
tcgatggcca gcaaatacgc gtgtacacgt gcttactacg gttggcgggc tcgcgaaatt  69600
```

-continued

```
tcattctgcc gaataagccg caggtgcgtg cgggaaccga gttcgaaaac agcatcgcca  69660
gtacggatga atttgaaggc gaaccttccc cttcgaatcc aaaggcatcc tcatcatttc  69720
atggaaatgg cggcagagtc gtcggttacc aaggagcgaa agtgttagat cccatttcgg  69780
gattccacgt cgaccccgtg gtagtctttg attttgccag cttgtatcct agcataattc  69840
aggcacataa cctgtgtttc accaccctaa taaacgacga cagaaaactc gccgatctac  69900
gtccacgcga tgattatatg gaaatcgacg tacaaggaaa atcgctgcat tttgccaaac  69960
cccatattcg agaaagttta ctgggtatcc tattaaagga ctggttggcc atgagaaaag  70020
cgatccgagc taaaatcccc gctagctctg atgatacagc tgttcttttg gataagcagc  70080
aggcagccat caaagtggtc tgcaattccg tgtacgggtt ttgcggtgtg gcaaacgggc  70140
tattaccttg cattgatgtg gccgcgaccg tgaccacaat tggtcgtgac atgttgctta  70200
cagtacgtga ctacgttaag gttaagtggg gaaccagaga tgccctcctc cgcgaatttc  70260
ccgcgctgac gaattatatg ttgggcgacg attactccgt gagcgtgatt tacggtgata  70320
ccgattcggt gttcattaag ttcaaagggg tagcgataca gggcctcgtc gcaaatggag  70380
acgatatggc aaaacgcata tcgtccgatt tatttcccaa acctatcaag ttggagtgtg  70440
aaaagacatt cgacaagctg ttgcttataa cgaaaaagaa atacatgggg acgattcacg  70500
gtgggaggat gttaatgaag ggagtggaca ttgttcgaaa gaataattgc cgcttcatta  70560
acacatacgc aaaaaagtta agtgatttgc tatttcagga cgatgcggtg gcaaaagcag  70620
ccgccctcgt cgcggaaagg ccttcgtcat tttgggcaac ggctccccta ccagaaggct  70680
tgaagccctt cggggacata ttggctgagg catacggtca aatgacggca agcacgttgt  70740
ccgacgtggg agatttcgtc atgtcggccg aactaagtcg gccaccgcag gcctacgcta  70800
acaaaagaat agctcatctc accgtgtatc acaaattggc catgcggtcc gaacagttgc  70860
ccatggtaaa agaccggatt tcctatgtca tagctgccgc aacgccggag gtactgcgcg  70920
atgccgagcg ggtagcagaa gccagagggg aaaggaaatt ccgctttagc gaggtctctg  70980
tcccggaggt tccagggacg tttagcaaca gcgccaagac gcgggccgtc caaaaaccca  71040
aggtattgat ctctgacatg gcggaagacc cgacatatct aatcgaaaac aatattcccc  71100
tcaacacaga ttattatcta tcacatctat taggaactct atgtgtaatt ttcaaggctt  71160
tattcggcaa tgacaccaaa acaacggata ctgtattaaa gcgatttatt cccgaaactt  71220
atacagagga tcgcgcctac gcgacgcgag ttgcgcgcgc cgtctttgcg gagatacgca  71280
gcggggccgg tctaagttct agcgaggagg aagaaactct tcaaagactg aatagagctt  71340
tccgtattct aacagaagtt cgccgtcgat attaatgtcg catagcttac agtacacgtc  71400
gtcggcgttg acggctggga catcactcga atctgtttga cgatcgtatt cttttctaat  71460
gactaataaa aagttaccgc gccacacgtg agcgattatg ctgtaattct tacaggccgt  71520
ttttaaacaa tcaatcaatt tgtagtggag gtggagagct ttcccgggga acacgacata  71580
catcatgtat tcaagggagc ctgcttcctg atccaagtaa aacaacacct tcacattttt  71640
cattccagaa tcgagtagca catagtatgc gaaaaaaagt tccgggattg ccaaaatacg  71700
agaaagggca atttcgctat ctttcccccg ctcctctccg caccccattc tgccgcccaa  71760
ggccacgata gaagccatga aattcctata atgataaatg ttgtttatct gttggacata  71820
tgccaatatc aaagaggcac gatcgtttcg ccccaatcgc gggtctccgc tagccgtgca  71880
cgtagggcaa cagccaccaa ctccgagata ataccccatt cccgacaaag acaaacagtt  71940
```

-continued

```
atctgcgaca gcttccgaca tattgaacgg caacgagact ggcgttgtct tgatgatcgg  72000
cacagccaaa tccttgacta ccattagttc ctccgatggg gactcttcaa cgaaatcgaa  72060
gtaagcgcga tacaaatcga catctggttt tcgagacccg cgtttcgtac cgcatgccgg  72120
cgcttgtaga tctcgccatt gccgccgcga ccgtcttgct atccctccgc tacgccctac  72180
agatctgcgt cgtatgaaaa tgcaaccggt catgccggga attacgatgt cacacgtagg  72240
tttgtagcgt gtgctcgaga gatatcaggg atatagagtg tctttgaaga aatgcgccag  72300
cgtctttgac gaacgcggat aaagtagtcg gccggggagg gaaaacctga tatgtcttga  72360
acgtgtacgc caaggcccaa aacccggcgc atacgcgacc ttcgaaacgg ttatggcttg  72420
cgagccgagc tttatggagt gccaattctt cccggctcgc taggtccggg tggtcgaaca  72480
atgaccgtgg attggtctgc gctatccgcg cagcacacat cgggtcgcaa aagaagtgtt  72540
tgtagattgc ttccgttccc gtgcctttga gcagcgccac gaagtatccg tcatcttcaa  72600
aatcggcatt tctctcctgc gtcccccacg cctccaacac cggttctatg ctatggaaaa  72660
tgccgatgtt gttagctgaa taggcaatga tatcgcgctt aaattgccgc attgcaagcc  72720
agtacgtgcg gattagtagg aagttgcaca ataagcattc cgcggacgtt ccccctttgg  72780
ttatcgcgtg ctttaattgt gttaccatta agggtcctaa ctccaaatca ggttctgagt  72840
catcttcgta acagtgacta tatgcccgag tcgcccctct agcaagatct attctgttgt  72900
ctttccaaaa cttgctgacc gtctccttcc taaatttcgc tgccataaga gcgagttcgc  72960
tcgccccatc tggtgcagat cccgtgcccg aaagcaataa taggacgaga ttcgtataac  73020
ccatagtaga gtcctcgccg ctcgaccgtt ccgtatactg agaccgatta gtgcacggtg  73080
ctagtgcacc aagatcgttc tccccgtcag gcagtgcttt gctcaaacga agctgcaatt  73140
cgcgctcgta aatatcgtcg tccgacaatg cgcgtataat gcaactttcc gtttgagaaa  73200
aattacattc tacgcttctc gcgcagtcct tccagcctgc caaagcgacg gaaagcgagg  73260
tgggaattga gccgaccgtt tgacccgttt gtgggacttt ccttttactt tcgtgtccag  73320
ctgccgtgtc gcattggccc tcgtacgacg agtgacccat gtcggacacc gtcgtcaaca  73380
tggcccgcgt agcgctttgg gccaaatacg aatagttact gtacaacact ttagcgtcac  73440
ccgcgcacag cgaccgtcct cttttccccg ccgaacggcc ttgatttgca cggggcacga  73500
taacctcgtt atgccgtctt cccggtaccc ccccgtcagt tcgaaaacaa ccatgcagaa  73560
agaagtgtct ctggatatcc tcaaaagtta aatgctttct cccaaacgag cctaccaacg  73620
tgcaaccgtg atcgaccaga aaatgcttat ccattatata cacgaattcg aacgctgcta  73680
taaacattgt tgtagcgcat ggtggagaac caagacattt ggaacacaaa aatgcgtaat  73740
cggccatcca tatagccgat aatccgaatt tgtgcttata tatatctaaa acacggcaaa  73800
cgagacattg tctatctaga gcaaaaacct cggctgccgt cccgataaac gtcgccagct  73860
cttgatgctc gattccgtct tcgcaatctt ctgcgctttc gctaccactg caactctgac  73920
cagcctgaag actgttggtc ttaatagcgt gggcggagag tagcaattcg ttaaagagcg  73980
tatcgttgta cgtcaatatt tcaggatcga acgctatgta agggcatttt aaggactcct  74040
cgacccatcc ttccgacgcg gatgctcccg gagatcgaat aaacggtagt tcgacagtac  74100
gatgggccat ggccgctgag acaaacactc ggcaagtaga tacgcctcgg ttagccgacg  74160
cgatcccaga cgtagagttg ctgtcggacg atgtcgataa attagctgaa cgctatattt  74220
gcgacgggat cgtatatcgc gtatggttcg aatacctaat acccgatgaa ttagatttga  74280
ttttcccgac aaccgacggg aagtttaatt atctatcatt cactagaaga cttgcttctg  74340
```

-continued

```
ccatccgaca tggtcgtgcc ggagctggga gtgcgacccc tacgtcgttt atcagtgccg  74400
agcgtgtctg tgaccatggg gccgttttga gagggcggag cgagagattt gcatccgtaa  74460
ttaataggtt ccttgacttg catcaaattc tgaaggattg ttagaaacta gcaagccgaa  74520
cataattgct ccgccgtata tctttttttc ttttacgaag gcatacagcg aatgatgagc  74580
gcgcctcaga gtaagccctg tcgtcgtgca ggactaatag cacggatcag gctcatcgtc  74640
ggcggagatt taactatggg caattccgat cccggactcg cggagtcttt ttccggtcgc  74700
gttccggcac gttgcgtatt tcaattcagt ggggcagacg gcgtggagag cgcgtttccc  74760
gttgaatacg taatgagaat gatgaacgat tgggcggggg gtgagtgcga tccctacatt  74820
aaaatacaga ataccggcgt ctccgttcta atcgaagggt ttttcgctcc tccgacaaac  74880
gccgctagag cgccgctgtg cgccgacaaa gtgaacgtcc tgttaaacac taccgattct  74940
acgggcgtcg ttttatctga tatcaaaagg tttaaaaaat cagtgggtgt ggattgcagg  75000
cctttccagg cttgcctaaa cgttcattgc tttgtaaggc taccaaatgt tcagctggcc  75060
ttcagattcg tcggcccgac cgatccggcc agaacatcaa aactgctcga ctcggccgta  75120
gcgtcttaca attcgaaagc gaaacagcgg ttcaaaaaca gttcgagggc tatcgataac  75180
gaatcgagac cctgcgcact tcatgagtgt gttccgatcc cggtaagaga tgaaacgcag  75240
aaactgacta gccaatctga tataaggacc cctaggcgcg tgctgaccat actcaagaaa  75300
atttcgagcg gtgagtacgt aacgaccgta cgcgtctcga tccgcaaaat tatactgtgc  75360
ctggtcagtg tattcgtagt tataaccgcc tggtggtgct acccgctcta aaacctcgcg  75420
acgcggcgtc acgtttccag tcggaacacc gcaccacaga gtcatcatcg gcgccactac  75480
atcgcgcgag actgcaatgt ctcgcacgcc ctctccccag ctttcgcctg tttcacaagc  75540
gttcgatccc tccgacttga gcacttacaa gttggatgtg ctggttaact accccctctc  75600
ggatttggtg catcacctta atgccatacc gcgaaacctg caagtttccg acaggcattc  75660
cgacctgaac gcagctaaaa tcaacgtttt acgggctctt tgtgtgggat tttctgacgt  75720
gcggcgcaaa aatgatactc gcactttaca acgcacgccc atgttcgcaa tcggcgacgc  75780
cgcatcgcgc ttgagaccgt ccattggatt gaaacggaca ttccccacgg gcatattctc  75840
aacaactatc ataaactctc ccgcagacga tgatgcatag cttttgtgag tcgacatgct  75900
ttaataaaaa attatccaaa tcgaacgagt ctacttccct atgtcagtta tccggtcagg  75960
agcattttga ttttaaatat ctctatcgtt aatgtatcga ttctggctct caattgttgt  76020
cgtgcgtgtg cgatttgcct ggccatcttt tcgcatgccc tagtgagtgc gtaaagcgcg  76080
ctgcgtccca cctgcctaaa atcgcgcctt gtcaataatc tatcggcaga gattactcgg  76140
gacgcgctcg attcgtccgt gctggagcga tcgctatcag gaacactaga ttgcgactcg  76200
ccatccgtgt tagaatccac ggacgataga gactccagcg caaacagata tcgctctggg  76260
tcgatattgg agtcctgttg cttattttgc cctgcttctg cttccgtgac cacgaaccct  76320
ctgtacatgt tgtgatggtc gtgctttgcc gttgtcgcct tgcatggcga acgtcggcac  76380
gtattaatgg gtttcgactg cgaactagac ggctgcgcgg gtctcgacag aatgtttccc  76440
agaaccgcac tactcggcga cgaaggctcc gctaatataa cgtccggggg cgcaaatgcg  76500
aagtggtcgt acagtccgtg ctgcgccgga ctcccgaccg ccgcctgctt tttgccacca  76560
ggtgccgtcg agatatcgac ggagcggtca accggttcca ggttaagatc cgcggtaata  76620
acggctggcg acgctcgttg taacaaggga gacgagtcgc ggcgcacgga agcgagtccc  76680
```

-continued cctaaagtat cgcatcttgg ccttgacgca ttgttaggac gaacacgggc ggcgcccttg 76740
tccgagatcc gtccgattga atcaatcctc gttccggcac gcgacggctt cagcgctctt 76800
atccctattc ctccgtcttc gtcgtcggga atcagggatt ttgtcgaaga cgcgacaaca 76860
aatggtgttg aggtcgaatc ggagtcagat cgatgtggaa tgtttggagt tccatgcttt 76920
ttcctatcat cgcgtaccga gttatccgaa ataactacgg caggggactt ttggtcgaga 76980
gcgcagccgg gtgcgttaca cgcggctgcc gtatcggtaa attttagcct cccacgatag 77040
acaggctttg gcatatcgtg cgcccgttcg ctgacatcga tatgttttac ggggcgcccc 77100
ttctgcctct cctcgatccc gactgctgcg taggtagatt gctcgttatg tgttttttta 77160
gttacgacga gtttttgagt ggctggagat aacagggacg ggctcaatgt ttcattattt 77220
gggggggcga gcttatagtg aaaggcgagt ttggaagagg cgccatcgga agcatcggtg 77280
ctaaccgtag aaggacactc gacattctcg ggaactaccc ggtcgctacg atcgttcaac 77340
tctttatgaa acaaaaaacc cgtttcagca ttgtcgtaga cgtccttctc tgcagccatc 77400
ccatcccaca tgctctctct atcccgacta aagtcattcc ctggtaattc ttcatcttcc 77460
gacgccgttc caatagatag tacatcctcg acatcgccgt ctcggctctt gttgtacacg 77520
gggatcggat attgtctaga ttcgtcggaa aaaaaattag ccgcgtcctg tcggtcgagc 77580
acggcgatgt catcatatga cgcgcccgtt tccacgcgaa tgcccgcatc tatgtatggc 77640
agttccgaga gaacagcgtc atcgctggaa gttagccgta ttacggggat agggtcgaat 77700
accgtcttag gccatagaac tttcacggga accattcccg tgtccactat cactaaacac 77760
ggaggagcgg aagaaagggg cttggaggct atgagatggg acaagtgttc cagctgttgg 77820
ccgaggcatg catttttcgat tggattgctg tcgtctgcca acaatttccc cccccaggaa 77880
gtcgtgtcgg atgaaacggc ggcaggttcg agaaagcagc cctcggagcc gcttctcgag 77940
tcgaaaagac ggacacacag attcagtcca gagccggagg aatacgcttc tggacattct 78000
gcggcgatca cgatccgtgc cccgaataat gtagctgcgg ctgccagatc catagcgttt 78060
acttttaaga ctccgctagg gggtgtggac gtgacggtaa atgtcatcgc cactcctgtg 78120
ggttcatata aattgggacc gtctgaacct ttcgggatag ttttgtcggc gggacgtaac 78180
acggacgatg tggtcacgtc taaagtcgaa gcagcgtccc cgcgggctgt gacgacgtca 78240
tcgtagcttc tacagctttg ctctatctcc gcgggtagaa gcgaggacca catcaccgcc 78300
aatgcggttg gcggaatgca catacgagcc agcactgttg tcgttgtcaa aagattcgac 78360
ggcacgaccg cacgaatttt ggcaaggccc gtactcgtag ccccacctac accttcccag 78420
ggtttaaggg ggtctgtttc ggaaaggctg ccttgtttcc aatcagaata ccgcaaagca 78480
aaaagggatc cgcctgacgg gtcccacgct ccgccccgtta aactcatcgg tcggcaattc 78540
gagtccgacg gggcatcttt ggatagctgc gtagataaac agttgataaa cgccgtagtg 78600
gacagcgact cattgatagc gccatagagc gtcttatcca taaaatcgta ctggctaata 78660
agatcgagct gggaaaaggt caagacgtgc cccggcatgc acgtcataat agcaaccatc 78720
acgtcggcca actccagccg aacgggtcgt ccatttgcag ctattttttt aagccccttt 78780
ttgtcggcgg caggggcgac ttgccccgga agaaaaaaaa tatcagacaa gctagcaccc 78840
gttttacgcg tgagcgtaat ggccattaat gcgcaataaa tggacccgat cgcttttact 78900
gtgccatccg ccagccaatc gtagttttgc gtacgtacat acttggtgaa ggcgcggaaa 78960
ttatccgccg cggcttgaac gaaacccagc ctcaaggcca tgatgtcgcc tagcatgccc 79020
gcggcaacta ccatatctct agttgacata acttttgaag ggatcgcggg cctcaggctt 79080

-continued

```
aggccggagg gctcgcacaa acacgcggcc attttttcac caacagttcg atagcagaca  79140
gaatatctca ggggcgcgtc ggaggcgtct aaatatgtat ggatgcctgg gatatctatt  79200
tcagaaaacg cctcctgcag cgtgacaaca actgatggtc tgatccaagc agctactcgg  79260
tgtttaagat atcgatccac gaaccccgcg gccggtctgt tgttcgcgtc agcattcaat  79320
cctgtatcag aggggaggag cgatggacac ccggcaactc ccggcaaaat ggcggaatat  79380
gcagcataca gcgccaatct cagctttaca agccgcgagt atcgagttac gtgccgaacg  79440
taccacttgg ggagccgttt agagagaata tcgaattgcg aggctattgt actgagatcg  79500
tttaagacaa aggttggcgg gatctttgca cacagagtgt ccatctgttt ttgaatcgat  79560
tccgtttctt tgagggccgc cagaaaagca tccatgactc cggctctgtc tctgtatttc  79620
gcatcgataa gtccgatgat tttagccggc agcctagcat actctgcgtt atcgcgcaaa  79680
gcgttgatcg tattggaaga gactttagcg cgagcagcac tatctcgggc ggcggcaaac  79740
ccctctgagc tcttgtccat cctgtcctta tcgtgcataa acgtggacca tgtgtcatcc  79800
caagcgactt cggcaagcgc tagttcggat tttaactcgt ccaatcggct cgctaagtcc  79860
gcgagagcat cgatccgctc cgcgtatata gtcatcggac cgctttcgtc gatccgggaa  79920
gttagctcgt gcgaatctat gacagatcgg gcgtgtttta gccactctac cgtttgggta  79980
tccaattctt tagtttcttc gactttactc aaaagtattg ccgcttgagt gactatgtcg  80040
ttcgcagttt cagccttttc aatagctttc gctatatgcg gaggcatcgc gaccagccgc  80100
agcaggtttt ttaaattggc caattgctcc gccgtctctc tgtctgcggc ataagaaact  80160
tcggccaaac tcttcagaat aacttcagct ctcgatttcg cgccctcaat agctgtcgtt  80220
acccgcagct ttattgagga gacggcttct atatcgcgtt ggagagtatg agcgctatac  80280
tctgcatagg ctgtcccgtt gaacgccgta atgtcttcct tttccaaatc gttggttatt  80340
gtcagtatgg cgttcgccga aggaatcacg atagagaccc catattcaag agcgcgacgc  80400
gccccctcag ggctatacat tctagccaga ttctccaatg cctctctaat ttctatatct  80460
accctccccg ctgcgtgaag agcctctacc ctcatttgtt catgccgagc taaaaagccc  80520
gtaaattcct catgcccgtt acgataaaaa tccacgtatt tggccaacgt tgggaccgct  80580
cttacgtctg gttcaatttc gcccaataac gtgtaatagt ccaagttccc gccgcgggca  80640
tccgcgtgcc ttaatatagc gagtactatc ttgattaact gtagcaaggc gtcgcagcta  80700
actccgaaaa gttttgtgta ataaggagcc gccgctataa acgcgtctag ccaggtcata  80760
tttttcaaaa atgctatagg aggcagaatt ccatgaattc tattcggggt ggaaaacggg  80820
ttgaacttca atacagtttc tatcgcatcg tgaatcgcac gaccatgcga cataacaatt  80880
ttctcggctc tggctctgaa acggatagtg tcgtagccgg ccaccacggc ccttttctcc  80940
aaatcactca tctccatagc atcaaattcg gatttcagct cggcattgga tagtagggaa  81000
tgaatcgagg aaacccaaac gtcttcgcta tgcgatctct gggcacttat cagatttctc  81060
tcgtaggttg taacggccgc ctccaattct acggtccgct gatttacaag ccctaccgat  81120
tttgccaggt cggcaatttt acgttggatg tgggggtccg taacatgcgc gtgactctcg  81180
agagctgcga tggctgtatt ggcgtctctc gcgctctgca gcgcgtgagc tatttcagtt  81240
ctggcgctca ttataacact ggcgtcgcta tcagcggctg ctgttttggg atctgaagtt  81300
ttgaccttgg ttattgacgc gatcacgcta ttgagtgccg cgcgcactgc ccgatgtaga  81360
ccatctaaac ggtccccgtg ctgcgccacg cccgcggcca cctcagcgtc ggataacagc  81420
```

-continued

```
accgttaaga acgaaaacgc gtcatcctgg cctgcgggta gatcggccat tattcccgta  81480
gagggagtgt ctgcagtcgc cctgtttaca tcggatacgg cgttctgcag cgccgtaaca  81540
gccgccgtag ttttttcgac cgacatcggt tcgaggcgcg cagcggcgac tgctgcagaa  81600
agcgtatcgg catgtttccc gaaaaaaacc gacgcggccg gataaccccc aattggaccc  81660
aatattacgc gtatggccag agagaaagga atgccgaggc cagataactc tgcggcagtg  81720
ctcgtactgg ggtgtgacaa aattgtccta tactgagaga acaacagcca caaatccgtt  81780
cgcaaagtcc caataacatc gggtggtgcg agagctagaa aggtctctag cggccccgta  81840
tctccaggga tggattgcgt tatggttttg actgtcgagt ccaatgcgcg caacccagca  81900
aacctttgta gaggacgcag catcagctta atcgaagaat ataaagttct gatctcctcg  81960
taacgatatt gaagtgccgc aattaaggtt tcggcatcca gccgcctacg ggcgatagcc  82020
gcgcggtcat ccgaacttag caaatttgca aatttgtcgc cccctaaagc atttgacaat  82080
tttactaact caaccacatc cttcataact tcctccagtt tttgaagatc ggccgttgtc  82140
tccaaatcag tgtatgacgc aactctagct tccaactcat gtaagcggtc caaatccgcc  82200
agggctgttt cacggcgggc ggcgttgttg ttaacggcat cgacttcttt gatcagtgtt  82260
tcaaactctt gtcgactaat ccacccgccc gcttgaacgg ctgccattgc cgttttccat  82320
accgccagat tttctggatt ttctaaatta gagtcatttt ccagcagatc cccgagcaat  82380
ttagattccg gtgcagttgt tacgggcggc ggggcctgcg cgccactacg cgccgctact  82440
agggcaataa catcatcgag cacagataat gatgcgaaca gcctggccat tttttcatgt  82500
tgctcgacaa cgaccatttt aaatctagat gtgctagcca cgttggctcg aagcgcattc  82560
gcgctataga gagccccctt caagtaatat tcgtgtagtg cgttgccgac tgcatcaacg  82620
gctgccctct caatagcagt caagcgctgt gtaacgacag atggggagac tttagctatg  82680
ctctcgtcgt cgcgcgatcc agaagtaccc ccagatcctc ccattataaa tgcatcaaat  82740
gaggcgtgca tcaatcgaac gccggcgtcg agggcctcca attcagctag tatgagttcc  82800
gccttcctcc tggcaacagt ttccctatca cgtatgaacc tgcacagcga tgcgactctg  82860
tcggtcaagc tctgttcggc atgcaaagac gtcttctctg agtatatctt tcctggatta  82920
ctattaaacg cgcttactaa cgatgtcgcc atcctttcgt agattctatc tgcatccgca  82980
gtgctcgcct ctctctctat agagtccaaa gttttgtgaa gggcatctgt gagctcctcc  83040
acttccagag ccactaatac cagcttgctt agggccaatt tgcctatctt ggaattttca  83100
gaaagtacag attctatgag gtctgcagat tctccggctc gcgaaaccgc cattcccgta  83160
gaatcaatga acgcgctaaa gtgggcgggc ctcgtaaatg ctttaaataa tgatgccatc  83220
tcggcttcta cgacagatcc tatttccgtt gtggttcgag cgccgttttc gataacgtag  83280
ttgaacaatc tggtaaaagt atccagccca catatatcca gaagtccgtc atagtcaccc  83340
gaccgtgaca agtggatggt cattcccata cttaaagcta tagattgctc taaatcatcg  83400
atgttagcat tgatgtcgct cagaatagag ctagggacgt gttcgcttgt ccatagcccg  83460
tctcgtagcg actcgtcccc ttcccccgct accgtgtgag gattaaaagg tggccggtct  83520
cgcaacgatt ggccgtgcac gaagtgctca gcacgcgcct gagaacttat aaactcattg  83580
aaggagacat tgtccggccg ggtagcttct tcttgaccag gtatattatg tgtcgtgctc  83640
gatccactat ctgcttgttc agacaaactt atcgatggag ccaccggatt gtccgtatag  83700
gtcaaacatc gtttagtttt ccgggacggt tttctgctcg aagattgacc ttggccatcg  83760
acggataagt tctctgaact tgacggagga gtccatacag ggcgcctcct cttatgtctc  83820
```

-continued

```
tcaaaagact gtttgggcgg ggagctagat ttcgtgtcag tttcaagccg aactacattt  83880
tcccgcgttt tgggcaaatc aggccttgtt agcaccgaca gatcatcgcc gatgtccggg  83940
aatgcagtgg tccacgcatt tacgatggac tcatgattgg ttatatcaca tatggcatca  84000
actggagcct cctcgggagg caggacgtat gcgtcctcct ccgcatagcc catttcccgc  84060
ctaacatcca catcccctgc agcgacggga gaacgatcac ttctggaatc gacagcgact  84120
ttgatgtcct cgctacgtga cgtggaggtt ccaatgatga tcctagttgt tgtaggctgt  84180
ggcctgtaag ggggatcgag attggccagc actactttaa tgttctcttc ctcgttaacc  84240
ctgcctagat ccaaaacgat gtccgctgta ccgtacagcc gtgatacggc tgatattatt  84300
tcttcctttg gcggtgtact ggagatcata gatacaaagt aaacaaaggt cgcggaccac  84360
tctggcgccg tcgagggatc cgcataggac gtgagatatt gataaaaata accctcgctt  84420
actcgaacga tacacgcttg gcctatgtgg ccatgaccgt gtggatcgaa aatgtagatt  84480
ccgttatcgg atctgtacac ccctattcct atgacgccga tgacgatcag gcaataaata  84540
tcacctcgtt tctgcttcca tactttttct atgaatgtcc gcgcagatat ttgggtttct  84600
aagatagtgg aggtgttttc atctacgtag aagtccaatt ctccatagga gctcgaaaac  84660
gcaacacaca agttgccgtc gggctcattt gataagatcc tgtttggtaa atcgtgaggg  84720
acgcaagtcg tataccttcc atcgcgagag gtttctattg tccattcctt tccctgcaat  84780
aacagtctat ctatggcctc ggtcgacaat accgcatcca acccatacgc aaaaactacg  84840
cgcagaaacg ccaatgacga ccgcaagcat gaaaccgatg accccggact caagtccggg  84900
gcaaattgat tcctgttgcc aacggcaact agtgtaaagt cggtggcatc aaccaccatt  84960
cttgcccatt catctaggat tacctccgaa tccatgtttg ttcccgaacg catggcgcgg  85020
ttttgcatgt tcgagacgga gctgtccctc gaattatccg atgtttccaa gcgccgcgtc  85080
gagggactcg gttgtaaccg cgtagatttc ttggatgggc gtgtagtgct ccctctactc  85140
tcactagcag ccatatagac gatggggcgg aatggcgcgt cttttcagat tgcgctttgt  85200
cattgagcga gttagacatt aaaagttgat taactccaaa attgtgatca atcagttgcg  85260
gccgcgtaag tggcgtggct gcaacatcca agtcggcacg aacgaacgat acgccaggcc  85320
gtaaaacgat agacgtgtgc gtcacgcatt gcgatctctc gcctgccttt cgttattaaa  85380
caccgtatcg acaatgtcga ccaaaccgtc tacagttact ctcggtttta tgaggaagtc  85440
cttcgcaaaa ttggcaaggt ccacatcatc gtgtgccacc gtatccaaat ccaatgtatc  85500
aaaattgagt tcgtcacgat gagttaaatt gtgcctcgat gtcagttcga ctactagggc  85560
ggggctatcg tcggttacta cgggcagacg gcccagcagg gtcgctacag ctgcgtcgat  85620
ttcgtcgttc gtgacacggt cttccatatc acgcggaacc tcgatccgat cagctatttt  85680
ttgccatact actcccacat tctctatagc actggccaag tcctgcgaac ttctgtcacg  85740
aaacgtagaa tttatttccg acaacgtttg ccatttgtcc agcagccaca cgatatcgcc  85800
ggtcccgggc ggcgtggaac acgatgtcaa ggctctgacg tgcaggtcca gcgaattctg  85860
caggcgagcc aatctggcat agtcggttcc gagggtagaa aaatagcttg ctgcctttac  85920
gctaaataaa attgcgcgct ccattaaatt atcgcatgta tgaacttgtt tcccagtttc  85980
ttctattaaa gtccgcaaca ccattgattt gagtcttaca ttcgccatta catcacccga  86040
ggagtcgtag aattccctga gagccgacag cacatcaacg attttccatg tgccaaaatt  86100
ggcacgcggc tcgccacggc ggtaaaccgt tacagtacct cctgctgtac cagctgcgaa  86160
```

-continued

```
tttacacgca aagaaatgct taaatatgta cgcaaattta accaactgcc tggatcgctc  86220
cgctaaatat gccgcacact tcaacgttct atccgctaag taattgaatt gaagtcctag  86280
ggccgttcca tgcatactaa tcaaaagcaa actattcgat atctctggac ggggggggcat  86340
aatcggtctg gtctctggcg gtaccatctg cacggccgca tagaccacgt cgtacaattc  86400
gcccatcagc atttccagat tatacgcatc gtccgtggta ggcttggccg tcagatctct  86460
agcaaacgga gcgagtgagg aaattagagc attgagcttg tttctatgat tcacgaaact  86520
gccaatgtac ggcgcgccgt aatccctggc ccaagtcaaa atttcgataa cagtgtttat  86580
cgggcgttca gaaaagacag atgtcgtgat agccgacaat gcgtccacgc aaacggtagc  86640
tagaatatat cttagaaaat ggggagttgt gctttcaggt gtgatgggca tggattcagg  86700
atagcgaatt gtcatggcca gacgaatcat acggctctcc aggtctgggt ccactgcatt  86760
tggtccagag atactctcta aatccgaatg gtccacacta gctagatgtt ccgacggttc  86820
acctccaatt aactcttccg gtggcacgat tccccatata tgctcggctc tggagtcgaa  86880
ccatagcatg agtgactcct ttgcaaattg tattgctcga ttggcagtcc cggccccgct  86940
ctggcggatt gcgctatcca tttccgcggc gaggatcgct cgtgcagact ttacatagtc  87000
ctcgtgggga tttggcggta tacatcgccc taatatctga gctatgattg cgctatctaa  87060
cccaagtact tttatgaaat ctgaatcggc gtccggagga aggccattgt ccatataatt  87120
ggttaagtaa gtcatgccgg gaccataact ttccatgagt ccgaaaacga tgtttccgat  87180
gacagctatg catccgataa cctgttgtac gtcgtcaaat gtgtcgagtt cattaacagt  87240
accacgagtt tttcccaaat ttgcctttag cgccgattca taaacccggc atgcctgtct  87300
cacaaaacct ctttctataa gcgcttccaa taactgtctc ggcgacgaac tgtgttgtac  87360
agccccccat gcccgcctag ccgattcgga gagtttcgct ttagcagcat cgagagcgcc  87420
cccgccgtca tttaagtcgc catcggtaat aagccggacc acggcagaca tatggatcgc  87480
taaggcatct tctgttaatg cgtgatcagc taatataatg tctggtccgt tccgcaactt  87540
ttccgctacc atacccggct gaactgcata tacatacggg tctccgtatg ctatggcggc  87600
agatgctcta acatcatatg ctgttctttt catattgttt gcctctacgg ccgagataag  87660
ttcgcgcgag cccaatgcgc tggcatcttc tgcgaataga tcctttaact gagaaggatg  87720
gggcgatcgc ggacttttaa aatattgatc gacaagggcc agcgtaaata gtattcgagt  87780
gagtggcgta aaggccctat ttgttgtaca tcgagacata ataacaaacg gggtgatcca  87840
cccgacggct atagaaatta atcgaattcc ttcctgaaca aacgggaaat cgtaaataag  87900
tttaaagcgc gtctgcgtca aggaagctgg tagttccaaa gcattaggag caggttgacg  87960
tccggataac aacccttcgg aagtataatc aaacgcgtcc gtggcgatct cttcaaaaat  88020
tgtcagccac tcacttatta ggggccacaa aacactcggt ccaaaaggac atgatctgcg  88080
cagaccgttt cgggtaagcc acgcaatggc ttcttctccc gtcatttcgg ccgccaatct  88140
acgcaaccta cgagaatcgt ctttccagga cattttatcc caccttacgg aggtacgcca  88200
caagatgaat ccgacaaaat tttgggccag cattgccgct tctgggcttc ctgtttgttt  88260
gtagacctcg agcacagccg cgaatgcatc gcgccacgtc gattccactt gctgaatact  88320
cattgtttct agagcctgga aaaatgatcc gatagcagtt cttgcttccg cagctgtagc  88380
atttccccac ggttccagtg gcgccgttcc agccgataaa gaccttagtg tatccagtaa  88440
agttttcaac gggaatctcg cttcgccctg ggtttcagac atggcgcgcc aataggtagg  88500
gatggatcta cgtatgtcaa tggaggccgt ataaagcttc aataataata cgttccctaa  88560
```

-continued aatgctgtgc tccgcaccgc agaaaaatat cgtgtgatcc gcagttacac cataccgtac 88620
tttatcatct ccatgacgca tcgagatccc gtataggccg gcccacgtaa gaggcacacg 88680
cgctacataa ctttgttgcg tttaactaca ccgccagtcc tgtattgcag tatactaggt 88740
gacatacagc gatttttatg tgcagtagtg cacacgcagt tgtcgcaaaa cgggcttgca 88800
aacgatcatc gccaatacag gatctcttta taactggttg ttgatagtgg acgtcatgaa 88860
aaccactttt cgaacaagcg acgtgcaggc atccaacacg cagtcaaatg cctcggacag 88920
gctgcatgac atcttacgga gcatcaataa ctcaatgcac tccggcattg ttcggcgcat 88980
caacataggc tatccgcatg cgggcaacag gcgcgggacg ttgaccgccg gattggaact 89040
gttgagcaat acgatcacaa cgacccctcc cggggcaaac atacaccgct ccattgcaaa 89100
ttcggcaggc gaagctacgg caacgatcat acaatcttta cgaacatatt ccggaagtgg 89160
agatctgaac acgaatggtg ataataacgt cctttcccga cagatcagcc tgacagattt 89220
ctgtttcccc gatgcggaga tgccaggact aattgtctta tctatgcgac atccactgga 89280
tataaacagc gaagcattat acagcacacc tgccggacgg gacccacggg cattggagtc 89340
agcgtggtat gaattatctg aactggccgc ggtatcggta aacagattag acggaagtgg 89400
tgtccggccg tccctattat cgctctcatt tcttattgct tcccgcgcgg gagactatgc 89460
ggataaatgt ggtgctgagg ctgtaagagc tcacgtgatt agcaattacg gccgccggcg 89520
gatagaggac aggctcgaca ggttcggaag ctgccaagca gcaatgttga gatgtcacgt 89580
gttcccacac cgacatatgc aagtattagg gggaatggtg tcgtggatcg cacagcgcga 89640
aatcgccagt ataaccgccg tggtcaaggg ctctcaagag agcgccagga cagaacagac 89700
caacaatcca agatcgtcgg tatacgttcc cgcatgcgcc tatctcgatt tagataaaga 89760
gattcacatg ctccatgatg acagagcttc ttcgctacta tacctcgttt tcgtttatgc 89820
acaacacctc ggacgcgaga gcatccgtgt atatctcatg cggagtcgtt taggggaatc 89880
ggtgttcaga gaaggcctcg gttacctgta ctccgggcta agagccggta acgctattaa 89940
cggtctggcc ggtataatag cgccacatgg agtagacgcg aatacggaat ttccattatc 90000
aaaagctttc gaggtacaca aacacgcctg tcgaaacacc ggaatcggac ctcgagactc 90060
cgagaaagtg gactggcgtt tagatctccg aggccgccct acaaagaatt cctgcatgta 90120
cgcagcatac tgtcgcgtag ggcacttgaa cgagtattcg atgccggcga agaagtctga 90180
acgttgtggc gggtctgtgg aggtccctgt tgtatgggtg ccgggagtag tgtgggatat 90240
cggagaatgg accgagtgtt atcagtagag agttggctac accgagatcc ggcatcatac 90300
cttacgtgaa ctgcttacgt ttggggatgt ttttgcgtcg gtgtttgggg aggagtcaat 90360
cttataaaaa gcctatttgt ggtacgcttc ggtctcgcgc tcactgagca acccgtattt 90420
tatccagtct gaaatcagaa tctaaaatgc agcgatccga tgaaaacgaa tccctcgaag 90480
cgaatagaaa tttggacacc gcctcgcgta actgtactga tgtgcaggta gccttgataa 90540
tggcaacgaa attgcatcgc atccagcagc aacttgcgag catgggatat ttatctggct 90600
acgattccgt gcccgatatt actacacccg tgaaagttct gcgcgagcgc attacccatc 90660
tagtaaatac attgaaaccc gtttgccgtt tcgatgagcg cgtgtactac gcctgcgggg 90720
agctggtgca tttacggatc aaatcacagg aagctacttt tgatgcgtgg ttgatgtcga 90780
aaaaattaag cctgaaaggc gagatcgtag ataacataca gcgccacaga ggtcacgtag 90840
agacggatat gctgcgcttt tacggagtaa cctatccctg gctgaaacga ctgggtttac 90900

-continued

```
agtcggcgtt gaaatacgaa gaatatctga ctgagttgga agacggcaaa aaagaatctc  90960
tttgccagtt ttttgttcgg ctggccgcgg cggcagcaac cgaagcgtca aacaaaaaag  91020
ctttcatgtc ggctttgggt accgaagtgt cgacctggga aacggctttc acggcttttt  91080
ttttcgctct cgctcgtcag atatttgtcc catcgactcc ctgtatgctt tttttggggc  91140
gcgaaggaac ctcaaccgcg agctgttatc tcatggaccc cagaactata aatacacacg  91200
atacccttaa agcgatcgcc gacgatatag ttccccatct cctagcgaga ggagggatag  91260
ggatatcgtt gcagcattta aaccaaaaaa caggccttat gcctgtgatg aaagtattgg  91320
attccttagt gatggccgcg aatgcggggg agcgtcgacc cacgggggta tgcgtttatc  91380
tcgaaccgtg gcacgcggac atcatgtctg cattaaatat gcgcggcatg atggcgacgg  91440
aagagtcccg taggtgcgat aacgtattta tcgccctttg gacttgcgat ttactgttta  91500
agcgctacga gagacacgca aacggggaga aaaatgtgac gtggacctta ttcgattccc  91560
gcgcgtcgat attggccacg cttcacggat cggaattcga aaaggagtat aaccgtttag  91620
aagcggaagg tttaggcgta gctagcctcc ctgtaaggga tttgatgttc gcaataatca  91680
aaagtgcggc gtccaccggt agccccttta ttctctttaa agacgcgtgc aacaagcact  91740
acattacaga tactcaagga gacgccattg caggctctaa tctgtgtacc gaaatcattc  91800
aaaaaaccga cggaaataca aacggggtgt gcagcttagt aagcgtcaac ctcgcccgat  91860
gtgttttcga cgagaacgga gagaaaaaat ttgatttttc cgcccttaga cgcgccgtgc  91920
ggctggctac ggtgttcgtt aactcgataa tgtctagcag cgatgttccg actgcgaaat  91980
ctcgttccgg taaagatcga cacagatcca tgggcatagg cgttcagggg cttcatacag  92040
ctctgttgtc aatgggtctc gatttgagcg atgaacgcgt caagcccctc aacaagcaga  92100
tttttgaatt gatgttgtta gaggccatga cggtcagttg tgaattttgc gaaggcgggt  92160
tgcccgcctt cgccgacttc tccaacagct attactcacg gggcgcctg cattttgatg  92220
gctgggcaaa cgtaggctta agtatgcccg aagagtggaa tgcgctgcgg gagagaatac  92280
aggcgtccgg gttatacaat gcccagttcg tagcgttgat gccgacagcc gcatccgcac  92340
aagtaaccga agtgagtgag agttttttgc ccgtgttcag caacatgttt aacaaagtga  92400
cgacggcggg ggaactactg cggcccaata atcaattaat gggagagttg agggagatct  92460
atgcggataa tgaggatcgg cgattgaaag ccatagcagc gttggagtgc gcgaactggt  92520
gcgtggagac cgctctggga aataagcccg aatgctctca attacttaaa tacaaaacgg  92580
cgttcgagta cgaccaatcc ctcctaatag atttgtgtgc cgatagggcg ccttttgtgg  92640
atcaaagcca gtcgatgact ctgtttgtga cggaagcggc tgacggaacg ctgctggcgt  92700
ctcacgtcat gaacctactc ttacgcgcct ataaagccgg cctgaaaaca ggaatgtatt  92760
actgcaagat acgcaaggcg actaatgccg gagtattcag cggtaacggc gaattgacct  92820
gctcgtcctg catactataa tctccaagca tcccggcatt ttgaccatgg ccacgcaagc  92880
acgcgggaac gaatttgtca gcggccaaac cgcacctctg cacaaaaacc cgtgtcccga  92940
aaacgcggcg gccgtcctaa agatggaagg tatcgagatc gaaccttcga ctagttccgc  93000
tagagataat tacaaagtgt cacggtactt ctacgtcccc gaatgcccag atatagggca  93060
cctccgagct ttgagtatta tgaaccgatg gacggagacc gaatttgtcg tcgccgagga  93120
tctcggggac gtcgccaagc ttagcgaaga agaaaaaaat ttctaccgat tcctctttac  93180
gtttctctct gctgcagacg atttggttaa ccttaatata gacaatctgt taggtttatt  93240
cgaacaaaag gatattcacc actattactt cgagcaggaa tgtatagaag ctgtccactc  93300
```

```
tcgggcctat agcattattc agctgatgtt attcgacaac gactcctcgg cgcgcgcaaa  93360
atatgttcag tctgcgttag agtcccccgt catccaatct aaattggaat ggttagaccg  93420
acgtatacta gagtgcacgt ctataccaga aaaatatatc cttatgattt taacagaagg  93480
cattttcttt tcagcatcct tcgcggctat cgcttatttg cgcacgaata acctctttgt  93540
cgttacatgc cagattaaca acctgatcag cagagacgaa gcgatacacg tagaggcgtc  93600
gtgctgcatt ttcaagaatt atatcgctgg caacaagcca tccaccgctc gcatccaagc  93660
cttatttagc gaagccgtcg acttggaatg tgcatttctc cgcgcagccg caccacgcga  93720
ctctcgctta ttggatattg gctcaatctg tagctatgtt cgttacagcg ccgacagatt  93780
attgagaatg ttggacgtgc caccgattta cggcgaaccc agccccgctg ccgactttcc  93840
gctatctcta atgtccgctt caaataatac aaatttcttc gaaagaagaa gcaccgcgta  93900
ctccgggagt gtatcgaacg atctttaatt agcctgtgtg caactgtact ttctacccct  93960
acccacaaga attaataaat gaattcaaat tatcgctttt cgcaccgtgt agtttgtgat  94020
gcatcccttc cccagtacct tatcagcacg gagtcgaaag gccgtacctc cgggatacac  94080
cttagaaatg cggttgaaat aactgaagct tcggcctcat tgggtatact gcgaaacacc  94140
aattcttcaa ccgctacatc gtcacgtata tcctgcatta tggggaatcg ttttaaaata  94200
ctaattctgg gcgttctgcg ctcgggcatt atagtcgcaa tgacgtgctt tatgaacttg  94260
tattcgagaa cttcgcatct cgtttttggg gggtgcaaag atcttaacaa gctgtaattg  94320
gacgcgagat ccctgttcgc atcgggcata tcagccggtc tctcgtaatg atggccgccc  94380
gtgatctcag gattgcaaca attcatcaac gacgaccggc cacgctcgtt atcgctcgct  94440
ttaccgcaga tagtgcccga accctgcttc aatgtcccta gatctattat ctcttgcatg  94500
gatttcagtg tgtgttcgca atggaggtct gtttgacacc gaacgaagtt agacaaaaac  94560
gtgaaatagt ccatttttaa cgccgccaaa acatctctgc agtagatagt cggcggaaat  94620
attctagtaa ggtcgatgat tatatcacat cccatcaata gcatgtctgt atctgaagat  94680
aacacatacg caaccgtttt ggtgtgaaag aggttagcac agatatcgtc cgcttccatc  94740
atggccacat cgacataagg gtatcccata tagcgaatgg tatccatgca gagcctatgt  94800
agaattttgg gcgtatcaga cttatcgctc catctgcgtg gtcttttccg cttccgcgtt  94860
cttttgttcc gcgcttctcc ggtatccgca ttctcgcatt cgtcgcgcga acgtacttgc  94920
agcctcccag aacctcctcc cctcgcgatg cgagtagctg ctagcgcctt tgctccataa  94980
agcgttttcc catacttcga aaacccccgg tccgatacaa acaccggata atacgaccgt  95040
tggtgtaaca aacgcagcag acagtataag caccgcagcg tggcgaccga gttgtcgact  95100
ccgtcgacct taccagggta aattttttcc agcagtccat acataacatt ccataaatcc  95160
acggcaatgg gcgtcatagc cccgccggat atcgaacccg aaatgtgact tctcactaat  95220
ccgttcgcat aggcgaagtg catgcaaccg tacacgccca tggcaacttt cggagtcgca  95280
gtgtaagaga cacggggtaa tacgaatttt gaattttggg agtatctgtc aagtatattc  95340
aactcttgaa taaccacgac caggcgtagc tatccaaatg ccgaaacgtt aagccgctcc  95400
ataaaacctt gattccacta ttcaattgtg caatagttgg attagggcag gtattcggct  95460
ctatctgttc accgtataca cgctataccg tcctttaaat tagacaaggt gcgcgtctct  95520
aaacctataa ttcccggtag cggtataagc gacacttatt acatgcctat ccaccacgtg  95580
atgcaaccca cacgattcac gttgaagaca tgtgacattt gctgtaaata tacgcaggta  95640
```

-continued acaatgtgtg cggcgaatta gacttacagc caatagtaag cgcgacataa cactaaatgg 95700
gcggcgcgac attcgagtgc ctataggaga ccgatatacg taaccacgcg tggtgcgatt 95760
gcgacccagg ctccttcgat ataagctttc cccctcacat ccggagccat ccgttagatt 95820
gactctgcct cagcctatac aacgcgccaa agaacagtgt gctacggaca gaagtgacgc 95880
cgacttgagt tcacggcatc gagaccccag aaccggtctc ggcgatggcg cgaataacta 95940
tgagcgatga acacatcata gacgatgcag gggccacttc taacgattcg cccaattcct 96000
ggaaagtcgt cttggccgga gagaaattta gaacggtatc ggctgcagta cgcgcaatag 96060
tagattctgt gaagaatccc ctaatcatat tcagcgacga cggattaatg atacagggca 96120
cgatttgcgg tcagcaaaca ttcgttccta tcgagtgcgc cgcctttagt gaatttgaat 96180
ggcgcgggtc cgcggccata ttcctggcgc taacagattc gaggcgtact ttattagacg 96240
cgtttaaatg cgacaagaaa aaagcaatcg aggtctcctt tacgttccga ggggaaccgc 96300
cgtcgcgaca tctaacccag acagtcacgt atgtaactga taacggatcg ttctcgagtg 96360
ctatcatcaa gtatgaactg tggtgcgcct cagttttatt cccgcaaaaa attcccgatg 96420
ttacgttctc agtaaacaaa cagcaattaa acaagatttt ggctatagcc gccaagagac 96480
ggcacgagca actaacattt gcgttgaaag cagaaggggg gttttatgcc ggaactgtgt 96540
gcgatgttat aagtttcgat gtagacggga gcgcaatgac tcagtatccg tataatgcca 96600
cgactgcggt ctcgtctgcc ctcgtcttag catgcgggaa gaaaagagcc gcccgtaatg 96660
cacccgtgac tgcatatggg agcggaaaac ctttctgcct cgcactggaa gacacgaccg 96720
cgttccgaaa cgtcgtacag aaaattaaaa ccggctcggc aggggcagat ttgggatttt 96780
atacggcgtg caatccaccg atgctatgcg tgcgtccgca cgcgttcggc agcctgaccg 96840
cttttctatt ttgcaactcg gattgcatgt ctatatacga attggaggaa gcgagtgtag 96900
cggtcggcgc agtaacatcg aaacgcataa acgaatattt tcccagagta tcgaccatcg 96960
attcccggaa aaggcgcccg tcttcggtcc tctcggaggg ggatgggaaa ctccttaaac 97020
ccgacggcca ataggtctcg tgtccgcgcg cggaccacag tcatgacgcg gggaggtcaa 97080
actgatataa gatgtgataa gactgcttag atttcattcg acctggttat tcggacatac 97140
atggagcccg tcgacaacgc gtctccgtta cctccgactg gcgcgggaca ctgtcttcat 97200
aggattgttt gcatcgaccc tccatgtaca gcaaccattg gcagcgggag gagcggcaat 97260
aggtgcataa aatgtattat ggttacgacg ggctccctgt tatcgatggc cgcacacttg 97320
accgtcaccg tattttgcgt ttccgtgatt ccgtgtatag atcgaaccgc agcctatcca 97380
cgctgcacta tgggcgccat cttcgcattc ctattctttt ttaacatgcg gcttactgca 97440
cgatcatcgg aaatagtgct gctcattggc agaccgacac aatttttatg cgctctgaca 97500
gcatcaatcg ccgacacggt cgccaaacat ctagcggcta cccataagga ttacctgacg 97560
acattgcgag caatagaagt aatgtctctg ttgacttttg tcatgctcgg agctctgatc 97620
gcatcttatc attacgtctg catagcaacg tctggagacg tgacgtggaa gaccgggttt 97680
ttagttgtgg cggcagggac gattgccggc atcacggctc cgtatggaga catttctcct 97740
ctagccggct ttctttcggc gtatacggcg ttagctattc acgtggtcag agacgccagt 97800
cggtctctaa tgaacacgtg ctactaccgt gcacgtcggg aaattactgt gaacggtgca 97860
tatcgcctcg gtcgcgcgcg tctcccgccc agcacggacg ccgaggcgac gcgcgaagaa 97920
gacgtatcca gttacgatac gctggggggg aatattccta cgataattct gagcctcata 97980
gcggtcatct cgattccagc catagccagc tttcaaaagt acatgtcgaa cgcaactaag 98040
caccagtcaa cattgactga cacgttacgc agtatatgcg gtttcttggt gggtacaagt 98100
gtcgcgatat tccttccgtc gcgctaccac gaggttctgt tccgtccaat tcttgtatta 98160
ctgttaatat tcggggcaat ggctactacc ttagccggct tcggtttact tctcgggccg 98220
acattgtttt ccgcgacagc cgcggttctg tgctgctaca cttgtataaa tgtacgcaac 98280
gcgaatagcg gaataaagca attggcggcc gccgcagctg gtaaatgcat attaggaact 98340
gccatctcga gcatgttggt ttgcgtgtta atacaatatt cctgatcgcg gagcgattaa 98400
tttttatatc atgtgctcat agcgttcttt cgaactgcga ataaaacttt cgtggctact 98460
aaaggggcct atcgtgggtt tatgcgctgt cgaaaacatg aaagggccga tttaaagcta 98520
agttgcgcag gcagaggcca ctccatatac gctctcggag acgcggctcg cacgccagct 98580
gaaatatttt ccccatgcac gcgtcacgcg cgttgcgagc tttggggtgg acgagactct 98640
tatttgtcgt tttattttcg ggccgcgtcc taagcgctag cattaacccc gatctagcta 98700
cacccccggt cattgctttc aacccgtcaa gtattccggc cgatgatggg cctttggcca 98760
aagttcctgc atccccgccg gcaggggaga aagaggagag ccacaagaat gcaagcgacg 98820
cgcgtaggat gcctagtata gtttgcgata aagaagaagt tttcgttttc ctgaacaaga 98880
ccgggcgttt cgtgtgcact cttaagatcg cccctccctc cgacaacgaa tggtcgaact 98940
ttgctctgga ccttattttc aatccgatcg aataccatgc taatgagaag aacgtggaag 99000
cagcgcgtat tgctggcctc tatggggtgc ccggatcaga ttacgcctac ccgcgtcctt 99060
ctgaattaat ctcttctatt cggcgagacc cccaagggac cttttggaca agcccatcgg 99120
cacatggaga caagtacttc atatggctaa acaaaacgac gaatacgatg ggcgtggaaa 99180
ttaggaacgt cgactacgca gacaacggtt acatccaagt tgccatgcgg gatcctttca 99240
atcggccttt actagataag cacgtgtaca tccgcgtgtg tcaacgaccc gcctcggtcg 99300
acgttctagc cccccccgtc ctcagtggcg ataagtacaa ggcttcatgc atcgttaggc 99360
atttttatcc accgggctcc gtctatgtgt tctggaggca agatgggaat atcgttacac 99420
cacgtaagga cacggacgga agtttttggt ggtttgaatc agcccgggga gccaccctgg 99480
tatctacgat aacgctgggc aactcggcca tcgaccctcc tcccaagatt tcatgtctgg 99540
tagcctggaa gcagggaaat atgatgagta ctacgaacgc cactgcaatc ccgaccgtat 99600
atcatcatcc ccggatatcc ctggctttca aagatgggta tgcaatatgt actacgcaat 99660
gtgtgccgtt cggaattacc atacgatggt tagtacacga tgaacccaaa cctaatacaa 99720
cttatgatac tgtggttaca ggtctttgca ggaccctcaa gcggcataga aatatcatca 99780
gccgaatatt actccaagat gactggcaga aaacaaagta tacatgtcgt ctcatcggct 99840
atcctttcga cgaagacaaa tttcaagctt tcgattactt cgacgcgacg ccatcgacga 99900
gggggtcccc catggttctc gcgatagcgg ctgttgtggg actagctttg attttgggaa 99960
tgggtacact cctgacggct ctgtgtttct acgcctccgg gaaaaaatac atattacttt 100020
cgtccgtcta gtttgcggtg acattgatct ggctcattat atgccccgag ctcttgtaac 100080
atcgcggacg cgatttccgt agtaggcaca tctcaaatgc aaaagcggca tgtcaaccgt 100140
ataggtacat ccggccctgc ttacagtcgg tagggcatat atccaccgga aaacttcagc 100200
tttagactcc tcaggtgatg aggaatagta tgtaaccctc tagcagtacg gtatttctaa 100260
aaaaaggtag atccttttcc acacggcaca gactaaataa cgtacactac acaggttctc 100320
tcgaacttcg tttggaccgg aattattccc tcggcagcgc ctaaaaagca aacctctaga 100380

-continued gtagataagt gtcagtgaac ctaggccttc tttgttccac ggctggaaag ctaagggacg 100440
aggtacacgc gaccccagcc acgcacgaac agagtttaac ggaagcgtcg tttgcgggat 100500
aaggttgtcg gaccccgcgg gtccgttgaa aagtggctgc gcgcctaccg acgaatacgt 100560
cggtaacaat tttagaaatc gaatatgact gcgagtaccg tacaatcgcg aaatacggtc 100620
tctatatagc tactcggtcc ttaaatatgt aagtatgatg tcccctactc ccgaagacga 100680
ccgcgacttg gtcgcagtac gtgggctgct ccggatgatg gacgagacca catctgagcg 100740
acacaaacgt tcgcgttcag gatgcccccg gttgttatgc ggttgtacga tcgggatcgc 100800
tcttactgtg ttcgtcatca cagctacggt cgtgctagct tcgctgtttg cattctctta 100860
catgtccctg gagtccggta catgtcctca cgaatggatc ggtttaggct atagttgtat 100920
gcgcgcgatg gggagcaacg ctaccgagct agaagcccta gatacgtgct cccgacataa 100980
cagcaagctt gtcgacttta ctcatgcgaa aattctaatc gaagctatcg cgccgttcgc 101040
ctccacggac gccaatagca gcaacgtctt ccgactacgc gatagtagaa caacgtgcgt 101100
acgccccact gccgcaggac cggtggccgt cgactgcccg aggacctgta ccgccatatg 101160
ccagcggccg cgcccattga gtatcgtcgc ttcgataatc agggacgccc gtacttctct 101220
tcgtctagaa cgtcgcgaat attacgaagt ttatacggcc attctctcaa atggcagcgt 101280
gaaataaacg cgagagaccg agcattagag tagcacttat ttattctatc gcagagaaac 101340
accgcgcgcg ttcaaaaaaa acacaggcgg ggtacgataa atttacgcgg ccgcgctatg 101400
tttactttat acatcagagg tcatcgtcaa cctgcgcaaa atttccgtta ccgtaaccgt 101460
gccgccacga tgcttgcgca cggcttttgg gcgtggaccg gtcggtgcct ccaaaaggcg 101520
ttcgggggc gtttcgggga ccgtactggg agatccgaca gccacggcgt tgcacatatc 101580
tgccggaatc gccaatcccg tcgtagaagc acaaccattc ctttcaatcg aaaaagtggc 101640
agggagggtt gcggctcggt ccgatgcggg cgaaggctcc gcatctgtgc gggtcccatt 101700
tgacgtagat gccgtagtcg gtgtcgggga gcggagataa gttagcgagc actgagcggg 101760
aggcggggag tcttgagtga agtgcatagt gaagatggac tgtccattag aggcaggcgc 101820
ttcactggtc tcgcccccgt cctctaccca cgcacgcttc gattgctggg gcgagtcttg 101880
caagcatcta acgactgagt cacctccctt agccgcgggt tggtaggtga ccgtcgactt 101940
aactcgtgcg tgtttgaacc agagcgccac cgtggattcc gtgtcagccc acgtgcacga 102000
gttcatggtc ggaaatagct cccccaggaa gcactggaac cgtttctgtt gccggagagc 102060
acgtctcaat gttgagttag ccatgccgcc ctgcagccat accgcatacc cgttaaagac 102120
catgttgagg atatattgac agcggtaatt caaaagacca accaacgcca caatagcgac 102180
tacaggccgc gatacttcac tttctgggct gcttcgccac gcgcagcacg tccacaaagc 102240
gcccatgtga acaagagggg ctaaaacggt tccgataaaa tggcataaca tcgtagtgtc 102300
ggcccagctt tccgatggta gggaactcac ggcttcggca agggccaaaa atacggtatc 102360
aaagtcgctc ggggcccgag ggccgaagac gttagggcac gcgcgcagat ctaacacgtc 102420
cattagccac accgcccacg tatacaacgt ccttacataa ctcagcaata gttgcaagcg 102480
tatcgacgta tcggcactag gcgccgttac atcatcgggt ctcatgtagt aggcgtattt 102540
ttgaataagc tctgtcccgt cccgaatctc tcgccaacat ctgagataca gtgcattatc 102600
tttcgcgagt tggaacggtt tcttgaccaa ggcgttacga ttaatgatag ggtaaaagag 102660
caatgctgct tcacgtctag tcggatcgca ggtctcgggc gaaccggcac ggcatccatc 102720
gcgtctcatc tctaaataat tcatgtaaga ggcctgataa cacctcttga ccgacgcacg 102780

-continued agtcagcttc ttttttttca tacggcgcgc aatgcgcgcg cggtagggcc tcgtatactc 102840
ttccgaggca tcccctaacg cgaggtagac gacgatacat tccggaactt tgttagaagg 102900
agcgtcgcgc aacagcgttt gtcgcaaagc agagagaaat cctgagggga gcacttctac 102960
gagcgcgtct tcttgagctc ggatacccga aagagatgta cccgttgttt ccgatagctg 103020
acacgggtac tcctggacgc gcgtcggcga acctcgtgac cgggaattta acgccaacga 103080
atccgtctcc ggctcgggag aagttggcgt aaacaactcc ggcgacatgc tagcgcaagc 103140
atatcggtcc atcggaatct atacagatta ggcgcagtac ggaaaggccg acttttggga 103200
cgcgaagtgg ccagaagcat cgctttcctt agcacaacta ttcttaaatg cgatgcttac 103260
tcagggcgga ttgatagtcc cgcccatacg gcgcgtcacc acgatctgca cgccgctccg 103320
tgcgcttttt ttttaccggt ccgttttttt gaagatcgcc tccttcgcat cttctaacac 103380
atcctgcagc gaggctagcg tgccgagaag gttatacccg ctcggaggcg gtactagctt 103440
tagagcttcc aactctccat tcttctcctc tccacgaatc gctgtcgcaa tgccgtcggg 103500
cgggtctcct cgctcaaatt ccaattctaa atactccata gcgtcgtcgc ggtcggctat 103560
atattcatct acgctaacag gtcgatacaa gcctttacat acgtagcaca ggtggcggta 103620
tagcttaaac gtttccgacc aaacgtctac agcgaggtcg tggtacatgg cggcgatcgt 103680
gaggtgcgcg acgccgatat tcaaatgccc tagcagacgt tgcagaacaa tggtagtggc 103740
taccacggtt gcggttaagg tgtctcccga ctcgatatct ctctcattcg ccgaggtgct 103800
gcgcgatacg aactcgttca taagctccgt aagcgcagat ctagtagcga cataagcccc 103860
gacgaaagtc tcccctagcg gcgcgccccc ggtaccataa gaagctgatt ccaatctccc 103920
caggcacatt ccttccgcat aaagaacatc gaggctctcc attgggagct ttttatgacc 103980
acggcctagc agtcgcgccc acgcgcgaac acgattagct ttgaaacggt gaagcattcg 104040
acccgacgaa acatacagga actgcgcggc gatactagca gccacacatc ccacagtaac 104100
gcacgacgat agcatttcaa gttcttcttt cgtcacagac accgtgtcag acgacactct 104160
cgacaataaa aacacttctg cccgtagcat agcggcagcg gcatagcgca ctgcactttt 104220
acacttcgat cccaaaatgc aacggagttc tggccagtac gccagagagc cgtaggaagc 104280
acgtaaaatt gcagcagcgg ggcccttcgc cttacggata gcgccgcctt caaacatttt 104340
agcgtcaccc gtaggaacgc gtggcaaaga cgacaataat ttggcgcgac cgaatttgga 104400 aaagcccct ttatgtatcc tcaccgctag ctccaaagcc gaggtaatta agaaaataat 104460
agcgtctttc tgattcagct cgccagacac tacggcactc ctcagggcat ctatcccgag 104520
gcagagaata agcgcgtgtg cttgcttcgc cgtccgtttc caggcgagag cgccttttgg 104580
tggcgcggac gtatacatat ccccccttggc atagtctgat ctgctgtcag aatgccaaag 104640
tggaccgtcc ccgaaagtat tgccccgggt atgtagtaat ttgtcttctc gtatagcctc 104700
gactcgaggc acgggttcca acagccgccg caacggaatg aacgtgccaa ggctctcgat 104760
aaacgtcgga ctcgtgcctt cgaccttgat gctattgaga tcgggttcgg ccgataaagg 104820
ggaagggacc gtgtaagcag atacgacccg ctcgtaaggc cgtaaatcgt catcatctcc 104880
cgaaaagctg tcgcttccca gagattgact cttttctcta gacgatgcac ccgagccttt 104940
acttatccag ttctgtttta agtcagacgg cgcacgctcc aagctgctgt cgcgattaaa 105000
tgaggttcga tcctcatgac cgccggctct cggtcctcgc ctgcgtgacg atccgcggcg 105060
tcgtccgcgc acgcgcccag accgagccgc atgtgtgtat tcccccccctc tagatgatct 105120

-continued

```
tcctctaaac tggacccatc ttctggatcg atggcgacct tcagagccat tcgagcctat 105180
cgaagaccgg ccagaacccc tagaataatg cgtgcgcacg ctagcgtttc gatgtcgccg 105240
tctagatgac gacctccgac gtctagacct aggtctcgac ctcgatgagg cgtctgtcat 105300
gtcgcgcgac gcatcccggc ctgaacgatc cgaagagcgt ccctcccgat ctctgcgata 105360
gtgcgtatga gcactagcgt tgcgatgacg acgcctagac gaagaccttc gccgtttaga 105420
ccgaggttta gatctcgacg atgcgtctat cgcatcacgc ggtacatccc gtcccgtatg 105480
ctccaaaggg cgtctatccc gaaaagtatc tcgaatgtag ccaataaacc cttgtccgtt 105540
gcgacgactc gtagatccgg cagagctcct atatccatca gtctctaggc gatcgtacgt 105600
atcgtcgtag ttcgtctctg atggtcccac gtgtatgctt gccatgttat agggacttcg 105660
cgataatcgg acacgcgttt tagttccgcg cgttacataa tctcggaccg aaccggttct 105720
ctgtcgctgc tcttgaccga catccccatg acggtgtaga gccagcattc gccttcccgt 105780
cacaactcac cggcaaagta cggcggccgt ccatcgccgt ctcattttat acggtgccta 105840
atcgaacggc ggaaccgtag ctatatcgac cgcgttccat tgagaagggg gcgcgaggaa 105900
cggtaacgaa gtaaatataa taaaatcatt tattagctgt cgcttttacg tacaacattg 105960
ttttaactac aaaatcgtac cgtcgcatca agtattacat caccgtttac cgttcgcggc 106020
ttacattgtg cgagcagcag cgatatcctc ggcaatcgcg ggcccgggat gtgtagaatc 106080
ccgcaacatc gctttcacga tagtcccatg gccacacgac gggccggcct tcccagcgcg 106140
gccgctctct ccccgcgctg atgatcgcgg tcttggaggg tgcatgagag agtacacttc 106200
cagctttgat ttgatgcact ggaatagata cgcggatgcc ctaggcgcgt ttgctaaaaa 106260
tgcaggcggg gctgtcaaag gcataccccg ctcttccact aactcgcatc gcatcaccgg 106320
cagtccgagt tcggaccgta cgtaattttg tgttcttaat tcggcggcgg ttaacgcacg 106380
cccttcaact atcacaacgc cgtggttaaa aataaccggt tgaaataaac actgaaagtg 106440
tcgtaattgg tgccaatcgc accgcaggtg tgcaaataag ttttgccttt tcctctgact 106500
ggcttcgagt cgccgcgata catctcttgt aaccgaaagg tataaatgca tatacagaag 106560
tcttgcgaac cttgccgctt cccggtaata cgcccccggcg atagatcgcc ggggcgtctc 106620
tgacctgccg acgcacatat cgcatcgcga gggttcgttc gctccctgcc taagataaca 106680
tgccaaagca cgacaataac cgcaaagtag agtgacatag gatttttctc tagcttccaa 106740
ttccatcgaa aagaattttt gaatctccgt aacataaaca ggcaagccgt cctttgttaa 106800
tgggggccgc gggacttcca tcccgcaatg ttcgtttaga tttatcgccg tatatgccca 106860
tttctcttcg gacgccgcat ctaggacttc gctaggagag acggacagta gggttgcatg 106920
ttcgtataag tgcccattaa tcggaaagca cgagaacaag tctacgttta gtttttccag 106980
ccgagataac agggacgggc cctctgtaaa atccagttcg tgcaagagcc tgttgtacaa 107040
gcggttcgga ggattcggat ttggggacgg aagcgaaatt ttgatcgaaa atggagcact 107100
caaagagaac gaggcagatt gctccgcgca tctcgtttga gagcaaagag tttcgctaaa 107160
gctttcaatg ccgcggagga tgtccgaatc caaacagtcc gtcattccgt ttacgggcgc 107220
ttcgatctcg gcggataagt ccgtactgtc gcggcgagca tctcgactcc ccggtcccat 107280
tctccgcgtc gccatccatc tgcttagtag cgcccgcccc actaccgata ctttatgtga 107340
cgctattcac tctcgctact atagttacca cgggaacttg agtagtggcg acgtgaagtc 107400
gtcggagcgc gaccgggggt ttttgagcga cgatctctct tatctaccgg agtgctctcg 107460
tcaccgtcgc gttttccata ttgggatctg gacttagggt ttcccatatc cggcgacagt 107520
```

ccggactcct ccgataattt tcgcgtacat gcctcagctt catccaatag gtttgcccct 107580
tcttgaatcg tgatcttgat tatagccctg gcgaggaatt cctcgagctc cgcattggtc 107640
ctcggggcgt tccgacgcca aagggaaagc gctcccctat atgcatggta ctgggccaca 107700
gcagctacgg ctccgcagaa tatacgctcg ttatagacga gcgtgtttga tcgccaggta 107760
ctagttgctg acgccggagt cgtactaaag gcaaatttcc ctttttctat tgccctggct 107820
ccgggtttgg cacgaacttt ggaggacagc gactcccctc tttgggtttc cgatgaggaa 107880
tcttttcttt cgatctttac agatctgcgt ctttgtaatg aatgagacgg gggggagatc 107940
cggtccggcg actcgttctt ggacgaatct cgtcgagcgc gggtcgacga tatatgggca 108000
ctattatccg gtgacgtgcg catagttgag cgacgtcgac tcgacttacg tctatccgaa 108060
tctcccattg tatctcgtat taggcagccg attacagacg cgacgggccg ttacgtttca 108120
ccgtgttgcg tctccgacac tgatcaagct gttcacggca atgacattct tatacgggaa 108180
cagtagcgcc cacgcccaca cgatcttacc agccgtcatc gaacatactt gccgtgaata 108240
gtcggaagca tgcatggtac gacccggcca agagggcgga gattaccgcc accagaccta 108300
gataaaaaag gaccgagaag ccagaagaaa aggctataga cacgcctacg gcggaacacg 108360
tagattccca gaaatttcct gccacggcga tcggccttcc cgaatcgatc gaagtagctc 108420
gcgactccac gagggacgca attacgcaaa ttaacacttt acagaccaca tgatggatgt 108480
cggacaaacc catccctgcg gtaacgcttt ggaaaagatg tcctcgcacg cgtcgggggc 108540
tccgtggcgc atgcagttct ccgtcgatga agcgatatat gcgaggaacc cagaaggttg 108600
gacctgttat atagaagaac gcgacccgcg ctgtcttcgc gttatcaacg actgtgcgat 108660
ctcgttgccc aaacgcgatg ttaagcggaa gtatgaaata tgtgcgttag atctaggtgt 108720
acgagtggca gttcctcgga attatgtcgt tgtgctggcg aaattgacgg acccggatcc 108780
aacgtctcgg ggcgtacccg taatccgcgt tgccaatgga ctaatagatt ctggatacag 108840
ggggaacgtt cgagtggtac ttttgtacga agcagcttgc accattccta aaaacgggct 108900
ggttatacgt ctggcgctcg tgcagttggc ctatccggat ttcaacagtc gcgtgctttt 108960
tgacctcgct gatatcacgc cccacttgga ttgcgggcct aacttttcga tgtcgattgc 109020
aaccgctgct aaatcgcaca gcgctcaggc tcgaccgcta ttgccccctg gcggcgagaa 109080
actatggccg ggaaccgggt gtcgggcact cgtctgtttg tacagcgatc gcgtgtctcg 109140
ggcaactcat tataacactt tagacagcaa tgtcatattt gccgtaaggt acaatgattc 109200
tacgaccgtt atcggcttaa aagatgtccc gaagtatgtg cataaaacat ttgtacggtt 109260
ttatacatcc ggtcaatttg caacgttcgt tcctttttac gagacattta atacaaagcg 109320
gcacgaagat gcggcttacg atatattcgc tccgagcgac attgtattgg aatcaatgtc 109380
ttctgtaact atcgcgatac agcagcgata tgcatgtgcg gataagtcaa tggttccttg 109440
gatcttcgga cggtcgtcca tgaatttgcg cgggttgatt atttccccat ctaggtggat 109500
gcccgattcg tggttaacgc tgactttatg caacttaacg gaagcaaaag cgaccattaa 109560
acgcggagat aggatcgccc agctgttgtt agtcaatcag gaagccgctg cgttgcttcc 109620
aacggaaggc ggcacggctg cgctgttccc tacagtaggt aaatgccgtc gtcccgcagc 109680
gtccgcggaa gctaagtgga gggaaacggc agcattcgat acggaatcgg gcaggagcga 109740
gagagagtgt gccggcttcg ggtcgagcgg gcaataatgt atagttgcgc acgattacat 109800
acaaaacaat aaacacgaac accacgctgc gttctggaca atcagtttat tcagttacac 109860

-continued agtccggtaa catgccctcg ttgactccac atgtcttagc ccttctaccg cttcccttac 109920
ttacatcaca tgacgttgca catgccgctt gctcggcttc agagtgcggc ggcgaaggta 109980
gccctcccac ccgaccgtaa atatctgctc cactttcgtc cccgcagtta cgggggtcag 110040
tagcttccga tagctctaag ttttccgttt cgggacacgc ggccaacgct tcgagcgagc 110100
aatcatttgg ggaagatttt aagcctaacg ctctttccac tagagcgata tcattcatag 110160
cagtctctgt agcagcagtt atttgtatcg cgtgttctac gaaggcatcc gttcgtcccg 110220
tgccgacaga catgtagatc tgcaagaggg cggcggcaca cgtgtccacc attcgctgcg 110280
catttttgcg atgggtctcg acgaccgcgt cgagcccagg ggttccttgt cccgaaacat 110340
gacgagatag gcaatcgaga ttacggagac acgcactgta cattctagcc aacgactggc 110400
cacgaaccag ttttcgcact ccgtcggcag acaatatcgc catttctaat gtgatgggcg 110460
tggggagcat aagattgacg gcttgtaccg cctccctgaa acgatgcata actctgtcgg 110520
aggaagacga ggtagacagt gctgtgtatt ccggctgaat ttttctagag cgccttctta 110580
acccggcgtg cattgtggcc aaatcttcta ttatgtccga tataccggag gatgccgacc 110640
ctgggatcaa agttttgttt gccgttgatg gttgcgccgt ctcgttctcc cttgcacttc 110700
ttacgggtca ggtcccatct atcaatcccg tctacgttat cagccactgg gatccgggca 110760
atcgtttgtt agatgtcctt tgccaccgcg cagacgatcg cgactgcgga agaataccga 110820
atgaacgagg agatttaaac gcggtctccg accctctaaa agtagagttt tgccttctca 110880
gtcaaatgac acgcggtttg ggcggcgccg atttaaaatt gcggacgcga gcgatattcg 110940
tgtgccggtt tacttcgcat tccgagatta actccatcgt ggcttctata gcttccggag 111000
cgcctattca aacagactta ttaatagcca ccctctccga atatgacaca tttcgcctac 111060
atgatgactt caacatcgcc ctccacatct ctctcgcctg tttatcgcaa aagcgccgca 111120
atgggaaaga gccggcaaaa tcaccggatc gaaatctgct atcgattatg gcgggaacct 111180
tttctggagg tcggcgcggt ctagccgggc tgtatttaca atacgagcaa aaagtcaccg 111240
cggcctaccg acgtgtatat ggggggtcga cgacgacagc gttctggtac gtgtctaaat 111300
ttggaccgga agaaaagagc ctggtcttgg cgctacgtta ttaccttttg caagctcagg 111360
ccgaacctac tgggattgct acgggttacg atttacaggc cataaaagat atctgcgaca 111420
cgtacgctgt acccgtagag gccaatccta ccgggttttc gacggcagac ttgacatcgt 111480
ttgccagatt atcgcgtttc tgttgcgtga gcaattatgc caacggtccc gtagctaggg 111540
cgtttcccct atacgtggaa cacagaattg cagccgacgt gacagaagtg gatgcattga 111600
aagagtatat agaaagagac cggtccgggt taaagatttc ggatttggaa tttgtcaaat 111660
atatttactt ggcttacttc gagtgctaca atcgtgctca attaagacgt catttgcgag 111720
acgtgaccgt gcgttgtccc gaagaagatg tctacaaacg ctcgtctctg ggaaacacg 111780 cagtcgataa tttctttacg catgtgagat ccagactaaa cgtgaacgat cacatagcat 111840
gtaacgtatc tccggatcaa gtggaaatgg gaaacgtttt gacccgagca ttttgtaggg 111900
ccaggaccta tccaccgagt accatggaaa gcgatgcgcg tttcaccggg atttgcgaac 111960
cctcgtcggt gattataaag cgtctggatg ccctagaatc gacattacac aaatacggat 112020
ggccgcgcgc acggtctgaa acagttaaca tgatgtcaga gtgcgcgaat ttgcccatcg 112080
cttcatctgc cgatagtctt aggccacccg gcctgccgct agaacatcca ggcactcatt 112140
gccggggtgg tccaatgatc gtaaagcgcc tactagcgct agtatccgca gatgcacgtg 112200
tcggggacat aggaccgaca aacatgctca ccggcattcg ggaatcggcc gtcaagggcc 112260
ctcttccgat ttaccggata ggcatgtcca aaggcaaaca agcgtttgcc gtgatggtgg 112320
ccgattgttg ggacaaaatc atcccgtctc cgggaattgt gaaagcccat ctctctaaac 112380
tcggcagatc cggtagagcc cccgaagacg atgtgatcgc ccgagatatt ttttttacat 112440
cagaacttga gcgagtcacg ggccatgctg cggaactgcc gtactttacc tgcggccctg 112500
ccgaagaaca acagtacata aatcgcaacg aagtgttcaa tgacaatctt attgtgggga 112560
acataatcct ggatgtcgat gtgcacttac gaacccccgt acccgtcaaa cttttgcatg 112620
tggcaatgag aggttttagg accggtgcgc tcaaagcgtt gtctctatta cttccaaaag 112680
caaaaataga tcacggctcg tacccgtgct acttttacaa aacctcgtgc aagaaatctc 112740
gagtcgtgca cgtaaaacat tggatgtcgt ctactaccga cttcgctctc gactgcgacg 112800
gtcccgccgt cgaaagtgca gactgcgaac tagaaatggg cttcgatgac ccgttactta 112860
tggatcaaat tgatgattcc atcagtagat gtgagtcaga tgcatcaagt ttgccgtcgg 112920
acgccgatct gccttgtaac tgtcacgaaa aaataggatt gcgggtctgc attccggtgc 112980
cgcccccgta tctactcgta ggtagcagaa caatgagcgg tctggctagg gtactgcaac 113040
aatcggttct gttagaacgt agtttcgtag aacctatcgg ttcgtatctc aaaaactatg 113100
atatagttga tagcggagta tatggtcacg gtcgcagctt gcggcttcct ttttttggca 113160
agatagacga gaccgggctt atatcaggcc gcctgcttcc gttttgcgtg ataccggagc 113220
gctgcggtga cgcagaacag ttcgttctgt ctcatttaca gcctaaaacc tttcacttcc 113280
acagtcccat gcccgaagaa gatcacgcgt ctgtagttct gaagggccta ggcggagagt 113340
atgccggatt ctttgaaaaa aaaatcacga tcaatagaga tacgtttttc ggaatcagat 113400
tatccttagc ggtagctctg aaagccaggg gggttgacat taacgactct gcggcaatcg 113460
tatcattcgt aacggagcac attttagatg acataattca gtacatgcat gaccacatac 113520
ccgatcacgc tgcggaatat aatcacgttt ctgtttcgtg ctgcgtcatt agaccagatt 113580
ggatcctctt gcagctaatg gccaataaaa cattgggacg cgctcacggg tttacgtgcg 113640
tgaggtttaa gcatacaaga acgactcgaa tgagttcgcg ttcgtatttg tctttaaaca 113700
tcgacgcaca tggtaggttg tgcgcgtgtg tgattcagca gtgttttgcg gccaagtgtg 113760
gaaacaataa actccgtact ctttttacgg tggatgtcga ttcgaaatgc caggcagaac 113820
atcgatagcc ctttcgggaa ttatactctg catctcgaca tacgccatcg ctttggtgat 113880
ctacacgacg atgatagcta aacacggttc tgggtgcatc tatgccgtcc tggtagacag 113940
cgatcatcgc gatgccaaaa attttacatg ggagccatac aattctacac tggtatacac 114000
gccgctgggg aataaattac cattggacgg aggatttggc ggttttagcg atgtatgtaa 114060
cacatatctg atcaacgcga cggatttatt cggacgcgcg tctcacgcgt ccgccaagtc 114120
gaaaatccgt tcggtggtag gaacgcgcaa ttgcgcagcc tacttttgga agacgcatat 114180
acaagccttg accttttccc taagttcgta cattatgttt tgcgtcatta gagaatggag 114240
acgcatgttt ggggtggtgc gatctgaaaa cgacagaata ccgccgacga cgtacacgaa 114300
gaattatact gccagggtaa tcgctaacgg attgctaaaa acggtatata ctagaatgtc 114360
tgaatttatg tgcgagatta ctatatacaa aaattctatg tgcagaatat ttacagacga 114420
ccctatctcg tttatcttac gtcacccttt ggctgcgatt ctccttataa ccgagcggct 114480
cataaggctc ggcgcacagt gtctgtgtgt actaacggta tcgatttttt ttgtaccgtg 114540
taaaatagtt ttatcgaaat ggttcttgtc tatcaccgga gttttcttag gaatcgttat 114600

-continued

```
ttgcaccgag atgggcctgc tgatagaccc gggaccggct gaaaaacctg tcatgtttgc 114660
agaagttgcc ccagccccca aaacccagca gaacggcgtg gctgtcccgt tcggtgcaca 114720
cgctgtatgt tccaattgct gcgcctccat aatctccagc atagtcatca aagttctgta 114780
cgtgttattc atggttaccc tcatcgttac cctcgtgcga tatgaacgag cgctccagat 114840
tgccctgttc gggcgtgcgt acctacccta aaacattagt ggccaagcct cctatttgca 114900
tcgcgcggat gtgacacgct aaccgcgaga ccttataaat ggttccaatg agtcattcgc 114960
ccctcgggtg tacgcggtat tctacagcag cgtattagat aaactacacg ggtttgccgt 115020
cgcgcctcaa ggaaaatgtc agtgggagct ttctctcgtg attgggacga tataatgagt 115080
ttgtcagact acgattttac agaggaagaa tccttagatg aaagcggcga actgaaagaa 115140
ttcaagaaca cgtccgcgtt gaatgctatt gagacagccc gcgacgcaat tgaaagatca 115200
gccaattcaa acccccccat cgaagaaccg tcgttcatct ccaaatctca tgcaggcgag 115260
acctcggcct cgaaatatag aagcttgccc ctcgacatcg aaaaggcaga acggtgtgat 115320
gacactcgag gctacaacgt gagttcggga aaacgaatgc gtttggcagt ttcggccact 115380
gttgacctgt gcgagtctga gatcgaacgg caatgtctga atacggaaac gcgggaccgt 115440
gcacggtccc ccaaacattt tgcatcccat tatgaaatcg ccgccaaaat acacgatctt 115500
cccagatcta cgggaaaaag gcaacggcat cgcacgttag attctcgctc acgacgccac 115560
ttagcgggag agcatcggcg gcggggagct catgacgagg aaagcagaca cttttccctc 115620
agaatgcgtg accctcattc agcacccggc aagagcccgc tgtcgaaaag gcgcagtccc 115680
gttaggctcc gtaacctctc tgtgcaggag gaacttaacg cgatgctaca acgagagaaa 115740
ctgaagctcg acatgatttc gagagagcgc aatttccgca cttctagcaa aaaccgctgg 115800
gcctcagtac tggcattctc ctgtaccgga aaaagtgggg catacgggtc tcagataacg 115860
tggcaatatt tgcttcaaga gggaccggag cttagaaaga cgttcgaaaa tagacctaga 115920
acctcattgc tggcgtctgc ggcgcgcgaa gctgtgttgc ggggcgaaaa cttagttgcg 115980
gcattggaga gcgccgagga aaccctggca tggctgaaat tacactctgt tctaaaactg 116040
cgtttaatga accatgaccc tattttcagg acggcgggtg ccgtcttaga taatctcaag 116100
ctgaaactcg cacccataat gatgtgtaga aatggtacag acaaacggtc gttaggagac 116160
atgctgagaa gatccgccac ggacgatatc gccgattcat tgaccttatg cttaattttg 116220
ctatcgcgta ttcatcgcat gatgatgtat cgcgtgtcgg gtagaaaaga tagttccatg 116280
atagatcctc ggggatacat gagagagtat actcctggtg aatgtatggc gggtatattg 116340
cattacgtag acgcgcatgc aaaaacgtgt tccgacagag cgtgcaattt atatattagc 116400
tgtaccctta tgcctgttta cgtacacggc aggtactttc gatgcaattc cgcgtttgat 116460
atgtaaccta ctacagacgg gcaattttgt attcttcaat agctttattt gatatccatt 116520
aaacttaaat aaagacaccg atattcaatt ggacatgaac agcgtgcgtt ttattttaca 116580
cttagcctgt gtgctttcga caccgagtag gaaaacgaag gacctgaaat tgcacgcacg 116640
accgaaggaa ataagccatc gcaatcgcat ttgaaatcca agtaggcaaa ttcaggagaa 116700
cctatcactt cattgaacaa gttctcgagt attcttatga atgataagca ctggagcccg 116760
ccagggcgat cgcagacaca actaattaac atgccgtgag tgctgaagtt ctctctcatg 116820
gcagattcgc ataagtaaat agtcttcctt cgagttccta tctccgtgaa tctgcggggg 116880
ttcatcagaa gcgcaggttt gatttccgac gtgtgattag aatgaaattg tcgaaagaca 116940
gtctttagag tcattggcat gtctgtcagt actatggaca cttccttgcg gcagcgatcg 117000
```

-continued gtaaggaacc acagtagttc cttaggtagt atgtttctac ctaggaacca cggtgttccc 117060
acggccaaaa accaagcgtg gtcaaacgat ccggtgctcg gagaagaacg ctgcgtatcc 117120
gctacccaaa gcagtatcct ttcgcagata gacgacgttg ccgtgaccat tctccctttc 117180
caacctcccg tcagtacact gtttattggg cccccggcgt gcgtgaggag taccggtcta 117240
gcgactattc cataaacgtt agtcggtgag agttctctcg gggtgagcca cattgggaag 117300
cccgtctggg ttggagcgtc cgatgtagag tcgtaattgg cgcagcgctg accctgcggt 117360
ctacaatgca tggtcatgct agacgggaca actagtcgcc cggtgcattt ttcattacgg 117420
ccatccctta cgtccacgta ccacgtgccg tgagtgtgta ggtaacacgt agtgggcgtg 117480
gaaaaactta tataacaccc ggcagaaacc acgtgcgccc agcggtggca gatcctcagt 117540
tctacagtgt ccaatggcgg aaagtacagc tgaaccgtca gcttcaccgg tacgaattcc 117600
gtacgtttgg caagtgatcg ctccgttagc aattgacgtg ccgtccgcct ctactcaact 117660
agctacgggc gaacatgtgt catgtgccgc atccgttatt cctcgttcgt acgtcatacg 117720
ggcagcgtgt aaatcgtcga cgactttcca cgcgttcttc tttggattgg cgacggatcc 117780
gtctgagaac atgtcccaat gcggtgcctc gtatatcgcg tatagaatga acaagaagtt 117840
acggactggt cgattgacag gcgaccaatg cgagtcgcct ttttctcatg cgacgatcat 117900
cgactcactg gatgaaaact acagcatggc tatagaggga ctgtgttttc attgccactg 117960
cgaaaataag ttttcgctcg agtgttggag atcggctttt agcgctgccg aaaaaatcgc 118020
atcgcagtgc agagctattc gcgagtacgg acactgaata aaaacgaatc atgatttgat 118080
ctaccatttc agcatttatt ggtttataca ttctcgggtt cgtatgtata caaaatctta 118140
tggcaacccg cgataacaat tcatttacgc ataccaattg cgagagctag gggcgcaccc 118200
tcaggttcgc ctacgccggt atagcgttga gatctaatac gggagtagtg attttgcagg 118260
aatgtaagtg gtagtaacac ctaaagaaaa ccacatacta acgctctact gttcactcgt 118320
atctacgtgc agtgaggttc ccgcatatgt ttgcgcgtca tcaatcgctc tcgccagtat 118380
cgccacaatg cgtttttcgc gcgcgggtat tgggacgcag tgtaagtgga atagcattcc 118440
gcaggcaaaa aagttgtttg tcatgcaagc atccatcaag tagcaatcac atagtgggac 118500
cagacgcctc aaagcgacgt agtgggggga accctcttcc cattgcaacc actttcgaaa 118560
tctgtaggta tatgctgcca gccagcgcct tgttctgacg gttattaccc tgaacccctt 118620
aaatgggaag aagaatccaa ggtaccaatc gttggcgact ggcccgtgcg gacaacgggt 118680
taaggatgtg acaaactgtg tttgcgtggg tacgtttacg atgtatttcg aatcccgcac 118740
gacgcattcc tcccagtgag atagtagtat cccataattc atgcatctga ctaccttggg 118800
ggtgagacac gctgtaatat gaggcgtcgc ttgtaaaacg cacctgtatg gaaccgttcc 118860
gagttcgggg attgattcta tgatagcaag tctacttatt ccggaaaccg ccatgacatc 118920
gcacaaagga agcagttggt taattgcatg aatcagaatg tttgtttcca gcacggcacc 118980
tccaaaggaa aataatgttt cgatgcacgt tcgtgccccg ttctctgtat tacagcttac 119040
tagcgcaagg ctgaggacaa aaacgagttc gggctttgta tgttcgagcg gaacaccaat 119100
gcgacatacc gtatcgctta agtttttcat aaaagtggat cttgcacgtt tgccagatct 119160
gctccaatcg gccgaaaaaa atttgcgcac aatcggatgc atgtctgtgc ctacaaatac 119220
catgaaacat aattcttgtg ctggaccccc atccccgcta tctatatcta cattgtctga 119280
catgtgttgt gccgacaaca aacggtgtct tgtatcccca tcaatccagc gctttctgag 119340

-continued

```
gtttacgggc tttaggatgg acacatcacc gcatttcggc acgcataacg cgggcatgtc 119400
tgaacgggca acgattctct ctgtgagcag atcgagacgg ccgtgacgca caccacgtgc 119460
cggtacatta ggcacgactg tagcaaaagg atggtagcga tggagccagc ctaccgacag 119520
tcccgcaaaa aatcttatcg gcggaatgtc tcttttaagg ggtagtgtgt tacgaaccga 119580
tgaattcaat ttctctgtcc aaccacttat cgcttccgca acagaaaaat cgtttctaag 119640
ttgcgaatat gtttctacca cccacttgag atcgctgcga agggcttccg acattttttt 119700
agcgtattcc tcatctccat cacaatcaca gtcgtgtctt tcatttgcaa gtgtgggcgc 119760
gcagatgtct acgcgacgac ttaaccgaga cactgtttct ctagtgtacc ggtaacatgg 119820
actggcgccc gctctgaccg ttagcatgcg tttggatgca accgaggtta gataaacgtc 119880
tggagaactg cccaattctt tgctttcact ggcacatatc caaccgtatg tatcctctgt 119940
ctgtcctgcc gcctcaaagt taccggggag aggtccggga ctcgctagac agaagtcgat 120000
ttgggaaaat tctgtgtcat tgttgtaggg actgtgcggc ctatctacca tagttgcaga 120060
atcgtgcatt agaatttcag cgagcatgga atcgatacgt tcgtcggcac ccgcatatac 120120
ggcacctatt cctattcgcg tacaagagtc atcttctaca tcaagcttcc agaacgttgt 120180
caggtattcg ccataggctg caaagtctgc atctgtggtt cttcttacaa attcaatctc 120240
cgggttccaa cgtccacgtc ccatacatag gttgcgcaac gtgatcgagt acgccaacgt 120300
attgaaatca tttatgctag atgcttcgct attatcttcg aacaaaatta tcgtatacaa 120360
tttcgattga tgcatcgatc gaaggactga caaatctgtc gcatatgtct cctcggggag 120420
aggtgtgacg gtgataggct cgtccctacg ttcgaaccgg ataaggccta ctgtagcggt 120480
ggtttcagta gtcctgatgc atcgtaaaat tgtggcctcg gttctaattt tcccgagtaa 120540
ggcccacgga ggtccgcaat tactattaca cagggcctgg attacggagg aagtgccagt 120600
tggtgcacac cgaaactctg gaaaccattc cttggacgga ataggagggt ggaatttttg 120660
tcgtttagtc cactccatct gttcgtacat ggaaaatcgt gttaattcct gatcgtcgaa 120720
atgtgctaat ggagctatag tgctgcgttc ggctggtgcg gaacctatag acacgacata 120780
ttttggttgc acgtgcagtt ctctgagctg attaggaaat aatactgcgt ttgatgatag 120840
caaagacctt tcgggatcga gctccggagt gcagtgcgaa gcgtgaacaa ttctactttt 120900
cttccgagac ggtgtgaagc aaaacatctt gacgatgcta cgttctatgg cattctgcaa 120960
caataaagta tcaaattatt ttgacattat catctatagt atgagcggtg tgttatataa 121020
gaggacgaaa cacttgtgaa gtagacacgt tttattcagg aactcacatt ttcactacta 121080
cgctgttgtg agcagagaga taagcgcggc ggaaaaaaca gtcacaaata ctactgttaa 121140
tataatgatc gcagccgcat cctgtcgggc attaaacaac caatcctctt catcattagt 121200
ttccgaagag ctagtctcat aaggcggcgg aggagagtcg taggtaggag gtggtccatt 121260
tgaggcttca tacggaggca aatatgcagc gtcgcattga ccgtccccca gttgtaattc 121320
gaaatgttca tataccgatt ccccgggagc gtctaaaaat ggttgctcct catgtaacgc 121380
ttgcgcttcg ctcgtcagac cgcggtctag ctctgcgctc gtaagttcgg tttgcggtcg 121440
gtcgctatcc attttccctc gcccgcagta actgtgtcga tggttcacta ctctcgaagg 121500
agttaaattg cctactttct cctcgaatct cgaatgtggc tatgcagcat cagggtcatt 121560
agcgtcagta ttttcctctt tggagtctat ggctctaccc caaatacctc ccgcgattgc 121620
tcctgtgcat aaggccataa acaggccggc cctctgccaa cccgttgaat ccaccttcac 121680
tgctctgcca attagtattc ctgcaaaaaa tgccatgcat gatcccatta ctaatgatct 121740
```

tgcggaccga ataagcgtga ttaccattaa ggagcgcatt gtagcattct cagattccac 121800
agataaaaca gtacgaggta ctgtaggagc aaggcgctga cctacgaggt tttgttgcac 121860
ctttcccgct cctttttctg ctatcatcag taagttaatg gactgcacga tttcgctttc 121920
ggcccggagg aggcggcggg catcttgtac cgcgcgctcg gcgcgccgga gcaggcgcgc 121980
gtgcgcctcg tccgcgtccg cgcccgcgtc cgcgcccggg tcgtcgcccg ggtcgtcgcc 122040
cgggtcggcg cccgggtcgt cgcccgcgcc cgcgcccgcg tcgtcgcccg ggtcgtcgcc 122100
cgggtcgtcg cccgggtccg cgcccggtcc gcgccctccg gcgtcgttct ctccggcgtc 122160
cgggtcgccc cctccgtccc cggctccgct ctcgcgctcc gcatccctct cggcgtccgg 122220
aggggcgcgc ggatcagcgg tcgggtcgcg atcgcgtccg tcggatcggc gccttttccc 122280
ccgccgcatc gcgttccgcc gggccggtcg gacgggagaa gaagggggag ggggggaagg 122340
aggagagggg ggagggaggg tagccggccg gcctgcagtt cgggaagagc gggggaggcg 122400
ccgtccgagg ccgccgggga ggaggttgtg gggggcggga ggatgtgtgg gggaagggaa 122460
gggggagacg gccgaaacct acgcgttcgc cgcggcgtcc gatccgggat cgctcccgac 122520
ggggctctcg ttcggcgatc gcttatcctc tgccgccacc ttgcgtccgt tcgcgggaag 122580
cgccggaccg gcgctctaag cggagatccg gcgcctccgc ttcttatgac cgggccggtc 122640
gtgagggcgt aacgatcacg tgatgcaatg caaacgagcg gggcgaacgc gtcagcgttc 122700
gcaccgcgaa ccaatataag attatatata taatatatta ttggcgcaag gtgcgaacgc 122760
ccgtccgggc caatcgggaa gcgggatcct atgccacgtg ttcgtgtccg gccgcggccc 122820
gcgccggggg ctagaaacgc cgcccccctc ccacgggggc ggattcgggg acctccggcc 122880
tacaaatacg cgagcggagg tccggcgggg accgtcgttc cgctggccgg cccgccgtcc 122940
gaaagcgcgg gaccgcggta ataaagcgcc cgccgtcgcg gatcggattt tctggtcgtt 123000
cttttaccgc cgggcgaacc gcgcggcgaa cgaacccgtc ccgttgggat cgcaggcggc 123060
cgggaagcga tcgcgcgccg tcccgagaac gtcgtctacg gctcgcgttc gcgggggtcg 123120
ccgacgggtg gaagggggat gggtaccgag ggcatcgaac tggccgagct cggcatctcc 123180
gccttcgggc cgcgaccctc gcggcgtccg gaaccgtcgg acgtcgaggg aggacgcccc 123240
atcgttctcg tccgcggatc gtcccgatcc ctcgcacgag aacgagatcc gaccccgcgt 123300
cggcgacgcg gccgaacgcc gctcgcggaa cacggtcgcg ggtcgccccc cgactttccc 123360
cccggccccg cacccgcggc gaggtcggaa cctcgggaat cgattgaaaa cgggccggtc 123420
gagataggac cgctctctcg ttcggaagcg gagcaataaa gccgttcggc gtgagctcgg 123480
gatgagtctc ggacgcgcgt cggtccgttt ctgcccttgc ggcgctctac gaaagaaccc 123540
gatgaggccg cgttctgttc gggagcggtc ccgagctgta gggatcggct cagtagtaac 123600
tcgtctcggg tttcgatcga gttctagcga accccgaaag gggggtacga ggaagcttgc 123660
ggcctgccgc aaaaagactc cgaggagaat agcttatccg cgatacgccg ccccctcaac 123720
cgttcagcac tcacttcggc gtcagttccg aagtgacttt gtctggccgg ctcggcgcga 123780
gccggcctcg gagagaacgc gtacatagcg atcgtgggct gggcaacgag ataggagtag 123840
agggatgggg aaaaagtgaa gtcccgcgct ggctctggac gaggcggaac gaaatggggg 123900
aggggacggc ctctcgaacg agagcggggg tggggcatgg tcggtggagg ggtgtgggaa 123960
acgccgcgac gccgcggccc gtccatgtgg taatgcgggg aatagagttc cctgacgggg 124020
aggagttgtc agctcaccgg tcccgtgatc aacgcatatg ccacatatat gcaaccccgc 124080

-continued

```
gaccctctcc tcacgaacag ggtagagggt ctcgctttgt tgcacacaca agcacactca 124140
cttttgcggc gacaatgaaa atcgtgagcc cagaccaatt gcccctatat gtgttaacgg 124200
cctccgacgg aacaacggag ttcagtattc gagattggtc gctatgggat cgggatccgg 124260
aatcccgtgc aggtacgcac cgcgggctcc gtcaaacgga acgctctctt ttggagcgat 124320
gtcgtttggg tccgggcccg agtagggttc ggccggctat ttccctcccc cccccccccc 124380
caagcccgtg cgggaccgag gttgagtggg aaggtctcgc ctgccggatc ggggggggagg 124440
ggaaaagacg tttgcgttat ccggaatcga gccggaccgt tttacgtttc agagttcgaa 124500
cacgctctca cgagctgcag ccaccggctc aagccctcag accgcgtccg cgccccgggc 124560
cagcctagcg tcgcaaacgt ctggaagagt ctgtggagtt tggtttcgag ggccgtgcgg 124620
ggaaacgcag agggctccta cggacgaccg gaggagggag acgccgaaac tgccgtgtaa 124680
acgaatgctt agcggagccg cgcccgggac gcgtcgtttc ttgcgaaacg gggtggatcg 124740
ctcgcccgct cttagccctc gcgtacagtg cgtcgatcgt taaggtgtac gtgcgtgtac 124800
gagaccgcgt gcgagcggtc tcgtcgtagt gcgtatgaac gtgtttatta aaaagtcttt 124860
ctcgcttcgg tcccgtttcg gtgtctggcg atggcgcggg cgggggagtc cgtcgcgtaa 124920
gtcggggaac gtactttgtc ctctcctctc ccccgaggcg ggatgtgcga ggggggggggc 124980
gacgggcgac cgggaatgcg tgcgattagt gttgtggaga acgtaccgcg ccgaggcccg 125040
cggtgcgcgc gaagggttag ttgggggagg ggcacgcgca tcataagtcg ctcgcggatc 125100
gtccaggtgt ttgtgcgggg gatacagttt cgcgacgggg aggagccgtt agctcaccgg 125160
ccccgcggga gacgcagatg cgatataaac agccccgcgg tccacctcct tgttcgcgac 125220
ctgctactta gcctcgcttc gttcccacgt ataagcacca ctgacttacg cggcgaccgt 125280
ggaagtcgcg agttccgacc agtgtcgcgt atatgtgtta acggcccccg tcggaaccga 125340
attccacatt cgagatgaag tgctacggaa tcaggaatcc cgtcccggcc gcgcgcacac 125400
ccacacacac ccccacacac acccccacac acccccacac acaccgcggc tacagagcgg 125460
ctgtcgtagt acgtataggc gcgagcgcga acacttgcac ggactctcgt cgtagcacgt 125520
tcaaatcggt ttattaaagc cctcatgctc agactccgtg tcgatggcgg gggggggggg 125580
gtggtgagtg acacgaactt actttcctgc gacgctcccg agaggaggtg tgcaccgggc 125640
cgttttctcc gagactgaaa agagaaagaa aagctccgcc gttcgcccgg ccgagcgccc 125700
ggacgcaccg gtgtccgtac ggccttcgga cgcttagaga gcgcgggcgt ttcgcgccgc 125760
tgcggcgttt aggcgcgcag cggcgcgttt gcaaaaaaaa agaatgtacg gagagacccg 125820
cccgccagcc tctccggccc ggagcggaaa cgccgcgtta tctctacgcc cccgacccgc 125880
acatccgaat gcgcggtcgg atcgcgaggt taactccctg cccgcgcccg cgctccgcgc 125940
tccccctgcg ttgtttaccg gttcgcgatc gcgatcgcgg aagtcgcagg gccgacttcc 126000
ttgtttacat tgaatacgtc gacggaagcg caactgcgta tgtccgccgc gcagacgcag 126060
aagcgccggg gccgaatccg ggaagaagag taatacgggg cttctccagc gcgtaagtac 126120
cggcgttccg ggcggtcggc gagtcggcgg agaaaaggtg gatcgcgagc gcgatccgaa 126180
tccgcgggcc gaggggaaat tcttcctatc ccctgtgcgt tgagcgcccc gtgccgtgcc 126240
gcctttttcc gtttccggtc ggactcggag ccttcccgcc gcacggttcg gactcccccc 126300
cccccccgca acggttttat tttcccgcgt tcgaccccgg cgtgatgtcc gcttttctgt 126360
taaaccgtgc gttcgtctta tagggaagcc atcttaattc tgacatgcgc gaatgcgtct 126420
ttccccccttc caaggcctaa cccccccgc gctttctcgt ttccgccgtg ggccatttat 126480
```

-continued cttccccccc gcgtaaacaa ttatccctcc cccgcgcgtc ctacttttct tctgagacct 126540
atcgcctttg gcgattctag tcagattgcc ttttatagtc aagtttcgag cagatcctaa 126600
gcaagcatgc cctgtacccc acccccccttc taaataaatt tccgatccct ggaggtttcc 126660
ggagtatttg tcccaggagc ggggtcctat gcagtaatcg taggtctttc atgtatgggg 126720 ggggggggagg ggggggggaga tgcgaacgcc cacactggtg ttggttcgtc cgccacggaa 126780
gctggaaccc catcggacgt ctcggcgccc tgtttgcaaa atgtcaggta cttgtagtgc 126840
attccacgta ggaaaatggt cgtgagggga gggggggctg agtttttctg ttatgggtat 126900
cctgaggggt ctacgtgaaa gtgactggcc ttccgttttc ccacagaaac gttgtgtggt 126960
acggtgcacc ctgagagatg atctatattc tcaggaagtt ccgtgcccga aacgctctga 127020
acgataagct tctagattgc atcggggatt cctctgagaa gagcgggtgg ggaaatacat 127080
agccgttaaa gtctcgcggt ccgatatccc cgtttggccg gtggatgagt cgcgatggcc 127140
ggacggggcc ggaaatgcga tccttctttt gcgggctatt tgcgatggaa gggaaaggca 127200
aaccggaaaa cttaaggccg tttggtgtgt ttttcccttc catcgcaggt cgtgccgcag 127260
tacttttgaa tcggagggag acgtcgggcg agtgggaatg ggcatcgcgg ggtcatcctt 127320
tattctggga cgaccgcgaa tctacgtgtc gtctcagtct ggacggccca tggaaaaaaa 127380
aaagagtcga gaggcgtggg ggggggggga ggcctgaacg gccggcgcga taagggatac 127440
gtggtcaatc ttggcgatta agcctagata ttgcgcgggg agtggggcgg cggtccaatg 127500
cctagaaggg cattattcga aatttggagt cgggctgcgt agcgacgggt ggcgcgcatt 127560 aatacccccta tcttttttttt ttttgcttcg tttcttgtgg ccggcttggg aaatgtcagc 127620
ggaaaacatg cacccgctgt gtgaatgtaa accgcgtaag taaacccgtg ttagactaga 127680
tttcgcaagt tgcgaagggg ggcgattggg gaggaggaag tctgaacgga gggggggagaa 127740 gggagggggg agggggaagg ctgaacggag gggggagaag ggaggggggga gggggaaggc 127800 tgaacggagg tgggagaagg gggaagaagg gagggagtgg ggaggggggg gggagaagag 127860
gggaaggggg aagggggggaa gggagggggg gaagggaggg ggggaaggga gggggggaag 127920
ggaggggggg aagggagggg gggaagggag ggggaaggga ggaagagggg agggggggggg 127980 aagggaggaa gaagggaggg gggaagaagg gagggggggaa gaagggaggg gggaagaagg 128040 gagggggggaa gaagggaggg gggaagaagg gagggggggaa gaagggaggg gggaagaagg 128100 gagggggggaa gaagggaggg gggagaaggg agggggggag aagggagggg ggaagaaggg 128160 agggggggaga aggggccctg gcgagatcgg ctctgaattc ttcgttgtag atagcagacg 128220
accgtaaacc tgaagtacct gtgacttgga cggtgatgag atgtttggcc tagttacagg 128280
gactggcctt tgttagacac gatggccttt ggaaacgcat ccagtctgtt ttggcatctg 128340
agtggcgcgt agccgttgtc agatgccaga gagactgaaa tgtttctcga ggactctaac 128400
cgtaatctga ataggcccgg accttaatcc caataggccg tgccgggata tcagaggaga 128460
gccgctcgga ccgctgcgat tccatccttc gactagcgac ttgttatggc gggtaatagc 128520
cggacgacgg agtctcggcg gttcgacctt agcgggcccc ggataggttt ctcggttggg 128580
gacaaagggg aggtagaggc gtcggatgcg gggcgatgag cgggtattta ggccacgaga 128640
tcaggtgttg tgaggaaggg gtaacgacgc cgtattgcgg tcggaccgca cgacggcgcg 128700
tcgtccagtc cttcccgggt cccctagagg tgtcacgttc taggacaacc gggacggaca 128760
gggcgacgcg cgcgaaatgc ctcgtatcgc ctgatatgct cggaacgagt cggggaaggg 128820

-continued cgcgaaagcg agagttacta ctcggaactc gggactgttc gtatgttttc tctcaggctg 128880
gcattgcacg tgtcattgcc gttgtgcaat gcctgcggag agaaagacga attgattccc 128940
cgtgccgctc cccgtcgtgt gggacaaggt tgggagggct ctgggcgaag aaccggctga 129000
gcatcggcgc gcgcgccgtg tccccccctcg gcggtgtgca cgggagtatc gggcgccgtc 129060
ctcatgcccc cctccgaggg tagcacgcgg tggtcgctgc ggtcttttca aaacaggttc 129120
tgcgaagcag agatgcgtcg gcgcgcgagc gaagcgaacc gagctctgct ccgtccttag 129180
cgtggtgcct gagattttaa cacgtatcgt ctcaagtact gcgcgcaagg accgaggcgg 129240
cgttccaaac gtcggacggg acggcgcggc gtcgtcgcgc gccgcggaaa tcgttacacg 129300
ctccgcttcc tccttcgcgg ggtgcttgag atcaccgaat gacgggatcg agcaccacgc 129360
cgatggacgg agatggcgcg cggtacgttc actgaatcgc aacgaggccg ggccgcgctg 129420
cagggatggc cgcgggtacg cgcgccgagt atgggggggc gcgtgctctc ctacggccga 129480
ctcttgggag cgtgcatcgt tcgggggtcg gctgttgggt aagacgtggt ctctttcagg 129540
tcggtgctgt tattttcggc ggggcgcggg acttcgtcct gggccgtctt acacgcacgt 129600
cactctggtc gtatcggtag tcctagtggc ttgcttgtag gctgtccgtc ggaggaagac 129660
agcaccgccg cccagctgcc tgtgcgagcg caggactcgt gtccacgtcc tgcgtgactg 129720
ttcgcccgcc gttcggatgg tccgtggtac ggtgtcctgt gttgtgtgag aggtctccgt 129780
acaccggacc atcgaagggg ggtggggggg atatgcgacc gcagagcgac ttttaggctg 129840
ccgctgtgca gtgttcggtt gggtggggag ggaggaatgt ctgtaaatct tacggcgata 129900
tgctggatcg tgagaggtga gtacgtgtct gtgcgggtag gtgggagcat aaccacaaaa 129960
agactagaat tctgcccgcg gggaaatggc ggtgtgtgta atgcttctgt tccaaacgaa 130020
ggtgcggaat aggagcgaaa tggaccgacc ttcccccgcg acgacgtaag tggcttgtta 130080
cgacctggga ggcctagctg tgttctcgct cgttgccagt ggataggctc gcccttttttt 130140 gtaacagatg gcgatggaac agaggttcct atgtgggggg gggggggcgg gaaggataac 130200
gtctatcgat cccgaagtct tcgttgcgga tatgagacga tcagtactct caccgatctg 130260
catatcggac gcggaggggc gagagagggc ccgtggttag gcgtctgtac tccgaactgc 130320
ttccattttt tcccttacgg tgcctgacgt cgtattttaa cggttagatg ccgtcaggga 130380
aagatgggag tttgtttgct cgagccctgc cggcggactg caggcgaaga agtagccggg 130440
cgcgaagcgg ctgggaatcg ggtcgcgtgg cgtgtcctcc ttcggacgag tgcttgccgg 130500
ggagtaaccg tcatgcacta ctccggggggt aggacgcgac gtgcgacgcg ctctccggat 130560
cggtgccgtg ctgcctgaga tcgagagcat cggacggagc ccagcgccgt cctttgtgct 130620
gtgtgtgaga ggtcgtcatc ccttctcggg caccgcaccg aaggatggag tgggccctcg 130680
aaacgtcatc cggaacgccg cgggacgaag ccgccccggt aaagtccaga cgcgcgcagt 130740
tccctccttc gtccggtgtt cgaggcgtga gacttttgta ttgccgcgtc gagcaccgtg 130800
ctggaggaag gagatggcgc tctactccgg gacgaaggcg ctgcggagcg catcgcgtgg 130860
tgttagaggt ggatcctgtc atcaagcacc acgtcgatgg acggagactg ggcgcgaagc 130920
gttctgcggg atcgcgtgga acgagggcgc accctcggtc gcgattttct cgacgcctac 130980
cctcggcgtt gttcgtcggc cgagggtagg cgcagaggaa atcgcggtcg ctgtggactc 131040
cggtgtctgg tatcatgtcc ggctcgagtc gtacgtcctg aaatgttgct tctgattccg 131100
acgggtcttc ttcacgtacc tctctatggc tgcatcttta tggccatagt gaggtacgtg 131160
taggctacct gccggagaaa ggcggtcccg acgaatacgc gtcccgtgta gcggtcgccc 131220
gctctgcgat gggctggttc cggcatcaat attgcagggt ctatttttgt ggtgggcgtg 131280
accgcgcatc gcatcgaaat aaatctttaa accggccgag ttcattgttg ggctatgctc 131340
ggttttcggg gggggggtgt ggaaggaggg tactaggtta gggttagggt cgggccctta 131400
gggtcatggt cagggttagg cctttaaggt catgcttagg tctttagggg cagggtcggg 131460
cctttagggt gatggttggg cccttagggg caggggctcg gggtaagggt tagtgccagg 131520
gtcgggtgtc agggtcatgg acagggatat gccgttaagg ttagggttgg ggtccaaagt 131580
taggcgttta ggggtcgggt cgggttcggg gttaggcctt taggggtgt gtctggttta 131640
gggttaggcc tttaggggca gtctcggggt cgtggttagg cgtttagggg tcgggtcgag 131700
ttcggggtta gacctttagg ggtagtgtcg ggtttagggt taggccttta ggggtagtgt 131760
cgttgtcggg gttaggcctg taggggtagt gtcgttgtcg gggttaggcc tttaggggta 131820
gtgtcggggt cggggttagg cctttagggg caagctcagg tgcagggtcg gggttaggcc 131880
tttaggggca gggttagggt cagggtcggg gttaggcttc tggatcgggt ctttagggtc 131940
ggggttaggc ttctggatcg ggtctttagg gtcggggtga ttatgatcag agactaagag 132000
cgcgaaggcc tatcagtgtt aggttctctg ggtcagggtt aaggcctcgg ggttagggtc 132060
tcaagggcgg cgtttggctt aggggcccgg ggttaggacc tgtcaaggtc agggttatgg 132120
cctatcagag ttcgtggtca caggtgtaag ggttattagg gcctattaat gtcaggccct 132180
attcgggtta ggctcccacc gagtactaag gttagggtct tgtaagggtt ggggcccgta 132240
agggtagggg ctggggtctg ttacgggcag ggcccccccc acacggttcg acctgccacg 132300
cttaggttcc catccccccct cccccccccg agtagggtta gggcctggca ggggtagggt 132360
aggcgcgaag gttgggcccg ttagggctag gagcgaccct cctccccccc cccattattg 132420
ttagtctgtt aaggaggcgt tccccctccc cgtcagggtt agggcctgtt aggggtaggg 132480
taacagggtt aggttagggg ttaaggtctc tcggaattag ggcggggcgt gtaatggtta 132540
tagggtcagg gcgtgccgcg gattgagggt cggggccggc gagggtgtcg ttccggtgtt 132600
tacggaaacg gcggatgtgc gcgcatgcgc tcgcgcgcga gccagacgga cggacggacg 132660
gacgcgtctc gtagcagcat tccatgggcg tttttattcg tactggccga cggcttcagc 132720
ccgggtcggg gctaggagcg cccgcgtgcg cgatgaagcc gccgtctccc ggcggcgacg 132780
caaaggctgc ggtccgcggt tcccaagcgt cctgcgtccc cgccattgct gcaccgctgc 132840
cggaaaaaga aaaacatcct gtacgcactt cccgagcgcc gggacagagg cggtctccgc 132900
cagccccccg cgaaattcca aaaagccggt gtggcggact cggccatgga atctacgggg 132960
ggggggttga ggggggggatg cggcgctgta gtcgccggat gcagtcagga cacggaaatt 133020
aagcgcgtcc ggacgtgccg gacaatcgcg tacgcggaag tgcttgcacg ggaagtaaac 133080
agtggaccgc ggcttacctt cccagcagga gtacggtgtt cgcggagaaa actgtaaggc 133140
gggagcccat cgtcgtgcgc tcccggtcct ctcggaatcg gctgcgagtc tcaaaaaaac 133200
aggaaagggg atcggcctca caaaaccact tcctcattcg tgactgcgcg tagcctccgt 133260
tcttgaaagc ggttggcgtt cgcacagacc tgagtcgaca ccgcctacct gttgtttact 133320
ttcaatgtag tgcgttgcac agagacgctc ggggccgggt acaagttgcc cgggtccgcg 133380
ggtctgaagc acgcactctt ccgttgaagg acggggtggg aaagcggatt attggacccc 133440
gcgatagggt ctgttagggt cgggggttcg gcctgtcatc acggtcgggg ttagggcctg 133500
tcttattcgt tttagtgcct gttagggcca cattaagggc ttgggccagg gccgtttacg 133560

-continued gtggcggtta gggcctctcg gggtcggcgt caggactgtt agggtcactg ttatggcctt 133620
tcagggttag ggtaatagtc catagtcggg gtcaggacat attaagggta gcggctttgg 133680
cggttacggc atgtagggct aggacctttt aatgtaacgg gcagcgttgg tgtcatgtat 133740
cacggtcggg gtgactgtta ggcctcgccg ggcctcattt cacggtcggg gctatggcag 133800
ggtcagagtc tgtggtggtg tgcttcggtc acccactgtg tccgcgcaat gctgcgcgtt 133860
cattctgcct gtagccgaca gttcgcgggg tgcggcagcc cgcgggctga gtgcacctgt 133920
ggcggcggga ggctgcggcc cagccgcgtt aattgttgtg ctatgttcct tttttggggg 133980
gggggtgaaa tgcagggggg gatattaagt tggttagggt tagggttagg gttagggtta 134040
gggttagggt tagggttagg gttagggtta gggttagggt tagggttagg gttagggtta 134100
ggccgttagg gttagggtta ggcctttagg gttagggtta ggcctttagg gttagggtta 134160
gggtgaattt tttttattca gttcgccgcc gcgagagttt tggtatgacg tttggtggtg 134220
gccagggtcc gccgcgcgca tgctccctac ggtccgccgc gcgcatgctc cctacggtcc 134280
gccgcgcgca tgctcgctag ggtccgccgc gcgcatgctc gcaaatgtcg actgcgcgca 134340
tgcgcgcacg ggtccgctac gcatttccgg gcggcctagc gagcgcccgc gcggccggcg 134400
ggcatgtccg gcggggatgc agcgtgcggc tcggcctact ggccgcgcgg agccgccggc 134460
ggtcggcggt ctaacgcttg gagtcgcgcc cccccccccc ccccgatcag acgcaaggct 134520
ttttcaggcg cccgtctcgg tcacttagga cagccgcggt tcgtctcgaa aaaggtctgc 134580
ggcgtgggtg gtgggggaaa gggggagggg cagaacagtc cagagaccgt cacgggcgaa 134640
cgattggggt ccgcgggggg cgcgaggtgg actcggtagc cgccgcggtc cgatccggaa 134700
accgtgtccc ccctgcgctt tcttcgggcc cgctcgccga cgcgaatggg gtgggggagg 134760
ggggtgcgcg ggcgaacaat tagggaccgc ggagtgcgac agcgggcctc ggtagccgcc 134820
gcggtccgat ccggaaaccc tgtcccgctg ccgctttcct cgggcccgct cgccgactcg 134880
atcagaaacc cgtctccccc gccattttta tgtctcccgt atgcgcgctc gttcccgcca 134940
ctttctggtg ccgctgcgga agaggatagc cgggcgggcg agcgggcgag cgcgccgcgg 135000
accgaaccgc tccgcgggct gcgcagggga ccgcagagat tgctcccgcg cgagggatcg 135060
atccgcgggg tagagggctc tccgcgaaca gcgtaagaac agaggtgtcc ccgcgcgccg 135120
ctgcctccgg acgcaccccc cgcccccccc cccccggcca cccagggcga ccgaaacccc 135180
ctgccgccgc cggcaagagt cggtcagaga gcgcgaatga tgtctgtcgc atctggtccc 135240
ttcattcatt cattcattca ttcattcatt cattcattca tttatttatt tatttattcg 135300
ccagcgctac atctcaatcc cagctaccgt taaccctacc accacccccc cccccccccc 135360
cgaccttgag cggttctatc cgttcgagat gaccttcacg gagcggagct cgttgcagga 135420
tccggaggag cggtttccgc agccctaggg atcgcgattc ttcggtacag ccgcgcaggc 135480
cttcggaaag gacgcggcga tctgagtcca gggggccacg gctccgcgcc cgcggtttcg 135540
gttcccgggc agaccgccgt cggggacccc cgggagcttt cggagaaggt agggcggagt 135600
tctgaggctt gagggacaat gagcggcggg tcggttcggt tcacgtcgcc gtcgggatcc 135660
ggtgcggccc cgtccgactt tgccgtggga ggctccattg tccgtcccct cccccctttg 135720
gcggagcgca gggcgaaagg accccgcttt cgccgccgct cctcctcgta caggccacgg 135780
gtcttctagg cgctgtcgcc gcgcggtctt ccttttacga aactttctct accgcgtttg 135840
cgggagaaca ctacggcgaa cgcgcccgcg ggctcgccgg cgcttctgcg ctactgaatg 135900
gccgggcgaa ggtgcgcgcg gggcattcgt tctgggaaca ggtatagagg cgtggccacg 135960
gccgaccaat ggaccaggcg gtgacgcatc cgcacggcag accgcggccc gtacgactaa 136020
cagcgcggaa cgcaaccgag ccgcggggtt ccgctggccc cctaatttat ttgtccgtct 136080
ccccgctcgc ggatgatatg tcgtacccgc ggggctgctt gtccagatag cccttaaaag 136140
tccgccgagt gactccccc gcccccccc ccccgaccct gacttagcct tcactcgccg 136200
aagacttcag agtcgctgag ggccaagggc gaaggaggac cgggcagcgt cggaggatga 136260
attatcctct gtcgcgcgcc ctgttcctcc tggacggtgg tctccggcgg accgccgtcc 136320
ccttccagcc acactacaga cgagctacgt aggtgagcga gcatctcgcg ggccaataaa 136380
ctgcacgtcg cttcgggaac gtgaacgacg actggctggg cgtgcggatc ggggggggagg 136440
actacggagc ggcaaacgtc gcagacggtc ctatttaaga aatcggggga aactatggcg 136500
ttctttttgg gctccaagac gtacacggga cgcagcgggg cgtacagtcc ccacttgaga 136560
gcggctcggt gggagtgcga ctctccagct aaaaagtcgg ggccgggcgg cctctggcgc 136620
ccggccacaa gggccgagga ggctgcgagg taggagagag cggtcattgg gaccgtcgcg 136680
acgcggtcca gtcgcgtcgc gaccttgtat cggacgttgc ttccgcagca cagactgatg 136740
tcgccggccg cggggttttc gcggcgaaag tgcgtttcca gctcacgtag gaccacgggg 136800
cccagcacgt cccgcgaggt tatgaccgtc gtagctagat cggggtggcc aggccatcgg 136860
acggagcatt ggctgcgggg cgagacggtg cacctgacgt agcggacggc ttcttccacg 136920
aggcgcgggc cgttctccgg gcgatcttga tcctctagcg tgtccaggac cacgagcctt 136980
ttttctcgtt tcaaacagag gcgttgcagg tgttccagga cgcccgcaaa accgaggtcc 137040
tgaggggaca ggaacatgac gccggccgcg gtcagcgccg aaacgtccgg cgccgctctc 137100
caccggcccg cccaggcggc gctctccggt aggcagaggc ggttggcgag tgcggcgagc 137160
aggaaagaga gtcctccccg gttcgggtcg aaccggggtc ccccgggggg cgagccgggc 137220
gccggtacgc aaaacaggtg ctcgcctggg ttggccgtgt acaggatgac gagagcgaca 137280
tcttcaggcg aagcctgctg atgccgcatc caagcggtgc gcgctctgag agagacgacg 137340
gccgtgcggc acaacactcc ctcggacgca gcagtgtctg ggcttctgct gacgtgcgag 137400
ggagtgctcg ccacgcgagc gatctccgcc atggcctccg gagaacgcgc caacggctga 137460
cgccacagag tcggtatttg ggcgaagctg gtcagctcgt cgactccttc gcctggacaa 137520
taggcgtcga ggtgcggggg gccggcatag ccagcaatcg gagttccaat ggggggcttc 137580
ctaaaggcgg cgccacgatg ccgtcgatcg cctaacgaca gggaaccgtc cataatgcgc 137640
gcggggtcgc gccacggaaa gcaacgtggg cgcttgggcg ggaaaggccc ggcgtcgcgg 137700
cacgcttcag ggggggtggg gggccttgtg cagctggcga caggcggagg tccggcgcct 137760
gtccgggacc ttcccaaacg cggacgcggg ttctcgacgg cgttgtccgc gccgtcgaga 137820
accgccgcgg gagctgattt tctcttcctt gactcggctg acgtttgggc gcaaagggcc 137880
cgcacgggct cgggagaact tgcggggccg gggtcgtaac aaggctccgc ggagcgcgac 137940
cggccctcgg acgttccgga agaggccgcg tcggcgtccg cgagaaggcg cgccacgcgt 138000
tgcagccgtc gggccttctc gcgggatcgt accggttcgc ccctcgaccc acattcgcgc 138060
aggagcacgg aagtaatgtc cctcgaccca gggcatcgcc aaggccgagc ggggtctttg 138120
ctaagcaacg ggccgatcgc ttccgttatc agggccaccg cattagccgc gagagttcgc 138180
tcctggcgcc cccgaggagc cgaaccgttc gcgtaggccg cgtacacggc gctcctgaga 138240
tcaagcaggt ctcggagcca cgacccgagc agagcccggc atttttccca ctgttcgtgg 138300

-continued ccggcgggtc gagggaaggg cccgtcctcg caagacgaca gcatttccgc gaccgcgccc 138360
ggaccgtcgg gtccgcgcag aagcgccgcc acgacccccct cgcactccag cgcgcaagcg 138420
tccaccagct cgttcagcgg ccgggtagac gcgaaaccgt ccccggcagg gatgtccgga 138480
cgcgcgggcg cgaccaatcg gtattcgggg acgtccagca ggccctcctc tagcgcggaa 138540
ttgaaggccg cgacgccccg gcgcacgcgg tcgtggatcg tggacacgtc tattaccggg 138600
atgagcccgg ccgccgtact ttgggcagtg acgggtgccc gatttgaaat aggcgatgcc 138660
gaggggcgtc gcatttcggc gctggctgca gacgccatag gcgcgtaggc tttcctgagg 138720
gagcggaaca tgaactcttt ctgatctttg cagtacctgc gagtcataga cacgctggcg 138780
gcgatgtgcg gtagcgccca aagcagattt cgcttcttca tggcgctggc tatgtggggt 138840
atgcatttgt tgaccgtccc cgtgacggcc gcgcccggcg aactgtgcga gctctgaaac 138900
ttcgtgacat agatgtgatt gagcgctgcg tcggtgggcg agagcttgcc gtggtgtgcc 138960
cagttcaggg ggttcgcctt cacgtctttg ttaagcatgg cgcttacgag cgcctcgtac 139020
tgtttggcgc agttccccat ttcctccacg tacaccggga ggggaccggg agtagagagg 139080
aatctaacgg cggcctgctc tacttcaggg atgccccgga gcgcctgtcg gtgtccgccg 139140
agaggcccga accagcaccg gccggccggc ggggagggaa tttgccacca cacctcttgg 139200
tcgaggtcat ccggcggtgg cggcgcagca gtttccgagg acggtgatgg cgcccgccgg 139260
ccgcggccgc gccgtcctcc gcggccgcgg ccgcggcctc tggcagcgca ttgaggcgct 139320
cctgcctcgc gggtcggcga cctggatgag gtgcgcgaag aaggggcggc agacgactgt 139380
tccgatgaag agggcgcgga cgacgaagag gacgaggaag aggaagcgga cgaggaggag 139440
gaagatctgg agcgacaccc gagcgaaggg tacgaggccg ggggaggccg gggtagggga 139500
tgggaagcgc gggtcgccgg cgtgccaacc tcctgttgta atgcctgttt tagaacagca 139560
ggtggagctg ttgtgtgcga accatcggag cccgatcccg gctggactct gcggtaacgt 139620
tcctgcgtac cggtggggct gctaacgagg cccggcctcg gagacggccc gttccagtct 139680
ggaacgggaa ggggggggaaa catgggcgct ccgtcgtccc tcgcgccgga cggctgacgg 139740
aggtgtctga atcggcgtag cgccgcggcg gtgacggcgg cgcgccaatc aagtatggct 139800
ttgtacagag gtctgacccg tttttcgatg gccggaccgc aggcggggaa ccccagttcg 139860
accatagcga cggcgagctg ctgcaccatg aatccgtagg cgcgtgcggg acgagagccg 139920
tggggcgtcc cgccgggttc cggatttccg ttccgcagcg ccaacttcga ttccctgacg 139980
gccgcggaaa gcgcgggagg gagcgcggtg gcgggcgggg ggggcatttc gaaaggcacc 140040
tcgaagccgg gccgcacgtc ggggccgacg atgtagtcgt ctggggccag cagtaacccc 140100
cgacgcactt tgaaaaaaag acacctgtaa tgtagcatct tgaaatcgtt ccaggtgagc 140160
ccggtccagg ggttcgggct gccttcccgg ccttccaccc accgaatctc ctcgagcaga 140220
ggacagaagt tggaggcata gaagccgccg cggcgccggc tgcagtcgag accgcggggg 140280
gattcagagg gcggcgttcc gttccagtcc tcgtccaagg gagtacccgc gcccggcggc 140340
ggcgcgcacg ccggaaagca cggcagacca cgagccgctt gtaattgata ggaaaagtcg 140400
cgtgtcagaa cgtgggccat gtactggacg cgcctgacgc agcggagtcg gtccagccag 140460
cggtatgaaa ggcggggaac cttcgacacg aaatcggggg tgacttgaag gccgaggaag 140520
cgaaggagcg ccgacaaaat gtaagcgtac gtcggggtgc gcggagccgg tctcgggagc 140580
cgtgttaccg cttcccagat gcgcgttggc agcactatcg gggcggggag ggggagcggg 140640
cactcgttct gcgggcccca tccgcaaccc tgcgattcta acacgctttc cccgtcctcg 140700
gacggcgaca tatcgtccag ggtcgagaga acgaggcgcg cgcatcgaga aaacaaccac 140760
atcttgcagg ccgcccagtc attccccagc tcgttcggag ggcacgggaa gaccggctcc 140820
tggggcagcg ggcgaccctt cgcgcaacgc cattcgaacg gccggtagtc gctgtcgagt 140880
aaaggggcct ctctcggcag ttcgatagac cccggtgagg tccgcagagg gctgccgcgc 140940
ggagtaggta agatttctct gagtaccgct tccctcgcca gccgatccca gtaggaaggg 141000
caccggcgag cgtccgacaa cgcgaggaga aaaaccttag ggttgtctcc ggaggacggc 141060
tccgtcgcgc cgtcgcgagc cccgcgcgc cacaacatag cgtggctccc cggctggcgg 141120
gccaccaact cgagctcttc tcgagggggg gatgggatcc tggcggatgc ggataggcgg 141180
cagacgtact ggaagcccgc gcccctggta cgggggcccc cgccctcgga aacgctcgat 141240
ttacggcggg ctgggactcg gtcgctccgg aggggagcgg gtgcgaggcg gggggctgaa 141300
ggggacaacg gaggggaagg acgctgacaa gaagcagaga gggctggggg gtccggggaa 141360
agaggcctgt cgtggagagg ggttggcgga ggtggggtag acgccggagg cgagtcaagc 141420
ggtagagacg cagacgggga ggatgtctgc gtagagggag gggaggtaga cggcagaggc 141480
gtggggggag gggaaccgtg cggagggggg gtatgcggag gtggcgtagg aggaggggg 141540
ctaaggggag gtggcgtagg aggaggggg ctaaggggg gtggcgtagg aggaggggg 141600
ctaaggggag gtggtgtagg gggagtgggt gaatggtgtt gagcgaacgg tcccggcgtc 141660
agcggagaaa atgtccatgg gaagttcacg ataggttcgg ggggggtgg ggggggcacg 141720
cccgagggag gggggagagt ttcgacacag acggcgagcg gcgtgcaggc gccggtgggc 141780
ttacagggcg cgtcagatac gcagcggacg gggtcgtttg atttgcgggg atccataggg 141840
ctcggttcgc cccgttccga acccgcgggg actagatcgc cgactgtctt ttgccaagaa 141900
caggaccgcg gggccgccgc ggccgtttcg tttccacaga cgtccacgat gtccgcggtg 141960
gaactgacga cctcgccagg agacccctga tgcgcgccgt cggggggttc ggcggaacgg 142020
agacccgtat ccgaaccctc cgaaacggca ccctcaatgc cgaaaggggc tcgtgcgccg 142080
gcaaggctgc ccgcgacggg agccgcgcgg gcaggggatt tagaccgtgg cgggacgggc 142140
tgccgaccgg gcgtcggggg cacggccacg ctcggtgtat tcaagcacac gtcctggtac 142200
ggatctcccg gggtggcggg tggctgcgga gaaaatccgc cgttgtcggc taacatctct 142260
aacaggctgt agaaatcggg cgggttctcc atgtccgagc aatgggggaa acgcgcgccg 142320
gtccaaccgt ggcgacgccg gcagcactgg cgatccgctc cttacagggg cgtaaatgca 142380
ggggttaatc gggcggatgg ggaccagcgc agggagcgcg gaaggagtcc tgctctgaaa 142440
aaaatgaggg ggaaccgtga gaaagcgttc cccgcagttc gcatcgcttc ttgccccccg 142500
cccaacacca ccaccacccc gcccctacac acaccacagc cacggctccg gcagtgccgg 142560
cctggctact cctttaatca ttaactccca tcaacgcgat ttgatccccg ggctgctctc 142620
cgaatcagcc gagccccata ggtaaacatt ccgccgccca caacgtttct tgtcaaacaa 142680
acgcttatcg gccggattgc gaaacgagca ggttttgcca ttagatatgc tgcggtcagc 142740
gctgctaggc tccccggggg caaacattct cctagcgacg ccgaggtaag gagacattaa 142800
ccctcgacac gctcctgcga gcgactgtgc ggttcgtgcg gtttgtttct ctcgctcccg 142860
acgttcctac cgccctcggg agagtgctcg cccgggggct agaacccgaa gcggaccggc 142920
ccttgagcat cgagacgctt aggctcgggc gaaccgcccg gctctaaaaa gtcaagcgcg 142980
cgcgtgtatt tcttttttt gggggggggg ggggggtgg tggtggtggt tggagacaga 143040

-continued agaggagaga aacggagggg gtggtggtgg ttggagacag aagaggagag aaacggaggg 143100
ggtggtggtg gttggagaca gaagaggaga gaaacggagg gggcggtggt ggttggagac 143160
agaagaggag agaaatggag ggggtggtgg tgggagagaa ataccgacgg ccggacagag 143220
cgaattatta agcacccaac gctcacgcca acacgtccca cctctttccc cgacccgcgc 143280
cgcccccccc ccccccgata ttcgcgtcgg gggtcaggga caaagagagg cgacggggca 143340
ataggcgctg cgtgggggag ggggggccgg ccctacttgc ccctaacgca ccggcgtcca 143400
cgcgatcgcg cgacccgaca gcacctacca ggagcgcggt gccggcggca gccccttctc 143460
gattcggctc ggagctagcc gggagagacg gccgcggtca cgtctccctt tccgaacgcc 143520
tagcgatata gttacagacc gaagcgagcc gtgtcacacc aagtcactta gccgcaattc 143580
tgttcccctt cccccacaca cataacagga gacatagcgc atgggagggg ctttccttat 143640
ctctcgagca gaggtcgccg acacgtcaac gaagggcggt acgtgtgtgg taagtagcag 143700
agatcggagt tggtcccgat ttactaacat ctaataccga tcgttcatag ccgcctggaa 143760
tttgcgggca taacccgcgg ataacggtac tggtcaggga agcaacgcag cgcagacacg 143820
acccgatata aaagactgca aacgaggttt tgtaggggta atgagatgat gtggaaaaga 143880
aatgggtcag gggcgctgt ttgttgtgac acatttgcgc ctagtgtggg accggggcgt 143940
gcggcgagca cccagcgcgg aacgactcgc aagctgacgg tgcagggcta actcgcatta 144000
gaggaagtgt ttgctgattt cttcgtagac gctctgcgcc gagagcgtct cctcgtttaa 144060
cctttatgaa gaaggaagtc gctcccatct ggtgcggaac gatggggtac ttctctccgt 144120
aatggggaac cgaaaactga accaaataca gaaattagaa gaggaacatc ggcttttccc 144180
gttatgtaaa aggaccatgg ggtcgcgtcc gggaggaggg ggagagtttg gggaactcgg 144240
ggccctaaga gcgctacacc agactcttca taataccata tgtcaaggca gttgcggtaa 144300
atatagcgac gaccgcaacc gaacgggtat ttcttctaca ggttagaacc atcccatgac 144360
ccatgcgaaa agtgttacgg cacagagaag gccagaggga aactccgcgt ccggcaaagc 144420
gcacggtaag acactcgcga ggttgtgcaa cagcgcatcg ccccgggtag aaccgacagg 144480
tttatcttca gatggctatc gcggacaact cgtcgtcggg gctgggggag gggggggtat 144540
gtgtcagcca cttccatcct cgtcgctgtc gtcgctcgca aatgtgggct atcaacgctt 144600
ctcgattaaa aaaagacaaa ctagaggggc atccgcaata aacgacaatg tttcatcaca 144660
aaacaaatgg cgtggtctat tctttttcgt ttgcctctga tcctgggcgg tccgtactgc 144720
ggggtgatag ataaaagaag acaacagcag ggaatcgagg tggcgagctc acaaattgcg 144780
aagctcagcc tatgccggcg atgatggccg atgagggaat gtaggaagag agggcgtatc 144840
cccgattgac gatggtgcga ccaccaaccg agtccgtgta ctcctatctt ccattctcac 144900
gacaccggac atgagaaacg atgcgcggag caagtcgggg gggggggggg gaatgaatcc 144960
acggcacgcg cagcgcttcc tttacattgc accacgtgac catattccca taatgacggc 145020
aggcgttatc tatataatgc caggcagaag tcttacttcc gctcgcgatc actattgtcg 145080
tcacacgggg agtctgacta ggcggtatgg acggcgtacg agacagagta ttacctgata 145140
cgtcaacgga caacgagatc taccttgggt cggggtatcc ggtgcaatta catgatgaat 145200
atgggcaaat ttctctaggc tcgccggtcg aaagcagcaa tagcacagga aatttttgtg 145260
ctccgccatg gatgccggat atccctcgtt taagtaatga tacatgtaag atatttcggt 145320
gtctgactag ctgtcgtctc aattgcgcac cgttccacga tgctctcaga agagccttgc 145380
tcgatatgca catgttaggt cgaatgggat tccgtctacg acagcacgaa tgggaacgta 145440
tcatgcagtt gactccagat gagagcatta acctgcggag aactctcctg gaagccgacg 145500
agcggagcag tcattgtatg ccgaacgtgt acgcatctga cattagtaat tccctcgaag 145560
ctggtacaat gcaagttacc tccagctcca atatccgggg tatcagcaac aagtccgtaa 145620
atcactgatt acaaaactca ctgatgtaga cgaacaataa atgtcctatt gccagtaatc 145680
actttgcctg ttatttattg aatgagtatg tcgcgttaat taagtaacgc agtgtgggcg 145740
tgacttgtac catatagatt tctattgact acaacgttat ccgacctgac atttgggagc 145800
tgggtgtcta tagagacaga aggtgcacca ccgcgcaaga taatattgtg atatgtccag 145860
tgaggtatgt gaagtaccat caccgcaaaa gcaaatgggc ctgtggtcgg tgtgccgcaa 145920
acttcgcaga acatctcatc tgtggccgga tcctgcgaat gagaaagtat acggtatact 145980
ttctgctggt ggagtacata tatcatccct gccaaagtct gtacgcggtt tggcccgaac 146040
tgtattgacc gctgccatgg tctctttcgc ggcaatgaaa gctggtatgc cgccatccat 146100
tcacctgtgg cgtgagataa tggatttaac tgacgcaaca atccgccgcg aacaacggtc 146160
cacatcaaat ttctacgtag ccggttcgtt gaggaaaata gtaagtgttg cattgcgaaa 146220
ttataagcat gcacctgaaa cgcatggaga aatggatagc cgtctgactg ctattatgta 146280
ttggtgttgt cttgggcatc ctggctgctg tattgtttcc catttatatg aggaaaacag 146340
tgatctgatt aagttgttgg gaatggcaac aggctgtgga gaaagcccgc ttactgaagt 146400
agagtcttat tggaagcctt tatgccgggc tgtagcagcg aaggggaatg cattaattta 146460
cgacgacgtc gaagtggcac attacctgat caacgtgcga caatcgtctg aatcttcgcc 146520
tccagacgat ggggaagaca ttgagtaaat ttgcgcgaat gacagggctc ggaaacaatg 146580
tatagagttt tgcaaataaa cactttattg acttaccaga agttattgca tcttattgta 146640
atctgcgtca atattctcta acttcagtta aaacgtagca atcgcagagg ggcaaactag 146700
agaaaaatgg acccgcgacc taaatctcgt ctaaaacgct ccagtgcttt acagttcgat 146760
aatctggacc tggggacgcg tataggatcg ttcctccaca tgcgctgctg tcggtatctc 146820
gaatccccgg tattcagttg aatcgttggc ggagtgtcct cctggactct gcaatgttcc 146880
ctagccgtct tcactatctc gtgcaaggct ctataataca gttcctctgc agacccgtcg 146940
ttgctcttcc cttctgcgtc gttagttatt tctgtaggct ccagacgatt tgcctgcatt 147000
tgtgcgcaac ataatctgat tgcattccct atctcgtctt ccggtaatcc cataggtgtt 147060
cggtattcgc agataggtag agaaagcacc actgcaaatc gtgcaatttc cattgcccca 147120
accaatattt tttttaagaa cggcatcgcc gttaatgtac ctcgggcatt gtgacgatcg 147180
aaacccttat ggatgcctaa agagagcatt gcggtccagt tctccaggtg aaaagagaat 147240
agcgcgggta gaaacgggcc gattagtttt atcttcgccg cgtccctaat atcccaagtt 147300
ctgcagtata acttccatcg tccgttttcg acaaggtccg gcgcgacata gtttgaaatg 147360
tcatctatca gaaacatctc gcccatcgta gaaaaaaacc tgtacgcaga ccataaaacc 147420
attcggtacc acatatcctt gtgtatatca aacgatatgt tggttatgtc gttggcggat 147480
gttgtatgaa atagagctaa gcgttctctg gattccacgc actgaacgat tccgttagtc 147540
aattcatctg ctaacatagg ccaaaagttt attcgtgtta cttttctcgg cggtttggca 147600
aaacgccccc ttggcacatc catgtcatta aatacagcgg cataactcct actcatgtgt 147660
tccatagccc aggtttctgt tcggtctgct actacgatca gatcagtggc gcgatcagat 147720
gcgtgggatg aatgaagtgt atccgaaagc agttttgaga tatacgctaa actgtacgac 147780
gattgtggca ctaaacgaag ctttgcgcga cccccatccc acgcggagtc tgtgcaaggt 147840
taatgaccct cgcagttcat tcggaagtta taactgccgc cttcgcacat ttctttttgt 147900
cctgttttgt attgccataa cagataggaa ttgaaacctg atcctcctgt tttttgcagc 147960
atggccagca acagaatact ttgtcggatc gactacttgc gcgagatggt tccgttcttg 148020
gaggtttcgg cgggtcgggt ggagaaccta ttattttata cacacacgtc ataccgttgt 148080
cgcgaaaatg ttctttgtct tctgccgtct cgaacgtcgg ttcccacgta gacgttagga 148140
gcgttggaat ggtatcagga agagcccacg gcatgccgga ccaagtaccc gctactttga 148200
ccgcgagcag tctcttcggt aatgggatgt attccagagc agcgcggcag agatcagcgg 148260
cccccactat ccacagactg tatgaagtgt tttctgaaac atcggactcc aacatcaaat 148320
atccagacat aacatcttgc cattcggaag cacatccgcc gacatcttca aatagcctaa 148380
ctataaacga gtctctagtt cctgctaacc cagtacctcg aatgccagtc ccatccggtg 148440
ggttcgtcct gataatcggt ctctgacgcc gaggaagaac taaaaggggt ctggaaaagc 148500
ggaacagatc tgcagaccga acgactacag acacgcccac atcatcatgt atctgttcca 148560
tgcattgctt tatgagaaaa atccataagg ccgaggcggc atctctagat ctcccgggga 148620
gtctctcgca ctcatctagg agagtgacga cagttatcat agacacgccc atttgtgcac 148680
caaacgaaaa gttcctgtac tggtggagcg tcggcgcggg aatcggtccg tgctctgaaa 148740
ccagtgtcta gacagaagac catccggtaa attctggtgt atgaactgac ggtctccaga 148800
cgaacgtcga agacattaac gatggaaact aacgagcttt cttcaaaagt gtctgattac 148860
aacgctaata gaccttacga aactatacgc agcgatacca gtgacacaga tccgtcggtg 148920
tcgtgtggga ctctctccga caaagacggg gacgacgaag aatctataga tttaagcaag 148980
gtcccgaatg caacgaatgt cggcgcaggt gaagattgca catcccccaa cgacgggcgc 149040
acagagttat gccgtacgac ttcggttacc ggaccggcct cggtcgtgag gatgcaatac 149100
aatattattt caccattacc gcccagctcg gagggccgcg tattcgtctg tacccgttgg 149160
gacgatgtca gcaataagaa ggtgattgtt aaagtcgtca ccggaggtag agacccaggg 149220
agagaaatcg agatcgtaaa gacactttcc cattgcgcga ttatacagct aattcatgca 149280
tatagttgga aatctacggt atgtatggta atgcctaagt ataaatgcga tctgtttacc 149340
tatgtggata gaaaggaatc aatacctttg aaagacgtta ttgtcattga acgacgtttg 149400
ttggaagctc tggtttatct gcacggcaaa ggtgtaattc atcgcgatgt aaagacagaa 149460
aacatatttc tggactaccc cggaaacgct gttttgggag atttcggggc agcgtgcaaa 149520
ttagacatgc atgataatag tcccaagtgc tatggttggg ccggaactat ggaaacaaat 149580
tccccagagc tcctcgcgct agatccttat tgtgccaaaa cagatatctg gagtgccggg 149640
cttgtgttat tcgagatgtc tgccaaaaaa aggacactgt ttggaaaaca agtaaaaacc 149700
tccagttctc aactgagagc attgattaga tgtttgcaga tccacgcttt agaatttcca 149760
caggatgaat ccacgactct atgcaaacaa ttcaaacaat atgcaatccc actgcggcct 149820
cctttctcca ttccagaagt tgtaagaaga aatatcccgt caatggatgt tgagtataca 149880
attgcaaaaa tgctcacatt tgatcaagag tttagacctt cggctcaaga catcctggcg 149940
ttccccctct ttgtgaaaga agccccccaa aatctccagg ccctatttgt tccctgagtg 150000
ctaacagcac atgcaatcga atcccattag aagccgtgct atttaaattt taatgtcgca 150060
tagaaatata tggtatacgg cgccacgcag agctctatac ggcttccact ttagaagcca 150120
atgttttgtc atcagtgagt aatacgactt gggttacaag agacaaacat aatacgtcga 150180

-continued acttaacaaa tgccggaatc tgtacccgtt ttctcatcgc cgctgctgca tattaacggc 150240
aggaagccct taggtatagc ctgagcgttt ttacgtccac tgcattgcca tattcgctac 150300
atcacgtatt tctacaagaa gatgagagtg tctattcaac gggcaatttt cctgatatac 150360
atatgtacag tctccatgtc cagctcggaa aaaactcgta atgaggacgc ctctcgtatt 150420
agttcttcgg acacctttcg cctaaaagaa ttccccgtat ctgcgatacc atcgcctcta 150480
ctcgacgtag tcgataactc gtacccgacg aaacacgtca tatacactga cacttgcggt 150540
ttcgctgttt tgaatcccac cggcgatccg aaatacacaa tcctcagctt acttttgatg 150600
ggacgacata gatacgatgc tactgttgca tggtacgtcc tgggtaagac atgtgctaga 150660
ccaatttatc tacgcgtatt ttcagattgt catacaaatg aacaatttgg gatgtgcact 150720
tcaaaatctc cgggatggtg ggatattggt tatgcaaaaa ctgcgtatat tgaccgtgat 150780
gagttgacgt tagtattagc tgctcctgct ccagagttgg gtgggctata cacacgttta 150840
atcataatta atggcgagcc aatatctagt gacatacttc taacgattga ggggacgtgt 150900
agtttttcgc tcaaaggccc aatcgacgac cggctctgta aaccattcaa ctttttttgta 150960 aatgggacca cgcttgacat aggcatgttt cctgcacgaa ctccccgacc ccatgaagaa 151020
aacgtaaaac agtggcttac gcgccaaagc ggaaaactgg atacggttat tggtgaagcg 151080
tccatgcgtc atgcagcaga tttgccacgt gcttttagag attcgtattt gaaatcgcct 151140
aaagataacc tacctgacga ccctggaagg cctacagttt caattagcag tatccatgcc 151200
aatgatgcct atgtaggaag cacctctctg tatgaccaat cgctacgcgc aactgaagag 151260
ccagtattgc catctgtaga tgaggcccgt cctgcgcttt atacaaatgc agagaggaac 151320
cccaggatgc aactaataat ttctgccatt gttgttgcta gtactgtaat ggtcgcactg 151380
attgggataa gtgcatgtat tgttaggaaa tgctgtaaaa ggaaaatcaa aagagggata 151440
cctcaacgcc cgtccaggaa agtgtattcc cgcctatgat tacgtatgga cttgggcgtg 151500
tcgacacaga cacaaaaccc agtttgcggc cttcttgaaa ctatcgatgt aatgtctctg 151560
tcgaacgggc acatggcaca ttggagtgcg gcgtccaaaa aacatatact atgtttccta 151620
tttcttgtca cggggagcca ttctctaatc ttcaccggga cttcgttatc cgcatcgacg 151680
gatcaatcgg ccatcgttgc cttctgtgga ctcgacaaaa cggtgaatgt ttacggtaga 151740
cttttcttct tgggtgactc ggttggtgtt atttcttacg atggaacgac agaaattctg 151800
agatggaacg aaaaactaaa gtgtttctcg gtcatgtatg ccgcgttgta tacggactgc 151860
ccccttgcag ggtctgcttt atttagagga tgtagaagcg cggtggtgta tgctacccct 151920
catgacaggg tgaagccggt ttccgaaaaa ggattactgc tgtgcatttc agatcccaga 151980
atttctgaca ccggtacata ttacatccgc gtgtccctcg ccggcagaaa tgtcagtgat 152040
attttcagaa ttgacgtcgt tgtgacgagt agcagtattc atacatgcgg ccatgcggat 152100
aaaggtatac aggaatgtat taggtatgcc gaccgtgtgt cattcgagaa ctatctaatt 152160
ggacacgtgg gacaattgct gcctgtcgac tcagagctac acgccgtgta taatgtcact 152220
cccagatcgg tcgttgggac aaatactgat accatgtcag cttttactaa ttcgacaaca 152280
aaatctgctt cgacgaattt aatcgctatg aagactactc atccaccaag tacgcggcgc 152340
tgtaacttga ggcgtgccct tccaaaatta atatacatgt cttcattggc aggcctgtgc 152400
cttctcgtac tattaattgg tagagcggtt gtaaagtgca aaacgcccaa acccaaaatc 152460
tacaagggcg actccacctc tgacggcatc tcgcttatca attctgcagt aaacgacgca 152520

```
tttgggtgta atcctgcaaa agaggttgat ccctcgaata tttctgaagg cgagaagctg 152580
gaaaacatgc agaaaacgac cggaaatgta gaaaagtaac cgtgcgagtt atgagctgga 152640
atggacgtta catgcgggaa gaagtagggc gtaactaagt acatgttaga aggggagggg 152700
cgggttttga cttttaaaag cacaccgcgg gaccacggcg gaattatgct tgatataccc 152760
gggctacgtg gcataatgtc ttgtccgcga atgccccttt tcctaatggc ggcgatgatg 152820
tgcagtgcaa ccaccgtaaa tcgtatacta attccccagg ggaattcggc aacacttaag 152880
atctccagat atccgccggt tgtagatggg actccatata cagagacgtg gacatggatc 152940
tctaatcgct gcaacgaaac ggcgactgga tacgtatgtt tggacagcgt taattgtttt 153000
catgacttaa tcgttaaaat ggcctgttgg cggtattcca aagaggtaat actgcgcact 153060
gccagattcg tggtagagag gggcgtgtta aaaacgatag agaccgctaa gctgcgcaac 153120
gctccgcgtg tattgattgt ggacaacgtg gacactcaat ggactgtttt gaatgcgagc 153180
gagcaaaacg cgggcattta tattcgatat tcccgaaatg gaacgagaac cgctcacgta 153240
gatgccatag tccttgccgt ttctggtcga aagagaggca gggtgccacc gacagtttat 153300
cctgttggac catttttgca caaattccaa atctccctta aaaattttaa aacgttctta 153360
tatcaggtgg gggataccgt tacaatatcg ataactacac gcctggagac gacggttcgt 153420
gcgttcaagt tggagtttcg ggtaatgttt ctcccctaca gtccaaactg taagtcgttc 153480
actatttacg agccgtgtat tttccacccc aaagagccag agtgcatatc tccgtcggag 153540
ctatcggaat gtcggtttgc atcaaacgcg caggtcctgg aaattgccgc cgcacgctcg 153600
gtgaactgca gcgcgggccg cgcgtgccat tacgatgccg aggtcgacga atcgatgcag 153660
caaaggttcg cattccttta ttcggaaatc ccctcgttta caattggcaa tgccgggccg 153720
ggggacgcgg gtctgtacgt cgtcgtcgct ctgtgcgatg agcggccgac aacttggact 153780
cacgtctatc tatcgacctt ggacaagatc ctagatgtgc acgagatcgc tcacaagccg 153840
ggatttgatg acagagtctt atcgagcaat gacgacgccg ctcgcggtgt aagacccgga 153900
gcggccatcg agaaagaatc aggtaggctc cgtctaagcg gagccctaat tgcatcgatc 153960
gtgctggtgg ccgcggccgt cgtaactacg gtaagctttt gcggagcttg cgtcttccgg 154020
tggcgtcgca ggtgccaccg gaagacgcaa gctcccggca actcttgcaa gtacatgtcg 154080
ttgccccaaa atcattggga agagttttac gacgacgtta gggttggcag cgcccctcag 154140
tatgagcagt ttaaccaaag gttgcccgag agaacgagat caggctacac cgcttggctc 154200
tcgtctgata tagccgccgt aagaaagcgt ctcgattgaa atcgccgaga cgtgcgtgcc 154260
gattgttgtt tttattgtat cgcccgtact taacggtcct ttatccccgc gcgaaataaa 154320
actgtccgac tcagtctact ggtgctcgcg tttacctcca ctgcgtaccg cgcgccaatt 154380
ttcgtgtagg tgtgcgtatg gtggagtggt ttgggggacc ctgtctctaa gccggcacac 154440
tccacgctat ttcccccgc ccggtgggca caagcgcttg cgggaggaac cagttgtcgg 154500
tttttatgc gggctcctca gcaccttcgc cacccaccca cactccgcgc cccgactgcg 154560
cgaagctgcc ccgtttaggc aaacggggcc cggccggcgc gacgcagaag aataaagcag 154620
actccgtcgt ttcttctata atggagggta tactcgttta ttgcgacatc acaccccgtg 154680
ttgctatttt aaattgaagg ccgttgataa cccgcatcat ccactaacgt cgttagcgat 154740
aacgattgta tcttccccc cccccccacc tacggtttgt cgacagctat gataagcgga 154800
ggaaaacctg cctgattcct tgggcgggga tccttgtgcg ctgtcttgct ctgtatgcgc 154860
cgacccaaag ccgcctcctc ctcaacgtaa atttaaccgc ccaggccgcg tagttgcgtg 154920
```

tcctgaacgg gaaagaagtt cgttcgctgt tattgtggtc attaccgtaa ctgtcccggc 154980
gtgcctccat ctgctgagtc ccgtgcagac tggcatgagg atggttgttc ggcggcaggc 155040
aactcccccc tcatccctac taatcccgaa tgcctttaat gatcacgcaa taacccctcc 155100
tcttaacaat atctcttttt cgatgaagat ttcagttccc ccataacacg gcagaacgag 155160
tctgatccct gatcaattgg aacgacttcc ttcttcagaa aggttaaacg aggacacagt 155220
ctgcgacgag agggcttaac acttcctcct gtgcgagagc gcgtctctgc gatgtggctt 155280
cgccgcaaag tcctttccca tactaggcgt aaaccgcact ataacaactc cccctccccc 155340
cagcacccaa ggggcccgtg aaaccgcgac tggtttcttc ttcactggct cagtactgca 155400
aatgtgctgc ttacctcgtg attgctgtcg tcggggctcg ttcgcacttt ccaggccacc 155460
aaagaaagcg agaccagagc caatcgggac catctccgaa ccttgttcgc taccacacac 155520
gtgccgccct ttgttgacgt ggccgcaaac agagctcgtg gccacgccaa cgaactgctc 155580
gtcctataaa accccctcca tactcaatgc cccctgaaat gtttgcaggg gggaaagtga 155640
agccttctgc ttcattcagg tgttcgcaat cgttagggac tcaacggtct gtccatctac 155700
ccaggtgcac accaatgtgg tgaatggtaa aatggcgttt atttgatggt ggcaacagct 155760
tatataatcg tgcatagctt cgtctacgcc catatgtcct tgcgtcattc cttccttatc 155820
tagttgccac caatgagcat atggaatgtc ttgctttttc cttatttggt ctttagacta 155880
ttcaagttgc ctctggctct atttgactac atttcccccct ccctatcgtt agggactcaa 155940
cggtctgtcc atctacccag gtgcacacca atgtggtgaa tggtaaaatg gcgtttattt 156000
gatggtggca acagcttata taatcgtgca tagcttcgtc tacgcccata tgtccttgcg 156060
tcattccttc cttatctagt tgccaccaat gagcatatgg aatgtcttgc tttttcctta 156120
tttggtcttt agactattca agttgcctct ggctctattt gactacattt ccccctccct 156180
atcgttaggg actcaacggt ctgtccatct acccaggtgc acaccaatgt ggtgaatggt 156240
aaaatggcgt ttatttgatg gtggcaacag cttatataat cgtgcatagc ttcgtctacg 156300
cccatatgtc cttgcgtcat tccttcctta tctagttgcc accaatgagc atatggaatg 156360
tcttgctttt tccttatttg gtctttagac tattcaagtt gcctctggct ctatttgact 156420
acaggaaagg gagacgtgac cgcggccgtc tctcccggct agctccgagc cgaatcgaga 156480
aggggctgcc gccggcaccg cgctcctggt aggtgctgtc gggtcgcgcg atcgcgtgga 156540
cgccggtgcg ttaggggcaa gtagggccgg cccccccctcc cccacgcagc gcctattgcc 156600
ccgtcgcctc tctttgtccc tgaccccgac gcgaatatcg gggggggggg gggcggcgcg 156660
ggtcggggaa agaggtggga cgtgttggcg tgagcgttgg gtgcttaata attcgctctg 156720
tccggccgtc ggtatttctc tcccaccacc accccctcca tttctctcct cttctgtctc 156780
caaccaccac cgccccctcc gtttctctcc tcttctgtct ccaaccacca ccaccccctc 156840
cgtttctctc ctcttctgtc tccaaccacc accacccccct ccgtttctct cctcttctgt 156900
ctccaaccac caccaccacc cccccccccc cccccaaaaa aaagaaatac acgcgcgcgc 156960
ttgacttttt agagccgggc ggttcgcccg agcctaagcg tctcgatgct caagggccgg 157020
tccgcttcgg gttctagccc ccgggcgagc actctcccga gggcggtagg aacgtcggga 157080
gcgagagaaa caaaccgcac gaaccgcaca gtcgctcgca ggagcgtgtc gagggttaat 157140
gtctccttac ctcggcgtcg ctaggagaat gtttgccccc ggggagccta gcagcgctga 157200
ccgcagcata tctaatggca aaacctgctc gtttcgcaat ccggccgata agcgtttgtt 157260

-continued tgacaagaaa cgttgtgggc ggcggaatgt ttacctatgg ggctcggctg attcggagag 157320
cagcccgggg atcaaatcgc gttgatggga gttaatgatt aaaggagtag ccaggccggc 157380
actgccggag ccgtggctgt ggtgtgtgta ggggcggggt ggtggtggtg ttgggcgggg 157440
ggcaagaagc gatgcgaact gcggggaacg ctttctcacg gttccccctc atttttttca 157500
gagcaggact ccttccgcgc tccctgcgct ggtccccatc cgcccgatta acccctgcat 157560
ttacgcccct gtaaggagcg gatcgccagt gctgccggcg tcgccacggt tggaccggcg 157620
cgcgtttccc ccattgctcg gacatggaga acccgcccga tttctacagc ctgttagaga 157680
tgttagccga caacggcgga ttttctccgc agccacccgc caccccggga gatccgtacc 157740
aggacgtgtg cttgaataca ccgagcgtgg ccgtgccccc gacgcccggt cggcagcccg 157800
tcccgccacg gtctaaatcc cctgcccgcg cggctcccgt cgcgggcagc cttgccggcg 157860
cacgagcccc tttcggcatt gagggtgccg tttcggaggg ttcggatacg ggtctccgtt 157920
ccgccgaacc ccccgacggc gcgcatcagg ggtctcctgg cgaggtcgtc agttccaccg 157980
cggacatcgt ggacgtctgt ggaaacgaaa cggccgcggc ggccccgcgg tcctgttctt 158040
ggcaaaagac agtcggcgat ctagtccccg cgggttcgga acggggcgaa ccgagcccta 158100
tggatccccg caaatcaaac gaccccgtcc gctgcgtatc tgacgcgccc tgtaagccca 158160
ccggcgcctg cacgccgctc gccgtctgtg tcgaaactct ccccccctccc tcgggcgtgc 158220
cccccccacc cccccccgaa cctatcgtga acttcccatg gacattttct ccgctgacgc 158280
cgggaccgtt cgctcaacac cattcaccca ctccccctac accacctccc cttagccccc 158340
ctcctcctac gccacccccc cttagccccc ctcctcctac gccacctccc cttagccccc 158400
ctcctcctac gccacctccg cataccccccc ctccgcacgg ttcccctccc cccacgcctc 158460
tgccgtctac ctcccctccc tctacgcaga catcctcccc gtctgcgtct ctaccgcttg 158520
actcgcctcc ggcgtctacc ccacctccgc caacccctct ccacgacagg cctctttccc 158580
cggacccccc agccctctct gcttcttgtc agcgtccttc ccctccgttg tccccttcag 158640
ccccccgcct cgcacccgct cccctccgga gcgaccgagt cccagcccgc cgtaaatcga 158700
gcgtttccga gggcgggggc ccccgtacca ggggcgcggg cttccagtac gtctgccgcc 158760
tatccgcatc cgccaggatc ccatcccccc ctcgagaaga gctcgagttg gtggcccgcc 158820
agccggggag ccacgctatg ttgtggcgcg cgggggctcg cgacggcgcg acggagccgt 158880
cctccggaga caaccctaag gtttttctcc tcgcgttgtc ggacgctcgc cggtgccctt 158940
cctactggga tcggctggcg agggaagcgg tactcagaga aatcttacct actccgcgcg 159000
gcagccctct gcggacctca ccggggtcta tcgaactgcc gagagaggcc cctttactcg 159060
acagcgacta ccggccgttc gaatggcgtt gcgcgaaggg tcgcccgctg ccccaggagc 159120
cggtcttccc gtgccctccg aacgagctgg ggaatgactg ggcggcctgc aagatgtggt 159180
tgttttctcg atgcgcgcgc ctcgttctct cgaccctgga cgatatgtcg ccgtccgagg 159240
acggggaaag cgtgttagaa tcgcagggtt gcggatgggg cccgcagaac gagtgcccgc 159300
tccccctccc cgccccgata gtgctgccaa cgcgcatctg ggaagcggta acacggctcc 159360
cgagaccggc tccgcgcacc ccgacgtacg cttacatttt gtcggcgctc cttcgcttcc 159420
tcggccttca agtcaccccc gatttcgtgt cgaaggttcc ccgcctttca taccgctggc 159480
tggaccgact ccgctgcgtc aggcgcgtcc agtacatggc ccacgttctg acacgcgact 159540
tttcctatca attacaagcg gctcgtggtc tgccgtgctt tccggcgtgc gcgccgccgc 159600
cgggcgcggg tactcccttg gacgaggact ggaacggaac gccgccctct gaatcccccc 159660
gcggtctcga ctgcagccgg cgccgcggcg gcttctatgc ctccaacttc tgtcctctgc 159720
tcgaggagat tcggtgggtg gaaggccggg aaggcagccc gaacccctgg accgggctca 159780
cctggaacga tttcaagatg ctacattaca ggtgtctttt tttcaaagtg cgtcgggggt 159840
tactgctggc cccagacgac tacatcgtcg gccccgacgt gcggcccggc ttcgaggtgc 159900
ctttcgaaat gcccccccg cccgccaccg cgctccctcc cgcgctttcc gcggccgtca 159960
gggaatcgaa gttggcgctg cggaacggaa atccggaacc cggcgggacg ccccacggct 160020
ctcgtcccgc acgcgcctac ggattcatgg tgcagcagct cgccgtcgct atggtcgaac 160080
tggggttccc cgcctgcggt ccggccatcg aaaaacgggt cagacctctg tacaaagcca 160140
tacttgattg gcgcgccgcc gtcaccgccg cggcgctacg ccgattcaga cacctccgtc 160200
agccgtccgg cgcgagggac gacggagcgc ccatgtttcc ccccttccc gttccagact 160260 ggaacgggcc gtctccgagg ccgggcctcg ttagcagccc caccggtacg caggaacgtt 160320
accgcagagt ccagccggga tcgggctccg atggttcgca cacaacagct ccacctgctg 160380
ttctaaaaca ggcattacaa caggaggttg gcacgccggc gacccgcgct tcccatcccc 160440
taccccggcc tcccccggcc tcgtaccctt cgctcgggtg tcgctccaga tcttcctcct 160500
cctcgtccgc ttcctcttcc tcgtcctctt cgtcgtccgc gccctcttca tcggaacagt 160560
cgtctgccgc cccttcttcg cgcacctcat ccaggtcgcc gacccgcgag gcaggagcgc 160620
ctcaatgcgc tgccagaggc cgcggccgcg gccgcggagg acggcgcggc cgcggccggc 160680
gggcgccatc accgtcctcg gaaactgctg cgccgccacc gccggatgac ctcgaccaag 160740
aggtgtggtg gcaaattccc tccccgccgg ccggccggtg ctggttcggg cctctcggcg 160800
gacaccgaca ggcgctccgg ggcatccctg aagtagagca ggccgccgtt agattcctct 160860
ctactcccgg tcccctcccg gtgtacgtgg aggaaatggg gaactgcgcc aaacagtacg 160920
aggcgctcgt aagcgccatg cttaacaaag acgtgaaggc gaaccccctg aactgggcac 160980
accacggcaa gctctcgccc accgacgcag cgctcaatca catctatgtc acgaagtttc 161040
agagctcgca cagttcgccg ggcgcggccg tcacggggac ggtcaacaaa tgcatacccc 161100
acatagccag cgccatgaag aagcgaaatc tgctttgggc gctaccgcac atcgccgcca 161160
gcgtgtctat gactcgcagg tactgcaaag atcagaaaga gttcatgttc cgctccctca 161220
ggaaagccta cgcgcctatg gcgtctgcag ccagcgccga aatgcgacgc ccctcggcat 161280
cgcctatttc aaatcgggca cccgtcactg cccaaagtac ggcggccggg ctcatcccgg 161340
taatagacgt gtccacgatc cacgaccgcg tgcgccgggg cgtcgcggcc ttcaattccg 161400
cgctagagga gggcctgctg gacgtccccg aataccgatt ggtcgcgccc gcgcgtccgg 161460
acatccctgc cggggacggt ttcgcgtcta cccggccgct gaacgagctg gtggacgctt 161520
gcgcgctgga gtgcgagggg gtcgtggcgg cgcttctgcg cggacccgac ggtccgggcg 161580
cggtcgcgga aatgctgtcg tcttgcgagg acgggccctt ccctcgaccc gccggccacg 161640
aacagtggga aaaatgccgg gctctgctcg ggtcgtggct ccgagacctg cttgatctca 161700
ggagcgccgt gtacgcggcc tacgcgaacg gttcggctcc tcgggggcgc caggagcgaa 161760
ctctcgcggc taatgcggtg gccctgataa cggaagcgat cggcccgttg cttagcaaag 161820
accccgctcg gccttggcga tgccctgggt cgagggacat tacttccgtg ctcctgcgcg 161880
aatgtgggtc gaggggcgaa ccggtacgat cccgcgagaa ggcccgacgg ctgcaacgcg 161940
tggcgcgcct tctcgcggac gccgacgcgg cctcttccgg aacgtccgag ggccggtcgc 162000
gctccgcgga gccttgttac gaccccggcc ccgcaagttc tcccgagccc gtgcgggccc 162060
tttgcgccca aacgtcagcc gagtcaagga agagaaaatc agctcccgcg gcggttctcg 162120
acggcgcgga caacgccgtc gagaacccgc gtccgcgttt gggaaggtcc cggacaggcg 162180
ccggacctcc gcctgtcgcc agctgcacaa ggccccccac ccccctgaa gcgtgccgcg 162240
acgccgggcc tttcccgccc aagcgcccac gttgctttcc gtggcgcgac cccgcgcgca 162300
ttatggacgg ttccctgtcg ttaggcgatc gacggcatcg tggcgccgcc tttaggaagc 162360
cccccattgg aactccgatt gctggctatg ccggcccccc gcacctcgac gcctattgtc 162420
caggcgaagg agtcgacgag ctgaccagct tcgcccaaat accgactctg tggcgtcagc 162480
cgttggcgcg ttctccggag gccatggcgg agatcgctcg cgtggcgagc actccctcgc 162540
acgtcagcag aagcccagac actgctgcgt ccgagggagt gttgtgccgc acggccgtcg 162600
tctctctcag agcgcgcacc gcttggatgc ggcatcagca ggcttcgcct gaagatgtcg 162660
ctctcgtcat cctgtacacg gccaacccag gcgagcacct gttttgcgta ccggcgcccg 162720
gctcgccccc cgggggaccc cggttcgacc cgaaccgggg aggactctct ttcctgctcg 162780
ccgcactcgc caaccgcctc tgcctaccgg agagcgccgc ctgggcgggc cggtggagag 162840
cggcgccgga cgtttcggcg ctgaccgcgg ccggcgtcat gttcctgtcc cctcaggacc 162900
tcggttttgc gggcgtcctg gaacacctgc aacgcctctg tttgaaacga gaaaaaaggc 162960
tcgtggtcct ggacacgcta gaggatcaag atcgcccgga gaacggcccg cgcctcgtgg 163020
aagaagccgt ccgctacgtc aggtgcaccg tctcgccccg cagccaatgc tccgtccgat 163080
ggcctggcca ccccgatcta gctacgacgg tcataacctc gcgggacgtg ctgggccccg 163140
tggtcctacg tgagctggaa acgcactttc gccgcgaaaa ccccgcggcc ggcgacatca 163200
gtctgtgctg cggaagcaac gtccgataca aggtcgcgac gcgactggac cgcgtcgcga 163260
cggtcccaat gaccgctctc tcctacctcg cagcctcctc ggcccttgtg gccgggcgcc 163320
agaggccgcc cggccccgac tttttagctg gagagtcgca ctcccaccga gccgctctca 163380
agtggggact gtacgccccg ctgcgtcccg tgtacgtctt ggagcccaaa aagaacgcca 163440
tagtttcccc cgatttctta aataggaccg tctgcgacgt ttgccgctcc gtagtcctcc 163500
cccccgatcc gcacgcccag ccagtcgtcg ttcacgttcc cgaagcgacg tgcagtttat 163560
tggcccgcga gatgctcgct cacctacgta gctcgtctgt agtgtggctg gaaggggacg 163620
gcggtccgcc ggagaccacc gtccaggagg aacagggcgc gcgacagagg ataattcatc 163680
ctccgacgct gcccggtcct ccttcgccct tggccctcag cgactctgaa gtcttcggcg 163740
agtgaaggct aagtcagggt cgggggggg ggggcggggg gagtcactcg gcggactttt 163800
aagggctatc tggacaagca gccccgcggg tacgacatat catccgcgag cggggagacg 163860
gacaaataaa ttagggggcc agcggaaccc cgcggctcgg ttgcgttccg cgctgttagt 163920
cgtacgggcc gcggtctgcc gtgcggatgc gtcaccgcct ggtccattgg tcggccgtgg 163980
ccacgcctct atacctgttc ccagaacgaa tgccccgcgc gcaccttcgc ccggccattc 164040
agtagcgcag aagcgccggc gagcccgcgg gcgcgttcgc cgtagtgttc tcccgcaaac 164100
gcggtagaga aagtttcgta aaaggaagac cgcgcggcga cagcgcctag aagacccgtg 164160
gcctgtacga ggaggagcgg cggcgaaagc ggggtccttt cgccctgcgc tccgccaaag 164220
gggggagggg acggacaatg gagcctccca cggcaaagtc ggacggggcc gcaccggatc 164280
ccgacggcga cgtgaaccga accgacccgc cgctcattgt ccctcaagcc tcagaactcc 164340
gccctacctt ctccgaaagc tcccgggggt ccccgacggc ggtctgcccg ggaaccgaaa 164400
ccgcgggcgc ggagccgtgg ccccctggac tcagatcgcc gcgtcctttc cgaaggcctg 164460
cgcggctgta ccgaagaatc gcgatcccta gggctgcgga aaccgctcct ccggatcctg 164520
caacgagctc cgctccgtga aggtcatctc gaacggatag aaccgctcaa ggtcgggggg 164580
gggggggggg gtggtggtag ggttaacggt agctgggatt gagatgtagc gctggcgaat 164640
aaataaataa ataaatgaat gaatgaatga atgaatgaat gaatgaatga atgaagggac 164700
cagatgcgac agacatcatt cgcgctctct gaccgactct tgccggcggc ggcagggggt 164760
ttcggtcgcc ctgggtggcc gggggggggg gggcgggggg tgcgtccgga ggcagcggcg 164820
cgcggggaca cctctgttct tacgctgttc gcggagagcc ctctaccccg cggatcgatc 164880
cctcgcgcgg gagcaatctc tgcggtcccc tgcgcagccc gcggagcggt tcggtccgcg 164940
gcgcgctcgc ccgctcgccc gcccggctat cctcttccgc agcggcacca gaaagtggcg 165000
ggaacgagcg cgcatacggg agacataaaa atggcggggg agacgggttt ctgatcgagt 165060
cggcgagcgg gcccgaggaa agcggcagcg ggacagggtt tccggatcgg accgcggcgg 165120
ctaccgaggc ccgctgtcgc actccgcggt ccctaattgt tcgcccgcgc accccccctcc 165180 cccaccccat tcgcgtcggc gagcgggccc gaagaaagcg caggggggac acggtttccg 165240
gatcggaccg cggcggctac cgagtccacc tcgcgccccc cgcggacccc aatcgttcgc 165300
ccgtgacggt ctctggactg ttctgcccct ccccctttcc cccaccaccc acgccgcaga 165360 ccttttcga gacgaaccgc ggctgtccta agtgaccgag acgggcgcct gaaaaagcct 165420
tgcgtctgat cggggggggg ggggggcgc gactccaagc gttagaccgc cgaccgccgg 165480
cggctccgcg cggccagtag gccgagccgc acgctgcatc cccgccggac atgcccgccg 165540
gccgcgcggg cgctcgctag gccgcccgga aatgcgtagc ggacccgtgc gcgcatgcgc 165600
gcagtcgaca tttgcgagca tgcgcgcggc ggaccctagc gagcatgcgc gcggcggacc 165660
gtagggagca tgcgcgcggc ggaccgtagg gagcatgcgc gcggcggacc ctggccacca 165720
ccaaacgtca taccaaaact ctcgcggcgg cgaactgaat aaaaaaaatt caccctaacc 165780
ctaaccctaa aggcctaacc ctaaccctaa aggcctaacc ctaaccctaa cggcctaacc 165840
ctaaccctaa ccctaaccct aaccctaacc ctaaccctaa ccctaaccct aaccctaacc 165900
ctaaccctaa ccctaaccct aaccaactta atatcccccc ctgcatttca cccccccccc 165960
aaaaaaggaa catagcacaa caattaacgc ggct 165994

<210> SEQ ID NO 15
<211> LENGTH: 22
<212> TYPE: DNA
<213> ORGANISM: artificial sequence
<220> FEATURE:
<223> OTHER INFORMATION: MB080 primer

<400> SEQUENCE: 15
cgaacaaact tcatcgctat gc 22

<210> SEQ ID NO 16
<211> LENGTH: 22
<212> TYPE: DNA
<213> ORGANISM: artificial sequence
<220> FEATURE:
<223> OTHER INFORMATION: MB081 primer

<400> SEQUENCE: 16
taactcaaat gcgaagcgtt gc 22

<210> SEQ ID NO 17
<211> LENGTH: 21
<212> TYPE: DNA
<213> ORGANISM: artificial sequence
<220> FEATURE:
<223> OTHER INFORMATION: SB-1 US10 primer

<400> SEQUENCE: 17
tcaacgtgcg acaatcgtct g 21

<210> SEQ ID NO 18
<211> LENGTH: 21
<212> TYPE: DNA
<213> ORGANISM: artificial sequence
<220> FEATURE:
<223> OTHER INFORMATION: SB-1 SORF4 primer

<400> SEQUENCE: 18
atgtggagga acgatcctat a 21

<210> SEQ ID NO 19
<211> LENGTH: 18
<212> TYPE: DNA
<213> ORGANISM: artificial sequence
<220> FEATURE:
<223> OTHER INFORMATION: ALLNDVFprimer

<400> SEQUENCE: 19
atggcttggg aataatac 18

<210> SEQ ID NO 20
<211> LENGTH: 18
<212> TYPE: DNA
<213> ORGANISM: artificial sequence
<220> FEATURE:
<223> OTHER INFORMATION: mCMVF primer

<400> SEQUENCE: 20
aactccgccc gttttatg 18

<210> SEQ ID NO 21
<211> LENGTH: 18
<212> TYPE: DNA
<213> ORGANISM: artificial sequence
<220> FEATURE:
<223> OTHER INFORMATION: SV40tailR primer

<400> SEQUENCE: 21
tcgactctag aggatccg 18

<210> SEQ ID NO 22
<211> LENGTH: 21
<212> TYPE: DNA
<213> ORGANISM: artificial sequence
<220> FEATURE:
<223> OTHER INFORMATION: newSB-1 UL55R primer

<400> SEQUENCE: 22
atggctatag agggactgtg t 21

<210> SEQ ID NO 23
<211> LENGTH: 21
<212> TYPE: DNA
<213> ORGANISM: artificial sequence
<220> FEATURE:
<223> OTHER INFORMATION: New SB-1 ORF5F primer

<400> SEQUENCE: 23
gatctcaacg ctataccggc g 21

<210> SEQ ID NO 24
<211> LENGTH: 21
<212> TYPE: DNA
<213> ORGANISM: artificial sequence
<220> FEATURE:
<223> OTHER INFORMATION: OptF primer

<400> SEQUENCE: 24
actgacaaca ccctacatgg c 21

<210> SEQ ID NO 25
<211> LENGTH: 19
<212> TYPE: DNA
<213> ORGANISM: artificial sequence
<220> FEATURE:
<223> OTHER INFORMATION: VIIoptF RP primer

<400> SEQUENCE: 25
gccagcacca ggctcaggg 19

<210> SEQ ID NO 26
<211> LENGTH: 18
<212> TYPE: DNA
<213> ORGANISM: artificial sequence
<220> FEATURE:
<223> OTHER INFORMATION: SV40promoterF primer

<400> SEQUENCE: 26
agcttggctg tggaatgt 18

<210> SEQ ID NO 27
<211> LENGTH: 21
<212> TYPE: DNA
<213> ORGANISM: artificial sequence
<220> FEATURE:
<223> OTHER INFORMATION: SB1 43.F primer

<400> SEQUENCE: 27
gctctcggag acgcggctcg c 21

<210> SEQ ID NO 28
<211> LENGTH: 21
<212> TYPE: DNA
<213> ORGANISM: artificial sequence
<220> FEATURE:
<223> OTHER INFORMATION: SB1 45.R primer

<400> SEQUENCE: 28
gctcttgtaa catcgcggac g 21

<210> SEQ ID NO 29
<211> LENGTH: 18
<212> TYPE: DNA
<213> ORGANISM: artificial sequence
<220> FEATURE:
<223> OTHER INFORMATION: SV40 promoter F primer

<400> SEQUENCE: 29
agcttggctg tggaatgt 18

<210> SEQ ID NO 30

<211> LENGTH: 20
<212> TYPE: DNA
<213> ORGANISM: artificial sequence
<220> FEATURE:
<223> OTHER INFORMATION: HVTUS10 FP primer

<400> SEQUENCE: 30
ccggcaacat acataatgtg 20

<210> SEQ ID NO 31
<211> LENGTH: 18
<212> TYPE: DNA
<213> ORGANISM: artificial sequence
<220> FEATURE:
<223> OTHER INFORMATION: HVTUS10 RP primer

<400> SEQUENCE: 31
ggcactatcc acagtacg 18

<210> SEQ ID NO 32
<211> LENGTH: 19
<212> TYPE: DNA
<213> ORGANISM: artificial sequence
<220> FEATURE:
<223> OTHER INFORMATION: CaoptF RP primer

<400> SEQUENCE: 32
gccagcacca ggctcatca 19

<210> SEQ ID NO 33
<211> LENGTH: 18
<212> TYPE: DNA
<213> ORGANISM: artificial sequence
<220> FEATURE:
<223> OTHER INFORMATION: SynTailR primer

<400> SEQUENCE: 33
atgttctggc acctgcac 18

<210> SEQ ID NO 34
<211> LENGTH: 1437
<212> TYPE: DNA
<213> ORGANISM: artificial sequence
<220> FEATURE:
<223> OTHER INFORMATION: DNA sequence encoding glycoprotein C of SB-1
strain with GenBank accession No. HQ840738

<400> SEQUENCE: 34
atgcacgcgt cacgcgcgtt gcgagctttg gggtggacga gactcttatt tgtcgtttta 60
ttttcgggcc gcgtcctaag cgctagcatt aaccccgatc tagctacacc cccggtcatt 120
gctttcaacc cgtcaagtat tccggccgat gatgggcctt tggccaaagt tcctgcatcc 180
ccgccggcag gggagaaaga ggagagccac aagaatgcaa gcgacgcgcg taggatgcct 240
agtatagttt gcgataaaga agaagttttc gttttcctga acaagaccgg gcgtttcgtg 300
tgcactctta agatcgcccc tccctccgac aacgaatggt cgaactttgc tctggacctt 360
attttcaatc cgatcgaata ccatgctaat gagaagaacg tggaagcagc gcgtattgct 420
ggcctctatg gggtgcccgg atcagattac gcctacccgc gtccttctga attaatctct 480
tctattcggc gagaccccca agggaccttt tggacaagcc catcggcaca tggagacaag 540
tacttcatat ggctaaacaa aacgacgaat acgatgggcg tggaaattag gaacgtcgac 600
tacgcagaca acggttacat ccaagttgcc atgcgggatc ctttcaatcg gcctttacta 660

```
gataagcacg tgtacatccg cgtgtgtcaa cgacccgcct cggtcgacgt tctagccccc    720

cccgtcctca gtggcgataa gtacaaggct tcatgcatcg ttaggcattt ttatccaccg    780

ggctccgtct atgtgttctg gaggcaagat gggaatatcg ttacaccacg taaggacacg    840

gacggaagtt tttggtggtt tgaatcagcc cggggagcca ccctggtatc tacgataacg    900

ctgggcaact cggccatcga ccctcctccc aagatttcat gtctggtagc ctggaagcag    960

ggaaatatga tgagtactac gaacgccact gcaatcccga ccgtatatca tcatccccgg   1020

atatccctgg ctttcaaaga tgggtatgca atatgtacta cgcaatgtgt gccgttcgga   1080

attaccatac gatggttagt acacgatgaa cccaaaccta atacaactta tgatactgtg   1140

gttacaggtc tttgcaggac cctcaagcgg catagaaata tcatcagccg aatattactc   1200

caagatgact ggcagaaaac aaagtataca tgtcgtctca tcggctatcc tttcgacgaa   1260

gacaaatttc aagctttcga ttacttcgac gcgacgccat cgacgagggg gtcccccatg   1320

gttctcgcga tagcggctgt tgtgggacta gctttgattt tgggaatggg tacactcctg   1380

acggctctgt gtttctacgc ctccgggaaa aaatacatat tactttcgtc cgtctag      1437
```

<210> SEQ ID NO 35
<211> LENGTH: 478
<212> TYPE: PRT
<213> ORGANISM: artificial sequence
<220> FEATURE:
<223> OTHER INFORMATION: glycoportein C of SB-1 strain with GenBank
      accession No. AEI00252

<400> SEQUENCE: 35

```
Met His Ala Ser Arg Ala Leu Arg Ala Leu Gly Trp Thr Arg Leu Leu
1               5                   10                  15

Phe Val Val Leu Phe Ser Gly Arg Val Leu Ser Ala Ser Ile Asn Pro
            20                  25                  30

Asp Leu Ala Thr Pro Pro Val Ile Ala Phe Asn Pro Ser Ser Ile Pro
        35                  40                  45

Ala Asp Asp Gly Pro Leu Ala Lys Val Pro Ala Ser Pro Pro Ala Gly
    50                  55                  60

Glu Lys Glu Glu Ser His Lys Asn Ala Ser Asp Ala Arg Arg Met Pro
65                  70                  75                  80

Ser Ile Val Cys Asp Lys Glu Glu Val Phe Val Phe Leu Asn Lys Thr
                85                  90                  95

Gly Arg Phe Val Cys Thr Leu Lys Ile Ala Pro Pro Ser Asp Asn Glu
            100                 105                 110

Trp Ser Asn Phe Ala Leu Asp Leu Ile Phe Asn Pro Ile Glu Tyr His
        115                 120                 125

Ala Asn Glu Lys Asn Val Glu Ala Ala Arg Ile Ala Gly Leu Tyr Gly
    130                 135                 140

Val Pro Gly Ser Asp Tyr Ala Tyr Pro Arg Pro Ser Glu Leu Ile Ser
145                 150                 155                 160

Ser Ile Arg Arg Asp Pro Gln Gly Thr Phe Trp Thr Ser Pro Ser Ala
                165                 170                 175

His Gly Asp Lys Tyr Phe Ile Trp Leu Asn Lys Thr Thr Asn Thr Met
            180                 185                 190

Gly Val Glu Ile Arg Asn Val Asp Tyr Ala Asp Asn Gly Tyr Ile Gln
        195                 200                 205

Val Ala Met Arg Asp Pro Phe Asn Arg Pro Leu Leu Asp Lys His Val
    210                 215                 220
```

```
Tyr Ile Arg Val Cys Gln Arg Pro Ala Ser Val Asp Val Leu Ala Pro
225                 230                 235                 240

Pro Val Leu Ser Gly Asp Lys Tyr Lys Ala Ser Cys Ile Val Arg His
                245                 250                 255

Phe Tyr Pro Pro Gly Ser Val Tyr Val Phe Trp Arg Gln Asp Gly Asn
            260                 265                 270

Ile Val Thr Pro Arg Lys Asp Thr Asp Gly Ser Phe Trp Trp Phe Glu
        275                 280                 285

Ser Ala Arg Gly Ala Thr Leu Val Ser Thr Ile Thr Leu Gly Asn Ser
    290                 295                 300

Ala Ile Asp Pro Pro Pro Lys Ile Ser Cys Leu Val Ala Trp Lys Gln
305                 310                 315                 320

Gly Asn Met Met Ser Thr Thr Asn Ala Thr Ala Ile Pro Thr Val Tyr
                325                 330                 335

His His Pro Arg Ile Ser Leu Ala Phe Lys Asp Gly Tyr Ala Ile Cys
            340                 345                 350

Thr Thr Gln Cys Val Pro Phe Gly Ile Thr Ile Arg Trp Leu Val His
        355                 360                 365

Asp Glu Pro Lys Pro Asn Thr Thr Tyr Asp Thr Val Val Thr Gly Leu
    370                 375                 380

Cys Arg Thr Leu Lys Arg His Arg Asn Ile Ile Ser Arg Ile Leu Leu
385                 390                 395                 400

Gln Asp Asp Trp Gln Lys Thr Lys Tyr Thr Cys Arg Leu Ile Gly Tyr
                405                 410                 415

Pro Phe Asp Glu Asp Lys Phe Gln Ala Phe Asp Tyr Phe Asp Ala Thr
            420                 425                 430

Pro Ser Thr Arg Gly Ser Pro Met Val Leu Ala Ile Ala Ala Val Val
        435                 440                 445

Gly Leu Ala Leu Ile Leu Gly Met Gly Thr Leu Leu Thr Ala Leu Cys
    450                 455                 460

Phe Tyr Ala Ser Gly Lys Lys Tyr Ile Leu Leu Ser Ser Val
465                 470                 475
```

<210> SEQ ID NO 36
<211> LENGTH: 4734
<212> TYPE: DNA
<213> ORGANISM: artificial sequence
<220> FEATURE:
<223> OTHER INFORMATION: plasmid pSB1 44cds for gC deletion

<400> SEQUENCE: 36

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgagctcggt acctcgcgaa    420

tgcatctaga tgccaatgaa ttcgcgatag cttcgattag aattttcgca tgagtaaagt    480

cgacaagctt gctgttatgt cgggagcacg tatctagggc ttctagctcg gtagcgttgc    540

tccccatcgc gcgcatacaa ctatagccta aaccgatcca ttcgtgagga catgtaccgg    600

actccaggga catgtaagag aatgcaaaca gcgaagctag cacgaccgta gctgtgatga    660
```

-continued

```
cgaacacagt aagagcgatc ccgatcgtac aaccgcataa caaccggggg catcctgaac    720
gcgaacgttt gtgtcgctca gatgtggtct cgtccatcat ccggagcagc ccacgtactg    780
cgaccaagtc gcggtcgtct tcgggagtag ggacatcat  acttacatat ttaaggaccg    840
agtagctata tagagaccgt atttcgcgat tgtacggtac tcgcagtcat attcgatttc    900
taaaattgtt accgacgtat tcgtcggtag gcgcgcagcc acttttcaac ggacccgcgg    960
ggtccgacaa ccttatcccg caaacgacgc ttccgttaaa ctctgttcgt gcgtggctgg   1020
ggtcgcgtgt acctcgtccc ttagctttcc agccgtggaa caaagaaggc ctaggttcac   1080
tgacacttat ctactctaga ggtttgcttt ttaggcgctg ccgagggaat aattccggtc   1140
caaacgaagt tcgagagaac ctgtgtagtg tacgttattt agtctgtgcc gtgtggaaaa   1200
ggatctacct ttttttagaa ataccgtact gctagagggt tacatactat tcctcatcac   1260
ctgaggagtc taaagctgaa gttttccggt ggatatatgc cctaccgact gtaagcaggg   1320
ccggatgtac ctatacggtt gacatgccgc ttttgcattt gagatgtgcc tactacggaa   1380
atcgcgtccg cgatgttaca agagctcggg gcatataatg agccagatca atgtcaccgc   1440
aaacctgcag ggatatcggg ccccctgcag gggggaaaat atttcagctg gcgtgcgagc   1500
cgcgtctccg agagcgtata tggagtggcc tctgcctgcg caacttagct ttaaatcggc   1560
cctttcatgt tttcgacagc gcataaaccc acgataggcc cctttagtag ccacgaaagt   1620
tttattcgca gttcgaaaga acgctatgag cacatgatat aaaaattaat cgctccgcga   1680
tcaggaatat tgtattaaca cgcaaaccaa catgctcgag atggcagttc ctaatatgca   1740
tttaccagct gcggcggccg ccaattgctt tattccgcta ttcgcgttgc gtacatttat   1800
acaagtgtag cagcacagaa ccgcggctgt cgcggaaaac aatgtcggcc cgagaagtaa   1860
accgaagccg gctaaggtag tagccattgc cccgaatatt aacagtaata caagaattgg   1920
acggaacaga acctcgtggt agcgcgacgg aaggaatatc gcgacacttg tacccaccaa   1980
gaaaccgcat atactgcgta acgtgtcagt caatgttgac tggtgcttag ttgcgttcga   2040
catgtacttt tgaaagctgg ctatggctgg aatcgagatg accgctatga ggctcagaat   2100
tatcgtagga atattccccc ccagcgtatc gtaactggat acgtcttctt cgcgcgtcgc   2160
ctcggcgtcc gtgctgggcg ggagacgcgc gcgaccgagg cgatatgcac cgttcacagt   2220
aatttcccga cgtgcacggt agtagcacgt gttcattaga gaccgactgg cgtctctgac   2280
cacgtgaata gctaacgccg tatacgccga aagaaagccg gctagaggag aaatgtctcc   2340
atacggagcc gtgatgccgg caatcgtccc tgccgccaca actaaaaacc cggtcttcca   2400
cgtcacgtct ccagacgttg ctatgcagac gtaatgataa gatgcgatca gagctccgag   2460
catgacaaaa gcccgactgc agaggcctgc atgcaagctt ggcgtaatca tggtcatagc   2520
tgtttcctgt gtgaaattgt tatccgctca caattccaca caacatacga gccggaagca   2580
taaagtgtaa agcctggggt gcctaatgag tgagctaact cacattaatt gcgttgcgct   2640
cactgcccgc tttccagtcg ggaaacctgt cgtgccagct gcattaatga atcggccaac   2700
gcgcggggag aggcggtttg cgtattgggc gctcttccgc ttcctcgctc actgactcgc   2760
tgcgctcggt cgttcggctg cggcgagcgg tatcagctca ctcaaaggcg gtaatacggt   2820
tatccacaga atcaggggat aacgcaggaa agaacatgtg agcaaaaggc cagcaaaagg   2880
ccaggaaccg taaaaaggcc gcgttgctgg cgtttttcca taggctccgc ccccctgacg   2940
agcatcacaa aaatcgacgc tcaagtcaga ggtggcgaaa cccgacagga ctataaagat   3000
```

```
accaggcgtt tccccctgga agctccctcg tgcgctctcc tgttccgacc ctgccgctta   3060

ccggatacct gtccgccttt ctcccttcgg gaagcgtggc gctttctcat agctcacgct   3120

gtaggtatct cagttcggtg taggtcgttc gctccaagct gggctgtgtg cacgaacccc   3180

ccgttcagcc cgaccgctgc gccttatccg gtaactatcg tcttgagtcc aacccggtaa   3240

gacacgactt atcgccactg gcagcagcca ctggtaacag gattagcaga gcgaggtatg   3300

taggcggtgc tacagagttc ttgaagtggt ggcctaacta cggctacact agaagaacag   3360

tatttggtat ctgcgctctg ctgaagccag ttaccttcgg aaaaagagtt ggtagctctt   3420

gatccggcaa acaaaccacc gctggtagcg gtggtttttt tgtttgcaag cagcagatta   3480

cgcgcagaaa aaaaggatct caagaagatc ctttgatctt ttctacgggg tctgacgctc   3540

agtggaacga aaactcacgt taagggattt tggtcatgag attatcaaaa aggatcttca   3600

cctagatcct tttaaattaa aaatgaagtt ttaaatcaat ctaaagtata tatgagtaaa   3660

cttggtctga cagttaccaa tgcttaatca gtgaggcacc tatctcagcg atctgtctat   3720

ttcgttcatc catagttgcc tgactccccg tcgtgtagat aactacgata cgggagggct   3780

taccatctgg ccccagtgct gcaatgatac cgcgagaccc acgctcaccg gctccagatt   3840

tatcagcaat aaaccagcca gccggaaggg ccgagcgcag aagtggtcct gcaactttat   3900

ccgcctccat ccagtctatt aattgttgcc gggaagctag agtaagtagt tcgccagtta   3960

atagtttgcg caacgttgtt gccattgcta caggcatcgt ggtgtcacgc tcgtcgtttg   4020

gtatggcttc attcagctcc ggttcccaac gatcaaggcg agttacatga tcccccatgt   4080

tgtgcaaaaa agcggttagc tccttcggtc ctccgatcgt tgtcagaagt aagttggccg   4140

cagtgttatc actcatggtt atggcagcac tgcataattc tcttactgtc atgccatccg   4200

taagatgctt ttctgtgact ggtgagtact caaccaagtc attctgagaa tagtgtatgc   4260

ggcgaccgag ttgctcttgc ccggcgtcaa tacgggataa taccgcgcca catagcagaa   4320

ctttaaaagt gctcatcatt ggaaaacgtt cttcggggcg aaaactctca aggatcttac   4380

cgctgttgag atccagttcg atgtaaccca ctcgtgcacc caactgatct tcagcatctt   4440

ttactttcac cagcgtttct gggtgagcaa aaacaggaag gcaaaatgcc gcaaaaaagg   4500

gaataagggc gacacggaaa tgttgaatac tcatactctt cctttttcaa tattattgaa   4560

gcatttatca gggttattgt ctcatgagcg gatacatatt tgaatgtatt tagaaaaata   4620

aacaaatagg ggttccgcgc acatttcccc gaaaagtgcc acctgacgtc taagaaacca   4680

ttattatcat gacattaacc tataaaaata ggcgtatcac gaggcccttt cgtc         4734
```

```
<210> SEQ ID NO 37
<211> LENGTH: 4085
<212> TYPE: DNA
<213> ORGANISM: artificial sequence
<220> FEATURE:
<223> OTHER INFORMATION: partial plasmid sequence of pSB1 44cds SV
      FCAopt for vSB1-009

<400> SEQUENCE: 37
```

```
cttttgtcat gctcggagct ctgatcgcat cttatcatta cgtctgcata gcaacgtctg     60

gagacgtgac gtggaagacc gggtttttag ttgtggcggc agggacgatt gccggcatca    120

cggctccgta tggagacatt tctcctctag ccggctttct ttcggcgtat acggcgttag    180

ctattcacgt ggtcagagac gccagtcggt ctctaatgaa cacgtgctac taccgtgcac    240

gtcgggaaat tactgtgaac ggtgcatatc gcctcggtcg cgcgcgtctc ccgcccagca    300
```

-continued

```
cggacgccga ggcgacgcgc gaagaagacg tatccagtta cgatacgctg ggggggaata    360
ttcctacgat aattctgagc ctcatagcgg tcatctcgat tccagccata gccagctttc    420
aaaagtacat gtcgaacgca actaagcacc agtcaacatt gactgacacg ttacgcagta    480
tatgcggttt cttggtgggt acaagtgtcg cgatattcct tccgtcgcgc taccacgagg    540
ttctgttccg tccaattctt gtattactgt taatattcgg ggcaatggct actaccttag    600
ccggcttcgg tttacttctc gggccgacat tgttttccgc gacagccgcg gttctgtgct    660
gctacacttg tataaatgta cgcaacgcga atagcggaat aaagcaattg gcggccgccg    720
cagctggtaa atgcatatta ggaactgcca tctcgagcat gttggtttgc gtgttaatac    780
aatattcctg atcgcggagc gattaatttt tatatcatgt gctcatagcg ttctttcgaa    840
ctgcgaataa aactttcgtg gctactaaag gggcctatcg tgggtttatg cgctgtcgaa    900
aacatgaaag ggccgattta aagctaagtt gcgcaggcag aggccactcc atatacgctc    960
tcggagacgc ggctcgcacg ccagctgaaa tattttcccc cctgcaggtc gacccaattc   1020
gagctcggta cagcttggct gtggaatgtg tgtcagttag ggtgtggaaa gtccccaggc   1080
tccccagcag gcagaagtat gcaaagcatg catctcaatt agtcagcaac caggtgtgga   1140
aagtccccag gctccccagc aggcagaagt atgcaaagca tgcatctcaa ttagtcagca   1200
accatagtcc cgcccctaac tccgcccatc ccgcccctaa ctccgcccag ttccgcccat   1260
tctccgcccc atggctgact aatttttttt atttatgcag aggccgaggc cgcctcggcc   1320
tctgagctat tccagaagta gtgaggaggc ttttttggag gcctaggctt ttgcaaaaag   1380
ctcccggggc ggccgccacc atgggcagca agcccagcac ctggatcagc gtgaccctga   1440
tgctgatcac cagaaccatg ctgatcctga gctgcatctg ccccacaagc agcctggacg   1500
gcagacccct ggccgctgcc ggcatcgtgg tgaccggcga caaggccgtg aacatctaca   1560
ccagcagcca gaccggcagc atcatcatca agctgctgcc caacatgccc aaggacaaag   1620
aggcctgcgc caaggccccc ctggaagcct acaacagaac cctgaccacc ctgctgaccc   1680
ccctgggcga cagcatcaga agaatccagg gcagcgccac cacaagcggc ggaggaaagc   1740
agggcagact ggtgggcgct atcatcggga gcgtggccct gggcgtggcc acagctgccc   1800
agattaccgc tgcagccgcc ctgattcagg ccaatcagaa cgccgccaac atcctgagac   1860
tgaaagagag cattgccgcc accaacgacg ccgtgcacga agtgacaaac ggactgtccc   1920
agctggctgt cgctgtcggc aagatgcagc agttcgtgaa caaccagttc aacaacaccg   1980
ccagagagct ggactgcatc aagatcgccc agcaggtggg cgtggagctg aacctgtacc   2040
tgaccgagct gaccacagtg ttcggccccc agatcacaag ccccgctctg acccagctga   2100
caatccaggc cctgtacaac ctggctggcg gcaacatgga ctatctgctg actaagctgg   2160
gagtgggcaa caaccagctg tccagcctga tcgggtccgg gctgatcaca ggcaacccca   2220
tcctgtacga cagccagaca cagctgctgg gcatccagat caacctgcca tccgtgggaa   2280
gcctgaacaa catgagagcc acctacctgg aaaccctgag cgtgtccacc accaagggct   2340
tcgccagcgc cctggtgccc aaggtggtga cacaggtggg cagcgtgatc gaggaactgg   2400
acaccagcta ctgcatcgag agcgacatcg acctgtactg caccagagtg gtgaccttcc   2460
caatgagccc cggcatctac agctgcctga gcggcaacac cagcgcctgc atgtacagca   2520
agaccgaagg agcactgaca acaccctaca tggccctgaa gggaagcgtg atcgccaact   2580
gcaagatgac cacctgcaga tgcgccgacc ccccaggcat catcagccag aactacggcg   2640
aggccgtgag cctgatcgac aaacattcct gtagcgtgct gtccctggat ggcatcacac   2700
```

```
tgagactgag cggcgagttc gacgccacct accagaagaa catcagcatc ctggacagcc      2760

aggtgatcgt gaccggcaac ctggacatca gcaccgagct gggcaacgtg aacaacagca      2820

tcagcagcac cctggacaag ctggccgagt ccaacaacaa gctgaacaaa gtgaacgtga      2880

acctgaccag cacaagcgcc ctgatcacct acatcgtgct ggccatcgtg tccctggcct      2940

tcggcgtgat cagcctggtg ctggcctgct acctgatgta caagcagaga gcccagcaga      3000

aaaccctgct gtggctgggc aataacaccc tggaccagat gagggccacc accagaacct      3060

gatgagcggc cgcgatacct gcaggtttgc ggtgacattg atctggctca ttatatgccc      3120

cgagctcttg taacatcgcg gacgcgattt ccgtagtagg cacatctcaa atgcaaaagc      3180

ggcatgtcaa ccgtataggt acatccggcc ctgcttacag tcggtagggc atatatccac      3240

cggaaaactt cagctttaga ctcctcaggt gatgaggaat agtatgtaac cctctagcag      3300

tacggtattt ctaaaaaaag gtagatcctt ttccacacgg cacagactaa ataacgtaca      3360

ctacacaggt tctctcgaac ttcgtttgga ccggaattat tccctcggca gcgcctaaaa      3420

agcaaacctc tagagtagat aagtgtcagt gaacctaggc cttctttgtt ccacggctgg      3480

aaagctaagg gacgaggtac acgcgacccc agccacgcac gaacagagtt taacggaagc      3540

gtcgtttgcg ggataaggtt gtcggacccc gcgggtccgt tgaaaagtgg ctgcgcgcct      3600

accgacgaat acgtcggtaa caattttaga aatcgaatat gactgcgagt accgtacaat      3660

cgcgaaatac ggtctctata tagctactcg gtccttaaat atgtaagtat gatgtcccct      3720

actcccgaag acgaccgcga cttggtcgca gtacgtgggc tgctccggat gatggacgag      3780

accacatctg agcgacacaa acgttcgcgt tcaggatgcc cccggttgtt atgcggttgt      3840

acgatcggga tcgctcttac tgtgttcgtc atcacagcta cggtcgtgct agcttcgctg      3900

tttgcattct cttacatgtc cctggagtcc ggtacatgtc ctcacgaatg gatcggttta      3960

ggctatagtt gtatgcgcgc gatggggagc aacgctaccg agctagaagc cctagatacg      4020

tgctcccgac ataacagcaa gcttgtcgac tttactcatg cgaaaattct aatcgaagct      4080

atcgc                                                                  4085
```

<210> SEQ ID NO 38
<211> LENGTH: 4344
<212> TYPE: DNA
<213> ORGANISM: artificial sequence
<220> FEATURE:
<223> OTHER INFORMATION: partial plasmid sequence of pHM103+Fopt for vHVT114

<400> SEQUENCE: 38

```
gagctcaggg tatgatactc agctgttatt gtggccgacc aggaggactc caatgcttag       60

cattcataag aacgctagag atgctattta acgatgtgct gtcgtctaaa gaatttgtgc      120

atttagcctt taaatgtaaa accaatgacg cattcactac gctcgtgcgt gcaatttctg      180

ggccagggta tgcatattcc ataacagaaa tcgacacttg agaagaggat ctgactgttt      240

gggataaagg tcgtttgggt ctgtcctagc gatataattt atatgacgat atacattaaa      300

catctgtgtg cagtacttag gtatttaatc atgtcgatga aatgttatgt gtaaatatcg      360

gacaatatag ataacgggca cgctgctatt gtaacgtgcg cccgcgcgct agtgctgact      420

aatagtgtgg atgatgtata cagtatatta caaacggaaa tgatacgtaa taaattatgt      480

actcttattg atttataaaa acatacatgc agtgttgcta tgtcacataa ttagcctcgc      540

ccgtctacgc tccactgaag ataatgggct cccgctgttc aaaaaaatca gcgtgcgtcg      600
```

ataagacttt ggtgcagtct cttcggggtc gcaatttaga tttgccgcat ggagggtatc 660
tggggatttt tgccaatgct ggagcgacga ctgtacgatt cgtcccatcg ggatctagca 720
gaccaatgat gttgacacac atcggccatg catgtacgga cggtctattg cgcgagtttg 780
ttattttcga aggacaagat ggaagtgtat atggaaccga caataatgtt agtttgcatt 840
tcttagggcg gaatctacat gatatcttat ccaagcgggg tatgagccag agagatgtga 900
tggtcataaa gggtaaattt tttagatctg aaataacgca gttgcccaaa caacgatcgc 960
gattaaaaga aaaatcggat ggttcaatta ggacatgcat ggattctgtg cgcataaacc 1020
ataaccgcag cactgttggg cacttcggta actcaaatgc gaagcgttgc acgtctgcga 1080
taactacgcc tactatgcac attgttactc ctgcatctta aaaatatatc ctgtagtaat 1140
tttcacagca atgtcataac atcatctcgc taaagaatga cctgggattg gagaagtaat 1200
gaatatttgc aaccaatgca ttgaataaac taacattaaa cgaattcgag ctcggtacag 1260
cttggctgtg gaatgtgtgt cagttagggt gtggaaagtc cccaggctcc ccagcaggca 1320
gaagtatgca aagcatgcat ctcaattagt cagcaaccag gtgtggaaag tccccaggct 1380
ccccagcagg cagaagtatg caaagcatgc atctcaatta gtcagcaacc atagtcccgc 1440
ccctaactcc gcccatcccg cccctaactc cgcccagttc cgcccattct ccgccccatg 1500
gctgactaat tttttttatt tatgcagagg ccgaggccgc ctcggcctct gagctattcc 1560
agaagtagtg aggaggcttt tttggaggcc taggcttttg caaaaagctg cggccgccac 1620
catgggcagc aagcccagca caagaatccc agccccctg atgctgatca cccgcatcat 1680
gctgatcctg ggctgcatca gacccacaag ctccctggat ggacgccccc tggccgctgc 1740
cggcatcgtg gtgaccggcg acaaggccgt gaacgtgtac accagcagcc agaccggcag 1800
catcatcgtg aagctgctgc ccaacatgcc cagagacaaa gaggcctgcg ccaaggcccc 1860
cctggaagcc tacaacagaa ccctgaccac cctgctgacc cccctgggcg acagcatcag 1920
aaagatccag ggctccgtga gcacaagcgg cggaggaaag cagggcagac tgatcggcgc 1980
cgtgatcggc agcgtggccc tgggagtggc tacagctgcc cagattaccg ctgcagccgc 2040
cctgatccag gccaaccaga acgccgccaa catcctgaga ctgaaagaga gcattgccgc 2100
caccaacgag gccgtgcacg aagtgaccga cggcctgagc cagctgtccg tggccgtggg 2160
caagatgcag cagttcgtga acgaccagtt caacaacacc gccagagagc tggactgcat 2220
caagatcacc cagcaggtgg gcgtggagct gaacctgtac ctgaccgagc tgaccacagt 2280
gttcggcccc cagatcacaa gcccagccct gacacagctg accatccagg ccctgtacaa 2340
cctggctggc ggcaacatgg actatctgct gacaaagctg ggaatcggca acaaccagct 2400
gtccagcctg atcggaagcg gcctgatcac cggctacccc atcctgtacg acagccagac 2460
acagctgctg ggcatccagg tgaacctgcc cagcgtgggc aacctgaaca acatgcgcgc 2520
cacctacctg gaaaccctga gcgtgtccac caccaagggc tacgccagcg ccctggtgcc 2580
caaggtggtg acacaggtgg gcagcgtgat cgaggaactg gacaccagct actgcatcga 2640
gagcgacctg gacctgtact gcaccagaat cgtgaccttc ccaatgagcc ccggcatcta 2700
cagctgcctg agcggcaaca ccagcgcctg catgtacagc aagaccgaag gcgcactgac 2760
aacaccctac atggccctga agggaagcgt gatcgccaac tgcaagatca ccacctgcag 2820
atgcaccgac ccccaggca tcatcagcca gaactacggc gaggccgtga gcctgatcga 2880
tcgccattcc tgtaacgtgc tgtccctgga cggcatcaca ctgagactga gcggcgagtt 2940

-continued cgatgccacc taccagaaga acatcagcat cctggacagc caggtgatcg tgaccggcaa 3000
cctggacatc agcaccgagc tgggcaacgt gaataacagc atcagcaacg ccctggacag 3060
actggccgag agcaacagca agctggaaaa agtgaacgtg cgcctgacat ccacttccgc 3120
tctgatcacc tacatcgtgc tgaccgtgat cagcctggtg ttcggcgccc tgagcctggt 3180
gctggcctgc tacctgatgt acaagcagaa ggcccagcag aaaaccctgc tgtggctggg 3240
caacaacacc ctggaccaga tgagagccac caccagagcc tgatgagcgg ccgcggggat 3300
ccagacatga taagatacat tgatgagttt ggacaaacca caactagaat gcagtgaaaa 3360
aaatgcttta tttgtgaaat ttgtgatgct attgctttat ttgtaaccat tataagctgc 3420
aataaacaag ttaacaacaa caattgcatt gattttatgt ttcaggttca gggggaggtg 3480
tgggaggttt tttcggatcc tctagagtcg acaattattt tatttaataa catatagccc 3540
aaagacctct atgaacattt agtttcccgt atactcaacg gcgcgtgtac acacgcatct 3600
ctttgcatag cgatgaagtt tgttcggcag cagaaaatgc agatatccaa caatctggag 3660
aaaacttatc atcacagtgg cagtggaaac ataccccctc tatattcatg gtataattat 3720
cgtctacagc gtccaggata gtggcgtgag aaaatggaga tctgcagccc tcctttccat 3780
ggcatgccgc tttattgttc attaaacgca caatggtctc aacgccagat atgggcatag 3840
attctgaaga acccgttgac aatccgaaga agaaggcgtg caggtctttg gaagactcgc 3900
acgttggtct tataatgtat gatcgagatg tcaccctaat gccacatggt acaggcttat 3960
cgcggtcatg gcgatcggac ttgtaatttg caacgatggg caaaggatcg acgacatgcc 4020
aaacattctg aacccgtaga gatgttaacg atgacgagga tgaatatccc atgctcgctg 4080
ccatagtatc aagtacaccg cgaataagga cgcgtccaac atcgttatat gcacacaatg 4140
ggctacacgt gactaacacc cccgaatatt agtcatatgt gagtttcagt ctggctccca 4200
tatagcctgt agactatttg tggtttaagt gtgaacgagg cgctgtgaac gagactcggg 4260
ccgattgtaa gaacaagcaa atgcactttc catttaacaa gaagtgtaga gagaatactc 4320
aacctctttg gatgtatcct cgag 4344

<210> SEQ ID NO 39
<211> LENGTH: 1362
<212> TYPE: DNA
<213> ORGANISM: artificial sequence
<220> FEATURE:
<223> OTHER INFORMATION: IBDV DNA encoding VP2 protein

<400> SEQUENCE: 39
atgacaaacc tgcaagatca aacccaacag attgttccgt tcatacggag ccttctgatg 60
ccaacaaccg gaccggcgtc cattccggac gacaccctgg agaagcacac tctcaggtca 120
gagacctcga cctacaattt gactgtgggg gacacagggt cagggctaat tgtctttttc 180
cctggattcc ctggctcaat tgtgggtgct cactacacac tgcagagcaa tgggaactac 240
aagttcgatc agatgctcct gactgcccag aacctaccgg ccagctacaa ctactgcaga 300
ctagtgagtc ggagtctcac agtgaggtca agcacactcc ctggtggcgt ttatgcacta 360
aacggcacca taaacgccgt gaccttccaa ggaagcctga gtgaactgac agatgttagc 420
tacaatgggt tgatgtctgc aacagccaac atcaacgaca aaattgggaa tgtcctggta 480
ggggaagggg tcactgtcct cagcctaccc acatcatatg atcttgggta tgtgaggctt 540
ggtgacccca ttcccgctat agggcttgac ccaaaaatgg tagctacatg cgacagcagt 600
gacaggccca gagtctacac cataactgca gccgatgatt accaattctc atcacagtac 660

```
caaccaggtg ggtaacaat  cacactgttc tcagccaaca ttgatgctat cacaagcctc    720

agcattgggg gagagctcgt gtttcaaaca agcgtccaag gccttgtact gggcgccacc    780

atctacctta taggctttga tgggactgcg gtaatcacca gagctgtagc cgcagataat    840

gggctgacgg ccggcaccga caatcttatg ccattcaatc ttgtcattcc aaccaatgag    900

ataacccagc caatcacatc catcaaactg gagatagtga cctccaaaag tggtggtcag    960

gcaggggatc agatgtcatg gtcggcaagt gggagcctag cagtgacgat ccatggtggc   1020

aactatccag ggccctccg  tcccgtcaca ctagtagcct acgaaagagt ggcaacagga   1080

tccgtcgtta cggtcgctgg ggtgagtaac ttcgagctga ttccaaatcc tgaactagca   1140

aagaacctgg ttacagaata cggccgattt gacccaggag ccatgaacta cacaaaattg   1200

atactgagtg agagggaccg tcttggcatc aagaccgtct ggccaacaag ggagtacact   1260

gattttcgtg agtacttcat ggaggtggcc gacctcaact ctcccctgaa gattgcagga   1320

gcatttggct tcaaagacat aatccgggct ataaggaggt aa                      1362
```

<210> SEQ ID NO 40
<211> LENGTH: 453
<212> TYPE: PRT
<213> ORGANISM: artificial sequence
<220> FEATURE:
<223> OTHER INFORMATION: IBDV VP2 protein

<400> SEQUENCE: 40

```
Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240
```

```
Ser Ile Gly Gly Glu Leu Val Phe Gln Thr Ser Val Gln Gly Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asp Asn Gly Leu Thr Ala Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg
    450
```

<210> SEQ ID NO 41
<211> LENGTH: 5178
<212> TYPE: DNA
<213> ORGANISM: artificial sequence
<220> FEATURE:
<223> OTHER INFORMATION: partial plasmid sequence of SB-1 US10mFwt SbfI for vSB1-004

<400> SEQUENCE: 41

```
gacataacca acatatcgtt tgatatacac aaggatatgt ggtaccgaat ggttttatgg      60

tctgcgtaca ggttttttc tacgatgggc gagatgtttc tgatagatga catttcaaac     120

tatgtcgcgc cggaccttgt cgaaaacgga cgatggaagt tatactgcag aacttgggat     180

attagggacg cggcgaagat aaaactaatc ggcccgtttc tacccgcgct attctctttt     240

cacctggaga actggaccgc aatgctctct ttaggcatcc ataagggttt cgatcgtcac     300

aatgcccgag gtacattaac ggcgatgccg ttcttaaaaa aaatattggt tggggcaatg     360

gaaattgcac gatttgcagt ggtgctttct ctacctatct gcgaataccg aacacctatg     420

ggattaccgg aagacgagat agggaatgca atcagattat gttgcgcaca aatgcaggca     480

aatcgtctgg agcctacaga aataactaac gacgcagaag ggaagagcaa cgacgggtct     540

gcagaggaac tgtattatag agccttgcac gagatagtga agacggctag ggaacattgc     600

agagtccagg aggacactcc gccaacgatt caactgaata ccggggattc gagataccga     660

cagcagcgca tgtggaggaa cgatcctata cgcgtcccca ggtccagatt atcgaactgt     720

aaagcactgg agcgttttag acgagattta ggtcgcgggt ccatttttct ctagtttgcc     780
```

-continued

```
cctctgcgat tgctacgttt taactgaagt tagagaatat tgacgcagat tacaataaga    840
tgcaataact tctggtaagt caataaagtg cctgcaggcc caattcaata gtggatcccc    900
caactccgcc cgttttatga ctagaaccaa tagtttttaa tgccaaatgc actgaaatcc    960
cctaatttgc aaagccaaac gccccctatg tgagtaatac ggggactttt tacccaattt   1020
cccacgcgga aagcccccta atacactcat atggcatatg aatcagcacg gtcatgcact   1080
ctaatggcgg cccataggga ctttccacat agggggcgtt caccatttcc cagcataggg   1140
gtggtgactc aatggccttt acccaagtac attgggtcaa tgggaggtaa gccaatgggt   1200
ttttcccatt actggcaagc acactgagtc aaatgggact ttccactggg ttttgcccaa   1260
gtacattggg tcaatgggag gtgagccaat gggaaaaacc cattgctgcc aagtacactg   1320
actcaatagg gactttccaa tgggtttttc cattgttggc aagcatataa ggtcaatgtg   1380
ggtgagtcaa tagggacttt ccattgtatt ctgcccagta cataaggtca ataggggggtg   1440
aatcaacagg aaagtcccat tggagccaag tacactgcgt caatagggac tttccattgg   1500
gttttgccca gtacataagg tcaatagggg atgagtcaat gggaaaaacc cattggagcc   1560
aagtacactg actcaatagg gactttccat tgggttttgc ccagtacata aggtcaatag   1620
ggggtgagtc aacaggaaag ttccattgga gccaagtaca ttgagtcaat agggactttc   1680
caatgggttt tgcccagtac ataaggtcaa tgggaggtaa gccaatgggt ttttcccatt   1740
actggcacgt atactgagtc attagggact ttccaatggg ttttgcccag tacataaggt   1800
caataggggt gaatcaacag gaaagtccca ttggagccaa gtacactgag tcaataggga   1860
ctttccattg ggttttgccc agtacaaaag gtcaataggg ggtgagtcaa tgggtttttc   1920
ccattattgg cacgtacata aggtcaatag ggtgagtca ttgggttttt ccagccaatt   1980
taattaaaac gccatgtact ttcccaccat tgacgtcaat gggctattga aactaatgca   2040
acgtgacctt taaacggtac tttcccatag ctgattaatg ggaaagtacc gttctcgagc   2100
caatacacgt caatgggaag tgaaagggca gccaaaacgt aacaccgccc cggttttccc   2160
ctggaaattc catattggca cgcattctat tggctgagct gcgttctacg tgggtataag   2220
aggcgcgacc agcgtcggta ccgtcgcagt cttcggtctg accaccgtag aacgcagagc   2280
tcctcgctgc aggcggccgc atgggctcca aaccttctac caggatccca gcacctctga   2340
tgctgatcac ccggattatg ctgatattgg gctgtatccg tccgacaagc tctcttgacg   2400
gcaggcctct tgcagctgca ggaattgtag taacaggaga taaggcagtc aatgtataca   2460
cttcgtctca gacagggtca atcatagtca agttgctccc gaatatgccc agggataagg   2520
aggcgtgtgc aaaagcccca ttagaggcat ataacagaac actgactact ttgctcactc   2580
ctcttggcga ctccatccgc aagatccaag ggtctgtgtc cacatctgga ggaggcaagc   2640
aaggccgcct gataggtgct gttattggca gtgtagctct tggggttgca acagcggcac   2700
agataacagc agctgcggcc ctaatacaag ccaaccagaa tgccgccaac atcctccggc   2760
ttaaggagag cattgctgca accaatgaag ctgtgcatga agtcaccgac ggattatcac   2820
aactatcagt ggcagttggg aagatgcagc agtttgtcaa tgaccagttt aataatacgg   2880
cgcgagaatt ggactgtata aaaatcacac aacaggttgg tgtagaactc aacctatacc   2940
taactgaatt gactacagta ttcgggccac agatcacctc ccctgcatta actcagctga   3000
ccatccaggc actttataat ttagctggtg gcaatatgga ttacttatta actaagttag   3060
gtatagggaa caatcaactc agctcgttaa ttggtagcgg cctgatcact ggttacccta   3120
```

-continued

```
tactgtatga ctcacagact caactcttgg gcatacaagt gaatttaccc tcagtcggga   3180
acttaaataa tatgcgtgcc acctatttgg agaccttatc tgtaagtaca accaaaggat   3240
atgcctcagc acttgtcccg aaagtagtga cacaagtcgg ttccgtgata gaagagcttg   3300
acacctcata ctgtatagag tccgatctgg atttatattg tactagaata gtgacattcc   3360
ccatgtcccc aggtatttat tcctgtttga gcggcaacac atcagcttgc atgtattcaa   3420
agactgaagg cgcactcact acgccgtata tggcccttaa aggctcagtt attgccaatt   3480
gtaaaataac aacatgtaga tgtacagacc ctcctggtat catatcgcaa aattatggag   3540
aagctgtatc cctgatagat agacattcgt gcaatgtctt atcattagac gggataactc   3600
taaggctcag tggggaattt gatgcaactt atcaaaagaa catctcaata ctagattctc   3660
aagtcatcgt gacaggcaat cttgatatat caactgaact tggaaacgtc aacaattcaa   3720
tcagcaatgc cttggatagg ttggcagaaa gcaacagcaa gctagaaaaa gtcaatgtca   3780
gactaaccag cacatctgct ctcattacct atattgttct aactgtcatt tctctagttt   3840
tcggtgcact tagtctggtg ttagcgtgtt acctgatgta caaacagaag gcacaacaaa   3900
agaccttgct atggcttggg aataataccc tcgatcagat gagagccact acaagagcat   3960
gagcggccgc ggggatccag acatgataag atacattgat gagtttggac aaaccacaac   4020
tagaatgcag tgaaaaaaat gctttatttg tgaaatttgt gatgctattg ctttatttgt   4080
aaccattata agctgcaata aacaagttaa caacaacaat tgcattgatt ttatgtttca   4140
ggttcagggg gaggtgtggg aggtttttc ggatcctcta gagtcgaggg tcgacgatat    4200
cctgcaggtt tatttgcaaa actctataca ttgtttccga gccctgtcat tcgcgcaaat   4260
ttactcaatg tcttccccat cgtctggagg cgaagattca gacgattgtc gcacgttgat   4320
caggtaatgt gccacttcga cgtcgtcgta aattaatgca ttccccttcg ctgctacagc   4380
ccggcataaa ggcttccaat aagactctac ttcagtaagc gggctttctc cacagcctgt   4440
tgccattccc aacaacttaa tcagatcact gttttcctca tataaatggg aaacaataca   4500
gcagccagga tgcccaagac aacaccaata cataatagca gtcagacggc tatccatttc   4560
tccatgcgtt tcaggtgcat gcttataatt tcgcaatgca acacttacta ttttcctcaa   4620
cgaaccggct acgtagaaat ttgatgtgga ccgttgttcg cggcggattg ttgcgtcagt   4680
taaatccatt atctcacgcc acaggtgaat ggatggcggc ataccagctt tcattgccgc   4740
gaaagagacc atggcagcgg tcaatacagt tcgggccaaa ccgcgtacag actttggcag   4800
ggatgatata tgtactccac cagcagaaag tataccgtat actttctcat tcgcaggatc   4860
cggccacaga tgagatgttc tgcgaagttt gcggcacacc gaccacaggc ccatttgctt   4920
ttgcggtgat ggtacttcac atacctcact ggacatatca caatattatc ttgcgcggtg   4980
gtgcaccttc tgtctctata gacacccagc tcccaaatgt caggtcggat aacgttgtag   5040
tcaatagaaa tctatatggt acaagtcacg cccacactgc gttacttaat taacgcgaca   5100
tactcattca ataaataaca ggcaaagtga ttactggcaa taggacattt attgttcgtc   5160
tacatcagtg agttttgt                                                  5178
```

<210> SEQ ID NO 42
<211> LENGTH: 4226
<212> TYPE: DNA
<213> ORGANISM: artificial sequence
<220> FEATURE:
<223> OTHER INFORMATION: partial plasmid sequence of SB1 UL55 SVFopt syn
tail SbfI for vSB1-006

-continued

<400> SEQUENCE: 42

```
gtcctcagcc ttgcgctagt aagctgtaat acagagaacg gggcacgaac gtgcatcgaa     60
acattatttt cctttggagg tgccgtgctg gaaacaaaca ttctgattca tgcaattaac    120
caactgcttc ctttgtgcga tgtcatggcg gtttccggaa taagtagact tgctatcata    180
gaatcaatcc ccgaactcgg aacggttcca tacaggtgcg ttttacaagc gacgcctcat    240
attacagcgt gtctcacccc caaggtagtc agatgcatga attatgggat actactatct    300
cactgggagg aatgcgtcgt gcgggattcg aaatacatcg taaacgtacc cacgcaaaca    360
cagtttgtca catccttaac ccgttgtccg cacgggccag tcgccaacga ttggtacctt    420
ggattcttct tcccatttaa ggggttcagg gtaataaccg tcagaacaag gcgctggctg    480
gcagcatata cctacagatt tcgaaagtgg ttgcaatggg aagagggttc cccccactac    540
gtcgctttga ggcgtctggt cccactatgt gattgctact tgatggatgc ttgcatgaca    600
aacaactttt ttgcctgcgg aatgctattc cacttacact gcgtcccaat acccgcgcgc    660
gaaaaacgca ttgtggcgat actggcgaga gcgattgatg acgcgcaaac atatgcggga    720
acctcactgc acgtagatac gagtgaacag tagagcgtta gtatgtggtt ttctttaggt    780
gttactacca cttacattcc tacaaaatca ctactcccgt attagatctc aacgctatac    840
cggcgtaggc gaacctgagg gtgcgcccct agctctcgca attggtatgc gtaaatgaat    900
tgttatcgcg ggttgccata agattttgta tacatacgaa cccgagaatg tataaaccaa    960
taaatgctga aatggtagac ctgcaggtcg acccaattcg agctcggtac agcttggctg   1020
tggaatgtgt gtcagttagg gtgtggaaag tccccaggct ccccagcagg cagaagtatg   1080
caaagcatgc atctcaatta gtcagcaacc aggtgtggaa agtccccagg ctccccagca   1140
ggcagaagta tgcaaagcat gcatctcaat tagtcagcaa ccatagtccc gcccctaact   1200
ccgcccatcc cgcccctaac tccgcccagt tccgcccatt ctccgcccca tggctgacta   1260
attttttta tttatgcaga ggccgaggcc gcctcggcct ctgagctatt ccagaagtag   1320
tgaggaggct tttttggagg cctaggcttt tgcaaaaagc tcccggggcg gccgccacca   1380
tgggcagcaa gcccagcaca agaatcccag cccccctgat gctgatcacc cgcatcatgc   1440
tgatcctggg ctgcatcaga cccacaagct ccctggatgg acgcccctg gccgctgccg   1500
gcatcgtggt gaccggcgac aaggccgtga acgtgtacac cagcagccag accggcagca   1560
tcatcgtgaa gctgctgccc aacatgccca gagacaaaga ggcctgcgcc aaggcccccc   1620
tggaagccta caacagaacc ctgaccaccc tgctgacccc cctgggcgac agcatcagaa   1680
agatccaggg ctccgtgagc acaagcggcg gaggaaagca gggcagactg atcggcgccg   1740
tgatcggcag cgtggccctg ggagtggcta cagctgccca gattaccgct gcagccgccc   1800
tgatccaggc caaccagaac gccgccaaca tcctgagact gaaagagagc attgccgcca   1860
ccaacgaggc cgtgcacgaa gtgaccgacg gcctgagcca gctgtccgtg gccgtgggca   1920
agatgcagca gttcgtgaac gaccagttca acaacaccgc cagagagctg gactgcatca   1980
agatcaccca gcaggtgggc gtggagctga acctgtacct gaccgagctg accacagtgt   2040
tcggccccca gatcacaagc ccagccctga cacagctgac catccaggcc ctgtacaacc   2100
tggctggcgg caacatggac tatctgctga caaagctggg aatcggcaac aaccagctgt   2160
ccagcctgat cggaagcggc ctgatcaccg gctaccccat cctgtacgac agccagacac   2220
agctgctggg catccaggtg aacctgccca gcgtgggcaa cctgaacaac atgcgcgcca   2280
cctacctgga aaccctgagc gtgtccacca ccaagggcta cgccagcgcc ctggtgccca   2340
```

aggtggtgac acaggtgggc agcgtgatcg aggaactgga caccagctac tgcatcgaga 2400
gcgacctgga cctgtactgc accagaatcg tgaccttccc aatgagcccc ggcatctaca 2460
gctgcctgag cggcaacacc agcgcctgca tgtacagcaa gaccgaaggc gcactgacaa 2520
caccctacat ggccctgaag ggaagcgtga tcgccaactg caagatcacc acctgcagat 2580
gcaccgaccc cccaggcatc atcagccaga actacggcga ggccgtgagc ctgatcgatc 2640
gccattcctg taacgtgctg tccctggacg gcatcacact gagactgagc ggcgagttcg 2700
atgccaccta ccagaagaac atcagcatcc tggacagcca ggtgatcgtg accggcaacc 2760
tggacatcag caccgagctg ggcaacgtga ataacagcat cagcaacgcc ctggacagac 2820
tggccgagag caacagcaag ctggaaaaag tgaacgtgcg cctgacatcc acttccgctc 2880
tgatcaccta catcgtgctg accgtgatca gcctggtgtt cggcgccctg agcctggtgc 2940
tggcctgcta cctgatgtac aagcagaagg cccagcagaa aaccctgctg tggctgggca 3000
acaacaccct ggaccagatg agagccacca ccagagcctg atgagcggcc gcgatatcaa 3060
taaaatatct ttattttcat tacatctgtg tgttggtttt ttgtgtgaat cgatagtact 3120
aacatacgct ctccatcaaa acaaaacgaa acaaaacaaa ctagcaaaat aggctgtccc 3180
cagtgcaagt gcaggtgcca gaacatttct cttctagacc tgcaggtcaa atcatgattc 3240
gtttttattc agtgtccgta ctcgcgaata gctctgcact gcgatgcgat tttttcggca 3300
gcgctaaaag ccgatctcca acactcgagc gaaaacttat tttcgcagtg gcaatgaaaa 3360
cacagtccct ctatagccat gctgtagttt tcatccagtg agtcgatgat cgtcgcatga 3420
gaaaaaggcg actcgcattg gtcgcctgtc aatcgaccag tccgtaactt cttgttcatt 3480
ctatacgcga tatacgaggc accgcattgg gacatgttct cagacggatc cgtcgccaat 3540
ccaaagaaga acgcgtggaa agtcgtcgac gatttacacg ctgcccgtat gacgtacgaa 3600
cgaggaataa cggatgcggc acatgacaca tgttcgcccg tagctagttg agtagaggcg 3660
gacggcacgt caattgctaa cggagcgatc acttgccaaa cgtacggaat tcgtaccggt 3720
gaagctgacg gttcagctgt actttccgcc attggacact gtagaactga ggatctgcca 3780
ccgctgggcg cacgtggttt ctgccgggtg ttatataagt ttttccacgc ccactacgtg 3840
ttacctacac actcacggca cgtggtacgt ggacgtaagg gatggccgta atgaaaaatg 3900
caccgggcga ctagttgtcc cgtctagcat gaccatgcat tgtagaccgc aggtccagcg 3960
ctgcgccaat tacgactcta catcggacgc tccaacccag acgggcttcc caatgtggct 4020
caccccgaga gaactctcac cgactaacgt ttatggaata gtcgctagac cggtactcct 4080
cacgcacgcc gggggcccaa taaacagtgt actgacggga ggttggaaag ggagaatggt 4140
cacggcaacg tcgtctatct gcgaaaggat actgctttgg gtagcggata cgcagcgttc 4200
ttctccgagc accggatcgt ttgacc 4226

<210> SEQ ID NO 43
<211> LENGTH: 4085
<212> TYPE: DNA
<213> ORGANISM: artificial sequence
<220> FEATURE:
<223> OTHER INFORMATION: partial plasmid sequence of pSB1 44cds SVOptF
for vSB1-007

<400> SEQUENCE: 43
gcgatagctt cgattagaat tttcgcatga gtaaagtcga caagcttgct gttatgtcgg 60
gagcacgtat ctagggcttc tagctcggta gcgttgctcc ccatcgcgcg catacaacta 120

```
tagcctaaac cgatccattc gtgaggacat gtaccggact ccagggacat gtaagagaat    180
gcaaacagcg aagctagcac gaccgtagct gtgatgacga acacagtaag agcgatcccg    240
atcgtacaac cgcataacaa ccgggggcat cctgaacgcg aacgtttgtg tcgctcagat    300
gtggtctcgt ccatcatccg gagcagccca cgtactgcga ccaagtcgcg gtcgtcttcg    360
ggagtagggg acatcatact tacatattta aggaccgagt agctatatag agaccgtatt    420
tcgcgattgt acggtactcg cagtcatatt cgatttctaa aattgttacc gacgtattcg    480
tcggtaggcg cgcagccact tttcaacgga cccgcggggt ccgacaacct tatcccgcaa    540
acgacgcttc cgttaaactc tgttcgtgcg tggctggggt cgcgtgtacc tcgtccctta    600
gctttccagc cgtggaacaa agaaggccta ggttcactga cacttatcta ctctagaggt    660
ttgcttttta ggcgctgccg agggaataat tccggtccaa acgaagttcg agagaacctg    720
tgtagtgtac gttatttagt ctgtgccgtg tggaaaagga tctacctttt tttagaaata    780
ccgtactgct agagggttac atactattcc tcatcacctg aggagtctaa agctgaagtt    840
ttccggtgga tatatgccct accgactgta agcagggccg gatgtaccta tacggttgac    900
atgccgcttt tgcatttgag atgtgcctac tacggaaatc gcgtccgcga tgttacaaga    960
gctcggggca tataatgagc cagatcaatg tcaccgcaaa cctgcaggtc gacccaattc   1020
gagctcggta cagcttggct gtggaatgtg tgtcagttag ggtgtggaaa gtccccaggc   1080
tccccagcag gcagaagtat gcaaagcatg catctcaatt agtcagcaac caggtgtgga   1140
aagtccccag gctccccagc aggcagaagt atgcaaagca tgcatctcaa ttagtcagca   1200
accatagtcc cgcccctaac tccgcccatc ccgcccctaa ctccgcccag ttccgcccat   1260
tctccgcccc atggctgact aattttttt atttatgcag aggccgaggc cgcctcggcc   1320
tctgagctat tccagaagta gtgaggaggc ttttttggag gcctaggctt ttgcaaaaag   1380
ctcccggggc ggccgccacc atgggcagca agcccagcac aagaatccca gcccccctga   1440
tgctgatcac ccgcatcatg ctgatcctgg gctgcatcag acccacaagc tccctggatg   1500
gacgcccct ggccgctgcc ggcatcgtgg tgaccggcga caaggccgtg aacgtgtaca   1560
ccagcagcca gaccggcagc atcatcgtga agctgctgcc caacatgccc agagacaaag   1620
aggcctgcgc caaggccccc ctggaagcct acaacagaac cctgaccacc ctgctgaccc   1680
ccctgggcga cagcatcaga aagatccagg gctccgtgag cacaagcggc ggaggaaagc   1740
agggcagact gatcggcgcc gtgatcggca gcgtggccct gggagtggct acagctgccc   1800
agattaccgc tgcagccgcc ctgatccagg ccaaccagaa cgccgccaac atcctgagac   1860
tgaaagagag cattgccgcc accaacgagg ccgtgcacga agtgaccgac ggcctgagcc   1920
agctgtccgt ggccgtgggc aagatgcagc agttcgtgaa cgaccagttc aacaacaccg   1980
ccagagagct ggactgcatc aagatcaccc agcaggtggg cgtggagctg aacctgtacc   2040
tgaccgagct gaccacagtg ttcggccccc agatcacaag cccagccctg acacagctga   2100
ccatccaggc cctgtacaac ctggctggcg gcaacatgga ctatctgctg acaaagctgg   2160
gaatcggcaa caaccagctg tccagcctga tcggaagcgg cctgatcacc ggctacccca   2220
tcctgtacga cagccagaca cagctgctgg gcatccaggt gaacctgccc agcgtgggca   2280
acctgaacaa catgcgcgcc acctacctgg aaaccctgag cgtgtccacc accaagggct   2340
acgccagcgc cctggtgccc aaggtggtga cacaggtggg cagcgtgatc gaggaactgg   2400
acaccagcta ctgcatcgag agcgacctgg acctgtactg caccagaatc gtgaccttcc   2460
```

caatgagccc cggcatctac agctgcctga gcggcaacac cagcgcctgc atgtacagca 2520
agaccgaagg cgcactgaca acaccctaca tggccctgaa gggaagcgtg atcgccaact 2580
gcaagatcac cacctgcaga tgcaccgacc ccccaggcat catcagccag aactacggcg 2640
aggccgtgag cctgatcgat cgccattcct gtaacgtgct gtccctggac ggcatcacac 2700
tgagactgag cggcgagttc gatgccacct accagaagaa catcagcatc ctggacagcc 2760
aggtgatcgt gaccggcaac ctggacatca gcaccgagct gggcaacgtg aataacagca 2820
tcagcaacgc cctggacaga ctggccgaga gcaacagcaa gctggaaaaa gtgaacgtgc 2880
gcctgacatc cacttccgct ctgatcacct acatcgtgct gaccgtgatc agcctggtgt 2940
tcggcgccct gagcctggtg ctggcctgct acctgatgta caagcagaag gcccagcaga 3000
aaaccctgct gtggctgggc aacaacaccc tggaccagat gagagccacc accagagcct 3060
gatgagcggc cgcgatacct gcaggggggga aaatatttca gctggcgtgc gagccgcgtc 3120
tccgagagcg tatatggagt ggcctctgcc tgcgcaactt agctttaaat cggccctttc 3180
atgttttcga cagcgcataa acccacgata ggcccccttta gtagccacga aagttttatt 3240
cgcagttcga aagaacgcta tgagcacatg atataaaaat taatcgctcc gcgatcagga 3300
atattgtatt aacacgcaaa ccaacatgct cgagatggca gttcctaata tgcatttacc 3360
agctgcggcg gccgccaatt gctttattcc gctattcgcg ttgcgtacat ttatacaagt 3420
gtagcagcac agaaccgcgg ctgtcgcgga aaacaatgtc ggcccgagaa gtaaaccgaa 3480
gccggctaag gtagtagcca ttgccccgaa tattaacagt aatacaagaa ttggacggaa 3540
cagaacctcg tggtagcgcg acggaaggaa tatcgcgaca cttgtaccca ccaagaaacc 3600
gcatatactg cgtaacgtgt cagtcaatgt tgactggtgc ttagttgcgt tcgacatgta 3660
cttttgaaag ctggctatgg ctggaatcga gatgaccgct atgaggctca gaattatcgt 3720
aggaatattc ccccccagcg tatcgtaact ggatacgtct tcttcgcgcg tcgcctcggc 3780
gtccgtgctg ggcgggagac gcgcgcgacc gaggcgatat gcaccgttca cagtaatttc 3840
ccgacgtgca cggtagtagc acgtgttcat tagagaccga ctggcgtctc tgaccacgtg 3900
aatagctaac gccgtatacg ccgaaagaaa gccggctaga ggagaaatgt ctccatacgg 3960
agccgtgatg ccggcaatcg tccctgccgc cacaactaaa aacccggtct tccacgtcac 4020
gtctccagac gttgctatgc agacgtaatg ataagatgcg atcagagctc cgagcatgac 4080
aaaag 4085

<210> SEQ ID NO 44
<211> LENGTH: 4226
<212> TYPE: DNA
<213> ORGANISM: artificial sequence
<220> FEATURE:
<223> OTHER INFORMATION: partial plasmid sequence of SB-1 UL55 CAFopt syn tail SbfI for vSB1-008

<400> SEQUENCE: 44
gtcctcagcc ttgcgctagt aagctgtaat acagagaacg gggcacgaac gtgcatcgaa 60
acattatttt cctttggagg tgccgtgctg gaaacaaaca ttctgattca tgcaattaac 120
caactgcttc ctttgtgcga tgtcatggcg gtttccggaa taagtagact tgctatcata 180
gaatcaatcc ccgaactcgg aacggttcca tacaggtgcg ttttacaagc gacgcctcat 240
attacagcgt gtctcacccc caaggtagtc agatgcatga attatgggat actactatct 300
cactgggagg aatgcgtcgt gcgggattcg aaatacatcg taaacgtacc cacgcaaaca 360

-continued

```
cagtttgtca catccttaac ccgttgtccg cacgggccag tcgccaacga ttggtacctt    420
ggattcttct tcccatttaa ggggttcagg gtaataaccg tcagaacaag gcgctggctg    480
gcagcatata cctacagatt tcgaaagtgg ttgcaatggg aagagggttc cccccactac    540
gtcgctttga ggcgtctggt cccactatgt gattgctact tgatggatgc ttgcatgaca    600
aacaactttt ttgcctgcgg aatgctattc cacttacact gcgtcccaat acccgcgcgc    660
gaaaaacgca ttgtggcgat actggcgaga gcgattgatg acgcgcaaac atatgcggga    720
acctcactgc acgtagatac gagtgaacag tagagcgtta gtatgtggtt ttctttaggt    780
gttactacca cttacattcc tacaaaatca ctactcccgt attagatctc aacgctatac    840
cggcgtaggc gaacctgagg gtgcgcccct agctctcgca attggtatgc gtaaatgaat    900
tgttatcgcg ggttgccata agattttgta tacatacgaa cccgagaatg tataaaccaa    960
taaatgctga aatggtagac ctgcaggtcg acccaattcg agctcggtac agcttggctg   1020
tggaatgtgt gtcagttagg gtgtggaaag tccccaggct ccccagcagg cagaagtatg   1080
caaagcatgc atctcaatta gtcagcaacc aggtgtggaa agtccccagg ctccccagca   1140
ggcagaagta tgcaaagcat gcatctcaat tagtcagcaa ccatagtccc gcccctaact   1200
ccgcccatcc cgcccctaac tccgcccagt tccgcccatt ctccgcccca tggctgacta   1260
attttttta tttatgcaga ggccgaggcc gcctcggcct ctgagctatt ccagaagtag    1320
tgaggaggct tttttggagg cctaggcttt tgcaaaaagc tcccggggcg gccgccacca   1380
tgggcagcaa gcccagcacc tggatcagcg tgaccctgat gctgatcacc agaaccatgc   1440
tgatcctgag ctgcatctgc cccacaagca gcctggacgg cagacccctg gccgctgccg   1500
gcatcgtggt gaccggcgac aaggccgtga acatctacac cagcagccag accggcagca   1560
tcatcatcaa gctgctgccc aacatgccca aggacaaaga ggcctgcgcc aaggcccccc   1620
tggaagccta caacagaacc ctgaccaccc tgctgacccc cctgggcgac agcatcagaa   1680
gaatccaggg cagcgccacc acaagcggcg gaggaaagca gggcagactg gtgggcgcta   1740
tcatcgggag cgtggccctg ggcgtggcca cagctgccca gattaccgct gcagccgccc   1800
tgattcaggc caatcagaac gccgccaaca tcctgagact gaaagagagc attgccgcca   1860
ccaacgacgc cgtgcacgaa gtgacaaacg gactgtccca gctggctgtc gctgtcggca   1920
agatgcagca gttcgtgaac aaccagttca acaacaccgc cagagagctg gactgcatca   1980
agatcgccca gcaggtgggc gtggagctga acctgtacct gaccgagctg accacagtgt   2040
tcggccccca gatcacaagc cccgctctga cccagctgac aatccaggcc ctgtacaacc   2100
tggctggcgg caacatggac tatctgctga ctaagctggg agtgggcaac aaccagctgt   2160
ccagcctgat cgggtccggg ctgatcacag gcaaccccat cctgtacgac agccagacac   2220
agctgctggg catccagatc aacctgccat ccgtgggaag cctgaacaac atgagagcca   2280
cctacctgga aaccctgagc gtgtccacca ccaagggctt cgccagcgcc ctggtgccca   2340
aggtggtgac acaggtgggc agcgtgatcg aggaactgga caccagctac tgcatcgaga   2400
gcgacatcga cctgtactgc accagagtgg tgaccttccc aatgagcccc ggcatctaca   2460
gctgcctgag cggcaacacc agcgcctgca tgtacagcaa gaccgaagga gcactgacaa   2520
caccctacat ggccctgaag ggaagcgtga tcgccaactg caagatgacc acctgcagat   2580
gcgccgaccc cccaggcatc atcagccaga actacggcga ggccgtgagc ctgatcgaca   2640
aacattcctg tagcgtgctg tccctggatg gcatcacact gagactgagc ggcgagttcg   2700
acgccaccta ccagaagaac atcagcatcc tggacagcca ggtgatcgtg accggcaacc   2760
```

-continued

```
tggacatcag caccgagctg ggcaacgtga acaacagcat cagcagcacc ctggacaagc   2820

tggccgagtc caacaacaag ctgaacaaag tgaacgtgaa cctgaccagc acaagcgccc   2880

tgatcaccta catcgtgctg gccatcgtgt ccctggcctt cggcgtgatc agcctggtgc   2940

tggcctgcta cctgatgtac aagcagagag cccagcagaa aaccctgctg tggctgggca   3000

ataacaccct ggaccagatg agggccacca ccagaacctg atgagcggcc gcgatatcaa   3060

taaaatatct ttattttcat tacatctgtg tgttggtttt ttgtgtgaat cgatagtact   3120

aacatacgct ctccatcaaa acaaaacgaa acaaaacaaa ctagcaaaat aggctgtccc   3180

cagtgcaagt gcaggtgcca gaacatttct cttctagacc tgcaggtcaa atcatgattc   3240

gtttttattc agtgtccgta ctcgcgaata gctctgcact gcgatgcgat tttttcggca   3300

gcgctaaaag ccgatctcca acactcgagc gaaaacttat tttcgcagtg gcaatgaaaa   3360

cacagtccct ctatagccat gctgtagttt tcatccagtg agtcgatgat cgtcgcatga   3420

gaaaaaggcg actcgcattg gtcgcctgtc aatcgaccag tccgtaactt cttgttcatt   3480

ctatacgcga tatacgaggc accgcattgg gacatgttct cagacggatc cgtcgccaat   3540

ccaaagaaga acgcgtggaa agtcgtcgac gatttacacg ctgcccgtat gacgtacgaa   3600

cgaggaataa cggatgcggc acatgacaca tgttcgcccg tagctagttg agtagaggcg   3660

gacggcacgt caattgctaa cggagcgatc acttgccaaa cgtacggaat tcgtaccggt   3720

gaagctgacg gttcagctgt actttccgcc attggacact gtagaactga ggatctgcca   3780

ccgctgggcg cacgtggttt ctgccgggtg ttatataagt ttttccacgc ccactacgtg   3840

ttacctacac actcacggca cgtggtacgt ggacgtaagg gatggccgta atgaaaaatg   3900

caccgggcga ctagttgtcc cgtctagcat gaccatgcat tgtagaccgc aggtccagcg   3960

ctgcgccaat tacgactcta catcggacgc tccaacccag acgggcttcc caatgtggct   4020

caccccgaga gaactctcac cgactaacgt ttatggaata gtcgctagac cggtactcct   4080

cacgcacgcc gggggcccaa taaacagtgt actgacggga ggttggaaag ggagaatggt   4140

cacggcaacg tcgtctatct gcgaaaggat actgctttgg gtagcggata cgcagcgttc   4200

ttctccgagc accggatcgt ttgacc                                        4226
```

<210> SEQ ID NO 45
<211> LENGTH: 4335
<212> TYPE: DNA
<213> ORGANISM: artificial sequence
<220> FEATURE:
<223> OTHER INFORMATION: partial plasmid sequence of pHVT US2
      SV-Fopt-synPA for vHVT306

<400> SEQUENCE: 45

```
taaaatggga tctatcatta cattcgttaa gagtctggat aattttactg tttgccagct     60

tcgatcttgg aacgtactgt ggatagtgcc ttacttggaa tcgtgaaaat ttgaaacgtc    120

cattatttgg atatcttccg gttgtcccat atcccgccct ggtaccgctc ggataccttg    180

cccgtatgga ttcgtattga cagtcgcgca atcggggacc aacaacgcgt gggtccacac    240

tcattcggaa attttccgat gattctgaat atttattgcc gctcgttacg agtcgttgga    300

catatctgta atacatttct tcttctgaag gatcgctgca catttgatct atacattggc    360

caggatgttc aagtctcaga tgttgcattc tggcacagca caactttatg gcatttccga    420

tgtaatcgtc cggcagccct gggggagttc tatattcgca tattgggatg gtaaggacaa    480

tagcagatct cgcaacctcc agggaggcta ataataacgtt tttaaaggat ggatttctca    540
```

-continued

```
taaaaatctg tcgcaaatta cactgagaat atcctttact agcgccgatt gagagcatcg    600
tcgtccaatt ttctaaatgg aaagaaaaca aggcgggcaa gagtgttcca aacattttca    660
ttttcggcga atctctcaaa tcccatggcg tgcaattgat tgcaaaattg gcacttccgt    720
tcacgtttgt atctccaaac tctaagacac ttttaattga aaaactacgt tctagtgtgg    780
aaagaaacct ataggcagac catagaacta tttgacacca catatctttt tgtatgtcaa    840
actgaccatg atcgtatgtt gctgaatgca ctagggcaat tcgctcgcgc gactccatac    900
attgaataat tccacacgtc agctcatcgg ttagcaaggt ccagtagttg aagtcattta    960
tttttccccg cggctggcca aatctacctc tgggaatatc caagttgtcg aatatgatcg   1020
caccggctct ggtcatggtg aaggaacttg tagcataaag acgcaggtat catagggta   1080
atatttttt attcactcac atactaaaag taacgcatat tagcaccatg tatgggctat   1140
caattgacat ttgcgtagca ctacatcacg attatgtaca acataatggg acaacatatg   1200
cctgcaggtc gacccaattc gagctcggta cagcttggct gtggaatgtg tgtcagttag   1260
ggtgtggaaa gtccccaggc tccccagcag gcagaagtat gcaaagcatg catctcaatt   1320
agtcagcaac caggtgtgga aagtccccag gctccccagc aggcagaagt atgcaaagca   1380
tgcatctcaa ttagtcagca accatagtcc cgcccctaac tccgcccatc ccgcccctaa   1440
ctccgcccag ttccgcccat tctccgcccc atggctgact aattttttt atttatgcag   1500
aggccgaggc cgcctcggcc tctgagctat tccagaagta gtgaggaggc ttttttggag   1560
gcctaggctt ttgcaaaaag ctcccggggc ggccgccacc atgggcagca agcccagcac   1620
aagaatccca gccccctga tgctgatcac ccgcatcatg ctgatcctgg gctgcatcag   1680
acccacaagc tccctggatg gacgcccct ggccgctgcc ggcatcgtgg tgaccggcga   1740
caaggccgtg aacgtgtaca ccagcagcca gaccggcagc atcatcgtga agctgctgcc   1800
caacatgccc agagacaaag aggcctgcgc caaggccccc ctggaagcct acaacagaac   1860
cctgaccacc ctgctgaccc ccctgggcga cagcatcaga aagatccagg gctccgtgag   1920
cacaagcggc ggaggaaagc agggcagact gatcggcgcc gtgatcggca gcgtggccct   1980
gggagtggct acagctgccc agattaccgc tgcagccgcc ctgatccagg ccaaccagaa   2040
cgccgccaac atcctgagac tgaaagagag cattgccgcc accaacgagg ccgtgcacga   2100
agtgaccgac ggcctgagcc agctgtccgt ggccgtgggc aagatgcagc agttcgtgaa   2160
cgaccagttc aacaacaccg ccagagagct ggactgcatc aagatcaccc agcaggtggg   2220
cgtggagctg aacctgtacc tgaccgagct gaccacagtg ttcggccccc agatcacaag   2280
cccagccctg acacagctga ccatccaggc cctgtacaac ctggctggcg gcaacatgga   2340
ctatctgctg acaaagctgg gaatcggcaa caaccagctg tccagcctga tcggaagcgg   2400
cctgatcacc ggctacccca tcctgtacga cagccagaca cagctgctgg gcatccaggt   2460
gaacctgccc agcgtgggca acctgaacaa catgcgcgcc acctacctgg aaaccctgag   2520
cgtgtccacc accaagggct acgccagcgc cctggtgccc aaggtggtga cacaggtggg   2580
cagcgtgatc gaggaactgg acaccagcta ctgcatcgag agcgacctgg acctgtactg   2640
caccagaatc gtgaccttcc caatgagccc cggcatctac agctgcctga gcggcaacac   2700
cagcgcctgc atgtacagca agaccgaagg cgcactgaca acaccctaca tggccctgaa   2760
gggaagcgtg atcgccaact gcaagatcac cacctgcaga tgcaccgacc ccccaggcat   2820
catcagccag aactacggcg aggccgtgag cctgatcgat cgccattcct gtaacgtgct   2880
```

-continued gtccctggac ggcatcacac tgagactgag cggcgagttc gatgccacct accagaagaa 2940
catcagcatc ctggacagcc aggtgatcgt gaccggcaac ctggacatca gcaccgagct 3000
gggcaacgtg aataacagca tcagcaacgc cctggacaga ctggccgaga gcaacagcaa 3060
gctggaaaaa gtgaacgtgc gcctgacatc cacttccgct ctgatcacct acatcgtgct 3120
gaccgtgatc agcctggtgt tcggcgccct gagcctggtg ctggcctgct acctgatgta 3180
caagcagaag gcccagcaga aaaccctgct gtggctgggc aacaacaccc tggaccagat 3240
gagagccacc accagagcct gatgagcggc cgcgatatca ataaaatatc tttattttca 3300
ttacatctgt gtgttggttt tttgtgtgaa tcgatagtac taacatacgc tctccatcaa 3360
aacaaaacga aacaaaacaa actagcaaaa taggctgtcc ccagtgcaag tgcaggtgcc 3420
agaacatttc tcttctagac ctgcaggccc gggcaagtag atgcaatttc ctcacactag 3480
ttgggtttat ctactattga attttcccct atctgtgata cacttgggag cctctacaag 3540
catattgcca tcatgtacgt tttatctac tgtcttaacg cccatgggaa cggaggcgtc 3600
gtcgtcatgt attggacggc aacataggca gcaacacaaa ttgcgtttag gtggggtgca 3660
tgtggactcg ataccaagcc cctgcagctg gggaacgtct ggtggagagc cgataatttg 3720
atatacgcac gccatattac tgtcgttgaa gtacgcctta tcttctatgt tttcaaattt 3780
aggttcccaa gtggacgtga gaagtgtttg tatctcacat ggaatggccc aaggcattcc 3840
agcccaggtg cctggtactt taatggcaaa caaacgtttt ggtagaggta ttgattctat 3900
tgcagttctg cagatatctg cagccccgag tatccacagg ctatacgata cgttatcgga 3960
ggcctccgat tctagcatta catagccggt cagtagatcc tgccattcgg tagcgcaacc 4020
ggctacatct tcaaacagtc tcacaataaa tgcatctctc gttcctgcca atccggaacc 4080
gggcatacca ctcccgcctg ccgatttaat tctcacaatt gggcgatgcc ggcggggcaa 4140
aacgaatgtg gatttggcaa accgacacag gtctgctgta cggactaata tgggcacacc 4200
cacatcattc ttcagatgct ccatgcattg ttctatgaga aagatccata gggtggaggc 4260
agcgtcacga gatcgcccag gcaatcgatc gcattcgtct agtaaagtga cgagagttat 4320
catgcacaca cccat 4335

<210> SEQ ID NO 46
<211> LENGTH: 5381
<212> TYPE: DNA
<213> ORGANISM: artificial sequence
<220> FEATURE:
<223> OTHER INFORMATION: Partial plasmid pCD046+NDV-F VII YZCQ sequence
for vHVT112

<400> SEQUENCE: 46
gagctcaggg tatgatactc agctgttatt gtggccgacc aggaggactc caatgcttag 60
cattcataag aacgctagag atgctattta acgatgtgct gtcgtctaaa gaatttgtgc 120
atttagcctt taaatgtaaa accaatgacg cattcactac gctcgtgcgt gcaatttctg 180
ggccagggta tgcatattcc ataacagaaa tcgacacttg agaagaggat ctgactgttt 240
gggataaagg tcgtttgggt ctgtcctagc gatataattt atatgacgat atacattaaa 300
catctgtgtg cagtacttag gtatttaatc atgtcgatga aatgttatgt gtaaatatcg 360
gacaatatag ataacgggca cgctgctatt gtaacgtgcg cccgcgcgct agtgctgact 420
aatagtgtgg atgatgtata cagtatatta caaacggaaa tgatacgtaa taaattatgt 480
actcttattg atttataaaa acatacatgc agtgttgcta tgtcacataa ttagcctcgc 540

-continued

```
ccgtctacgc tccactgaag ataatgggct cccgctgttc aaaaaaatca gcgtgcgtcg    600
ataagacttt ggtgcagtct cttcggggtc gcaatttaga tttgccgcat ggagggtatc    660
tggggatttt tgccaatgct ggagcgacga ctgtacgatt cgtcccatcg ggatctagca    720
gaccaatgat gttgacacac atcggccatg catgtacgga cggtctattg cgcgagtttg    780
ttattttcga aggacaagat ggaagtgtat atggaaccga caataatgtt agtttgcatt    840
tcttagggcg gaatctacat gatatcttat ccaagcgggg tatgagccag agagatgtga    900
tggtcataaa gggtaaattt tttagatctg aaataacgca gttgcccaaa caacgatcgc    960
gattaaaaga aaaatcggat ggttcaatta ggacatgcat ggattctgtg cgcataaacc   1020
ataaccgcag cactgttggg cacttcggta actcaaatgc gaagcgttgc acgtctgcga   1080
taactacgcc tactatgcac attgttactc ctgcatctta aaaatatatc ctgtagtaat   1140
tttcacagca atgtcataac atcatctcgc taaagaatga cctgggattg gagaagtaat   1200
gaatatttgc aaccaatgca ttgaataaac taacattaaa cgaattcaat agtggatccc   1260
ccaactccgc ccgttttatg actagaacca atagttttta atgccaaatg cactgaaatc   1320
ccctaatttg caaagccaaa cgccccctat gtgagtaata cggggacttt ttacccaatt   1380
tcccacgcgg aaagccccct aatacactca tatggcatat gaatcagcac ggtcatgcac   1440
tctaatggcg gcccataggg actttccaca tagggggcgt tcaccatttc ccagcatagg   1500
ggtggtgact caatggcctt tacccaagta cattgggtca atgggaggta agccaatggg   1560
tttttcccat tactggcaag cacactgagt caaatgggac tttccactgg gttttgccca   1620
agtacattgg gtcaatggga ggtgagccaa tgggaaaaac ccattgctgc caagtacact   1680
gactcaatag ggactttcca atgggttttt ccattgttgg caagcatata aggtcaatgt   1740
gggtgagtca atagggactt tccattgtat tctgcccagt acataaggtc aataggggt    1800
gaatcaacag gaaagtccca ttggagccaa gtacactgcg tcaataggga ctttccattg   1860
ggttttgccc agtacataag gtcaataggg gatgagtcaa tgggaaaaac ccattggagc   1920
caagtacact gactcaatag ggactttcca ttgggttttg cccagtacat aaggtcaata   1980
gggggtgagt caacaggaaa gttccattgg agccaagtac attgagtcaa tagggacttt   2040
ccaatgggtt ttgcccagta cataaggtca atgggaggta agccaatggg tttttcccat   2100
tactggcacg tatactgagt cattagggac tttccaatgg gttttgccca gtacataagg   2160
tcaatagggg tgaatcaaca ggaaagtccc attggagcca agtacactga gtcaataggg   2220
actttccatt gggttttgcc cagtacaaaa ggtcaatagg gggtgagtca atgggttttt   2280
cccattattg gcacgtacat aaggtcaata ggggtgagtc attgggtttt tccagccaat   2340
ttaattaaaa cgccatgtac tttcccacca ttgacgtcaa tgggctattg aaactaatgc   2400
aacgtgacct ttaaacggta ctttcccata gctgattaat gggaaagtac cgttctcgag   2460
ccaatacacg tcaatgggaa gtgaaagggc agccaaaacg taacaccgcc ccggttttcc   2520
cctggaaatt ccatattggc acgcattcta ttggctgagc tgcgttctac gtgggtataa   2580
gaggcgcgac cagcgtcggt accgtcgcag tcttcggtct gaccaccgta gaacgcagag   2640
ctcctcgctg caggcggccg catgggctct aaaccttcta ccaggatccc agcacctctg   2700
atgctgatca cccggattat gctgatattg gactgtatcc gtccgacaag ctctcttgac   2760
ggcaggcctc ttgcagctgc aggaattgta gtaacaggag ataaggcagt caatgtatat   2820
acctcgtctc agacagggtc aatcatagtc aagttgctcc cgaatatgcc caaggataag   2880
gaggcgtgtg cgaaagaccc attagaggca tataacagaa cactgactac tttgctcact   2940
```

-continued

```
cctcttggcg aatccatccg caagatccaa gggtctgtgt ccacgtctgg aggaggcaag   3000
caaggccgcc tgataggtgc tgttattggt agtgtagctc ttggggttgc aacagcggca   3060
caaataacag cagctgcggc cctaatacaa gccaaccaga atgctgccaa catccttcgg   3120
cttaaggaga gcattgctgc aaccaatgaa gctgtgcatg aagtcaccga cggattatca   3180
caactatcag tggcagttgg gaagatgcag cagtttgtca atgaccagtt taataataca   3240
gcgcgagaat tggactgtat aaaaatcaca caacaggttg gtgtagaact caacctatac   3300
ctaactgaat tgactacagt attcgggcca cagatcacct cccctgcatt aactcagctg   3360
accatccagg cactttataa tttagctggt ggcaatatgg attacttatt aactaagtta   3420
ggtataggga acaatcaact cagctcatta attggcagcg gcctgatcac tggttaccct   3480
atattgtatg actcacagac tcaactcttg ggcatacaag tgaatttgcc ctcagtcggg   3540
aacttaaata atatgcgtgc cacctattta gagaccttat ctgtaagtac agccaaagga   3600
tatgcctcag cacttgttcc aaaagtagtg acacaagtcg gttctgtgat agaagagctt   3660
gacacctcat actgtataga gtccgatctg gatttatatt gtactagaat agtgacattc   3720
cccatgtccc caggtattta ttcctgttta agcggcaaca catcagcttg catgtattca   3780
aagactgaag gcgcactcac tacgccgtat atggccctta aaggctcagt tattgccaat   3840
tgtaagataa caacatgtag atgtacagac cctcctggta tcatatcgca aaattatgga   3900
gaagctgtat ccctgataga tagacattcg tgcaatgtct tatcattaga cgggataact   3960
ctgaggctca gtggagaatt tgatgcaact tatcaaaaga acatctcaat actagattct   4020
caagtcatcg tgacaggcaa tcttgatata tcaactgaac ttggaaacgt caacaattca   4080
atcagcaatg ccttggataa gttggcaaaa agcaacagca agctagaaaa agtcaatgtc   4140
agactaacca gcacatccgc tctcattacc tatattgttc tgactgtcat ttctctagtt   4200
ttcggtgcac taagtctggg tttaacatgt tacctgatgt acaaacaaaa ggcacaacaa   4260
aagaccttgc tatggcttgg gaataatacc ctcgatcaga tgagagccac tacaagagca   4320
tgagcggccg cggggatcca gacatgataa gatacattga tgagtttgga caaaccacaa   4380
ctagaatgca gtgaaaaaaa tgctttattt gtgaaatttg tgatgctatt gctttatttg   4440
taaccattat aagctgcaat aaacaagtta acaacaacaa ttgcattgat tttatgtttc   4500
aggttcaggg ggaggtgtgg gaggtttttt cggatcctct agagtcgaca attattttat   4560
ttaataacat atagcccaaa gacctctatg aacatttagt ttcccgtata ctcaacggcg   4620
cgtgtacaca cgcatctctt tgcatagcga tgaagtttgt tcggcagcag aaaatgcaga   4680
tatccaacaa tctggagaaa acttatcatc acagtggcag tggaaacata ccccctctat   4740
attcatggta taattatcgt ctacagcgtc caggatagtg gcgtgagaaa atggagatct   4800
gcagccctcc tttccatggc atgccgcttt attgttcatt aaacgcacaa tggtctcaac   4860
gccagatatg ggcatagatt ctgaagaacc cgttgacaat ccgaagaaga aggcgtgcag   4920
gtctttggaa gactcgcacg ttggtcttat aatgtatgat cgagatgtca ccctaatgcc   4980
acatggtaca ggcttatcgc ggtcatggcg atcggacttg taatttgcaa cgatgggcaa   5040
aggatcgacg acatgccaaa cattctgaac ccgtagagat gttaacgatg acgaggatga   5100
atatcccatg ctcgctgcca tagtatcaag tacaccgcga ataaggacgc gtccaacatc   5160
gttatatgca cacaatgggc tacacgtgac taacaccccc gaatattagt catatgtgag   5220
tttcagtctg gctcccatat agcctgtaga ctatttgtgg tttaagtgtg aacgaggcgc   5280
```

tgtgaacgag actcgggccg attgtaagaa caagcaaatg cactttccat ttaacaagaa 5340
gtgtagagag aatactcaac ctctttggat gtatcctcga g 5381

<210> SEQ ID NO 47
<211> LENGTH: 5381
<212> TYPE: DNA
<213> ORGANISM: artificial sequence
<220> FEATURE:
<223> OTHER INFORMATION: Partial plasmid pCD046+NDV Texas F sequence for vHVT113

<400> SEQUENCE: 47
gagctcaggg tatgatactc agctgttatt gtggccgacc aggaggactc caatgcttag 60
cattcataag aacgctagag atgctattta acgatgtgct gtcgtctaaa gaatttgtgc 120
atttagcctt taaatgtaaa accaatgacg cattcactac gctcgtgcgt gcaatttctg 180
ggccagggta tgcatattcc ataacagaaa tcgacacttg agaagaggat ctgactgttt 240
gggataaagg tcgtttgggt ctgtcctagc gatataattt atatgacgat atacattaaa 300
catctgtgtg cagtacttag gtatttaatc atgtcgatga aatgttatgt gtaaatatcg 360
gacaatatag ataacgggca cgctgctatt gtaacgtgcg cccgcgcgct agtgctgact 420
aatagtgtgg atgatgtata cagtatatta caaacggaaa tgatacgtaa taaattatgt 480
actcttattg atttataaaa acatacatgc agtgttgcta tgtcacataa ttagcctcgc 540
ccgtctacgc tccactgaag ataatgggct cccgctgttc aaaaaaatca gcgtgcgtcg 600
ataagacttt ggtgcagtct cttcggggtc gcaatttaga tttgccgcat ggagggtatc 660
tggggatttt tgccaatgct ggagcgacga ctgtacgatt cgtcccatcg ggatctagca 720
gaccaatgat gttgacacac atcggccatg catgtacgga cggtctattg cgcgagtttg 780
ttattttcga aggacaagat ggaagtgtat atggaaccga caataatgtt agtttgcatt 840
tcttagggcg gaatctacat gatatcttat ccaagcgggg tatgagccag agagatgtga 900
tggtcataaa gggtaaattt tttagatctg aaataacgca gttgcccaaa caacgatcgc 960
gattaaaaga aaaatcggat ggttcaatta ggacatgcat ggattctgtg cgcataaacc 1020
ataaccgcag cactgttggg cacttcggta actcaaatgc gaagcgttgc acgtctgcga 1080
taactacgcc tactatgcac attgttactc ctgcatctta aaaatatatc ctgtagtaat 1140
tttcacagca atgtcataac atcatctcgc taaagaatga cctgggattg gagaagtaat 1200
gaatatttgc aaccaatgca ttgaataaac taacattaaa cgaattcaat agtggatccc 1260
ccaactccgc ccgttttatg actagaacca atagttttta atgccaaatg cactgaaatc 1320
ccctaatttg caaagccaaa cgccccctat gtgagtaata cggggacttt ttacccaatt 1380
tcccacgcgg aaagcccccct aatacactca tatggcatat gaatcagcac ggtcatgcac 1440
tctaatggcg gcccataggg actttccaca tagggggcgt tcaccatttc ccagcatagg 1500
ggtggtgact caatggcctt tacccaagta cattgggtca atgggaggta agccaatggg 1560
tttttcccat tactggcaag cacactgagt caaatgggac tttccactgg gttttgccca 1620
agtacattgg gtcaatggga ggtgagccaa tgggaaaaac ccattgctgc caagtacact 1680
gactcaatag ggactttcca atgggttttt ccattgttgg caagcatata aggtcaatgt 1740
gggtgagtca atagggactt tccattgtat tctgcccagt acataaggtc aatagggggt 1800
gaatcaacag gaaagtccca ttggagccaa gtacactgcg tcaataggga ctttccattg 1860
ggttttgccc agtacataag gtcaataggg gatgagtcaa tgggaaaaac ccattggagc 1920

-continued

```
caagtacact gactcaatag ggactttcca ttgggttttg cccagtacat aaggtcaata   1980
gggggtgagt caacaggaaa gttccattgg agccaagtac attgagtcaa tagggacttt   2040
ccaatgggtt ttgcccagta cataaggtca atgggaggta agccaatggg tttttcccat   2100
tactggcacg tatactgagt cattagggac tttccaatgg gttttgccca gtacataagg   2160
tcaatagggg tgaatcaaca ggaaagtccc attggagcca agtacactga gtcaataggg   2220
actttccatt gggttttgcc cagtacaaaa ggtcaatagg gggtgagtca atgggttttt   2280
cccattattg gcacgtacat aaggtcaata ggggtgagtc attgggtttt tccagccaat   2340
ttaattaaaa cgccatgtac tttcccacca ttgacgtcaa tgggctattg aaactaatgc   2400
aacgtgacct ttaaacggta ctttcccata gctgattaat gggaaagtac cgttctcgag   2460
ccaatacacg tcaatgggaa gtgaaagggc agccaaaacg taacaccgcc ccggttttcc   2520
cctggaaatt ccatattggc acgcattcta ttggctgagc tgcgttctac gtgggtataa   2580
gaggcgcgac cagcgtcggt accgtcgcag tcttcggtct gaccaccgta gaacgcagag   2640
ctcctcgctg caggcggccg catgggctcc agatcttcta ccaggatccc ggtacctcta   2700
atgctgatca tccgaaccgc gctgacactg agctgtatcc gtctgacaag ctctcttgat   2760
ggcaggcctc ttgcggctgc agggatcgtg gtaacaggag ataaagcagt caacatatac   2820
acctcatccc agacagggtc aatcatagtt aagttactcc cgaatatgcc caaggacaaa   2880
gaggtgtgtg caaaagcccc attggaggca tacaacagga cactgactac tttactcacc   2940
ccccttggtg attctatccg caggatacaa gagtctgtga ctacttccgg aggaggcaag   3000
caaggccgcc tgataggtgc cattatcggc agtgtagctc ttggggttgc gacagctgca   3060
cagataacag cagcttcggc cctgatacaa gccaaccaga atgctgccaa catcctccgg   3120
cttaaagaga gcattgctgc aaccaatgaa gctgtgcacg aggtcactga cggattatca   3180
caactagcag tggcagtagg gaagatgcaa cagtttgtca atgaccagtt caataataca   3240
gcgcaagaat tggactgtat aaaaattgca cagcaggtcg gtgtagaact caacttgtac   3300
ctaactgaat tgactacagt atttgggcca caaatcactt cccctgcctt aactcagctg   3360
actatccaag cgctttacaa tctagctggt ggtaatatgg attacttgct gactaagtta   3420
ggtgtaggga acaaccaact cagctcatta attggtagcg gcttgatcac cggcaaccct   3480
attctgtacg actcacagac tcagatcttg ggtatacagg taactttgcc ttcagttggg   3540
aacctgaata atatgcgtgc cacctacctg gagaccttat ctgtaagcac aaccaaggga   3600
tttgcctcag cacttgtccc aaaagtggtg acacaggtcg gttccgtgat agaagaactt   3660
gacacctcat actgtatagg gaccgacttg gatttatact gtacaagaat agtgacattc   3720
cctatgtctc ctggtattta ttcttgtctg agcggtaata catcggcttg catgtattca   3780
aagactgaag gcgcacttac tacgccatat atggctctca aaggctcagt tattgccaat   3840
tgcaagctga caacatgtag atgtgcagat cccccaggta tcatatcgca aaattatgga   3900
gaagctgtgt ccttaataga taggcactca tgcaacgtct tatccttaga cgggataact   3960
ctgaggctca gtggggaatt tgatgcaacc tatcaaaaga atatctctat actagattct   4020
caagttatag tgacaggcaa tcttgatata tcaactgagc ttgggaatgt caacaactca   4080
ataagtaatg ccctgaataa gttagaggaa agcaacagca aactagacaa agtcaatgtc   4140
aaactgacca gcacatctgc tctcattacc tacatcgttt taactgtcat atctcttgtt   4200
tttggtgtac ttagcctggt tctagcatgc tacctgatgt acaagcaaaa ggcacaacaa   4260
aagaccttgt tatggcttgg gaataatacc cttgatcaga tgagagccac tacaaaaata   4320
```

tgagcggccg cggggatcca gacatgataa gatacattga tgagtttgga caaaccacaa 4380
ctagaatgca gtgaaaaaaa tgctttattt gtgaaatttg tgatgctatt gctttatttg 4440
taaccattat aagctgcaat aaacaagtta acaacaacaa ttgcattgat tttatgtttc 4500
aggttcaggg ggaggtgtgg gaggtttttt cggatcctct agagtcgaca attattttat 4560
ttaataacat atagcccaaa gacctctatg aacatttagt ttcccgtata ctcaacggcg 4620
cgtgtacaca cgcatctctt tgcatagcga tgaagtttgt tcggcagcag aaaatgcaga 4680
tatccaacaa tctggagaaa acttatcatc acagtggcag tggaaacata ccccctctat 4740
attcatggta taattatcgt ctacagcgtc caggatagtg gcgtgagaaa atggagatct 4800
gcagccctcc tttccatggc atgccgcttt attgttcatt aaacgcacaa tggtctcaac 4860
gccagatatg ggcatagatt ctgaagaacc cgttgacaat ccgaagaaga aggcgtgcag 4920
gtctttggaa gactcgcacg ttggtcttat aatgtatgat cgagatgtca ccctaatgcc 4980
acatggtaca ggcttatcgc ggtcatggcg atcggacttg taatttgcaa cgatgggcaa 5040
aggatcgacg acatgccaaa cattctgaac ccgtagagat gttaacgatg acgaggatga 5100
atatcccatg ctcgctgcca tagtatcaag tacaccgcga ataaggacgc gtccaacatc 5160
gttatatgca cacaatgggc tacacgtgac taacaccccc gaatattagt catatgtgag 5220
tttcagtctg gctcccatat agcctgtaga ctatttgtgg tttaagtgtg aacgaggcgc 5280
tgtgaacgag actcgggccg attgtaagaa caagcaaatg cactttccat ttaacaagaa 5340
gtgtagagag aatactcaac ctctttggat gtatcctcga g 5381

<210> SEQ ID NO 48
<211> LENGTH: 4600
<212> TYPE: DNA
<213> ORGANISM: artificial sequence
<220> FEATURE:
<223> OTHER INFORMATION: Partial plasmid pHM119 sequence for vHVT039

<400> SEQUENCE: 48
gagctcaggg tatgatactc agctgttatt gtggccgacc aggaggactc caatgcttag 60
cattcataag aacgctagag atgctattta acgatgtgct gtcgtctaaa gaatttgtgc 120
atttagcctt taaatgtaaa accaatgacg cattcactac gctcgtgcgt gcaatttctg 180
ggccagggta tgcatattcc ataacagaaa tcgacacttg agaagaggat ctgactgttt 240
gggataaagg tcgtttgggt ctgtcctagc gatataattt atatgacgat atacattaaa 300
catctgtgtg cagtacttag gtatttaatc atgtcgatga aatgttatgt gtaaatatcg 360
gacaatatag ataacgggca cgctgctatt gtaacgtgcg cccgcgcgct agtgctgact 420
aatagtgtgg atgatgtata cagtatatta caaacggaaa tgatacgtaa taaattatgt 480
actcttattg atttataaaa acatacatgc agtgttgcta tgtcacataa ttagcctcgc 540
ccgtctacgc tccactgaag ataatgggct cccgctgttc aaaaaaatca gcgtgcgtcg 600
ataagacttt ggtgcagtct cttcggggtc gcaatttaga tttgccgcat ggagggtatc 660
tggggatttt tgccaatgct ggagcgacga ctgtacgatt cgtcccatcg ggatctagca 720
gaccaatgat gttgacacac atcggccatg catgtacgga cggtctattg cgcgagtttg 780
ttattttcga aggacaagat ggaagtgtat atggaaccga caataatgtt agtttgcatt 840
tcttagggcg gaatctacat gatatcttat ccaagcgggg tatgagccag agagatgtga 900
tggtcataaa gggtaaattt tttagatctg aaataacgca gttgcccaaa caacgatcgc 960

-continued

```
gattaaaaga aaaatcggat ggttcaatta ggacatgcat ggattctgtg cgcataaacc   1020
ataaccgcag cactgttggg cacttcggta actcaaatgc gaagcgttgc acgtctgcga   1080
taactacgcc tactatgcac attgttactc ctgcatctta aaaatatatc ctgtagtaat   1140
tttcacagca atgtcataac atcatctcgc taaagaatga cctgggattg gagaagtaat   1200
gaatatttgc aaccaatgca ttgaataaac taacattaaa cgaattccga tgtttagtca   1260
cgatagacat cggttcgccc agccgtcgaa tacagcatta tattttagtg ttgaaaatgt   1320
agggctgctt cctcacttaa aggaggaaat ggctcgattc atgtttcata gcagtagaaa   1380
aacagattgg accgtcagta agtttagagg gttttatgac tttagcacta tagataatgt   1440
aactgcggcc catcgcatgg cttggaaata tatcaaagaa ctgatttttg caacagcttt   1500
attttcttct gtatttaaat gtggcgaatt gcacatctgt cgtgccgaca gtttgcagat   1560
caacagcaat ggagactatg tatggaaaaa tggaatatat ataacatatg aaaccgaata   1620
tccacttata atgattctgg ggtcagaatc aagcacttca gaaacgcaaa atatgactgc   1680
aattattgat acagatgttt tttcgttgct ttattctatt ttgcagtata tggccccccgt   1740
tacggcagat caggtgcgag tagaacagat taccaacagc cacgcccccca tctgacccgt   1800
ccaatattct tgtgtccctg cattttatct cacacaattt atgaacagca tcattaagat   1860
catctcactg cggccgcaag atgggctcca gatcttctac caggatcccg gtacctctaa   1920
tgctgatcat ccgaaccgcg ctgacactga gctgtatccg tctgacaagc tctcttgatg   1980
gcaggcctct tgcggctgca gggatcgtgg taacaggaga taaagcagtc aacatataca   2040
cctcatccca gacagggtca atcatagtta agttactccc gaatatgccc aaggacaaag   2100
aggtgtgtgc aaaagcccca ttggaggcat acaacaggac actgactact ttactcaccc   2160
cccttggtga ttctatccgc aggatacaag agtctgtgac tacttccgga ggaaggagac   2220
agagacgctt tataggtgcc attatcggca gtgtagctct tggggttgcg acagctgcac   2280
agataacagc agcttcggcc ctgatacaag ccaaccagaa tgctgccaac atcctccggc   2340
ttaaagagag cattgctgca accaatgaag ctgtgcacga ggtcactgac ggattatcac   2400
aactagcagt ggcagtaggg aagatgcaac agtttgtcaa tgaccagttc aataatacag   2460
cgcaagaatt ggactgtata aaaattgcac agcaggtcgg tgtagaactc aacttgtacc   2520
taactgaatt gactacagta tttgggccac aaatcacttc ccctgcctta actcagctga   2580
ctatccaagc gctttacaat ctagctggtg gtaatatgga ttacttgctg actaagttag   2640
gtgtagggaa caaccaactc agctcattaa ttggtagcgg cttgatcacc ggcaacccta   2700
ttctgtacga ctcacagact cagatcttgg gtatacaggt aactttgcct tcagttggga   2760
acctgaataa tatgcgtgcc acctacctgg agaccttatc tgtaagcaca accaagggat   2820
ttgcctcagc acttgtccca aaagtggtga cacaggtcgg ttccgtgata gaagaacttg   2880
acacctcata ctgtataggg accgacttgg atttatactg tacaagaata gtgacattcc   2940
ctatgtctcc tggtatttat tcttgtctga gcggtaatac atcggcttgc atgtattcaa   3000
agactgaagg cgcacttact acgccatata tggctctcaa aggctcagtt attgccaatt   3060
gcaagctgac aacatgtaga tgtgcagatc ccccaggtat catatcgcaa aattatggag   3120
aagctgtgtc cttaatagat aggcactcat gcaacgtctt atccttagac gggataactc   3180
tgaggctcag tggggaattt gatgcaacct atcaaaagaa tatctctata ctagattctc   3240
aagttatagt gacaggcaat cttgatatat caactgagct tgggaatgtc aacaactcaa   3300
taagtaatgc cctgaataag ttagaggaaa gcaacagcaa actagacaaa gtcaatgtca   3360
```

aactgaccag cacatctgct ctcattacct acatcgtttt aactgtcata tctcttgttt 3420
ttggtgtact tagcctggtt ctagcatgct acctgatgta caagcaaaag gcacaacaaa 3480
agaccttgtt atggcttggg aataataccc ttgatcagat gagagccact acaaaaatat 3540
gagcggccgc ggggatccag acatgataag atacattgat gagtttggac aaaccacaac 3600
tagaatgcag tgaaaaaaat gctttatttg tgaaatttgt gatgctattg ctttatttgt 3660
aaccattata agctgcaata aacaagttaa caacaacaat tgcattcatt ttatgtttca 3720
ggttcagggg gaggtgtggg aggtttttc ggatcctcta gagtcgacaa ttattttatt 3780
taataacata tagcccaaag acctctatga acatttagtt tcccgtatac tcaacggcgc 3840
gtgtacacac gcatctcttt gcatagcgat gaagtttgtt cggcagcaga aaatgcagat 3900
atccaacaat ctggagaaaa cttatcatca cagtggcagt ggaaacatac cccctctata 3960
ttcatggtat aattatcgtc tacagcgtcc aggatagtgg cgtgagaaaa tggagatctg 4020
cagccctcct ttccatggca tgccgcttta ttgttcatta aacgcacaat ggtctcaacg 4080
ccagatatgg gcatagattc tgaagaaccc gttgacaatc cgaagaagaa ggcgtgcagg 4140
tctttggaag actcgcacgt tggtcttata atgtatgatc gagatgtcac cctaatgcca 4200
catggtacag gcttatcgcg gtcatggcga tcggacttgt aatttgcaac gatgggcaaa 4260
ggatcgacga catgccaaac attctgaacc cgtagagatg ttaacgatga cgaggatgaa 4320
tatcccatgc tcgctgccat agtatcaagt acaccgcgaa taaggacgcg tccaacatcg 4380
ttatatgcac acaatgggct acacgtgact aacacccccg aatattagtc atatgtgagt 4440
ttcagtctgg ctcccatata gcctgtagac tatttgtggt ttaagtgtga acgaggcgct 4500
gtgaacgaga ctcgggccga ttgtaagaac aagcaaatgc actttccatt taacaagaag 4560
tgtagagaga atactcaacc tctttggatg tatcctcgag 4600

<210> SEQ ID NO 49
<211> LENGTH: 1662
<212> TYPE: DNA
<213> ORGANISM: artificial sequence
<220> FEATURE:
<223> OTHER INFORMATION: NDV Texas F gene (wild type non-modified)

<400> SEQUENCE: 49
atgggctcca gatcttctac caggatcccg gtacctctaa tgctgatcat ccgaaccgcg 60
ctgacactga gctgtatccg tctgacaagc tctcttgatg gcaggcctct tgcggctgca 120
gggatcgtgg taacaggaga taaagcagtc aacatataca cctcatccca gacagggtca 180
atcatagtta agttactccc gaatatgccc aaggacaaag aggtgtgtgc aaaagcccca 240
ttggaggcat acaacaggac actgactact ttactcaccc cccttggtga ttctatccgc 300
aggatacaag agtctgtgac tacttccgga ggaaggagac agagacgctt tataggtgcc 360
attatcggca gtgtagctct tggggttgcg acagctgcac agataacagc agcttcggcc 420
ctgatacaag ccaaccagaa tgctgccaac atcctccggc ttaaagagag cattgctgca 480
accaatgaag ctgtgcacga ggtcactgac ggattatcac aactagcagt ggcagtaggg 540
aagatgcaac agtttgtcaa tgaccagttc aataatacag cgcaagaatt ggactgtata 600
aaaattgcac agcaggtcgg tgtagaactc aacttgtacc taactgaatt gactacagta 660
tttgggccac aaatcacttc ccctgcctta actcagctga ctatccaagc gctttacaat 720
ctagctggtg gtaatatgga ttacttgctg actaagttag gtgtagggaa caaccaactc 780

-continued

```
agctcattaa ttggtagcgg cttgatcacc ggcaacccta ttctgtacga ctcacagact    840

cagatcttgg gtatacaggt aactttgcct tcagttggga acctgaataa tatgcgtgcc    900

acctacctgg agaccttatc tgtaagcaca accaagggat ttgcctcagc acttgtccca    960

aaagtggtga cacaggtcgg ttccgtgata gaagaacttg acacctcata ctgtataggg   1020

accgacttgg atttatactg tacaagaata gtgacattcc ctatgtctcc tggtatttat   1080

tcttgtctga gcggtaatac atcggcttgc atgtattcaa agactgaagg cgcacttact   1140

acgccatata tggctctcaa aggctcagtt attgccaatt gcaagctgac aacatgtaga   1200

tgtgcagatc ccccaggtat catatcgcaa aattatggag aagctgtgtc cttaatagat   1260

aggcactcat gcaacgtctt atccttagac gggataactc tgaggctcag tggggaattt   1320

gatgcaacct atcaaaagaa tatctctata ctagattctc aagttatagt gacaggcaat   1380

cttgatatat caactgagct tgggaatgtc aacaactcaa taagtaatgc cctgaataag   1440

ttagaggaaa gcaacagcaa actagacaaa gtcaatgtca aactgaccag cacatctgct   1500

ctcattacct acatcgtttt aactgtcata tctcttgttt ttggtgtact tagcctggtt   1560

ctagcatgct acctgatgta caagcaaaag gcacaacaaa agaccttgtt atggcttggg   1620

aataataccc ttgatcagat gagagccact acaaaaatat ga                      1662
```

```
<210> SEQ ID NO 50
<211> LENGTH: 553
<212> TYPE: PRT
<213> ORGANISM: artificial sequence
<220> FEATURE:
<223> OTHER INFORMATION: NDV Texas F protein (wild type non-modified;
      cleavage site underlined)

<400> SEQUENCE: 50

Met Gly Ser Arg Ser Ser Thr Arg Ile Pro Val Pro Leu Met Leu Ile
1               5                   10                  15

Ile Arg Thr Ala Leu Thr Leu Ser Cys Ile Arg Leu Thr Ser Ser Leu
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Met Pro Lys Asp Lys Glu Val Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Arg
            100                 105                 110

Arg Gln Arg Arg Phe Ile Gly Ala Ile Ile Gly Ser Val Ala Leu Gly
        115                 120                 125

Val Ala Thr Ala Ala Gln Ile Thr Ala Ala Ser Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Asn
            180                 185                 190

Thr Ala Gln Glu Leu Asp Cys Ile Lys Ile Ala Gln Gln Val Gly Val
        195                 200                 205
```

```
Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Ile Leu Gly Ile Gln Val Thr
        275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Gly Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Ala Leu Lys Gly Ser Val Ile Ala Asn Cys Lys Leu Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
    450                 455                 460

Thr Glu Leu Gly Asn Val Asn Asn Ser Ile Ser Asn Ala Leu Asn Lys
465                 470                 475                 480

Leu Glu Glu Ser Asn Ser Lys Leu Asp Lys Val Asn Val Lys Leu Thr
                485                 490                 495

Ser Thr Ser Ala Leu Ile Thr Tyr Ile Val Leu Thr Val Ile Ser Leu
            500                 505                 510

Val Phe Gly Val Leu Ser Leu Val Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Ile
545                 550
```

<210> SEQ ID NO 51
<211> LENGTH: 1662
<212> TYPE: DNA
<213> ORGANISM: artificial sequence
<220> FEATURE:
<223> OTHER INFORMATION: NDV-F YZCQ wildtype DNA

<400> SEQUENCE: 51

```
atgggctcca gatcttctac caggatcccg gtacctctaa tgctgatcat ccgaaccgcg      60
```

ctgacactga gctgtatccg tctgacaagc tctcttgatg gcaggcctct tgcggctgca 120
gggatcgtgg taacaggaga taaagcagtc aacatataca cctcatccca gacagggtca 180
atcatagtta agttactccc gaatatgccc aaggacaaag aggtgtgtgc aaaagcccca 240
ttggaggcat acaacaggac actgactact ttactcaccc cccttggtga ttctatccgc 300
aggatacaag agtctgtgac tacttccgga ggaggcaagc aaggccgcct gataggtgcc 360
attatcggca gtgtagctct tggggttgcg acagctgcac agataacagc agcttcggcc 420
ctgatacaag ccaaccagaa tgctgccaac atcctccggc ttaaagagag cattgctgca 480
accaatgaag ctgtgcacga ggtcactgac ggattatcac aactagcagt ggcagtaggg 540
aagatgcaac agtttgtcaa tgaccagttc aataatacag cgcaagaatt ggactgtata 600
aaaattgcac agcaggtcgg tgtagaactc aacttgtacc taactgaatt gactacagta 660
tttgggccac aaatcacttc ccctgcctta actcagctga ctatccaagc gctttacaat 720
ctagctggtg gtaatatgga ttacttgctg actaagttag gtgtagggaa caaccaactc 780
agctcattaa ttggtagcgg cttgatcacc ggcaacccta ttctgtacga ctcacagact 840
cagatcttgg gtatacaggt aactttgcct tcagttggga acctgaataa tatgcgtgcc 900
acctacctgg agaccttatc tgtaagcaca accaagggat ttgcctcagc acttgtccca 960
aaagtggtga cacaggtcgg ttccgtgata gaagaacttg acacctcata ctgtataggg 1020
accgacttgg atttatactg tacaagaata gtgacattcc ctatgtctcc tggtatttat 1080
tcttgtctga gcggtaatac atcggcttgc atgtattcaa agactgaagg cgcacttact 1140
acgccatata tggctctcaa aggctcagtt attgccaatt gcaagctgac aacatgtaga 1200
tgtgcagatc ccccaggtat catatcgcaa aattatggag aagctgtgtc cttaatagat 1260
aggcactcat gcaacgtctt atccttagac gggataactc tgaggctcag tggggaattt 1320
gatgcaacct atcaaaagaa tatctctata ctagattctc aagttatagt gacaggcaat 1380
cttgatatat caactgagct tgggaatgtc aacaactcaa taagtaatgc cctgaataag 1440
ttagaggaaa gcaacagcaa actagacaaa gtcaatgtca aactgaccag cacatctgct 1500
ctcattacct acatcgtttt aactgtcata tctcttgttt ttggtgtact tagcctggtt 1560
ctagcatgct acctgatgta caagcaaaag gcacaacaaa agaccttgtt atggcttggg 1620
aataataccc ttgatcagat gagagccact acaaaaatat ga 1662

<210> SEQ ID NO 52
<211> LENGTH: 553
<212> TYPE: PRT
<213> ORGANISM: artificial sequence
<220> FEATURE:
<223> OTHER INFORMATION: NDV-F protein from wildtype YZCQ strain (Amino Acid Sequence of NDV-F of Texas strain with lentogenic cleavage site sequence)

<400> SEQUENCE: 52

Met Gly Ser Arg Ser Ser Thr Arg Ile Pro Val Pro Leu Met Leu Ile
1               5                   10                  15

Ile Arg Thr Ala Leu Thr Leu Ser Cys Ile Arg Leu Thr Ser Ser Leu
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Met Pro Lys Asp Lys Glu Val Cys Ala Lys Ala Pro

-continued

```
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Gly
            100                 105                 110

Lys Gln Gly Arg Leu Ile Gly Ala Ile Ile Gly Ser Val Ala Leu Gly
        115                 120                 125

Val Ala Thr Ala Ala Gln Ile Thr Ala Ala Ser Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Asn
            180                 185                 190

Thr Ala Gln Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Ile Leu Gly Ile Gln Val Thr
        275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Gly Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Ala Leu Lys Gly Ser Val Ile Ala Asn Cys Lys Leu Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
    450                 455                 460

Thr Glu Leu Gly Asn Val Asn Asn Ser Ile Ser Asn Ala Leu Asn Lys
465                 470                 475                 480

Leu Glu Glu Ser Asn Ser Lys Leu Asp Lys Val Asn Val Lys Leu Thr
                485                 490                 495
```

-continued

```
Ser Thr Ser Ala Leu Ile Thr Tyr Ile Val Leu Thr Val Ile Ser Leu
            500                 505                 510

Val Phe Gly Val Leu Ser Leu Val Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Ile
545                 550


<210> SEQ ID NO 53
<211> LENGTH: 1662
<212> TYPE: DNA
<213> ORGANISM: artificial sequence
<220> FEATURE:
<223> OTHER INFORMATION: NDV-F Texas wildtype DNA

<400> SEQUENCE: 53

atgggctcta aaccttctac caggatccca gcacctctga tgctgatcac ccggattatg     60

ctgatattgg actgtatccg tccgacaagc tctcttgacg gcaggcctct tgcagctgca    120

ggaattgtag taacaggaga taaggcagtc aatgtatata cctcgtctca gacagggtca    180

atcatagtca agttgctccc gaatatgccc aaggataagg aggcgtgtgc gaaagaccca    240

ttagaggcat ataacagaac actgactact ttgctcactc ctcttggcga atccatccgc    300

aagatccaag ggtctgtgtc cacgtctgga ggaggcaagc aaggccgcct gataggtgct    360

gttattggta gtgtagctct tggggttgca acagcggcac aaataacagc agctgcggcc    420

ctaatacaag ccaaccagaa tgctgccaac atccttcggc ttaaggagag cattgctgca    480

accaatgaag ctgtgcatga agtcaccgac ggattatcac aactatcagt ggcagttggg    540

aagatgcagc agtttgtcaa tgaccagttt aataatacag cgcgagaatt ggactgtata    600

aaaatcacac aacaggttgg tgtagaactc aacctatacc taactgaatt gactacagta    660

ttcgggccac agatcacctc ccctgcatta actcagctga ccatccaggc actttataat    720

ttagctggtg gcaatatgga ttacttatta actaagttag gtatagggaa caatcaactc    780

agctcattaa ttggcagcgg cctgatcact ggttacccta tattgtatga ctcacagact    840

caactcttgg gcatacaagt gaatttgccc tcagtcggga acttaaataa tatgcgtgcc    900

acctatttag agaccttatc tgtaagtaca gccaaaggat atgcctcagc acttgttcca    960

aaagtagtga cacaagtcgg ttctgtgata gaagagcttg acacctcata ctgtatagag   1020

tccgatctgg atttatattg tactagaata gtgacattcc ccatgtcccc aggtatttat   1080

tcctgtttaa gcggcaacac atcagcttgc atgtattcaa agactgaagg cgcactcact   1140

acgccgtata tggcccttaa aggctcagtt attgccaatt gtaagataac aacatgtaga   1200

tgtacagacc ctcctggtat catatcgcaa aattatggag aagctgtatc cctgatagat   1260

agacattcgt gcaatgtctt atcattagac gggataactc tgaggctcag tggagaattt   1320

gatgcaactt atcaaaagaa catctcaata ctagattctc aagtcatcgt gacaggcaat   1380

cttgatatat caactgaact tggaaacgtc aacaattcaa tcagcaatgc cttggataag   1440

ttggcaaaaa gcaacagcaa gctagaaaaa gtcaatgtca gactaaccag cacatccgct   1500

ctcattacct atattgttct gactgtcatt tctctagttt tcggtgcact aagtctgggt   1560

ttaacatgtt acctgatgta caaacaaaag gcacaacaaa agaccttgct atggcttggg   1620

aataataccc tcgatcagat gagagccact acaagagcat ga                      1662
```

<210> SEQ ID NO 54
<211> LENGTH: 553
<212> TYPE: PRT
<213> ORGANISM: artificial sequence
<220> FEATURE:
<223> OTHER INFORMATION: NDV-F protein from wildtype Texas strain (Amino Acid Sequence of NDV-F VIId wt YZCQ with lentogenic cleavage site sequence)

<400> SEQUENCE: 54

```
Met Gly Ser Lys Pro Ser Thr Arg Ile Pro Ala Pro Leu Met Leu Ile
1               5                   10                  15

Thr Arg Ile Met Leu Ile Leu Asp Cys Ile Arg Pro Thr Ser Ser Leu
            20                  25                  30

Asp Gly Arg Pro Leu Ala Ala Ala Gly Ile Val Val Thr Gly Asp Lys
        35                  40                  45

Ala Val Asn Val Tyr Thr Ser Ser Gln Thr Gly Ser Ile Ile Val Lys
    50                  55                  60

Leu Leu Pro Asn Met Pro Lys Asp Lys Glu Ala Cys Ala Lys Asp Pro
65                  70                  75                  80

Leu Glu Ala Tyr Asn Arg Thr Leu Thr Thr Leu Leu Thr Pro Leu Gly
                85                  90                  95

Glu Ser Ile Arg Lys Ile Gln Gly Ser Val Ser Thr Ser Gly Gly Gly
            100                 105                 110

Lys Gln Gly Arg Leu Ile Gly Ala Val Ile Gly Ser Val Ala Leu Gly
        115                 120                 125

Val Ala Thr Ala Ala Gln Ile Thr Ala Ala Ala Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ser
                165                 170                 175

Val Ala Val Gly Lys Met Gln Gln Phe Val Asn Asp Gln Phe Asn Asn
            180                 185                 190

Thr Ala Arg Glu Leu Asp Cys Ile Lys Ile Thr Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Tyr
            260                 265                 270

Pro Ile Leu Tyr Asp Ser Gln Thr Gln Leu Leu Gly Ile Gln Val Asn
        275                 280                 285

Leu Pro Ser Val Gly Asn Leu Asn Asn Met Arg Ala Thr Tyr Leu Glu
    290                 295                 300

Thr Leu Ser Val Ser Thr Ala Lys Gly Tyr Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
```

355 360 365

Ala Cys Met Tyr Ser Lys Thr Glu Gly Ala Leu Thr Thr Pro Tyr Met
370 375 380

Ala Leu Lys Gly Ser Val Ile Ala Asn Cys Lys Ile Thr Thr Cys Arg
385 390 395 400

Cys Thr Asp Pro Pro Gly Ile Ile Ser Gln Asn Tyr Gly Glu Ala Val
405 410 415

Ser Leu Ile Asp Arg His Ser Cys Asn Val Leu Ser Leu Asp Gly Ile
420 425 430

Thr Leu Arg Leu Ser Gly Glu Phe Asp Ala Thr Tyr Gln Lys Asn Ile
435 440 445

Ser Ile Leu Asp Ser Gln Val Ile Val Thr Gly Asn Leu Asp Ile Ser
450 455 460

Thr Glu Leu Gly Asn Val Asn Asn Ser Ile Ser Asn Ala Leu Asp Lys
465 470 475 480

Leu Ala Lys Ser Asn Ser Lys Leu Glu Lys Val Asn Val Arg Leu Thr
485 490 495

Ser Thr Ser Ala Leu Ile Thr Tyr Ile Val Leu Thr Val Ile Ser Leu
500 505 510

Val Phe Gly Ala Leu Ser Leu Gly Leu Thr Cys Tyr Leu Met Tyr Lys
515 520 525

Gln Lys Ala Gln Gln Lys Thr Leu Leu Trp Leu Gly Asn Asn Thr Leu
530 535 540

Asp Gln Met Arg Ala Thr Thr Arg Ala
545 550

<210> SEQ ID NO 55
<211> LENGTH: 622
<212> TYPE: DNA
<213> ORGANISM: artificial sequence
<220> FEATURE:
<223> OTHER INFORMATION: MDV gB promoter

<400> SEQUENCE: 55
cgatgtttag tcacgataga catcggttcg cccagccgtc gaatacagca ttatatttta 60
gtgttgaaaa tgtagggctg cttcctcact taaaggagga aatggctcga ttcatgtttc 120
atagcagtag aaaaacagat tggaccgtca gtaagtttag agggttttat gactttagca 180
ctatagataa tgtaactgcg gcccatcgca tggcttggaa atatatcaaa gaactgattt 240
ttgcaacagc tttattttct tctgtattta aatgtggcga attgcacatc tgtcgtgccg 300
acagtttgca gatcaacagc aatggagact atgtatggaa aaatggaata tatataacat 360
atgaaaccga atatccactt ataatgattc tggggtcaga atcaagcact tcagaaacgc 420
aaaatatgac tgcaattatt gatacagatg ttttttcgtt gctttattct attttgcagt 480
atatggcccc cgttacggca gatcaggtgc gagtagaaca gattaccaac agccacgccc 540
ccatctgacc cgtccaatat tcttgtgtcc ctgcatttta tctcacacaa tttatgaaca 600
gcatcattaa gatcatctca ct 622

<210> SEQ ID NO 56
<211> LENGTH: 4850
<212> TYPE: DNA
<213> ORGANISM: artificial sequence
<220> FEATURE:
<223> OTHER INFORMATION: Partial plasmid HVT SORF3-US2 gpVar-Ewtsyn
sequence for vHVT202

-continued

<400> SEQUENCE: 56

```
taaaatggga tctatcatta cattcgttaa gagtctggat aattttactg tttgccagct     60
tcgatcttgg aacgtactgt ggatagtgcc ttacttggaa tcgtgaaaat ttgaaacgtc    120
cattatttgg atatcttccg gttgtcccat atcccgccct ggtaccgctc ggataccttg    180
cccgtatgga ttcgtattga cagtcgcgca atcggggacc aacaacgcgt gggtccacac    240
tcattcggaa attttccgat gattctgaat atttattgcc gctcgttacg agtcgttgga    300
catatctgta atacatttct tcttctgaag gatcgctgca catttgatct atacattggc    360
caggatgttc aagtctcaga tgttgcattc tggcacagca caactttatg gcatttccga    420
tgtaatcgtc cggcagccct gggggagttc tatattcgca tattgggatg gtaaggacaa    480
tagcagatct cgcaacctcc agggaggcta taataacgtt tttaaaggat ggatttctca    540
taaaaatctg tcgcaaatta cactgagaat atcctttact agcgccgatt gagagcatcg    600
tcgtccaatt ttctaaatgg aaagaaaaca aggcgggcaa gagtgttcca aacattttca    660
ttttcggcga atctctcaaa tcccatggcg tgcaattgat tgcaaaattg gcacttccgt    720
tcacgtttgt atctccaaac tctaagacac ttttaattga aaaactacgt tctagtgtgg    780
aaagaaacct ataggcagac catagaacta tttgacacca catatctttt tgtatgtcaa    840
actgaccatg atcgtatgtt gctgaatgca ctagggcaat tcgctcgcgc gactccatac    900
attgaataat tccacacgtc agctcatcgg ttagcaaggt ccagtagttg aagtcattta    960
tttttccccg cggctggcca aatctacctc tgggaatatc caagttgtcg aatatgatcg   1020
caccggctct ggtcatggtg aaggaacttg tagcataaag acgcaggtat catagggggta   1080
atattttttt attcactcac atactaaaag taacgcatat tagcaccatg tatgggctat   1140
caattgacat ttgcgtagca ctacatcacg attatgtaca acataatggg acaacatatg   1200
cctgcaggtt agtcatatgt tacttggcag aggccgcatg gaaagtccct ggacgtggga   1260
catctgatta atacgtgagg aggtcagcca tgttcttttt ggcaaaggac tacggtcatt   1320
ggacgtttga ttggcatggg atagggtcag ccagagttaa cagtgttctt ttggcaaagg   1380
gatacgtgga aagtcccggg ccatttacag taaactgata cggggacaaa gcacagccat   1440
atttagtcat gtattgcttg gcagagggtc tatggaaagt ccctggacgt gggacgtctg   1500
attaatatga aagaaggtca gccagaggta gctgtgtcct ttttggcaaa gggatacggt   1560
tatgggacgt ttgattggac tgggataggg tcagccagag ttaacagtgt tcttttggca   1620
aaggaaacgt ggaaagtccc gggccattta cagtaaactg atactgggac aaagtacacc   1680
catatttagt catgttcttt ttggcaaaga gcatctggaa agtcccgggc agcattatag   1740
tcacttggca gagggaaagg gtcactcaga gttaagtaca tctttccagg gccaatattc   1800
cagtaaatta cacttagttt tatgcaaatc agccacaaag gggattttcc cggtcaatta   1860
tgactttttc cttagtcatg cggtatccaa ttactgccaa attggcagta catactaggt   1920
gattcactga catttggccg tcctctggaa agtccctgga aaccgctcaa gtactgtatc   1980
atggtgactt tgcatttttg gagagcacgc cccactccac cattggtcca cgtaccctat   2040
gggggagtgg tttatgagta tataaggggc tccggtttag aagccgggca gagcggccgc   2100
atgacaaacc tgcaagatca aacccaacag attgttccgt tcatacggag ccttctgatg   2160
ccaacaaccg gaccggcgtc cattccggac gacaccctgg agaagcacac tctcaggtca   2220
gagacctcga cctacaattt gactgtgggg gacacagggt cagggctaat tgtctttttc   2280
cctggattcc ctggctcaat tgtgggtgct cactacacac tgcagagcaa tgggaactac   2340
```

aagttcgatc agatgctcct gactgcccag aacctaccgg ccagctacaa ctactgcagg 2400
ctagtgagtc ggagtctcac agtaaggtca agcacactcc ctggtggcgt ttatgcacta 2460
aacggcacca taaacgccgt gaccttccaa ggaagcctga gtgaactgac agatgttagc 2520
tacaacgggt tgatgtctgc aacagccaac atcaacgaca aaattgggaa cgtcctagta 2580
ggggaagggg taaccgtcct cagcttaccc acatcatatg atcttgggta tgtgaggctt 2640
ggtgacccca tacccgctat agggcttgac ccaaaaaatgg tagcaacatg tgacagcagt 2700
gacaggccca gagtctacac cataactgca gccgataatt accaattctc atcacagtac 2760
caaacaggtg gggtaacaat cacactgttc tcagccaaca ttgatgccat cacaagtctc 2820
agcgttgggg gagagctcgt gttcaaaaca agcgtccaaa gccttgtact gggcgccacc 2880
atctacctta taggctttga tgggactgcg gtaatcacca gagctgtggc cgcaaacaat 2940
gggctgacgg ccggcatcga caatcttatg ccattcaatc ttgtgattcc aaccaatgag 3000
ataacccagc caatcacatc catcaaactg gagatagtga cctccaaaag tgatggtcag 3060
gcaggggaac agatgtcatg gtcggcaagt gggagcctag cagtgacgat ccatggtggc 3120
aactatccag gagccctccg tcccgtcaca ctagtggcct acgaaagagt ggcaacagga 3180
tctgtcgtta cggtcgctgg ggtgagcaac ttcgagctga tcccaaatcc tgaactagca 3240
aagaacctgg ttacagaata tggccgattt gacccaggag ccatgaacta cacgaaattg 3300
atactgagtg agagggaccg ccttggcatc aagaccgtct ggccaacaag ggagtacact 3360
gactttcgtg agtacttcat ggaggtggcc gacctcaact ctcccctgaa gattgcagga 3420
gcatttggct tcaaagacat aatccgggcc ataaggaggt gagcggccgc gatatcaata 3480
aaatatcttt attttcatta catctgtgtg ttggtttttt gtgtgaatcg atagtactaa 3540
catacgctct ccatcaaaac aaaacgaaac aaaacaaact agcaaaatag gctgtcccca 3600
gtgcaagtgc aggtgccaga acatttctct tctagacctg caggcccggg gcaagtagat 3660
gcaatttcct cacactagtt gggtttatct actattgaat tttcccctat ctgtgataca 3720
cttgggagcc tctacaagca tattgccatc atgtacgttt ttatctactg tcttaacgcc 3780
catgggaacg gaggcgtcgt cgtcatgtat tggacggcaa cataggcagc aacacaaatt 3840
gcgtttaggt ggggtgcatg tggactcgat accaagcccc tgcagctggg gaacgtctgg 3900
tggagagccg ataatttgat atacgcacgc catattactg tcgttgaagt acgccttatc 3960
ttctatgttt tcaaatttag gttcccaagt ggacgtgaga agtgtttgta tctcacatgg 4020
aatggcccaa ggcattccag cccaggtgcc tggtacttta atggcaaaca aacgttttgg 4080
tagaggtatt gattctattg cagttctgca gatatctgca gccccgagta tccacaggct 4140
atacgatacg ttatcggagg cctccgattc tagcattaca tagccggtca gtagatcctg 4200
ccattcggta gcgcaaccgg ctacatcttc aaacagtctc acaataaatg catctctcgt 4260
tcctgccaat ccggaaccgg gcataccact cccgcctgcc gatttaattc tcacaattgg 4320
gcgatgccgg cggggcaaaa cgaatgtgga tttggcaaac cgacacaggt ctgctgtacg 4380
gactaatatg ggcacaccca catcattctt cagatgctcc atgcattgtt ctatgagaaa 4440
gatccatagg gtggaggcag cgtcacgaga tcgcccaggc aatcgatcgc attcgtctag 4500
taaagtgacg agagttatca tgcacacacc catgcccacg ccttccgaat aactggagct 4560
gtggaagatc ggaaacgtct tttgactgc cggtctcgta ctactttcgc acaggtgtat 4620
acccggacgc gtactatata ttttatatca tccaacgtcc cgaaattaca tacgtggcgg 4680
cgatggaagt agatgttgag tcttcgaaag taagtgcctc gaatatgggt attgtctgtg 4740
aaaatatcga aagcggtacg acggttgcag aaccgtcgat gtcgccagat actagtaaca 4800
atagcttcga taacgaagac ttccgtgggc ctgaatacga tgtggagata 4850

<210> SEQ ID NO 57
<211> LENGTH: 4943
<212> TYPE: DNA
<213> ORGANISM: artificial sequence
<220> FEATURE:
<223> OTHER INFORMATION: Partial plasmid SB1US2 gpVIIdwtsyn sequence for vSB1-010

<400> SEQUENCE: 57
tctcgtctaa aacgctccag tgctttacag ttcgataatc tggacctggg gacgcgtata 60
ggatcgttcc tccacatgcg ctgctgtcgg tatctcgaat ccccggtatt cagttgaatc 120
gttggcggag tgtcctcctg gactctgcaa tgttccctag ccgtcttcac tatctcgtgc 180
aaggctctat aatacagttc ctctgcagac ccgtcgttgc tcttcccttc tgcgtcgtta 240
gttatttctg taggctccag acgatttgcc tgcatttgtg cgcaacataa tctgattgca 300
ttccctatct cgtcttccgg taatcccata ggtgttcggt attcgcagat aggtagagaa 360
agcaccactg caaatcgtgc aatttccatt gccccaacca atattttttt taagaacggc 420
atcgccgtta atgtacctcg ggcattgtga cgatcgaaac ccttatggat gcctaaagag 480
agcattgcgg tccagttctc caggtgaaaa gagaatagcg cgggtagaaa cgggccgatt 540
agttttatct tcgccgcgtc cctaatatcc caagttctgc agtataactt ccatcgtccg 600
ttttcgacaa ggtccggcgc gacatagttt gaaatgtcat ctatcagaaa catctcgccc 660
atcgtagaaa aaaacctgta cgcagaccat aaaaccattc ggtaccacat atccttgtgt 720
atatcaaacg atatgttggt tatgtcgttg gcggatgttg tatgaaatag agctaagcgt 780
tctctggatt ccacgcactg aacgattccg ttagtcaatt catctgctaa cataggccaa 840
aagtttattc gtgttacttt tctcggcggt ttggcaaaac gccccccttgg cacatccatg 900 tcattaaata cagcggcata actcctactc atgtgttcca tagcccaggt ttctgttcgg 960
tctgctacta cgatcagatc agtggcgcga tcagatgcgt gggatgaatg aagtgtatcc 1020
gaaagcagtt ttgagatata cgctaaactg tacgacgatt gtggcactaa acgaagcttt 1080
gcgcgacccc catcccacgc cctgcaggtt agtcatatgt tacttggcag aggccgcatg 1140
gaaagtccct ggacgtggga catctgatta atacgtgagg aggtcagcca tgttcttttt 1200
ggcaaaggac tacggtcatt ggacgtttga ttggcatggg atagggtcag ccagagttaa 1260
cagtgttctt ttggcaaagg gatacgtgga aagtcccggg ccatttacag taaactgata 1320
cggggacaaa gcacagccat atttagtcat gtattgcttg gcagagggtc tatggaaagt 1380
ccctggacgt gggacgtctg attaatatga aagaaggtca gccagaggta gctgtgtcct 1440
ttttggcaaa gggatacggt tatgggacgt ttgattggac tgggataggg tcagccagag 1500
ttaacagtgt tcttttggca aaggaaacgt ggaaagtccc gggccattta cagtaaactg 1560
atactgggac aaagtacacc catatttagt catgttcttt ttggcaaaga gcatctggaa 1620
agtcccgggc agcattatag tcacttggca gagggaaagg gtcactcaga gttaagtaca 1680
tctttccagg gccaatattc cagtaaatta cacttagttt tatgcaaatc agccacaaag 1740
gggattttcc cggtcaatta tgactttttc cttagtcatg cggtatccaa ttactgccaa 1800
attggcagta catactaggt gattcactga catttggccg tcctctggaa agtccctgga 1860

-continued

```
aaccgctcaa gtactgtatc atggtgactt tgcatttttg gagagcacgc cccactccac   1920
cattggtcca cgtaccctat gggggagtgg tttatgagta tataaggggc tccggtttag   1980
aagccgggca gagcggccgc atgggctcca aaccttctac caggatccca gcacctctga   2040
tgctgatcac ccggattatg ctgatattgg gctgtatccg tccgacaagc tctcttgacg   2100
gcaggcctct tgcagctgca ggaattgtag taacaggaga taaggcagtc aatgtataca   2160
cttcgtctca gacagggtca atcatagtca agttgctccc gaatatgccc agggataagg   2220
aggcgtgtgc aaaagcccca ttagaggcat ataacagaac actgactact ttgctcactc   2280
ctcttggcga ctccatccgc aagatccaag ggtctgtgtc cacatctgga ggaggcaagc   2340
aaggccgcct gataggtgct gttattggca gtgtagctct tggggttgca acagcggcac   2400
agataacagc agctgcggcc ctaatacaag ccaaccagaa tgccgccaac atcctccggc   2460
ttaaggagag cattgctgca accaatgaag ctgtgcatga agtcaccgac ggattatcac   2520
aactatcagt ggcagttggg aagatgcagc agtttgtcaa tgaccagttt aataatacgg   2580
cgcgagaatt ggactgtata aaaatcacac aacaggttgg tgtagaactc aacctatacc   2640
taactgaatt gactacagta ttcgggccac agatcacctc ccctgcatta actcagctga   2700
ccatccaggc actttataat ttagctggtg gcaatatgga ttacttatta actaagttag   2760
gtatagggaa caatcaactc agctcgttaa ttggtagcgg cctgatcact ggttacccta   2820
tactgtatga ctcacagact caactcttgg gcatacaagt gaatttaccc tcagtcggga   2880
acttaaataa tatgcgtgcc acctatttgg agaccttatc tgtaagtaca accaaaggat   2940
atgcctcagc acttgtcccg aaagtagtga cacaagtcgg ttccgtgata gaagagcttg   3000
acacctcata ctgtatagag tccgatctgg atttatattg tactagaata gtgacattcc   3060
ccatgtcccc aggtatttat tcctgtttga gcggcaacac atcagcttgc atgtattcaa   3120
agactgaagg cgcactcact acgccgtata tggcccttaa aggctcagtt attgccaatt   3180
gtaaaataac aacatgtaga tgtacagacc ctcctggtat catatcgcaa aattatggag   3240
aagctgtatc cctgatagat agacattcgt gcaatgtctt atcattagac gggataactc   3300
taaggctcag tggggaattt gatgcaactt atcaaaagaa catctcaata ctagattctc   3360
aagtcatcgt gacaggcaat cttgatatat caactgaact tggaaacgtc aacaattcaa   3420
tcagcaatgc cttggatagg ttggcagaaa gcaacagcaa gctagaaaaa gtcaatgtca   3480
gactaaccag cacatctgct ctcattacct atattgttct aactgtcatt tctctagttt   3540
tcggtgcact tagtctggtg ttagcgtgtt acctgatgta caaacagaag gcacaacaaa   3600
agaccttgct atggcttggg aataataccc tcgatcagat gagagccact acaagagcat   3660
gagcggccgc gatatcaata aaatatcttt attttcatta catctgtgtg ttggtttttt   3720
gtgtgaatcg atagtactaa catacgctct ccatcaaaac aaaacgaaac aaaacaaact   3780
agcaaaatag gctgtcccca gtgcaagtgc aggtgccaga acatttctct tctagacctg   3840
caggggagtc tgtgcaaggt taatgaccct cgcagttcat tcggaagtta taactgccgc   3900
cttcgcacat ttctttttgt cctgttttgt attgccataa cagataggaa ttgaaacctg   3960
atcctcctgt tttttgcagc atggccagca acagaatact ttgtcggatc gactacttgc   4020
gcgagatggt tccgttcttg gaggtttcgg cgggtcgggt ggagaaccta ttattttata   4080
cacacacgtc ataccgttgt cgcgaaaatg ttctttgtct tctgccgtct cgaacgtcgg   4140
ttcccacgta gacgttagga gcgttggaat ggtatcagga agagcccacg gcatgccgga   4200
ccaagtaccc gctactttga ccgcgagcag tctcttcggt aatgggatgt attccagagc   4260
```

agcgcggcag agatcagcgg cccccactat ccacagactg tatgaagtgt tttctgaaac 4320
atcggactcc aacatcaaat atccagacat aacatcttgc cattcggaag cacatccgcc 4380
gacatcttca aatagcctaa ctataaacga gtctctagtt cctgctaacc cagtacctcg 4440
aatgccagtc ccatccggtg ggttcgtcct gataatcggt ctctgacgcc gaggaagaac 4500
taaaaggggt ctggaaaagc ggaacagatc tgcagaccga acgactacag acacgcccac 4560
atcatcatgt atctgttcca tgcattgctt tatgagaaaa atccataagg ccgaggcggc 4620
atctctagat ctcccgggga gtctctcgca ctcatctagg agagtgacga cagttatcat 4680
agacacgccc atttgtgcac caaacgaaaa gttcctgtac tggtggagcg tcggcgcggg 4740
aatcggtccg tgctctgaaa ccagtgtcta gacagaagac catccggtaa attctggtgt 4800
atgaactgac ggtctccaga cgaacgtcga agacattaac gatggaaact aacgagcttt 4860
cttcaaaagt gtctgattac aacgctaata gaccttacga aactatacgc agcgatacca 4920
gtgacacaga tccgtcggtg tcg 4943

<210> SEQ ID NO 58
<211> LENGTH: 1362
<212> TYPE: DNA
<213> ORGANISM: artificial sequence
<220> FEATURE:
<223> OTHER INFORMATION: IBDV DNA encoding VP2 protein of IBDV E strain

<400> SEQUENCE: 58
atgacaaacc tgcaagatca aacccaacag attgttccgt tcatacggag ccttctgatg 60
ccaacaaccg gaccggcgtc cattccggac gacaccctgg agaagcacac tctcaggtca 120
gagacctcga cctacaattt gactgtgggg gacacagggt cagggctaat tgtctttttc 180
cctggattcc ctggctcaat tgtgggtgct cactacacac tgcagagcaa tgggaactac 240
aagttcgatc agatgctcct gactgcccag aacctaccgg ccagctacaa ctactgcagg 300
ctagtgagtc ggagtctcac agtaaggtca agcacactcc ctggtggcgt ttatgcacta 360
aacggcacca taaacgccgt gaccttccaa ggaagcctga gtgaactgac agatgttagc 420
tacaacgggt tgatgtctgc aacagccaac atcaacgaca aaattgggaa cgtcctagta 480
ggggaagggg taaccgtcct cagcttaccc acatcatatg atcttgggta tgtgaggctt 540
ggtgacccca tacccgctat agggcttgac ccaaaaatgg tagcaacatg tgacagcagt 600
gacaggccca gagtctacac cataactgca gccgataatt accaattctc atcacagtac 660
caaacaggtg gggtaacaat cacactgttc tcagccaaca ttgatgccat cacaagtctc 720
agcgttgggg gagagctcgt gttcaaaaca agcgtccaaa gccttgtact gggcgccacc 780
atctacctta taggctttga tgggactgcg gtaatcacca gagctgtggc cgcaaacaat 840
gggctgacgg ccggcatcga caatcttatg ccattcaatc ttgtgattcc aaccaatgag 900
ataacccagc caatcacatc catcaaactg gagatagtga cctccaaaag tgatggtcag 960
gcaggggaac agatgtcatg gtcggcaagt gggagcctag cagtgacgat ccatggtggc 1020
aactatccag gagccctccg tcccgtcaca ctagtggcct acgaaagagt ggcaacagga 1080
tctgtcgtta cggtcgctgg ggtgagcaac ttcgagctga tcccaaatcc tgaactagca 1140
aagaacctgg ttacagaata tggccgattt gacccaggag ccatgaacta cacgaaattg 1200
atactgagtg agagggaccg ccttggcatc aagaccgtct ggccaacaag ggagtacact 1260
gactttcgtg agtacttcat ggaggtggcc gacctcaact ctcccctgaa gattgcagga 1320

```
gcatttggct tcaaagacat aatccgggcc ataaggaggt ga                    1362


<210> SEQ ID NO 59
<211> LENGTH: 453
<212> TYPE: PRT
<213> ORGANISM: artificial sequence
<220> FEATURE:
<223> OTHER INFORMATION: IBDV VP2 protein of IBDV E strain

<400> SEQUENCE: 59

Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asn Tyr Gln Phe Ser Ser Gln Tyr Gln Thr Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Ser Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asn Asn Gly Leu Thr Ala Gly Ile Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Asp Gly Gln
305                 310                 315                 320

Ala Gly Glu Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
```

```
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg
    450


<210> SEQ ID NO 60
<211> LENGTH: 884
<212> TYPE: DNA
<213> ORGANISM: artificial sequence
<220> FEATURE:
<223> OTHER INFORMATION: Guinea pig CMV promoter

<400> SEQUENCE: 60

ttagtcatat gttacttggc agaggccgca tggaaagtcc ctggacgtgg gacatctgat      60

taatacgtga ggaggtcagc catgttcttt ttggcaaagg actacggtca ttggacgttt     120

gattggcatg ggatagggtc agccagagtt aacagtgttc ttttggcaaa gggatacgtg     180

gaaagtcccg ggccatttac agtaaactga tacggggaca aagcacagcc atatttagtc     240

atgtattgct tggcagaggg tctatggaaa gtccctggac gtgggacgtc tgattaatat     300

gaaagaaggt cagccagagg tagctgtgtc ctttttggca aagggatacg gttatgggac     360

gtttgattgg actgggatag ggtcagccag agttaacagt gttcttttgg caaaggaaac     420

gtggaaagtc ccgggccatt tacagtaaac tgatactggg acaaagtaca cccatattta     480

gtcatgttct tttggcaaa gagcatctgg aaagtcccgg gcagcattat agtcacttgg      540

cagagggaaa gggtcactca gagttaagta catctttcca gggccaatat tccagtaaat     600

tacacttagt tttatgcaaa tcagccacaa aggggatttt cccggtcaat tatgactttt     660

tccttagtca tgcggtatcc aattactgcc aaattggcag tacatactag gtgattcact     720

gacatttggc cgtcctctgg aaagtccctg gaaaccgctc aagtactgta tcatggtgac     780

tttgcatttt tggagagcac gccccactcc accattggtc cacgtaccct atgggggagt     840

ggtttatgag tatataaggg gctccggttt agaagccggg caga                      884


<210> SEQ ID NO 61
<211> LENGTH: 30
<212> TYPE: DNA
<213> ORGANISM: artificial sequence
<220> FEATURE:
<223> OTHER INFORMATION: primer HM101

<400> SEQUENCE: 61

ccggaattcc gatgtttagt cacgatagac                                      30


<210> SEQ ID NO 62
<211> LENGTH: 35
<212> TYPE: DNA
<213> ORGANISM: artificial sequence
<220> FEATURE:
<223> OTHER INFORMATION: Primer HM102
```

-continued

```
<400> SEQUENCE: 62

ataagagcgg ccgcagtgag atgatcttaa tgatg                      35


<210> SEQ ID NO 63
<211> LENGTH: 38
<212> TYPE: DNA
<213> ORGANISM: artificial sequence
<220> FEATURE:
<223> OTHER INFORMATION: primer F-ATG

<400> SEQUENCE: 63

tatagcggcc gcaagatggg ctccagatct tctaccag                   38


<210> SEQ ID NO 64
<211> LENGTH: 34
<212> TYPE: DNA
<213> ORGANISM: artificial sequence
<220> FEATURE:
<223> OTHER INFORMATION: Primer F-STOP

<400> SEQUENCE: 64

cgaggcggcc gctcatattt ttgtagtggc tctc                       34
```

RECOMBINANT GALLID HERPESVIRUS 3 (MDV SEROTYPE 2) VECTORS EXPRESSING ANTIGENS OF AVIAN PATHOGENS AND USES THEREOF

CROSS-REFERENCE TO RELATED APPLICATIONS

This application claims priority to U.S. provisional application 61/564,877 filed on Nov. 30, 2011 and U.S. provisional application 61/694,957 filed on Aug. 30, 2012.

FIELD OF THE INVENTION

The invention relates to recombinant viral vectors for the insertion and expression of foreign genes for use as safe immunization vehicles to protect against a variety of pathogens. It also relates to multivalent composition or vaccine comprising one or more recombinant viral vectors for protection against a variety of pathogens. The present invention relates to methods of making and using the recombinant viral vectors.

BACKGROUND OF THE INVENTION

Poultry vaccination is widely used to protect poultry flocks against devastating diseases including Newcastle disease (ND), infectious bursal disease (IBD), Marek's disease (MD), infectious bronchitis (IB), infectious laryngotracheitis (ILT) and avian influenza (AI). ND is caused by the avian paramyxovirus 1 (APMV-1) also designated ND virus (NDV) belonging to the Paramyxoviridae family. MD is caused by Gallid herpesvirus 2 (Herpesviridae family) also designated as MD virus serotype 1 (MDV1). IB is caused by IB virus (IBV) belonging to the Coronaviridae family, ILT is caused by Gallid herpesvirus 1 (Herpesviridae family) also designated ILT virus (ILTV) and AI is caused by AI virus (AIV) belonging to the Orthomyxoviridae family.

A number of recombinant avian viral vectors have been proposed with a view to vaccinating birds against these avian pathogens. The viral vectors used comprise avipox viruses, especially fowlpox (EP-A-0,517,292), Marek's virus, such as serotypes 2 and 3 (HVT) (WO-A-87/04463), or alternatively the ITLV, NDV and avian adenovirus. When some of these recombinant avian viral vectors were used for vaccination, they display variable levels of protection.

Several recombinant herpesvirus of turkeys (HVT, also designated Meleagrid herpesvirus 1 or MDV serotype 3) vectors expressing antigens from various pathogens (U.S. Pat. Nos. 5,980,906, 5,853,733, 6,183,753, 5,187,087) including IBDV, NDV, ILTV and AIV have been developed and licensed. Of particular interest is a HVT vector-expressing IBDV VP2 protective gene that has shown clear advantages over classical IBD vaccines (Bublot et al J. Comp. Path. 2007, Vol. 137, S81-S84). Other HVT vectors of interest are those expressing either NDV (Morgan et al 1992, Avian dis. 36, 858-70) or ILTV (Johnson et al, 2010 Avian Dis 54, 1251-1259) protective gene(s). One of the practical problems of using several HVT-based recombinant vaccines together is their interference. Lower protection is induced at least against one of the disease when two HVT recombinants expressing different antigens are mixed (Rudolf Heine 2011; Issues of the Poultry Recombinant Viral Vector Vaccines which May Cause an Effect on the Economic Benefits of those Vaccines; paper presented at the XVII World Veterinary Poultry Association (WVPA) Congress in Cancun, Mexico, Aug. 14-18, 2011; Slacum G, Hein R. and Lynch P., 2009, The compatibility of HVT recombinants with other Marek's disease vaccines, 58$^{th}$ Western Poultry Disease Conference, Sacramento, Calif., USA, March 23-25, p 84).

The combination of HVT and SB-1, a Gallid herpesvirus 3 (MDV serotype 2 or MDV-2) vaccine strain, has shown a synergistic effect on MD protection (Witter and Lee, 1984, Avian Pathology 13, 75-92). To address the interference problem, it is of interest to evaluate the SB-1 virus as a vaccine vector to express protective antigen(s) that could be compatible with HVT vector and improve MD protection.

The SB-1 genome was cloned and characterized in bacterial artificial chromosome (BAC) (Petherbridge, et al., J. Virol. Methods 158, 11-17, 2009; Singh et al., Research in Veterinary Science 89, 140-145, 2010). The MDV2 SB-1 sequence was recently obtained and analyzed (Spatz and Schat, Virus Gene 42, 331-338, 2011). A glycoprotein E deletion of SB-1 virus was described by Petherbridge et al. (J. Virol. Methods 158, 11-17, 2009). However, no research has been reported using SB-1 as a viral vector expressing foreign protective genes.

It has been shown that both $U_L$13 protein kinase and glycoprotein C ($U_L$44) genes individually are essential for horizontal transmission of MDV in chickens (Jarosinski, et al., J. of Virology 81, 10575-10587, 2007; Jarosinski, et al., J. of Virology 84, 7911-7916, 2010).

Considering the potential effect of animal pathogens, such as NDV and IBDV on veterinary public health and the economy, efficient methods of preventing infection and protecting animals are needed. There is a need for a solution of combined effective vector vaccines and a suitable method for making the vaccine that could alleviate the problem of interference observed between 2 HVT-based vector vaccines.

SUMMARY OF THE INVENTION

The present invention demonstrated for the first time a recombinant Gallid Herpesvirus-3 (MDV-2) viral vector protecting against a poultry pathogen beyond Marek's disease virus.

The present invention showed surprising result when multivalent vaccines were used to protect animals against a variety of avian pathogens.

The present invention relates to a recombinant Gallid Herpesvirus-3 (MDV-2) vector comprising one or more heterologous polynucleotides coding for and expressing at least one antigen of an avian pathogen. The present invention further relates to a recombinant Gallid Herpesvirus-3 (MDV-2) vector comprising a mutated glycoprotein C (gC) gene.

The present invention provides a composition or vaccine comprising one or more recombinant Gallid Herpesvirus-3 (MDV-2) vectors comprising one or more heterologous polynucleotides coding for and expressing at least one antigen of an avian pathogen. The present invention further provides a composition for vaccine comprising one or more Gallid Herpesvirus-3 (MDV-2) vectors comprising a mutated glycoprotein C (gC) gene.

The present invention provides a polyvalent composition or vaccine comprising: i) a recombinant Gallid Herpesvirus-3 (MDV-2) vector comprising heterologous polynucleotides coding for and expressing at least one antigen of an avian pathogen, or comprising a mutated glycoprotein C (gC) gene; and ii) at least one of: a recombinant HVT vector (or MDV-3 or Meleagrid herpesvirus-1) comprising heterologous polynucleotides coding for and expressing at least one antigen of an avian pathogen; or wild type HVT (MDV-3); or recombinant MDV serotype 1 vector (i.e., MDV-1, Gallid herpesvirus-2) comprising heterologous polynucleotides coding for and expressing at least one antigen of an avian pathogen; or any wild type MDV-1.

The present invention relates to a method of vaccinating an animal, or inducing an immunogenic or protective response in an animal, comprising at least one administration of the composition or vector of the present invention.

The present invention further provides specific insertion loci for the introduction of one or more isolated polynucleotide into nonessential regions of the SB-1 genome.

BRIEF DESCRIPTION OF THE DRAWINGS

The following detailed description, given by way of example, and which is not intended to limit the invention to specific embodiments described, may be understood in conjunction with the accompanying figures, incorporated herein by reference, in which:

FIG. 1 is a table showing the SEQ ID NO assigned to each DNA and protein sequence.

FIG. 8 shows the PCR results of vSB1-006.

FIG. 14 shows the PCR results of vSB1-008.

FIG. 17 depicts the clinical analysis (percentage of birds shedding challenge virus) of the recombinants against CA02 and ZJ1 NDV challenge.

FIG. 18 depicts the clinical analysis (oropharyngeal shedding) of the recombinants against NDV challenge.

FIGS. 19A-19F depict the DNA sequence alignment of NDV-F genes. FIG. 19G shows the sequence identity percentage.

FIGS. 20A-20B depict the DNA sequence alignment between SEQ ID NO:3 and SEQ ID NO:4 (AY337464.1) highlighting the differences at nucleotide level. FIGS. 21A-21C depict protein sequence alignment of NDV-F and the sequence identity percentage. FIG. 22 depicts the protein sequence alignment of IBDV VP2 and the sequence identity percentage. FIGS. 23A-23C depict DNA sequence alignment of IBDV VP2 genes and the sequence identity percentage. FIG. 24 depicts the protein sequence alignment between SEQ ID NO:2 and SEQ ID NO:5 (AAP97877.1) highlighting the differences at amino acid level. FIG. 25 depicts the protein sequence alignment between SEQ ID NO:2 and SEQ ID NO:9 highlighting the differences at amino acid level.

DETAILED DESCRIPTION OF THE INVENTION

Figure 2:
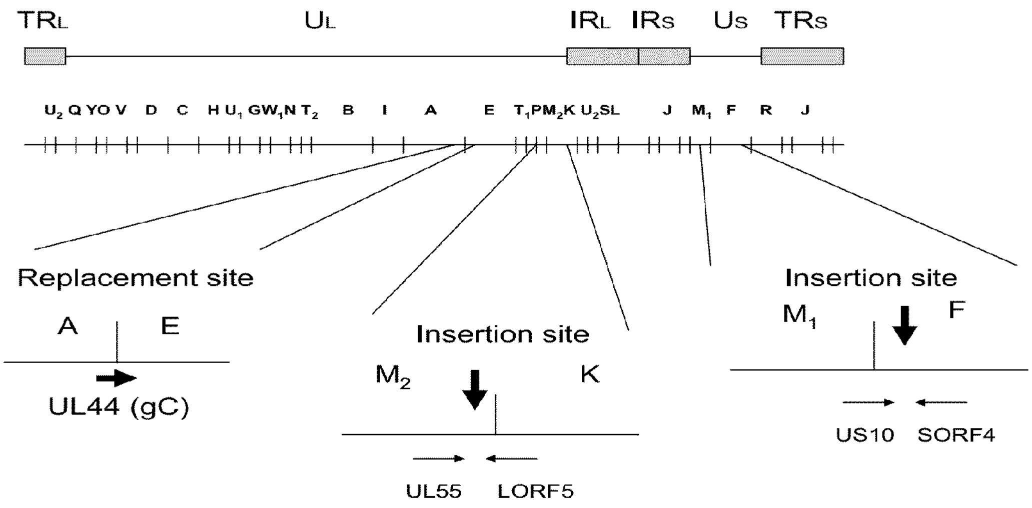
FIG. 2 depicts a schematic diagram of SB-1 genome organization.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise noted, technical terms are used according to conventional usage. Definitions of common terms in molecular biology may be found in Benjamin Lewin, Genes V. published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle), porcine (e.g., pig), ovine (e.g., sheep, goats, lamas, bisons), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "animal" also includes an individual animal in all stages of development, including embryonic and fetal stages.

The terms "polypeptide" and "protein" are used interchangeably herein to refer to a polymer of consecutive amino acid residues.

The term "nucleic acid", "nucleotide", and "polynucleotide" are used interchangeably and refer to RNA, DNA, cDNA, or cRNA and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "genomic DNA", or "genome" is used interchangeably and refers to the heritable genetic information of a host organism. The genomic DNA comprises the DNA of the nucleus (also referred to as chromosomal DNA) but also the DNA of the plastids (e.g., chloroplasts) and other cellular organelles (e.g., mitochondria). The genomic DNA or genome contemplated in the present invention also refers to the RNA of a virus. The RNA may be a positive strand or a negative strand RNA. The term "genomic DNA" contemplated in the present invention includes the genomic DNA containing sequences complementary to those described herein. The term "genomic DNA" also refers to messenger RNA (mRNA), complementary DNA (cDNA), and complementary RNA (cRNA).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al.; Pandher K et al.; Chung J Y et al.), transcription terminators (in general the terminator is located within approximately 50 nucleotides downstream of the stop codon of the coding sequence or gene; Ward C K et al.). Gene or polynucleotide also refers to a nucleic acid fragment that expresses mRNA or functional RNA, or encodes a specific protein, and which includes regulatory sequences.

The term "heterologous DNA" as used herein refers to the DNA derived from a different organism, such as a different cell type or a different species from the recipient. The term also refers to a DNA or fragment thereof on the same genome of the host DNA wherein the heterologous DNA is inserted into a region of the genome which is different from its original location.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

The term "immunogenic protein or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "recombinant" and "genetically modified" are used interchangeably and refer to any modification, alteration or engineering of a polynucleotide or protein in its native form or structure, or any modification, alteration or engineering of a polynucleotide or protein in its native environment or surrounding. The modification, alteration or engineering of a polynucleotide or protein may include, but is not limited to, deletion of one or more nucleotides or amino acids, deletion of an entire gene, codon-optimization of a gene, conservative substitution of amino acids, insertion of one or more heterologous polynucleotides.

The terms "polyvalent vaccine or composition", "combination or combo vaccine or composition" and "multivalent vaccine or composition" are used interchangeably to refer to a composition or vaccine containing more than one composition or vaccines. The polyvalent vaccine or composition may contain two, three, four or more compositions or vaccines. The polyvalent vaccine or composition may comprise recombinant viral vectors, active or attenuated or killed wild-type viruses, or a mixture of recombinant viral vectors and wild-type viruses in active or attenuated or killed forms.

One embodiment of the present invention provides a recombinant Gallid herpesvirus 3 (MDV-2) vector that comprises a mutated Glycoprotein C (gC or UL44) gene. The term "mutated gC gene" refers to the gC gene of Gallid herpesvirus 3 (MDV-2) that is altered or engineered which results in a non-functional gC protein upon expression. The alteration or engineering of the gC gene includes mutation or deletion of a segment of the gC gene which is essential for the expression of a functional gC protein. The term "mutated gC gene" also includes deletion of the entire gC gene of Gallid herpesvirus 3 (MDV-2) wherein gC protein is not expressed. Another embodiment of the present invention provides a recombinant Gallid herpesvirus 3 (MDV-2) wherein the Glycoprotein C (gC) gene in the native (wild-type) Gallid herpesvirus 3 (MDV-2) genome encoding the gC protein is deleted. The term "Glycoprotein C (gC) gene" includes any gene or polynucleotide that encodes the Glycoprotein C (gC) of Gallid herpesvirus 3 (MDV-2), and homologs, fragments or variants thereof. The gC gene may encode a gC protein having at least 75%, 80%, 85%, 90%, 95%, 95%, 96%, 97%, 98%, 99%, 99.1%, 99.2%, 99.3%, 99.4%, 99.5%, 99.6%, 99.7%, 99.8% or 99.9% sequence identity to SEQ ID NO: 35, or a variant thereof. The gC gene having at least 75%, 80%, 85%, 90%, 95%, 95%, 96%, 97%, 98%, 99%, 99.1%, 99.2%, 99.3%, 99.4%, 99.5%, 99.6%, 99.7%, 99.8% or 99.9% sequence identity to SEQ ID NO:34 is also encompassed in the present invention.

Another embodiment of the invention provides a recombinant Gallid herpesvirus 3 (MDV-2) viral vector comprising one or more heterologous polynucleotides coding for and expressing at least one antigen or polypeptide of an avian pathogen. The Gallid herpesvirus 3 (MDV-2) strains used for the recombinant viral vector may be any SB-1 strains, including, but not limited to, the commercial Marek's Disease Vaccine (SB-1 vaccine) (Merial Select Inc., Gainesville, Ga. 30503, USA), the SB-1 strain having the genome sequence as defined by GenBank Accession Number HQ840738.1. The Gallid herpesvirus 3 (MDV-2) strains used for the recombinant viral vector may be any other Gallid herpesvirus 3 isolate including the HPRS24 strain having the genome sequence as defined by GenBank Accession Number AB049735.1, or the HPRS24 strain having the genome sequence as defined by GenBank Accession Number NC_002577.1. The genomes of HPRS24 and SB-1 share 98.4% sequence identity (Spatz and Schat, 2011; Virus Gene 42, 331-338). The Gallid herpesvirus 3 (MDV-2) strains used for the recombinant viral vector may be the 301B/1 isolate described by Witter (1987 Avian Dis 31, 752-765) or by Witter et al. (1987 Avian Dis 31, 829-840). The Gallid herpesvirus 3 (MDV-2) strains may be any Gallid herpesvirus 3 (MDV-2) strains comprising the genome sequence having at least 90%, 91%, 92%, 93%, 94%, 95%, 96%, 97%, 98%, or 99% sequence identity to the sequence as defined in GenBank Accession Number HQ840738.1 (SEQ ID NO:14), AB049735.1, or NC_002577.1.

The genes coding for antigen or polypeptide may be those coding for Newcastle Disease Virus fusion protein (NDV-F), Newcastle Disease Virus hemagglutinin neuraminidase (NDV-HN), Marek's Disease Virus glycoprotein C (gC), Marek's Disease Virus glycoprotein B (gB), Marek's Disease Virus glycoprotein E (gE), Marek's Disease Virus glycoprotein I (gI), Marek's Disease Virus glycoprotein H (gH) or Marek's Disease Virus glycoprotein L (gL), IBDV VP2, IBDV VPX, IBDV VP3, IBDV VP4, ILTV glycoprotein B, ILTV glycoprotein I, ILTV UL32, ILTV glycoprotein D, ILTV glycoprotein E, ILTV glycoprotein C, influenza hemagglutinin (HA), influenza neuraminidase (NA), protective genes derived from *Mycoplasma gallisepticum* (MG), or *Mycoplasma* synoviae (MS), or combinations thereof. The antigen or polypeptide may be any antigen from the poultry pathogen selected form the group consisting of avian encephalomyelitis virus, avian reovirus, avian paramyxovirus, avian metapneumovirus, avian influenza virus, avian adenovirus, fowl pox virus, avian coronavirus, avian rotavirus, chick anemia virus, avian astrovirus, avian parvovirus, coccidiosis (*Eimeria* sp.), *Campylobacter* sp., *Salmonella* sp., *Pasteurella* sp., *Avibacterium* sp., *Mycoplasma gallisepticum, Mycoplasma synoviae, Clostridium* sp., and *E. coli.*

Moreover, homologs of aforementioned antigen or polynucleotides are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type polypeptide can differ from the wild-type polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the polynucleotide or polypeptide sequences of antigens described above, and will exhibit a similar function.

In one embodiment, the present invention provides a recombinant Gallid Herpesvirus-3 (MDV-2) viral vector comprising one, two or more heterologous polynucleotides coding for and expressing the NDV-F antigen or polypeptide. In one aspect of the embodiment, the NDV-F antigen or polypeptide has at least 70%, 75%, 80%, 85%, 90%, 95%, 96%, 97%, 98% or 99% sequence identity to a polypeptide having the sequence as set forth in SEQ ID NO:2, 9, 50, 52, or 54, or a conservative variant, an allelic variant, a homolog or an immunogenic fragment comprising at least eight or at east ten consecutive amino acids of one of these polypeptides, or a combination of these polypeptides. In another aspect of the embodiment, the heterologous polynucleotide encoding an NDV-F antigen or polypeptide has at least 70%, 75%, 80%, 85%, 90%, 95%, 96%, 97%, 98% or 99% sequence identity to a polypeptide having the sequence as set forth in SEQ ID NO:2, 9, 50, 52, or 54. In yet another aspect of the embodiment, the heterologous polynucleotide has at least 70%, 75%, 80%, 85%, 90%, 95%, 96%, 97%, 98% or 99% sequence identity to a polynucleotide having the sequence as set forth in SEQ ID NO:1, 8, 49, 51, or 53.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

The term "identity" with respect to sequences can refer to, for example, the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman). The sequence identity or sequence similarity of two amino acid sequences, or the sequence identity between two nucleotide sequences can be determined using Vector NTI software package (Invitrogen, 1600 Faraday Ave., Carlsbad, Calif.). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for NDV-F polypeptides, the DNA sequence of the NDV-F protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of NDV F protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the NDV-F polypeptide encoded by the nucleotide sequence is functionally unchanged.

In another embodiment, the present invention provides a method for producing a recombinant Gallid Herpesvirus-3 or SB-1 viral vector comprising the introduction into the SB-1 genome of one, two or more isolated polynucleotides in a nonessential region of the SB-1 genome. In yet another embodiment, the present invention provides a method for producing a recombinant Gallid Herpesvirus-3 or SB-1 viral vector comprising the steps of altering, engineering, or deleting the gC gene from the SB-1 genome. The term "nonessential region" refers to a region of a virus genome which is not essential for replication and propagation of the virus in tissue culture or in chickens. Any nonessential region or portion thereof can be deleted from the SB-1 genome or a foreign sequence can be inserted in it, and the viability and stability of the recombinant Gallid Herpesvirus-3 or SB-1 vector resulting from the deletion or insertion can be used to ascertain whether a deleted region or portion thereof is indeed nonessential. In one aspect of the embodiment, the non-essential regions are located in the unique long (UL) and unique short (US) regions of the SB-1 genome (see Spatz et al., Virus Genes 42:331-338, 2011). The UL region of SB-1 is about 109,744 bp to about 109,932 bp in length and may extend from positions 12,209 to 121,952 of SEQ ID NO:14 (GenBank accession No, HQ840738.1) or equivalent positions of other SB1-genomes, for example, from 11,826 bp to 121,757 bp of HPRS24 genome. The US region of SB-1 is about 12,109 bp to about 12,910 bp in length and may extend from positions 143,514 to 156,423 of SEQ ID NO:14 (GenBank accession No, HQ840738.1) or equivalent positions of other SB1-genomes, for example from 142,681 bp to 154,789 bp of HPRS24 genome (Spatz et al., 2011). In one aspect of the embodiment, the non-essential region is between ORF of UL55 and ORF of LORF5 in the unique long (UL) region of SB-1. In another aspect, the polynucleotide is inserted into or to replace SB-1 glycoprotein C gene (also designated UL44). The use of the gC locus may allow the generation of recombinant virus unable to produce a functional gC protein and unable to be transmitted horizontally. In yet another embodiment, the nonessential region may be in the intergenic regions between UL7 and UL8, between UL 21 and UL22, between UL40 and UL41, between UL50 and UL51, between UL54 and LORF4, between US10 and SORF4, or within the UL43, US2, US10 or US6 (coding for gD) gene (see GenBank accession No, HQ840738.1). In yet another embodiment, the nonessential regions may be in the region of nucleotide positions 118057-118306 (intergenic UL55-LORF5), 98595-100031 (gC or UL44), 25983-26038 (intergenic UL7-UL8), 49865-50033 (intergenic UL21-UL22), 75880-75948 (intergenic UL35-UL36), 93928-93990 (intergenic UL40-UL41), 109777-109847 (intergenic UL50-UL51), 116466-116571 (intergenic UL54-LORF4), 146548-146697 (intergenic US10-SORF4), 97141-98385 (UL43), 147857-148672 (US2), 145853.146548 (US10) or 150322-151479 (gD or US6) of SEQ ID NO:14.

Construction of recombinant virus is well known in the art as described in, e.g., U.S. Pat. Nos. 4,769,330, 4,722,848, 4,603, 112, 5,174, 993, and 5,756,103, 6,719,979. Specifically, a recombinant Gallid Herpesvirus-3 (MDV-2) viral vector may be constructed in two steps. First, the Gallid Herpesvirus-3 (MDV-2) or SB-1 genomic regions flanking the locus of insertion are cloned into an *E. coli* plasmid construct; unique(s) restriction site(s) is (are) placed between the two flanking regions (insertion plasmid) in order to allow the insertion of the donor expression cassette DNA. Separately, the cDNA or DNA gene sequence to be inserted is preceded by a promoter region (gene start region) and a terminator (or poly-adenylation, polyA) sequence which is specific for the Gallid Herpesvirus-3 (MDV-2) or SB-1 vector and/or eukaryotic cells. The whole expression cassette (promoter-foreign gene-poly-A) is then cloned into the unique(s) restriction site(s) of the insertion plasmid to construct the "donor plasmid" which contains the expression cassette flanked by Gallid Herpesvirus-3 (MDV-2) or SB-1 "arms" flanking the insertion locus. The resulting donor plasmid construct is then amplified by growth within *E. coli* bacteria and plasmid DNA is extracted. This plasmid is then linearized using a restriction enzyme that cut the plasmid backbone (outside the Gallid Herpesvirus-3 (MDV-2) or SB-1 arms and expression cassette). Chicken embryo fibroblasts are then co-transfected with parental Gallid Herpesvirus-3 (MDV-2) or SB-1 DNA and linearized donor plasmid DNA. The resulting virus population is then cloned by multiple limiting dilution steps where viruses expressing the foreign gene are isolated from the non-expressing viral population. Similarly, another foreign cassette can be inserted in another locus of insertion to create a double Gallid Herpesvirus-3 (MDV-2) or SB-1 recombinant expressing two genes. The second cassette can also be inserted into the same locus. The Gallid Herpesvirus-3 (MDV-2) or SB-1 recombinant is produced in primary chicken embryo fibroblasts similarly to the parental Gallid Herpesvirus-3 (MDV-2) or SB-1 MD vaccine. After incubation, infected cells are harvested, mixed with a freezing medium allowing survival of infected cells, and frozen usually in cryovial or glass ampoules and stored in liquid nitrogen.

Successful expression of the inserted cDNA genetic sequence by the modified infectious virus requires two conditions. First, the insertion must be introduced into a region of the genome of the virus in order that the modified virus remains viable. The second condition for expression of inserted cDNA is the presence of a regulatory sequences allowing expression of the gene in the viral background (for instance: promoter, enhancer, donor and acceptor splicing sites and intron, Kozak translation initiation consensus sequence, polyadenylation signals, untranslated sequence elements).

In general, it is advantageous to employ a strong promoter functional in eukaryotic cells. The promoters include, but are not limited to, an immediate early cytomegalovirus (CMV) promoter, guinea pig CMV promoter, an SV40 promoter, Pseudorabies Virus promoters such as that of glycoprotein X promoter, Herpes Simplex Virus-1 such as the alpha 4 promoter, Marek's Disease Viruses (including MDV-1, MDV-2 and HVT) promoters such as those driving glycoproteins gC, gB, gE, or gI expression, Infectious Laryngotracheitis Virus promoters such as those of glycoprotein gB, gE, gI, gD genes, or other herpesvirus promoters. When the insertion locus consists of a SB-1 gene (for instance, gC, gD, US2 or US10 genes), the foreign gene can be inserted into the vector with no additional promoter sequence since the promoter of the deleted gene of the vector will drive the transcription of the inserted foreign gene.

In one embodiment, the present invention relates to a pharmaceutical composition or vaccine comprising one or more recombinant Gallid Herpesvirus-3 (MDV-2) rival vectors of the present invention and a pharmaceutically or veterinarily acceptable carrier, excipient, vehicle or adjuvant. The Gallid herpesvirus 3 (MDV-2) strains used for the recombinant Gallid Herpesvirus-3 viral vector may be any SB-1 strains, the HPSR24 strains, or the 301B/1 strains. The Gallid Herpesvirus-3 (MDV-2) strains may also include those described in Witter et al (Avian Diseases 34, 944-957; 1990), Witter (Avian Pathology 21, 601-614, 1992) and Witter (Avian Pathology 24, 665-678, 1995): 280-5/1, 281MI/1, 287C/1, 298B/1, 301A/1, 401/1, 437A/1, 437B/1, 468A/1, 468A/2, 468B/1, 471B/1, or HN-1/1.

In another embodiment, the present invention provides a composition or vaccine comprising: i) a recombinant Gallid Herpesvirus-3 vector (MDV-2) comprising heterologous polynucleotides coding for and expressing at least one antigen of an avian pathogen; and ii) at least one of: a recombinant HVT vector (or MDV-3 or Meleagrid Herpesvirus-1) comprising heterologous polynucleotides coding for and expressing at least one antigen of an avian pathogen; or wild type MDV-3; or recombinant MDV-1 vector (or Gallid herpesvirus-2) comprising heterologous polynucleotides coding for and expressing at least one antigen of an avian pathogen; or wild type MDV-1. The composition or vaccine may further comprise a pharmaceutically or veterinarily acceptable carrier, excipient, vehicle or adjuvant. This composition may further contain a recombinant fowlpox vector comprising heterologous polynucleotides coding for and expressing at least one antigen of an avian pathogen; or wild type fowlpox.

In one aspect of the embodiment, the composition or vaccine comprises one (or more) recombinant Gallid Herpesvirus-3 (MDV-2) vectors and one or more wild type HVT (MDV-3). In another aspect, the composition or vaccine comprises one (or more) recombinant Gallid Herpesvirus-3 (MDV-2) vectors and one or more recombinant HVT (MDV-3). In another aspect, the composition or vaccine comprises one or more recombinant Gallid Herpesvirus-3 (MDV-2) vectors and one or more wild type or genetically modified MDV-1. In another aspect, the composition or vaccine comprises one or more recombinant Gallid Herpesvirus-3 (MDV-2) vectors and one or more recombinant MDV-1. In another aspect, the composition or vaccine comprises one or more recombinant Gallid Herpesvirus-3 (MDV-2) vectors, one or more wild type HVT (MDV-3) and one or more wild type MDV-1. In another aspect, the composition or vaccine comprises one or more recombinant Gallid Herpesvirus-3 (MDV-2) vectors, one or more recombinant HVT (MDV-3) and one or more wild type MDV-1. In another aspect, the composition or vaccine comprises one or more recombinant Gallid Herpesvirus-3 (MDV-2) vectors, one or more wild type HVT (MDV-3) and one or more recombinant MDV-1. In yet another aspect, the composition or vaccine comprises one or more recombinant Gallid Herpesvirus-3 (MDV-2) vectors, one or more recombinant HVT (MDV-3) and one or more recombinant MDV-1. The wild type HVT (MDV-3) or wild type MDV-1 may be live, attenuated or genetically modified. The heterologous polynucleotides in recombinant Gallid Herpesvirus-3 (MDV-2) vectors, recombinant HVT (MDV-3) vectors, and recombinant MDV-1 vectors may encode same or different antigens from the same or different avian pathogens.

The pharmaceutically or veterinarily acceptable carriers or adjuvant or vehicles or excipients are well known to the one skilled in the art. For example, a pharmaceutically or veterinarily acceptable carrier or adjuvant or vehicle or excipient can be Marek's disease vaccine diluent used for MD vaccines. Other pharmaceutically or veterinarily acceptable carrier or adjuvant or vehicle or excipients that can be used for methods of this invention include, but are not limited to, 0.9% NaCl (e.g., saline) solution or a phosphate buffer, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro), or facilitating transfection or infection and/or improve preservation of the vector (or protein). Doses and dose volumes are herein discussed in the general description and can also be determined by the skilled artisan from this disclosure read in conjunction with the knowledge in the art, without any undue experimentation.

Optionally other compounds may be added as pharmaceutically or veterinarily acceptable carriers or adjuvant or vehicles or excipients, including, but not limited to, alum; CpG oligonucleotides (ODN), in particular ODN 2006, 2007, 2059, or 2135 (Pontarollo R. A. et al., *Vet. Immunol. Immunopath,* 2002, 84: 43-59; Wernette C. M. et al., *Vet. Immunol. Immunopath,* 2002, 84: 223-236; Mutwiri G. et al., *Vet. Immunol. Immunopath,* 2003, 91: 89-103); polyA-polyU, dimethyldioctadecylammonium bromide (DDA) ("Vaccine Design The Subunit and Adjuvant Approach", edited by Michael F. Powell and Mark J. Newman, *Pharmaceutical Biotechnology,* 6: p. 03, p. 157); N,N-dioctadecyl-N',N'-bis (2-hydroxyethyl) propanediamine (such as AVRIDINE®) (Ibid, p. 148); carbomer, chitosan (see U.S. Pat. No. 5,980, 912 for example).

The pharmaceutical compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

Another aspect of the invention relates to a method for inducing an immunological response in an animal against one or more antigens or a protective response in an animal against one or more avian pathogens, which method comprises inoculating the animal at least once with the vaccine or pharmaceutical composition of the present invention. Yet another aspect of the invention relates to a method for inducing an immunological response in an animal to one or more antigens or a protective response in an animal against one or more avian pathogens in a prime-boost administration regimen, which is comprised of at least one primary administration and at least one booster administration using at least one common polypeptide, antigen, epitope or immunogen. The immunological composition or vaccine used in primary administration may be same, may be different in nature from those used as a booster.

The avian pathogens may be Newcastle Disease Virus (NDV), Infectious Bursal Disease Virus (i.e., IBDV or Gumboro Disease virus), Marek's Disease Virus (MDV), Infectious Laryngotracheitis Virus (ILTV), avian encephalomyelitis virus and other picornavirus, avian reovirus, avian paramyxovirus, avian metapneumovirus, avian influenza virus, avian adenovirus, fowl pox virus, avian coronavirus, avian rotavirus, avian parvovirus, avian astrovirus and chick anemia virus, coccidiosis (*Eimeria* sp.), *Campylobacter* sp., *Salmonella* sp., *Mycoplasma gallisepticum, Mycoplasma synoviae, Pasteurella* sp., *Avibacterium* sp., *E. coli* or *Clostridium* sp.

Usually, one administration of the vaccine is performed either at one day-of-age by the subcutaneous or intramuscular route or in ovo in 17-19 day-old embryo. A second administration can be done within the first 10 days of age. The animals are preferably at least 17-day-embryo or one day old at the time of the first administration.

A variety of administration routes in day-old chicks may be used such as subcutaneously or intramuscularly, intradermally, transdermally. The in ovo vaccination can be performed in the amniotic sac and/or the embryo. Commercially available in ovo and SC administration devices can be used for vaccination.

The invention will now be further described by way of the following non-limiting examples.

EXAMPLES

Construction of DNA inserts, plasmids and recombinant viral vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989).

Example 1

Construction of Recombinant vSB1-004 Expressing NDV-F

The aim of the work is to construct a recombinant SB-1 virus in which an expression cassette containing mouse cytomegalovirus (mCMV) promoter, Newcastle disease virus fusion protein (NDV-F), and Simian virus 40 (SV40) poly A tail is inserted into the intergenic site between US10 and SORF4 site of SB-1 virus (Table 1 and FIG. 2).

TABLE 1

Characteristics of vSB1-004

| Name | Parental virus | Promoter | gene | Poly-A | Locus |
|---|---|---|---|---|---|
| vSB1-004 | SB-1* | mCMV IE | Wt-NDV-F of VIId | SV40 | SORF4/US10 |

SB-1*: Merial's commercial Marek's Disease Vaccine SB-1(Merial Select Inc., Gainesville, GA 30503, USA). Vaccine Lot# JV505.

A Newcastle disease virus Fusion Protein (NDV-F) corresponding to genotype VIId sequence (SEQ ID NO:2 encoded by SEQ ID NO:3) was chemically synthesized (GenScript, Piscataway, N.J., USA). The F protein cleavage site of this synthetic gene was altered to match with a lentogenic F cleavage site sequence and the resultant NDV-F gene sequence has 99% nucleotide as well as 99% amino acid sequence identity to NDV-F sequence deposited in GenBank under accession number AY337464 (for DNA) and AAP97877.1 (for protein), respectively.

Donor Plasmid SB-1 US10mFwt SbfI Construction

A fragment containing the synthetic NDV-F gene was excised from pUC57 NDV-F VIId wt plasmid (synthesized by GeneScript) using NotI and inserted into the same site of pCD046 plasmid containing mCMV promoter and SV40 polyA tail. The resultant plasmid, pCD046+NDV-F wt was digested with EcoRI and SalI and blunt ended with Klenow. A 3.3 kb fragment was gel extracted and ligated to a SmaI digested and dephosphorylated (CIPed) vector (SB1 US10-SORF4 SbfI pUC57) containing flanking arms. Ligated material was transformed using Top10 Oneshot kit (Invitrogen, CA, USA). Bacterial colonies were grown in LBamp broth, plasmid extracted by using Qiagens MiniSpin Prep kit, and screened for insert orientation using PstI digestion. The correct donor plasmid was designated SB-1 10mFwt SbfI. Large scale cultures were grown and plasmid extraction was done using Qiagens Maxi Prep kit. Transient expression of the maxi preps was verified using Fugene Transfection Reagent in Chicken Embryo Fibroblast Cells (CEF's) and chicken polyclonal sera against NDV.

Recombinant Generation

A standard homologous recombination procedure was followed by co-electroporation of secondary CEF cells using SB-1 US10 mFwt SbfI donor plasmid and viral DNA isolated from vaccine strain of SB-1 virus. Co-electroporation was performed using $1\times10^7$ 2° CEF in 300 μl Opti-MEM and shocked at 150 volts with 950 capacitance in a 2 mm electroporation cuvette. The transfected cells were seeded into 96-well plate and incubated for 5-7 days. The cells grown in the 96-well plate were then treated with trypsin and transferred into two "sisters" 96-well plates and incubated for 5 more days. One set of 96-well plates was used for IFA using chicken polyclonal sera against NDV-F to identify positive wells containing recombinants and another set of 96-well plates was used for recovering the infected cells from the positive wells.

The recombinant viral purification methods were performed first by 96-well plate duplication and IFA selection for the wells containing the most IFA positive plaques with the least amount of IFA negative plaques. Wells matching those criteria were then harvested and adjusted to 1 ml in DMEM+ 2% FBS. From the 1 ml stock, 5-20 μl (depending on the number of visible plaques) were removed and mixed with $1\times10^7$ CEFs in 10 ml DMEM+2% FBS and aliquoted onto a new 96-well plate to have single SB-1 plaques per well. The 96-well plates were duplicated after 5 days of incubation and wells that contained plaques were tested for the presence of recombinant SB-1 and absence of parental virus by IFA and PCR. Again the wells that appeared to have more recombinant virus, by comparing the PCR banding results, were harvested and adjusted to 1 ml and aliquoted onto new 96-well plates. After three to five rounds of purification of virus infected cells, recombinant SB-1 expressing NDV-F protein was isolated and the purity of the recombinant virus was tested by IFA and PCR to confirm the absence of parental virus. Selected recombinant virus was then passed from one well of a 96-well plate (P0) to 2×T-25 flasks (P1), then 2×T-75 flasks (P2), 2×T-175 flasks (P3), and finally 2×850 $cm^2$ roller bottles (pre-MSV stock or P4). Vials with 2 ml aliquot were stored in liquid nitrogen. Titrations were performed in triplicate on CEFs and a titer of $1\times10^5$ pfu/ml was obtained for SB1-004.

Expression Analysis

Figure 3:
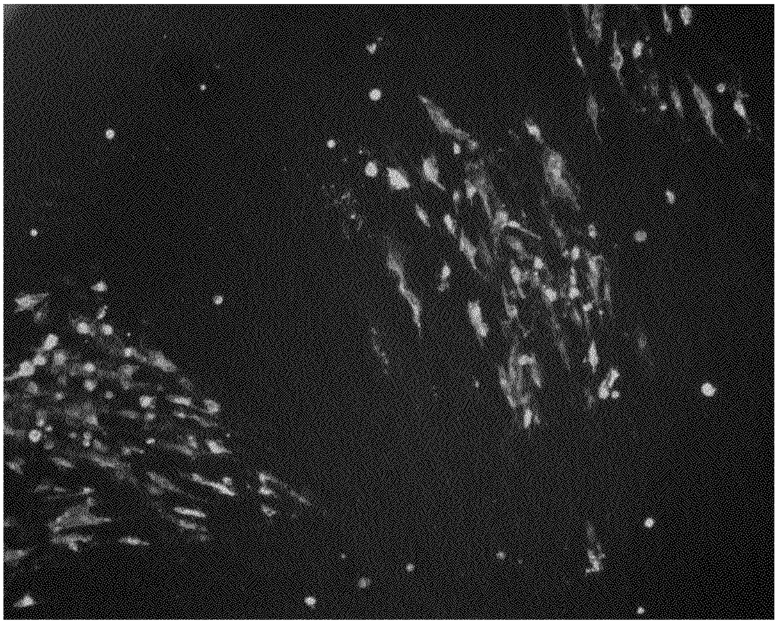
FIG. 3 depicts the immunofluorescent staining of recombinant vSB1-004 virus expressing NDV-F protein.

For immunofluorescence testing, the P3 material was diluted 1:100 in media. Approximately 50 μA of the diluted virus was added to 10 ml of DMEM+2% FBS with $1\times10^7$ CEFs and then aliquoted onto a 96 well plate (100 μl/well). The plates were incubated for 5 days at 37° C.+5% $CO_2$ until viral plaques were visible. The plates were fixed with 95% ice-cold acetone for three minutes and washed three times with PBS. Chicken anti-sera against Newcastle Disease Virus (lot#C0139, Charles Rivers Laboratory) at 1:1000 was added and the plates were incubated at 37° C. for 1 hour. After one hour incubation, the plates were washed three times with PBS and FITC anti-chicken (cat# F8888, Sigma) was added at 1:500. Again the plates were incubated at 37° C. for 1 hour. After one hour incubation the cells were rinsed three times with PBS and visualized with a fluorescent microscope using fluorescein isothiocyanate (FITC) filter. All examined plaques of vSB1-004 were found to express NDV-F protein (FIG. 3).

Analysis of Recombinant by PCR

Figure 4:
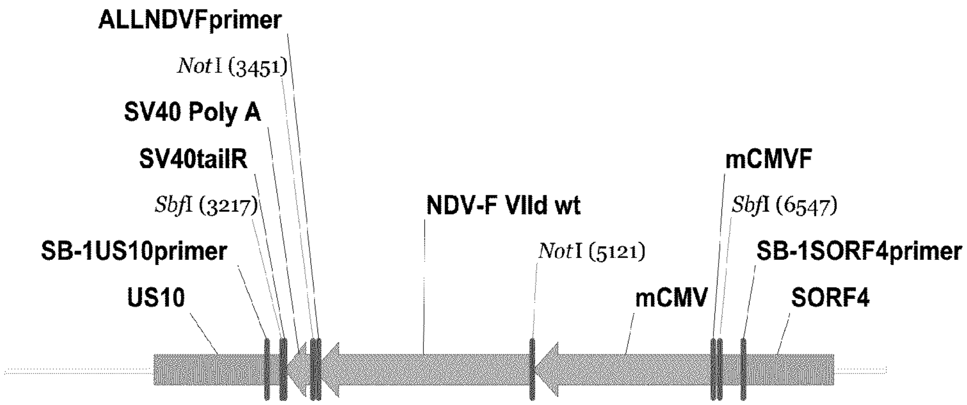
FIG. 4 depicts the schematic representation of primer binding sites.

DNA was extracted from a stock virus by phenol/chloroform extraction, ethanol precipitated, and resuspended in 20 mM HEPES. PCR primers were designed to specifically identify the NDV-F VIId gene, the promoter, the SV40 poly A and the SB-1 flanking arms (see FIG. 4). Primers, specific to HVT (strain FC126), MDV serotype 3 (MB080+MB081) were also included in the analysis to check the purity of the recombinant virus from SB-1 parental virus. PCR was performed using 200 μg of DNA template along with the specified primers pairs.

Figure 5:
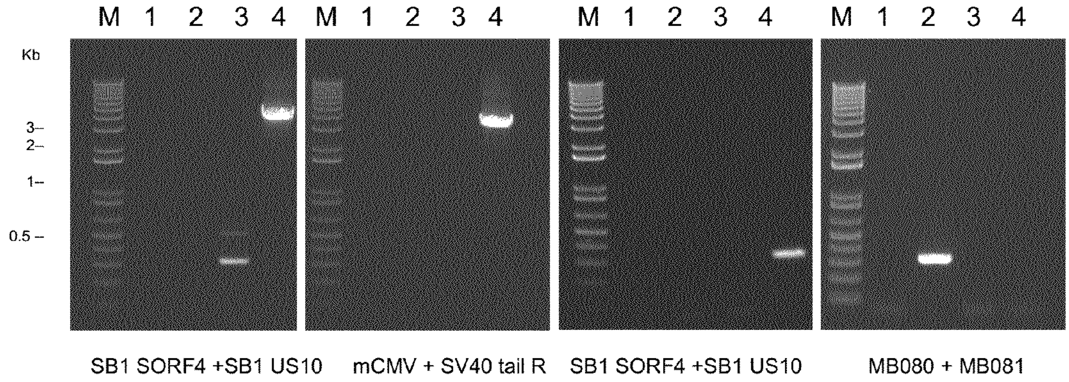
FIG. 5 shows the PCR results of identifying vSB1-004.

The PCR reactions with all primer pairs resulted in the expected PCR products and banding patterns. The PCR results demonstrate that recombinant virus vSB1-004 carries the intended expression cassette and the virus stock is free from detectable amounts of parental SB-1 virus (FIG. 5).

The nucleotide sequence of the donor plasmid SB-1 US10mFwt SbfI (SEQ ID NO:41) is shown in FIG. 20.

Based on PCR testing and immunofluorescence analysis, vSB1-004 is a recombinant SB-1 expressing a NDV-F gene under the control of mCMV promoter. Recombinant vector vSB1-004 is free of any detectable parental SB-1 virus or potential HVT contaminant.

Example 2

Construction of Recombinant vSB1-006 Expressing NDV-F

The aim of the work is to construct a recombinant SB-1 virus in which an expression cassette containing SV40 promoter, Newcastle disease virus fusion protein (NDV-F), and synthetic polyA tail is inserted between the UL55 and LORF5 site of SB-1 virus (Table 2).

TABLE 2

Characteristics of vSB1-006

| Name | Parental virus | Promoter | gene | Poly-A | Locus |
|---|---|---|---|---|---|
| vSB1-006 | SB-1 | SV40 | Opt-NDV-F of VIId | Syn | UL55/ LORF5 |

A Newcastle disease virus Fusion Protein (NDV-F) corresponding to a consensus codon-optimized genotype VIId sequence (SEQ ID NO:2 encoded by SEQ ID NO:1) was chemically synthesized (GeneArt).

Donor Plasmid SB-1 UL55 SV Fopt Syn Tail SbfI Construction

A synthetic SB-1 UL55-LOrf5 SbfI plasmid covering approximately 1 kb sequence on each side of the insertion site (GenScript) was digested with SbfI and dephosphorylated. A synthetic SV OptF syn tail pUC57 plasmid (Genscript) was digested with SbfI and a 2239 base pair fragment was gel extracted and ligated to the SbfI digested vector to create the new SB1 UL55 SVFopt syn tail SbfI donor plasmid.

Recombinant Generation, Expression Analysis and PCR Testing

A standard homologous recombination procedure was followed by co-electroporation of secondary CEF cells using donor plasmid SB1 UL55 SV Fopt syn tail SbfI and viral DNA isolated from vaccine strain of SB-1 virus. Essentially the procedure described in example 1 for vSB1-004 was followed to generate, plaque purify and characterize recombinants by immunofluorescence and PCR.

The nucleotide sequence of the donor plasmid SB1 UL55 SVFopt syn tail SbfI (SEQ ID NO:42) is shown in FIG. 20.

Recombinant Generation and Expression Analyses

Genomic DNA of SB-1 virus was co-electroporated with SB-1 UL55 SV Fopt syn tail SbfI donor plasmid to generate recombinant SB-1 using homologous recombination technique. Recombinant virus was separated from parental SB-1 virus by immunofluorescent positive well selection and PCR screening in multiple rounds of plaque purification. A plaque purified recombinant SB-1 virus expressing the NDV-F protein, designated vSB1-006, was scaled up from tissue culture flasks to 2×850 $cm^2$ roller bottles. After about 72 hrs post infection in roller bottles, the infected CEFs were harvested. Aliquots were frozen in liquid nitrogen containing 10% FBS and 10% DMSO. Titrations were performed in triplicate on CEFs and a titer of $8\times10^5$ pfu/ml was obtained for SB1-006.

Figure 6:
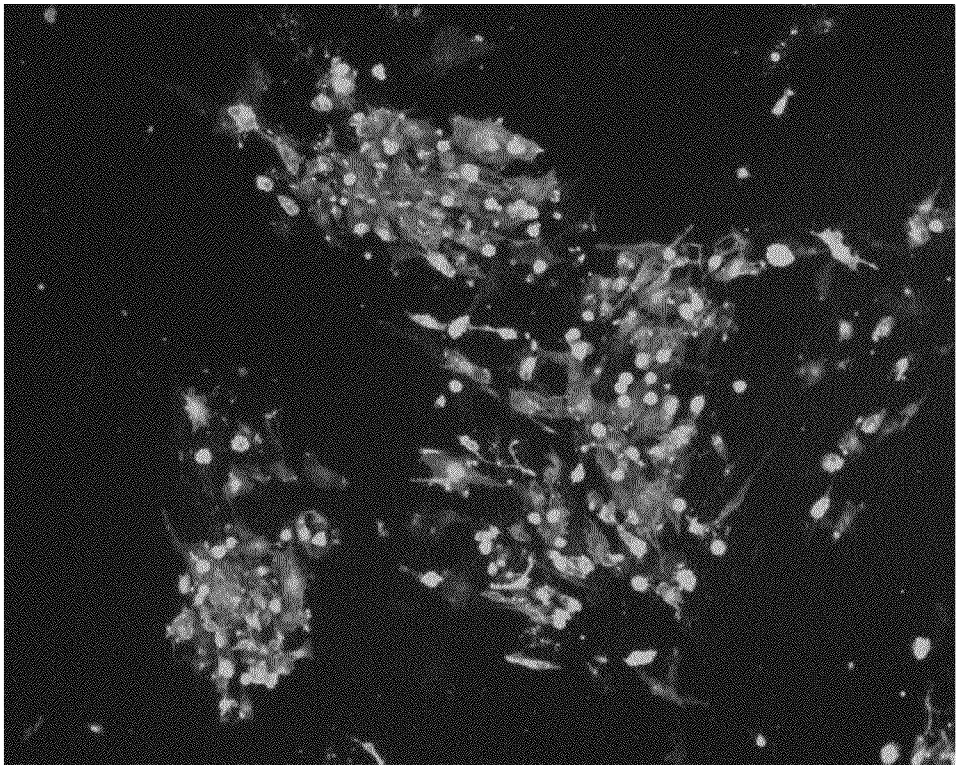
FIG. 6 shows the immunofluorescent staining of recombinant vSB1-006 virus expressing NDV-F protein.

Immunofluorescence was preformed using chicken antisera (lot# C0139, Charles Rivers Laboratories) followed by a FITC labeled anti-chicken IgG (cat#02-24-06, KPL). All examined plaques of vSB1-006 were found to express NDV-F protein (FIG. 6).

PCR Analysis of vSB1-006

Figure 7:
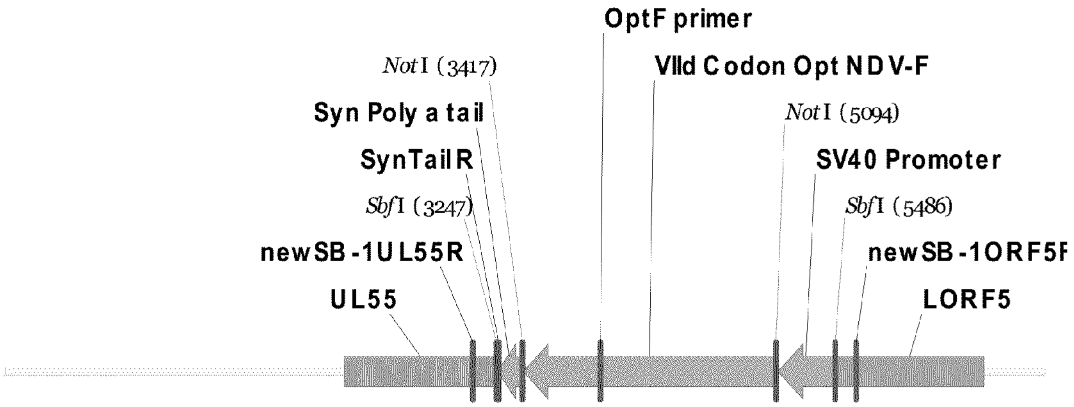
FIG. 7 depicts the schematic representation of primer binding sites on vSB1-006.

Purity of recombinant virus was verified by PCR using primer pairs that are specific to the SB-1 flanking arms, codon-optimized NDV-F VIId, SV40 promoter as well as primer pairs specific to HVT (see FIG. 7). PCR reactions with all primer pairs resulted in the expected PCR products and banding patterns. In addition, there was no evidence of the parental SB-1 virus in vSB1-006 (FIG. 8).

Based on PCR testing and immunofluorescence analysis, it is confirmed that vSB1-006 is a recombinant SB-1 expressing a codon-optimized NDV-F gene under the control of SV40 promoter. Recombinant vector vSB1-006 is free of any detectable amount of parental SB-1 virus and potential HVT contaminant.

Example 3

Construction of Recombinant vSB1-007 Expressing NDV-F

The aim of the work is to construct a recombinant SB-1 virus in which an expression cassette containing SV40 promoter, NDV-F gene corresponding to the F sequence of genotype VIId of NDV is used to replace the coding sequence of glycoprotein C (gC or UL44) of SB-1 virus (Table 3).

TABLE 3

Characteristics of vSB1-007

| Name | Parental virus | Promoter | gene | Poly-A | Locus |
|---|---|---|---|---|---|
| vSB1-007 | SB-1 | SV40 | Opt-NDV-F of VIId | (endogeneous from gC gene) | gC |

A Newcastle disease virus Fusion Protein (NDV-F) corresponding to a consensus codon-optimized genotype VIId sequence (SEQ ID NO:2 encoded by SEQ ID NO:1) was chemically synthesized (GeneArt).

Donor Plasmid pSB1 44 Cds SVOptF Construction

A synthetic pSB1 44 cds plasmid containing flanking arms was generated by gene synthesis (GenScript). The pSB1 44 cds was digested with SbfI, dephosphorylated. Another plasmid named SV-OptF-syn no polyA tail-pUC57 was digested with SbfI and 2.1 kb fragment containing SV40 promoter and NDV-F gene was gel extracted, ligated into the SbfI digested vector and transformed using the Top10 Oneshot kit (Invitrogen). Bacterial colonies were grown in LB-ampicillin media (100 ug/ml), and plasmids were extracted by using Qiagen Mini Spin Prep kit, and screened for insertions by EcoRI and NcoI digestion. The resultant donor plasmid was designated pSB1 44 cds SVOptF.

The synthetic plasmid pSB1 44 cds (SEQ ID NO:36 in FIG. 20) can also be used as a donor plasmid without further modification (without inserting NDV-F expression cassette) to generate a recombinant SB-1 lacking the glycoprotein (gC) gene.

Recombinant Generation and Expression Analyses

A standard homologous recombination procedure was followed by co-electroporation of secondary CEF cells using donor plasmid pSB1 44 cds SVOptF and viral DNA isolated from vaccine strain of SB-1 virus. Essentially the procedure described in example 1 for vSB1-004 was followed to generate, plaque purify and characterize recombinants by immunofluorescence. A plaque purified recombinant SB-1 virus expressing the NDV-F protein, designated vSB1-007, was scaled up from T-25 tissue culture flasks to 10×T-150 $cm^2$ flasks. Infected CEF cells were harvested and aliquots were frozen in liquid nitrogen containing 10% FBS and 10% DMSO. Titrations were performed in triplicate on CEFs and a titer of $7.2\times10^4$ pfu/ml was obtained for SB1-007.

Figure 9:
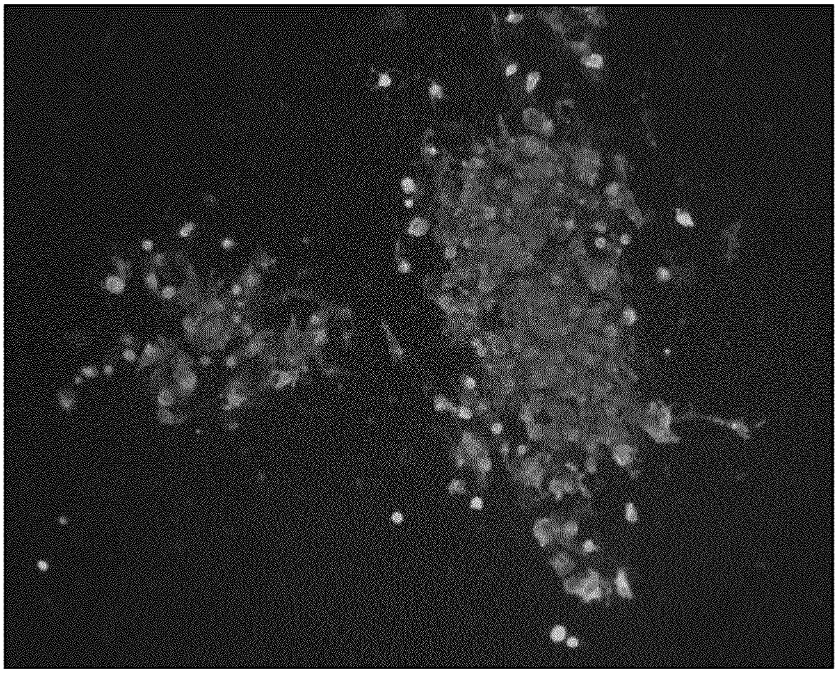
FIG. 9 depicts the immunofluorescent staining of recombinant SB1-007 virus expressing NDV-F protein.

Immunofluorescents was performed using chicken antisera (lot# C0139, Charles Rivers Laboratories) followed by a FITC labeled anti-chicken IgG (cat#02-24-06, KPL). All examined plaques of vSB1-007 were found to express NDV-F protein (FIG. 9).

PCR Analysis of vSB1-007

Figure 10:
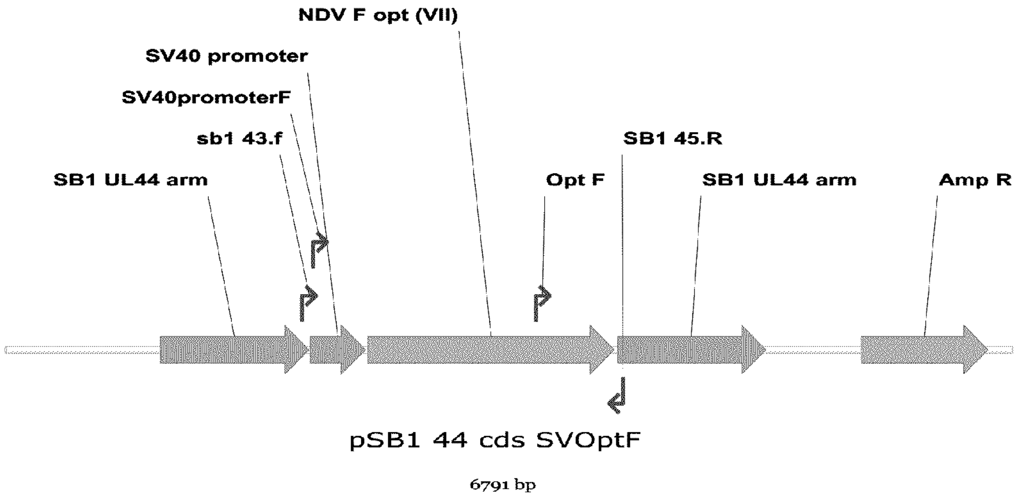
FIG. 10 depicts the schematic diagram of primer location on pSB1 44 cds SVOptF donor plasmid.

Viral DNA was extracted from SB1-007 from P.1 through P.6 by QIA DNeasy Blood & Tissue Kit (Qiagen). PCR primers were designed to specifically identify the presence of NDV F (codon-optimized), the SV40 promoter and the flanking arms of UL44 (see FIG. 10). PCR amplifications were preformed using 200 ng of DNA template along with the specified primer pairs.

Similarly, a standard homologous recombination procedure using synthetic plasmid pSB1 44 cds and viral DNA isolated from vaccine strain of SB-1 virus will generate a recombinant SB-1 in which the coding region of gC gene is deleted. Two PCR primers (SB1 43.F and SB1 45.R, Table 4) will produce a PCR product of 103 nucleotides for a gC-deleted recombinant SB-1 versus a 1540 nucleotides for the parent SB-1 virus.

Figure 11:
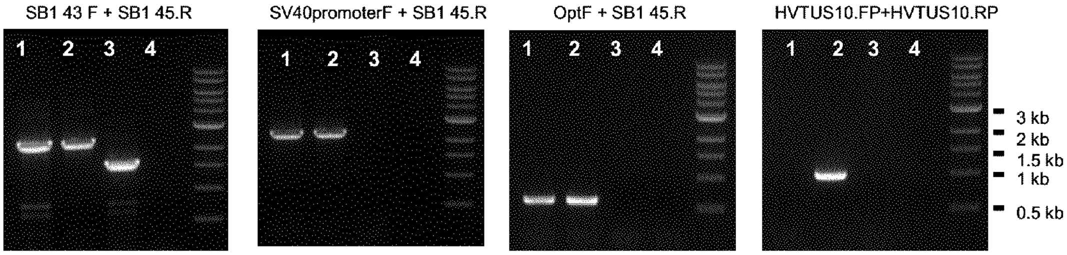
FIG. 11 shows the PCR results of vSB1-007.

Purity of recombinant virus was verified by PCR using primer pairs that are specific to the SB-1 flanking arms, codon-optimized NDV-F VIId, SV40 promoter as well as primer pairs (MB080+MB081) specific to HVT. PCR reactions with all primer pairs resulted in the expected PCR products and banding patterns. In addition, there is no evidence of the parental SB-1 virus in vSB1-007 (Tables 4-5 and FIG. 11).

TABLE 4

PCR primers

| Primer | SEQ ID NO: | Sequence (5' to 3') |
|---|---|---|
| SB1 43.F | 27 | GCTCTCGGAGACGCGGCTCGC |
| SB1 45.R | 28 | GCTCTTGTAACATCGCGGACG |
| SV40 promoter.F | 29 | AGCTTGGCTGTGGAATGT |
| Opt F | 24 | ACTGACAACACCCTACATGGC |
| HVTUS10.FP | 30 | CCGGCAACATACATAATGTG |
| HVTUS10.RP | 31 | GGCACTATCCACAGTACG |

TABLE 5

| Expected amplicon size | | |
|---|---|---|
| | Expected amplicon size (bp) | |
| Primer pairs | SB-1 | vSB1-007/pSB1 44 cds SVOptF |
| SB1 43.F + SB1 45.R | 1540 | 2188 |
| SV40promoterF + SB1 45.R | None | 2113 |
| Opt F + SB1 45.R | None | 611 |
| HVTUS10.FP + HVTUS10.RP | None | None |

Based on PCR testing and immunofluorescence analysis, it is confirmed that vSB1-007 is a recombinant SB-1 expressing a codon-optimized NDV-F gene under the control of SV40 promoter. The NDV-F expression cassette was successfully used to replace the gC gene of SB1, demonstrating that gC is dispensable for in vitro propagation of SB-1 virus. Recombinant vector vSB1-007 is free of any detectable amount of parental SB-1 virus or HVT.

The nucleotide sequence of the donor plasmid pSB1 44 cds SVOptF (SEQ ID NO:43) is shown in FIG. 20.

Example 4

Construction of Recombinant vSB1-008 Expressing NDV-F

The aim of the work is to construct a recombinant SB-1 virus in which an expression cassette containing SV40 promoter, NDV-F gene corresponding to the F sequence of CA02 strain of NDV, and synthetic polyA tail is inserted between the UL55 and LORF5 site of SB-1 virus (Table 6).

TABLE 6

| Characteristics of vSB1-008 | | | | | |
|---|---|---|---|---|---|
| Name | Parental virus | Promoter | gene | Poly-A | Locus |
| vSB1-008 | SB-1 | SV40 | Opt-NDV-F of CA02 | Syn | UL55/ LORF5 |

An NDV-F corresponding to a codon-optimized genotype V (CA02 strain) sequence (SEQ ID NO:9 encoded by SEQ ID NO:8) was chemically synthesized (GeneArt). The F protein cleavage site of this synthetic gene was altered to match a lentogenic F cleavage site sequence and the resultant NDV-F gene sequence has 99% amino acid sequence identity to NDV-F sequence deposited in GenBank (ABS84266).

Donor Plasmid SB1 UL55 SV CaFopt Syn Tail SbfI Construction

A synthetic SB-1 UL55-LOrf5 SbfI plasmid (Genscript) containing approximately 1 kb sequence of each side of the insertion site was digested with SbfI and dephosphorylated. A synthetic SV OptF syn tail pUC57 plasmid (Genscript) was digested with SbfI and a 2239 base pair fragment containing syn tail was gel extracted and ligated to the SbfI digested vector to create the new SB1 UL55 SVFopt syn tail SbfI donor plasmid. This donor plasmid was then digested with NotI, CIPed, and a 5196 base pair fragment was gel extracted. A synthetic NDV-F CAO2 CSmut 0813005 pVR101 donor plasmid (GeneArt) was digested with NotI and a 1677 base pair fragment was gel extracted and ligated to the NotI digested and CIPed UL55 vector resulting in donor plasmid SB1 UL55 SV CaFopt syn tail SbfI.

Recombinant Generation and Expression Analysis

A standard homologous recombination procedure was followed by co-electroporation of secondary CEF cells using donor plasmid SB-1 UL55 SV CaFopt syn tail SbfI and viral DNA isolated from vaccine strain of SB-1 virus. Essentially the procedure described in example 1 was followed to generate and characterize recombinants by immunofluorescence and PCR.

Recombinant virus was separated from parental SB-1 virus by immunofluorescent positive well selection and PCR screening in multiple rounds of plaque purification. A plaque purified recombinant SB-1 virus expressing the NDV-F protein, designated vSB1-008, was scaled up from tissue culture flasks to 2×850 $cm^2$ roller bottles. After about 72 hrs post infection in roller bottles, the infected CEFs were harvested. Aliquots were frozen in liquid nitrogen containing 10% FBS and 10% DMSO.

Figure 12:
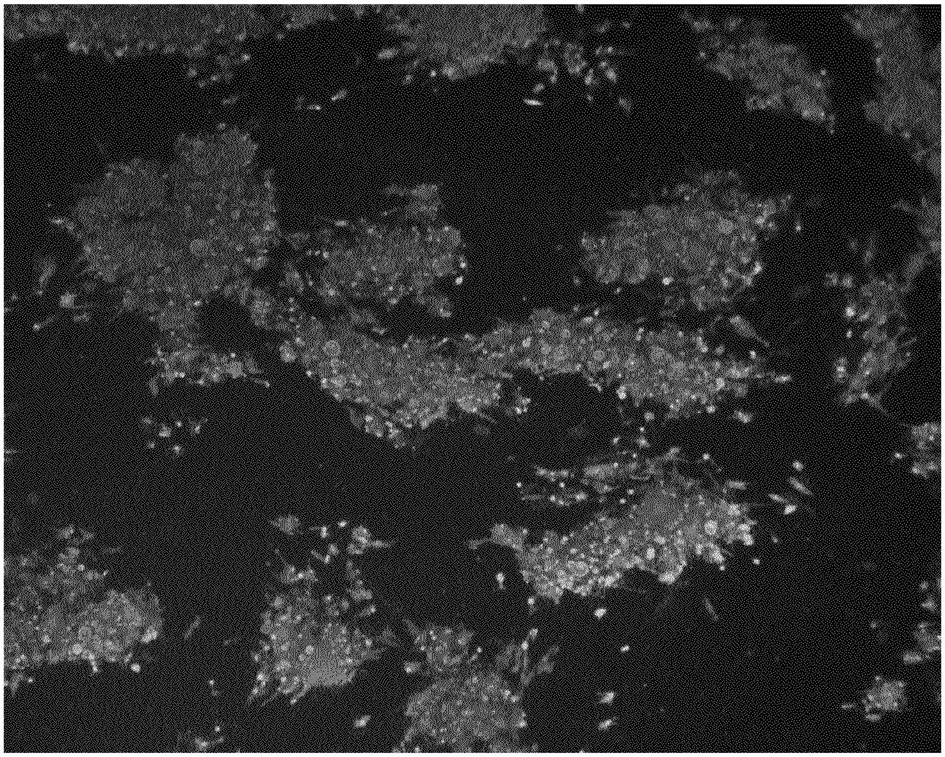
FIG. 12 depicts the immunofluorescent staining of recombinant SB1-008 virus expressing NDV-F protein.

Immunofluorescence was performed using chicken antisera (Charles Rivers Laboratories) followed by a FITC labeled anti-chicken IgG (KPL) (FIG. 12).

PCR Analysis of vSB1-008

Figure 13:
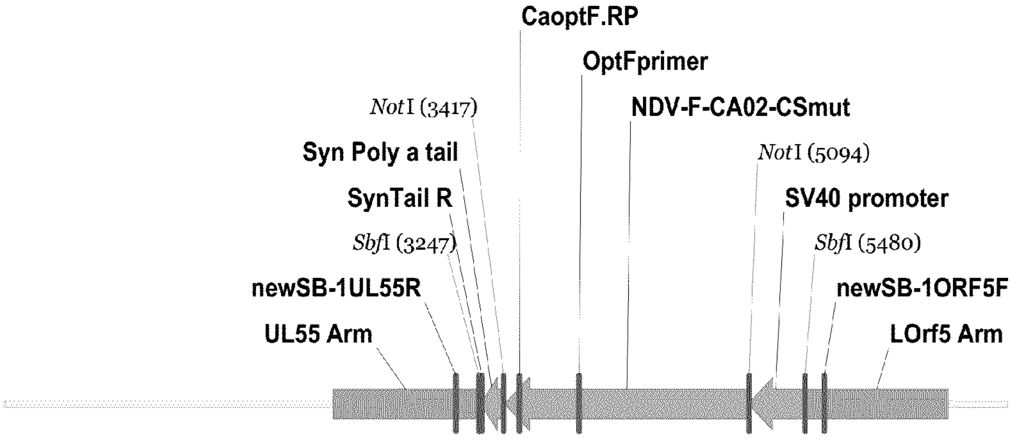
FIG. 13 depicts the schematic representation of primer binding sites.

Purity of recombinant virus was verified by PCR using primer pairs that are specific to the SB-1 flanking arms, codon-optimized NDV-F VIId, SV40 promoter (see FIG. 13) as well as primer pairs (MB080+MB081) specific to HVT, MDV serotype 3. PCR reactions with all primer pairs resulted in the expected PCR products and banding patterns. In addition, there is no evidence of the parental SB-1 virus in vSB1-008 (FIG. 14).

The nucleotide sequence of the donor plasmid SB-1 UL55 CaFopt syn tail SbfI (SEQ ID NO:44) is shown in FIG. 20.

Based on PCR testing and immunofluorescence analysis, it is confirmed that vSB1-008 is a recombinant SB-1 expressing a codon-optimized NDV-F gene under the control of SV40 promoter. Recombinant vector vSB1-008 is free of any detectable parental SB-1 virus or HVT.

Example 5

Construction of Recombinant vSB1-009 and vSB1-010 Expressing NDV-F

The aim of the study is to construct a recombinant SB-1 viral vector vSB1-009 in which an expression cassette containing SV40 promoter and Newcastle disease virus fusion (NDV-F) gene is inserted to replace UL44 coding (gC) sequence of SB-1 and to construct a recombinant SB-1 viral vector vSB1-010 in which an additional expression cassette containing guinea pig CMV promoter and NDV-F gene is inserted in SORF-US2 locus of SB1-009 vector backbone.

Example 5.1

Construction of vSB1-009

A donor plasmid pSB1 44 cds SV FCAopt was constructed containing UL44 flanking arms of SB1 virus, SV40 promoter and NDV F codon optimized gene sequence (SEQ ID NO:8, coding for SEQ ID NO:9) (Table 7).

TABLE 7

Characteristics of vSB1-009

| Name | Parental virus | Promoter | F gene | Poly-A | Locus |
|---|---|---|---|---|---|
| vSB1-009 | SB1 | SV40 | Opt-NDV-F of CA02 | (endogeneous from gC gene) | UL44 (gC) |

Generation of Recombinant Virus

A standard homologous recombination procedure was followed by co-electroporation of secondary CEF cells using donor plasmid pSB1 44 cds SV FCAopt and viral DNA isolated from SB-1 virus infected CEFs. Essentially the procedure described in example 1 was followed to generate, plaque purify and characterize recombinants by immunofluorescence.

After two rounds of plaque purification, pure recombinant virus (vSB1-009) was isolated and the purity of vSB1-009 was tested by IFA and PCR to validate the appropriate insertion as well as no remnant parental virus.

PCR Analysis

Viral DNA was extracted from vSB1-009 pre-master seed virus (pre-MSV) stock by QIA DNeasy Blood & Tissue Kit (Qiagen). PCR primers were designed to identify the presence of the NDV F optimized, the NDV F wild type, the SV40 promoter, the mCMV promoter, the UL44 flanking arms of SB-1 virus and HVT virus. PCR amplifications were performed using approximately 200 ng of DNA template along with the primer pairs.

PCR amplification with various primers confirmed that the vSB1-009 has the expected amplification patterns and amplicons.

Expression Analysis

Indirect immunofluorescent assay (IFA) was performed on the vSB1-009 pre-MSV stock to examine the expression of NDV F gene and SB-1 virus antigen. The CEFs that were inoculated with vSB1-009 were fixed with ice-cold 95% acetone for three minutes at room temperature and air-dried for 10 min. The plates were washed with PBS, then two primary antibodies, chicken anti-Newcastle Disease Virus sera (Charles Rivers Laboratories cat#10100641, lot#C0117A) at 1:500 dilution and Y5.9 monoclonal antibody against SB-1 virus (Merial Select, Gainesville, Ga.) at 1:3000 dilution were added and the plates were incubated for 45 min at 37° C. After three washes with PBS, two secondary antibodies, goat anti-chicken IgG-fluorescein (KPL) at 1:500 dilution and donkey anti-mouse IgG-Alexa Fluor 568 (Molecular Probe) at 1:250 dilution were added. The plates were incubated at 37° C. for 45 min and followed by three washes with PBS. The wells were screened for IFA positive plaques with a fluorescent microscope using fluorescein isothiocyanate (FITC) and tetramethylrhodamine isothiocyanate (TRITC)-filters of Nikon Eclipse Ti inverted microscope. Similarly, reactivity of vSB1-009 with NDV F Mab was examined by Dual IFA using anti-MDV serum (Charles River Laboratories (1/300 dilution) and anti-NDV F monoclonal antibody (1/300 dilution) as primary antibody. The goat anti-chicken IgG-fluorescein (KPL) (1:500 dilution) and donkey anti-mouse IgG-Alexa Fluor 568 (Molecular Probe) (1:250 dilution) were used as secondary antibodies. The wells were observed to identify the IFA positive plaques with a fluorescent microscope using FITC- and TRITC-filters of Nikon Eclipse Ti inverted microscope.

IFA results indicate that vSB1-009 expresses the NDV F protein in virus-infected CEF. Over 500 vSB1-009 plaques were counted for NDV F protein expression as well as SB-1 virus specific protein expression with dual IFA. The expression of NDV F protein completely matched with SB-1 virus antigen expression in each virus plaque (Table 8).

TABLE 8

Dual IFA of vSB1-009

| | Dual IFA plate#1 (total 189 plaques) | | Dual IFA plate#2 (total 361 plaques) | |
|---|---|---|---|---|
| Virus | Anti-NDV serum positive plaques | Anti-SB-1 Mab positive plaques | Anti-NDV serum positive plaques | Anti-SB-1 Mab positive plaques |
| vSB1-009 | 189 | 189 | 361 | 361 |

NDV F Mab reactivity was confirmed by Dual IFA. Over 200 vSB1-009 plaques were examined for NDV F Mab reactivity as well as anti-MDV serum reactivity. The reactivity with NDV F Mab completely matched with anti-MDV serum reactivity in each virus plaque (Table 9).

TABLE 9

Reactivity of vSB1-009 with anti-NDV F Mab

| | Dual IFA (total 254 plaques) | |
|---|---|---|
| Virus | Anti-MDV serum positive plaques | Anti-NDV F Mab positive plaques |
| vSB1-009 | 254 | 254 |

Southern Blot Analysis

Total genomic DNA was extracted from vSB1-009 pre-MSV stock infected CEFs. The genomic DNA of vSB1-009, SB-1 virus (negative control), pSB1 44 cds SV FCA opt donor plasmid were digested at 37° C. with EcoRI, NcoI, and KpnI restriction endonucleases separately. The restriction fragments were separated by a 0.8% agarose gel electrophoresis and transferred onto a positively charged Nylon membrane. After transfer, the membrane was treated with 0.4M NaOH and then neutralized with 2×SSC—HCl buffer. The membrane was then air dried and UV crosslinked.

Following the North2South Chemiluminescent Hybridization and Detection Kit (Thermo Scientific cat#89880) manufacturers' instructions, the membrane was pre-hybridized for 1 hr and then hybridized with the probe at 55° C. for overnight. For hybridization, two probes were used; 1) the SbfI fragment of pSB1 44 cds SV FCA opt as NDV F cassette probe, 2) the SmaI-EcoRI fragment of pUC57 SB1 44 arm (GenScript) as recombination arm probe. After the overnight hybridization, several stringency washes were conducted until the membrane was placed in blocking buffer with the addition of Streptavidin-HRP. After rinsing the membrane of any unbound Streptavidin-HRP, the substrate solution of Luminal and peroxide were added. The membrane was then exposed to X-ray film and the film was developed.

The Southern blot results were as expected based on Vector NTI map analysis. The NDV F cassette (SV40 promoter, NDV-F CA02 codon optimized gene) replaced the UL44 coding sequences of SB-1 virus.

Genomic Analysis

The genomic DNA of vSB1-009 pre-MSV stock was conducted by nucleotide sequence determination of the region of recombination arm as well as inserted gene cassette. Primers were designed and used to amplify the entire NDV-F gene cassette including the recombination arms.

The vSB1-009 sequence (donor plasmid pSB1 44 cds SV FCAopt) containing the recombinant arms, SV40 promoter and NDV F codon-optimized gene was confirmed to be correct as shown in SEQ ID NO:37 (FIG. 20).

Western Blot Analysis

The CEF monolayer was infected with vSB1-009 pre-MSV at MOI ~0.1. After a 5-day incubation, the CEFs were pelleted and washed with PBS followed by lysis with IP Lysis/Wash buffer of Pierce Classic IP Kit (Thermo Scientific cat#26146) according to the manufacturers' protocols. The lysate was pre-cleared and incubated with 100 ul of anti-NDV F monoclonal antibody to make the immune complex. The immune complex was captured by Protein A/G Plus Agarose and after removing of the un-bounded immune complex by washing steps, the 50 ul of sample buffer was used to elute under non-reducing conditions. The uninfected CEFs were included as a control. The 20 ul of eluted samples were separated in 10% Bis-Tris gels by electrophoresis. After the electrophoresis, the separated proteins in a gel were transferred onto PVDF membrane. The Protein Detection TMB Western Blot Kit (KPL cat#54-11-50) was used to detect the NDV antigens onto PVDF membrane with chicken anti-NDV serum (Charles River Laboratories Laboratories cat#10100641, lot#C0117A), and goat anti-chicken IgG-peroxidase conjugate (KM, cat#14-24-06) following the manufacturers' protocols.

Figure 15:
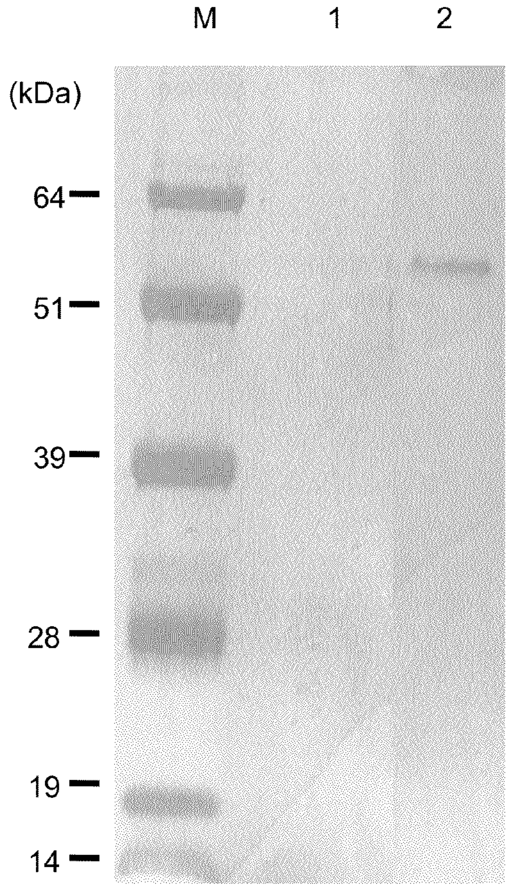
FIG. 15 depicts the Western blot analysis of immunoprecipitated sample from vSB1-009 infected cells.

The NDV F protein expression of vSB1-009 was confirmed by two-step immunodetection. First, the expressed NDV F proteins from vSB1-009 infected CEF lysate were captured by the immunoprecipitation using anti-NDV F monoclonal antibody 001C3. Subsequently Western blot analysis using anti-NDV polyclonal serum (Charles River Laboratories cat#10100641, lot#C0117A) was applied to detect the NDV F protein in the captured samples (NDV F protein-monoclonal antibody complex) (FIG. 15). An approximately 55 kDa protein in vSB1-007 pre-MSV lysates was detected by anti-NDV serum that corresponding the expected size of NDV F1 fusion protein (FIG. 15).

Example 5.2

Construction of vSB1-010

Donor Plasmid SB1US2 gpVIIdwtsyn Construction

Using the plasmid HVT SOrf3-US2 gpVar-Ewt Syn, the gpCMV, Varient E, Syn tail was removed by SbfI digestion. This fragment was ligated into the SB1 US2 donor plasmid. The Varient E gene was cut out by NotI and replaced by NDV-F VIId wt. The synthetic NDV-F VIId wild type gene (SEQ ID NO:3 encoding SEQ ID NO:2) was excised from pUC57 NDV-F VIId wt plasmid (synthesized by GeneScript) using NotI digestion. Ligated material was transformed using Top10 Oneshot kit (cat#C404002, Invitrogen). Bacterial colonies were grown in LBamp broth, plasmid extracted by using Qiagens MiniSpin Prep kit, and screened for insert orientation using NcoI+SalI digestion. The correct donor plasmid was designated pSB1 US2 gpVIIdwt Syn. Table 10.1 shows the features unique to the construct around the expression cassettes, including the respective sequences. Large scale cultures were grown and plasmid extraction was done by using Qiagens Maxi Prep kit. Transient expression of the maxi preps was verified using Fugene Transfection Reagent in Chicken Embryo Fibroblast Cells (CEF's) and chicken polyclonal sera against NDV-F.

Recombinant Generation

A standard homologous recombination procedure was followed by co-electroporation of secondary CEF cells using pSB1 US2 gpVIIdWt Syn donor plasmid and viral DNA isolated from vSB1-009 (vSB1-009 is already a recombinant virus expressing CA02 F gene of NDV). Essentially the procedure described in example 1 for was followed to generate, plaque purify and characterize recombinants by immunofluorescence.

After five rounds of plaque purification, pure recombinant virus (vSB1-010) was isolated and the purity of vSB1-010 was tested by IFA and PCR to validate the appropriate insertion as well as no remnant parental virus.

TABLE 10.1

Characteristics of vSB1-010

| Name | Parental virus | Promoter | F gene | Poly-A | Locus |
|---|---|---|---|---|---|
| vSB1-010 | vSB1-009 | Guinea pig CMV | NDV-F VIId | Synthetic | SORF4-US2 |

Sequencing of the insert region confirmed that vSB1-010 contains the correct sequences of guinea pig CMV promoter and the NDV-F VIId wt gene as shown in the sequence of the donor plasmid SB1US2 gpVIIdwtsyn (SEQ ID NO:57).

Analysis of Recombinant by PCR

DNA was extracted from a stock virus by phenol/chloroform extraction, ethanol precipitated, and resuspended in 20 mM HEPES. PCR primers were designed to specifically identify the NDV-F VIId wt gene, the promoter, the polyA, as well as, the purity of the recombinant virus from SB1 parental virus. PCR was performed using 200 μg of DNA template along with the specified primers pairs indicted in Table 1. PCR cycling conditions are as follows (unless otherwise noted): 94° C.—2 min; 30 cycles of 94° C.—30 sec, 55° C.—30 sec, 68° C.—3 min; 68° C.—5 min.

Purity of recombinant virus was verified by PCR using primer pairs that are specific to the SB1 flanking arms, the gpCMV promoter, the NDV-F VIId wt gene and the syn tail. Primers, specific to HVT, MDV serotype 3 (MB080+MB081) were also included in the analysis. The PCR results demonstrate that recombinant virus vSB1-010 carries the intended expression cassette and the virus stock is free from detectable amounts of parental SB1-009 virus.

Immunofluorescent Staining of Recombinant vSB1-010 Virus Expressing Two NDV-F Proteins For immunofluorescence testing, the P3 material was diluted 1:100 in media. Approximately 50 μl of the diluted virus was added to 10 ml of DMEM+2% FBS with $1\times10^7$ CEFs and then aliquoted onto a 96 well plate (100 μl/well). The plates were incubated for 5 days at 37° C.+5% $CO_2$ until viral plaques were visible. The plates were fixed with 95% ice-cold acetone for three minutes and washed three times with PBS. Chicken anti-sera against Newcastle Disease Virus (lot#C0139, Charles Rivers Laboratory) at 1:1000 was added and the plates were incubated at 37° C. for 1 hour. After one hour incubation, the plates were washed three times with PBS and FITC anti-chicken (cat# F8888, Sigma) was added at 1:500. Again the plates were incubated at 37° C. for 1 hour. After one hour incubation the cells were rinsed three times with PBS and visualized with a fluorescent microscope using fluorescein isothiocyanate (FITC) filter.

The immunofluorescent staining results indicate that vSB1-010 exhibited a very strong expression of the NDV-F protein when the polyclonal sera against both CA02 and VIId F proteins of NDV were used.

Conclusion

Based on PCR testing and immunofluorescence analysis, vSB1-010 is a recombinant SB-1 in which VIId-F gene of NDV under the control of gpCMV promoter was successfully inserted into a vSB1-009, which already expresses the CA02-F gene of NDV. Consequently vSB1-010 carries both VIId and CA02 F genes of NDV genotypes and it is free of any detectable parental vSB1-009.

Example 6

Construction of Recombinant vHVT Vectors Expressing NDV-F

Preparation of Donor Plasmid pHM103+Fopt for vHVT114

The plasmid pHM103 (Merial Limited) containing the Intergenic I arms of HVT FC126, SV40 promoter and SV40 poly A was digested with NotI, dephosphorylated, and the 5.6 kb fragment was gel extracted. A NotI flanked 1.7 kb fragment of a chemically synthesized codon-optimized genotype VIId NDV-F gene (SEQ ID NO:1, coding for SEQ ID NO:2) was also NotI digested and the 1.7 kb fragment was gel extracted. The 5.6 and 1.7 kb fragments were ligated to create pHM103+Fopt (Table 10.2).

TABLE 10.2

Characteristics of vHVT114

| Name | Parental virus | Promoter | F gene | Poly-A | Locus |
|---|---|---|---|---|---|
| vHVT114 | HVT FC126 strain | SV40 | Opt-VIId | SV40 | IG1 |

Generation of Recombinant HVT Viral Vector

A standard homologous recombination procedure was followed by co-electroporation of secondary CEF cells using donor plasmid pHM103+Fopt and viral DNA isolated from the HVT strain FC126 (Igarashi T. et al., J. Gen. Virol. 70, 1789-1804, 1989). Essentially the procedure described in example 1 was followed to generate, plaque purify and characterize recombinants by immunofluorescence.

After five rounds of plaque purification, a recombinant virus designated as vHVT114 was isolated and the purity was tested by IFA and PCR to confirm NDV-F expression and the absence of parental virus.

PCR Analysis of Recombinant vHVT114

DNA was extracted from vHVT114 by phenol/chloroform extraction, ethanol precipitated, and was resuspended in 20 mM HEPES. PCR primers were designed to specifically identify the presence of the codon optimized NDV-F, the SV40 promoter, as well as, the purity of the recombinant virus from FC126 CL2 parental virus.

The PCR results showed that the sizes of PCR products after gel electrophoresis correspond well with the expected sizes and the banding patterns.

Sequence Analysis of the Inserted Region in Recombinant vHVT114

Analysis of vHVT114 genomic DNA region was performed by PCR amplification. Total of 10 primers were used to amplify the entire cassette, as well as, beyond the flanking BamHI-I arms used in the donor plasmid. The 4.727 kb PCR product was gel purified and the entire fragment was sequenced using the sequencing primers. The sequence result confirmed that the vHVT114 contains the correct SV40 promoter, the codon-optimized NDV-F and the SV40 polyA sequences that match exactly the sequence described for the donor plasmid pHM103+Fopt in SEQ ID NO:38 (see FIG. 20).

Western Blot Analysis of Recombinant vHVT114

Approximately $2\times10^6$ chicken fibroblast cells were infected at ~0.1 MOI with vHVT114 Pre-MSV. After two days of incubation at 37° C., infected as well as uninfected cells were harvested using a cell scraper after removing the media and rinsing with PBS. The cells were harvested with 1 ml of PBS and centrifuged. The cell pellets were lysed by following the Pierce Classic IP Kit (Thermo Scientific). 100 μl of the anti-NDV-F monoclonal antibody 001C3 (Merial Limited) was used to form the immune complex. The antibody/lysate sample was added to Protein A/G Plus Agarose to capture the immune complex. The immune complex was washed three times to remove non-bound material and then eluted in 50 ul volume using sample buffer elution under non-reducing condition. After boiling for 5 minutes, 10 μl of the samples were loaded into a 10% Acrylamide gel (Invitrogen). The PAGE gel was run in MOPS buffer (Invitrogen) at 200 volts for 1 hour. Then the gel was transferred onto a PVDF membrane.

The Protein Detector Western Blot Kit TMB System (KPL, cat#54-11-50) was used for blotting the PVDF membrane by using the reagents and following manufacturer's directions. After blocking the membrane for 1 hour at room temperature, the membrane was then rinsed three times in 1× Wash Buffer, five minutes each and then soaked in blocking buffer containing 1:1000 dilution of chicken serum raised against NDV virus (Lot # C0139, Charles River Laboratories). After washing three times in a washing buffer, the membrane was incubated with a peroxidase labeled goat anti-chicken IgG (KPL, cat#14-24-06) at a dilution of 1:2000 for 1 hour at room temperature. The membrane was then rinsed three times in 1× Wash Buffer, five minutes each. 5 ml of TMB membrane peroxidase substrate was added to the membrane and gently rocked for about 1 minute. The developing reaction was stopped by placing the membrane into water.

Figure 16:
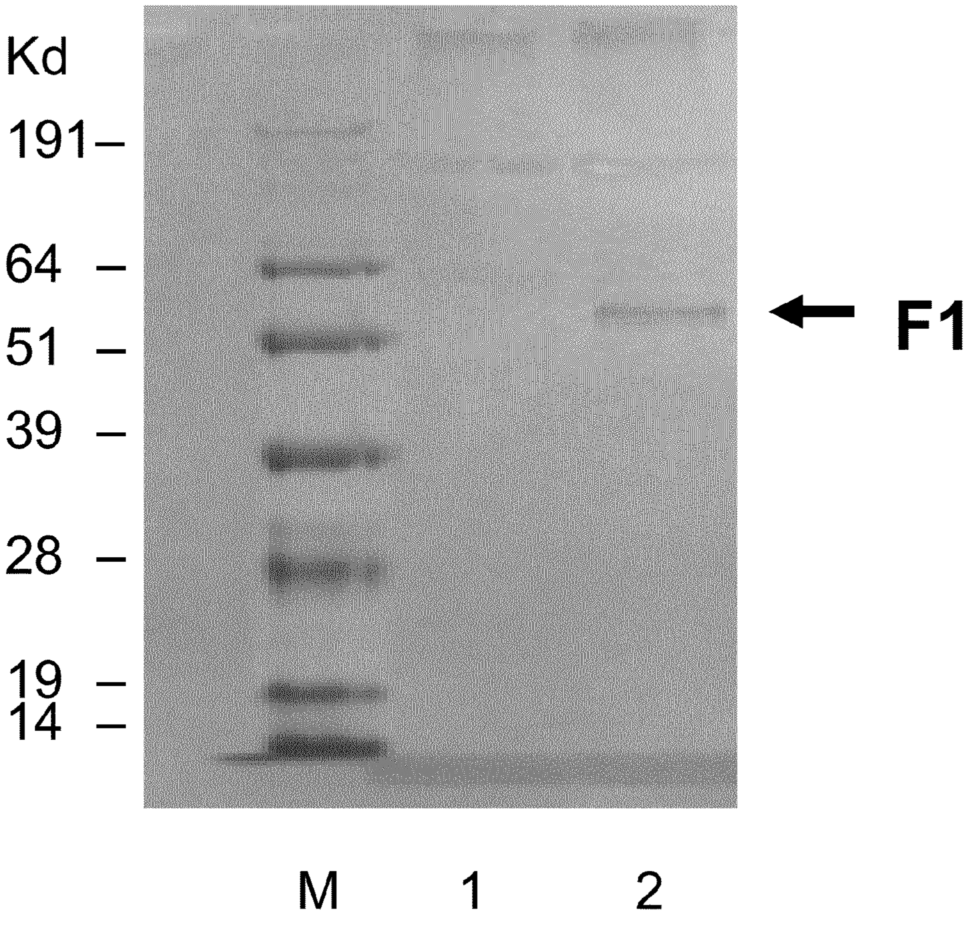
FIG. 16 depicts the Immunoprecipitation and Western Blot of vHVT114.

The immunoprecipitation and Western blot technique detected an approximately 55 kD protein in vHVT114 sample that corresponds to the expected size of F1 component of the NDV-F protein (FIG. 16).

Generation and Characterization of Other HVT Recombinants

Generation and characterization of other HVT recombinants, such as vHVT039, vHVT110, vHVT111, vHVT112, vHVT113, and vHVT116 were essentially done in the same way as for vHVT114 described above. The generation and characterization of recombinant HVT viral vectors were also described in U.S. patent application Ser. No. 13/689,625 filed on Nov. 29, 2012 (Merial limited), which is incorporated herein by reference in its entirety. Table 11 shows the features unique to each construct around the expression cassettes, including the respective sequences.

TABLE 11

Characteristics of the expression cassettes of single HVT recombinants

| Name | Parental virus | Promoter | F gene | Poly-A | Locus |
|---|---|---|---|---|---|
| vHVT039 | HVT | MDV gB | Wtnm-Texas | SV40 | IG1 |
| vHVT110 | HVT | mCMV IE | Wt-VIId | SV40 | IG1 |
| vHVT111 | HVT | SV40 | Wt-VIId | SV40 | IG1 |
| vHVT112 | HVT | MCMV IE | Wt-YZCQ | SV40 | IG1 |
| vHVT113 | HVT | MCMV IE | Wt-Texas | SV40 | IG1 |

TABLE 11-continued

| Characteristics of the expression cassettes of single HVT recombinants | | | | | |
|---|---|---|---|---|---|
| Name | Parental virus | Promoter | F gene | Poly-A | Locus |
| vHVT114 | HVT | SV40 | Opt-VIId | SV40 | IG1 |
| vHVT116 | HVT | SV40 | Opt-NDV-F of CA02 | SV40 | IG1 |

Example 7

Construction of Double HVT Vectors Expressing NDV-F and IBDV VP2, and Double HVT Vectors Expressing IBDV VP2 Variants Preparation of Donor Plasmid pHVT US2 SV-Fopt-synPA for vHVT306

The donor plasmid pHVT US2 SV-Fopt-synPA was constructed containing SV40 promoter, synthetic NDV F codon optimized VII gene, synthetic polyA tail flanked by the SORF3 and US2 arm sequences of HVT FC126.

Generation of Recombinant Virus

A standard homologous recombination procedure was followed by co-electroporation of secondary CEF cells using donor plasmid pHVT US2 SV-Fopt-synPA and viral DNA isolated from vHVT13 (an HVT vector expressing the IBDV VP2 gene, Merial Limited). Essentially the procedure described in example 1 was followed to generate, plaque purify and characterize recombinants by immunofluorescence.

After two rounds of plaque purification, pure recombinant virus (vHVT306) was isolated and the purity of vHVT306 was tested and confirmed by IFA and PCR.

PCR Analysis

Viral DNA was extracted from vHVT306 pre-master seed virus (pre-MSV) stock by QIA DNeasy Blood & Tissue Kit (Qiagen). PCR primers were designed to identify the presence of the NDV F optimized, the NDV F wild type, the SV40 promoter, the mCMV promoter, the flanking arms of US2 HVT virus and SB-1 virus.

PCR amplification with various primers confirmed that the vHVT306 had the expected amplification patterns and amplicons.

Genomic Analysis

The genomic DNA of vHVT306 pre-MSV stock was sequenced to verify the sequence of the recombination arm region as well as inserted gene cassette.

Primers were designed to amplify the entire inserted gene cassette including recombination arm used in donor plasmid. Analysis of vHVT306 genomic DNA was performed by PCR amplification and followed by nucleotide sequence determination.

The vHVT306 (donor plasmid pHVT US2 SV-Fopt-synPA) containing the recombinant arms, SV40 promoter and NDV F codon-optimized gene was confirmed to be correct as shown in SEQ ID NO:45 (FIG. 20).

Western Blot Analysis

The NDV F protein expression of vHVT306 was confirmed by two-step immunodetection. First, the expressed NDV F proteins from vHVT306 infected CEF were captured by the immunoprecipitation using anti-NDV F monoclonal antibody 001C3 (Merial Limited). Subsequently Western blot analysis using anti-NDV polyclonal serum (Charles River Laboratories) was applied to detect the NDV F protein in the captured samples (NDV F protein-monoclonal antibody complex). A 55 kDa protein in vHVT306 pre-MSV lysates was detected by anti-NDV serum which corresponds to the expected size of NDV F1 fusion protein.

Generation and Characterization of Other Double HVT Recombinants

Generation and characterization of double HVT recombinants, such as vHVT301, vHVT302, vHVT303, vHVT304, vHVT202, and vHVT307 were essentially done in the same way as for vHVT306 described above. The generation and characterization of recombinant HVT viral vectors were also described in U.S. patent application Ser. No. 13/689,625 filed on Nov. 29, 2012 (Merial limited), which is incorporated herein by reference in its entirety. Table 12 shows the features unique to each construct around the expression cassettes, including the respective sequences.

TABLE 12

| Characteristics of the expression cassettes of double HVT recombinants | | | | | |
|---|---|---|---|---|---|
| Name | Parental virus | Promoter | NDV-F gene or IBDV VP2 gene | Poly-A | Locus |
| vHVT301 | vHVT13 | SV40 | Wt-VIId NDV-F | SV40 | IG2 |
| vHVT302 | vHVT13 | US10 | Opt-VIId NDV-F | US10 | US10 |
| vHVT303 | vHVT13 | US10 | Opt-V (CA02) NDV-F | US10 | US10 |
| vHVT304 | vHVT13 | SV40 | Opt-VIId NDV-F | Synthetic | IG2 |
| vHVT306 | vHVT13 | SV40 | Opt-VIId NDV-F | Synthetic | SORF3-US2 |
| vHVT307 | vHVT13 | SV40 | Opt-V (CA02) NDV-F | Synthetic | SORF3-US2 |
| vHVT202 | vHVT306 | Guinea pig CMV | IBDV E VP2 | Synthetic | SORF3-US2 |

Example 8

Lack of Horizontal Transmission of gC-Deleted SB-1 Mutant

The objective of the study was to compare the level of viremia and horizontal transmission induced by the parental SB-1 with that of a recombinant SB-1 virus in which the gC gene was deleted (see example 3).

Two groups (A and B) of thirty one-day-old specific pathogen free (SPF) white Leghorn chicks were randomly constituted. Twenty birds from groups A were vaccinated (D0) by the subcutaneous route (nape of the neck; 0.2 ml/bird) with 2000 PFU of parental SB-1 and twenty from groups B with 2000 PFU of the SB-1 gC-deleted mutant. Ten birds were kept unvaccinated in the same isolator as the vaccinated birds (groups Ac and Bc). At 2-weeks-of-age (D14), the spleen as well as 2 feathers of twenty vaccinated birds of groups A and B were removed after euthanasia. At 4-weeks-of-age (D28) the spleen of the 10 contact birds of groups Ac and Bc were also removed for viral isolation. White blood cells were collected from the buffy coat of ground spleens which had added to lymphocyte separation medium and centrifuged. For each bird, $10^6$ leucocytes were added to a 60 mm tissue culture dish that contained confluent monolayers of primary chicken embryo fibroblasts (CEF) prepared the day before. Five days post-infection, MDV plaques were counted on each dish and the number of positive birds and mean number of plaques was calculated. For feather follicles samples, the feather pulp was added to SPGA medium and sonicated for 10 seconds before placing on confluent monolayers of primary CEF from which the media had been removed. The pulp suspension was allowed to absorb for 45 minutes prior to adding fresh media with 1% calf serum.

Results of virus isolation from spleen and from feather follicles of vaccinated birds at D14 are reported in Table 13. All birds from both groups were positive for virus isolation from spleen with a similar mean number of plaques of 142.5 and 176.0 for groups A and B, respectively. Virus could be isolated from feather follicles of all birds in group A and from 90% of birds in group B.

Results of virus isolation from spleen of unvaccinated contact birds at D28 are reported in Table 14. Seven out of ten birds from group Ac were positive for virus isolation from spleen indicating that the parental SB-1 spread horizontally to contact birds. Virus could not be isolated from birds of group Bc suggesting that the gC-deleted mutant did not spread to contact birds.

TABLE 13

Results of viral isolation from spleen buffy coat (BC) and from feather follicles (FF) of vaccinated birds from groups A and B at D 14

| Sample No. | Group A - SB1 | | Group B - SB-1 gC deleted | |
|---|---|---|---|---|
| | Spleen BC* | FF** | Spleen BC* | FF |
| 1 | 46 | + | 179 | + |
| 2 | 92 | + | 129 | + |
| 3 | 80 | + | 108 | + |
| 4 | 135 | + | 111 | + |
| 5 | 18 | + | 38 | + |
| 6 | 55 | + | 109 | − |
| 7 | 187 | + | 83 | − |
| 8 | 233 | + | 383 | + |
| 9 | 51 | + | 31 | + |
| 10 | 213 | + | 251 | + |
| 11 | 100 | + | 345 | + |
| 12 | 50 | + | 44 | + |
| 13 | 271 | + | 331 | + |
| 14 | 128 | + | 106 | + |
| 15 | 155 | + | 80 | + |
| 16 | 226 | + | TNTC (563) | + |
| 17 | 145 | + | 145 | + |
| 18 | 114 | + | 224 | + |
| 19 | 88 | + | 181 | + |
| 20 | TNTC*** (462) | + | 78 | + |
| Mean or positive/total | 142.5 | 20/20 | 176.0 | 18/20 |
| Standard deviation | 103.3 | − | 137.6 | − |

*Average plaque counts from spleen buffy coat (BC)
**positive sample from feather follicles
***TNTC too numerous to count

TABLE 14

Results of viral isolation from spleen buffy coat (BC) of unvaccinated contact birds from groups Ac and Bc at D 28

| Sample No. | Group Ac - SB-1 Spleen BCE* | Group Bc - SB-1 gC deleted Spleen BCE* |
|---|---|---|
| 1 | 0 | 0 |
| 2 | 0 | 0 |
| 3 | 0 | 0 |
| 4 | 8 | 0 |
| 5 | 129 | 0 |
| 6 | 3 | 0 |

TABLE 14-continued

Results of viral isolation from spleen buffy coat (BC) of unvaccinated contact birds from groups Ac and Bc at D 28

| Sample No. | Group Ac - SB-1 Spleen BCE* | Group Bc - SB-1 gC deleted Spleen BCE* |
|---|---|---|
| 7 | 25 | 0 |
| 8 | 1 | 0 |
| 9 | 108 | 0 |
| 10 | 1 | 0 |

*Average plaque counts

This study indicates that the level of viremia of the gC-deleted SB-1 mutant measured at D14 post-vaccination was similar to that of the parental SB-1 virus suggesting that the gC deletion did not impair the ability of the SB-1 virus to replicate in vaccinated birds. The level of virus at the feather follicle was slightly lower with the gC-deleted mutant since 2/20 birds did not have detectable amount of virus. Horizontal transmission could be detected in 7/10 birds in contact with birds vaccinated with the parental SB-1. In contrast, no virus could be detected from the birds in contacts with birds vaccinated with the gC-deleted mutant indicating that the gC deletion severely impaired horizontal transmission.

Example 9

ND Efficacy Induced by SB-1 Recombinant Alone or in Combination with an HVT-IBD Vector Vaccine in One Day-Old SPF Chickens The objective of the study was to evaluate the efficacy of the vSB1-004 recombinant expressing NDV F gene against an ND challenge performed at 4 week-of-age in SPF chicks vaccinated with vSB1-004 alone or in combination with an HVT-IBD vector vaccine.

Three groups (1, 2 and 3) of fifteen one-day-old specific pathogen free (SPF) white Leghorn chicks were randomly constituted. Two vectored vaccines were used: the vSB1-004 described in example 1 and vHVT13, an herpesvirus of turkey (HVT) vector expressing the VP2 gene of infectious bursal disease virus Faragher 52/70 strain (active ingredient of the Merial licensed VAXXITEK® HVT+IBD vaccine, U.S. Pat. No. 5,980,906 and EP 0 719 864). Birds from groups 1, 2 and 3 received vHVT13 only (control group), vSB1-004 only and a mix of vHVT13 and vSB1-004, respectively (see Table 6). All birds were vaccinated by the subcutaneous route (nape of the neck) with 2000 PFU of vSB1-004 and/or vHVT13 (D0). Twenty seven days after vaccination (D27), birds of each group were challenged with the genotype V Mexican Chimalhuacan (Mex V) velogenic NDV strain. The challenge was performed by the intramuscular (IM) route using $10^5$ Egg Infectious Dose 50 (EID50) diluted in 0.2 ml of physiological sterile water. Birds were observed daily during 14 days after challenge for clinical signs and mortality. Oropharyngeal swabs were also sampled from 10 birds per group 5, 7 and 9 days after challenge. The viral RNA load was evaluated in these swabs after RNA extraction by using a quantitative reverse transcriptase real time polymerase chain reaction (qRT-PCR) based on the M gene and described by Wise et al. (2004; Development of a Real-Time Reverse-Transcription PCR for Detection of Newcastle Disease Virus RNA in Clinical Samples; J. Clin. Microbiol. 42, 328-338). Shedding levels were expressed as log 10 egg infectious dose 50% (EID50) per mL. Blood was also sampled at the time of challenge (D27). The serums were tested with the anti-IBD ELISA (Synbiotics ELISA ProFlok PLUS IBD) to evaluate the impact of vSBA-004 on the vHVT13-induced IBDV antibodies.

Results of protection and serology are summarized in Table 15. All control birds died within 5 days after ND challenge. The vSB1-004 recombinant virus induced full clinical protection either alone or when combined with vHVT13. The number of birds shedding detectable amount of challenge ND virus was very low in both vaccinated groups. The mean IBD ELISA titers in groups 1 and 3 were nearly identical indicating the lack of vSB1-004 interference on vHVT13-induced IBDV antibodies.

group were challenged with the genotype V Mexican Chimalhuacan (Mex V) velogenic NDV strain and the other half with the genotype VIId Malaysia 04-1 (Mal VIId) velogenic NDV strain. The challenge was performed by the intramuscular (IM) route using $10^5$ Egg Infectious Dose 50 (EID50) diluted in 0.2 ml of physiological sterile water. Birds were observed daily during 14 days after challenge for clinical signs and mortality.

Results of protection are summarized in Table 16. All control birds died within 5 days after ND challenges. The vSB1-004 recombinant virus induced partial protection against mortality (70% and 40% protection after challenge with Mal VIId and Mex V, respectively) and against morbidity (50% and 30% protection after challenge with Mal VIId and Mex V, respectively) in these severe early challenge conditions.

TABLE 15

Results of ND protection induced by SB-1 recombinants expressing NDV F gene in SPF day-old chicks (15/group) challenged at D27

| Group | Vaccine (D0) | ND protection | IBD ELISA titer (log10 ± SD*) | Shedding in oropharyngeal swabs** D5*** | D7 | D9 |
|---|---|---|---|---|---|---|
| 1 | vHVT13 | 0% | 4.04 ± 0.15 | —**** | — | — |
| 2 | vSB1-004 | 100% | 0.26 ± 0.50 | 1/10 (2.2) | 0/10 | 0/10 |
| 3 | vSB1-004 + vHVT13 | 100% | 4.02 ± 0.08 | 3/10 (4.1) | 2/10 (2.8) | 1/9 (3.4) |

*Standard deviation

**number of birds shedding/total (mean log10 EID50 equivalent/mL)

***day post-challenge

****all birds of group 1 died before D5 and therefore, shedding was not evaluated in this group The ND challenge model with the genotype V Chimalhuacan velogenic NDV is very severe. In these severe challenge conditions, vSB1-004 induced full clinical protection and excellent protection against shedding of challenge virus by the oropharyngeal route. It is worth noting that the F gene inserted in vSB1-004 is from a genotype VIId NDV strain and the challenge strain used here is a genotype V. It shows therefore that the genotype VIId F gene inserted into the SB-1 vector is cross-protecting birds against a genotype V challenge. The addition of vHVT13 did not impair the ND protection induced by vSB1-004 and the vSB1-004 did not interfere on vHVT13-induced IBD antibody titers, demonstrating compatibility of SB-1 vector with HVT vector.

Example 10

ND Early Efficacy Induced by SB-1 Recombinant in One-Day-Old SPF Chickens

The objective of the study was to evaluate the efficacy of the vSB1-004 recombinant expressing NDV F gene against an early (D14) ND challenge in SPF chicks performed with two different NDV challenge strains.

Two groups (1 and 2) of twenty one-day-old specific pathogen free (SPF) white Leghorn chicks were randomly constituted. Birds from group 2 were vaccinated by the subcutaneous route (nape of the neck) with 2000 PFU of vSB1-004. Chicks from group 1 were not vaccinated and were kept as control birds. At 2 week-of-age, half of the birds of each

TABLE 16

Results of early ND protection induced by SB-1 recombinants expressing NDV F gene in SPF day-old chicks

| Group | Vaccine | Challenge strain | Protection against mortality | Protection against morbidity |
|---|---|---|---|---|
| 1 | — | Mal VIId | 0/10 | 0/10 |
| | | Mex V | 0/9 | 0/9 |
| 2 | vSB1-004 | Mal VIId | 7/10 | 5/10 |
| | | Mex V | 4/10 | 3/10 |

The early ND challenge model that was used to evaluate the efficacy of vSB1-004 recombinant was chosen because Marek's disease virus vectors expressing NDV F gene do not generally provide full protection in this model. Indeed, their onset of immunity is delayed compared to live NDV vaccines (Morgan et al. (1993) Avian Dis 37, 1032-40; Heckert et al. (1996) Avian Dis 40, 770-777). It is therefore a good model to evaluate and compare the vaccine candidates. In these severe early challenge conditions, vSB1-004 recombinant induced partial protection that was only slightly higher against the Malaysian genotype VIId challenge than against the Mexican Chimalhuacan genotype V one indicating a broad protection against the 2 most prevalent genotypes circulating in the Americas and Eurasia/Africa, respectively.

Example 11

ND Efficacy Induced by SB-1 Recombinant Alone or in Combination with an HVT-IBD Vector Vaccine in 1 Day-Old Broiler Chickens with Maternal Antibodies The objective of the study was to evaluate the efficacy of the vSB1-004 recombinant expressing NDV F gene against two ND challenges performed at 4 week of age in broiler chicks vaccinated with vSB1-004 alone or in combination with an HVT-IBD vector vaccine.

Six groups (1a, 1b, 2a, 2b, 3a, 3b) of twelve one-day-old broilers (Hubbard JA957 line) were randomly constituted. Two vectored vaccines were used: the vSB1-004 described in example 1 and vHVT13, an herpesvirus of turkey (HVT) vector expressing the VP2 gene of infectious bursal disease virus Faragher 52/70 strain (active ingredient of the Merial licensed VAXXITEK® HVT+IBD vaccine). Birds from groups 1 (1a & 1b) were vaccinated with vHVT13 only (control group); those from groups 2 with vSB1-004 only and those from groups 3 with a mix of vHVT13 and vSB1-004 (see Table 17). All birds were vaccinated by the subcutaneous route (nape of the neck) with 2000 PFU of vSB1-004 and/or vHVT13 (D0). Twenty eight days after vaccination (D28), all birds of each subgroup "a" were challenged with the genotype VIId Malaysia 04-1 (Mal VIId) velogenic NDV strain and all birds of each subgroup "b" with the genotype V Mexican Chimalhuacan (Mex V) velogenic NDV strain. The challenge was performed by the intramuscular (IM) route using $10^5$ Egg Infectious Dose 50 (EID50) diluted in 0.2 ml of physiological sterile water. Birds were observed daily during 14 days after challenge for clinical signs and mortality. Blood was also sampled from 5 birds in each group at the time of challenge (D28). The serums were tested with the anti-IBD ELISA (Synbiotics ELISA ProFlok PLUS IBD) to evaluate the impact of vSB1-004 on the vHVT13-induced IBDV antibodies in broilers.

Results of protection and serology are summarized in Table 17. All control birds died within 5 days after ND challenges. The vSB1-004 recombinant virus induced significant level of clinical protection when combined or not with vHVT13. The number of birds shedding detectable amount of virus was very low in both vaccinated groups. The mean IBD antibody titers in groups 2 was still high (3 log 10) at D27 indicating a high level of maternally-derived IBD antibodies; nevertheless, vHVT13 induced a clear IBD antibody response which was not affected when mixed with vSB1-004.

TABLE 17

Results of ND protection induced by SB-1 recombinants expressing NDV F gene in broiler day-old chicks (12 per group except group 1b: 11) challenged at D 28

| Group | Vaccine (D0) | ND challenge | ND protection | IBD ELISA titer (log10 ± SD*) |
|---|---|---|---|---|
| 1a | vHVT13 | Mal VIId | 0% | 3.94 ± 0.24 |
| 1b | vHVT13 | Mex V | 0% | |
| 2a | vSB1-004 | Mal VIId | 83% | 3.03 ± 0.44 |
| 2b | vSB1-004 | Mex V | 75% | |
| 3a | vSB1-004 + vHVT13 | Mal VIId | 75% | 4.02 ± 0.23 |
| 3b | vSB1-004 + vHVT13 | Mex V | 83% | |

*Standard deviation

Results of this study indicated significant levels of protection induced by vSB1-004 in broilers with NDV MDA. The addition of vHVT13 did not have negative impact on vSB1-004-induced ND protection indicating the lack of vHVT13 interference. Furthermore, vSB1-004 did not interfere on vHVT13-induced IBD antibodies, confirming in broilers the compatibility between these two vectors.

Example 12

Lack of Interference of vSB1-004 on IBD Early Efficacy Induced by an HVT-IBD Vector Vaccine in 1 Day-Old SPF Chicks The objective of the study was to evaluate the potential interference of the vSB1-004 recombinant on the IBD efficacy induced by an HVT-IBD vector vaccine (vHVT13) in an early (D14) IBD challenge model in SPF chicks.

Three groups (1 to 3) of ten one-day-old specific pathogen free (SPF) white Leghorn chicks were randomly constituted. Birds from group 1 were vaccinated by the subcutaneous route (nape of the neck) with 2000 PFU of vSB1-004 (control group). Chicks from group 2 were vaccinated with 2000 PFU of vHVT13 and birds from group 3 were vaccinated with 2000 PFU of vHVT13 and 2000 PFU of vSB1-004. At 2 week of age, all birds of each group were challenged by the ocular route with 50 μL containing 2.5 log 10 EID50 of the IBDV classical strain Faragher 52/70. Birds were observed daily during 10 days after challenge for clinical signs and mortality. All birds were euthanized 10 days after challenge and body and bursa of Fabricius weights were recorded in order to evaluate the bursa/body weight ratio. Their bursa was also checked for histological lesions typical of IBD. A score was assigned to each bursa based on the severity of the lesions as shown in Table 18. The number of affected birds (non-protected) in each group was calculated. A bird was considered as affected if it died and/or showed notable sign of disease and/or intermediate or severe lesions of the bursa of Fabricius (i.e., histology score ≥3).

TABLE 18

Scoring scale of histological lesions of the bursa of Fabricius

| Score | Histology observation/lesions |
|---|---|
| 0 | No lesion, normal bursa |
| 1 | 1% to 25% of the follicles show lymphoid depletion (i.e., less than 50% of depletion in 1 affected follicle), influx of heterophils in lesions |
| 2 | 26% to 50% of the follicles show nearly complete lymphoid depletion (i.e., with more than 75% of depletion in 1 affected follicle), the affected follicles show necrosis lesions and severe influx of heterophils may be detected |
| 3 | 51% to 75% of the follicles show lymphoid depletion; affected follicles show necrosis lesions and a severe influx of heterophils is detected |
| 4 | 76% to 100% of the follicles show nearly complete lymphoid depletion; hyperplasia and cyst structures are detected; affected follicles show necrosis lesions and severe influx of heterophils is detected |
| 5 | 100% of the follicles show nearly complete lymphoid depletion; complete loss of follicular structure; thickened and folded epithelium; fibrosis of bursal tissue |

Results of protection are summarized in Table 19. All control birds became sick and one died after challenge whereas all vaccinated birds remained healthy. The bursal body weight ratios of groups 2 and 3 were similar and significantly higher than that of group 1. All 8 birds that survived challenge from group 1 had bursa lesion scores of 4 or 5

TABLE 19

Results of early (D14) IBD protection induced by vHVT13 alone or in combination with vSB1-004 recombinant expressing NDV F gene in SPF day-old chicks.

| Group | Vaccine | Mortality | Morbidity | Bursal/Body weight ratio* 100 | Bursa with score ≥3 | Protection |
|---|---|---|---|---|---|---|
| 1 | vSB1-004 | 1/9* | 9/9 | 0.14 ± 0.02 | 8/8 | 0% |
| 2 | vHVT13 | 0/10 | 0/10 | 0.47 ± 0.10 | 0/10 | 100% |
| 3 | vHVT13 + vSB1-004 | 0/9* | 0/9 | 0.46 ± 0.20 | 1/9 | 89% |

*One bird in these groups died before challenge.

The early IBD challenge model that was used to evaluate the lack of interference of vSB1-004 recombinant on vHVT13-induced IBD protection was chosen because it is very sensitive to detect interference on vHVT13 protection. Results obtained with vSB1-004+vHVT13 indicated an excellent level of IBD protection (89%) indicating compatibility between vSB1-004 and vHVT13 even when measured in an early IBD challenge.

Example 13

Efficacy of vHVT114, vHVT116, vSB1-007, vSB1-008 (Alone or with vHVT13) and vHVT304 Against Challenges with NDV ZJ1 (Genotype VIId) and California/02 (Genotype V) at 21 Days of Age in SPF Chickens The aim of the study was to assess the efficacy of 2 single HVT recombinant constructs (vHVT114 and vHVT116), 2 SB1 recombinant constructs (vSB1-007 & vSB1-008) expressing the NDV F gene and a double HVT recombinant (vHVT304) against Newcastle disease challenge with NDV ZJ1 (genotype VIId) and California/02 (genotype V) performed at 21 days of age in SPF chickens.

The characteristics of these 5 vaccine candidates are described in Table 20 below.

TABLE 20

Characteristics of the vectors used in the challenge study

| Name | Parental virus | Promoter | F gene | Poly-A | Locus |
|---|---|---|---|---|---|
| vHVT114 | HVT | SV40 | Opt-VIId | SV40 | IG1 |
| vHVT116 | HVT | SV40 | Opt-V | SV40 | IG1 |
| vSB1-007 | SB-1 | SV40 | Opt-VIId | gC | gC |
| vSB1-008 | SB-1 | SV40 | Opt-V | SV40 | IG1 |
| vHVT304 | vHVT13* | SV40 | Opt-VIId | Synth | IG2 |

*vHVT13 is the active ingredient of the licensed Vaxxitek HVT-IBD vaccine based on an HVT vector expressing the IBDV VP2 gene (see U.S. Pat. No. 5,980,906 and EP 0 719 864).

On D0, 158 one-day-old SPF chickens were randomly allocated into 6 groups of 24 birds (vaccinated) and 1 group of 12 birds (non-vaccinated controls). The birds were injected by subcutaneous injection in the neck at D0 with 0.2 mL of recombinant vaccines containing a target dose of 1000 pfu as described in Table 21 below. The birds were then separated into two sub-groups, each sub-group being challenged by the intramuscular route on D21 with 5 log 10 EID50 of either NDV ZJ1 (genotype VIId) or California/02 (genotype V) velogenic strain.

TABLE 21

Results of efficacy

| Group | Vaccine at day-old (D0) | % clinical protection: CA/02 (genotype V) | ZJ1 (genotype VIId) |
|---|---|---|---|
| G1 | — | 0% | 0% |
| G2 | vHVT114 | 100% | 100% |
| G3 | vHVT116 | 100% | 90% |
| G4 | vSB1-007 | 92% | 100% |
| G5 | vSB1-008 | 100% | 100% |
| G6 | vSB1-008 + vHVT13 | 100% | 83% |
| G7 | vHVT304 | 92% | 75% |

Each group was monitored before and after challenge. Technical problems observed with isolators reduced the number of birds in group 2 (vHVT114: from 24 to 14) and in group 3 (vHVT116: from 24 to 20). NDV clinical signs were recorded after challenge. Serum was collected from blood samples taken from birds of groups 2 and 7 before challenge (D21) for NDV serology by HI test using each challenge strains as antigen.

Percentages of protection against mortality and morbidity are reported in the table above. Full susceptibility was observed in the non-vaccinated challenged control group G1 thus validating the high severity of both challenges. All vaccines induced high levels (≥75%) of protection against both challenges. Full clinical protection against both challenges was induced by vHVT114 and vSB1-008.

The shedding was evaluated after challenge by real time RT-PCR in oral and cloacal swabs taken 2 and 4 days post-challenge. Percentage of positive (Ct<40) birds are shown for both challenges in FIGS. 17A and 17B. Note that all 6 birds were dead at 4 dpch in the control group challenged with the CA/02 isolate and only one bird (out of 6) was still alive at 4 dpch in the control group challenged with ZJ1. Shedding was detected in all control birds. Reduction of the percentage of birds positive for shedding was observed in all vaccinated groups.

In conclusion, the results of this study showed the very good ND protection at 3 weeks of age induced by tested Marek's disease vector vaccines.

Example 14

Efficacy of vHVT114, vSB1-007, vSB1-009, vHVT306 and vHVT307 Vaccines Against Challenges with NDV Texas GB Strain at 28 Days of Age in SPF Chickens The aim of the study was to assess the efficacy of combinations of different Marek's disease vector vaccines expressing the NDV F and/or the IBDV VP2 gene against Newcastle disease challenge (Texas GB strain, genotype II) performed at 28 days of age in SPF chickens.

The characteristics of the 5 recombinant vaccine candidates tested in this study are described in Table 22 below.

TABLE 22

Characteristics of the vectors used in the challenge study

| Name | Parental virus | Promoter | F gene | Poly-A | Locus |
|---|---|---|---|---|---|
| vHVT114 | HVT | SV40 | Opt-VIId | SV40 | IG1 |
| vSB1-007 | SB-1 | SV40 | Opt-VIId | gC | gC |

TABLE 22-continued

Characteristics of the vectors used in the challenge study

| Name | Parental virus | Promoter | F gene | Poly-A | Locus |
|---|---|---|---|---|---|
| vSB1-009 | SB-1 | SV40 | Opt-V (CA02) | gC | gC |
| vHVT306 | vHVT13 | SV40 | Opt-VIId | Synth | SORF3-US2 |
| vHVT307 | vHVT13 | SV40 | Opt-V (CA02) | Synth | SORF3-US2 |

The Marek's disease virus serotype 1 (CVI988 (or Rispens) strain; Gallid herpesvirus 2) and serotype 2 (SB-1 strain; gallid herpesvirus 3) vaccines were used also in combination with recombinant viruses in some of the groups.

On D0, 135 one-day-old SPF chickens were randomly allocated into 9 groups of 15 birds. The birds were injected by subcutaneous injection in the neck at D0 with 0.2 mL containing a target dose of 2000 pfu for recombinant vaccines (vSB1-007, vSB1-009, vHVT13, vHVT306, vHVT307, vHVT114), and 1000 pfu for parental Marek's disease vaccine strains (SB-1 and CVI988). The design of the study is shown in Table 23 below. The birds were challenged by the intramuscular route on D28 with 4.0 log 10 EID50 velogenic ND Texas GB (genotype II) strain.

TABLE 23

Results of efficacy

| Group | Vaccine at day-old (D0) | % ND protection after Newcastle disease challenge at 28 days of age |
|---|---|---|
| G1 | — | 0% |
| G2 | vSB1-007 + vHVT13 | 80% |
| G3 | vSB1-009 | 100% |
| G4 | vSB1-009 + vHVT13 | 86% |
| G5 | vSB1-009 + vHVT13 + CVI988 | 93% |
| G6 | vHVT306 + SB-1 | 100% |
| G7 | vHVT307 | 100% |
| G8 | vHVT307 + SB-1 | 93% |
| G9 | vHVT114 + vHVT13 + SB-1 | 100% |

Each group was monitored before and after challenge. NDV clinical signs after challenge were recorded.

Percentages of protection against mortality and morbidity are reported in the table 23 above. Full susceptibility was observed in the non-vaccinated challenged control group G1 thus validating the high severity of challenge. Excellent levels of protection were observed in all vaccinated groups. Birds from G3, G6, G7 and G9 were fully protected. This study shows that the vSB1-ND candidates can be co-administered with vHVT13 and CVI988 and still provide a very good ND protection. Similarly, double HVT-IBD+ND are compatible with SB-1 and vHVT-ND (vHVT114) is compatible with vHVT13 and SB-1.

In conclusion, the results of this study showed the lack of interference on ND protection induced by the tested Marek's disease parental and vector vaccines.

Example 15

Efficacy of vHVT114, vHVT307, vSB1-007 and vSB1-009 in Combination with vHVT13 Against Challenges with NDV Chimalhuacan Strain (Genotype V) at D28 in SPF Chickens The aim of the study was to assess the efficacy of one HVT recombinant construct (vHVT114) and two SB1 recombinant constructs (vSB1-007 and vSB1-009) expressing the NDV F gene in combination with vHVT-IBD (vHVT13), as well as a double HVT vHVT307 expressing both NDV F and IBDV VP2 against Newcastle disease challenge (Chimalhuacan, genotype V) performed at 28 days of age in SPF chickens.

The characteristics of these 4 vaccine candidates are described in Table 24 below.

TABLE 24

Characteristics of the vectors used in the challenge study

| Name | Parental virus | Promoter | F gene | Poly-A | Locus |
|---|---|---|---|---|---|
| vHVT114 | HVT | SV40 | Opt-VIId | SV40 | IG1 |
| vSB1-007 | SB-1 | SV40 | Opt-VIId | gC | gC |
| vSB1-009 | SB-1 | SV40 | Opt-V (CA02) | gC | gC |
| vHVT307 | vHVT13* | SV40 | Opt-V (CA02) | Synth | SORF3-US2 |

On D0, 45 one-day-old SPF chickens were randomly allocated into 4 groups of 10 birds and 1 group of 5 birds (unvaccinated control group). The birds were injected by subcutaneous injection in the neck at D0 with 0.2 mL of recombinant vaccines containing a target dose of 2000 pfu as described in Table 25 below. The birds were challenged by the intramuscular route on D28 with 5.0 log 10 EID50 velogenic Chimalhuacan (genotype V) strain.

TABLE 25

Study design and results of ND efficacy

| Group | Vaccine at day-old (D0) | % protection against mortality | % protection against morbidity |
|---|---|---|---|
| G1 | — | 0% | 0% |
| G2 | vHVT114 + vHVT13 | 100% | 100% |
| G3 | vHVT307 | 80% | 80% |
| G4 | vSB1-007 + vHVT13 | 90% | 90% |
| G5 | vSB1-009 + vHVT13 | 90% | 90% |

Each group was monitored before and after challenge. NDV clinical signs were recorded after challenge. Oropharyngeal swabs were taken in the vaccinated groups at 5 and 7 days post-challenge to evaluate the viral load by real time RT-PCR.

Percentages of protection against mortality and morbidity are reported in the table above. Full susceptibility was observed in the non-vaccinated challenged control group G1 thus validating the high severity of challenge. Very good protection was observed in all 4 vaccinated groups, a full clinical protection being induced by vHVT114+vHVT13. The percentage of positive birds and the mean shedding titer (expressed as log 10 EID50 equivalent per mL) are shown in FIGS. 18A and 18B. Surprisingly, no shedding was detected in G2 indicating a complete (against both clinical signs and shedding) ND protection induced by vHVT114 even if co-administered with vHVT13, in the tested conditions. The shedding levels detected in the other vaccinated groups were low with a slightly higher level detected in G3 (vHVT307) at 5 days post-infection (pi) only.

In conclusion, this example further illustrates the excellent ND protection induced by double HVT-IBD+ND recombinant or a combination of SB1-ND or HVT-ND and HVT-IBD (vHVT13) recombinant viruses. Contrary to the general belief in the field that a second HVT vaccine (regular HVT vaccines or recombinant HVT vaccines) interferes with the immunity to the foreign genes inserted into the first recombinant HVT vaccine, the present invention showed surprising result that vHVT114 in combination with vHVT13 offered excellent protection against NDV and no interference effect was observed.

Example 16

Efficacy of vHVT306, vSB1-008 in Combination with vHVT13 Administered by SC or in Ovo Route Against Challenge with NDV Chimalhuacan Strain (Genotype V) at D28 in SPF Chickens The aim of the study was to assess the efficacy of the vHVT306 double HVT expressing both NDV F and IBDV VP2 genes, and the vSB1-008 SB1 recombinant expressing the NDV F gene in combination with vHVT-IBD (vHVT13), administered by the in ovo or by the subcutaneous route against Newcastle disease challenge (Chimalhuacan, genotype V) performed at 28 days of age in SPF chickens.

The design of the groups is shown on Table 26. Sixty SPF embryonated eggs (after approximately 18 days and 18 hours of incubation; D-3) were used for the in ovo administration (20 per group for G1, G2 and G3). Fifty microliters of vaccine containing 2000 PFU were administered by the in ovo route using the IntelliLab System device from AviTech LLC (Salisbury, Md., USA). Hatchability and survival were recorded after in ovo administration. On D0, 20 one-day-old SPF chickens were randomly allocated into 2 groups of 10 birds (G4 and G5). The birds were injected by subcutaneous (SC) injection in the neck at D0 with 0.2 mL of recombinant vaccines containing a target dose of 2000 pfu as described in Table 26 below. Ten birds per group were challenged by the intramuscular route on D28 with 5.0 log 10 EID50 velogenic Chimalhuacan (genotype V) strain.

TABLE 26

Study design and results of ND efficacy

| Group | Vaccine at day-old (D0) | Admin. route | % protection against mortality | % protection against morbidity |
|---|---|---|---|---|
| G1 | vHVT13 | In ovo | 0% | 0% |
| G2 | vHVT306 | In ovo | 100% | 100% |
| G3 | vSB1-008 + vHVT13 | In ovo | 78% | 68% |
| G4 | vHVT306 | SC | 100% | 100% |
| G5 | vSB1-008 + vHVT13 | SC | 100% | 70% |

Each group was monitored before and after challenge. NDV clinical signs were recorded after challenge. Oropharyngeal swabs were taken in the vaccinated groups at 5 and 7 days post-challenge to evaluate the viral load by real time RT-PCR.

Full hatchability and viability were recorded up to D28 (challenge day) for birds of groups G1 and G2. Hatchability in G3 was 85% and one additional bird died after hatching in this group. The lower hatchability of that group may be due to egg incubator problems. Body weights of males and females in G1, G2 and G3 were similar at D1 and at D28.

Percentages of protection against mortality and morbidity are reported in the table 26. Full susceptibility was observed in the non-vaccinated challenged control group G1 thus validating the high severity of challenge. Very good protection was observed in all 4 vaccinated groups, a full clinical protection being induced by vHVT306 administered by both routes.

The percentage of positive birds and the mean shedding titer (expressed as log 10 EID50 equivalent per mL) are shown in Table 27. Absence of detectable or very low shedding was observed in G2 and G4 vaccinated with vHVT306. The shedding levels detected in the groups vaccinated with vSB1-008+vHVT13 were higher especially at 5 days post-infection (pi).

TABLE 27

Results of protection against shedding (percentage of birds with detectable shedding and mean viral load in log10) evaluated at D5 and D7 after NDV challenge

| Group | Vaccine at day-old (D0) | Admin. Route | Percent of positive birds (D5/D7 pi) | Mean viral load* (D5/D7 pi) |
|---|---|---|---|---|
| G2 | vHVT306 | In ovo | 0/0% | 2.7/2.7 |
| G3 | vSB1-008 + vHVT13 | In ovo | 100/38% | 5.2/3.2 |
| G4 | vHVT306 | SC | 20/10% | 3.2/2.9 |
| G5 | vSB1-008 + vHVT13 | SC | 80/50% | 4.6/3.4 |

*Mean quantitative real time PCR value expressed in equivalent log10 EID50; the threshold is set at 2.7 log10.

In conclusion, this example shows excellent ND protection induced by vHVT306 double HVT recombinant administered either by in ovo or by SC routes. The performance of vSB1-008+vHVT13 was slightly lower especially after in ovo administration, but it may be at least partially due to egg incubator problems. Indeed, the in ovo safety testing of another SB1-ND recombinant (vSB1-009) at 1000 or 4000 PFU associated with 6000 PFU of vHVT13 did not show any difference in hatchability and early survival with a group receiving 6000 PFU of vHVT13 only.

Example 17

Efficacy of vHVT304, vHVT306, vSB1-007 and vSB1-008 in Combination with vHVT13 Against Challenge with NDV Chimalhuacan Strain (Genotype V) at D42 in Commercial Broiler Chickens The aim of the study was to assess the efficacy of two double HVT (vHVT304 and vHVT306) expressing both NDV F and IBDV VP2 genes, and two SB1 recombinants (vSB1-007 and vSB1-008) expressing the NDV F gene in combination with vHVT-IBD (vHVT13) against Newcastle disease challenge (Chimalhuacan, genotype V) performed at 42 days of age in commercial broiler chickens.

The design of the groups is shown on Table 28. On D0, 55 one-day-old commercial broiler chickens were randomly allocated into 5 groups of 11 birds. The birds were injected by subcutaneous (SC) injection in the neck at D0 with 0.2 mL of recombinant vaccines containing a target dose of 2000 pfu as described in Table 28 below. Ten birds per group were challenged by the intramuscular route on D42 with 5.0 log 10 EID50 velogenic Chimalhuacan (genotype V) strain.

TABLE 28

Study design and results of ND efficacy

| Group | Vaccine at day-old (D0) | % protection against mortality | % protection against morbidity |
|---|---|---|---|
| G1 | vHVT13 | 0% | 0% |
| G2 | vHVT304 | 82% | 82% |

TABLE 28-continued

| Study design and results of ND efficacy | | | |
|---|---|---|---|
| Group | Vaccine at day-old (D0) | % protection against mortality | % protection against morbidity |
| G3 | vHVT306 | 100% | 100% |
| G4 | vSB1-007 + vHVT13 | 100% | 100% |
| G5 | vSB1-008 + vHVT13 | 91% | 91% |

Each group was monitored before and after challenge. NDV clinical signs were recorded during 14 days after challenge. Oropharyngeal swabs were taken in the vaccinated groups at 5 and 7 days post-challenge to evaluate the viral load by real time RT-PCR.

Percentages of protection against mortality and morbidity are reported in the table 28. Full susceptibility was observed in the non-vaccinated challenged control group G1 thus validating the high severity of challenge. Very good protection was observed in all 4 vaccinated groups, a full clinical protection being induced by vHVT306 and by vSB1-007+ vHVT13.

The percentage of positive birds and the mean shedding titer (expressed as log 10 EID50 equivalent per mL) are shown in Table 29. The best reduction of shedding was induced by vHVT306 and vSB1-007+vHVT13, which were also the best candidates for clinical protection.

TABLE 29

| Results of protection against shedding (percentage of birds with detectable shedding and mean viral load in log10) evaluated at D5 and D7 after NDV challenge (pi) | | | |
|---|---|---|---|
| Group | Vaccine at day-old (D0) | Percent of positive birds (D5/D7 pi) | Mean viral load* (D5/D7 pi) |
| G2 | vHVT304 | 100/100% | 5.4/4.6 |
| G3 | vHVT306 | 40/50% | 3.5/3.7 |
| G4 | vSB1-007 + vHVT13 | 80/70% | 3.8/4.8 |
| G5 | vSB1-008 + vHVT13 | 100/100% | 4.8/4.3 |

*Mean quantitative real time PCR value expressed in equivalent log10 EID50; the threshold is set at 2.7 log10.

The vSB1-007+vHVT13 performed better than vSB1-008+vHVT13. The vSB1-007 genomic structure differs from that of vSB1-008 in different aspects: locus of insertion, promoter, poly-adenylation signal and F gene origin. The combination of these foreign sequences and locus of insertion in vSB1-007 were likely responsible for its better ND protection performances.

In summary, this example illustrates the importance of the locus of insertion and other regulatory sequences of the NDV expression cassette in the ND protection induced by HVT and MDV serotype 2 vectors.

Example 18

Efficacy of Double HVT-ND+IBD (vHVT304 and vHVT306) or SB1-ND (vSB1-008) in Combination with vHVT13 Recombinant Vaccines, Against Challenge with a Classical IBDV Isolate on D14 in SPF Chickens The aim of the study was to assess the early IBD efficacy of double HVT recombinants vHVT304 and vHVT306 as well as that of vHVT13 co-administered with a SB1-ND (vSB1-008) recombinant constructs against a virulent infectious bursal disease virus (vIBDV) challenge (Faragher 52/70 strain) performed at 14 days of age in SPF chickens.

On D0, 95 one-day-old SPF chickens were randomly allocated into 9 groups of 10 birds and 1 group of 5 birds (unvaccinated unchallenged control group). The birds were injected by subcutaneous injection in the neck at D0 with 0.2 mL of recombinant vaccines containing a target dose of 300 or 1000 pfu as described in the Table 30 below. On D14, blood sample was collected from 5 birds per group for serological testing with the Kit ProFLOK® plus IBD (Synbiotics Corp). The birds (10 birds per group except for group 7 in which 1 bird died before challenge) were challenged by the eye drop (0.05 mL per bird) with 2.5 log 10 EID50.

TABLE 30

| Study design and results of IBD efficacy | | | | | |
|---|---|---|---|---|---|
| Group | Vaccine at day-old (dose in PFU) | IBD+ ELISA titer at D 14[1] | Number Dead/ Sick[2] | % protection[3] | Mean bursal/body weight ratio[4] |
| G1 | vSB1-008 (1000) | 0.2 | 7/10 | 0% | 0.0013 |
| G2 | vHVT13 (300) | 2.7 | 0/0 | 100% | 0.0051 |
| G3 | vHVT13 (1000) | 2.7 | 0/0 | 90% | 0.0049 |
| G4 | vHVT13 + vSB1-008 (300) | 1.9 | 1/1 | 60% | 0.0041 |
| G5 | vHVT13 + vSB1-008 (1000) | 2.4 | 0/0 | 70% | 0.0041 |
| G6 | vHVT304 (300) | 2.9 | 0/0 | 60% | 0.0037 |
| G7 | vHVT304 (1000) | 2.2 | 0/0 | 67% | 0.0047 |
| G8 | vHVT306 (300) | 2.4 | 0/0 | 80% | 0.0033 |
| G9 | vHVT306 (1000) | 2.7 | 0/0 | 40% | 0.0026 |

[1]Mean IBD+ ELISA titers expressed in log10 in the serum of 5 birds per group sampled at D14 before challenge;
[2]Birds sick for more than 2 days or still sick on D25 were considered as sick.
[3]Protection against clinical signs and severe bursal lesion (bursal score <3)
[4]The bursal/body weight ratio of the unvaccinated/unchallenged group was 0.0047.

Each group was monitored before and after challenge. IBDV clinical signs were recorded for 11 days after challenge (from D15 to D25). At the end of the post-challenge observation period (D25), all the surviving birds were euthanized and necropsied. Body and bursal weights were recorded. Each bursa of Fabricius (BF) was weighted then stored in individual recipients containing 4% formaldehyde for histology. Histological lesions of the bursa were scored according to the scale presented in Table 31.

TABLE 31

| Scoring scale of histological lesions of the bursa of Fabricius* | |
|---|---|
| Score | Histology observation/lesions |
| 0 | No lesion, normal bursa |
| 1 | 1% to 25% of the follicles show lymphoid depletion (i.e. less than 50% of depletion in 1 affected follicle), influx of heterophils in lesions |
| 2 | 26% to 50% of the follicles show nearly complete lymphoid depletion (i.e. more than 75% of depletion in 1 affected follicle), affected follicles show necrosis and severe influx of heterophils may be detected |
| 3 | 51% to 75% of the follicles show lymphoid depletion; affected follicles show necrosis lesions and a severe influx of heterophils is detected |
| 4 | 76% to 100% of the follicles show nearly complete lymphoid depletion; hyperplasia and cyst structures are detected; affected follicles show necrosis and severe influx of heterophils is detected |

TABLE 31-continued

| Scoring scale of histological lesions of the bursa of Fabricius* | |
|---|---|
| Score | Histology observation/lesions |
| 5 | 100% of the follicles show nearly complete lymphoid depletion; complete loss of follicular structure, thickened and folded epithelium, fibrosis of bursal tissue |

*sourced from Monograph No. 01/2008: 0587 of EU Pharmacopoeia "Avian Infectious Bursal Disease vaccine (live)

A bird was considered as affected if it died and/or showed notable sign of disease and/or severe lesions of the bursa of Fabricius (i.e., histology score ≥3).

The mean ELISA IBD+ antibody titer expressed in log 10 before challenge is shown in Table 30. Significant titers were detected in all vaccinated groups that were significantly higher than that of the control group G1. The serology titer was not dose-dependent.

Severe clinical signs were observed after challenge in all birds of the control group G1. Seven out of 10 birds of that group died within the 11 days observation period indicating the high severity of challenge. None of the vaccinated birds showed severe clinical signs after challenge except 1 bird of G4 that died. Percentages of protection against severe bursal lesions are shown in the table 30 above. Significant IBD protection was observed in all groups, the best protection being observed in G2 and G3 (vHVT13 alone). The co-administration of vSB1-008+vHVT13 and the double vHVT304 and vHVT306 constructs induced similar levels of IBD protection. The protection was not dose-dependent at the tested doses. The mean bursal/body weight ratios are also shown in Table 30. Ratios in all vaccinated groups were higher than those of the challenged control group.

In conclusion, these data indicate that both the combination of a SB1-ND vector with a single HVT-IBD or double HVT expressing both NDV-F and IBDV-VP2 induce IBD antibodies and early IBD protection in a severe IBDV challenge model.

Example 19

Efficacy of Single HVT-ND (vHVT114) or SB1-ND (vSB1-007 and vSB1-009) in Combination with vHVT13 Recombinant Vaccines, Against Challenge with a Very Virulent IBDV Isolate on D23 in Commercial Broiler Chickens The aim of the study was to assess the IBD efficacy of vHVT13 co-administered with an HVT-ND (vHVT114) or SB1-ND (vSB1-007 and vSB1-009) recombinant constructs against a very virulent infectious bursal disease virus (vvIBDV) challenge (91-168/980702 isolate) performed at 23 days of age in commercial broiler chickens.

On D0, 90 one-day-old broiler chickens were randomly allocated into 7 groups of 12 birds and 1 group of 6 birds (unvaccinated unchallenged control group). The birds were injected by subcutaneous injection in the neck at D0 with 0.2 mL of recombinant vaccines containing a target dose of 3000 pfu as described in the Table 32. On D14, blood sample was collected from 5 birds per group for serological testing with the Kit ProFLOK® plus IBD (Synbiotics Corp). The serum of 10 extra one-day-old broiler chickens was tested at D0 with the same kit to evaluate the level of IBDV maternal antibody. The birds (10 birds per group) were challenged by the eye drop (0.05 mL per bird) on D23 with 4.3 log 10 EID50 of the vvIBDV 91-168 isolate.

Each group was monitored before and after challenge. IBDV clinical signs were recorded for 11 days after challenge (from D23 to D33). At the end of the post-challenge observation period (D33), all the surviving birds were euthanized and necropsied. Body and bursal weights were recorded. Each bursa of Fabricius (BF) was weighted then stored in individual recipients containing 4% formaldehyde for histology. Histological lesions of the bursa were scored according to the scale presented in Table 31.

A bird was considered as affected if it died and/or showed notable signs of disease and/or severe lesions of the bursa of Fabricius (i.e., histology score ≥3).

TABLE 32

Study design and serology results

| Group | Vaccine at day-old (D0) | IBD+ ELISA titer at D23[1] | Mean bursal/body weight ratio[2] |
|---|---|---|---|
| G1 | — | 3.9 | 0.0007 |
| G2 | vHVT13 | 4.0 | 0.0015 |
| G3 | vHVT114 + vHVT13 | 4.1 | 0.0015 |
| G4 | vSB1-007 + vHVT13 | 3.8 | 0.0018 |
| G5 | vSB1-009 + vHVT13 | 4.0 | 0.0019 |

[1]Mean IBD+ ELISA titers expressed in log10 in the serum of 5 birds per group sampled at D23 before challenge;
[2]The bursal/body weight ratio of the unvaccinated/unchallenged group was 0.0047

The mean ELISA IBD+ serological titer at D0 was 4.36±0.01 log 10 indicating a very high level of IBD maternal antibody at hatch. At D23, the mean ELISA IBD+ titer was still high (3.9) in the control G1. ELISA mean titers in the vaccinated groups were not significantly different from those of the control group.

Neither morbidity nor mortality was observed in any of the groups after challenge. Percentages of protection against severe bursal lesions are shown in Table 32 above. The result showed that co-administration of vHVT114, vSB1-007 or vSB1-009 did not interfere with vHVT13-induced IBD protection indicating a lack of interference. Similarly, the mean bursal/body weight ratios of the vaccinated groups were similar and clearly higher than that of the control group, indicating IBD protection and no difference between the vaccination regimens.

In conclusion, the data indicate the compatibility between vHVT114, vSB1-007 or vSB1-009 and vHVT13 for IBD protection.

Example 20

Efficacy of Double HVT-ND+IBD (vHVT304 and vHVT306) Associated or not with SB-1 and of SB1-ND (vSB1-007 and vSB1-008) in Combination with vHVT13 Recombinant Vaccines, Against Challenge with a Variant E IBDV Isolate on D28 in SPF Chickens The aim of the study was to assess the efficacy of two double HVT (HVT-ND+IBD: vHVT304 and vHVT306) or two vSB-1-NDV in combination with vHVT13 (vSB1-007+vHVT13, vSB1-008+vHVT13) vectored vaccines administered subcutaneously (SC) to day-old SPF chicks and challenged with IBDV-Variant (VAR-E) 28 days post-vaccination.

On D0, 105 one-day-old SPF chickens were randomly allocated into 7 groups of 15 birds including a group of challenged controls (G6) and unchallenged controls (G7).

The birds of groups G1 to G5 were injected by subcutaneous injection in the neck at D0 with 0.2 mL of recombinant and/or SB-1 vaccines containing each a target dose of 2000 pfu. The design of the study is shown in Table 33 below. On D28, all birds from groups G1 to G6 were challenged by the eye drop (0.03 mL containing 3 log 10 EID50 per bird) of the IBDV variant E isolate from University of Delaware (USA). Each group was monitored before and after challenge. Eleven days post-challenge, birds were weighed and necropsied. The bursa were collected and weighed. The bursal/body weight ratio (bursa weight/body weight ratio×100) was calculated.

TABLE 33

Study design and results of IBD efficacy

| Group | Vaccine at day-old | Mean bursal/body weight ratio (*100) |
|---|---|---|
| G1 | vHVT304 | 0.33 |
| G2 | vHVT304 + SB-1 | 0.33 |
| G3 | vHVT306 | 0.29 |
| G4 | vHVT13 + vSB1-007 | 0.49 |
| G5 | vHVT13 + vSB1-008 | 0.47 |
| G6 | - (challenged) | 0.13 |
| G7 | - (unchallenged) | 0.46 |

The mean bursal/body weight ratios are shown in Table 33. The challenged control birds had a severe bursal atrophy compared to unchallenged ones. The vSB1-007 and vSB1-008 vaccines did not interfere on vHVT13-induced protection (G4 and G5). The bursal/body weight ratios of birds vaccinated with the double HVT (HVT-ND+IBD) were slightly lower than the unchallenged control group but were clearly higher than the challenged control groups. Furthermore, the SB-1 serotype 2 Marek's disease vaccine did not interfere with vHVT304-induced IBD protection.

In conclusion, these data indicate that both the combination of a SB1-ND vector with a single HVT-IBD or double HVT expressing both NDV-F and IBDV-VP2 induce IBD protection in a variant E IBDV challenge model.

Example 21

Lack of Interference of vHVT114, vSB1-009 and/or SB-1 on vHVT13 Induced Variant E IBD Protection in SPF Chickens The aim of the study was to assess the IBD efficacy of vHVT13 when administered by SC or in ovo route concomitantly with vHVT114, vSB1-009 and/or SB-1 in SPF chicks in an IBDV-Variant (VAR-E) at D28 challenge model.

75 one-day-old SPF chickens and 75 SPF 18 to 19 day-old chicken embryo were randomly allocated into 5 groups (G1 to G5 and G6 to G10, respectively) including a group of challenged controls (G4 and G9, respectively) and unchallenged controls (G5 and G10, respectively). The birds of groups G1 to G3 were injected by subcutaneous injection in the neck at D0 with 0.2 mL of vaccines containing each a target dose of 3000 pfu except for SB-1 which had a target dose of 1000 PFU. Birds from G6 to G8 received the same vaccine doses but in 0.05 mL volume by the in ovo route 2-3 days before hatch. The design of the study is shown in Table 34 below. At 28 days of age, all birds from groups G1 to G4 and G6 to G9 were challenged by the eye drop (0.03 mL containing 3 log 10 EID50 per bird) of the IBDV variant E isolate from University of Delaware (USA). Each group was monitored before and after challenge. Eleven days post-challenge, birds were weighed and necropsied. The bursa were collected and weighed. The bursal/body weight ratio (bursa weight/body weight ratio×100) was calculated.

TABLE 34

Study design and results of IBD efficacy

| Group | Vaccine at day-old | Administration route | Mean bursal/ body weight ratio (*100) |
|---|---|---|---|
| G1 | vHVT13 + vHVT114 + SB-1 | SC | 0.56 |
| G2 | vHVT13 + vHVT114 + vSB1-009 | SC | 0.58 |
| G3 | vHVT13 + vSB1-009 | SC | 0.52 |
| G4 | - (challenged) | SC | 0.13 |
| G5 | - (unchallenged) | SC | 0.51 |
| G6 | vHVT13 + vHVT114 + SB-1 | In ovo | 0.54 |
| G7 | vHVT13 + vHVT114 + vSB1-009 | In ovo | 0.47 |
| G8 | vHVT13 + vSB1-009 | In ovo | 0.53 |
| G9 | - (challenged) | In ovo | 0.14 |
| G10 | - (unchallenged) | In ovo | 0.58 |

The mean bursal/body weight ratios are shown in Table 34. The challenged control birds (G4 and G9) had a severe bursal atrophy compared to unchallenged ones. The bursal/body weight ratios of the vaccinated groups (G1 to G3 and G6 to G8) were similar to those of the unchallenged control groups (G5 and G10) and well above those of the challenged control groups (G4 and G9). The lack of interference of vHVT114 on vHVT13-induced IBD protection after both SC or in ovo routes was surprising and confirmed data obtained in examples 15 and 19.

In conclusion, these data indicate clearly the compatibility of vHVT114+vSB1-009 or +SB-1 and of vSB1-009 with vHVT13 when administered by SC or in ovo route in a variant E IBDV challenge model.

Example 22

Efficacy of vHVT114 and vHVT13 and SB1 or vSB1-009 Vectors Against Very Virulent Plus Marek's Disease Challenge The aim of this study was to evaluate the Marek's disease efficacy induced by different combinations of vaccines including vHVT114, vHVT13, SB-1 and/or vSB1-009 administered by the SC route to one-day-old SPF chicks and challenged 4 days later with the very virulent plus Marek's disease virus (vv+MDV) T-King isolate.

On D0, 100 one-day-old SPF chickens were randomly allocated into 5 groups of 20 birds. The birds from groups 1 to 3 were injected by subcutaneous injection in the neck at D0 with 0.2 mL of vaccines containing a target dose of 2000 pfu for each vaccine except for SB-1 for which the target dose was 1000 pfu. Birds from groups 4 and 5 were non-vaccinated and were used as sham controls challenged (group 4) or unchallenged (group 5). The study design is shown in the Table 35. On D4, All birds from groups 1 to 4 were challenged with 0.2 mL of the vv+MDV T-King isolate using the intraperitoneal route of administration.

TABLE 35

Study design and MD protection results

| Group | Vaccine at day-old (D0) | Number of MD positive/total | Percentage of protection |
|---|---|---|---|
| G1 | vHVT13 + SB-1 | 7/20 | 65% |
| G2 | vHVT114 + SB-1 | 7/20 | 65% |

TABLE 35-continued

| Study design and MD protection results | | | |
|---|---|---|---|
| Group | Vaccine at day-old (D0) | Number of MD positive/total | Percentage of protection |
| G3 | vHVT13 + vHVT114 + vSB1-009 | 7/20 | 65% |
| G4 | - (challenged) | 20/20 | 0% |
| G5 | - (unchallenged) | 0/20 | 100% |

Each group was monitored daily for any unfavourable reactions before and after challenge. At day 49, all live birds were terminated and necropsied to examine for gross lesions associated with Marek's disease. Chickens were classified as positive for infection with Marek's disease if nervous signs, such as paralysis, locomotive signs attributable to the disease, and severe emaciation or depression are observed, if mortality directly attributable to Marek's Disease occurs, or if gross lesions are observed at necropsy. Lesions might include, but not be limited to, the following: liver, heart, spleen, gonads, kidneys, and muscle lesions Results of protection are shown in the Table 35 above. All vaccinated groups (G1 to G3) performed equally, inducing a partial (65%) MD protection as expected in this very severe and early challenge model. These results indicated that the vector vaccine candidates retain their ability to protect against Marek's disease.

Example 23

Evaluation of Marek's Disease Efficacy of the SB1-ND Vector Combined with HVT-IBD Vector The synergy between parental HVT and SB-1 in inducing a protection against Marek's disease is well known. The SB-1 vector expressing a foreign gene can therefore be mixed with either parental HVT or vectored HVT expressing another foreign gene in order to get a bivalent or a trivalent vaccine solution, respectively. An example of evaluation of Marek's disease efficacy induced by a combination of vSB1-009 with vHVT114 and vHVT13 is shown above (example 22). Marek's disease (MD) efficacy is also demonstrated for Marek's disease vectored recombinants either alone or in combination in other MD challenge models including virulent Marek's disease (vMD) challenge such as GA22, very virulent Marek's disease (vvMD) challenge such as RB1B and/or very virulent plus Marek's disease (vv+MD) challenge such as the T. King virus. One-day-old chickens are inoculated subcutaneously or 18-19-day-old embryonated eggs are inoculated with a 0.2 ml dose or 0.05 ml dose, respectively, of the test viruses. At five days of age the vaccinated chickens and naïve controls are challenged with the relevant Marek's challenge virus (v, vv, or vv+MDV). The challenged birds are observed until seven weeks of age. All birds are terminated and necropsied to observe for grossly visible lesions associated with Marek's disease as described in Example 22.

Example 24

Efficacy of vSB1-004, vSB1-006, vSB1-007, vSB1-008, SB1-Vectored ND Vaccine Alone or in Association with vHVT13 HVT-Vectored IBD Vaccine, and the vHVT302 and vHVT304 Vaccines Against Challenges with NDV Texas GB Strain at 14 and/or 28 Days of Age in SPF Chickens The aim of the study was to assess the efficacy of combinations of different Marek's disease vector vaccines expressing the NDV F and/or the IBDV VP2 gene against Newcastle disease challenge (Texas GB strain, genotype II) performed at 14 and/or 28 days of age in SPF chickens.

The characteristics of the 6 NDV recombinant vaccine candidates tested in this study are described in the Table 36 below.

TABLE 36

| characteristics of the 6 NDV recombinant vaccine candidates tested in this study | | | | | |
|---|---|---|---|---|---|
| Name | Parental virus | Promoter | F gene | Poly-A | Locus |
| vSB1-004 | SB-1* | mCMV IE | Wt-VIId | SV40 | SORF4/US10 |
| vSB1-006 | SB-1 | SV40 | Opt-VIId | Synthetic | UL55/LORF5 |
| vSB1-007 | SB-1 | SV40 | Opt-VIId | (endogeneous from gC gene) | gC |
| vSB1-008 | SB-1 | SV40 | Opt-CA02 | Synthetic | UL55/LORF5 |
| vHVT302 | vHVT13 | US10 | Opt-VIId | US10 | US10 |
| vHVT304 | vHVT13 | SV40 | Opt-VIId | Synthetic | IG2 |

On D0, 225 one-day-old SPF chickens were randomly allocated into 9 groups of 15 birds (G1 to G9a challenged at D14) and 6 groups of 15 birds (G1b, G3b, G4b, G5b, G8b, G9b challenged at D28). The birds were injected by subcutaneous injection in the neck at D0 with 0.2 mL containing a target dose of 2000 pfu for recombinant vaccines. The design of the study is shown in Table 37 below. The birds were challenged by the intramuscular route on D14 or D28 with 4.3 and 4.2 log 10 EID50 (0.1 mL) velogenic ND Texas GB (genotype II) strain, respectively.

TABLE 37

| Results of ND efficacy | | | |
|---|---|---|---|
| Group | Vaccine at day-old (D0) | % ND protection after ND challenge at 14 days of age | % ND protection after ND challenge at 28 days of age |
| G1a & 1b | — | 0% | 0% |
| G2a | vSB1-004 | 20% | ND* |
| G3a & 3b | vSB1-006 | 26.6% | 73.3% |
| G4a & 4b | vSB1-007 | 33.3% | 93.3% |
| G5a & 5b | vSB1-008 | 46.6% | 86.6% |
| G6a | vSB1-006 + vHVT13 | 14% | ND |
| G7a | vSB1-008 + vHVT13 | 21.4% | ND |
| G8a & 8b | vHVT302 | 13.3% | 80% |
| G9a & 9b | vHVT304 | 33.3% | 93.3% |

*ND = not done

Each group was monitored before and after challenge. NDV clinical signs after challenge were recorded. One bird died in G6 and G7 before challenge reducing the number of birds from 15 to 14 in these groups.

Percentages of clinical protection (including protection against both mortality and morbidity) are reported in Table 37 above. Full susceptibility was observed in the non-vaccinated challenged control group G1a and G1b thus validating the high severity of challenge. Partial protections ranging from 13.3 to 46.6% were observed after challenge at D14, the highest levels of protection being induced by vSB1-008, vSB1-007 and vHVT304. Protection levels after ND challenge at D28 were much higher for all vaccinated groups and were again slightly higher in the groups vaccinates with vSB1-008, vSB1-007 or vHVT304. These results indicated that ND protection levels were dependent on the date of challenge and on the construct. The vSB1-008 and vSB1-007 constructs performed slightly better than vSB1-004 and vSB1-006, and the vHVT304 performed slightly better than vHVT302, indicating that different characteristics of the constructs are playing a role in the performances of MDV-based vector vaccines.

In conclusion, the results of this study showed that ND protection levels induced by Marek's disease vectors expressing NDV F gene may depend on different parameters including the vector, the locus of insertion, the F gene, the promoter, the poly-adenylation site and the challenge conditions.

Example 25

Efficacy of Double HVT-ND+IBD vHVT304 and vHVT306 Vaccines Against Challenges with NDV Texas GB Strain at 14 and/or 28 Days of Age in SPF Chickens The aim of the study was to assess the efficacy of HVT-vectored vaccine expressing both NDV F and IBDV VP2 genes against Newcastle disease challenge (Texas GB strain, genotype II) performed at 14 and/or 28 days of age in SPF chickens.

The characteristics of the 2 recombinant vaccine candidates tested in this study are described in the Table 38 below.

TABLE 38

Characteristics of the recombinant vaccine candidates used in this study

| Name | Parental virus | Promoter | F gene | Poly-A | Locus |
|---|---|---|---|---|---|
| vHVT304 | vHVT13 | SV40 | Opt-VIId | Synthetic | IG2 |
| vHVT306 | vHVT13 | SV40 | Opt-VIId | Synthetic | SORF3-US2 |

On D0, 90 one-day-old SPF chickens were randomly allocated into 3 groups of 15 birds (G1a to G3a challenged at D14) and 3 groups of 15 birds (G1b to G3b challenged at D28). The birds were injected by subcutaneous injection in the neck at D0 with 0.2 mL containing a target dose of 2000 pfu for recombinant vaccines. The design of the study is shown in Table 39 below. The birds were challenged by the intramuscular route on D14 or D28 with a target dose of 4.0 log 10 EID50 (0.1 mL) velogenic ND Texas GB (genotype II) strain.

TABLE 39

Results of ND efficacy

| Group | Vaccine at day-old (D0) | % ND protection after ND challenge at 14 days of age | % ND protection after ND challenge at 28 days of age |
|---|---|---|---|
| G1a & 1b | — | 0% | 0% |
| G2a & 2b | vHVT304 | 26.7% | 92.9% |
| G3a & 3b | vHVT306 | 33.3% | 86.7% |

Each group was monitored before and after challenge. NDV clinical signs after challenge were recorded. One bird died in G2b before challenge reducing the number of birds from 15 to 14 in this group.

Percentages of clinical protection (including protection against both mortality and morbidity) are reported in Table 39 above. Full susceptibility was observed in the non-vaccinated challenged control group G1a and G1b thus validating the high severity of challenge. Protections levels after challenge at D14 were much lower than those obtained after challenge at D28. These vaccine candidates had the same NDV F expression cassette inserted into 2 different loci of vHVT13 genome. They performed equally in terms of ND protection in the tested conditions, indicating that both insertion loci (IG2 and SORF3-US2) are equally suitable for NDV F cassette insertion.

In conclusion, the results of this study showed that ND protection levels induced by Marek's disease vectors expressing NDV F gene depend on different parameters including the vector, the locus of insertion, the F gene, the promoter, the poly-adenylation site and the challenge conditions.

Example 26

ND Early Efficacy Induced by Double HVT-ND+IBD (vHVT302, vHVT303, and vHVT304) or SB1-vectors (vSB1-006 and vSB1-007) in One Day-Old SPF Chickens Against a Velogenic Genotype V NDV Challenge The objective of the study was to evaluate the efficacy of three double HVT-ND+IBD (vHVT302, vHVT303, and vHVT304) and two SB1-ND vectors (vSB1-006 and vSB1-007) in one day-old SPF chickens against a velogenic genotype V (Chimalhuacan) NDV challenge performed at D14.

The characteristics of the 5 recombinant vaccine candidates tested in this study are described in the Table 40 below.

TABLE 40

Characteristics of the recombinant vaccine candidates used in this study

| Name | Parental virus | Promoter | F gene | Poly-A | Locus |
|---|---|---|---|---|---|
| vHVT302 | vHVT13 | US10 | Opt-VIId | US10 | US10 |
| vHVT303 | vHVT13 | US10 | Opt-V (CA02) | US10 | US10 |
| vHVT304 | vHVT13 | SV40 | Opt-VIId | Synthetic | IG2 |
| vSB1-006 | SB-1 | SV40 | Opt-VIId | Synthetic | UL55/ LORF5 |
| vSB1-007 | SB-1 | SV40 | Opt-VIId | (endogeneous from gC gene) | gC |

Six groups (1 and 2) of ten one-day-old specific pathogen free (SPF) white Leghorn chicks were randomly constituted. Birds from groups 2 to 6 were vaccinated by the subcutaneous route (nape of the neck) with a target dose of 2000 PFU as shown in the Table 41 below. Chicks from group 1 were not vaccinated and were kept as control birds. At 2 week-of-age, all birds were challenged with the genotype V Mexican Chimalhuacan (Mex V) velogenic NDV strain. The challenge was performed by the intramuscular (IM) route using $10^5$ Egg Infectious Dose 50 (EID50) diluted in 0.2 ml of physiological sterile water. All birds were monitored until 14 days post-challenge. After challenge, health status of each bird was scored daily as follows: healthy/with specific symptoms (ruffled feathers, prostration, torticollis, tremor)/dead. Any bird that showed specific symptoms for more than 2 days or was noted sick on D28 was taken into account for calculation of morbidity.

TABLE 41

Results of early ND protection induced by different MDV vectored candidates expressing NDV F gene in SPF day-old chicks

| Group | Vaccine | Target dose (PFU) under 0.2 mL (actual dose) | Protection against mortality | Protection against morbidity |
|---|---|---|---|---|
| G1 | — | — | 0% | 0% |
| G2 | vHVT302 | 2000 (4427) | 50% | 10% |
| G3 | vHVT303 | 2000 (ND) | 10% | 0% |
| G4 | vHVT304 | 2000 (1169) | 80% | 60% |
| G5 | vSB1-006 | 2000 (1720) | 60% | 40% |
| G6 | vSB1-007 | 2000 (1564) | 80% | 50% |

Results of protection are summarized in Table 41. All control birds died after ND challenge. Variable levels of ND protection were induced by the different tested vaccines ranging from 10% to 80% and from 0% and 60% in terms of protection against mortality and morbidity, respectively. The vHVT304 candidate induced a better protection than the vHVT303 and vHVT302 candidates; this may be due to the exogenous SV40 promoter placed in front of the NDV F gene. The vSB1-007 performed slightly better than the vSB1-006. Furthermore, performances obtained with vHVT304 were comparable to those obtained with vSB1-007 indicating that different Marek's disease vectors can reach the same level of ND protection.

In conclusion, this study demonstrates that both double HVT-ND$^+$ IBD and SB1-ND vectored vaccines can reach significant levels of ND protection in a very severe and early NDV challenge model.

Example 27

ND Efficacy Induced by the Double HVT-ND+IBD vHVT306 Administered by In Ovo or SC Route to One Day-Old SPF Chickens Against a Velogenic Genotype V NDV Challenge Performed at D28

The objective of the study was to evaluate the efficacy of one double HVT-ND+IBD (vHVT306) administered by the in ovo or SC route to SPF chickens against a velogenic genotype V (Chimalhuacan) NDV challenge performed at 28 days of age.

The characteristics of the vHVT306 recombinant vaccine candidate tested in this study are described in Table 42 below. The single HVT-IBD vector vaccine vHVT13 was used as a control.

TABLE 42

Characteristics of the recombinant vaccine candidate used in this study

| Name | Parental virus | Promoter | F gene | Poly-A | Locus |
|---|---|---|---|---|---|
| vHVT306 | vHVT13 | SV40 | Opt-VIId | Synthetic | SORF3-US2 |

On day −3, 40 SPF embryonated eggs aged around 18 days and 18 hours of incubation were randomly allocated into 2 groups of 20 eggs each. On D0, one group of 12 day-old SPF chicks was added. The definition of groups is given in Table 43 below. The vaccination was performed on D-3 (in ovo route) or on D0 (SC route, in the back of the neck) and the target dose of vHVT306 and vHVT13 was 2000 PFU/bird. For the in ovo route, hatchability, viability (until D28) and growth of the birds (between hatching and D28) were monitored.

On D28, 10 birds per group were challenged with virulent ND Chimalhuacan strain. The challenge was performed by the intramuscular (IM) route using $10^5$ Egg Infectious Dose 50 (EID50) diluted in 0.2 ml of physiological sterile water. Birds were monitored until 14 days post-challenge. Specific clinical signs and mortality were recorded. Any bird that showed specific symptoms for more than 2 days or was noted sick on D42 was taken into account for calculation of morbidity. Five and seven days post-challenge (i.e. on D33 and D35), oropharyngeal swab was taken from each surviving bird. All the swabs were analyzed by specific NDV qRT-PCR.

TABLE 43

Results of ND protection induced by vHVT306 MDV vectored candidate expressing both NDV F and IBDV VP2 genes administered by the SC or in ovo route into SPF chicks

| Group | Vaccine/route | Hatch-ability/viability (%) | Protection against mortality/morbidity | % birds shedding at 5 dpi/7 dpi (mean log10 titer*) |
|---|---|---|---|---|
| G1 | vHVT13/in ovo | 100%/100% | 0%/0% | (not tested) |
| G2 | vVHT306/in ovo | 100%/100% | 100%/100% | 0% (2.7)/ 0% (2.7) |
| G3 | vHVT306/SC | — | 100%/100% | 20% (3.2)/ 10% (2.9) |

*The threshold titer of the real time RT PCR was set at 2.7 log10 equivalent EID50

Full hatchability was recorded after in ovo vaccination in groups 1 and 2 and all hatched birds survived up to D28. No difference in body weights was detected between the two groups at both D0 and D28 confirming the perfect safety of vHVT306 when administered in ovo. Results of protection are summarized in Table 43. All vHVT13-vaccinated control birds died by 4 days after ND challenge. Full clinical ND protection was induced by vHVT306 administered by both routes. Furthermore, no shedding was detected after in ovo administration whereas only a few birds shed detectable amount of challenge virus after SC administration.

In conclusion, this study demonstrates that the double HVT-ND+IBD vHVT306 induce excellent level of ND protection by SC or in ovo administration routes in a very severe heterologous NDV challenge model.

Example 28

Efficacy of Double HVT-ND+IBD (vHVT302, vHVT303 and vHVT304) Recombinant Vaccines, Against Challenge with a Classical IBDV Isolate on D15 in SPF Chickens The aim of the study was to assess the early IBD efficacy of double HVT recombinants vHVT302, vHVT303 and vHVT304 recombinant constructs against a virulent infectious bursal disease virus (vIBDV) challenge (Faragher 52/70 strain) performed at 15 days of age in SPF chickens.

The characteristics of the 3 double HVT-ND+IBD recombinant vaccine candidates tested in this study are described in the Table 44 below.

TABLE 44

| Characteristics of the expression cassettes of double HVT recombinants | | | | | |
|---|---|---|---|---|---|
| Name | Parental virus | Promoter | F gene | Poly-A | Locus |
| vHVT302 | vHVT13 | US10 | Opt-VIId | US10 | US10 |
| vHVT303 | vHVT13 | US10 | Opt-V (CA02) | US10 | US10 |
| vHVT304 | vHVT13 | SV40 | Opt-VIId | Synthetic | IG2 |

On D0, 40 one-day-old SPF chickens were randomly allocated into 4 groups of 10 birds including one control groups (G1) that was vaccinated with vSB1-004, a SB-1 vector expressing NDV F gene. Five other SPF birds were kept unvaccinated and unchallenged for bursal/body weights evaluation. The birds were injected by subcutaneous injection in the neck at D0 with 0.2 mL of recombinant vaccines containing a target dose of 2000 pfu as described in the Table 45 below. On D15, blood sample was collected from all birds per group (10 birds per group except for groups 1 and 3 in which 1 bird died before blood sampling) for serological testing with the Kit ProFLOK® plus IBD (Synbiotics Corp). On D15, birds from all 4 groups were challenged by the eye drop (0.05 mL per bird) with 2.5 log 10 EID50.

TABLE 45

| Study design and results of IBD efficacy | | | | | |
|---|---|---|---|---|---|
| Group | Vaccine at day-old | ELISA IBD+ titer (log10) | Number Dead/Sick (total)[1] | % protection[2] | Mean bursal/ body weight ratio[4] |
| G1 | vSB1-004 | 0.25 | 1/9 (9) | 0% | 0.0014 |
| G2 | vHVT302 | 2.6 | 0/1 (10) | 80% | 0.0043 |
| G3 | vHVT303 | 3.0 | 0/0 (9) | 100% | 0.0053 |
| G4 | vHVT304 | 2.4 | 0/0 (10) | 80% | 0.0034 |

[1]Birds sick for more than 2 days or still sick on D25 were considered as sick. The number in brackets is the total number of birds in the group that were challenged.
[2]Protection against clinical signs and severe bursal lesion (bursal score <3)
[4]The bursal/body weight ratio of the unvaccinated/unchallenged group was 0.0043.

Each group was monitored before and after challenge. IBDV clinical signs were recorded for 11 days after challenge (from D15 to D25). At the end of the post-challenge observation period (D25), all the surviving birds were euthanized and necropsied. Body and bursal weights were recorded. Each bursa of Fabricius (BF) was weighted then stored in individual recipients containing 4% formaldehyde for histology. Histological lesions of the bursa were scored according to the scale presented in Table 46.

TABLE 46

| Scoring scale of histological lesions of the bursa of Fabricius* | |
|---|---|
| Score | Histology observation/lesions |
| 0 | No lesion, normal bursa |
| 1 | 1% to 25% of the follicles show lymphoid depletion (i.e. less than 50% of depletion in 1 affected follicle), influx of heterophils in lesions |
| 2 | 26% to 50% of the follicles show nearly complete lymphoid depletion (i.e. more than 75% of depletion in 1 affected follicle), affected follicles show necrosis and severe influx of heterophils may be detected |
| 3 | 51% to 75% of the follicles show lymphoid depletion; affected follicles show necrosis lesions and a severe influx of heterophils is detected |

TABLE 46-continued

| Scoring scale of histological lesions of the bursa of Fabricius* | |
|---|---|
| Score | Histology observation/lesions |
| 4 | 76% to 100% of the follicles show nearly complete lymphoid depletion; hyperplasia and cyst structures are detected; affected follicles show necrosis and severe influx of heterophils is detected |
| 5 | 100% of the follicles show nearly complete lymphoid depletion; complete loss of follicular structure, thickened and folded epithelium, fibrosis of bursal tissue |

*sourced from Monograph No. 01/2008: 0587 of EU Pharmacopoeia "Avian Infectious Bursal Disease vaccine (live)

A bird was considered as affected if it died and/or showed notable sign of disease and/or severe lesions of the bursa of Fabricius (i.e., histology score ≥3).

The mean ELISA IBD+ antibody titer expressed in log 10 before challenge is shown in Table 45. Significant titers were detected in all vaccinated groups that were significantly higher than that of the control group G1. The serology titer was slightly higher in G3 (vHVT303).

Severe clinical signs were observed after challenge in all 9 birds of the control group G1, which lead to the death of 1 bird. Only one vaccinated bird in G2 (vHVT302) showed clinical signs after challenge. Percentages of protection against severe bursal lesions are shown in Table 45 above. Significant IBD protection was observed in all vaccinated groups, a full protection being observed in G3 (vHVT303). The mean bursal/body weight ratios are also shown in Table 45. Ratios in all vaccinated groups were higher than those of the challenged control group G1 and not significantly different from the unvaccinated and unchallenged control group.

In conclusion, these data indicate that the three double HVT-IBD+ND tested in this study induced IBD antibodies and early IBD protection in a severe IBDV challenge model.

Example 29

Efficacy of Five Different HVT-ND Vaccine Candidates Against Challenges with Velogenic NDV ZJ1 (Genotype VIId) Isolate at 14 Days of Age in SPF Chickens The aim of the study was to assess the efficacy of 5 single HVT recombinant constructs (vHVT39, vHVT110, vHVT111, vHVT112 and vHVT113) expressing the NDV F gene against Newcastle disease challenge with velogenic NDV ZJ1 (genotype VIId) isolate performed at 14 days of age in SPF chickens.

The characteristics of these 5 vaccine candidates are described in Table 47 below.

TABLE 47

| Characteristics of the HVT-ND recombinant viruses used in the challenge study | | | | | |
|---|---|---|---|---|---|
| Name | Parental virus | Promoter | F gene* | Poly-A | Locus |
| vHVT039 | HVT | MDV gB | Wtnm-Texas | SV40 | IG1 |
| vHVT110 | HVT | MCMV IE | Wt-VIId | SV40 | IG1 |
| vHVT111 | HVT | SV40 | Wt-VIId | SV40 | IG1 |
| vHVT112 | HVT | MCMV IE | Wt-YZCQ | SV40 | IG1 |
| vHVT113 | HVT | MCMV IE | Wt-Texas | SV40 | IG1 |

*Wt means that the wild type velogenic F gene sequence was used but the cleavage site was modified to that of a lentogenic virus. Wtnm means that the cleavage site of the wild type sequence was not modified. The Texas velogenic strain belongs to genotype IV and YZCQ to the genotype VIId.

On D0, 72 one-day-old SPF chickens were randomly allocated into 5 groups of 12 birds (vaccinated) and 1 group of 12 birds (non-vaccinated controls). The birds were injected by subcutaneous injection in the neck at D0 with 0.2 mL of recombinant vaccines containing a target dose of 6000 pfu as described in Table 48 below. The birds were challenged by the intramuscular route on D14 with 5 log 10 EID50 of NDV ZJ1/2000 (genotype VIId) velogenic strain.

TABLE 48

Results of ND efficacy

| Group | Vaccine at day-old (D0) | % clinical protection: Protection against mortality/morbidity | Mean shedding titer (log10) at 2/4 dpi |
|---|---|---|---|
| G1 | — | 0%/0% | 3.5/— (all dead) |
| G2 | vHVT039 | 25%/8% | 2.5/4.8 |
| G3 | vHVT110 | 100%/83% | 1.8/2.0 |
| G4 | vHVT111 | 100%/67% | 1.8/2.8 |
| G5 | vHVT112 | 75%/42% | 1.7/3.4 |
| G6 | vHVT113 | 83%/25% | 1.4/3.3 |

Each group was monitored before and after challenge. NDV clinical signs and mortality were recorded after challenge. Oropharyngeal swabs were taken at 2 and 4 days post-infection (dpi) for evaluation of viral load by real time RT-PCR using the method described by Wise et al. (2004; Development of a Real-Time Reverse-Transcription PCR for Detection of Newcastle Disease Virus RNA in Clinical Samples. J Clin Microbiol 42, 329-338).

Percentages of protection against mortality and morbidity are reported in Table 48 above. Full susceptibility was observed in the non-vaccinated challenged control group G1 thus validating the high severity of the challenge. Vaccines induced variable levels of protection against mortality (25-100%) or against morbidity (8%-83%). The best protection level was induced by vHVT110 whereas the lowest one was induced by vHVT039, the other candidates giving intermediate results. Results of oropharyngeal shedding at 2 and 4 dpi are also shown in Table 48 above and are in line with those of clinical protection. These vaccine candidates differ in their promoter and F gene sequence. These results show that both of these parameters are important for the design of optimal HVT-ND vaccine candidate.

In conclusion, the results of this study showed the importance of promoter and F gene sequence in the ND efficacy induced by HVT-vectored ND vaccine candidates.

Example 30

Evaluation of the Newcastle Disease Efficacy Induced by Double SB1 Constructs Expressing IBDV VP2 and NDV F The aim of the study is to assess the efficacy of double SB1 constructs expressing IBDV VP2 and NDV F against Newcastle disease challenge.

On D0, one-day-old SPF chickens are randomly allocated into several groups of 10-20 birds, including vaccinated and non-vaccinated groups. The birds of the vaccinated groups are injected by subcutaneous injection in the neck at D0 with 0.2 mL containing a target dose of 1000 to 5000 pfu of recombinant vaccines. Alternatively, the same dose in 0.05 mL may be administered in ovo 2 or 3 days before hatch. The birds (at least one vaccinated and one non vaccinated group) are challenged by the intramuscular route at different time after vaccination: for instance, D14, D28 or D42 with about 4.0 log 10 EID50 (0.1 mL) of a velogenic NDV strain such as Texas GB (genotype II), ZJ1 (genotype VIId), Chimalhuacan (genotype V) strain.

Each group is monitored clinically before and after challenge. NDV clinical signs (morbidity) and mortality are recorded after challenge. Percentages of clinical protection in all groups are calculated. At least 90% of non-vaccinated challenged SPF birds should die or be severely sick after challenge to validate the severity of challenge. Oropharyngeal and cloacal swabs can be samples at different times after challenge such as 3, 5, 7 and 9 days post-challenge and the viral load can be estimated by real-time RT-PCR. The best candidates will be those who induced the highest level of clinical protection and the lowest level of viral load in the swabs. A similar study can be performed in broilers containing NDV maternal antibodies; however, these maternal antibodies may potentially protect the non-vaccinated birds if the challenge is performed early. The double SB1 construct may also be tested in combination with other Marek's disease vaccine or vector vaccines.

Example 31

Evaluation of the Infectious Bursal Disease Efficacy Induced by Double SB1 Constructs Expressing IBDV VP2 and NDV F The aim of the study is to assess the IBD efficacy of double SB1 expressing both the IBDV VP2 and the NDV F.

One-day-old SPF chickens are randomly allocated into several groups of 10 to 20 birds including vaccinated and non-vaccinated controls. Non-vaccinated controls will be separated into 2 subgroups including challenged and unchallenged birds. The birds of vaccinated groups are injected by subcutaneous injection in the neck at D0 with 0.2 mL of vaccines containing each a target dose of 1000 to 5000 pfu. Alternatively, the same dose in 0.05 mL may be administered in ovo 2 or 3 days before hatch. At different times after vaccination such as 14, 21, 28 or 42 days post-vaccination, all birds from vaccinated groups and the challenged controls are challenged by the eye drop (0.03 mL containing 2 to 4 log 10 EID50 per bird) of a virulent IBDV (such as the Faragher or the US standard strain), a very virulent IBDV such as the 91-168 isolate or a variant IBDV isolate such as the US Delaware variant E isolate. Each group is clinically monitored before and after challenge. Birds can be necropsied 4 or 5 days post-challenge for bursal gross lesions evaluation. They can also be necropsied 10 to 11 days post-challenge. Gross and/or histological lesions can be evaluated. Furthermore, birds and bursa are weighed the bursal/body weight ratios (bursa weight/body weight ratio×100) are calculated compared to those of the non-vaccinated unchallenged group. Control SPF challenged birds must show clinical signs and/or have significant gross and/or histological lesions, and/or should have a bursal/body weight ratio significantly lower than the unvaccinated unchallenged control birds to validate the severity of challenge. The efficacy of the vaccine is evaluated by comparing these parameters with unvaccinated/challenged and unvaccinated/unchallenged groups. Such study may be performed in broiler chickens containing IBDV maternal antibodies; however, these maternal antibodies may potentially protect the non-vaccinated birds if the challenge is performed early. The double SB1 construct may also be tested in combination with other Marek's disease vaccine or vector vaccines.

Example 32

Evaluation of the Marek's Disease Efficacy Induced by Double SB1 Constructs Expressing IBDV VP2 and NDV F The aim of the study is to evaluate Marek's disease efficacy induced by the SB1 vectors expressing both IBDV VP2 and NDVF.

One-day-old SPF chickens are randomly allocated into several groups of 20 to 50 birds including vaccinated and non-vaccinated controls. Non-vaccinated controls may be separated into 2 subgroups including challenged and unchallenged birds. The birds of vaccinated groups are injected by subcutaneous injection in the neck at D0 with 0.2 mL of vaccines containing each a target dose of 1000 to 5000 pfu. Alternatively, the same dose in 0.05 mL may be administered in ovo 2 or 3 days before hatch. At different times after vaccination such as 3 to 10 days post-vaccination, all birds from vaccinated groups and the challenged controls are challenged by the intraperitoneal route with 0.2 mL of a Marek's disease virus (MDV) strain. MDV strain may be of several pathotypes such as virulent MDV (vMDV) including the JM or GA22 isolate, very virulent MDV (vvMDV) such as the RB-1B or Md5 isolate, very virulent plus (vv+MDV) such as the T-King or 648A isolate. MDV challenge strain inoculum are prepared by infecting chickens, harvesting and freezing their blood cells into liquid nitrogen in presence of a cryopreservative such as DMSO. The chicken infectious dose 50 (CID50) is established for each challenge batch before performing vaccination/challenge studies. Each group is clinically monitored before and after challenge. Birds are necropsied after at least 7 weeks post-vaccination and the presence Marek's disease gross lesions is checked in each bird. Lesions might include, but not be limited to, the following: liver, heart, spleen, gonads, kidneys, nerve and muscle lesions. Such study may be performed in broiler chickens containing MDV maternal antibodies. The double SB1 construct may also be tested in combination with other Marek's disease vaccine (for instance HVT and or CVI988 Rispens strains) or MD vector vaccines. MD challenge may also be performed by contact between vaccinated birds and MDV infected non-vaccinated SPF chicks.

```
NDV-F codon optimized gene from modified wt VIId
                                                          (SEQ ID NO: 1)
atgggcagcaagcccagcacaagaatcccagccccctgatgctgatcacccgcatcatgctgatcctgggctgcatcagacc

cacaagctccctggatggacgccccctggccgctgccggcatcgtggtgaccggcgacaaggccgtgaacgtgtacaccag

cagccagaccggcagcatcatcgtgaagctgctgcccaacatgcccagagacaaagaggcctgcgccaaggccccctgga

agcctacaacagaaccctgaccaccctgctgacccccctgggcgacagcatcagaaagatccagggctccgtgagcacaagc

ggcggaggaaagcagggcagactgatcggcgccgtgatcggcagcgtggccctgggagtggctacagctgcccagattacc

gctgcagccgccctgatccaggccaaccagaacgccgccaacatcctgagactgaaagagagcattgccgccaccaacgag

gccgtgcacgaagtgaccgacggcctgagccagctgtccgtggccgtgggcaagatgcagcagttcgtgaacgaccagttca

acaacaccgccagagagctggactgcatcaagatcacccagcaggtgggcgtggagctgaacctgtacctgaccgagctgac

cacagtgttcggcccccagatcacaagcccagccctgacacagctgaccatccaggccctgtacaacctggctggcggcaac

atggactatctgctgacaaagctgggaatcggcaacaaccagctgtccagcctgatcggaagcggcctgatcaccggctaccc

catcctgtacgacagccagacacagctgctgggcatccaggtgaacctgcccagcgtgggcaacctgaacaacatgcgcgcc

acctacctggaaaccctgagcgtgtccaccaccaagggctacgccagcgccctggtgcccaaggtggtgacacaggtgggca

gcgtgatcgaggaactggacaccagctactgcatcgagagcgacctggacctgtactgcaccagaatcgtgaccttcccaatg

agccccggcatctacagctgcctgagcggcaacaccagcgcctgcatgtacagcaagaccgaaggcgcactgacaacaccc

tacatggccctgaagggaagcgtgatcgccaactgcaagatcaccacctgcagatgcaccgacccccccaggcatcatcagcc

agaactacggcgaggccgtgagcctgatcgatcgccattcctgtaacgtgctgtccctggacggcatcacactgagactgagc

ggcgagttcgatgccacctaccagaagaacatcagcatcctggacagccaggtgatcgtgaccggcaacctggacatcagca

ccgagctgggcaacgtgaataacagcatcagcaacgccctggacagactggccgagagcaacagcaagctggaaaaagtga

acgtgcgcctgacatccacttccgctctgatcacctacatcgtgctgaccgtgatcagcctggtgttcggcgccctgagcctggtg

ctggcctgctacctgatgtacaagcagaaggcccagcagaaaaccctgctgtggctgggcaacaacaccctggaccagatga

gagccaccaccagagcctgatga

NDV-F protein encoded by codon-optimized NDV-F gene of wt VIId
                                                          (SEQ ID NO: 2)
mgskpstripaplmlitrimlilgcirptssldgrplaaagivvtgdkavnvytssqtgsiivkllpnmpr

dkeacakapleaynrtlttlltplgdsirkiqgsvstsgggkqgrligavigsvalgvataaqitaaali
```

-continued qanqnaanilrlkesiaatneavhevtdglsqlsvavgkmqqfvndqfnntareldcikitqqvgvelnly lteltttvfgpqitspaltqltigalynlaggnmdylltklgignnqlssligsglitgypilydsqtqllg iqvnlpsvgnlnnmratyletlsvsttkgyasalvpkvvtqvgsvieeldtsyciesdldlyctrivtfpm spgiysclsgntsacmysktegalttpymalkgsvianckittcrctdppgiisqnygeavslidrhscnv lsldgitlrlsgefdatyqknisildsqvivtgnldistelgnvnnsisnaldrlaesnsklekvnvrlts tsalityivltvislvfgalslvlacylmykqkaqqktllwlgnntldqmrattra NDV-F DNA wt VIId (SEQ ID NO: 3)

Atgggctccaaaccttctaccaggatcccagcacctctgatgctgatcacccggattatgctgatattggg ctgtatccgtccgacaagctctcttgacggcaggcctcttgcagctgcaggaattgtagtaacaggagata aggcagtcaatgtatacacttcgtctcagacagggtcaatcatagtcaagttgctcccgaatatgcccagg gataaggaggcgtgtgcaaaagccccattagaggcatataacagaacactgactactttgctcactcctct tggcgactccatccgcaagatccaagggtctgtgtccacatctggaggaggcaagcaaggccgcctgatag gtgctgttattggcagtgtagctcttggggttgcaacagcggcacagataacagcagctgcggccctaata caagccaaccagaatgccgccaacatcctccggcttaaggagagcattgctgcaaccaatgaagctgtgca tgaagtcaccgacggattatcacaactatcagtggcagttgggaagatgcagcagtttgtcaatgaccagt ttaataatacggcgcgagaattggactgtataaaaatcacacaacaggttggtgtagaactcaacctatac ctaactgaattgactacagtattcgggccacagatcacctcccctgcattaactcagctgaccatccaggc actttataatttagctggtggcaatatggattacttattaactaagttaggtatagggaacaatcaactca gctcgttaattggtagcggcctgatcactggttaccctatactgtatgactcacagactcaactcttgggc atacaagtgaatttaccctcagtcgggaacttaaataatatgcgtgccacctatttggagaccttatctgt aagtacaaccaaaggatatgcctcagcacttgtcccgaaagtagtgacacaagtcggttccgtgatagaag agcttgacacctcatactgtatagagtccgatctggatttatattgtactagaatagtgacattccccatg tccccaggtatttattcctgtttgagcggcaacacatcagcttgcatgtattcaaagactgaaggcgcact cactacgccgtatatggcccttaaaggctcagttattgccaattgtaaaataacaacatgtagatgtacag accctcctggtatcatatcgcaaaattatggagaagctgtatccctgatagatagacattcgtgcaatgtc ttatcattagacgggataactctaaggctcagtggggaatttgatgcaacttatcaaaagaacatctcaat actagattctcaagtcatcgtgacaggcaatcttgatatatcaactgaacttggaaacgtcaacaattcaa tcagcaatgccttggataggttggcagaaagcaacagcaagctagaaaaagtcaatgtcagactaaccagc acatctgctctcattacctatattgttctaactgtcatttctctagttttcggtgcacttagtctggtgtt agcgtgttacctgatgtacaaacagaaggcacaacaaaagaccttgctatggcttgggaataataccctcg atcagatgagagccactacaagagcatga NDV-F gene GenBank Accession No. AY337464.1 (SEQ ID NO: 4)

CTGGATCCCGGTTGGCTCATTCAGGACGCAATATGGGCTCCAAACCTTCTACCAGGATCCCAGCACCTCT

GATGCTGATCACCCGGATTATGCTGATATTGGGCTGTATCCGTCCGACAAGCTCTCTTGACGGCAGGCCT

CTTGCAGCTGCAGGAATTGTAGTAACAGGAGATAAGGCAGTCAATGTATACACTTCGTCTCAGACAGGGT

CAATCATAGTCAAGTTGCTCCCGAATATGCCCAGGGATAAGGAGGCGTGTGCAAAAGCCCCATTAGAGGC

ATATAACAGAACACTGACTACTTTGCTCACTCCTCTTGGCGACTCCATCCGCAAGATCCAAGGGTCTGTG

TCCACATCTGGAGGAAGGAGACAAAAACGCTTTATAGGTGCTGTTATTGGCAGTGTAGCTCTTGGGGTTG

CAACAGCGGCACAGATAACAGCAGCTGCGGCCCTAATACAAGCCAACCAGAATGCCGCCAACATCCTCCG

GCTTAAGGAGAGCATTGCTGCAACCAATGAAGCTGTGCATGAAGTCACCGACGGATTATCACAACTATCA

GTGGCAGTTGGGAAGATGCAGCAGTTTGTCAATGACCAGTTTAATAATACGGCGCGAGAATTGGACTGTA

-continued

TAAAAATCACACAACAGGTTGGTGTAGAACTCAACCTATACCTAACTGAATTGACTACAGTATTCGGGCC

ACAGATCACCTCCCCTGCATTAACTCAGCTGACCATCCAGGCACTTTATAATTTAGCTGGTGGCAATATG

GATTACTTATTAACTAAGTTAGGTATAGGGAACAATCAACTCAGCTCGTTAATTGGTAGCGGCCTGATCA

CTGGTTACCCTATACTGTATGACTCACAGACTCAACTCTTGGGCATACAAGTGAATTTACCCTCAGTCGG

GAACTTAAATAATATGCGTGCCACCTATTTGGAGACCTTATCTGTAAGTACAACCAAAGGATATGCCTCA

GCACTTGTCCCGAAAGTAGTGACACAAGTCGGTTCCGTGATAGAAGAGCTTGACACCTCATACTGTATAG

AGTCCGATCTGGATTTATATTGTACTAGAATAGTGACATTCCCCATGTCCCCAGGTATTTATTCCTGTTT

GAGCGGCAACACATCAGCTTGCATGTATTCAAAGACTGAAGGCGCACTCACTACGCCGTATATGGCCCTT

AAAGGCTCAGTTATTGCCAATTGTAGGATAACAACATGTAGATGTACAGACCCTCCTGGTATCATATCGC

AAAATTATGGAGAAGCTGTATCCCTGATAGATAGACATTCGTGCAATGTCTTATCATTAGACGGGATAAC

TCTAAGGCTCAGTGGGGAATTTGATGCAACTTATCAAAAGAACATCTCAATACTAGATTCTCAAGTCATC

GTGACAGGCAATCTTGATATATCAACTGAACTTGGAAACGTCAACAATTCAATCAGCAATGCCTTGGATA

GGTTGGCAGAAAGCAACAGCAAGCTAGAAAAAGTCAATGTCAGACTAACCAGCACATCTGCTCTCATTAC

CTATATTGTTCTAACTGTCATTTCTCTAGTTTTCGGTGCACTTAGTCTGGGTTTAGCGTGTTACCTGATG

TACAAACAGAAGGCACAACAAAAGACCTTGCTATGGCTTGGGAATAATACCCTCGATCAGATGAGAGCCA

CTACAAGAGCATGAA

NDV-F protein GenBank Accession No. AAP97877.1

(SEQ ID NO: 5)

MGSKPSTRIPAPLMLITRIMLILGCIRPTSSLDGRPLAAAGIVVTGDKAVNVYTSSQTGSIIVKLLPNMP

RDKEACAKAPLEAYNRTLTTLLTPLGDSIRKIQGSVSTSGGRRQKRFIGAVIGSVALGVATAAQITAAAA

LIQANQNAANILRLKESIAATNEAVHEVTDGLSQLSVAVGKMQQFVNDQFNNTARELDCIKITQQVGVEL

NLYLTELTTVFGPQITSPALTQLTIQALYNLAGGNMDYLLTKLGIGNNQLSSLIGSGLITGYPILYDSQT

QLLGIQVNLPSVGNLNNMRATYLETLSVSTTKGYASALVPKVVTQVGSVIEELDTSYCIESDLDLYCTRI

VTFPMSPGIYSCLSGNTSACMYSKTEGALTTPYMALKGSVIANCRITTCRCTDPPGIISQNYGEAVSLID

RHSCNVLSLDGITLRLSGEFDATYQKNISILDSQVIVTGNLDISTELGNVNNSISNALDRLAESNSKLEK

VNVRLTSTSALITYIVLTVISLVFGALSLGLACYLMYKQKAQQKTLLWLGNNTLDQMRATTRA

NDV-F gene of CA02 strain GenBank Accesion No. EF520718.1

(SEQ ID NO: 6)

ATGGGCTCCAAACCTTCTACCTGGATCTCAGTAACTCTGATGCTGATCACTCGGACCATGCTTATACTTA

GCTGTATCTGTCCGACAAGCTCTCTTGACGGTAGACCTCTCGCAGCCGCAGGGATTGTGGTGACGGGAGA

TAAAGCAGTCAATATATACACTTCATCTCAAACAGGGTCAATCATCATCAAGTTACTCCCAAATATGCCC

AAGGATAAAGAAGCGTGCGCAAAAGCCCCATTGGAAGCATACAATAGAACACTGACCACTTTACTCACCC

CTCTTGGTGACTCTATCCGCAGAATACAAGGGTCTGCGACTACATCTGGAGGAAGGAGACAGAAACGCTT

TGTAGGTGCCATTATCGGCAGTGTAGCTCTTGGGGTTGCAACAGCTGCACAGATAACAGCAGCCGCAGCT

CTGATACAAGCCAACCAAAATGCTGCCAACATCCTCCGGCTTAAGGAGAGCATTGCTGCAACCAATGACG

CTGTACACGAGGTCACTAACGGATTATCACAACTAGCGGTGGCGGTCGGGAAGATGCAGCAGTTTGTTAA

TAACCAGTTTAATAATACGGCGCGAGAATTGGACTGCATAAAAATTGCACAACAAGTGGGCGTCGAACTC

AATTTGTATCTAACTGAATTGACCACAGTGTTCGGGCCACAAATCACCTCCCCTGCTTTAACTCAGCTGA

CTATCCAGGCACTTTATAATTTAGCCGGTGGCAATATGGATTACCTGTTGACTAAGTTGGGTGTAGGGAA

TAATCAACTCAGTTCGTTAATTGGTAGTGGCTTGATAACTGGCAACCCTATACTATATGACTCACAGACC

CAACTCTTAGGCATACAGATAAATTTACCCTCAGTCGGGAGCCTAAATAATATGCGTGCCACCTACTTGG

AGACCTTATCCGTAAGCACGACCAAAGGGTTCGCCTCAGCACTTGTCCCGAAAGTTGTGACGCAAGTCGG

-continued

CTCTGTGATAGAAGAACTTGACACCTCATATTGTATAGAATCCGATATAGATCTATATTGTACAAGGGTA

GTGACATTCCCCATGTCTCCTGGTATTTACTCCTGTCTGAGCGGCAATACGTCAGCTTGTATGTATTCAA

AGACCGAAGGTGCACTCACTACACCATACATGGCCCTCAAAGGCTCAGTTATTGCCAATTGCAAGATGAC

TACATGCAGATGCGCAGATCCCCCAGGTATCATATCACAGAATTATGGGGAAGCTGTGTCTCTAATAGAT

AAACATTCATGCAGTGTCTTGTCCCTAGACGGGATAACTCTGAGGCTCAGTGGGGAATTTGATGCGACCT

ATCAAAAGAACATCTCAATACTAGATTCTCAAGTCATCGTGACAGGAAATCTCGATATATCAACTGAGCT

TGGGAATGTTAACAACTCGATAAGCAGTACCCTGGACAAATTAGCAGAAAGCAACAACAAGCTAAACAAG

GTCAATGTAAACCTAACCAGCACATCTGCTCTCATCACTTATATTGTCTTAGCTATCGTATCTCTTGCTT

TCGGCGTAATTAGCCTGGTTCTAGCATGCTACCTGATGTATAAACAAAGAGCACAACAAAAGACCTTACT

ATGGCTGGGGAACAACACCCTTGATCAGATGAGAGCCACCACAAGAACCTGA

NDV-F wildtype protein sequence of CA02 strain, GenBank Acession No. ABS84266.1

(SEQ ID NO: 7)

MGSKPSTWISVTLMLITRTMLILSCICPTSSLDGRPLAAAGIVVTGDKAVNIYTSSQTGSIIIKLLPNMP

KDKEACAKAPLEAYNRTLTTLLTPLGDSIRRIQGSATTSGGRRQKRFVGAIIGSVALGVATAAQITAAAA

LIQANQNAANILRLKESIAATNDAVHEVTNGLSQLAVAVGKMQQFVNNQFNNTARELDCIKIAQQVGVEL

NLYLTELTTVFGPQITSPALTQLTIQALYNLAGGNMDYLLTKLGVGNNQLSSLIGSGLITGNPILYDSQT

QLLGIQINLPSVGSLNNMRATYLETLSVSTTKGFASALVPKVVTQVGSVIEELDTSYCIESDIDLYCTRV

VTFPMSPGIYSCLSGNTSACMYSKTEGALTTPYMALKGSVIANCKMTTCRCADPPGIISQNYGEAVSLID

KHSCSVLSLDGITLRLSGEFDATYQKNISILDSQVIVTGNLDISTELGNVNNSISSTLDKLAESNNKLNK

VNVNLTSTSALITYIVLAIVSLAFGVISLVLACYLMYKQRAQQKTLLWLGNNTLDQMRATTRT

NDV-F codon-optimized gene of modified CA02 strain (SEQ ID NO: 8)

Atgggcagcaagcccagcacctggatcagcgtgaccctgatgctgatcaccagaaccat gctgatcctgagctgcatctgccccacaagcagcctggacggcagacccctggccgctg ccggcatcgtggtgaccggcgacaaggccgtgaacatctacaccagcagccagaccggc agcatcatcatcaagctgctgcccaacatgcccaaggacaaagaggcctgcgccaaggc ccccctggaagcctacaacagaaccctgaccaccctgctgacccccctgggcgacagca tcagaagaatccagggcagcgccaccacaagcggcggaggaaagcagggcagactggtg ggcgctatcatcgggagcgtggccctgggcgtggccacagctgcccagattaccgctgc agccgccctgattcaggccaatcagaacgccgccaacatcctgagactgaaagagagca ttgccgccaccaacgacgccgtgcacgaagtgacaaacggactgtcccagctggctgtc gctgtcggcaagatgcagcagttcgtgaacaaccagttcaacaacaccgccagagagct ggactgcatcaagatcgcccagcaggtgggcgtggagctgaacctgtacctgaccgagc tgaccacagtgttcggcccccagatcacaagccccgctctgacccagctgacaatccag gccctgtacaacctggctggcggcaacatggactatctgctgactaagctgggagtggg caacaaccagctgtccagcctgatcgggtccgggctgatcacaggcaaccccatcctgt acgacagccagacacagctgctgggcatccagatcaacctgccatccgtgggaagcctg aacaacatgagagccacctacctggaaaccctgagcgtgtccaccaccaagggcttcgc cagcgccctggtgcccaaggtggtgacacaggtgggcagcgtgatcgaggaactggaca ccagctactgcatcgagagcgacatcgacctgtactgcaccagagtggtgaccttccca atgagccccggcatctacagctgcctgagcggcaacaccagcgcctgcatgtacagcaa gaccgaaggagcactgacaacaccctacatggccctgaagggaagcgtgatcgccaact gcaagatgaccaccctgcagatgcgccgacccccaggcatcatcagccagaactacggc -continued gaggccgtgagcctgatcgacaaacattcctgtagcgtgctgtccctggatggcatcac actgagactgagcggcgagttcgacgccacctaccagaagaacatcagcatcctggaca gccaggtgatcgtgaccggcaacctggacatcagcaccgagctgggcaacgtgaacaac agcatcagcagcaccctggacaagctggccgagtccaacaacaagctgaacaaagtgaa cgtgaacctgaccagcacaagcgccctgatcacctacatcgtgctggccatcgtgtccc tggccttcggcgtgatcagcctggtgctggcctgctacctgatgtacaagcagagagcc cagcagaaaaccctgctgtggctgggcaataacaccctggaccagatgagggccaccac cagaacctgatga Amino Acid Sequence of the codon optimized genotype V NDV-F gene in vSB1-008

(SEQ ID NO: 9)

mgskpstwisvtlmlitrtmlilscicptssldgrplaaagivvtgdkavniytssqtgsiiikllpnmpkdkeacakapleayn rtltttlltplgdsirriqgsattsgggkqgrlvgaiigsvalgvataaqitaaaaliqanqnaanilrlkesiaatndavhevtnglsq lavavgkmqqfvnnqfnntareldcikiaqqvgvelnlyltelttvfgpqitspaltqltiqalynlaggnmdylltklgvgnn qlssligsglitgnpilydsqtqllgiqinlpsvgslnnmratyletlsysttkgfasalvpkvvtqvgsvieeldtsyciesdidly ctrvvtfpmspgiysclsgntsacmysktegalttpymalkgsvianckmttcrcadppgiisqnygeayslidkhscsvlsl dgitlrlsgefdatyqknisildsqvivtgnldistelgnvnnsisstldklaesnnklnkvnvnltstsalityivlaivslafgvisl vlacylmykqraqqktllwlgnntldqmrattrt* mCMV IE promoter (SEQ ID NO: 10)

aattcaatagtggatcccccaactccgcccgttttatgactagaaccaatagtttttaa tgccaaatgcactgaaatcccctaatttgcaaagccaaacgcccccctatgtgagtaata cggggactttttacccaatttcccacgcggaaagccccctaatacactcatatggcata tgaatcagcacggtcatgcactctaatggcggcccatagggactttccacatagggggc gttcaccatttcccagcatagggggtggtgactcaatggcctttacccaagtacattggg tcaatgggaggtaagccaatgggtttttcccattactggcaagcacactgagtcaaatg ggactttccactgggttttgcccaagtacattgggtcaatgggaggtgagccaatggga aaaacccattgctgccaagtacactgactcaatagggactttccaatgggtttttccat tgttggcaagcatataaggtcaatgtgggtgagtcaatagggactttccattgtattct gcccagtacataaggtcaatagggggtgaatcaacaggaaagtcccattggagccaagt acactgcgtcaatagggactttccattgggttttgcccagtacataaggtcaatagggg atgagtcaatgggaaaaacccattggagccaagtacactgactcaatagggactttcca ttgggttttgcccagtacataaggtcaatagggggtgagtcaacaggaaagttccattg gagccaagtacattgagtcaatagggactttccaatgggttttgcccagtacataaggt caatgggaggtaagccaatgggtttttcccattactggcacgtatactgagtcattagg gactttccaatgggttttgcccagtacataaggtcaataggggtgaatcaacaggaaag tcccattggagccaagtacactgagtcaatagggactttccattgggttttgcccagta caaaaggtcaatagggggtgagtcaatgggtttttcccattattggcacgtacataagg tcaataggggtgagtcattgggtttttccagccaatttaattaaaacgccatgtacttt cccaccattgacgtcaatgggctattgaaactaatgcaacgtgacctttaaacggtact ttcccatagctgattaatgggaaagtaccgttctcgagccaatacacgtcaatgggaag tgaaagggcagccaaaacgtaacaccgccccggttttcccctggaaattccatattggc acgcattctattggctgagctgcgttctacgtgggtataagaggcgcgaccagcgtcgg -continued taccgtcgcagtcttcggtctgaccaccgtagaacgcagagctcctcgctgcag SV40 PolyA (SEQ ID NO: 11)

ggggatccagacatgataagatacattgatgagtttggacaaaccacaactagaatgca gtgaaaaaaatgctttatttgtgaaatttgtgatgctattgctttatttgtaaccatta taagctgcaataaacaagttaacaacaacaattgcattgattttatgtttcaggttcag ggggaggtgtgggaggttttttcggatcctctagagtcga SV40 promoter (SEQ ID NO: 12)

caattcgagctcggtacagcttggctgtggaatgtgtgtcagttagggtgtggaaagtccccaggctccccagcaggcagaagt atgcaaagcatgcatctcaattagtcagcaaccaggtgtggaaagtccccaggctccccagcaggcagaagtatgcaaagcat gcatctcaattagtcagcaaccatagtcccgcccctaactccgcccatcccgcccctaactccgcccagttccgcccattctccgc cccatggctgactaattttttttatttatgcagaggccgaggccgcctcggcctctgagctattccagaagtagtgaggaggcttttttt ggaggcctaggcttttgcaaaaagct Synthetic PolyA (SEQ ID NO: 13)

aataaaatatctttattttcattacatctgtgtgttggttttttgtgtgaatcgatagtactaacatacgctctccatcaaaacaaaacgaa acaaaacaaactagcaaaataggctgtccccagtgcaagtgcaggtgccagaacatttctct Gene coding for glycoprotein C of SB-1 strain from genome HQ840738 (98595 . . . 100031)

(SEQ ID NO: 34)

atgcac gcgtcacgcg cgttgcgagc tttggggtgg acgagactct tatttgtcgt tttattttcg ggccgcgtcc taagcgctag cattaacccc gatctagcta cacccccggt cattgctttc aacccgtcaa gtattccggc cgatgatggg cctttggcca aagttcctgc atccccgccg gcaggggaga aagaggagag ccacaagaat gcaagcgacg cgcgtaggat gcctagtata gtttgcgata aagaagaagt tttcgttttc ctgaacaaga ccgggcgttt cgtgtgcact cttaagatcg cccctccctc cgacaacgaa tggtcgaact ttgctctgga ccttattttc aatccgatcg aataccatgc taatgagaag aacgtggaag cagcgcgtat tgctggcctc tatggggtgc ccggatcaga ttacgcctac ccgcgtcctt ctgaattaat ctcttctatt cggcgagacc cccaagggac cttttggaca agcccatcgg cacatggaga caagtacttc atatggctaa acaaaaacgac gaatacgatg ggcgtggaaa ttaggaacgt cgactacgca gacaacggtt acatccaagt tgccatgcgg gatcctttca atcggccttt actagataag cacgtgtaca tccgcgtgtg tcaacgaccc gcctcggtcg acgttctagc ccccccgtc ctcagtggcg ataagtacaa ggcttcatgc atcgttaggc atttttatcc accgggctcc gtctatgtgt tctggaggca agatgggaat atcgttacac cacgtaagga cacggacgga agtttttggt ggtttgaatc agcccgggga gccaccctgg tatctacgat aacgctgggc aactcggcca tcgaccctcc tcccaagatt tcatgtctgg tagcctggaa gcagggaaat atgatgagta ctacgaacgc cactgcaatc ccgaccgtat atcatcatcc ccggatatcc ctggctttca aagatgggta tgcaatatgt actacgcaat gtgtgccgtt cggaattacc atacgatggt tagtacacga tgaacccaaa cctaatacaa cttatgatac tgtggttaca ggtctttgca ggaccctcaa gcggcataga aatatcatca gccgaatatt actccaagat gactggcaga aaacaaagta tacatgtcgt ctcatcggct -continued atcctttcga cgaagacaaa tttcaagctt tcgattactt cgacgcgacg ccatcgacga gggggtcccc catggttctc gcgatagcgg ctgttgtggg actagctttg attttgggaa tgggtacact cctgacggct ctgtgtttct acgcctccgg gaaaaaatac atattacttt cgtccgtcta g Glycoprotein C of SB-1 [Gallid herpesvirus 3] with GenBank Accession NO. AEI00252.1
(SEQ ID NO: 35)

MHASRALRALGWTRLLFVVLFSGRVLSASINPDLATPPVIAFNPSSIPADDGPLAKVPASPPAGEKEESH

KNASDARRMPSIVCDKEEVFVFLNKTGRFVCTLKIAPPSDNEWSNFALDLIFNPIEYHANEKNVEAARIA

GLYGVPGSDYAYPRPSELISSIRRDPQGTFWTSPSAHGDKYFIWLNKTTNTMGVEIRNVDYADNGYIQVA

MRDPFNRPLLDKHVYIRVCQRPASVDVLAPPVLSGDKYKASCIVRHFYPPGSVYVFWRQDGNIVTPRKDT

DGSFWWFESARGATLVSTITLGNSAIDPPPKISCLVAWKQGNMMSTTNATAIPTVYHHPRISLAFKDGYA

ICTTQCVPFGITIRWLVHDEPKPNTTYDTVVTGLCRTLKRHRNIISRILLQDDWQKTKYTCRLIGYPFDE

DKFQAFDYFDATPSTRGSPMVLAIAAVVGLALILGMGTLLTALCFYASGKKYILLSSV

Partial plasmid pSB1 44cds SV FCAopt sequence for vSB1-009 (6791 bp)
Green and Italic = UL44 Recombination Arms
BLUE AND UPPERCASE = SV40 PROMOTER
Black and Bold = NDV-F-CAO2-CSmut sequence
(SEQ ID NO: 37)

*Cttttgtcatgctcggagctctgatcgcatcttatcattacgtctgcatagcaacgtct*

*ggagacgtgacgtggaagaccgggtttttagttgtggcggcagggacgattgccggcat*

*cacggctccgtatggagacatttctcctctagccggctttctttcggcgtatacggcgt*

*tagctattcacgtggtcagagacgccagtcggtctctaatgaacacgtgctactaccgt*

*gcacgtcgggaaattactgtgaacggtgcatatcgcctcggtcgcgcgcgtctcccgcc*

*cagcacggacgccgaggcgacgcgcgaagaagacgtatccagttacgatacgctggggg*

*ggaatattcctacgataattctgagcctcatagcggtcatctcgattccagccatagcc*

*agctttcaaaagtacatgtcgaacgcaactaagcaccagtcaacattgactgacacgtt*

*acgcagtatatgcggtttcttggtgggtacaagtgtcgcgatattccttccgtcgcgct*

*accacgaggttctgttccgtccaattcttgtattactgttaatattcggggcaatggct*

*actaccttagccggcttcggtttacttctcgggccgacattgttttccgcgacagccgc*

*ggttctgtgctgctacacttgtataaatgtacgcaacgcgaatagcggaataaagcaat*

*tggcggccgccgcagctggtaaatgcatattaggaactgccatctcgagcatgttggtt*

*tgcgtgttaatacaatattcctgatcgcggagcgattaattttatatcatgtgctcat*

*agcgttctttcgaactgcgaataaaactttcgtggctactaaaggggcctatcgtgggt*

*ttatgcgctgtcgaaaacatgaaagggccgatttaaagctaagttgcgcaggcagaggc*

*cactccatatacgctctcggagacgcggctcgcacgccagctgaaatattttcccccct* gcaggtcgaccCAATTCGAGCTCGGTACAGCTTGGCTGTGGAATGTGTGTCAGTTAGGG

TGTGGAAAGTCCCCAGGCTCCCCAGCAGGCAGAAGTATGCAAAGCATGCATCTCAATTA

GTCAGCAACCAGGTGTGGAAAGTCCCCAGGCTCCCCAGCAGGCAGAAGTATGCAAAGCA

TGCATCTCAATTAGTCAGCAACCATAGTCCCGCCCCTAACTCCGCCCATCCCGCCCCTA

ACTCCGCCCAGTTCCGCCCATTCTCCGCCCCATGGCTGACTAATTTTTTTTATTTATGC

AGAGGCCGAGGCCGCCTCGGCCTCTGAGCTATTCCAGAAGTAGTGAGGAGGCTTTTTTG

GAGGCCTAGGCTTTTGCAAAAAGCTcccggggcggccgccaccatgggcagcaagccca gcacctggatcagcgtgaccctgatgctgatcaccagaaccatgctgatcctgagctgc atctgccccacaagcagcctggacggcagacccctggccgctgccggcatcgtggtgac

-continued cggcgacaaggccgtgaacatctacaccagcagccagaccggcagcatcatcatcaagc tgctgcccaacatgcccaaggacaaagaggcctgcgccaaggccccccctggaagcctac aacagaaccctgaccaccctgctgaccccccctgggcgacagcatcagaagaatccaggg cagcgccaccacaagcggcggaggaaagcagggcagactggtgggcgctatcatcggga gcgtggccctgggcgtggccacagctgcccagattaccgctgcagccgccctgattcag gccaatcagaacgccgccaacatcctgagactgaaagagagcattgccgccaccaacga cgccgtgcacgaagtgacaaacggactgtcccagctggctgtcgctgtcggcaagatgc agcagttcgtgaacaaccagttcaacaacaccgccagagagctggactgcatcaagatc gcccagcaggtgggcgtggagctgaacctgtacctgaccgagctgaccacagtgttcgg cccccagatcacaagccccgctctgacccagctgacaatccaggccctgtacaacctgg ctggcggcaacatggactatctgctgactaagctgggagtgggcaacaaccagctgtcc agcctgatcgggtccgggctgatcacaggcaaccccatcctgtacgacagccagacaca gctgctgggcatccagatcaacctgccatccgtgggaagcctgaacaacatgagagcca cctacctggaaaccctgagcgtgtccaccaccaagggcttcgccagcgccctggtgccc aaggtggtgacacaggtgggcagcgtgatcgaggaactggacaccagctactgcatcga gagcgacatcgacctgtactgcaccagagtggtgaccttcccaatgagccccggcatct acagctgcctgagcggcaacaccagcgcctgcatgtacagcaagaccgaaggagcactg acaacaccctacatggccctgaagggaagcgtgatcgccaactgcaagatgaccacctg cagatgcgccgacccccccaggcatcatcagccagaactacggcgaggccgtgagcctga tcgacaaacattcctgtagcgtgctgtccctggatggcatcacactgagactgagcggc gagttcgacgccacctaccagaagaacatcagcatcctggacagccaggtgatcgtgac cggcaacctggacatcagcaccgagctgggcaacgtgaacaacagcatcagcagcaccc tggacaagctggccgagtccaacaacaagctgaacaaagtgaacgtgaacctgaccagc acaagcgccctgatcacctacatcgtgctggccatcgtgtccctggccttcggcgtgat cagcctggtgctggcctgctacctgatgtacaagcagagagcccagcagaaaaccctgc tgtggctgggcaataacaccctggaccagatgagggccaccaccagaacctgatgagcg gccgcgatacctgcagg*tttgcggtgacattgatctggctcattatatgccccgagctc*

*ttgtaacatcgcggacgcgatttccgtagtaggcacatctcaaatgcaaaagcggcatg*

*tcaaccgtataggtacatccggccctgcttacagtcggtagggcatatatccaccggaa*

*aacttcagctttagactcctcaggtgatgaggaatagtatgtaaccctctagcagtacg*

*gtatttctaaaaaaaggtagatccttttccacacggcacagactaaataacgtacacta*

*cacaggttctctcgaacttcgtttggaccggaattattccctcggcagcgcctaaaaag*

*caaacctctagagtagataagtgtcagtgaacctaggccttctttgttccacggctgga*

*aagctaagggacgaggtacacgcgaccccagccacgcacgaacagagtttaacggaagc*

*gtcgtttgcgggataaggttgtcggaccccgcgggtccgttgaaaagtggctgcgcgcc*

*taccgacgaatacgtcggtaacaattttagaaatcgaatatgactgcgagtaccgtaca*

*atcgcgaaatacggtctctatatagctactcggtccttaaatatgtaagtatgatgtcc*

*cctactcccgaagacgaccgcgacttggtcgcagtacgtgggctgctccggatgatgga*

*cgagaccacatctgagcgacacaaacgttcgcgttcaggatgcccccggttgttatgcg*

*gttgtacgatcgggatcgctcttactgtgttcgtcatcacagctacggtcgtgctagct*

-continued

*tcgctgtttgcattctcttacatgtccctggagtccggtacatgtcctcacgaatggat*

*cggtttaggctatagttgtatgcgcgcgatggggagcaacgctaccgagctagaagccc*

*tagatacgtgctcccgacataacagcaagcttgtcgactttactcatgcgaaaattcta*

*atcgaagctatcgc*

Partial plasmid pHM103 + Fopt DNA sequence for vHVT114
Green and Italic = Arms
Black and bold = NDV Fopt
BLUE AND UPPERCASE = SV40 PROMOTER
Red and Italic and underlined = SV40 polyA (SEQ ID NO: 38)

*gagctcagggtatgatactcagctgttattgtggccgaccaggaggactccaatgctta*

*gcattcataagaacgctagagatgctatttaacgatgtgctgtcgtctaaagaatttgt*

*gcatttagcctttaaatgtaaaaccaatgacgcattcactacgctcgtgcgtgcaattt*

*ctgggccagggtatgcatattccataacagaaatcgacacttgagaagaggatctgact*

*gtttgggataaaggtcgtttgggtctgtcctagcgatataatttatatgacgatataca*

*ttaaacatctgtgtgcagtacttaggtatttaatcatgtcgatgaaatgttatgtgtaa*

*atatcggacaatatagataacgggcacgctgctattgtaacgtgcgcccgcgcgctagt*

*gctgactaatagtgtggatgatgtatacagtatattacaaacggaaatgatacgtaata*

*aattatgtactcttattgatttataaaaacatacatgcagtgttgctatgtcacataat*

*tagcctcgcccgtctacgctccactgaagataatgggctcccgctgttcaaaaaaatca*

*gcgtgcgtcgataagactttggtgcagtctcttcggggtcgcaatttagatttgccgca*

*tggagggtatctggggatttttgccaatgctggagcgacgactgtacgattcgtcccat*

*cgggatctagcagaccaatgatgttgacacacatcggccatgcatgtacggacggtcta*

*ttgcgcgagtttgttattttcgaaggacaagatggaagtgtatatggaaccgacaataa*

*tgttagtttgcatttcttagggcggaatctacatgatatcttatccaagcggggtatga*

*gccagagagatgtgatggtcataaagggtaaatttttttagatctgaaataacgcagttg*

*cccaaacaacgatcgcgattaaaagaaaaatcggatggttcaattaggacatgcatgga*

*ttctgtgcgcataaaccataaccgcagcactgttgggcacttcggtaactcaaatgcga*

*agcgttgcacgtctgcgataactacgcctactatgcacattgttactcctgcatcttaa*

*aaatatatcctgtagtaattttcacagcaatgtcataacatcatctcgctaaagaatga*

*cctgggattggagaagtaatgaatatttgcaaccaatgcattgaataaactaacattaa*

*ac*GAATTCGAGCTCGGTACAGCTTGGCTGTGGAATGTGTGTCAGTTAGGGTGTGGAAAG

TCCCCAGGCTCCCCAGCAGGCAGAAGTATGCAAAGCATGCATCTCAATTAGTCAGCAAC

CAGGTGTGGAAAGTCCCCAGGCTCCCCAGCAGGCAGAAGTATGCAAAGCATGCATCTCA

ATTTAGTCAGCAACCATAGTCCCGCCCCTAACTCCGCCCATCCCGCCCCTAACTCCGCCC

AGTTCCGCCCATTCTCCGCCCCATGGCTGACTAATTTTTTTTATTTATGCAGAGGCCGA

GGCCGCCTCGGCCTCTGAGCTATTCCAGAAGTAGTGAGGAGGCTTTTTTGGAGGCCTAG

GCTTTTGCAAAAAGCTgcggccgccaccatgggcagcaagcccagcacaagaatcccag ccccctgatgctgatcacccgcatcatgctgatcctgggctgcatcagacccacaagc tccctggatggacgccccctggccgctgccggcatcgtggtgaccggcgacaaggccgt gaacgtgtacaccagcagccagaccggcagcatcatcgtgaagctgctgcccaacatgc ccagagacaaagaggcctgcgccaaggccccccctggaagcctacaacagaaccctgacc accctgctgacccccctgggcgacagcatcagaaagatccagggctccgtgagcacaag cggcggaggaaagcagggcagactgatcggcgccgtgatcggcagcgtggccctgggag -continued tggctacagctgcccagattaccgctgcagccgccctgatccaggccaaccagaacgcc gccaacatcctgagactgaaagagagcattgccgccaccaacgaggccgtgcacgaagt gaccgacggcctgagccagctgtccgtggccgtgggcaagatgcagcagttcgtgaacg accagttcaacaacaccgccagagagctggactgcatcaagatcacccagcaggtgggc gtggagctgaacctgtacctgaccgagctgaccacagtgttcggcccccagatcacaag cccagccctgacacagctgaccatccaggccctgtacaacctggctggcggcaacatgg actatctgctgacaaagctgggaatcggcaacaaccagctgtccagcctgatcggaagc ggcctgatcaccggctaccccatcctgtacgacagccagacacagctgctgggcatcca ggtgaacctgcccagcgtgggcaacctgaacaacatgcgcgccacctacctggaaaccc tgagcgtgtccaccaccaagggctacgccagcgccctggtgcccaaggtggtgacacag gtgggcagcgtgatcgaggaactggacaccagctactgcatcgagagcgacctggacct gtactgcaccagaatcgtgaccttcccaatgagccccggcatctacagctgcctgagcg gcaacaccagcgcctgcatgtacagcaagaccgaaggcgcactgacaacaccctacatg gccctgaagggaagcgtgatcgccaactgcaagatcaccacctgcagatgcaccgaccc cccaggcatcatcagccagaactacggcgaggccgtgagcctgatcgatcgccattcct gtaacgtgctgtccctggacggcatcacactgagactgagcggcgagttcgatgccacc taccagaagaacatcagcatcctggacagccaggtgatcgtgaccggcaacctggacat cagcaccgagctgggcaacgtgaataacagcatcagcaacgccctggacagactggccg agagcaacagcaagctggaaaaagtgaacgtgcgcctgacatccacttccgctctgatc acctacatcgtgctgaccgtgatcagcctggtgttcggcgccctgagcctggtgctggc ctgctacctgatgtacaagcagaaggcccagcagaaaaccctgctgtggctgggcaaca acaccctggaccagatgagagccaccaccagagcctgatgagcggccgc*ggggatccag*

*acatgataagatacattgatgagtttggacaaaccacaactagaatgcagtgaaaaaaa*

*tgctttatttgtgaaatttgtgatgctattgctttatttgtaaccattataagctgcaa*

*taaacaagttaacaacaacaattgcattgattttatgtttcaggttcagggggaggtgt*

*gggaggttttttcggatcctctagagtcgacaattattttatttaataacatatagccc*

*aaagacctctatgaacatttagtttcccgtatactcaacggcgcgtgtacacacgcatc*

*tctttgcatagcgatgaagtttgttcggcagcagaaaatgcagatatccaacaatctgg*

*agaaaacttatcatcacagtggcagtggaaacatacccccctctatattcatggtataat*

*tatcgtctacagcgtccaggatagtggcgtgagaaaatggagatctgcagccctccttt*

*ccatggcatgccgctttattgttcattaaacgcacaatggtctcaacgccagatatggg*

*catagattctgaagaacccgttgacaatccgaagaagaaggcgtgcaggtctttggaag*

*actcgcacgttggtcttataatgtatgatcgagatgtcaccctaatgccacatggtaca*

*ggcttatcgcggtcatggcgatcggacttgtaatttgcaacgatgggcaaaggatcgac*

*gacatgccaaacattctgaacccgtagagatgttaacgatgacgaggatgaatatccca*

*tgctcgctgccatagtatcaagtacaccgcgaataaggacgcgtccaacatcgttatat*

*gcacacaatgggctacacgtgactaacacccccgaatattagtcatatgtgagtttcag*

*tctggctcccatatagcctgtagactatttgtggtttaagtgtgaacgaggcgctgtga*

*acgagactcgggccgattgtaagaacaagcaaatgcactttccatttaacaagaagtgt*

*agagagaatactcaacctctttggatgtatcctcgag*

-continued

DNA coding for IBDV VP2 protein (SEQ ID NO: 39)

ATGACAAACCTGCAAGATCAAACCCAACAGATTGTTCCGTTCATACGGAGCCTTCTGAT

GCCAACAACCGGACCGGCGTCCATTCCGGACGACACCCTGGAGAAGCACACTCTCAGGT

CAGAGACCTCGACCTACAATTTGACTGTGGGGGACACAGGGTCAGGGCTAATTGTCTTT

TTCCCTGGATTCCCTGGCTCAATTGTGGGTGCTCACTACACACTGCAGAGCAATGGGAA

CTACAAGTTCGATCAGATGCTCCTGACTGCCCAGAACCTACCGGCCAGCTACAACTACT

GCAGACTAGTGAGTCGGAGTCTCACAGTGAGGTCAAGCACACTCCCTGGTGGCGTTTAT

GCACTAAACGGCACCATAAACGCCGTGACCTTCCAAGGAAGCCTGAGTGAACTGACAGA

TGTTAGCTACAATGGGTTGATGTCTGCAACAGCCAACATCAACGACAAAATTGGGAATG

TCCTGGTAGGGGAAGGGGTCACTGTCCTCAGCCTACCCACATCATATGATCTTGGGTAT

GTGAGGCTTGGTGACCCCATTCCCGCTATAGGGCTTGACCCAAAAATGGTAGCTACATG

CGACAGCAGTGACAGGCCCAGAGTCTACACCATAACTGCAGCCGATGATTACCAATTCT

CATCACAGTACCAACCAGGTGGGGTAACAATCACACTGTTCTCAGCCAACATTGATGCT

ATCACAAGCCTCAGCATTGGGGGAGAGCTCGTGTTTCAAACAAGCGTCCAAGGCCTTGT

ACTGGGCGCCACCATCTACCTTATAGGCTTTGATGGGACTGCGGTAATCACCAGAGCTG

TAGCCGCAGATAATGGGCTGACGGCCGGCACCGACAATCTTATGCCATTCAATCTTGTC

ATTCCAACCAATGAGATAACCCAGCCAATCACATCCATCAAACTGGAGATAGTGACCTC

CAAAAGTGGTGGTCAGGCAGGGGATCAGATGTCATGGTCGGCAAGTGGGAGCCTAGCAG

TGACGATCCATGGTGGCAACTATCCAGGGGCCCTCCGTCCCGTCACACTAGTAGCCTAC

GAAAGAGTGGCAACAGGATCCGTCGTTACGGTCGCTGGGGTGAGTAACTTCGAGCTGAT

TCCAAATCCTGAACTAGCAAAGAACCTGGTTACAGAATACGGCCGATTTGACCCAGGAG

CCATGAACTACACAAAATTGATACTGAGTGAGAGGGACCGTCTTGGCATCAAGACCGTC

TGGCCAACAAGGGAGTACACTGATTTTCGTGAGTACTTCATGGAGGTGGCCGACCTCAA

CTCTCCCCTGAAGATTGCAGGAGCATTTGGCTTCAAAGACATAATCCGGGCTATAAGGA

GGTAA

IBDV VP2 protein (SEQ ID NO: 40)

MTNLQDQTQQIVPFIRSLLMPTTGPASIPDDTLEKHTLRSETSTYNLTVGDTGSGLIVF

FPGFPGSIVGAHYTLQSNGNYKFDQMLLTAQNLPASYNYCRLVSRSLTVRSSTLPGGVY

ALNGTINAVTFQGSLSELTDVSYNGLMSATANINDKIGNVLVGEGVTVLSLPTSYDLGY

VRLGDPIPAIGLDPKMVATCDSSDRPRVYTITAADDYQFSSQYQPGGVTITLFSANIDA

ITSLSIGGELVFQTSVQGLVLGATIYLIGFDGTAVITRAVAADNGLTAGTDNLMPFNLV

IPTNEITQPITSIKLEIVTSKSGGQAGDQMSWSASGSLAVTIHGGNYPGALRPVTLVAY

ERVATGSVVTVAGVSNFELIPNPELAKNLVTEYGRFDPGAMNYTKLILSERDRLGIKTV

WPTREYTDFREYFMEVADLNSPLKIAGAFGFKDIIRAIRR

Partial plasmid pCD046 + NDV-F VII YZCQ for vHVT112
Green and Italic = Flanking Arms
BLUE AND UPPERCASE = mCMV IE
Black and Bold = NDV-F VIId wt YZCQ
Red and underlined = SV40 Poly A (SEQ ID NO: 46)

*gagctcagggtatgatactcagctgttattgtggccgaccaggaggactccaatgctta*

*gcattcataagaacgctagagatgctatttaacgatgtgctgtcgtctaaagaatttgt*

*gcatttagcctttaaatgtaaaaccaatgacgcattcactacgctcgtgcgtgcaattt*

*ctgggccagggtatgcatattccataacagaaatcgacacttgagaagaggatctgact*

-continued

*gtttgggataaaggtcgtttgggtctgtcctagcgatataatttatatgacgatataca*

*ttaaacatctgtgtgcagtacttaggtatttaatcatgtcgatgaaatgttatgtgtaa*

*atatcggacaatatagataacgggcacgctgctattgtaacgtgcgcccgcgcgctagt*

*gctgactaatagtgtggatgatgtatacagtatattacaaacggaaatgatacgtaata*

*aattatgtactcttattgatttataaaaacatacatgcagtgttgctatgtcacataat*

*tagcctcgcccgtctacgctccactgaagataatgggctcccgctgttcaaaaaaatca*

*gcgtgcgtcgataagactttggtgcagtctcttcggggtcgcaatttagatttgccgca*

*tggagggtatctggggattttgccaatgctggagcgacgactgtacgattcgtcccat*

*cgggatctagcagaccaatgatgttgacacacatcggccatgcatgtacggacggtcta*

*ttgcgcgagtttgttattttcgaaggacaagatggaagtgtatatggaaccgacaataa*

*tgttagtttgcatttcttagggcggaatctacatgatatcttatccaagcggggtatga*

*gccagagagatgtgatggtcataaagggtaaatttttagatctgaaataacgcagttg*

*cccaaacaacgatcgcgattaaaagaaaaatcggatggttcaattaggacatgcatgga*

*ttctgtgcgcataaaccataaccgcagcactgttgggcacttcggtaactcaaatgcga*

*agcgttgcacgtctgcgataactacgcctactatgcacattgttactcctgcatcttaa*

*aaatatatcctgtagtaattttcacagcaatgtcataacatcatctcgctaaagaatga*

*cctgggattggagaagtaatgaatatttgcaaccaatgcattgaataaactaacattaa*

*ac*GAATTCAATAGTGGATCCCCCAACTCCGCCCGTTTTATGACTAGAACCAATAGTTTT

TAATGCCAAATGCACTGAAATCCCCTAATTTGCAAAGCCAAACGCCCCCTATGTGAGTA

ATACGGGGACTTTTTACCCAATTTCCCACGCGGAAAGCCCCCTAATACACTCATATGGC

ATATGAATCAGCACGGTCATGCACTCTAATGGCGGCCCATAGGGACTTTCCACATAGGG

GGCGTTCACCATTTCCCAGCATAGGGGTGGTGACTCAATGGCCTTTACCCAAGTACATT

GGGTCAATGGGAGGTAAGCCAATGGGTTTTTCCCATTACTGGCAAGCACACTGAGTCAA

ATGGGACTTTCCACTGGGTTTTGCCCAAGTACATTGGGTCAATGGGAGGTGAGCCAATG

GGAAAAACCCATTGCTGCCAAGTACACTGACTCAATAGGGACTTTCCAATGGGTTTTTC

CATTGTTGGCAAGCATATAAGGTCAATGTGGGTGAGTCAATAGGGACTTTCCATTGTAT

TCTGCCCAGTACATAAGGTCAATAGGGGGTGAATCAACAGGAAAGTCCCATTGGAGCCA

AGTACACTGCGTCAATAGGGACTTTCCATTGGGTTTTGCCCAGTACATAAGGTCAATAG

GGGATGAGTCAATGGGAAAAACCCATTGGAGCCAAGTACACTGACTCAATAGGGACTTT

CCATTGGGTTTTGCCCAGTACATAAGGTCAATAGGGGGTGAGTCAACAGGAAAGTTCCA

TTGGAGCCAAGTACATTGAGTCAATAGGGACTTTCCAATGGGTTTTGCCCAGTACATAA

GGTCAATGGGAGGTAAGCCAATGGGTTTTTCCCATTACTGGCACGTATACTGAGTCATT

AGGGACTTTCCAATGGGTTTTGCCCAGTACATAAGGTCAATAGGGGTGAATCAACAGGA

AAGTCCCATTGGAGCCAAGTACACTGAGTCAATAGGGACTTTCCATTGGGTTTTGCCCA

GTACAAAAGGTCAATAGGGGGTGAGTCAATGGGTTTTTCCCATTATTGGCACGTACATA

AGGTCAATAGGGGTGAGTCATTGGGTTTTTCCAGCCAATTTAATTAAAACGCCATGTAC

TTTCCCACCATTGACGTCAATGGGCTATTGAAACTAATGCAACGTGACCTTTAAACGGT

ACTTTCCCATAGCTGATTAATGGGAAAGTACCGTTCTCGAGCCAATACACGTCAATGGG

AAGTGAAAGGGCAGCCAAAACGTAACACCGCCCCGGTTTTCCCCTGGAAATTCCATATT

GGCACGCATTCTATTGGCTGAGCTGCGTTCTACGTGGGTATAAGAGGCGCGACCAGCGT

-continued

CGGTACCGTCGCAGTCTTCGGTCTGACCACCGTAGAACGCAGAGCTCCTCGCTGCAG*gc*

*ggccgc*atgggctctaaaccttctaccaggatcccagcacctctgatgctgatcacccg gattatgctgatattggactgtatccgtccgacaagctctcttgacggcaggcctcttg cagctgcaggaattgtagtaacaggagataaggcagtcaatgtatatacctcgtctcag acagggtcaatcatagtcaagttgctcccgaatatgcccaaggataaggaggcgtgtgc gaaagacccattagaggcatataacagaacactgactactttgctcactcctcttggcg aatccatccgcaagatccaagggtctgtgtccacgtctggaggaggcaagcaaggccgc ctgataggtgctgttattggtagtgtagctcttggggttgcaacagcggcacaaataac agcagctgcggccctaatacaagccaaccagaatgctgccaacatccttcggcttaagg agagcattgctgcaaccaatgaagctgtgcatgaagtcaccgacggattatcacaacta tcagtggcagttgggaagatgcagcagtttgtcaatgaccagtttaataatacagcgcg agaattggactgtataaaaatcacacaacaggttggtgtagaactcaacctatacctaa ctgaattgactacagtattcgggccacagatcacctcccctgcattaactcagctgacc atccaggcactttataatttagctggtggcaatatggattacttattaactaagttagg tatagggaacaatcaactcagctcattaattggcagcggcctgatcactggttacccta tattgtatgactcacagactcaactcttgggcatacaagtgaatttgccctcagtcggg aacttaaataatatgcgtgccacctatttagagaccttatctgtaagtacagccaaagg atatgcctcagcacttgttccaaaagtagtgacacaagtcggttctgtgatagaagagc ttgacacctcatactgtatagagtccgatctggatttatattgtactagaatagtgaca ttccccatgtccccaggtatttattcctgtttaagcggcaacacatcagcttgcatgta ttcaaagactgaaggcgcactcactacgccgtatatggcccttaaaggctcagttattg ccaattgtaagataacaacatgtagatgtacagaccctcctggtatcatatcgcaaaat tatggagaagctgtatccctgatagatagacattcgtgcaatgtcttatcattagacgg gataactctgaggctcagtggagaatttgatgcaacttatcaaaagaacatctcaatac tagattctcaagtcatcgtgacaggcaatcttgatatatcaactgaacttggaaacgtc aacaattcaatcagcaatgccttggataagttggcaaaaagcaacagcaagctagaaaa agtcaatgtcagactaaccagcacatccgctctcattacctatattgttctgactgtca tttctctagttttcggtgcactaagtctgggtttaacatgttacctgatgtacaaacaa aaggcacaacaaaagaccttgctatggcttgggaataataccctcgatcagatgagagc cactacaagagcatga*gcggccgc*ggggatccagacatgataagatacattgatgagtt tggacaaaccacaactagaatgcagtgaaaaaaatgctttatttgtgaaatttgtgatg ctattgctttatttgtaaccattataagctgcaataaacaagttaacaacaacaattgc attgattttatgtttcaggttcagggggaggtgtgggaggttttttcggatcctctaga gtcgac*aattattttatttaataacatatagcccaaagacctctatgaacatttagttt*

*cccgtatactcaacggcgcgtgtacacacgcatctctttgcatagcgatgaagtttgtt*

*cggcagcagaaaatgcagatatccaacaatctggagaaaacttatcatcacagtggcag*

*tggaaacataccccctctatattcatggtataattatcgtctacagcgtccaggatagt*

*ggcgtgagaaaatggagatctgcagccctcctttccatggcatgccgctttattgttca*

*ttaaacgcacaatggtctcaacgccagatatgggcatagattctgaagaacccgttgac*

*aatccgaagaagaaggcgtgcaggtctttggaagactcgcacgttggtcttataatgta*

*tgatcgagatgtcaccctaatgccacatggtacaggcttatcgcggtcatggcgatcgg*

-continued

*acttgtaatttgcaacgatgggcaaaggatcgacgacatgccaaacattctgaacccgt*

*agagatgttaacgatgacgaggatgaatatcccatgctcgctgccatagtatcaagtac*

*accgcgaataaggacgcgtccaacatcgttatatgcacacaatgggctacacgtgacta*

*acacccccgaatattagtcatatgtgagtttcagtctggctcccatatagcctgtagac*

*tatttgtggtttaagtgtgaacgaggcgctgtgaacgagactcgggccgattgtaagaa*

*caagcaaatgcactttccatttaacaagaagtgtagagagaatactcaacctctttgga*

*tgtatcctcgag*

Partial plasmid pCD046 + NDV Texas F or vHVT113
Green and Italic = Flanking Arms
BLUE AND UPPERCASE = mCMV IE
Black and Bold = NDV Texas F
Red and underlined = SV40 Poly A (SEQ ID NO: 47)

*gagctcagggtatgatactcagctgttattgtggccgaccaggaggactccaatgctta*

*gcattcataagaacgctagagatgctatttaacgatgtgctgtcgtctaaagaatttgt*

*gcatttagcctttaaatgtaaaaccaatgacgcattcactacgctcgtgcgtgcaattt*

*ctgggccagggtatgcatattccataacagaaatcgacacttgagaagaggatctgact*

*gtttgggataaaggtcgtttgggtctgtcctagcgatataatttatatgacgatataca*

*ttaaacatctgtgtgcagtacttaggtatttaatcatgtcgatgaaatgttatgtgtaa*

*atatcggacaatatagataacgggcacgctgctattgtaacgtgcgcccgcgcgctagt*

*gctgactaatagtgtggatgatgtatacagtatattacaaacggaaatgatacgtaata*

*aattatgtactcttattgatttataaaaacatacatgcagtgttgctatgtcacataat*

*tagcctcgcccgtctacgctccactgaagataatgggctcccgctgttcaaaaaaatca*

*gcgtgcgtcgataagactttggtgcagtctcttcggggtcgcaatttagatttgccgca*

*tggagggtatctggggattttgccaatgctggagcgacgactgtacgattcgtcccat*

*cgggatctagcagaccaatgatgttgacacacatcggccatgcatgtacggacggtcta*

*ttgcgcgagtttgttattttcgaaggacaagatggaagtgtatatggaaccgacaataa*

*tgttagtttgcatttcttagggcggaatctacatgatatcttatccaagcggggtatga*

*gccagagagatgtgatggtcataaagggtaaatttttttagatctgaaataacgcagttg*

*cccaaacaacgatcgcgattaaaagaaaaatcggatggttcaattaggacatgcatgga*

*ttctgtgcgcataaaccataaccgcagcactgttgggcacttcggtaactcaaatgcga*

*agcgttgcacgtctgcgataactacgcctactatgcacattgttactcctgcatcttaa*

*aaatatatcctgtagtaattttcacagcaatgtcataacatcatctcgctaaagaatga*

*cctgggattggagaagtaatgaatatttgcaaccaatgcattgaataaactaacattaa*

*ac*GAATTCAATAGTGGATCCCCCAACTCCGCCCGTTTTATGACTAGAACCAATAGTTTT

TAATGCCAAATGCACTGAAATCCCCTAATTTGCAAAGCCAAACGCCCCCTATGTGAGTA

ATACGGGGACTTTTTACCCAATTTCCCACGCGGAAAGCCCCCTAATACACTCATATGGC

ATATGAATCAGCACGGTCATGCACTCTAATGGCGGCCCATAGGGACTTTCCACATAGGG

GGCGTTCACCATTTCCCAGCATAGGGGTGGTGACTCAATGGCCTTTACCCAAGTACATT

GGGTCAATGGGAGGTAAGCCAATGGGTTTTTCCCATTACTGGCAAGCACACTGAGTCAA

ATGGGACTTTCCACTGGGTTTTGCCCAAGTACATTGGGTCAATGGGAGGTGAGCCAATG

GGAAAAACCCATTGCTGCCAAGTACACTGACTCAATAGGGACTTTCCAATGGGTTTTTC

CATTGTTGGCAAGCATATAAGGTCAATGTGGGTGAGTCAATAGGGACTTTCCATTGTAT

-continued

TCTGCCCAGTACATAAGGTCAATAGGGGGTGAATCAACAGGAAAGTCCCATTGGAGCCA

AGTACACTGCGTCAATAGGGACTTTCCATTGGGTTTTGCCCAGTACATAAGGTCAATAG

GGGATGAGTCAATGGGAAAAACCCATTGGAGCCAAGTACACTGACTCAATAGGGACTTT

CCATTGGGTTTTGCCCAGTACATAAGGTCAATAGGGGGTGAGTCAACAGGAAAGTTCCA

TTGGAGCCAAGTACATTGAGTCAATAGGGACTTTCCAATGGGTTTTGCCCAGTACATAA

GGTCAATGGGAGGTAAGCCAATGGGTTTTTCCCATTACTGGCACGTATACTGAGTCATT

AGGGACTTTCCAATGGGTTTTGCCCAGTACATAAGGTCAATAGGGGTGAATCAACAGGA

AAGTCCCATTGGAGCCAAGTACACTGAGTCAATAGGGACTTTCCATTGGGTTTTGCCCA

GTACAAAAGGTCAATAGGGGGTGAGTCAATGGGTTTTTCCCATTATTGGCACGTACATA

AGGTCAATAGGGGTGAGTCATTGGGTTTTTCCAGCCAATTTAATTAAAACGCCATGTAC

TTTCCCACCATTGACGTCAATGGGCTATTGAAACTAATGCAACGTGACCTTTAAACGGT

ACTTTCCCATAGCTGATTAATGGGAAAGTACCGTTCTCGAGCCAATACACGTCAATGGG

AAGTGAAAGGGCAGCCAAAACGTAACACCGCCCCGGTTTTCCCCTGGAAATTCCATATT

GGCACGCATTCTATTGGCTGAGCTGCGTTCTACGTGGGTATAAGAGGCGCGACCAGGCT

CGGTACCGTCGCAGTCTTCGGTCTGACCACCGTAGAACGCAGAGCTCCTCGCTGCAGgc ggccgcatgggctccagatcttctaccaggatcccggtacctctaatgctgatcatccg aaccgcgctgacactgagctgtatccgtctgacaagctctcttgatggcaggcctcttg cggctgcagggatcgtggtaacaggagataaagcagtcaacatatacacctcatcccag acagggtcaatcatagttaagttactcccgaatatgcccaaggacaaagaggtgtgtgc aaaagccccattggaggcatacaacaggacactgactactttactcaccccccttggtg attctatccgcaggatacaagagtctgtgactacttccggaggaggcaagcaaggccgc ctgataggtgccattatcggcagtgtagctcttggggttgcgacagctgcacagataac agcagcttcggccctgatacaagccaaccagaatgctgccaacatcctccggcttaaag agagcattgctgcaaccaatgaagctgtgcacgaggtcactgacggattatcacaacta gcagtggcagtagggaagatgcaacagtttgtcaatgaccagttcaataatacagcgca agaattggactgtataaaaattgcacagcaggtcggtgtagaactcaacttgtacctaa ctgaattgactacagtatttgggccacaaatcacttcccctgccttaactcagctgact atccaagcgctttacaatctagctggtggtaatatggattacttgctgactaagttagg tgtagggaacaaccaactcagctcattaattggtagcggcttgatcaccggcaacccta ttctgtacgactcacagactcagatcttgggtatacaggtaactttgccttcagttggg aacctgaataatatgcgtgccacctacctggagaccttatctgtaagcacaaccaaggg atttgcctcagcacttgtcccaaaagtggtgacacaggtcggttccgtgatagaagaac ttgacacctcatactgtatagggaccgacttggatttatactgtacaagaatagtgaca ttccctatgtctcctggtatttattcttgtctgagcggtaatacatcggcttgcatgta ttcaaagactgaaggcgcacttactacgccatatatggctctcaaaggctcagttattg ccaattgcaagctgacaacatgtagatgtgcagatcccccaggtatcatatcgcaaaat tatggagaagctgtgtccttaatagataggcactcatgcaacgtcttatccttagacgg gataactctgaggctcagtggggaatttgatgcaacctatcaaaagaatatctctatac tagattctcaagttatagtgacaggcaatcttgatatatcaactgagcttgggaatgtc aacaactcaataagtaatgccctgaataagttagaggaaagcaacagcaaactagacaa agtcaatgtcaaactgaccagcacatctgctctcattacctacatcgttttaactgtca

-continued tatctcttgttttggtgtacttagcctggttctagcatgctacctgatgtacaagcaa aaggcacaacaaaagaccttgttatggcttgggaataatacccttgatcagatgagagc cactacaaaaatatgagcggccgcgggg<u>atccagacatgataagatacattgatgagtt</u>

<u>tggacaaaccacaactagaatgcagtgaaaaaaatgctttatttgtgaaatttgtgatg</u>

<u>ctattgctttatttgtaaccattataagctgcaataaacaagttaacaacaacaattgc</u>

<u>attgattttatgtttcaggttcagggggaggtgtgggaggttttttcggatcctctaga</u>

<u>gtcgac</u>*aattatttt atttaataacatatagcccaaagacctctatgaacatttagttt*

*cccgtatactcaacggcgcgtgtacacacgcatctctttgcatagcgatgaagtttgtt*

*cggcagcagaaaatgcagatatccaacaatctggagaaaacttatcatcacagtggcag*

*tggaaacataccccctctatattcatggtataattatcgtctacagcgtccaggatagt*

*ggcgtgagaaaatggagatctgcagccctcctttccatggcatgccgctttattgttca*

*ttaaacgcacaatggtctcaacgccagatatgggcatagattctgaagaacccgttgac*

*aatccgaagaagaaggcgtgcaggtctttggaagactcgcacgttggtcttataatgta*

*tgatcgagatgtcaccctaatgccacatggtacaggcttatcgcggtcatggcgatcgg*

*acttgtaatttgcaacgatgggcaaaggatcgacgacatgccaaacattctgaacccgt*

*agagatgttaacgatgacgaggatgaatatcccatgctcgctgccatagtatcaagtac*

*accgcgaataaggacgcgtccaacatcgttatatgcacacaatgggctacacgtgacta*

*acacccccgaatattagtcatatgtgagtttcagtctggctcccatatagcctgtagac*

*tatttgtggtttaagtgtgaacgaggcgctgtgaacgagactcgggccgattgtaagaa*

*caagcaaatgcactttccatttaacaagaagtgtagagagaatactcaacctctttgga*

*tgtatcctcgag*

```
Partial plasmid pHM119 sequence for vHVT039
Green and Italic = BamHI fragment I intergenic Recombination Arms
BLUE AND UPPERCASE = MDV gB PROMOTER
Black and Bold = NDV-F wild type unmodified Texas strain sequence
Red and Italic and Underlined = SV40 Poly A tail
```

(SEQ ID NO: 48)

*gagctcagggtatgatactcagctgttattgtggccgaccaggaggactccaatgctta*

*gcattcataagaacgctagagatgctatttaacgatgtgctgtcgtctaaagaatttgt*

*gcatttagccttt aaatgtaaaaccaatgacgcattcactacgctcgtgcgtgcaattt*

*ctgggccagggtatgcatattccataacagaaatcgacacttgagaagaggatctgact*

*gtttgggataaaggtcgtttgggtctgtcctagcgatataatttatatgacgatataca*

*ttaaacatctgtgtgcagtacttaggtatttaatcatgtcgatgaaatgttatgtgtaa*

*atatcggacaatatagataacgggcacgctgctattgtaacgtgcgcccgcgcgctagt*

*gctgactaatagtgtggatgatgtatacagtatattacaaacggaaatgatacgtaata*

*aattatgtactcttattgatttataaaaacatacatgcagtgttgctatgtcacataat*

*tagcctcgcccgtctacgctccactgaagataatgggctcccgctgttcaaaaaaatca*

*gcgtgcgtcgataagacttt ggtgcagtctcttcggggtcgcaatttagatttgccgca*

*tggagggtatctggggattttt gccaatgctggagcgacgactgtacgattcgtcccat*

*cgggatctagcagaccaatgatgttgacacacatcggccatgcatgtacggacggtcta*

*ttgcgcgagtttgttatttt cgaaggacaagatggaagtgtatatggaaccgacaataa*

*tgttagtttgcatttcttagggcgaatctacatgatatcttatccaagcggggtatga*

*gccagagagatgtgatggtcataaagggtaaatttttt agatctgaaataacgcagttg*

-continued

*cccaaacaacgatcgcgattaaaagaaaaatcggatggttcaattaggacatgcatgga*

*ttctgtgcgcataaaccataaccgcagcactgttgggcacttcggtaactcaaatgcga*

*agcgttgcacgtctgcgataactacgcctactatgcacattgttactcctgcatcttaa*

*aaatatatcctgtagtaattttcacagcaatgtcataacatcatctcgctaaagaatga*

*cctgggattggagaagtaatgaatatttgcaaccaatgcattgaataaactaacattaa*

*ac*gaattcCGATGTTTAGTCACGATAGACATCGGTTCGCCCAGCCGTCGAATACAGCAT

TATATTTTAGTGTTGAAAATGTAGGGCTGCTTCCTCACTTAAAGGAGGAAATGGCTCGA

TTCATGTTTCATAGCAGTAGAAAAACAGATTGGACCGTCAGTAAGTTTAGAGGGTTTTA

TGACTTTAGCACTATAGATAATGTAACTGCGGCCCATCGCATGGCTTGGAAATATATCA

AAGAACTGATTTTTGCAACAGCTTTATTTTCTTCTGTATTTAAATGTGGCGAATTGCAC

ATCTGTCGTGCCGACAGTTTGCAGATCAACAGCAATGGAGACTATGTATGGAAAAATGG

AATATATATAACATATGAAACCGAATATCCACTTATAATGATTCTGGGGTCAGAATCAA

GCACTTCAGAAACGCAAAATATGACTGCAATTATTGATACAGATTTTTTTCGGTTGCTT

TATTCTATTTTGCAGTATATGGCCCCCGTTACGGCAGATCAGGTGCGAGTAGAACAGAT

TACCAACAGCCACGCCCCCATCTGACCCGTCCAATATTCTTGTGTCCCTGCATTTTATC

TCACACAATTTATGAACAGCATCATTAAGATCATCTCACTgcggccgcaagatgggctc cagatcttctaccaggatcccggtacctctaatgctgatcatccgaaccgcgctgacac tgagctgtatccgtctgacaagctctcttgatggcaggcctcttgcggctgcagggatc gtggtaacaggagataaagcagtcaacatatacacctcatcccagacagggtcaatcat agttaagttactcccgaatatgcccaaggacaaagaggtgtgtgcaaaagccccattgg aggcatacaacaggacactgactactttactcacccccccttggtgattctatccgcagg atacaagagtctgtgactacttccggaggaaggagacagagacgctttataggtgccat tatcggcagtgtagctcttggggttgcgacagctgcacagataacagcagcttcggccc tgatacaagccaaccagaatgctgccaacatcctccggcttaaagagagcattgctgca accaatgaagctgtgcacgaggtcactgacggattatcacaactagcagtggcagtagg gaagatgcaacagtttgtcaatgaccagttcaataatacagcgcaagaattggactgta taaaaattgcacagcaggtcggtgtagaactcaacttgtacctaactgaattgactaca gtatttgggccacaaatcacttcccctgccttaactcagctgactatccaagcgcttta caatctagctggtggtaatatggattacttgctgactaagttaggtgtagggaacaacc aactcagctcattaattggtagcggcttgatcaccggcaaccctattctgtacgactca cagactcagatcttgggtatacaggtaactttgccttcagttgggaacctgaataatat gcgtgccacctacctggagaccttatctgtaagcacaaccaagggatttgcctcagcac ttgtcccaaaagtggtgacacaggtcggttccgtgatagaagaacttgacacctcatac tgtatagggaccgacttggatttatactgtacaagaatagtgacattccctatgtctcc tggtatttattcttgtctgagcggtaatacatcggcttgcatgtattcaaagactgaag gcgcacttactacgccatatatggctctcaaaggctcagttattgccaattgcaagctg acaacatgtagatgtgcagatcccccaggtatcatatcgcaaaattatggagaagctgt gtccttaatagataggcactcatgcaacgtcttatccttagacgggataactctgaggc tcagtggggaatttgatgcaacctatcaaaagaatatctctatactagattctcaagtt atagtgacaggcaatcttgatatatcaactgagcttgggaatgtcaacaactcaataag taatgccctgaataagttagaggaaagcaacagcaaactagacaaagtcaatgtcaaac

-continued tgaccagcacatctgctctcattacctacatcgttttaactgtcatatctcttgttttt ggtgtacttagcctggttctagcatgctacctgatgtacaagcaaaaggcacaacaaaa gaccttgttatggcttgggaataataccccttgatcagatgagagccactacaaaaatat gagcggccgc*<u>ggggatccagacatgataagatacattgatgagtttggacaaaccacaa</u>*

*<u>ctagaatgcagtgaaaaaaatgctttatttgtgaaatttgtgatgctattgctttattt</u>*

*<u>gtaaccattataagctgcaataaacaagttaacaacaacaattgcattcattttatgtt</u>*

*<u>tcaggttcagggggaggtgtgggaggttttttcggatcctctaga</u>*gtcgac*aattattt*

*tatttaataacatatagcccaaagacctctatgaacatttagtttcccgtatactcaac*

*ggcgcgtgtacacacgcatctctttgcatagcgatgaagtttgttcggcagcagaaaat*

*gcagatatccaacaatctggagaaaacttatcatcacagtggcagtggaaacatacccc*

*ctctatattcatggtataattatcgtctacagcgtccaggatagtggcgtgagaaaatg*

*gagatctgcagccctcctttccatggcatgccgctttattgttcattaaacgcacaatg*

*gtctcaacgccagatatgggcatagattctgaagaacccgttgacaatccgaagaagaa*

*ggcgtgcaggtctttggaagactcgcacgttggtcttataatgtatgatcgagatgtca*

*ccctaatgccacatggtacaggcttatcgcggtcatggcgatcggacttgtaatttgca*

*acgatgggcaaaggatcgacgacatgccaaacattctgaacccgtagagatgttaacga*

*tgacgaggatgaatatcccatgctcgctgccatagtatcaagtacaccgcgaataagga*

*cgcgtccaacatcgttatatgcacacaatgggctacacgtgactaacacccccgaatat*

*tagtcatatgtgagtttcagtctggctcccatatagcctgtagactatttgtggtttaa*

*gtgtgaacgaggcgctgtgaacgagactcgggccgattgtaagaacaagcaaatgcact*

*ttccatttaacaagaagtgtagagagaatactcaacctctttggatgtatcctcgag*

Partial plasmid SORF3-US2 gp Var-Ewtsyn sequence (for vHVT202)
Green and Italic = Flanking Arms
BLUE AND UPPERCASE = GPCMV
Black and Bold = Varient E wt
Red and Italic and Underlined = Syn Poly A (SEQ ID NO: 56)

taaaatgggatctatcattacattcgttaagagtctggataattttactgtttgccagc ttcgatcttggaacgtactgtggatagtgccttacttggaatcgtgaaaatttgaaacg tccattatttggatatcttccggttgtcccatatcccgccctggtaccgctcggatacc ttgcccgtatggattcgtattgacagtcgcgcaatcggggaccaacaacgcgtgggtcc acactcattcggaaattttccgatgattctgaatatttattgccgctcgttacgagtcg ttggacatatctgtaatacatttcttcttctgaaggatcgctgcacatttgatctatac attggccaggatgttcaagtctcagatgttgcattctggcacagcacaactttatggca tttccgatgtaatcgtccggcagccctgggggagttctatattcgcatattgggatggt aaggacaatagcagatctcgcaacctccagggaggctataataacgtttttaaaggatg gatttctcataaaaatctgtcgcaaattacactgagaatatcctttactagcgccgatt gagagcatcgtcgtccaattttctaaatggaaagaaaacaaggcgggcaagagtgttcc aaacattttcattttcggcgaatctctcaaatcccatggcgtgcaattgattgcaaaat tggcacttccgttcacgtttgtatctccaaactctaagacacttttaattgaaaaacta cgttctagtgtggaaagaaacctataggcagaccatagaactatttgacaccacatatc tttttgtatgtcaaactgaccatgatcgtatgttgctgaatgcactagggcaattcgct cgcgcgactccatacattgaataattccacacgtcagctcatcggttagcaaggtccag -continued tagttgaagtcatttatttttccccgcggctggccaaatctacctctgggaatatccaa gttgtcgaatatgatcgcaccggctctggtcatggtgaaggaacttgtagcataaagac gcaggtatcataggggtaatattttttattcactcacatactaaaagtaacgcatatt agcaccatgtatgggctatcaattgacatttgcgtagcactacatcacgattatgtaca acataatgggacaacatatgcctgcaggTTAGTCATATGTTACTTGGCAGAGGCCGCAT

GGAAAGTCCCTGGACGTGGGACATCTGATTAATACGTGAGGAGGTCAGCCATGTTCTTT

TTGGCAAAGGACTACGGTCATTGGACGTTTGATTGGCATGGGATAGGGTCAGCCAGAGT

TAACAGTGTTCTTTTGGCAAAGGGATACGTGGAAAGTCCCGGGCCATTTACAGTAAACT

GATACGGGGACAAAGCACAGCCATATTTAGTCATGTATTGCTTGGCAGAGGGTCTATGG

AAAGTCCCTGGACGTGGGACGTCTGATTAATATGAAAGAAGGTCAGCCAGAGGTAGCTG

TGTCCTTTTTGGCAAAGGGATACGGTTATGGGACGTTTGATTGGACTGGGATAGGGTCA

GCCAGAGTTAACAGTGTTCTTTTGGCAAAGGAAACGTGGAAAGTCCCGGGCCATTTACA

GTAAACTGATACTGGGACAAAGTACACCCATATTTAGTCATGTTCTTTTTGGCAAAGAG

CATCTGGAAAGTCCCGGGCAGCATTATAGTCACTTGGCAGAGGGAAAGGGTCACTCAGA

GTTAAGTACATCTTTCCAGGGCCAATATTCCAGTAAATTACACTTAGTTTTATGCAAAT

CAGCCACAAAGGGGATTTTCCCGGTCAATTATGACTTTTTCCTTAGTCATGCGGTATCC

AATTACTGCCAAATTGGCAGTACATACTAGGTGATTCACTGACATTTGGCCGTCCTCTG

GAAAGTCCCTGGAAACCGCTCAAGTACTGTATCATGGTGACTTTGCATTTTTGGAGAGC

ACGCCCCACTCCACCATTGGTCCACGTACCCTATGGGGGAGTGGTTTATGAGTATATAA

GGGGCTCCGGTTTAGAAGCCGGGCAGAgcggccgcatgacaaacctgcaagatcaaacc caacagattgttccgttcatacggagccttctgatgccaacaaccggaccggcgtccat tccggacgacaccctggagaagcacactctcaggtcagagacctcgacctacaatttga ctgtgggggacacagggtcagggctaattgtctttttccctggattccctggctcaatt gtgggtgctcactacacactgcagagcaatgggaactacaagttcgatcagatgctcct gactgcccagaacctaccggccagctacaactactgcaggctagtgagtcggagtctca cagtaaggtcaagcacactccctggtggcgtttatgcactaaacggcaccataaacgcc gtgaccttccaaggaagcctgagtgaactgacagatgttagctacaacgggttgatgtc tgcaacagccaacatcaacgacaaaattgggaacgtcctagtaggggaaggggtaaccg tcctcagcttacccacatcatatgatcttgggtatgtgaggcttggtgaccccataccc gctatagggcttgacccaaaaatggtagcaacatgtgacagcagtgacaggcccagagt ctacaccataactgcagccgataattaccaattctcatcacagtaccaaacaggtgggg taacaatcacactgttctcagccaacattgatgccatcacaagtctcagcgttgggga gagctcgtgttcaaaacaagcgtccaaagccttgtactgggcgccaccatctaccttat aggctttgatgggactgcggtaatcaccagagctgtggccgcaaacaatgggctgacgg ccggcatcgacaatcttatgccattcaatcttgtgattccaaccaatgagataacccag ccaatcacatccatcaaactggagatagtgacctccaaaagtgatggtcaggcagggga acagatgtcatggtcggcaagtgggagcctagcagtgacgatccatggtggcaactatc caggagccctccgtcccgtcacactagtggcctacgaaagagtggcaacaggatctgtc gttacggtcgctggggtgagcaacttcgagctgatcccaaatcctgaactagcaaagaa cctggttacagaatatggccgatttgacccaggagccatgaactacacgaaattgatac tgagtgagagggaccgccttggcatcaagaccgtctggccaacaagggagtacactgac

-continued tttcgtgagtacttcatggaggtggccgacctcaactctcccctgaagattgcaggagc atttggcttcaaagacataatccgggccataaggaggtgagcggccgcgatatc*aataa*

*aatatctttattttcattacatctgtgtgttggttttttgtgtgaatcgatagtactaa*

*catacgctctccatcaaaacaaaacgaaacaaaacaaactagcaaaataggctgtcccc*

*agtgcaagtgcaggtgccagaacatttctct*tctagacctgcaggcccggggcaagtag

*atgcaatttcctcacactagttgggtttatctactattgaattttcccctatctgtgat*

*acacttgggagcctctacaagcatattgccatcatgtacgtttttatctactgtcttaa*

*cgcccatgggaacggaggcgtcgtcgtcatgtattggacggcaacataggcagcaacac*

*aaattgcgtttaggtggggtgcatgtggactcgataccaagcccctgcagctggggaac*

*gtctggtggagagccgataatttgatatacgcacgccatattactgtcgttgaagtacg*

*ccttatcttctatgttttcaaatttaggttcccaagtggacgtgagaagtgtttgtatc*

*tcacatggaatggcccaaggcattccagcccaggtgcctggtactttaatggcaaacaa*

*acgttttggtagaggtattgattctattgcagttctgcagatatctgcagccccgagta*

*tccacaggctatacgatacgttatcggaggcctccgattctagcattacatagccggtc*

*agtagatcctgccattcggtagcgcaaccggctacatcttcaaacagtctcacaataaa*

*tgcatctctcgttcctgccaatccggaaccgggcataccactcccgcctgccgatttaa*

*ttctcacaattgggcgatgccggcggggcaaaacgaatgtggatttggcaaaccgacac*

*aggtctgctgtacggactaatatgggcacacccacatcattcttcagatgctccatgca*

*ttgttctatgagaaagatccatagggtggaggcagcgtcacgagatcgcccaggcaatc*

*gatcgcattcgtctagtaaagtgacgagagttatcatgcacacacccatgcccacgcct*

*tccgaataactggagctgtggaagatcggaaacgtctttttgactgccggtctcgtact*

*actttcgcacaggtgtatacccggacgcgtactatatattttatatcatccaacgtccc*

*gaaattacatacgtggcggcgatggaagtagatgttgagtcttcgaaagtaagtgcctc*

*gaatatgggtattgtctgtgaaaatatcgaaagcggtacgacggttgcagaaccgtcga*

*tgtcgccagatactagtaacaatagcttcgataacgaagacttccgtgggcctgaatac*

*gatgtggagata*

Partial plasmid SB1US2 gpVIIdwtsyn sequence (for vSB1-010)
Green and Italic = Flanking Arms
BLUE AND UPPERCASE = GPCMV
Black and Bold = NDV-F VIId wt
Red and Italic and Underlined = Syn Poly A (SEQ ID NO: 57)

*tctcgtctaaaacgctccagtgctttacagttcgataatctggacctggggacgcgtat*

*aggatcgttcctccacatgcgctgctgtcggtatctcgaatccccggtattcagttgga*

*tcgttggcggagtgtcctcctggactctgcaatgttccctagccgtcttcactatctcg*

*tgcaaggctctataatacagttcctctgcagacccgtcgttgctcttcccttctgcgtc*

*gttagttatttctgtaggctccagacgatttgcctgcatttgtgcgcaacataatctga*

*ttgcattccctatctcgtcttccggtaatcccataggtgttcggtattcgcagataggt*

*agagaaagcaccactgcaaatcgtgcaatttccattgccccaaccaatattttttttaa*

*gaacggcatcgccgttaatgtacctcgggcattgtgacgatcgaaacccttatggatgc*

*ctaaagagagcattgcggtccagttctccaggtgaaaagagaatagcgcgggtagaaac*

*gggccgattagttttatcttcgccgcgtccctaatatcccaagttctgcagtataactt*

*ccatcgtccgttttcgacaaggtccggcgcgacatagtttgaaatgtcatctatcagaa*

-continued

*acatctcgcccatcgtagaaaaaaacctgtacgcagaccataaaaccattcggtaccac*

*atatccttgtgtatatcaaacgatatgttggttatgtcgttggcggatgttgtatgaaa*

*tagagctaagcgttctctggattccacgcactgaacgattccgttagtcaattcatctg*

*ctaacataggccaaaagtttattcgtgttacttttctcggcggtttggcaaaacgcccc*

*cttggcacatccatgtcattaaatacagcggcataactcctactcatgtgttccatagc*

*ccaggtttctgttcggtctgctactacgatcagatcagtggcgcgatcagatgcgtggg*

*atgaatgaagtgtatccgaaagcagttttgagatatacgctaaactgtacgacgattgt*

*ggcactaaacgaagctttgcgcgaccccccatcccacgccc*tgcaggTTAGTCATATGTT

ACTTGGCAGAGGCCGCATGGAAAGTCCCTGGACGTGGGACATCTGATTAATACGTGAGG

AGGTCAGCCATGTTCTTTTTGGCAAAGGACTACGGTCATTGGACGTTTGATTGGCATGG

GATAGGGTCAGCCAGAGTTAACAGTGTTCTTTTGGCAAAGGGATACGTGGAAAGTCCCG

GGCCATTTACAGTAAACTGATACGGGGACAAAGCACAGCCATATTTAGTCATGTATTGC

TTGGCAGAGGGTCTATGGAAAGTCCCTGGACGTGGGACGTCTGATTAATATGAAAGAAG

GTCAGCCAGAGGTAGCTGTGTCCTTTTTGGCAAAGGGATACGGTTATGGGACGTTTGAT

TGGACTGGGATAGGGTCAGCCAGAGTTAACAGTGTTCTTTTGGCAAAGGAAACGTGGAA

AGTCCCGGGCCATTTACAGTAAACTGATACTGGGACAAAGTACACCCATATTTAGTCAT

GTTCTTTTTGGCAAAGAGCATCTGGAAAGTCCCGGGCAGCATTATAGTCACTTGGCAGA

GGGAAAGGGTCACTCAGAGTTAAGTACATCTTTCCAGGGCCAATATTCCAGTAAATTAC

ACTTAGTTTTATGCAAATCAGCCACAAAGGGGATTTTCCCGGTCAATTATGACTTTTTC

CTTAGTCATGCGGTATCCAATTACTGCCAAATTGGCAGTACATACTAGGTGATTCACTG

ACATTTGGCCGTCCTCTGGAAAGTCCCTGGAAACCGCTCAAGTACTGTATCATGGTGAC

TTTGCATTTTTGGAGAGCACGCCCCACTCCACCATTGGTCCACGTACCCTATGGGGGAG

TGGTTTATGAGTATATAAGGGGCTCCGGTTTAGAAGCCGGGCAGAgcggccgcatgggc tccaaaccttctaccaggatcccagcacctctgatgctgatcacccggattatgctgat attgggctgtatccgtccgacaagctctcttgacggcaggcctcttgcagctgcaggaa ttgtagtaacaggagataaggcagtcaatgtatacacttcgtctcagacagggtcaatc atagtcaagttgctcccgaatatgcccagggataaggaggcgtgtgcaaaagccccatt agaggcatataacagaacactgactactttgctcactcctcttggcgactccatccgca agatccaagggtctgtgtccacatctggaggaggcaagcaaggccgcctgataggtgct gttattggcagtgtagctcttggggttgcaacagcggcacagataacagcagctgcggc cctaatacaagccaaccagaatgccgccaacatcctccggcttaaggagagcattgctg caaccaatgaagctgtgcatgaagtcaccgacggattatcacaactatcagtggcagtt gggaagatgcagcagtttgtcaatgaccagtttaataatacggcgcgagaattggactg tataaaaatcacacaacaggttggtgtagaactcaacctatacctaactgaattgacta cagtattcgggccacagatcacctcccctgcattaactcagctgaccatccaggcactt tataatttagctggtggcaatatggattacttattaactaagttaggtatagggaacaa tcaactcagctcgttaattggtagcggcctgatcactggttaccctatactgtatgact cacagactcaactcttgggcatacaagtgaatttaccctcagtcgggaacttaaataat atgcgtgccacctatttggagaccttatctgtaagtacaaccaaaggatatgcctcagc acttgtcccgaaagtagtgacacaagtcggttccgtgatagaagagcttgacacctcat actgtatagagtccgatctggatttatattgtactagaatagtgacattccccatgtcc

-continued ccaggtatttattcctgtttgagcggcaacacatcagcttgcatgtattcaaagactga aggcgcactcactacgccgtatatggcccttaaaggctcagttattgccaattgtaaaa taacaacatgtagatgtacagaccctcctggtatcatatcgcaaaattatggagaagct gtatccctgatagatagacattcgtgcaatgtcttatcattagacgggataactctaag gctcagtggggaatttgatgcaacttatcaaaagaacatctcaatactagattctcaag tcatcgtgacaggcaatcttgatatatcaactgaacttggaaacgtcaacaattcaatc agcaatgccttggataggttggcagaaagcaacagcaagctagaaaaagtcaatgtcag actaaccagcacatctgctctcattacctatattgttctaactgtcatttctctagttt tcggtgcacttagtctggtgttagcgtgttacctgatgtacaaacagaaggcacaacaa aagaccttgctatggcttgggaataataccctcgatcagatgagagccactacaagagc atgagcggccgcgatatc*aataaaatatctttattttcattacatctgtgtgttggttt*

*tttgtgtgaatcgatagtactaacatacgctctccatcaaaacaaaacgaaacaaaaca*

*aactagcaaaataggctgtccccagtgcaagtgcaggtgccagaacatttctct*tctag acctgcag*gggagtctgtgcaaggttaatgaccctcgcagttcattcggaagttataac*

*tgccgccttcgcacatttctttttgtcctgttttgtattgccataacagataggaattg*

*aaacctgatcctcctgtttttttgcagcatggccagcaacagaatactttgtcggatcga*

*ctacttgcgcgagatggttccgttcttggaggtttcggcgggtcgggtggagaacctat*

*tattttatacacacacgtcataccgttgtcgcgaaaatgttctttgtcttctgccgtct*

*cgaacgtcggttcccacgtagacgttaggagcgttggaatggtatcaggaagagcccac*

*ggcatgccggaccaagtacccgctactttgaccgcgagcagtctcttcggtaatgggat*

*gtattccagagcagcgcggcagagatcagcggcccccactatccacagactgtatgaag*

*tgttttctgaaacatcggactccaacatcaaatatccagacataacatcttgccattcg*

*gaagcacatccgccgacatcttcaaatagcctaactataaacgagtctctagttcctgc*

*taacccagtacctcgaatgccagtcccatccggtgggttcgtcctgataatcggtctct*

*gacgccgaggaagaactaaaaggggtctggaaaagcggaacagatctgcagaccgaacg*

*actacagacacgcccacatcatcatgtatctgttccatgcattgctttatgagaaaaat*

*ccataaggccgaggcggcatctctagatctcccggggagtctctcgcactcatctagga*

*gagtgacgacagttatcatagacacgcccatttgtgcaccaaacgaaaagttcctgtac*

*tggtggagcgtcggcgcgggaatcggtccgtgctctgaaaccagtgtctagacagaaga*

*ccatccggtaaattctggtgtatgaactgacggtctccagacgaacgtcgaagacatta*

*acgatggaaactaacgagctttcttcaaaagtgtctgattacaacgctaatagacctta*

*cgaaactatacgcagcgataccagtgacacagatccgtcggtgtcg*

The nucleotide sequence of the cloned NDV Texas F gene (wild type non-modified)
(SEQ ID NO: 49)

ATGGGCTCCAGATCTTCTACCAGGATCCCGGTACCTCTAATGCTGATCATCCGAACCGC

GCTGACACTGAGCTGTATCCGTCTGACAAGCTCTCTTGATGGCAGGCCTCTTGCGGCTG

CAGGGATCGTGGTAACAGGAGATAAAGCAGTCAACATATACACCTCATCCCAGACAGGG

TCAATCATAGTTAAGTTACTCCCGAATATGCCCAAGGACAAAGAGGTGTGTGCAAAAGC

CCCATTGGAGGCATACAACAGGACACTGACTACTTTACTCACCCCCCTTGGTGATTCTA

TCCGCAGGATACAAGAGTCTGTGACTACTTCCGGAGGAAGGAGACAGAGACGCTTTATA

GGTGCCATTATCGGCAGTGTAGCTCTTGGGGTTGCGACAGCTGCACAGATAACAGCAGC

-continued

TTCGGCCCTGATACAAGCCAACCAGAATGCTGCCAACATCCTCCGGCTTAAAGAGAGCA

TTGCTGCAACCAATGAAGCTGTGCACGAGGTCACTGACGGATTATCACAACTAGCAGTG

GCAGTAGGGAAGATGCAACAGTTTGTCAATGACCAGTTCAATAATACAGCGCAAGAATT

GGACTGTATAAAAATTGCACAGCAGGTCGGTGTAGAACTCAACTTGTACCTAACTGAAT

TGACTACAGTATTTGGGCCACAAATCACTTCCCCTGCCTTAACTCAGCTGACTATCCAA

GCGCTTTACAATCTAGCTGGTGGTAATATGGATTACTTGCTGACTAAGTTAGGTGTAGG

GAACAACCAACTCAGCTCATTAATTGGTAGCGGCTTGATCACCGGCAACCCTATTCTGT

ACGACTCACAGACTCAGATCTTGGGTATACAGGTAACTTTGCCTTCAGTTGGGAACCTG

AATAATATGCGTGCCACCTACCTGGAGACCTTATCTGTAAGCACAACCAAGGGATTTGC

CTCAGCACTTGTCCCAAAAGTGGTGACACAGGTCGGTTCCGTGATAGAAGAACTTGACA

CCTCATACTGTATAGGGACCGACTTGGATTTATACTGTACAAGAATAGTGACATTCCCT

ATGTCTCCTGGTATTTATTCTTGTCTGAGCGGTAATACATCGGCTTGCATGTATTCAAA

GACTGAAGGCGCACTTACTACGCCATATATGGCTCTCAAAGGCTCAGTTATTGCCAATT

GCAAGCTGACAACATGTAGATGTGCAGATCCCCCAGGTATCATATCGCAAAATTATGGA

GAAGCTGTGTCCTTAATAGATAGGCACTCATGCAACGTCTTATCCTTAGACGGGATAAC

TCTGAGGCTCAGTGGGGAATTTGATGCAACCTATCAAAAGAATATCTCTATACTAGATT

CTCAAGTTATAGTGACAGGCAATCTTGATATATCAACTGAGCTTGGGAATGTCAACAAC

TCAATAAGTAATGCCCTGAATAAGTTAGAGGAAAGCAACAGCAAACTAGACAAAGTCAA

TGTCAAACTGACCAGCACATCTGCTCTCATTACCTACATCGTTTTAACTGTCATATCTC

TTGTTTTTGGTGTACTTAGCCTGGTTCTAGCATGCTACCTGATGTACAAGCAAAAGGCA

CAACAAAAGACCTTGTTATGGCTTGGGAATAATACCCTTGATCAGATGAGAGCCACTAC

AAAAATATGA

The amino acid sequence of the cloned NDV Texas F gene (wild type non-modified; cleavage site underlined)

(SEQ ID NO: 50)

MGSRSSTRIPVPLMLIIRTALTLSCIRLTSSLDGRPLAAAGIVVTGDKAVNIYTSSQTG

SIIVKLLPNMPKDKEVCAKAPLEAYNRTLTTLLTPLGDSIRRIQESVTTSG<u>GRRQRRF</u>I

GAIIGSVALGVATAAQITAASALIQANQNAANILRLKESIAATNEAVHEVTDGLSQLAV

AVGKMQQFVNDQFNNTAQELDCIKIAQQVGVELNLYLTELTTVFGPQITSPALTQLTIQ

ALYNLAGGNMDYLLTKLGVGNNQLSSLIGSGLITGNPILYDSQTQILGIQVTLPSVGNL

NNMRATYLETLSVSTTKGFASALVPKVVTQVGSVIEELDTSYCIGTDLDLYCTRIVTFP

MSPGIYSCLSGNTSACMYSKTEGALTTPYMALKGSVIANCKLTTCRCADPPGIISQNYG

EAVSLIDRHSCNVLSLDGITLRLSGEFDATYQKNISILDSQVIVTGNLDISTELGNVNN

SISNALNKLEESNSKLDKVNVKLTSTSALITYIVLTVISLVFGVLSLVLACYLMYKQKA

QQKTLLWLGNNTLDQMRATTKI

NDV-F YZCQ wildtype DNA sequence (SEQ ID NO: 51)

atgggctccagatcttctaccaggatcccggtacctctaatgctgatcatccgaaccgc gctgacactgagctgtatccgtctgacaagctctcttgatggcaggcctcttgcggctg cagggatcgtggtaacaggagataaagcagtcaacatatacacctcatcccagacaggg tcaatcatagttaagttactcccgaatatgcccaaggacaaagaggtgtgtgcaaaagc cccattggaggcatacaacaggacactgactactttactcaccccccttggtgattcta tccgcaggatacaagagtctgtgactacttccggaggaggcaagcaaggccgcctgata -continued ggtgccattatcggcagtgtagctcttggggttgcgacagctgcacagataacagcagc ttcggccctgatacaagccaaccagaatgctgccaacatcctccggcttaaagagagca ttgctgcaaccaatgaagctgtgcacgaggtcactgacggattatcacaactagcagtg gcagtagggaagatgcaacagtttgtcaatgaccagttcaataatacagcgcaagaatt ggactgtataaaaattgcacagcaggtcggtgtagaactcaacttgtacctaactgaat tgactacagtatttgggccacaaatcacttcccctgccttaactcagctgactatccaa gcgctttacaatctagctggtggtaatatggattacttgctgactaagttaggtgtagg gaacaaccaactcagctcattaattggtagcggcttgatcaccggcaaccctattctgt acgactcacagactcagatcttgggtatacaggtaactttgccttcagttgggaacctg aataatatgcgtgccacctacctggagaccttatctgtaagcacaaccaagggatttgc ctcagcacttgtcccaaaagtggtgacacaggtcggttccgtgatagaagaacttgaca cctcatactgtatagggaccgacttggatttatactgtacaagaatagtgacattccct atgtctcctggtatttattcttgtctgagcggtaatacatcggcttgcatgtattcaaa gactgaaggcgcacttactacgccatatatggctctcaaaggctcagttattgccaatt gcaagctgacaacatgtagatgtgcagatcccccaggtatcatatcgcaaaattatgga gaagctgtgtccttaatagataggcactcatgcaacgtcttatccttagacgggataac tctgaggctcagtggggaatttgatgcaacctatcaaaagaatatctctatactagatt ctcaagttatagtgacaggcaatcttgatatatcaactgagcttgggaatgtcaacaac tcaataagtaatgccctgaataagttagaggaaagcaacagcaaactagacaaagtcaa tgtcaaactgaccagcacatctgctctcattacctacatcgttttaactgtcatatctc ttgtttttggtgtacttagcctggttctagcatgctacctgatgtacaagcaaaaggca caacaaaagaccttgttatggcttgggaataataccccttgatcagatgagagccactac aaaaatatga NDV-F protein from wildtype YZCQ strain (Amino Acid Sequence of NDV-F of Texas strain with lentogenic cleavage site sequence)

(SEQ ID NO: 52)

mgsrsstripvplmliirtaltlscirltssldgrplaaagivvtgdkavnlytssqtg siivkllpnmpkdkevcakapleaynrtltttlltplgdsirriqesvttsgggkqgrli gaiigsvalgvataaqitaasaliqanqnaanilrlkesiaatneavhevtdglsqlav avgkmqqfvndqfnntaqeldciklaqqvgvelnlylteltt vfgpqitspaltqltiq alynlaggnmdyllltklgvgnnqlssligsglitgnpilydsqtqilgiqvtlpsvgnl nnmratyletlsysttkgfasalvpkvvtqvgsvieeldtsycigtdldlyctrivtfp mspgiysclsgntsacmysktegalttpymalkgsviancklttcrcadppgiisqnyg eavslidrhscnvlsldgitlrlsgefdatyqknisildsqvivtgnldistelgnvnn sisnalnkleesnskldkvnvkltstsalityivltvislvfgvlslvlacylmykqka qqktllwlgnntldqmrattki*

NDV-F Texas wildtype DNA sequence (SEQ ID NO: 53)

atgggctctaaaccttctaccaggatcccagcacctctgatgctgatcacccggattat gctgatattggactgtatccgtccgacaagctctcttgacggcaggcctcttgcagctg caggaattgtagtaacaggagataaggcagtcaatgtatatacctcgtctcagacaggg tcaatcatagtcaagttgctcccgaatatgcccaaggataaggaggcgtgtgcgaaaga cccattagaggcatataacagaacactgactactttgctcactcctcttggcgaatcca -continued tccgcaagatccaagggtctgtgtccacgtctggaggaggcaagcaaggccgcctgata ggtgctgttattggtagtgtagctcttggggttgcaacagcggcacaaataacagcagc tgcggccctaatacaagccaaccagaatgctgccaacatccttcggcttaaggagagca ttgctgcaaccaatgaagctgtgcatgaagtcaccgacggattatcacaactatcagtg gcagttgggaagatgcagcagtttgtcaatgaccagtttaataatacagcgcgagaatt ggactgtataaaaatcacacaacaggttggtgtagaactcaacctatacctaactgaat tgactacagtattcgggccacagatcacctcccctgcattaactcagctgaccatccag gcactttataatttagctggtggcaatatggattacttattaactaagttaggtatagg gaacaatcaactcagctcattaattggcagcggcctgatcactggttaccctatattgt atgactcacagactcaactcttgggcatacaagtgaatttgccctcagtcgggaactta aataatatgcgtgccacctatttagagaccttatctgtaagtacagccaaaggatatgc ctcagcacttgttccaaaagtagtgacacaagtcggttctgtgatagaagagcttgaca cctcatactgtatagagtccgatctggatttatattgtactagaatagtgacattcccc atgtccccaggtatttattcctgtttaagcggcaacacatcagcttgcatgtattcaaa gactgaaggcgcactcactacgccgtatatggcccttaaaggctcagttattgccaatt gtaagataacaacatgtagatgtacagaccctcctggtatcatatcgcaaaattatgga gaagctgtatccctgatagatagacattcgtgcaatgtcttatcattagacgggataac tctgaggctcagtggagaatttgatgcaacttatcaaaagaacatctcaatactagatt ctcaagtcatcgtgacaggcaatcttgatatatcaactgaacttggaaacgtcaacaat tcaatcagcaatgccttggataagttggcaaaaagcaacagcaagctagaaaaagtcaa tgtcagactaaccagcacatccgctctcattacctatattgttctgactgtcatttctc tagttttcggtgcactaagtctgggtttaacatgttacctgatgtacaaacaaaaggca caacaaaagaccttgctatggcttgggaataataccctcgatcagatgagagccactac aagagcatga NDV-F protein from wildtype Texas strain (Amino Acid Sequence of NDV-F VIId wt YZCQ with lentogenic cleavage site sequence)

(SEQ ID NO: 54)

mgskpstripaplmlitrimlildcirptssldgrplaaagivvtgdkavnvytssqtg siivkllpnmpkdkeacakdpleaynrtlttlltplgesirkiqgsvstsgggkqgrli gavigsvalgvataaqitaaaaliqanqnaanilrlkesiaatneavhevtdglsqlsv avgkmqqfvndqfnntareldcikitqqvgvelnlylteltt vfgpqitspaltqltiq alynlaggnmdylltklgignnqlssligsglitgypilydsqtqllgiqvnlpsvgnl nnmratyletlsystakgyasalvpkvvtqvgsvieeldtsyclesdldlyctrivtfp mspgiysclsgntsacmysktegalttpymalkgsvianckittcrctdppgiisqnyg eavslidrhscnvlsldgitlrlsgefdatyqknisildsqvivtgnldistelgnvnn sisnaldklaksnsklekvnvrltstsalityivltvislvfgalslgltcylmykqka qqktllwlgnntldqmrattra*

MDV gB promoter (SEQ ID NO: 55)

CGATGTTTAGTCACGATAGACATCGGTTCGCCCAGCCGTCGAATACAGCATTATATTTT

AGTGTTGAAAATGTAGGGCTGCTTCCTCACTTAAAGGAGGAAATGGCTCGATTCATGTT

TCATAGCAGTAGAAAAACAGATTGGACCGTCAGTAAGTTTAGAGGGTTTTATGACTTTA

GCACTATAGATAATGTAACTGCGGCCCATCGCATGGCTTGGAAATATATCAAAGAACTG

-continued

ATTTTTGCAACAGCTTTATTTTCTTCTGTATTTAAATGTGGCGAATTGCACATCTGTCG
TGCCGACAGTTTGCAGATCAACAGCAATGGAGACTATGTATGGAAAAATGGAATATATA
TAACATATGAAACCGAATATCCACTTATAATGATTCTGGGGTCAGAATCAAGCACTTCA
GAAACGCAAAATATGACTGCAATTATTGATACAGATGTTTTTTCGTTGCTTTATTCTAT
TTTGCAGTATATGGCCCCCGTTACGGCAGATCAGGTGCGAGTAGAACAGATTACCAACA
GCCACGCCCCCATCTGACCCGTCCAATATTCTTGTGTCCCTGCATTTTATCTCACACAA
TTTATGAACAGCATCATTAAGATCATCTCACT

IBDV DNA encoding VP2 protein of IBDV E strain (SEQ ID NO: 58)

Atgacaaacctgcaagatcaaacccaacagattgttccgttcatacggagccttctgat
gccaacaaccggaccggcgtccattccggacgacaccctggagaagcacactctcaggt
cagagacctcgacctacaatttgactgtgggggacacagggtcagggctaattgtcttt
ttccctggattccctggctcaattgtgggtgctcactacacactgcagagcaatgggaa
ctacaagttcgatcagatgctcctgactgcccagaacctaccggccagctacaactact
gcaggctagtgagtcggagtctcacagtaaggtcaagcacactccctggtggcgtttat
gcactaaacggcaccataaacgccgtgaccttccaaggaagcctgagtgaactgacaga
tgttagctacaacgggttgatgtctgcaacagccaacatcaacgacaaaattgggaacg
tcctagtaggggaaggggtaaccgtcctcagcttacccacatcatatgatcttgggtat
gtgaggcttggtgaccccatacccgctatagggcttgacccaaaaatggtagcaacatg
tgacagcagtgacaggcccagagtctacaccataactgcagccgataattaccaattct
catcacagtaccaaacaggtggggtaacaatcacactgttctcagccaacattgatgcc
atcacaagtctcagcgttggggggagagctcgtgttcaaaacaagcgtccaaagccttgt
actgggcgccaccatctaccttataggctttgatgggactgcggtaatcaccagagctg
tggccgcaaacaatgggctgacggccggcatcgacaatcttatgccattcaatcttgtg
attccaaccaatgagataacccagccaatcacatccatcaaactggagatagtgacctc
caaaagtgatggtcaggcaggggaacagatgtcatggtcggcaagtgggagcctagcag
tgacgatccatggtggcaactatccaggagccctccgtcccgtcacactagtggcctac
gaaagagtggcaacaggatctgtcgttacggtcgctggggtgagcaacttcgagctgat
cccaaatcctgaactagcaaagaacctggttacagaatatggccgatttgacccaggag
ccatgaactacacgaaattgatactgagtgagagggaccgccttggcatcaagaccgtc
tggccaacaagggagtacactgactttcgtgagtacttcatggaggtggccgacctcaa
ctctcccctgaagattgcaggagcatttggcttcaaagacataatccgggccataagga
ggtga IBDV VP2 protein of IBDV E strain (SEQ ID NO: 59)

mtnlqdqtqqivpfirsllmpttgpasipddtlekhtlrsetstynltvgdtgsglivf
fpgfpgsivgahytlqsngnykfdqmlltaqnlpasynycrlvsrsltvrsstlpggvy
alngtinavtfqgslseltdvsynglmsatanindkignylvgegvtvlslptsydlgy
vrlgdpipaigldpkmvatcdssdrprvytitaadnyqfssqyqtggvtitlfsanida
itslsvggelvfktsvqslvlgatlyligfdgtavitravaanngltagidnlmpfnlv
iptneitqpitsikleivtsksdgqageqmswsasgslavtihggnypgalrpvtlvay
ervatgsvvtvagvsnfelipnpelaknlyteygrfdpgamnytklilserdrlgiktv
wptreytdfreyfmevadlnsplkiagafgfkdiirairr*

-continued

Guinea pig CMV promoter (SEQ ID NO: 60)

```
ttagtcatatgttacttggcagaggccgcatggaaagtccctggacgtgggacatctga

ttaatacgtgaggaggtcagccatgttctttttggcaaaggactacggtcattggacgt

ttgattggcatgggatagggtcagccagagttaacagtgttcttttggcaaagggatac

gtggaaagtcccgggccatttacagtaaactgatacggggacaaagcacagccatattt

agtcatgtattgcttggcagagggtctatggaaagtccctggacgtgggacgtctgatt

aatatgaaagaaggtcagccagaggtagctgtgtcctttttggcaaagggatacggtta

tgggacgtttgattggactgggatagggtcagccagagttaacagtgttcttttggcaa

aggaaacgtggaaagtcccgggccatttacagtaaactgatactgggacaaagtacacc

catatttagtcatgttctttttggcaaagagcatctggaaagtcccgggcagcattata

gtcacttggcagagggaaagggtcactcagagttaagtacatctttccagggccaatat

tccagtaaattacacttagttttatgcaaatcagccacaaaggggatttcccggtcaa

ttatgactttttccttagtcatgcggtatccaattactgccaaattggcagtacatact

aggtgattcactgacatttggccgtcctctggaaagtccctggaaaccgctcaagtact

gtatcatggtgactttgcatttttggagagcacgccccactccaccattggtccacgta

ccctatgggggagtggtttatgagtatataaggggctccggtttagaagccgggcaga
```

Locus positions of SEQ ID NO:14 (GenBank Accession No. HQ840738.1, Gallid herpesvirus 3 strain SB-1, complete genome)

117554 . . . 118057 UL55 gene; product="UL55 protein"; protein id="AEI00266.1"

Complement (118306 . . . 120927) LORF5 gene; product="ORF996 protein"; protein id="AEI00267.1"

98595 . . . 100031 UL44 gene; product="glycoprotein C"; protein id="AEI00252.1"

25078 . . . 25983 UL7 gene; product="UL-7 like protein"; protein id="AEI00208.1"

Complement (26038 . . . 28332) UL8 gene; product="UL-8 like protein"; protein id="AEI00209.1"

48267 . . . 49865 UL21 gene; product="UL-21 like protein"; protein id="AEI00223.1"

Complement (50033 . . . 52549) UL22 gene; product="UL-22 like protein"; protein id="AEI00225.1"

75497 . . . 75880 UL35 gene; product="UL-35 protein"; protein id="AEI00241.1"

Complement (75498 . . . 85154) UL36 gene; product="UL-36 protein"; protein id="AEI00242.1"

92867 . . . 93928 UL40 gene; product="UL-40 protein"; protein id="AEI00248.1"

Complement (93990 . . . 95261) UL41 gene; product="UL-41 protein"; protein id="AEI00249.1"

108470 . . . 109777 UL50 gene; product="UL-50 protein"; protein id="AEI00260.1"

Complement (109847 . . . 110593) UL51 gene; product="UL-51 protein"; protein id="AEI00261.1"

115036 . . . 116466 UL54 gene; product="UL-54 protein"; protein id="AEI00264.1"

Complement (116571 . . . 117377) LORF4 gene; product="LORF4 protein"; protein id="AEI00265.1"

145853 . . . 146548 US10 gene; product="US10 protein"; protein id="AEI00292.1"

Complement (146697 . . . 147665) SORF4 gene; product="SORF4 protein"; protein id="AEI00294.1"

97141 . . . 98385 UL43 gene; product="UL43 protein"; protein id="AEI00251.1"

Complement (147857 . . . 148672) US2 gene; product="US2 protein"; protein id="AEI00297.1"

150322 . . . 151479 US6 gene; product="glycoprotein D"; protein id="AEI00299.1"

Having thus described in detail preferred embodiments of the present invention, it is to be understood that the invention defined by the above examples is not to be limited to particular details set forth in the above description as many apparent variations thereof are possible without departing from the spirit or scope of the present invention.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What we claim is:

1. A vaccine composition comprising:

1) a recombinant Gallid herpesvirus 3 (MDV-2) strain SB-1 vector, wherein said vector comprises a heterologous polynucleotide coding for and expressing in vivo, a Newcastle Disease Virus (NDV) Fusion protein (NDV-F), and 2) a pharmaceutically or veterinarily acceptable carrier, excipient, vehicle or adjuvant;

wherein the NDV-F protein has at least 99% sequence identity to a polypeptide having the sequence as set forth in SEQ ID NO:2 or wherein the NDV-F protein comprises SEQ ID NO:9.

2. A vaccine composition comprising:

1) a recombinant Gallid herpesvirus 3 (MDV-2) strain SB-1 vector, wherein said vector comprises a heterologous polynucleotide coding for and expressing in vivo, an NDV Fusion protein (NDV-F), 2) a recombinant Herpesvirus of Turkeys (HVT) vector, wherein HVT is also known as MDV-3 or Meleagrid herpesvirus 1, wherein the vector comprises a heterologous polynucleotide coding for and expressing in vivo, an Infectious bursal disease virus (IBDV) VP2, and 3) a pharmaceutically or veterinarily acceptable carrier, excipient, vehicle or adjuvant.

3. The vaccine composition of claim 1 or 2, wherein the heterologous polynucleotide coding for NDV-F is inserted into the region between ORF UL55 and ORF LORF5 in the unique long (UL) region of the recombinant MDV-2 strain SB-1 vector.

4. The vaccine composition of claim 1 or 2, wherein the recombinant MDV-2 strain SB-1 vector comprises a heterologous promoter, and expression of NDV-F is under the control of said promoter, wherein said promoter is selected from an immediate early CMV promoter, a mouse CMV promoter, a guinea pig CMV promoter, an SV40 promoter, a Pseudorabies Virus glycoprotein X promoter, a Herpes Simplex Virus-1 alpha 4 promoter, a Marek's Disease Virus glycoprotein C promoter, a Marek's Disease Virus glycoprotein B promoter, a Marek's Disease Virus glycoprotein E promoter, an Infectious Laryngotracheitis Virus glycoprotein B, an Infectious Laryngotracheitis Virus glycoprotein E promoter, an Infectious Laryngotracheitis Virus glycoprotein D promoter, an Infectious Laryngotracheitis Virus glycoprotein I promoter, or a Bovine Herpesvirus 1.1 VP8 promoter.

5. The vaccine composition of claim 2, wherein the NDV-F protein has at least 95% sequence identity to a polypeptide having the sequence as set forth in SEQ ID NOs: 2, 5, 7, or 9.

6. The vaccine composition of claim 2, wherein the polynucleotide encoding NDV-F has at least 95% sequence identity to SEQ ID NO: 1, 3, 4, 6, or 8.

7. The vaccine composition of claim 4, wherein the heterologous promoter comprises a mouse CMV promoter, a SV40 promoter, or a guinea pig CMV promoter.

8. The vaccine composition of claim 1 or 2, wherein the heterologous polynucleotide coding for NDV-F is in the region between ORF SORF4 and ORF US10 of the recombinant MDV-2 strain SB-1 vector.

9. The vaccine composition of claim 1 or 2, wherein heterologous polynucleotide coding for NDV-F is in the region between ORF SORF4 and ORF US2 of the recombinant MDV-2 strain SB-1 vector.

10. The vaccine composition of claim 1 or 2, wherein heterologous polynucleotide coding for NDV-F is in the region coding for glycoprotein C (UL44) of the recombinant MDV-2 strain SB-1 vector.

* * * * *